(12) United States Patent
Ramtohul et al.

(10) Patent No.: US 10,913,761 B2
(45) Date of Patent: Feb. 9, 2021

(54) 2,7-DIBROMOSPIRO[FLUORENE-9,4'-PIPERIDINE] COMPOUNDS

(71) Applicant: Vertex Pharmaceuticals Incorporated, Boston, MA (US)

(72) Inventors: Yeeman K. Ramtohul, Pierrefonds (CA); Sanjoy Kumar Das, Pierrefonds (CA); Caroline Cadilhac, Montreal (CA); Thumkunta Jagadeeswar Reddy, Pierrefonds (CA); Louis Vaillancourt, Laval (CA); Michel Gallant, Pierrefonds (CA); Bingcan Liu, Montreal (CA); Evelyne Dietrich, Laval (CA); Frederic Vallee, Montreal (CA); Julien Martel, Montreal (CA); Carl Poisson, Montreal (CA)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 16/837,191

(22) Filed: Apr. 1, 2020

(65) Prior Publication Data
US 2020/0270293 A1    Aug. 27, 2020

Related U.S. Application Data

(60) Continuation of application No. 15/945,221, filed on Apr. 4, 2018, now Pat. No. 10,669,298, which is a
(Continued)

(51) Int. Cl.
| | |
|---|---|
| C07D 495/04 | (2006.01) |
| C07H 7/02 | (2006.01) |
| C07D 407/14 | (2006.01) |
| C07D 405/14 | (2006.01) |
| C07D 309/10 | (2006.01) |
| C07H 15/26 | (2006.01) |
| C07D 409/14 | (2006.01) |
| C07H 19/056 | (2006.01) |
| C07D 417/14 | (2006.01) |
| C07H 7/04 | (2006.01) |
| C07H 7/06 | (2006.01) |
| C07H 19/02 | (2006.01) |
| A61K 31/7028 | (2006.01) |
| A61K 31/7034 | (2006.01) |
| A61K 31/7036 | (2006.01) |
| A61K 31/7042 | (2006.01) |
| A61K 31/7048 | (2006.01) |
| A61K 31/7056 | (2006.01) |

(Continued)

(52) U.S. Cl.
CPC ............ *C07H 7/02* (2013.01); *A61K 31/706* (2013.01); *A61K 31/7028* (2013.01); *A61K 31/7034* (2013.01); *A61K 31/7036* (2013.01); *A61K 31/7042* (2013.01); *A61K 31/7048* (2013.01); *A61K 31/7056* (2013.01); *A61K 31/7064* (2013.01); *C07D 309/10* (2013.01); *C07D 405/14* (2013.01); *C07D 407/14* (2013.01); *C07D 409/14* (2013.01); *C07D 413/14* (2013.01); *C07D 417/14* (2013.01); *C07D 495/04* (2013.01); *C07H 7/04* (2013.01); *C07H 7/06* (2013.01); *C07H 15/26* (2013.01); *C07H 19/02* (2013.01); *C07H 19/056* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 6,387,893 B1 * | 5/2002 | Evans | C07D 221/20 514/212.02 |
| 6,878,690 B2 | 4/2005 | Cowden et al. | |

(Continued)

FOREIGN PATENT DOCUMENTS

| | | |
|---|---|---|
| EP | 0619317 A1 | 10/1994 |
| EP | 1800134 A2 | 6/2007 |

(Continued)

OTHER PUBLICATIONS

Dietsch, P. , DE102008011868A1, machine translation, retrieved on Apr. 2, 2015 from h?p :lworldwide. espacenet. com.
(Continued)

*Primary Examiner* — Layla D Berry
(74) *Attorney, Agent, or Firm* — Banner & Witcoff, Ltd.

(57) ABSTRACT

The present invention relates to compounds useful for the treatment or prevention of bacteria infections. These compounds have formula I:

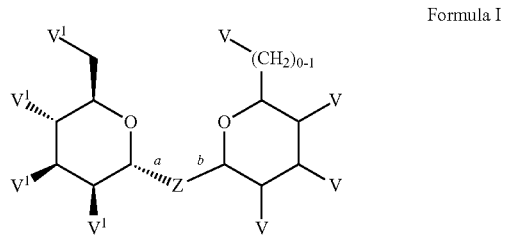

Formula I

The invention also provides pharmaceutically acceptable compositions containing the compounds and methods of using the compositions in the treatment of bacteria infections. Finally, the invention provides processes for making compounds of the invention.

12 Claims, 5 Drawing Sheets

Related U.S. Application Data continuation of application No. 15/140,045, filed on Apr. 27, 2016, now Pat. No. 9,963,478, which is a division of application No. 14/132,662, filed on Dec. 18, 2013, now Pat. No. 9,598,454.

(60) Provisional application No. 61/874,501, filed on Sep. 6, 2013, provisional application No. 61/788,241, filed on Mar. 15, 2013, provisional application No. 61/738,620, filed on Dec. 18, 2012.

(51) Int. Cl.
  *A61K 31/706* (2006.01)
  *A61K 31/7064* (2006.01)
  *C07D 413/14* (2006.01)

(56) References Cited

U.S. PATENT DOCUMENTS

| | | |
|---|---|---|
| 2010/0015600 A1 | 1/2010 | Bamich et al. |
| 2012/0309701 A1 | 12/2012 | Janetka et al. |
| 2013/0084292 A1 | 4/2013 | Darfeuille-Michaud et al. |
| 2013/0261077 A1 | 10/2013 | Bennani et al. |
| 2014/0107049 A1 | 4/2014 | Bennani et al. |
| 2014/0274930 A1 | 9/2014 | Dietrich et al. |

FOREIGN PATENT DOCUMENTS

| | | | |
|---|---|---|---|
| WO | 1998/031697 | A1 | 7/1998 |
| WO | 2004/091499 | A2 | 10/2004 |
| WO | 2005/089733 | A2 | 9/2005 |
| WO | 2006/077364 | A1 | 7/2006 |
| WO | 2006/077365 | A1 | 7/2006 |
| WO | 2006/077366 | A1 | 7/2006 |
| WO | 2006/077367 | A1 | 7/2006 |
| WO | 2006/135667 | A1 | 12/2006 |
| WO | 2007/095124 | A2 | 8/2007 |
| WO | 2011/050323 | A1 | 4/2011 |
| WO | 2011/073112 | A2 | 6/2011 |
| WO | 2012/109263 | A1 | 8/2012 |
| WO | 2012/163478 | A1 | 12/2012 |
| WO | 2012/164074 | A1 | 12/2012 |
| WO | 2013/134415 | A1 | 9/2013 |
| WO | 2014/055474 | A1 | 4/2014 |
| WO | 2014/165107 | A2 | 10/2014 |

OTHER PUBLICATIONS

Dominique, R., "Application of olefin metathesis reaction towards the synthesis of oligosaccharide mimics: A novel strategy in chemical glycobiology", (2003).
Weck, S., et al., "Monosaccharidic mimetics of the sialyl Lewis X tetrasaccharide based on 2, 7-dihydroxynaphthalene", ARKIVOC, 3, (2012), pp. 134-148.
Alzeer, J., and Vasella, A., Oligosaccharide analogs of polysaccharides. Part2. Regioselective deprotection of monosaccharide-derived monomers and dimers, Helvetica Chimica Acta, 1995, vol. 78, pp. 177-193.
Cendret, V., et al., "Design and synthesis of a "click" high-mannose oligosaccharide mimic emulating Man8 binding affinity towards Con A", Chem Commun (Camb) 48(31) : 3733-5 2012.
Dondoni, A., et al., Synthesis of all carbon-linked glycoside clusters round benzene scaffold via Sonogashira-Heck-Cassar cross-coupling of iodobenzenes with ethynyl C-glycosides, Synlett, 2002, No. 11 , pp. 1850-1854.
Espinosa, J.F., et al., "Conformational Differences Between C-and O-Glycosides: The alpha-C-Mannobiose/alpha-O-Mannobiose Case", Chemistry A European Journal, vol. 5, No. 2, 1999, pp. 1-32 (XP002716254).
Gottschaldt, M., et al., "Silver(I) complexes based on novel tripodal thioglycosides: synthesis, structure and antimicrobial activity", Tetrahedron, vol. 62, Issue 48, Nov. 27, 2006, pp. 11073-11080.
Han, J., et al., "Characterization of flavonoids in the traditional Chinese herbal medicine-Huangqin by liquid chromatography coupled with electrospray ionization mass spectrometry", J. Chromatography B., 2007, vol. 848, No. 2, pp. 355-362.
Han, Z., et al., "Structure-Based Drug Design and Optimization of Mannoside Bacterial FimH Antagonists", Journal of Medicinal Chemistry, American Chemical Society, vol. 53, No. 12, 2010, pp. 4779-4792 (XP002620405).
International Search Report for PCT/US2013/076086 dated Apr. 16, 2014.
Klein, T., et al., "FimH Antagonists for the Oral Treatment of Urinary Tract Infections: From Design and Synthesis to in Vitro and in Vivo Evaluation", Journal of Medicinal Chemistry, American Chemical Society, vol. 53, No. 24, 2010, pp. 8627-8864 (XP002620404).
Lövyova, Z., et al., "Stereoselective preparation of four 3-C-mannosylated d-and 1-glucals from a single starting compound", Tetrahedron, vol. 67, No. 27-28, 2011, pp. 4967-4979 (XP055087761).
Mikkelsen, L.M., et a l.?"Application of the anomeric samarium route for the convergent synthesis of the C-linked trisaccharide alpha-D-Man-(1→3)-[alpha-D-Man-(1→6)]-D-Man and the disaccharides alpha-D-Man-(1 ?>3)-D-Man and alpha-D-Man-(1→6)-D-Man.", J Org Chem 67(18): 6297-6308 2002.
Mikkelsen, L. M., et al., "Conformation of glycomimetics in the free and protein-bound state: structural and binding features of the C-glycosyl analogue of the core trisaccharide alpha-D-Man-(1→3)—[alpha-D-Man-(1 ?> 6)]-D-Man", Journal of the American Chemical Society, vol. 124, No. 50, 2002, pp. 14940-14951 (XP055087758).
Pang, L., et al., "FimH Antagonists: Structure-Activity and Structure-Property Relationships of Biphenyl [alpha]-DMannopyranosides", Chemmedchem, vol. 7, No. 8, 2012, pp. 1404-1422 (XP055087656).
Papadopoulos A., et al., "Diazo Transfer and Click Chemistry in the Solid Phase Syntheses of Lysine-Based Glycodendrimers as Antagonists against *Escherichia coli* FimH", Mol Pharm 9(3) : 394-403 2012.
Perez-Balderas, F. et al., "Click Multivalent Homogeneous Neoglycoconjugates—Synthesis and Evaluation of Their Binding Affinities", European Journal of Organic Chemistry 2009(15) : 2441-2453 2009.
Schmidt, R. R. And Beyerbach, A., AN1992:592188, Liebigs Annalen der Chemie, 1992, (9), 983-986.
Touaibia M., et al., "Mannosylated G{O) Dendrimers with Nanomolar Affinities to*Escherichia coil* FimH", ChemMedChem 2(8): 1190-1201 2007.
Zhang P., et al., "Synthesis and biological activities of novel isoxazoline-linked pseudodisaccharide derivatives", Carbohydr Res 351( ): 7-16 2012.
Hartmann, M. et al, The Bacterial Lectin FimH, a Target for Drug Discovery—Carbohydrate Inhibitors of Type 1 Fimbriae-Mediated Bacterial Adhesion, Eur J. Org. Chem., 2011, pp. 3583-3609.
Jinwang Xu et al., "Synthesis and Thermolysis of Acetylenosaccharidederived 1,2-dialkynylbenzenes", Helvetica Chimica Acta— vol. 79 (1996), pp. 2004-2022.

\* cited by examiner

DSC of Compound 162 Crystalline Form A

XRPD of Compound 162

DSC of Compound 202 Crystalline Form A

XRPD of Compound 202

TGA of Compound 202

2,7-DIBROMOSPIRO[FLUORENE-9,4'-PIPERIDINE] COMPOUNDS

CROSS REFERENCE TO RELATED APPLICATIONS

This application is a continuation application which claims priority to U.S. patent application Ser. No. 15/945,221, filed on Apr. 4, 2018, which is a continuation application which claims priority to U.S. patent application Ser. No. 15/140,045, filed on Apr. 27, 2016, which is a divisional application which claims priority to U.S. patent application Ser. No. 14/132,662, filed on Dec. 18, 2013, which claims the benefit, under 35 U.S.C. § 119, of U.S. Provisional Application No. 61/738,620, filed Dec. 18, 2012; U.S. Provisional Application No. 61/788,241, filed Mar. 15, 2013; and U.S. Provisional Application No. 61/874,501, filed Sep. 6, 2013, the entire contents of each of the above applications being incorporated herein by reference.

BACKGROUND OF THE INVENTION

Figure 1:
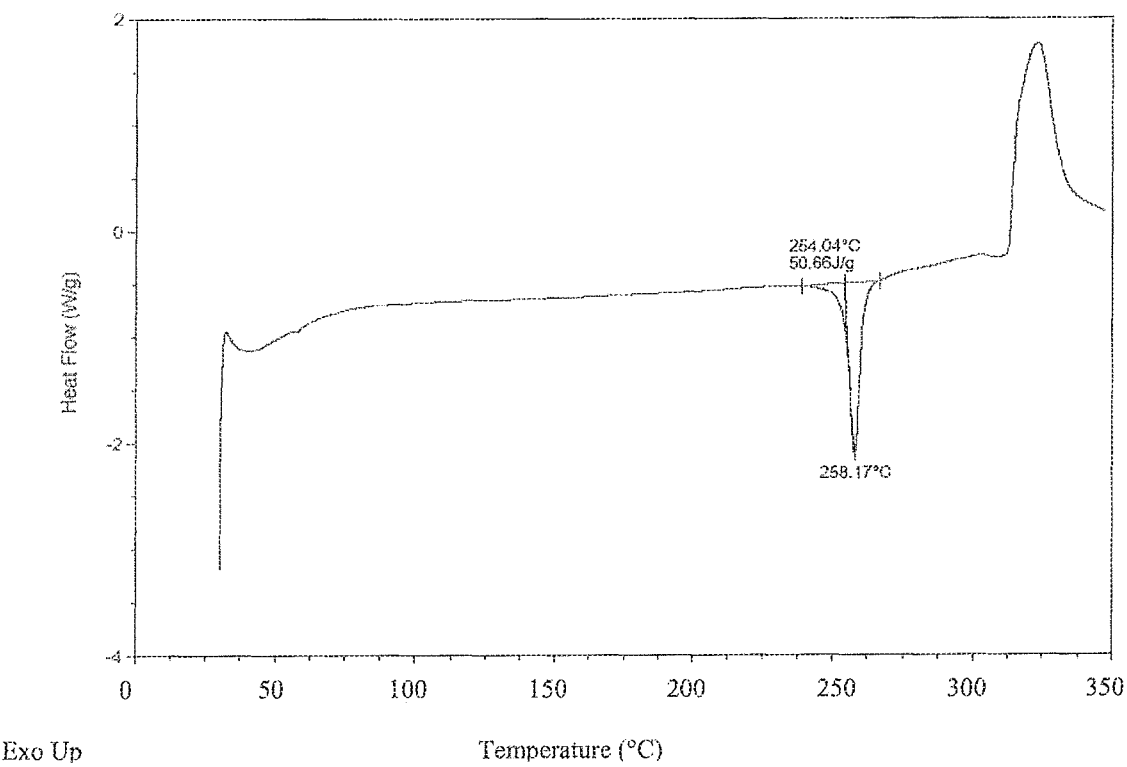
FIG. 1: Differential scanning calorimetry (DSC) of Compound 162, crystalline form A
Figure 2:
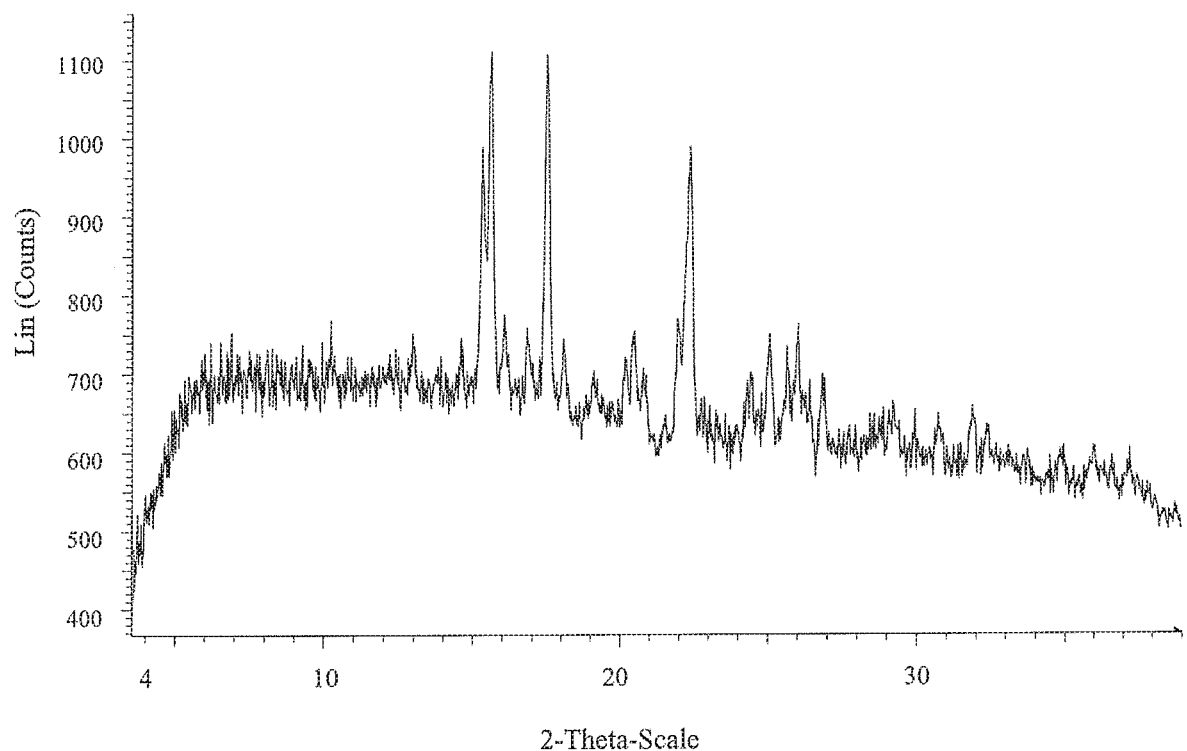
FIG. 2: X-ray powder diffractogram of Compound 162
Figure 3:
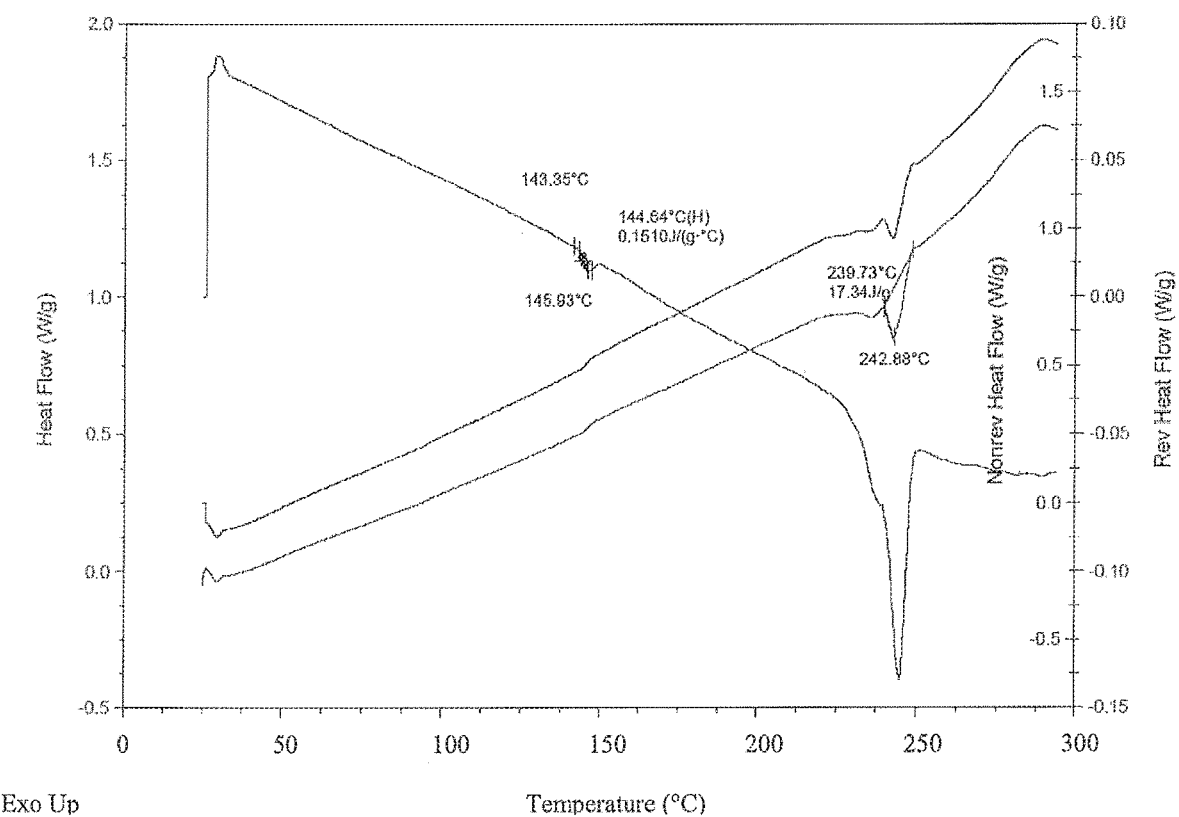
FIG. 3: Differential scanning calorimetry (DSC) of Compound 202, crystalline form A
Figure 4:
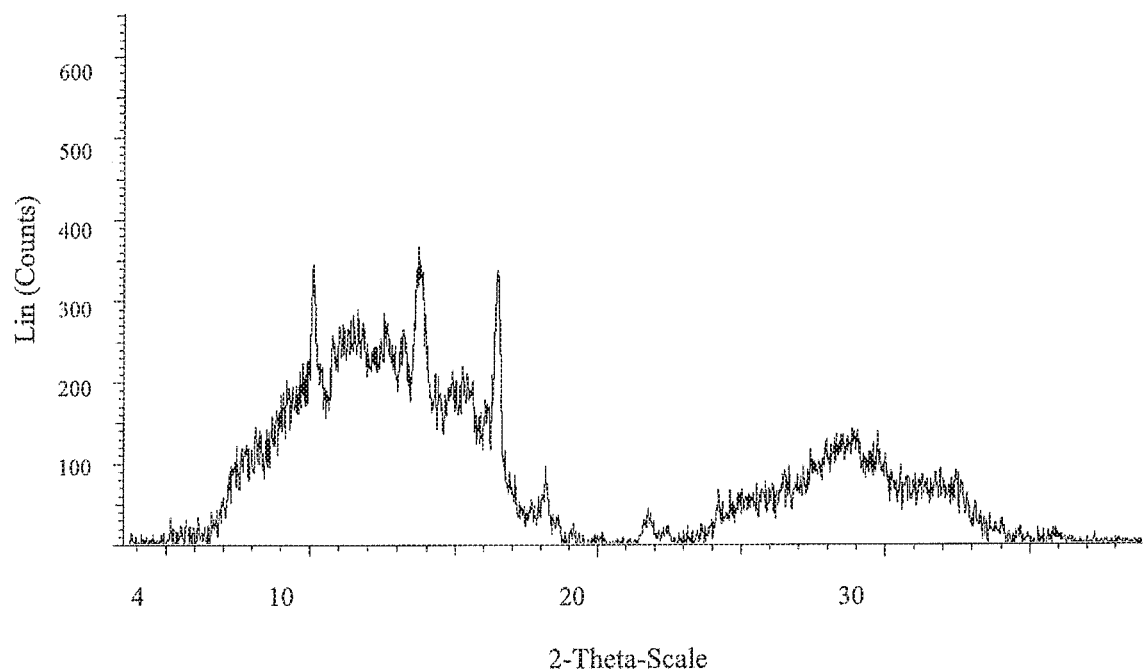
FIG. 4: X-ray powder diffractogram of Compound 202
Figure 5:
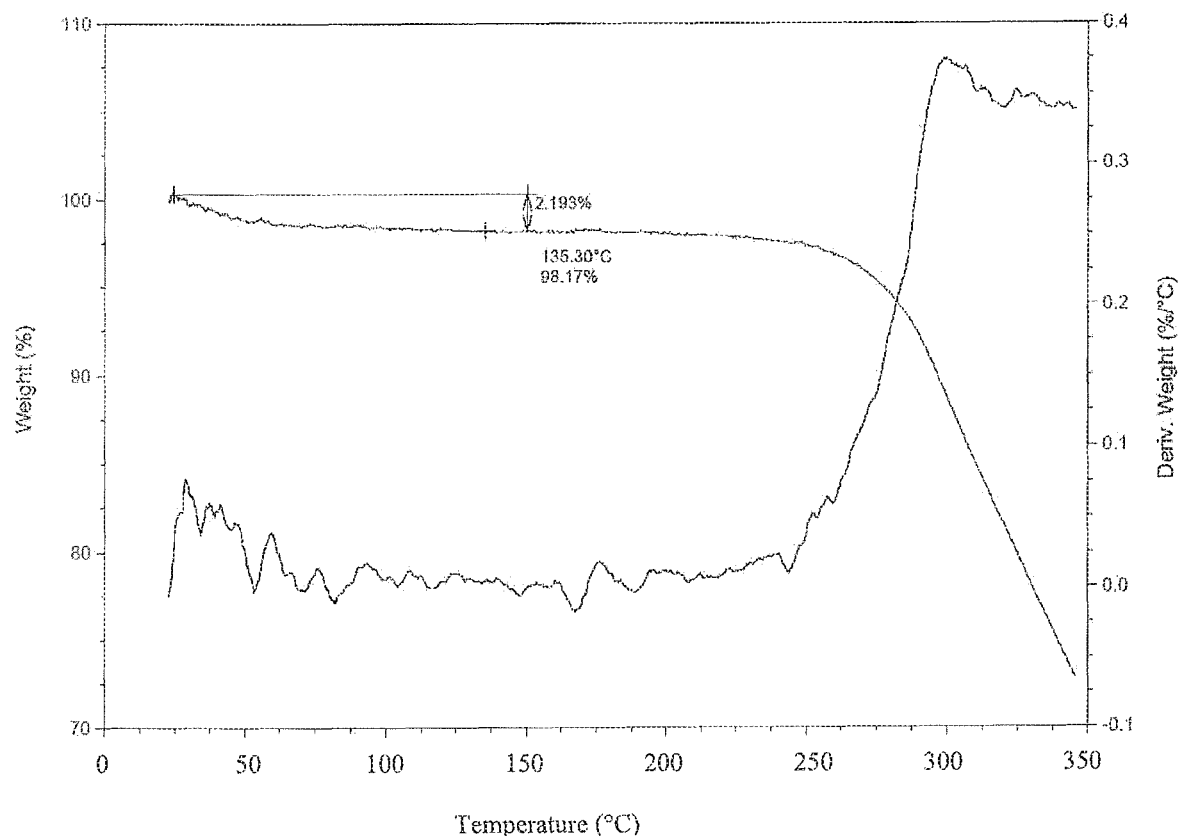
FIG. 5: Thermal gravimetric analysis (TGA) trace of Compound 202

Inflammatory bowel disease (IBD) is a complex chronic inflammatory disorder, with the two more common forms being ulcerative colitis (UC) and Crohn's disease (CD). IBD is a multifactorial disease that results from a combination of predisposing genetic factors, environmental triggers, dysbiosis of the gastrointestinal microbiota and an inappropriate inflammatory response (Man et al., 2011, Nat Rev Gastroenterol Hepatol, March, 8(3):152-68).

Several studies on fecal and mucosa-associated bacterial communities have shown that the microbiota of patients with Crohn's disease (CD) differ from those of healthy controls, as well as those of patients with ulcerative colitis (UC). Although the reported changes are not always consistent, numbers of *Escherichia coli* are generally increased, whereas Firmicutes are scarcer in CD patients (Peterson et al., 2008, Cell Host Microbe, 3: 17-27; Frank et al., 2007, Proc. Natl. Acad. Sci., 104:13780-13785). Whether these changes are causative factors or consequences of inflammation, it remains controversial. To date, several pathogens have been proposed as causative agents. In particular, adherent-invasive *E. coli* (AIEC) has been reported to be more prevalent in CD patients than in controls in several countries (United Kingdom, France and the USA) (Darfeuille-Michaud et al., 2004, Gastroenterology, 127:412-421; Martinez-Medina et al., 2009, Inflamm Bowel Dis., 15:872-882). AIEC strains have been isolated from ileal lesions in ~35% of CD patients compared to ~5% of healthy subjects. One of the features of AIEC is their ability to adhere and invade epithelial cells. It is known from various models that the binding of adhesins expressed on the bacterial cell surface to defined glycosylated receptors on the host tissue surface is considered to be an initial and critical step in pathogenesis, then opening a new avenue for therapy such as blocking the interaction between type 1 pili and CEACAM6, a known host receptor for FimH (Barnich et al., 2007, J. Clin. Invest., 117:1566-1574; Carvalho et al., 2009, JEM, vol. 206, no. 10, 2179-2189). Therefore, inhibition of adhesion, and consequently intracellular replication of AIEC in epithelial cells, may prevent establishment of a sub-mucosal infection leading to mucosal inflammation and epithelial barrier disruption.

It has also been demonstrated recently that FimH antagonists are potentially effective in treating urinary tract infections (J. Med. Chem. 2010, 53, 8627-8641).

SUMMARY OF THE INVENTION

The present invention provides compounds useful for the treatment or prevention of bacteria infections, such as urinary tract infection (UTI) and inflammatory bowel disease (IBD).

The compounds of the present invention are represented by the following structure of Formula (I), or a pharmaceutically acceptable salt thereof:

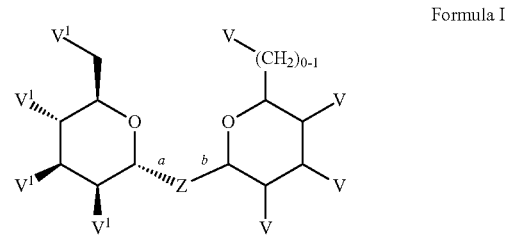

Formula I wherein $V^1$, Z, and V are as described herein.

The present invention also provides a composition comprising the compound described herein, and a pharmaceutically acceptable carrier, adjuvant, or vehicle.

The present invention also provides a method of treating or preventing bacteria infection in a subject, comprising administering to the subject an effective amount of the compound or the composition described herein. The present invention also provides processes for making compounds of the invention.

DETAILED DESCRIPTION OF THE INVENTION

The present invention relates to compounds useful for the treatment or prevention of bacteria infections, such as urinary tract infection (UTI) and inflammatory bowel diseases (IBD).

One aspect of the invention provides a compound of Formula I, or a pharmaceutically acceptable salt thereof:

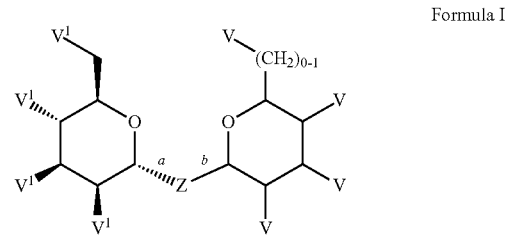

Formula I wherein
$V^1$ is halogen, $NH_2$, OH, or SH;
V is H, halogen, —$OR^7$, —$NR^5R^6$, —$SR^7$, or $C_1$-$C_6$aliphatic;
$R^5$ is —H; $X^5$; $Q^5$; $X^5$-$Q^5$; —C(O)$R^9$; —C(O)NH$R^9$; or —C(O)O$R^9$;
$R^6$ is —H; $X^6$; $Q^6$; $X^6$-$Q^6$; —C(O)$R^9$; —C(O)NH$R^9$; or —C(O)O$R^9$;
$R^7$ is —H; $X^7$; $Q^7$; $X^7$-$Q^7$; —C(O)$R^9$; or —C(O)NH$R^9$;
$R^9$ is —H; $X^9$; $Q^9$; or $X^9$-$Q^9$;
each $X^5$, $X^6$, $X^7$, and $X^9$ is independently $C_1$-$C_6$aliphatic optionally substituted with 1-3 halo;
each $Q^5$, $Q^6$, $Q^7$, and $Q^9$ is independently $C_6$-$C_{10}$ aryl, 5-10 membered heteroaryl, $C_3$-$C_8$ cycloaliphatic, or 3-12 membered heterocyclyl; wherein said $Q^5$, $Q^6$, $Q^7$, and $Q^9$ is independently and optionally substituted with 1-6 occurrences of J;
Z is

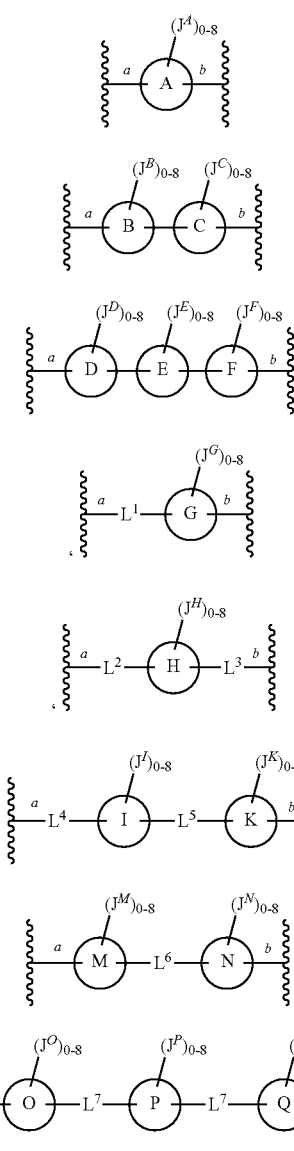

i ii iii iv v vi vii viii

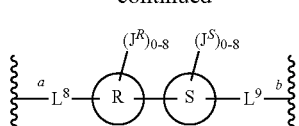

ix

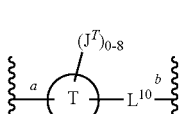

x

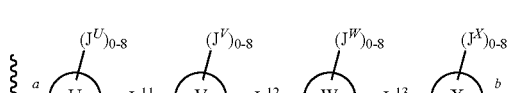

xi

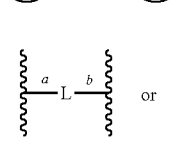

xii or xiii

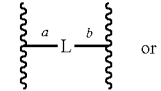

;

wherein Rings A, B, C, D, E, F, G, H, I, K, M, N, O, P, Q, R, S, T, U, V, W, X, Y, and Z are each independently a 5-6 membered saturated, fully unsaturated, partially unsaturated, or aromatic monocyclic ring optionally having 1-4 heteroatoms selected from oxygen, nitrogen, or sulfur; an 8-12 membered saturated, fully unsaturated, partially unsaturated, or aromatic bicyclic ring optionally having 1-6 heteroatoms selected from oxygen, nitrogen, or sulfur; or a 10-14 membered saturated, fully unsaturated, partially unsaturated, or aromatic tricyclic ring optionally having 1-6 heteroatoms selected from oxygen, nitrogen, or sulfur;

L is —X≡Y, wherein X is a $C_1$aliphatic or —C(O)— and Y is $C_1$-$C_{10}$aliphatic wherein up to two methylene units of the $C_1$-$C_{10}$aliphatic are optionally replaced with —C(O)—, NH, or NH($C_{1-6}$aliphatic); L is optionally substituted with 1-3 halo;

$L^1$ is —$X^1$≡$Y^1$— wherein $X^1$ is a $C_1$aliphatic or —C(O)— and $Y^1$ is $C_1$-$C_{10}$aliphatic wherein up to two methylene units of the $C_1$-$C_{10}$aliphatic are optionally replaced with —C(O)—, NH, or N($C_1$-$C_6$aliphatic); $L^1$ is optionally substituted with 1-3 halo;

$L^2$ is —$X^2$≡$Y^2$— wherein $X^2$ is a $C_1$aliphatic or —C(O)— and $Y^2$ is $C_1$-$C_{10}$aliphatic wherein up to two methylene units of the $C_1$-$C_{10}$aliphatic are optionally replaced with —C(O)—, NH, or N($C_1$-$C_6$aliphatic); $L^2$ is optionally substituted with 1-3 halo;

each $L^3$, $L^5$, and $L^{16}$ is independently $C_1$-$C_{12}$aliphatic wherein up to three methylene units of the $C_1$-$C_{12}$aliphatic are optionally replaced with —C(O)—, NH, or N($C_1$-$C_6$aliphatic); each $L^3$, $L^5$, and $L^{16}$ is independently and optionally substituted with 1-3 halo;

$L^4$ is —$X^4$≡$Y^4$— wherein $X^4$ is a $C_1$aliphatic or —C(O)— and $Y^4$ is $C_1$-$C_{10}$aliphatic wherein up to two methylene units of the $C_1$-$C_{10}$aliphatic are optionally replaced with —C(O)—, NH, or N($C_1$-$C_6$aliphatic); $L^4$ is optionally substituted with 1-3 halo;

$L^6$ is $C_1$-$C_{15}$aliphatic wherein up to six methylene units of the $C_1$-$C_{15}$aliphatic are optionally replaced with O, NH, N($C_1$-$C_6$aliphatic), S, —C(O)—, S(O), or S(O)$_2$; $L^6$ is optionally substituted with 1-3 halo;

each $L^7$ and $L^9$ is independently $C_1$-$C_6$aliphatic wherein up to two methylene units of the $C_1$-$C_6$aliphatic are optionally replaced with —C(O)—, NH, or N($C_1$-$C_4$aliphatic); each $L^7$ and $L^9$ is independently and optionally substituted with 1-3 halo;

$L^8$ is —$X^8$═$Y^8$— wherein $X^8$ is a $C_1$aliphatic and $Y^8$ is $C_1$-$C_{10}$aliphatic wherein up to two methylene units of the $C_1$-$C_{10}$aliphatic are optionally replaced with —C(O)—, NH, or N($C_1$-$C_6$aliphatic); $L^8$ is optionally substituted with 1-3 halo;

$L^{10}$ is $C_1$-$C_6$aliphatic wherein up to two methylene units of the $C_1$-$C_6$aliphatic are optionally replaced with O, NH, N($C_1$-$C_6$aliphatic), S, or —C(O)—; $L^{10}$ is optionally substituted with 1-3 halo;

$L^{11}$ is $C_1$-$C_6$aliphatic wherein up to two methylene units of the $C_1$-$C_6$aliphatic are optionally replaced with O, NH, N($C_1$-$C_6$aliphatic), S, or —C(O)—; $L^{11}$ is optionally substituted with 1-3 halo;

$L^{12}$ is $C_1$-$C_6$aliphatic wherein up to two methylene units of the $C_1$-$C_6$aliphatic are optionally replaced with O, NH, N($C_1$-$C_6$aliphatic), S, or —C(O)—; $L^{12}$ is optionally substituted with 1-3 halo;

$L^{13}$ is $C_1$-$C_6$aliphatic wherein up to two methylene units of the $C_1$-$C_6$aliphatic are optionally replaced with O, NH, N($C_1$-$C_6$aliphatic), S, or —C(O)—; $L^{13}$ is optionally substituted with 1-3 halo;

$L^{14}$ is —$X^{14}$═$Y^{14}$— wherein $X^{14}$ is a $C_1$aliphatic and $Y^{14}$ is $C_1$-$C_{10}$aliphatic wherein up to two methylene units of the $C_1$-$C_{10}$aliphatic are optionally replaced with —C(O)—, NH, or N($C_1$-$C_6$aliphatic); $L^{14}$ is optionally substituted with 1-3 halo;

$L^5$ is $C_1$-$C_6$aliphatic;

each J, $J^A$, $J^B$, $J^C$, $J^D$, $J^E$, $J^F$, $J^G$, $J^H$, $J^I$, $J^K$, $J^M$, $J^N$, $J^O$, $J^P$, $J^Q$, $J^R$, $J^S$, $J^T$, $J^U$, $J^V$, $J^X$, $J^Y$ and $J^Z$ is independently halogen, —CN, —NO$_2$, $X^J$, $Q^J$, or $X^J$-$Q^J$; or two J, $J^A$ B, j, $J^D$, $J^E$, $J^F$, $J^G$ $J^H$, $J^I$, $J^K$, $J^M$, $J^N$, $J^O$, $J^P$, $J^Q$, $J^R$, $J^S$, $J^T$, $J^U$, $J^V$, $J^W$, $J^Y$ or $J^Z$ groups bound to the same carbon atom, together with the carbon atom to which they are bound, optionally form —C═N—OH, —C(O)—, or Ring HH;

Ring HH is a 3-8 membered saturated monocyclic ring having 0-2 heteroatoms selected from oxygen, nitrogen, or sulfur; optionally substituted with 1-4 occurrences of $J^{HH}$;

$J^{HH}$ is halo, CN, oxo, $X^J$, $Q^J$, or $X^J$-$Q^J$;

$X^J$ is a $C_1$-$C_{10}$ aliphatic, wherein up to 4 methylene units of the $C_1$-$C_{10}$ aliphatic are optionally replaced with —O—, —NH, N($C_1$-$C_6$aliphatic), —S—, —C(O)—, —C(═NOH)—, —S(O)—, —S(O)$_2$—, P, or P(O); $X^J$ is optionally substituted with 0-6 occurrences of halo, OH, or $C_{1-4}$alkyl; or optionally substituted with 0-1 occurrences of CN;

$Q^J$ is a 3-7 membered monocyclic saturated, fully unsaturated, partially unsaturated, or aromatic ring optionally having 1-4 heteroatoms selected from oxygen, nitrogen, or sulfur; or an 8-12 membered saturated, fully unsaturated, partially unsaturated, or aromatic ring optionally having 1-6 heteroatoms selected from oxygen, nitrogen, or sulfur; wherein each $Q^J$ is optionally substituted with 1-6 occurrences of halo, oxo, CN, or $C_{1-6}$alkyl, wherein up to 2 methylene units of said $C_{1-6}$alkyl are optionally replaced with —O—, —NH, N($C_1$-$C_6$aliphatic), —S—, —C(O)—, —S(O)—, or —S(O)$_2$—;

provided that in some embodiments, Z is not CH$_2$CH$_2$,

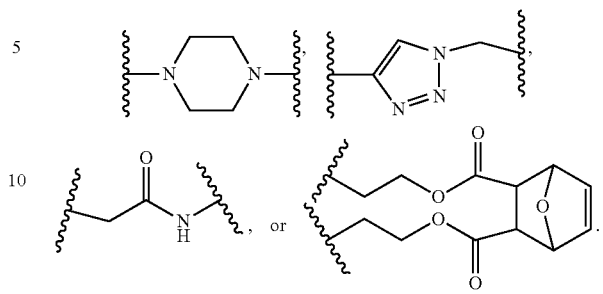

It shall be understood that a and b denote the bonds and indicate the specific connectivity and stereochemistry of the bond connecting the sugar ring to group Z. It shall further be understood that when X, $X^1$, $X^2$, $X^4$, $X^8$, and $X^{14}$ are C(O), the bond between X and Y; $X^1$ and $Y^1$; $X^2$ and $Y^2$; $X^4$ and $Y^4$; $X^8$ and $Y^8$ and $X^{14}$ and $Y^{14}$ respectively is a single bond. When X, $X^1$, $X^2$, $X^4$, $X^8$, and $X^{14}$ is a $C_1$ aliphatic, then the bond between X and Y; $X^1$ and $Y^1$; $X^2$ and $Y^2$; $X^4$ and $Y^4$; $X^8$ and $Y^8$ and $X^{14}$ and $Y^{14}$ respectively will change depending on the nature of X, $X^1$, $X^2$, $X^4$, $X^8$, and $X^{14}$. For example, if X is "CH", then the bond between X and Y is a double bond to result in —CH═Y.

Another aspect of the invention provides a compound of Formula I, or a pharmaceutically acceptable salt thereof:

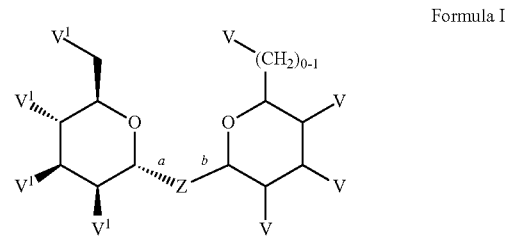

Formula I wherein $V^1$ is halogen, NH$_2$, OH, or SH;

V is H, halogen, —OR$^7$, —NR$^5$R$^6$, —SR$^7$, or $C_1$-$C_6$aliphatic;

R$^5$ is —H; X$^5$; Q$^5$; X$^5$-Q$^5$; —C(O)R$^9$; —C(O)NHR$^9$; or —C(O)OR$^9$;

R$^6$ is —H; X$^6$; Q$^6$; X$^6$-Q$^6$; —C(O)R$^9$; —C(O)NHR$^9$; or —C(O)OR$^9$;

R$^7$ is —H; X$^7$; Q$^7$; X$^7$-Q$^7$; —C(O)R$^9$; or —C(O)NHR$^9$;

R$^9$ is —H; X$^9$; Q$^9$; or X$^9$-Q$^9$;

each X$^5$, X$^6$, X$^7$, and X$^9$ is independently $C_1$-$C_6$aliphatic optionally substituted with 1-3 halo; each Q$^5$, Q$^6$, Q$^7$, and Q$^9$ is independently $C_6$-$C_{10}$ aryl, 5-10 membered heteroaryl, $C_3$-$C_8$ cycloaliphatic, or 3-12 membered heterocyclyl; wherein said Q$^5$, Q$^6$, Q$^7$, and Q$^9$ is independently and optionally substituted with 1-6 occurrences of J;

Z is

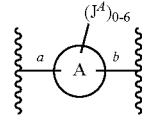

i

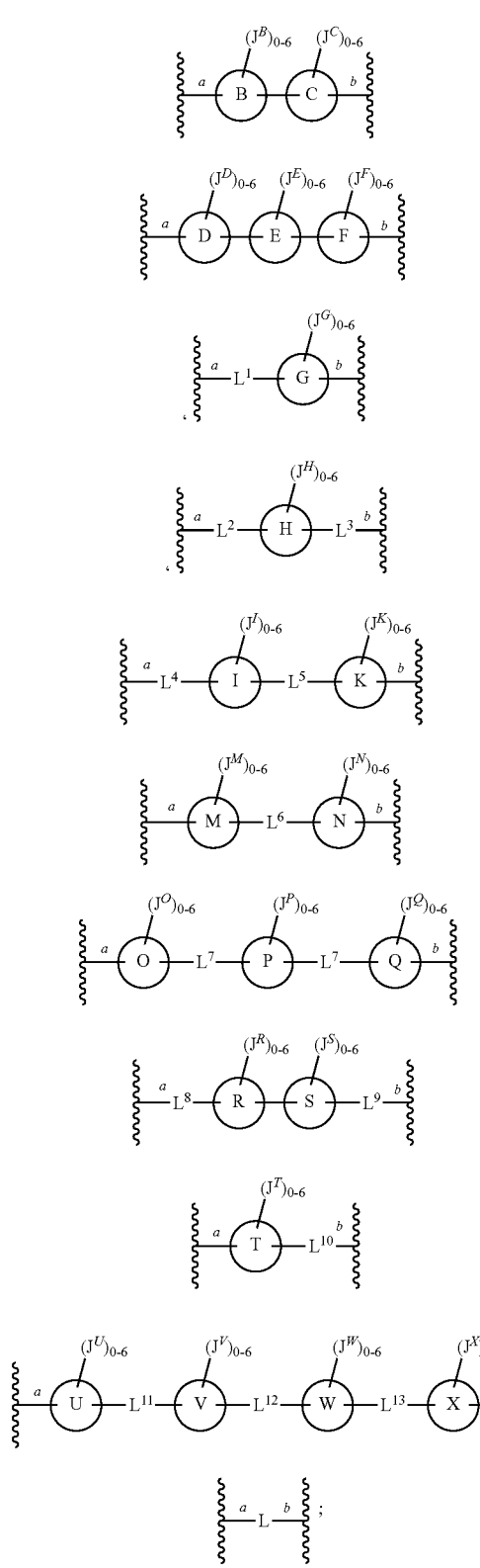

ii
membered fully unsaturated, partially unsaturated, or aromatic bicyclic ring optionally having 1-6 heteroatoms selected from oxygen, nitrogen, or sulfur; or a 10-14 membered fully unsaturated, partially unsaturated, or aromatic tricyclic ring optionally having 1-6 heteroatoms selected from oxygen, nitrogen, or sulfur;

L is —X═Y wherein X is a $C_1$ aliphatic or —C(O)— and Y is $C_1$-$C_{10}$ aliphatic wherein up to two methylene units of the $C_1$-$C_{10}$ aliphatic are optionally replaced with —C(O)—, NH, or NH($C_{1-6}$ aliphatic); L is optionally substituted with 1-3 halo;

iii $L^1$ is —$X^1$═$Y^1$— wherein $X^1$ is a $C_1$ aliphatic or —C(O)— and $Y^1$ is $C_1$-$C_{10}$ aliphatic wherein up to two methylene units of the $C_1$-$C_{10}$ aliphatic are optionally replaced with —C(O)—, NH, or N($C_1$-$C_6$ aliphatic); $L^1$ is optionally substituted with 1-3 halo;

iv $L^2$ is —$X^2$═$Y^2$— wherein $X^2$ is a $C_1$ aliphatic or —C(O)— and $Y^2$ is $C_1$-$C_{10}$ aliphatic wherein up to two methylene units of the $C_1$-$C_{10}$ aliphatic are optionally replaced with —C(O)—, NH, or N($C_1$-$C_6$ aliphatic); $L^2$ is optionally substituted with 1-3 halo;

v each $L^3$ and $L^5$ is independently $C_1$-$C_{12}$ aliphatic wherein up to three methylene units of the $C_1$-$C_{12}$ aliphatic are optionally replaced with —C(O)—, NH, or N($C_1$-$C_6$ aliphatic); each $L^3$ and $L^5$ is independently and optionally substituted with 1-3 halo;

vi $L^4$ is $X^4$═$Y^4$— wherein $X^4$ is a $C_1$ aliphatic or —C(O)— and $Y^4$ is $C_1$-$C_{10}$ aliphatic wherein up to two methylene units of the $C_1$-$C_{10}$ aliphatic are optionally replaced with —C(O)—, NH, or N($C_1$-$C_6$ aliphatic); $L^4$ is optionally substituted with 1-3 halo;

vii $L^6$ is $C_1$-$C_{15}$ aliphatic wherein up to six methylene units of the $C_1$-$C_{15}$ aliphatic are optionally replaced with O, NH, N($C_1$-$C_6$ aliphatic), S, —C(O)—, S(O), or S(O)$_2$; $L^6$ is optionally substituted with 1-3 halo;

viii each $L^7$ and $L^9$ is independently $C_1$-$C_6$ aliphatic wherein up to two methylene units of the $C_1$-$C_6$ aliphatic are optionally replaced with —C(O)—, NH, or N($C_1$-$C_4$ aliphatic); each $L^7$ and $L^9$ is independently and optionally substituted with 1-3 halo;

ix $L^8$ is —$X^8$═$Y^8$— wherein $X^8$ is a $C_1$ aliphatic and $Y^8$ is $C_1$-$C_{10}$ aliphatic wherein up to two methylene units of the $C_1$-$C_{10}$ aliphatic are optionally replaced with —C(O)—, NH, or N($C_1$-$C_6$ aliphatic); $L^8$ is optionally substituted with 1-3 halo;

x $L^{10}$ is $C_1$-$C_6$ aliphatic wherein up to two methylene units of the $C_1$-$C_6$ aliphatic are optionally replaced with O, NH, N($C_1$-$C_6$ aliphatic), S, or —C(O)—; $L^{10}$ is optionally substituted with 1-3 halo;

xi $L^{11}$ is $C_1$-$C_6$ aliphatic wherein up to two methylene units of the $C_1$-$C_6$ aliphatic are optionally replaced with O, NH, N($C_1$-$C_6$ aliphatic), S, or —C(O)—; $L^{11}$ is optionally substituted with 1-3 halo;

$L^{12}$ is $C_1$-$C_6$ aliphatic wherein up to two methylene units of the $C_1$-$C_6$ aliphatic are optionally replaced with O, NH, N($C_1$-$C_6$ aliphatic), S, or —C(O)—; $L^{11}$ is optionally substituted with 1-3 halo;

$L^{13}$ is $C_1$-$C_6$ aliphatic wherein up to two methylene units of the $C_1$-$C_6$ aliphatic are optionally replaced with O, NH, N($C_1$-$C_6$ aliphatic), S, or —C(O)—; $L^{11}$ is optionally substituted with 1-3 halo;

each J, $J^A$, $J^B$, $J^C$, $J^D$, $J^E$, $J^F$, $J^G$, $J^H$, $J^I$, $J^K$, $J^M$, $J^N$, $J^O$, $J^P$, $J^Q$, $J^R$, $J^S$, $J^T$, $J^U$, $J^V$, $J^W$ and $J^X$ is independently halogen, —CN, —NO$_2$, $X^J$, $Q^J$, or $X^J$-$Q^J$;

$X^J$ is a $C_1$-$C_{10}$ aliphatic, wherein up to 4 methylene units of the $C_1$-$C_{10}$ aliphatic are optionally replaced with —O—, —NH, N($C_1$-$C_6$ aliphatic), —S—, —C(O)—, wherein Rings A, B, C, D, E, F, G, H, I, K, M, N, O, P, Q, R, S, T, U, V, W, and X are each independently a 5-6 membered fully unsaturated, partially unsaturated, or monocyclic aromatic ring optionally having 1-4 heteroatoms selected from oxygen, nitrogen, or sulfur; an 8-12

—C(=NOH)—, —S(O)—, —S(O)₂—, P, or P(O); X$^J$ is optionally substituted with 0-6 occurrences of halo;

Q$^J$ is a 3-7 membered monocyclic fully unsaturated, partially unsaturated, or aromatic ring optionally having 1-4 heteroatoms selected from oxygen, nitrogen, or sulfur; or an 8-12 membered fully unsaturated, partially unsaturated, or aromatic ring optionally having 1-6 heteroatoms selected from oxygen, nitrogen, or sulfur; wherein each Q$^J$ is optionally substituted with 1-6 occurrences of halogen, CN, NO$_2$, C$_1$-C$_6$aliphatic, OH, NH$_2$, NH(C$_1$-C$_6$aliphatic), NH(C$_1$-C$_6$aliphatic)$_2$, phenyl, 5-6 membered heteroaryl, C$_3$-C$_6$ cycloaliphatic, or 3-8 membered heterocyclyl, wherein said phenyl, 5-6 membered heteroaryl, C$_3$-C$_6$ cycloaliphatic, or 3-8 membered heterocyclyl is optionally substituted with halo, CN, NO$_2$, or C$_1$-C$_6$aliphatic wherein up to 3 methylene units of the C$_1$-C$_6$aliphatic are optionally replaced with O, NH, S, or CO;

provided that Z is not CH$_2$CH$_2$,

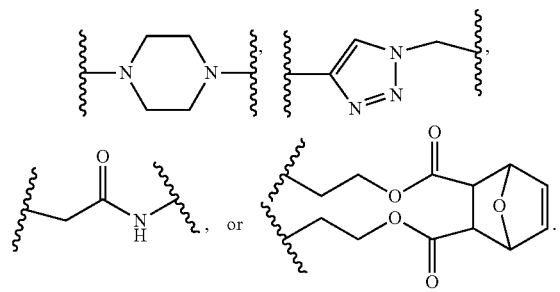

In some embodiments, the C$_6$-C$_{10}$ aryl of Q$^5$, Q$^6$, Q$^7$, and Q$^9$ is phenyl or napthyl; the 5-10 membered heteroaryl is a 5-6 membered monocyclic heteroaryl having 1-4 heteroatoms selected from oxygen, nitrogen, or sulfur; or an 8-10 bicyclic heteroaryl having 1-4 heteroatoms selected from oxygen, nitrogen, or sulfur; the C$_3$-C$_8$ cycloaliphatic is a monocyclic C$_3$-C$_8$ cycloalkyl or cycloalkenyl ring; and the 3-12 membered heterocyclyl is a 3-8 membered monocyclic heterocyclyl having 1-3 heteroatoms selected from oxygen, nitrogen, or sulfur; or an 8-12 membered bicyclic heterocyclyl having 1-6 heteroatoms selected from oxygen, nitrogen, or sulfur.

Some embodiments comprise one or more of the following:

a) Z is selected from formula i, ii, iii, iv, v, vi, vii, viii, ix, x, xi, or xii;
b) Rings A, B, C, D, E, F, G, H, I, K, M, N, O, P, Q, R, S, T, U, V, W, and X are each independently a 5-6 membered fully unsaturated, partially unsaturated, or aromatic monocyclic ring optionally having 1-4 heteroatoms selected from oxygen, nitrogen, or sulfur; or an 8-12 membered fully unsaturated, partially unsaturated, or aromatic bicyclic ring optionally having 1-6 heteroatoms selected from oxygen, nitrogen, or sulfur; and
c) X$^J$ is a C$_1$-C$_{10}$ aliphatic, wherein up to 4 methylene units of the C$_1$-C$_{10}$ aliphatic are optionally replaced with —O—, —NH, N(C$_1$-C$_6$aliphatic), —S—, —C(O)—, —C(=NOH)—, —S(O)—, —S(O)$_2$—, P, or P(O); X$^J$ is optionally substituted with 0-6 occurrences of halo.

In some embodiments, V$^1$ is OH. In other embodiments, V is OH.

In some embodiments, Ring A, B, C, D, E, F, G, H, I, K, M, N, O, P, Q, R, S, T, U, V, W, X, Y, and Z are aromatic.

In another embodiment, Z is selected from formula ii, iii, v, vii, or xiii. In some embodiments, Z is selected from formula ii, iii, or v.

In some embodiments, Ring A, B, C, D, E, F, G, H, I, K, M, N, O, P, Q, R, S, T, U, V, W, and X are aromatic. In other embodiments, Ring A, B, C, D, E, F, G, H, I, K, M, N, O, P, Q, R, S, T, U, V, W, X, Y, and Z are each independently phenyl, napthyl, or a 5-6 membered heteroaryl having 1-4 heteroatoms selected from oxygen, nitrogen, or sulfur. In yet other embodiments, Ring A, B, C, D, E, F, G, H, I, K, M, N, O, P, Q, R, S, T, U, V, W, and X are each independently phenyl, napthyl, or a 5-6 membered heteroaryl having 1-4 heteroatoms selected from oxygen, nitrogen, or sulfur. In some embodiments, each Ring A, B, D, M, O, T, and U is bonded to the mannose ring to which it is attached via a carbon atom.

In some embodiments, each J, J$^A$, J$^B$, J$^C$, J$^D$, J$^E$, J$^F$, J$^G$, J$^H$, J$^I$, J$^K$, J$^M$, J$^N$, J$^O$, J$^P$, J$^Q$, J$^R$, J$^S$, J$^T$, J$^U$, J$^V$, J$^W$, J$^X$, J$^Y$ and J$^Z$ is independently —NO$_2$, —CN, halogen, or C$_1$-C$_{10}$aliphatic wherein up to three methylene units of the C$_1$-C$_{10}$aliphatic is optionally replaced with O, NH, N(C$_{1-4}$alkyl), S, C(O), S(O), or S(O)$_2$ and optionally substituted with 1-3 halo or 1 CN. In other embodiments, each J, J$^A$, J$^B$, J$^C$, J$^D$, J$^E$, J$^F$, J$^G$, J$^H$, J$^I$, J$^K$, J$^M$, J$^N$, J$^O$, J$^P$, J$^Q$, J$^R$, J$^S$, J$^T$, J$^U$, J$^V$, J$^W$, and J$^X$ is independently —NO$_2$, —CN, halogen, or C$_1$-C$_{10}$aliphatic wherein up to three methylene units of the C$_1$-C$_{10}$aliphatic is optionally replaced with O, NH, N(C$_{1-4}$alkyl), S, C(O), S(O), or S(O)$_2$ and optionally substituted with 1-3 halo.

In one aspect of the invention, Z is

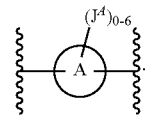

i

In some embodiments, Ring A is triazolyl, thienyl, or phenyl and J$^A$ is CF$_3$ or —O(C$_{1-6}$alkyl). In other embodiments, Ring A is phenyl and J$^A$ is CF$_3$ or OCH(CH$_3$)$_2$.

According to another aspect Z is

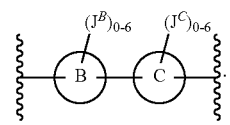

ii

In some embodiments, Ring B and Ring C are independently triazolyl or phenyl. In other embodiments, Ring B and Ring C are phenyl. In some embodiments, J$^B$ and J$^C$ are each independently halo, C$_{1-6}$alkyl, or O(C$_{1-6}$alkyl).

According to another aspect Z is

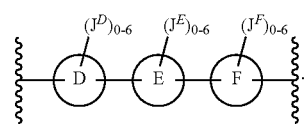

iii

In some embodiments, Ring D, Ring E, and Ring F are each independently triazolyl or phenyl. In other embodiments, Ring D and Ring E are phenyl and Ring E is an optionally substituted group selected from $C_{3-6}$cycloalkyl, phenyl, pyridinyl, or pyrazinyl. In some embodiments, Ring E is pyridinyl. In other embodiments, $J^D$, $J^E$, and $J^F$ are each independently $C_1$-$C_6$aliphatic wherein up to two methylene units of the $C_1$-$C_6$aliphatic is optionally replaced with O, NH, N($C_{1-4}$alkyl), or C(O). In some embodiments, these substituents are $C_1$-$C_6$alkyl, O($C_1$-$C_6$alkyl), halo, or $CH_2C(O)OCH_3$. In other embodiments, these substituents are $CH_3$, $OCH_3$, fluoro, or $CH_2C(O)OCH_3$.

According to another aspect Z is

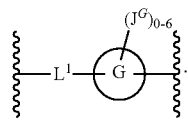

iv

In some embodiments, $L^1$ is —$C_1$-$C_6$aliphatic and Ring G phenyl. In other embodiments, Ring G is phenyl or indolyl; and $J^G$ is $C_{1-6}$alkyl, halo, or —O($C_{1-6}$alkyl). In another embodiment, $L^1$ is O. In other embodiments, $L^1$ is —C≡C—.

According to another aspect Z is

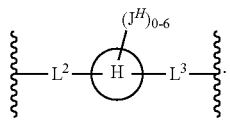

v

In some embodiments,
$L^2$ is $C_{1-6}$aliphatic or —($C_{1-4}$aliphatic)-C(O)NH—;
$L^3$ is $C_{1-6}$aliphatic or —C(O)NH—($C_{1-4}$aliphatic)-;
Ring H is phenyl or naphthyl; and
$J^H$ is halo, CN, $NO_2$, $C_{1-6}$aliphatic, —$OC_{1-6}$aliphatic, or C(O)O($C_{1-6}$aliphatic).

In other embodiments,
$L^2$ is $C_{1-6}$aliphatic or —($C_{1-4}$aliphatic)-C(O)NH—;
$L^3$ is $C_{1-6}$aliphatic or —NHC(O)—($C_{1-4}$aliphatic)-;
Ring H is phenyl or naphthyl; and
$J^H$ is halo, CN, $NO_2$, $C_{1-6}$aliphatic, —$OC_{1-6}$aliphatic, or C(O)O($C_{1-6}$aliphatic), wherein said $J^H$ is optionally substituted with 1-3 occurrences of halo.

In yet other embodiments, $J^H$ is halo, CN, $NO_2$, phenyl, or $C_{1-10}$aliphatic wherein up to 3 methylene units are optionally replaced with O, NH, N($C_{1-4}$alkyl), S, C(O), SO, or $SO_2$; wherein said $J^H$ is optionally substituted with 1-3 occurrences of CN, halo or phenyl.

According to another aspect Z is

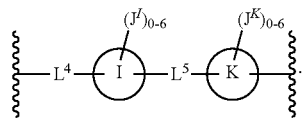

vi

In some embodiments,
$L^4$ and $L^5$ are each independently $C_{1-6}$aliphatic;
Ring I and Ring K are each independently phenyl;

$J^I$ and $J^K$ are each independently halo, CN, $NO_2$, $C_{1-6}$aliphatic, —$OC_{1-6}$aliphatic, or C(O)O($C_{1-6}$aliphatic).

In another embodiment, $L^4$ is —$CH_2CH$=$CH$— and $L^5$ is —C≡C—.

According to another aspect Z is

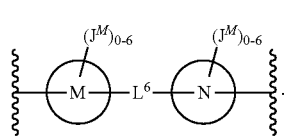

vii

In some embodiments, $L^6$ is $C_1$-$C_{15}$aliphatic wherein up to four methylene units of the $C_1$-$C_{15}$aliphatic are optionally replaced with —O— or C(O)NH. In other embodiments, $L^6$ is —C≡C—C≡C—, —C(O)NH—, —NHC(O)NH—, —($C_{1-6}$alkyl)-, —C(O)NH—($C_{1-8}$alkyl)-NHC(O)—. —C(O)NH—($CH_2CH_2$)—O—($CH_2CH_2$)—O—($CH_2CH_2$)—NHC(O)—, or —$CH_2N(CH_2C$≡$CH)CH_2$—. In yet other embodiment, M is phenyl; N is phenyl; and each $J^M$ and $J^N$ is each independently H or $C_{1-6}$alkyl.

Another aspect provides compounds wherein Z is

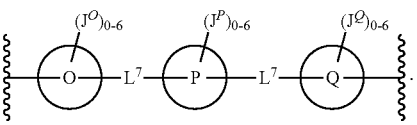

viii

In some embodiments, Ring O, Ring P, and Ring Q are each independently phenyl, triazolyl, or thienyl. In some embodiments, $L^7$ is —C(O)NH— or $C_{1-4}$alkyl. In other embodiments, Ring O, Ring P, and Ring Q are phenyl.

Another aspect provides compounds wherein Z is

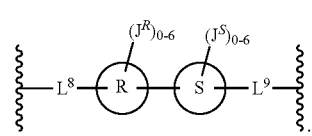

ix

In some embodiments, Ring R and Ring S are phenyl and $L^8$ is $C_1$-$C_6$alkyl. In other embodiments, Ring R and Ring S are thienyl. In some embodiments, $J^R$ is $C_{1-6}$alkyl.

According to another aspect Z is

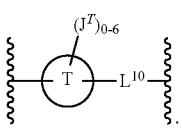

x

In some embodiments, Ring T is phenyl or naphthyl and $L^{10}$ is $C_1$-$C_6$aliphatic wherein up to one methylene unit of the $C_1$-$C_6$aliphatic is optionally replaced with —O—. In some embodiments, $L^{10}$ is —C≡C— or —$CH_2CH_2$—.

According to another aspect Z is

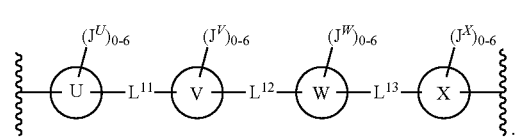

xi

In some embodiments, $L^{11}$, $L^{12}$, and $L^{13}$ are each independently —C(O)NH— or $C_{1-4}$alkyl and Ring U, V, W, and X are each independently phenyl.

According to another aspect Z is

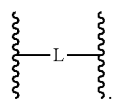

xii

In some embodiments, L is $C_3$-$C_6$ aliphatic. In some embodiments, L is an optionally substituted $C_{1-6}$aliphatic. In other embodiments, L is —C≡C—C≡C—.

According to another aspect Z is

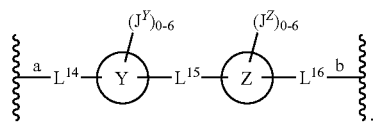

xiii

In some embodiments, Ring Y and Ring Z are phenyl. In some embodiments, $L^{14}$ and $L^{16}$ are C≡C—. In some embodiments, $L^{15}$ is $C_{1-4}$aliphatic. In some embodiments, $L^{15}$ is —C(CH$_3$)$_2$—. In certain embodiments, Ring Y and Ring Z are phenyl; $L^{14}$ and $L^{16}$ are C≡C—; and $L^{15}$ is —C(CH$_3$)$_2$—.

According to another aspect, $L^1$, $L^2$, $L^3$, $L^6$, and $L^{10}$ are each independently $C_1$-$C_4$ alkenyl or $C_1$-$C_4$ alkynyl.

Another aspect provides a compound having formula IA:

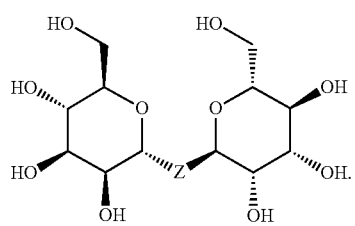

IA

Another aspect provides a compound having formula IB:

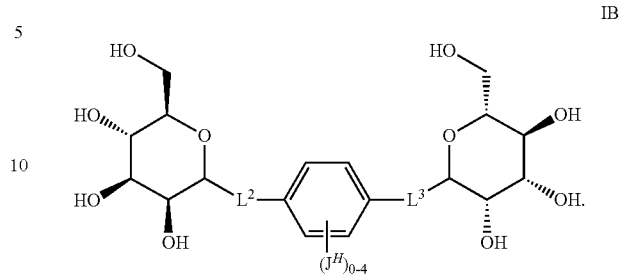

IB

In some embodiments, L and L are bonded to the mannose ring via a carbon atom. In some embodiments, $L^2$ and $L^3$ are each independently $C_1$-$C_6$ alkenyl or $C_1$-$C_6$ alkynyl. In some embodiments at least one of $L^2$ and $L^3$ is —C≡C—. In other embodiments, $L^2$ and $L^3$ are both —C≡C—.

Another aspect provides a compound having formula IC:

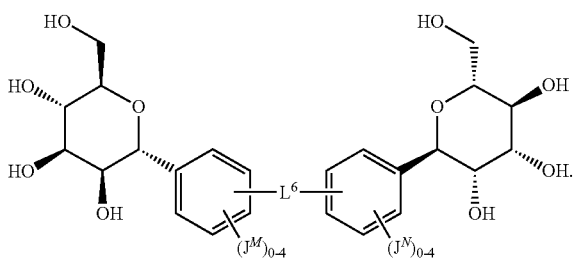

IC

In some embodiments, $L^6$ is bonded to the meta or para position of the phenyl ring(s) to which it is attached. In other embodiments, $L^6$ is bonded to the para position of the phenyl ring(s) to which it is attached. In yet other embodiments, $L^6$ is bonded to the meta position of the phenyl ring(s) as shown in Formula IC-a:

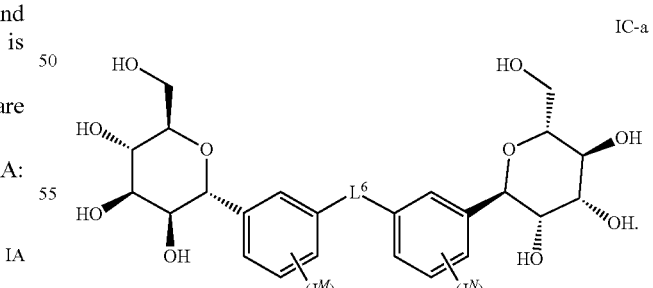

IC-a

In some embodiments $L^6$ is —C≡C—C≡C—. In other embodiments, $L^6$ is $C_{1-6}$aliphatic, —O—($C_{1-4}$alkyl)-O—, —C(O)NH—, —NHC(O)NH—, —C(O)NH—($C_{1-10}$alkyl)-NHC(O)—, —(CH$_2$CH$_2$OCH$_2$CH$_2$OCH$_2$CH$_2$)—. In yet other embodiments, $L^6$ is —CH$_2$— or —C(CH$_3$)$_2$—.

Another aspect provides a compound having formula ID:

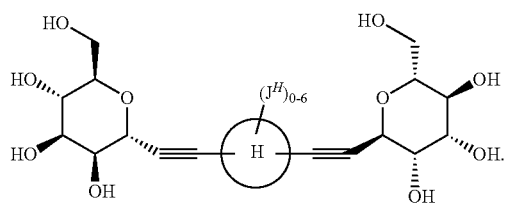

ID

In some embodiments, Ring H is an optionally substituted 5-6 membered monocyclic aromatic ring optionally having 1-4 heteroatoms selected from oxygen, nitrogen, or sulfur; or an 8-12 membered bicyclic aromatic ring optionally having 1-6 heteroatoms selected from oxygen, nitrogen, or sulfur; or a 10-14 tricyclic aromatic ring optionally having 1-6 heteroatoms selected from oxygen, nitrogen, or sulfur. For the sake of clarity, a bicyclic or tricyclic ring is considered an aromatic ring if it contains at least one aromatic ring.

In other embodiments, Ring H is optionally substituted phenyl, naphthyl, thienyl, isoxazolyl, pyridinyl, pyrazinyl, thienylthiophenyl, quinolinyl, quinazolinyl, benzothiadiazolyl, or fluorenyl. In other embodiments, Ring H is optionally substituted phenyl or naphthyl.

According to another embodiment, Ring H, together with $J^H$ and $J^{HH}$, is selected from the following:

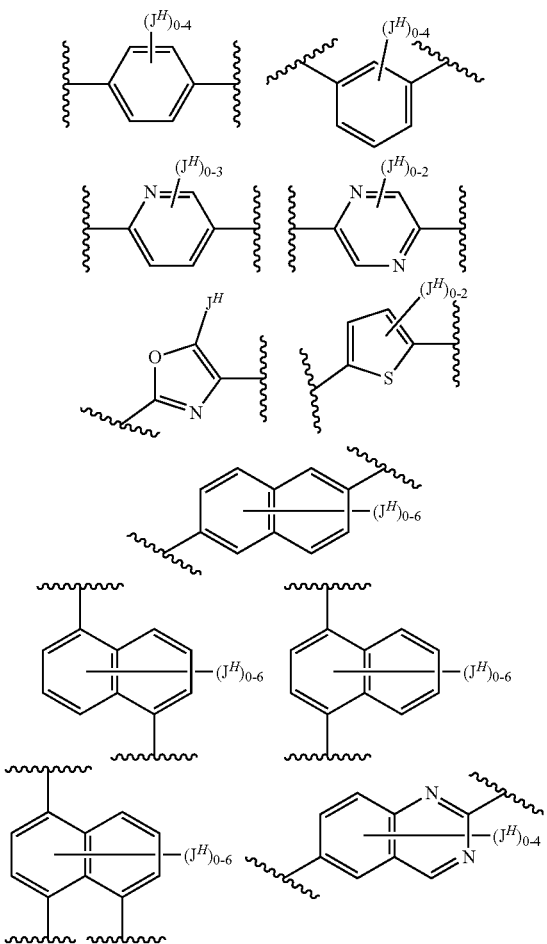

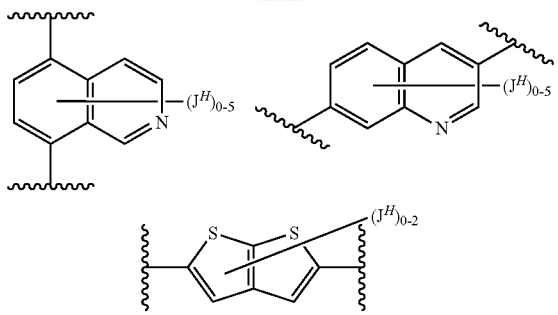

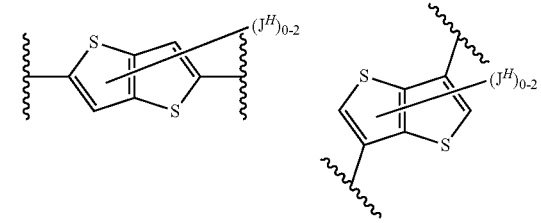

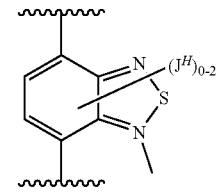

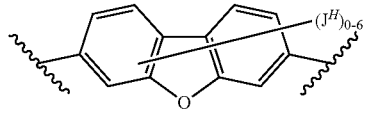

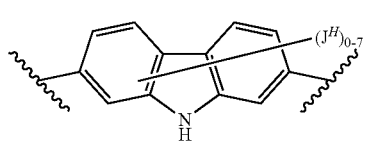

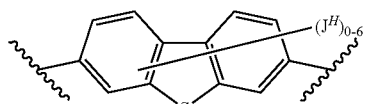

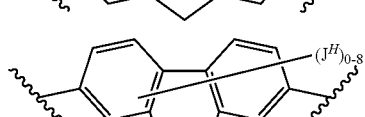

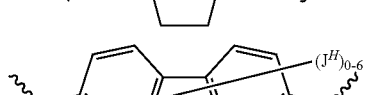

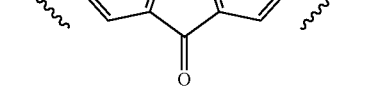

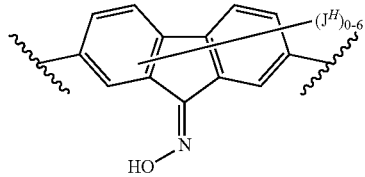

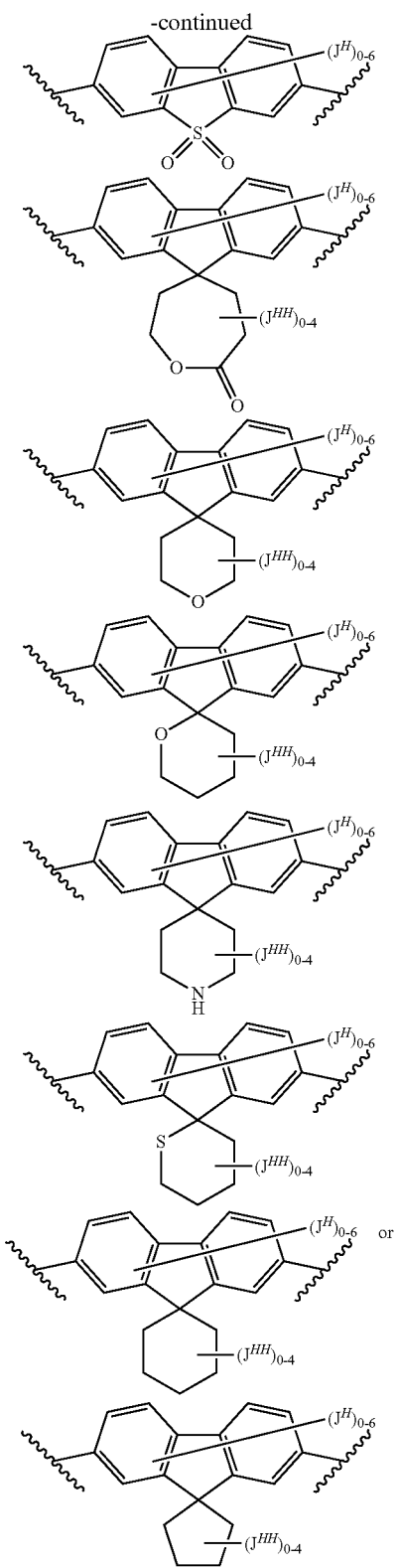

In some embodiments, $J^H$ is halogen, oxo, CN, $X^J$, $Q^J$, or $X^J\text{-}Q^J$; wherein $X^J$ is $C_1\text{-}C_{10}$ aliphatic, wherein up to 4 methylene units of the $C_1\text{-}C_{10}$ aliphatic are optionally replaced with —O—, —NH, $N(C_1\text{-}C_6\text{aliphatic})$, —S—, —C(O)—, —S(O)—, —S(O)$_2$—;

$Q^J$ is phenyl; and $J^H$ is optionally substituted with 0-3 occurrences of halo or 0-1 occurrences of CN.

In some embodiments, Ring H is optionally substituted phenyl or naphthyl.

In other embodiments, $J^H$ is halogen, CN, —C(CH$_3$)$_2$CN, $C_{3-6}$cycloalkyl, phenyl, —O—CH$_2$phenyl, or $C_{1-6}$alkyl wherein up to one methylene unit is optionally replaced with —O—, —S—, —NH—, —N(C$_{1-6}$alkyl)-, or —C(O)—. In yet other embodiments, Ring H is phenyl and $J^H$ is halo, CN, —C(CH$_3$)$_2$CN, $C_{3-6}$cycloalkyl, phenyl, CH$_2$phenyl, —O—CH$_2$phenyl, or $C_{1-6}$alkyl wherein up to one methylene unit is optionally replaced with —O—, —S—, —NH—, —N(C$_{1-6}$alkyl)-, or —C(=O)—. In some embodiments, $J^H$ is substituted with 0-3 halo or 0-1 CN.

According to another embodiment, Ring H is

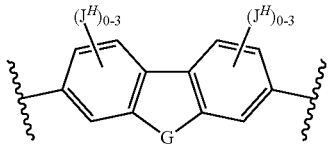

wherein G is O, S, S(O), S(O)$_2$, CF$_2$, C(J$^{H1}$)(J$^{H2}$), —C(J$^{H3}$)$_2$-C(J$^{H4}$)$_2$-, or N(J$^{H5}$);

$J^{H1}$ is H, OH, or $C_{1-6}$alkyl wherein up to 2 methylene units are optionally replaced with —O—, —NH—, —NH(C$_1$-C$_6$aliphatic)-, —S—, —C(O)—, —S(O)—, or —S(O)$_2$—; $J^{H1}$ is optionally and independently substituted with 1-3 occurrences of OH;

$J^{H2}$ is $X^{JH}$, $Q^{JH}$, or $X^{JH}\text{-}Q^{JH}$; $J^{H2}$ is optionally substituted with 1-3 occurrences of OH;

$X^{JH}$ is $C_{1-6}$alkyl wherein up to 3 methylene units of $C_{1-6}$alkyl is optionally replaced with —O—, —NH, N(C$_1$-C$_6$aliphatic), —S—, —C(O)—, —S(O)—, or —S(O)$_2$—;

$Q^{JH}$ is $C_{3-6}$cycloalkyl, phenyl, or a 5-7 membered monocyclic heterocyclyl having 1-3 heteroatoms selected from oxygen, nitrogen, or sulfur;

or $J^{H1}$ and $J^{H2}$, together with the carbon atom to which they are attached, form C=N—OH, C=O, or Ring HH;

Ring HH is a 5-7 membered saturated monocyclic ring having 0-2 heteroatoms selected from oxygen, nitrogen, or sulfur; wherein said ring is optionally substituted with 1-4 occurrences of $J^{HH}$;

$J^{HH}$ is halo, CN, $X^J$, $Q^J$, or $X^J\text{-}Q^J$;

$J^{H5}$ is $X^J$, $Q^J$, or $X^J\text{-}Q^J$;

$X^J$ is a $C_1\text{-}C_{10}$ aliphatic, wherein up to 4 methylene units of the $C_1\text{-}C_{10}$ aliphatic are optionally replaced with —O—, —NH, N(C$_1$-C$_6$aliphatic), —S—, —C(O)—, —S(O)—, or —S(O)$_2$—; $X^J$ is optionally substituted with 0-6 occurrences of halo or 0-1 occurrences of CN;

$Q^J$ is a 3-6 membered saturated, partially unsaturated, or aromatic monocyclic ring optionally having 1-4 heteroatoms selected from oxygen, nitrogen, or sulfur; or an 8-12 membered saturated, partially unsaturated, or aromatic bicyclic ring optionally having 1-6 heteroatoms selected from oxygen, nitrogen, or sulfur; wherein each $Q^J$ is optionally substituted with 1-6 occurrences of halogen, oxo, CN, NO$_2$ or a $C_1\text{-}C_6$aliphatic wherein up to 3 methylene units of the $C_1\text{-}C_6$aliphatic are optionally replaced with O, NR, S, or CO;

each $J^H$, $J^{H3}$, and $J^{H4}$ is independently H, halo, CN, or $C_1\text{-}C_{10}$ aliphatic, wherein up to 3 methylene units of the $C_1\text{-}C_{10}$ aliphatic are optionally replaced with —O—, —NH, N(C$_1$-C$_6$aliphatic), S, —C(O)—, —S(O)—, or SO$_2$—; each J$^H$, J$^{H3}$, and J$^{H4}$ is independently and optionally substituted with 0-2 occurrences of halo, OH, or C$_{1-4}$alkyl or with 1 occurrence of CN; and R is H or C$_{1-4}$alkyl.

In some embodiments,

G is C(J$^{H1}$)(J$^{H2}$);

J$^{H1}$ is OH, F, or —CH$_2$CH$_2$OH;

J$^{H2}$ is OH, CH$_3$, cyclopropyl, F, CH$_2$CH$_3$, —CH$_2$CH$_2$OH, —CH$_2$CH(OH)CH$_2$OH, or phenyl optionally substituted with OCH$_3$;

or J$^{H1}$ and J$^{H2}$, together with the carbon atom to which they are attached, form =N—OH or a 6-membered saturated monocyclic ring having 0-2 heteroatoms selected from oxygen, nitrogen, or sulfur; wherein said ring is optionally substituted with C$_{1-6}$alkyl, OH, NH$_2$, —C(O)OCH$_3$, —C(O)OC(CH$_3$)$_3$, —C(O)C(CH$_3$)$_2$OH, or —S(O)$_2$CH$_3$.

In some embodiments, Ring HH is selected from cyclopentyl, cyclohexyl, piperidinyl, piperazinyl, 1,3-dithianyl, or tetrahydropyranyl. In some embodiments, X$^{JH}$ is C$_{1-6}$alkyl and Q$^{JH}$ is C$_{3-6}$cycloaliphatic, oxetanyl, tetrahydropyrrolidinyl, piperidinyl, piperazinyl, or morpholinyl.

According to another embodiment, Ring H, together with Ring HH, is selected from one of the following formulae:

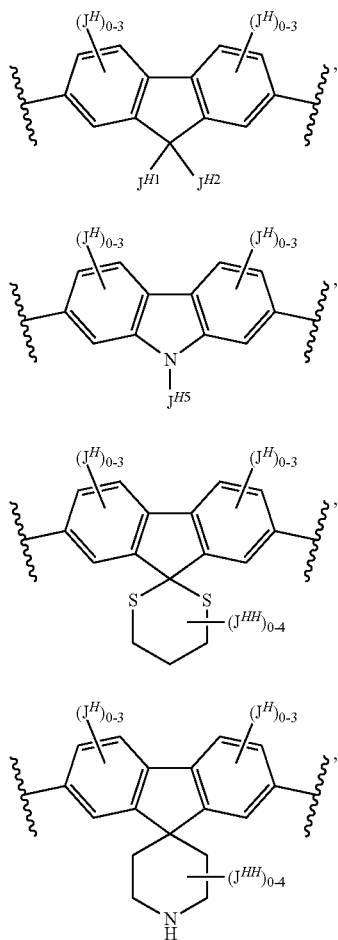

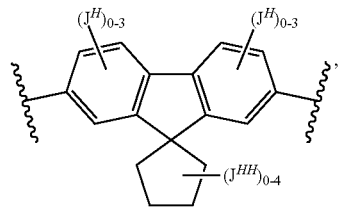

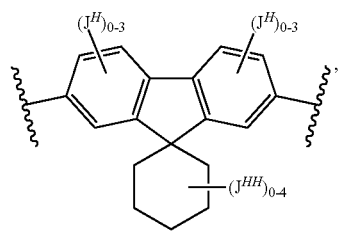

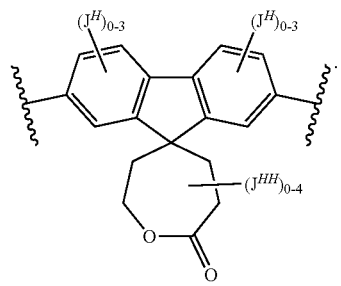

According to another embodiment, Ring H is H2:

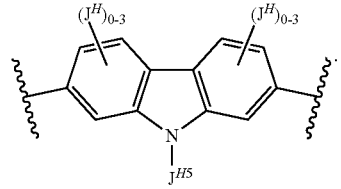

In some embodiments,

J$^{H5}$ is X$^J$, Q$^J$, or X$^J$-Q$^J$; wherein

X$^J$ is a C$_1$-C$_{10}$ aliphatic, wherein up to 4 methylene units of the C$_1$-C$_{10}$ aliphatic are optionally replaced with —O—, —NH, N(C$_1$-C$_6$aliphatic), or —S—; X$^J$ is optionally substituted with 1-2 occurrences of halo; and Q$^J$ is a monocyclic 3-6 membered saturated monocyclic ring having 1-2 heteroatoms selected from oxygen, nitrogen, or sulfur; Q$^J$ is optionally substituted with 1-4 occurrences of halo, CN, NO$_2$, oxo, or C$_1$-C$_6$aliphatic wherein up to 3 methylene units of the C$_1$-C$_6$aliphatic are optionally replaced with O, NR, S, or CO.

In some embodiments, J$^{H5}$ is H, phenyl, CH$_2$CH$_2$OH, CH$_2$CH$_2$OD$_3$, CH$_2$C(O)OH, CH$_2$C(O)OCH$_2$CH$_3$, CH$_2$C(O)N(CH$_3$)$_2$, CH$_2$CH(OH)CH$_2$OH, CH$_2$CH(OH)CH$_2$N(CH$_3$)$_2$,

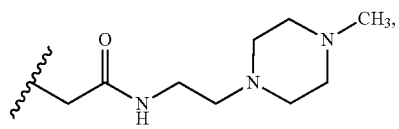

-continued

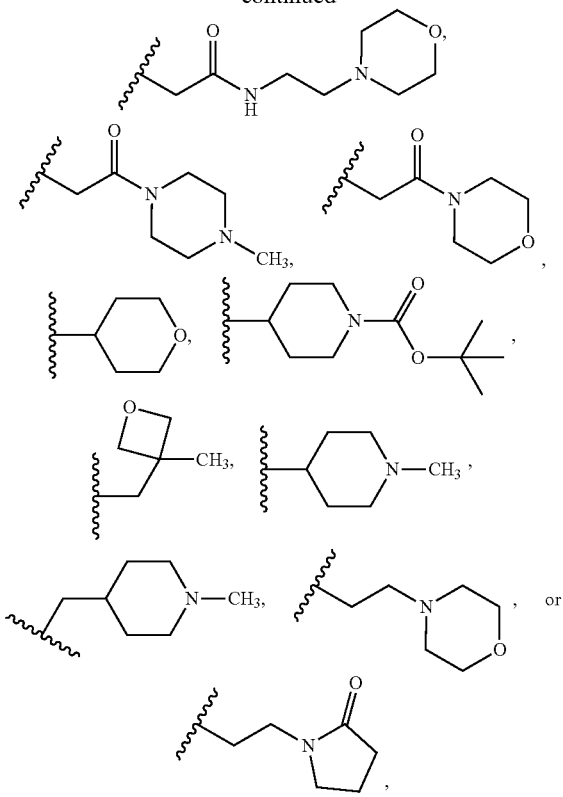

According to another embodiment, Ring H is H1;

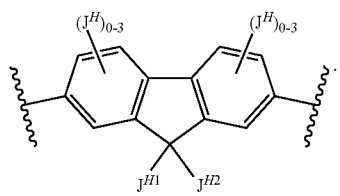

In some embodiments, $J^{H1}$ is H, OH, —($C_{1-4}$alkyl)OH, or —($C_{1-4}$alkyl)OC(O)($C_{1-4}$alkyl);

$J^{H2}$ is $X^J$H, $Q^J$H, or $X^J$H-$Q^J$H; wherein $X^{JH}$ is $C_{1-6}$alkyl wherein up to 3 methylene units of $C_{1-6}$alkyl is optionally replaced with —O—, —NH, N($C_1$-$C_6$aliphatic), or —C(O)—;

$Q^{JH}$ is $C_{3-6}$cycloalkyl, phenyl optionally substituted with —O($C_{1-4}$alkyl), or piperazinyl optionally substituted with $C_{1-4}$alkyl.

In other embodiments, $J^{H1}$ is H, OH, $CH_2OH$, $CH_2CH_2OH$, or $CH_2OC(O)CH_3$;

$J^{H2}$ is H, $CH_2CH_3$, $CH_2CH_2CH_3$, $CH(CH_3)_2$, $CH_2CH_2CH(CH_3)_2$, $CH_2OH$, $CH_2CH_2OH$, $CH_2CH_2C(O)OH$, $CH_2CH(OH)CH_2OH$, $CH_2OC(O)CH_3$, $N(CH_3)$ $CH_2CH_2N(CH_3)_2$, phenyl, 3-methoxyphenyl, 4-methylpiperazinyl, or $CH_2$-cyclohexyl; and $J^H$ is absent (i.e. $J^H$ is H or $J^H$ is absent).

In yet other embodiments, $X^{JH}$ is $C_{1-6}$alkyl and $Q^{JH}$ is $C_{3-6}$cycloaliphatic, oxetanyl, tetrahydropyrrolidinyl, piperidinyl, piperazinyl, or morpholinyl.

Another embodiment provides a compound having formula ID-a:

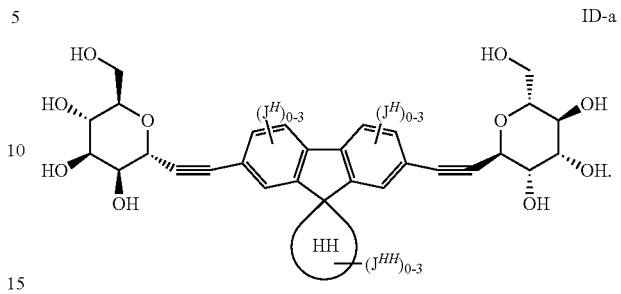

In some embodiments,

Ring HH is a 3-8 membered saturated monocyclic ring having 0-2 heteroatoms selected from oxygen, nitrogen, or sulfur;

$J^{HH}$ is $X^J$, $Q^J$, or $X^J$-$Q^J$;

$X^J$ is a $C_1$-$C_{10}$ aliphatic, wherein up to 4 methylene units of the $C_1$-$C_{10}$ aliphatic are optionally replaced with —O—, —NH, N($C_1$-$C_6$aliphatic), —S—, —C(O)—, —S(O)—, or —S(O)$_2$—; $X^J$ is optionally substituted with 0-6 occurrences of halo or 0-1 occurrences of CN;

$Q^J$ is a 3-7 membered monocyclic saturated, partially unsaturated, or aromatic ring optionally having 1-4 heteroatoms selected from oxygen, nitrogen, or sulfur; wherein each $Q^J$ is optionally substituted with 1-6 occurrences of halogen, CN, $NO_2$, or $C_1$-$C_6$aliphatic wherein up to three methylene units are optionally replaced with O, NH, NH($C_1$-$C_6$aliphatic), S, C(O), S(O), or S(O)$_2$; and $J^H$ is halogen, CN, $NO_2$, or $C_1$-$C_6$aliphatic wherein up to three methylene units are optionally replaced with O, NH, NH($C_1$-$C_6$aliphatic), S, C(O), S(O), or S(O)$_2$.

In some embodiments, Ring HH is cyclopentyl, cyclohexyl, tetrahydropyranyl, 1,3 dithianyl, piperazinyl, piperidinyl, or oxepanyl. In other embodiments, Ring HH is piperidinyl or tetrahydropyranyl.

Another embodiment provides a compound having formula ID-b:

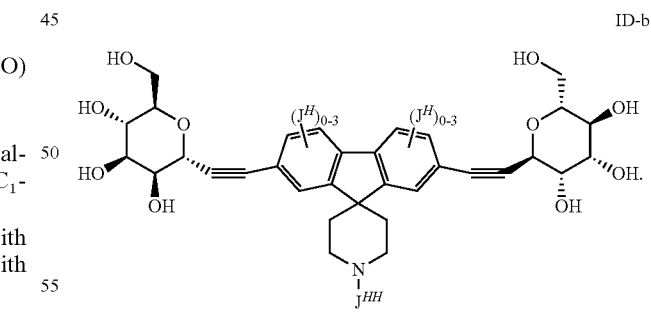

In some embodiments, $J^{HH}$ is $X^J$, $Q^J$, or $X^J$-$Q^J$;

$X^J$ is a $C_1$-$C_4$ aliphatic, wherein up to two methylene units of the $C_1$-$C_4$ aliphatic are optionally replaced with —O—, —NH, N($C_1$-$C_6$aliphatic), —S—, —C(O)—, —S(O)—, or —S(O)$_2$—;

$Q^J$ is a 3-6 membered monocyclic saturated, partially unsaturated, or aromatic ring optionally having 1-4 heteroatoms selected from oxygen, nitrogen, or sulfur; wherein each $Q^J$ is optionally substituted with 1-3 occurrences of halogen, CN, or $C_1$-$C_6$aliphatic wherein up to two methylene units of said $C_1$-$C_6$aliphatic are optionally replaced with O, NH, NH($C_1$-$C_6$aliphatic), S, C(O), S(O), or S(O)$_2$; and $J^H$ is halogen or $C_{1-4}$alkyl.

In some embodiments, $J^{HH}$ is H, C(O)($C_{1-6}$alkyl), C(O)O($C_{1-6}$alkyl), S(O)$_2$($C_{1-6}$alkyl), C(O)($C_{3-6}$cycloalkyl), C(O)(3-6 membered heterocyclyl), C(O)(5-6 membered heteroaryl), C(O)—($C_{1-4}$alkyl)-(5-6 membered heteroaryl), C(O)—($C_{1-4}$alkyl)-(heterocyclyl); wherein said heteroaryl or heterocyclyl has 1-3 heteroatoms selected from oxygen, nitrogen, or sulfur; $J^{HH}$ is optionally substituted with OH, O($C_{1-6}$alkyl), oxo, $C_{1-6}$alkyl, CN, or halo.

In other embodiments, $J^{HH}$ is H, C(O)CH$_3$, C(O)OC(CH$_3$)$_3$, C(O)OCH(CH$_3$)$_2$, C(O)OCH$_2$CH$_3$, C(O)OC(OH)(CH$_3$)$_2$, S(O)$_2$CH$_3$, C(O)CH(CH$_3$)$_2$, C(O)C(CH$_3$)$_3$, C(O)CH(CH$_3$)OCH$_3$,

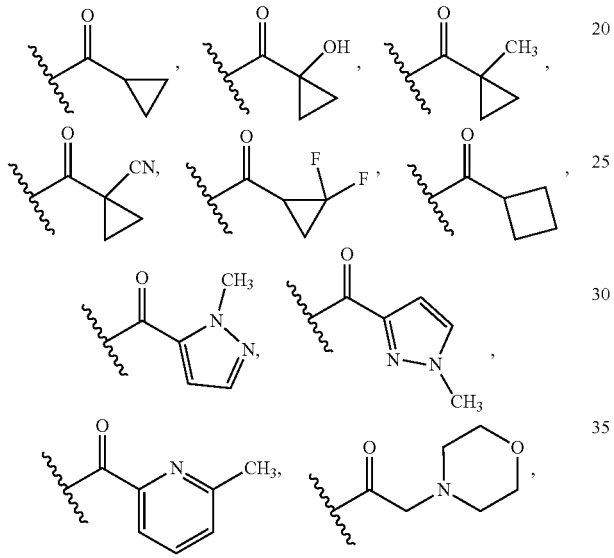

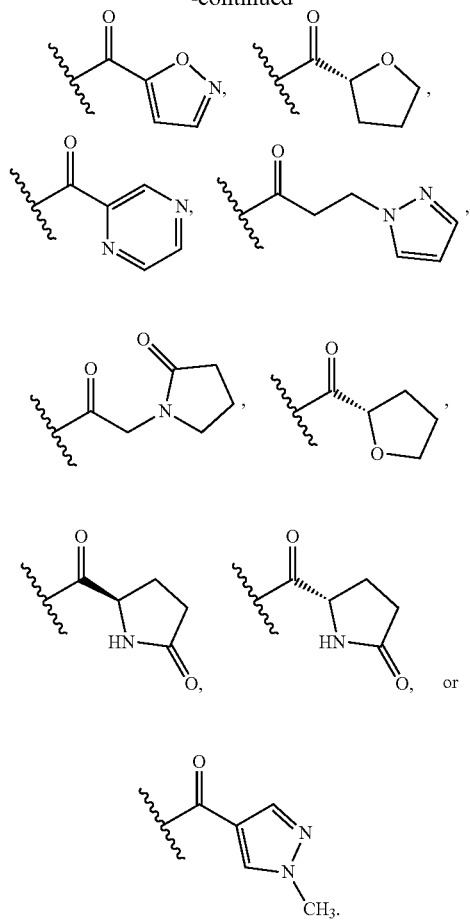

Another embodiment provides a compound represented by a structural formula selected from the group consisting of:

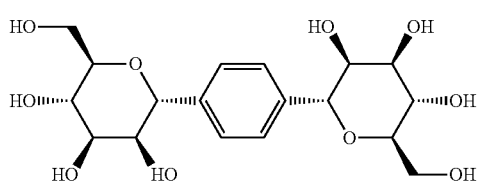

1

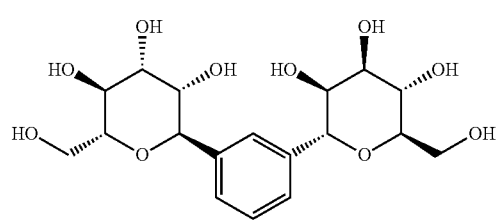

2

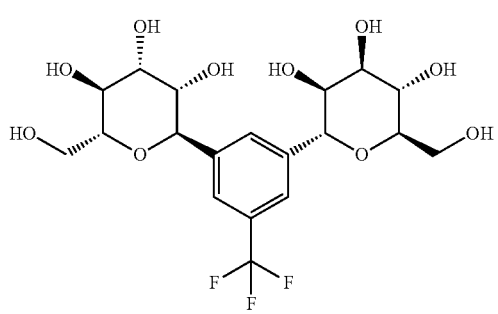

3

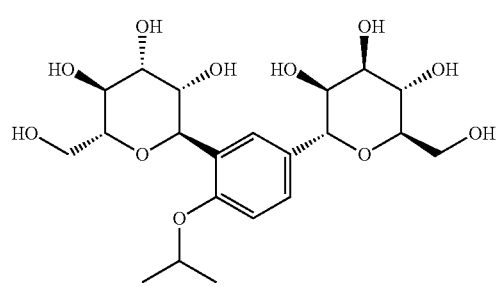

4

-continued
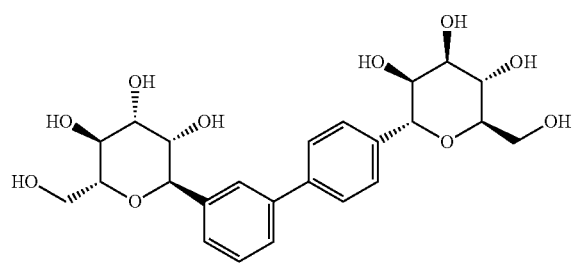
5
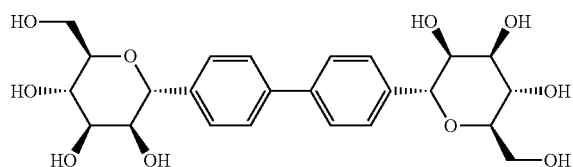
6
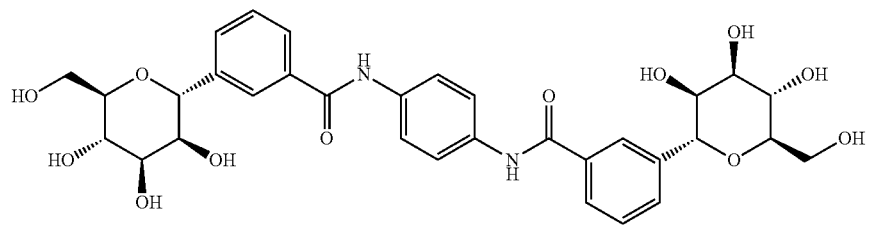
7
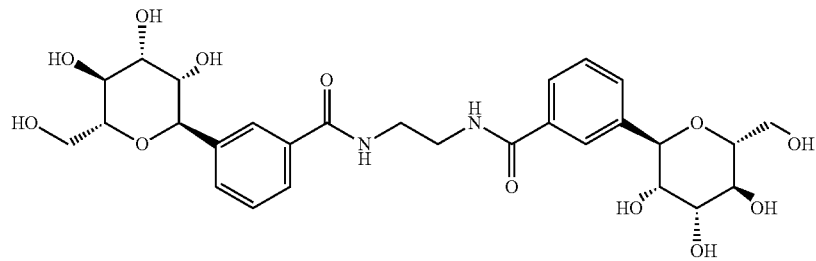
8
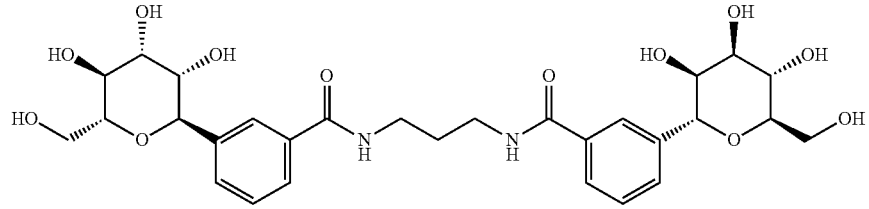
9
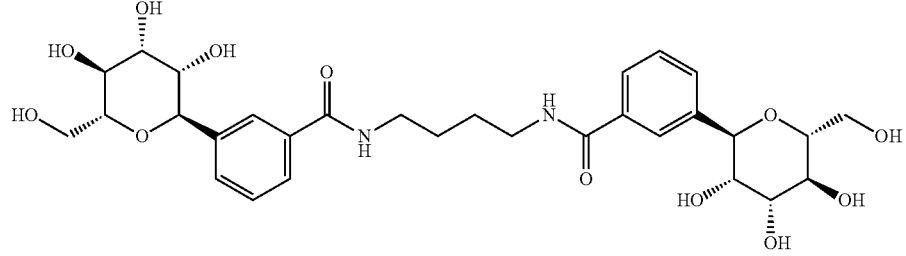
10
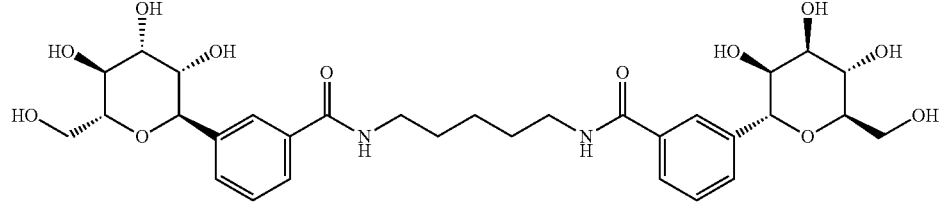
11

12
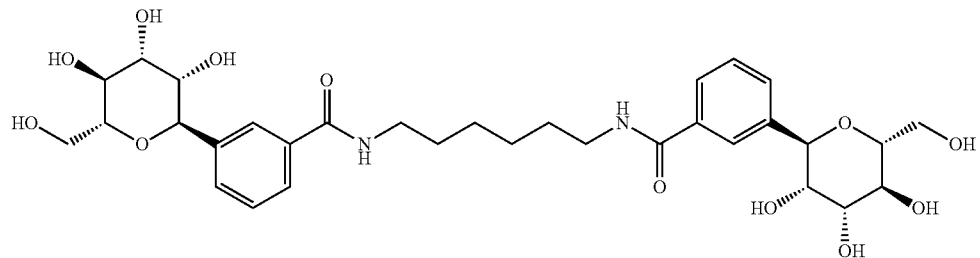
13
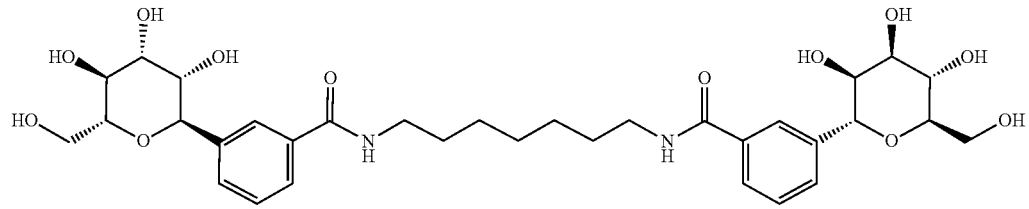
14
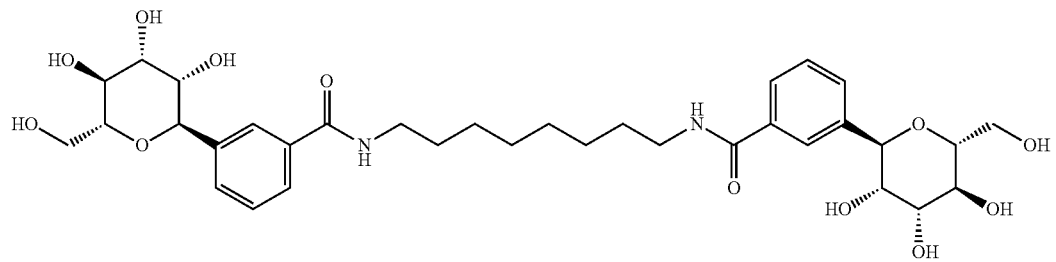
15
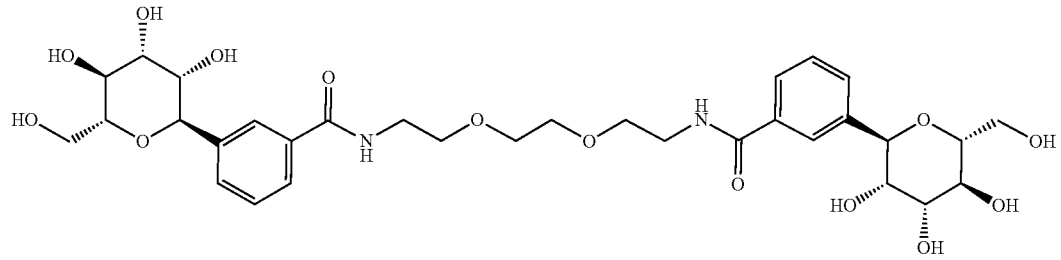
16
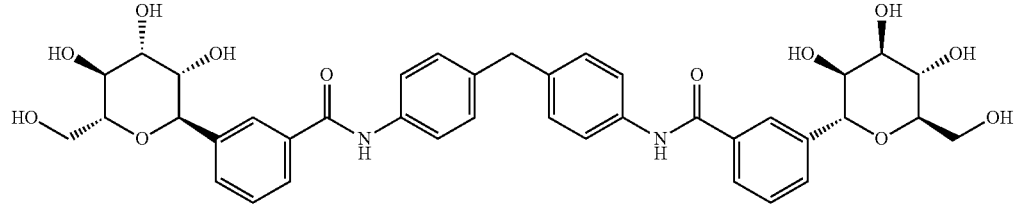
17
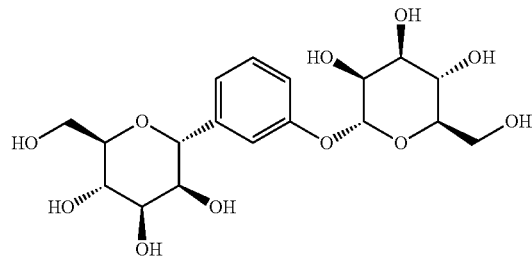
18
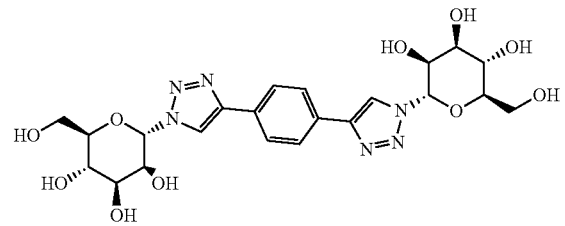

-continued
19 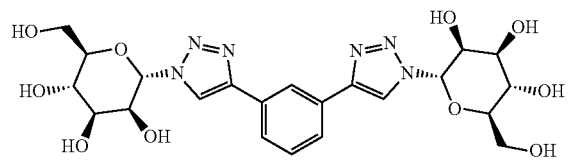
20 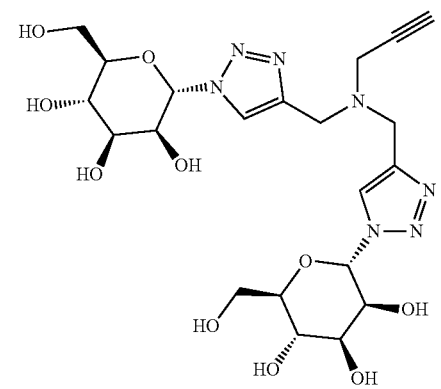
21 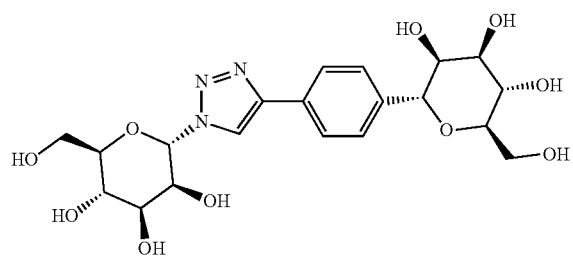
22 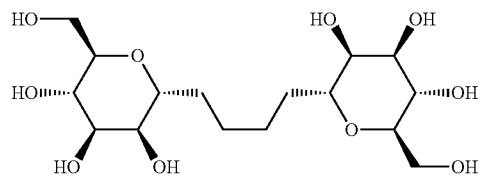
23 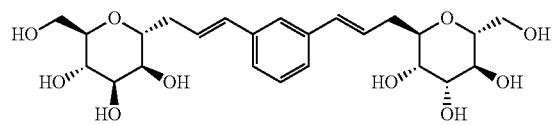
24
25 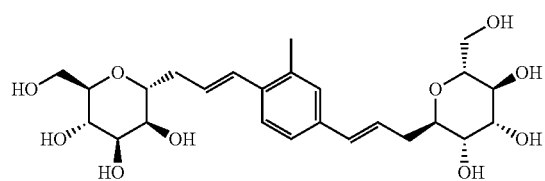
26
27 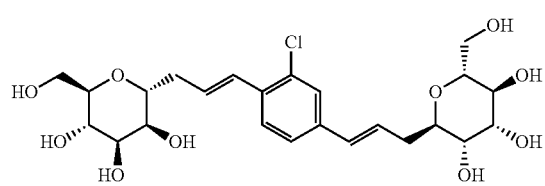
28
29 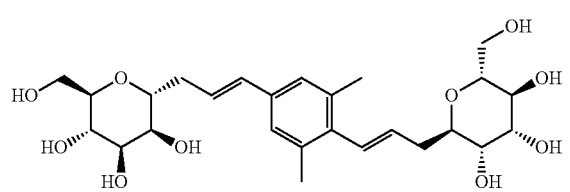
30 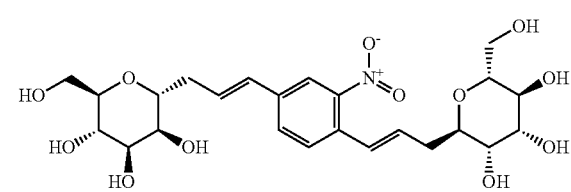
31
32

-continued
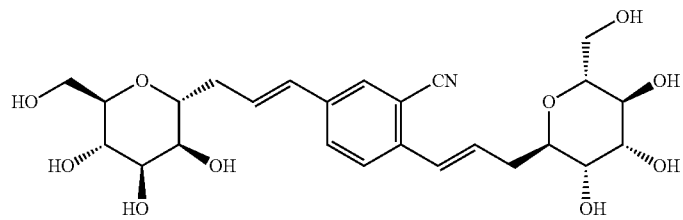
33
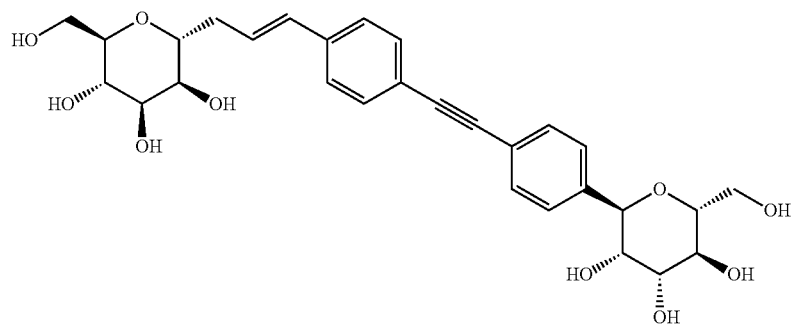
34
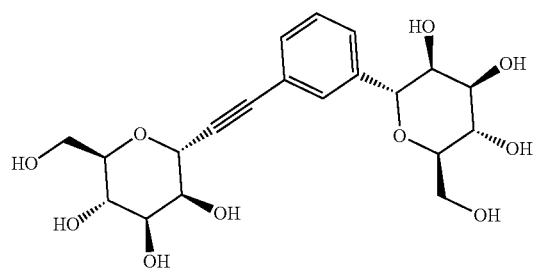
35
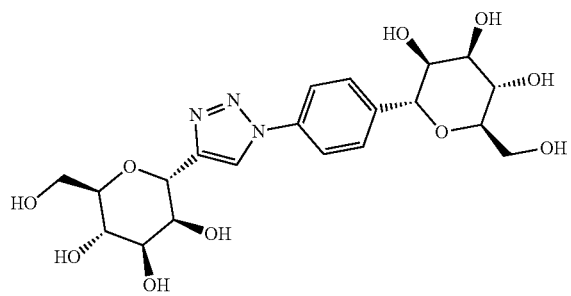
36
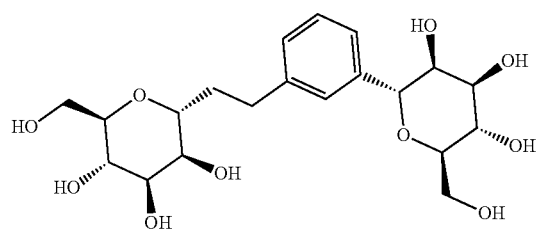
37
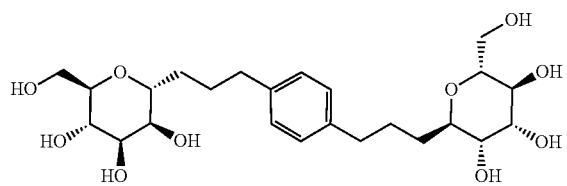
38
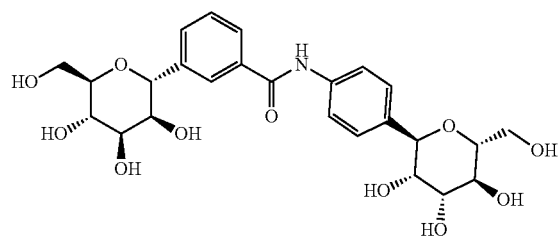
39
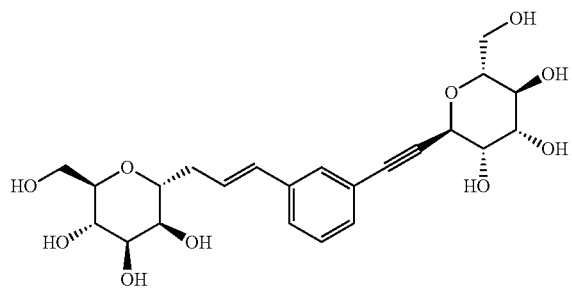
40

-continued
41 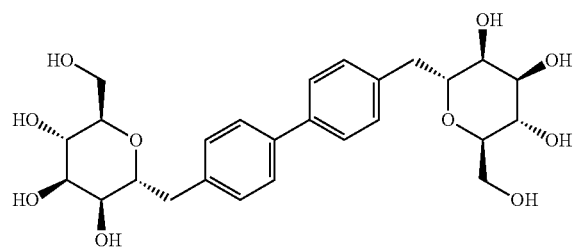
42 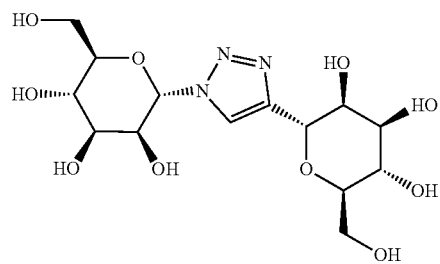
43 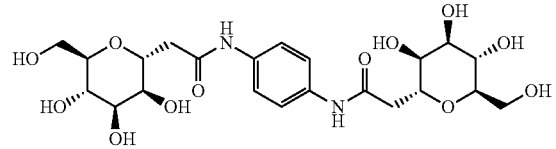
44 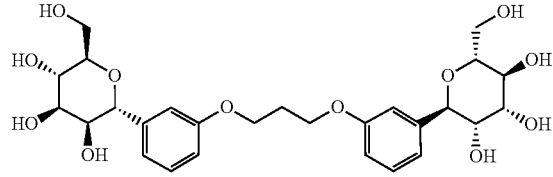
45 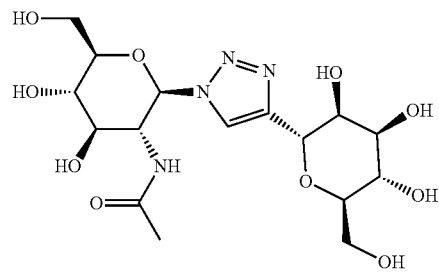
46 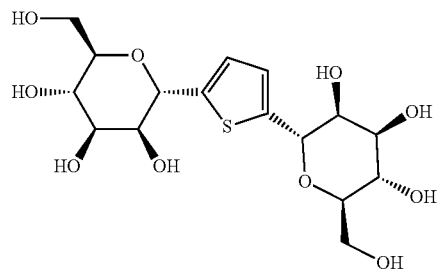
47 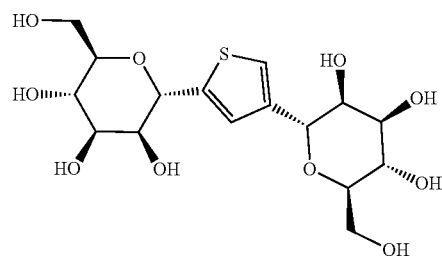
48 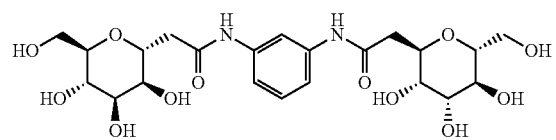
49 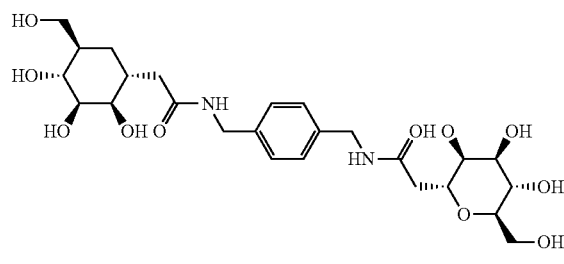
50 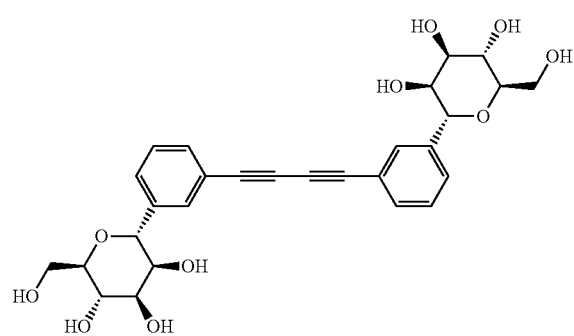
51 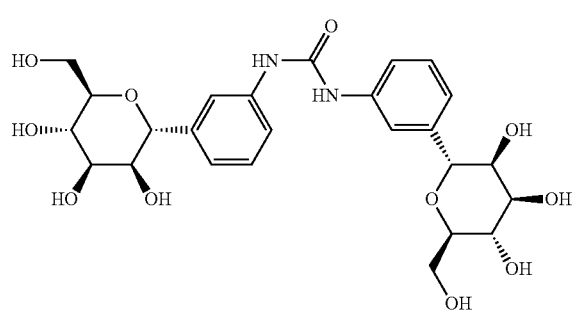

-continued
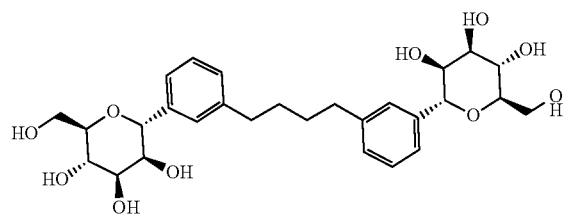
52
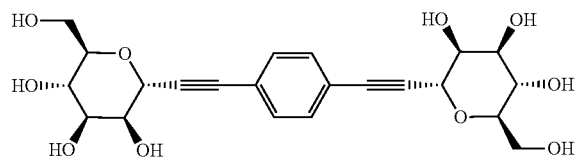
53
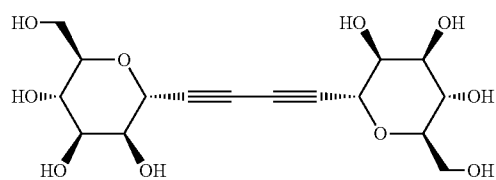
54
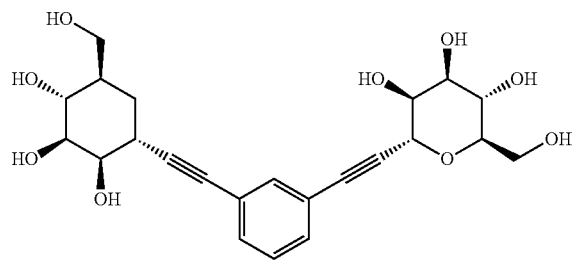
55
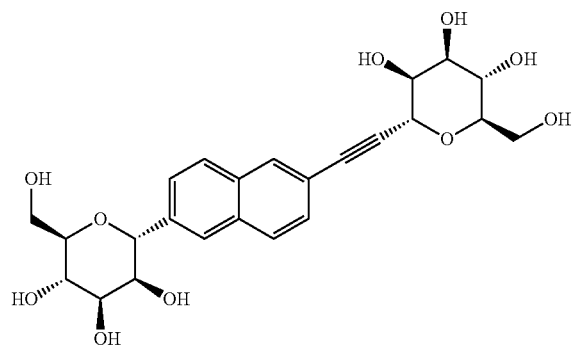
56
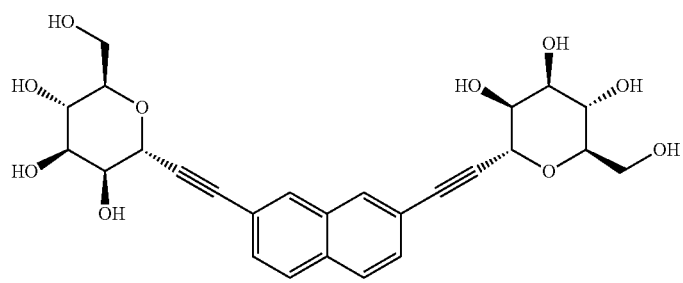
57
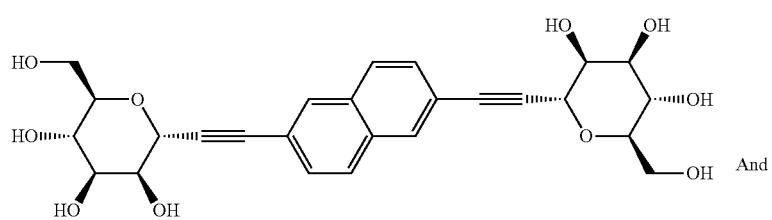
58
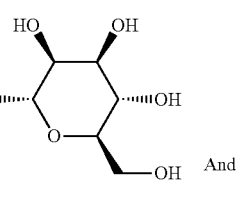
59
And -continued
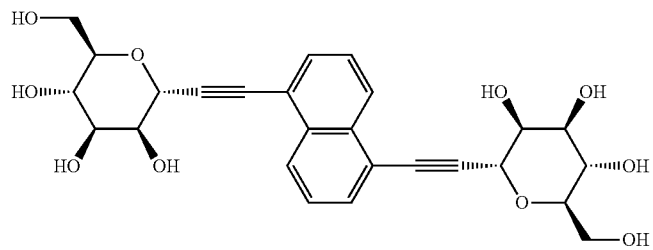
60
or a pharmaceutically acceptable salt thereof.
Another embodiment provides a compound represented by a structural formula selected from the group consisting of:
| # | Structure |
|---|---|
| 61 | |
| 62 | 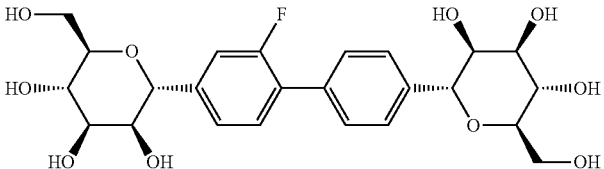 [SMILES: Cc1cc([C@H]2O[C@H](CO)[C@@H](O)[C@H](O)[C@@H]2O)ccc1-c1ccc([C@H]2O[C@H](CO)[C@@H](O)[C@H](O)[C@@H]2O)cc1] |
| 63 | 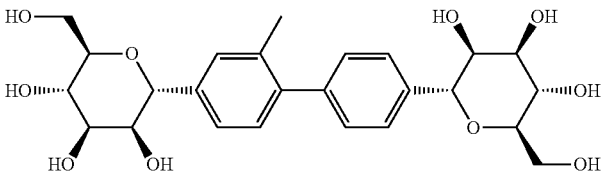 |
| 64 | 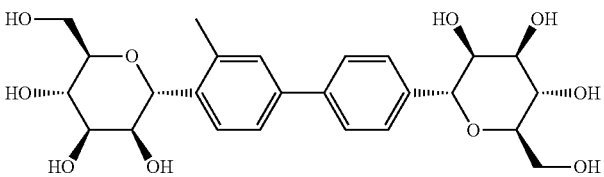 [SMILES: Cc1cc(-c2ccc([C@H]3O[C@H](CO)[C@@H](O)[C@H](O)[C@@H]3O)cc2)ccc1[C@H]1O[C@H](CO)[C@@H](O)[C@H](O)[C@@H]1O] |
| 65 | 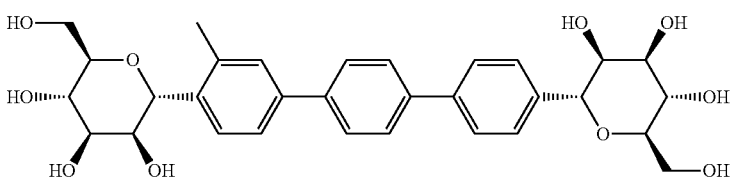 [SMILES: Cc1cc(-c2ccc(-c3ccc([C@H]4O[C@H](CO)[C@@H](O)[C@H](O)[C@@H]4O)cc3)cc2)ccc1[C@H]1O[C@H](CO)[C@@H](O)[C@H](O)[C@@H]1O] |
| 66 | 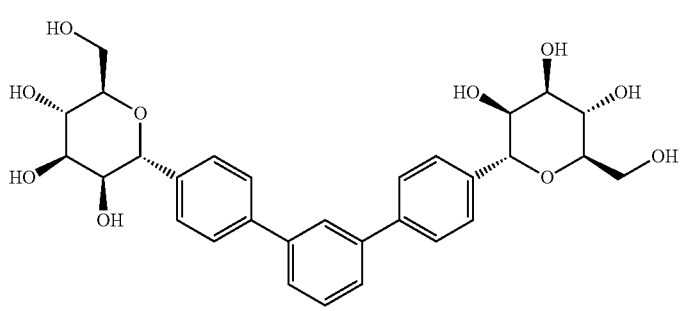 [SMILES: OC[C@H]1O[C@H](c2ccc(-c3cccc(-c4ccc([C@H]5O[C@H](CO)[C@@H](O)[C@H](O)[C@@H]5O)cc4)c3)cc2)[C@@H](O)[C@@H](O)[C@@H]1O] |

-continued

| # | Structure |
|---|---|
| 67 | 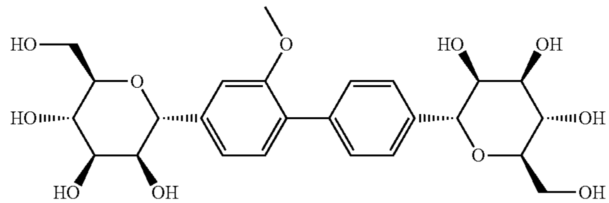 [SMILES: COc1cc([C@H]2O[C@H](CO)[C@@H](O)[C@H](O)[C@@H]2O)ccc1-c1ccc([C@H]2O[C@H](CO)[C@@H](O)[C@H](O)[C@@H]2O)cc1] |
| 68 | 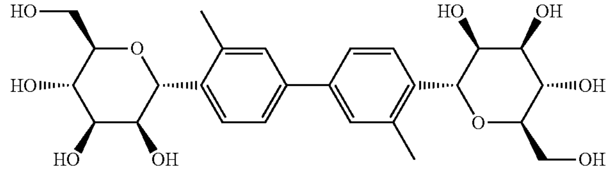 [SMILES: Cc1cc(-c2ccc([C@H]3O[C@H](CO)[C@@H](O)[C@H](O)[C@@H]3O)c(C)c2)ccc1[C@H]1O[C@H](CO)[C@@H](O)[C@H](O)[C@@H]1O] |
| 69 | 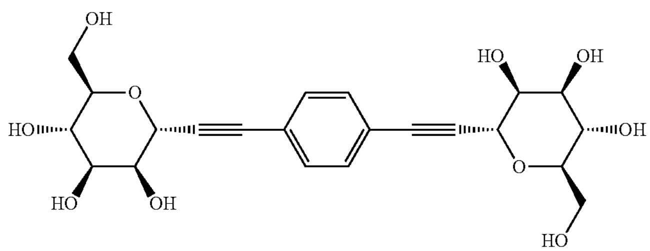 [SMILES: OC[C@H]1O[C@H](C#Cc2ccc(C#C[C@H]3O[C@H](CO)[C@@H](O)[C@H](O)[C@@H]3O)cc2)[C@@H](O)[C@@H](O)[C@@H]1O] |
| 70 | 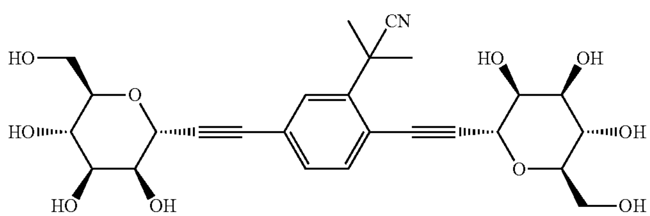 [SMILES: CC(C)(C#N)c1cc(C#C[C@H]2O[C@H](CO)[C@@H](O)[C@H](O)[C@@H]2O)ccc1C#C[C@H]1O[C@H](CO)[C@@H](O)[C@H](O)[C@@H]1O] |
| 71 | 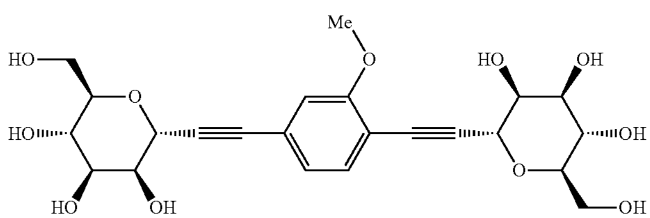 |
| 72 | 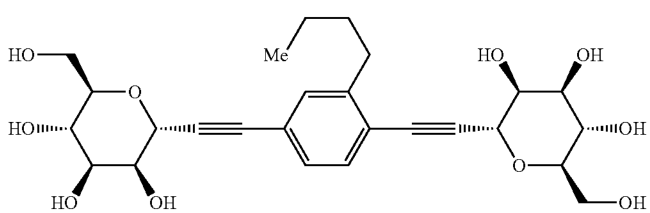 [SMILES: CCCCc1cc(C#C[C@H]2O[C@H](CO)[C@@H](O)[C@H](O)[C@@H]2O)ccc1C#C[C@H]1O[C@H](CO)[C@@H](O)[C@H](O)[C@@H]1O] |
| 73 | 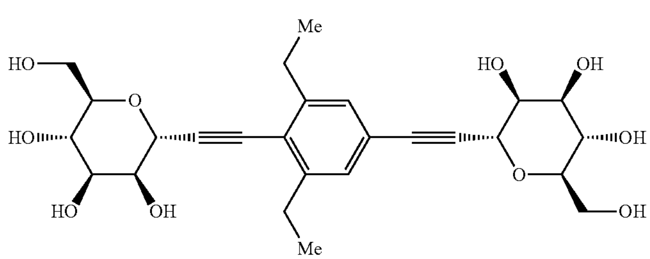 [SMILES: CCc1cc(C#C[C@H]2O[C@H](CO)[C@@H](O)[C@H](O)[C@@H]2O)cc(CC)c1C#C[C@H]1O[C@H](CO)[C@@H](O)[C@H](O)[C@@H]1O] |

-continued

| # | Structure |
|---|---|
| 74 | 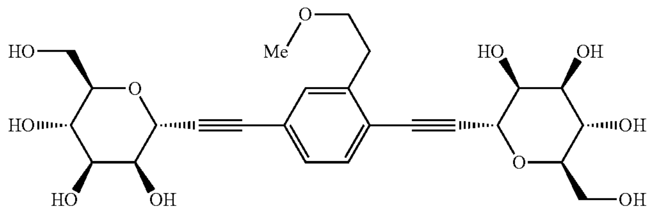 [SMILES: COCCc1cc(C#C[C@H]2O[C@H](CO)[C@@H](O)[C@H](O)[C@@H]2O)ccc1C#C[C@H]1O[C@H](CO)[C@@H](O)[C@H](O)[C@@H]1O] |
| 75 | 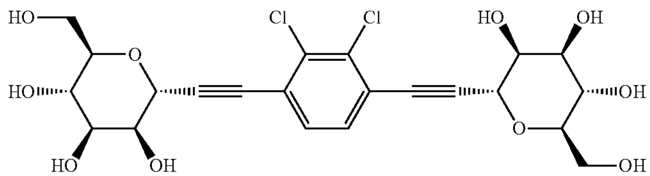 [SMILES: OC[C@H]1O[C@H](C#Cc2ccc(C#C[C@H]3O[C@H](CO)[C@@H](O)[C@H](O)[C@@H]3O)c(Cl)c2Cl)[C@@H](O)[C@@H](O)[C@@H]1O] |
| 76 | 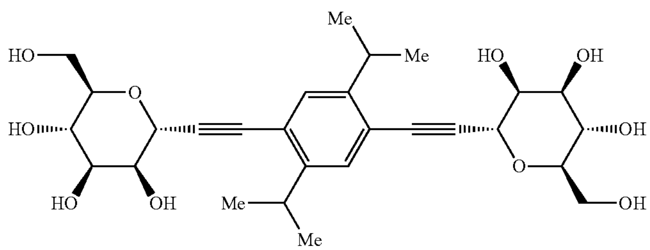 [SMILES: CC(C)c1cc(C#C[C@H]2O[C@H](CO)[C@@H](O)[C@H](O)[C@@H]2O)c(C(C)C)cc1C#C[C@H]1O[C@H](CO)[C@@H](O)[C@H](O)[C@@H]1O] |
| 77 | 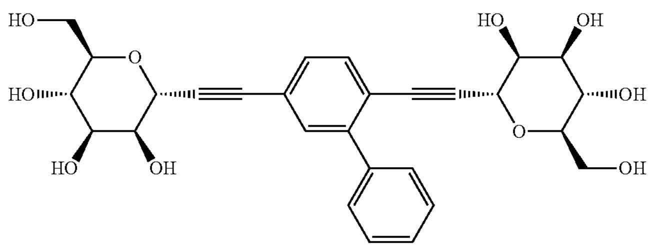 [SMILES: OC[C@H]1O[C@H](C#Cc2ccc(C#C[C@H]3O[C@H](CO)[C@@H](O)[C@H](O)[C@@H]3O)c(-c3ccccc3)c2)[C@@H](O)[C@@H](O)[C@@H]1O] |
| 78 | 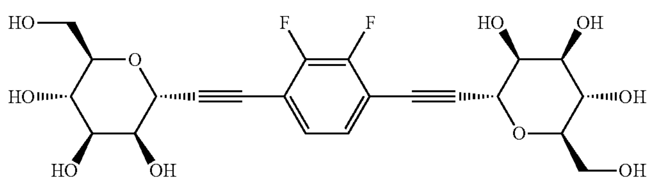 |
| 79 | 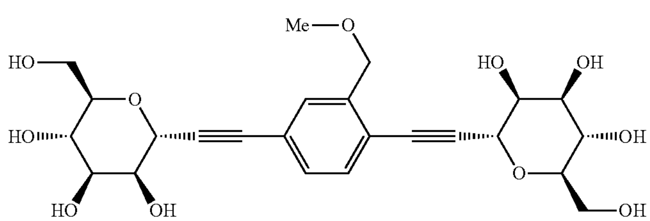 [SMILES: COCc1cc(C#C[C@H]2O[C@H](CO)[C@@H](O)[C@H](O)[C@@H]2O)ccc1C#C[C@H]1O[C@H](CO)[C@@H](O)[C@H](O)[C@@H]1O] |
| 80 | 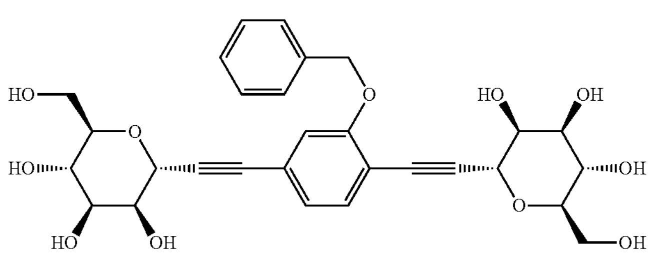 [SMILES: OC[C@H]1O[C@H](C#Cc2ccc(C#C[C@H]3O[C@H](CO)[C@@H](O)[C@H](O)[C@@H]3O)c(OCc3ccccc3)c2)[C@@H](O)[C@@H](O)[C@@H]1O] |

-continued

| # | Structure |
|---|---|
| 81 | 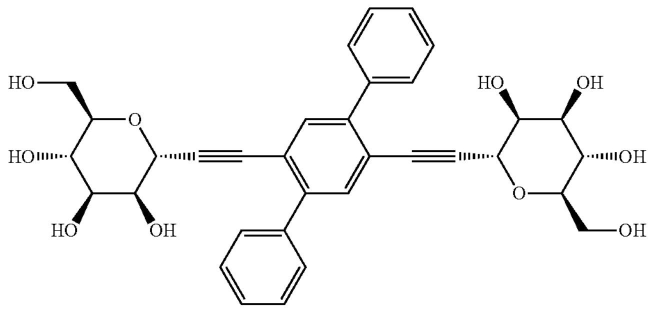 [SMILES: OC[C@H]1O[C@H](C#Cc2cc(-c3ccccc3)c(C#C[C@H]3O[C@H](CO)[C@@H](O)[C@H](O)[C@@H]3O)cc2-c2ccccc2)[C@@H](O)[C@@H](O)[C@@H]1O] |
| 82 | 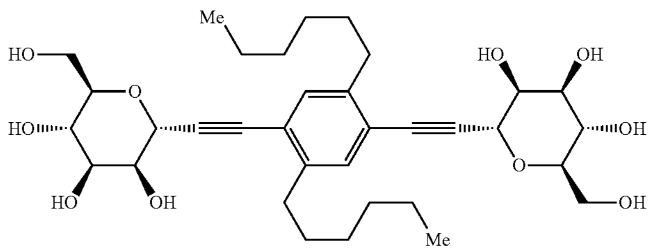 [SMILES: CCCCCCc1cc(C#C[C@H]2O[C@H](CO)[C@@H](O)[C@H](O)[C@@H]2O)c(CCCCCC)cc1C#C[C@H]1O[C@H](CO)[C@@H](O)[C@H](O)[C@@H]1O] |
| 83 | 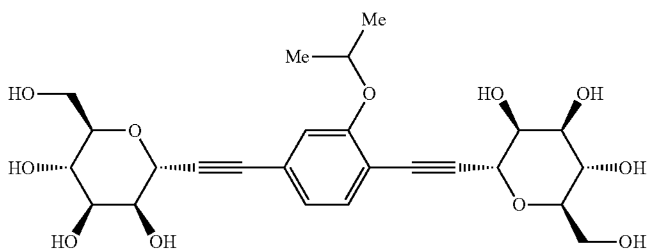 [SMILES: CC(C)Oc1cc(C#C[C@H]2O[C@H](CO)[C@@H](O)[C@H](O)[C@@H]2O)ccc1C#C[C@H]1O[C@H](CO)[C@@H](O)[C@H](O)[C@@H]1O] |
| 84 | 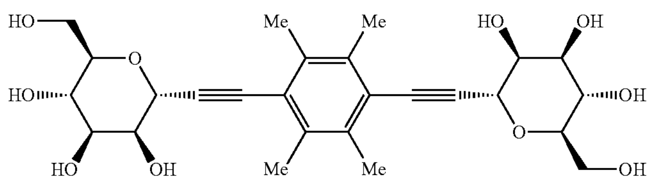 [SMILES: Cc1c(C)c(C#C[C@H]2O[C@H](CO)[C@@H](O)[C@H](O)[C@@H]2O)c(C)c(C)c1C#C[C@H]1O[C@H](CO)[C@@H](O)[C@H](O)[C@@H]1O] |
| 85 | 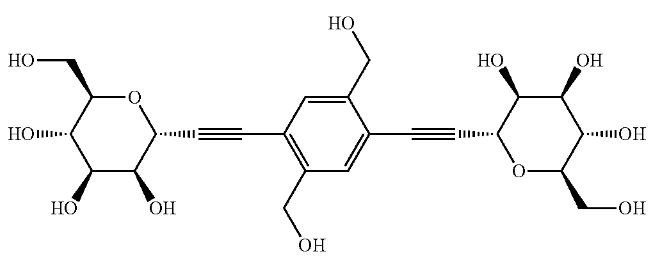 [SMILES: OCc1cc(C#C[C@H]2O[C@H](CO)[C@@H](O)[C@H](O)[C@@H]2O)c(CO)cc1C#C[C@H]1O[C@H](CO)[C@@H](O)[C@H](O)[C@@H]1O] |
| 86 | 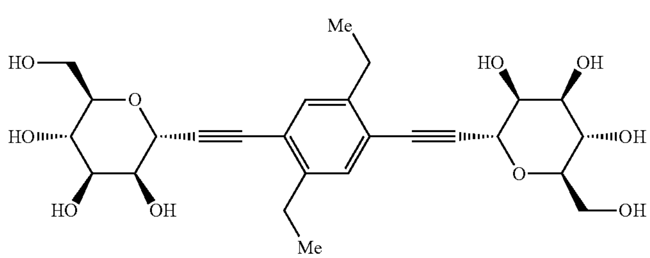 [SMILES: CCc1cc(C#C[C@H]2O[C@H](CO)[C@@H](O)[C@H](O)[C@@H]2O)c(CC)cc1C#C[C@H]1O[C@H](CO)[C@@H](O)[C@H](O)[C@@H]1O] |

-continued
| # | Structure |
|---|---|
| 87 | 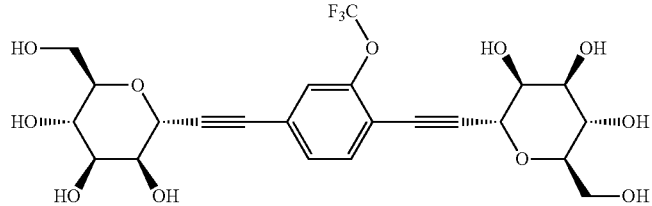 |
| 88 | 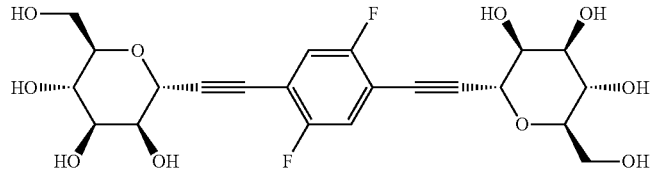 [SMILES: OC[C@H]1O[C@H](C#Cc2cc(F)c(C#C[C@H]3O[C@H](CO)[C@@H](O)[C@H](O)[C@@H]3O)cc2F)[C@@H](O)[C@@H](O)[C@@H]1O] |
| 89 | 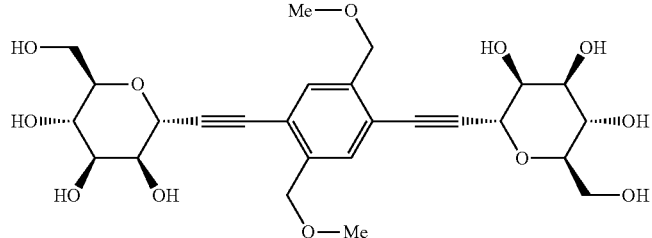 [SMILES: COCc1cc(C#C[C@H]2O[C@H](CO)[C@@H](O)[C@H](O)[C@@H]2O)c(COC)cc1C#C[C@H]1O[C@H](CO)[C@@H](O)[C@H](O)[C@@H]1O] |
| 90 | 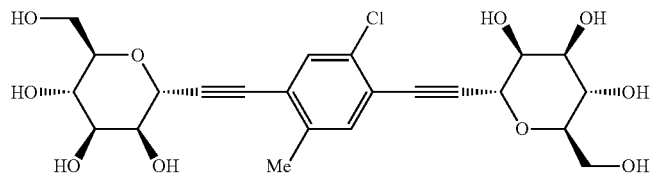 [SMILES: Cc1cc(C#C[C@H]2O[C@H](CO)[C@@H](O)[C@H](O)[C@@H]2O)c(C)cc1C#C[C@H]1O[C@H](CO)[C@@H](O)[C@H](O)[C@@H]1O] |
| 91 | 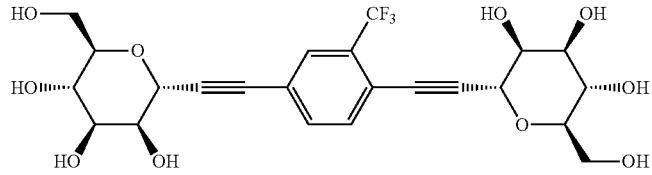 [SMILES: N#Cc1cc(C#C[C@H]2O[C@H](CO)[C@@H](O)[C@H](O)[C@@H]2O)ccc1C#C[C@H]1O[C@H](CO)[C@@H](O)[C@H](O)[C@@H]1O] |
| 92 | 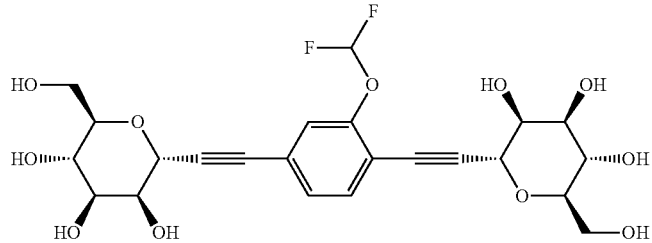 |
| 93 | 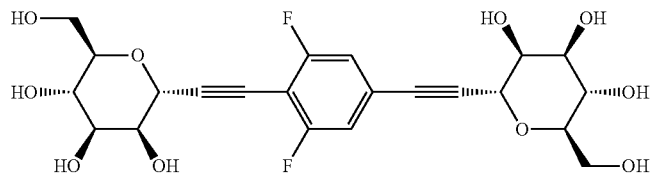 |

| # | Structure |
|---|---|
| 94 | (structure image) |
| 95 | (structure image) |
| 96 | (structure image) |
| 97 | (structure image) |
| 98 | (structure image) |
| 99 | (structure image) |
| 100 | (structure image) |

-continued

| # | Structure |
|---|---|
| 101 | (structure: glucose-C≡C-phenyl(CN)-C≡C-glucose) |
| 102 | (structure: glucose-C≡C-phenyl(Cl)-C≡C-glucose) |
| 103 | (structure: glucose-C≡C-phenyl(isopropyl)-C≡C-glucose) |
| 104 | (structure: glucose-C≡C-phenyl(Me)-C≡C-glucose) |
| 105 | (structure: glucose-C≡C-phenyl(F)-C≡C-glucose) |
| 106 | (structure: glucose-C≡C-dibenzofuran-C≡C-carbasugar) |

-continued

| # | Structure |
|---|---|
| 107 | 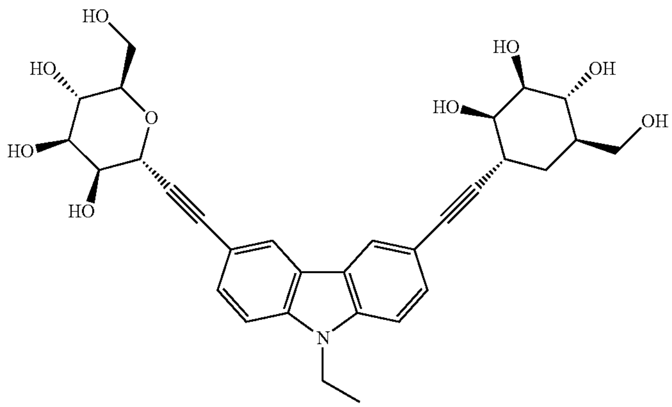 [SMILES: CCn1c2ccc(C#C[C@H]3C[C@H](CO)[C@@H](O)[C@H](O)[C@@H]3O)cc2c2cc(C#C[C@H]3O[C@H](CO)[C@@H](O)[C@H](O)[C@@H]3O)ccc21] |
| 108 | 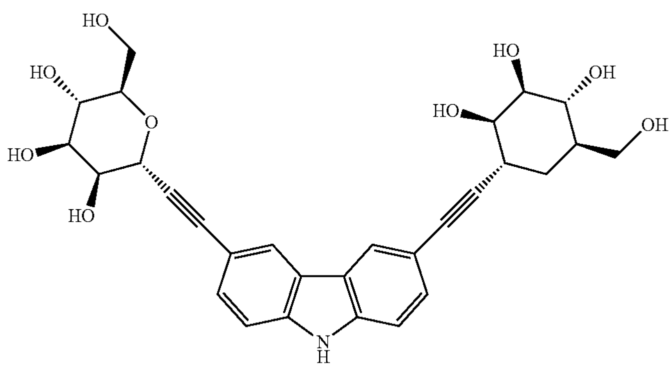 [SMILES: OC[C@H]1C[C@H](C#Cc2ccc3[nH]c4ccc(C#C[C@H]5O[C@H](CO)[C@@H](O)[C@H](O)[C@@H]5O)cc4c3c2)[C@@H](O)[C@@H](O)[C@@H]1O] |
| 109 | 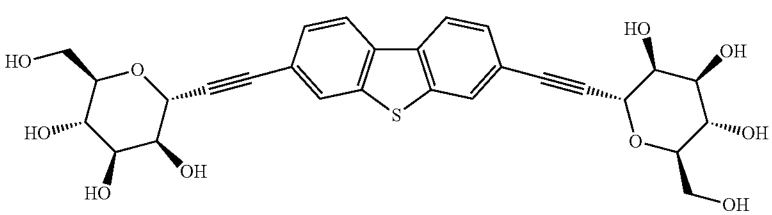 [SMILES: OC[C@H]1O[C@H](C#Cc2ccc3c(c2)sc2cc(C#C[C@H]4O[C@H](CO)[C@@H](O)[C@H](O)[C@@H]4O)ccc23)[C@@H](O)[C@@H](O)[C@@H]1O] |
| 110 | 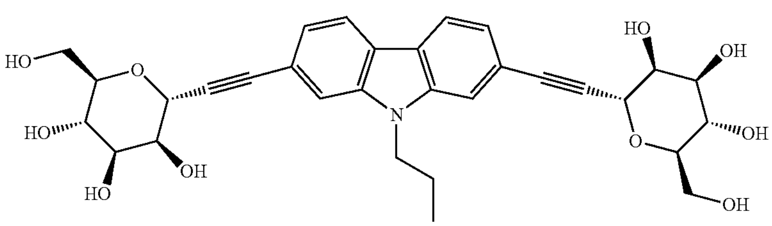 [SMILES: CCCn1c2cc(C#C[C@H]3O[C@H](CO)[C@@H](O)[C@H](O)[C@@H]3O)ccc2c2ccc(C#C[C@H]3O[C@H](CO)[C@@H](O)[C@H](O)[C@@H]3O)cc21] |
| 111 | 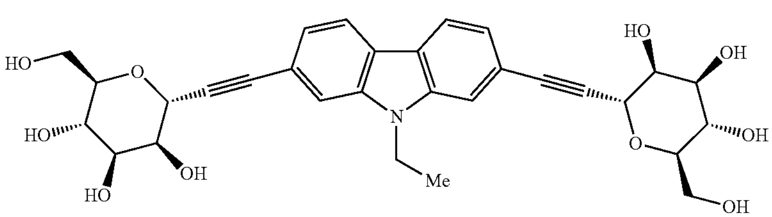 [SMILES: CCn1c2cc(C#C[C@H]3O[C@H](CO)[C@@H](O)[C@H](O)[C@@H]3O)ccc2c2ccc(C#C[C@H]3O[C@H](CO)[C@@H](O)[C@H](O)[C@@H]3O)cc21] |

-continued

| # | Structure |
|---|---|
| 112 | 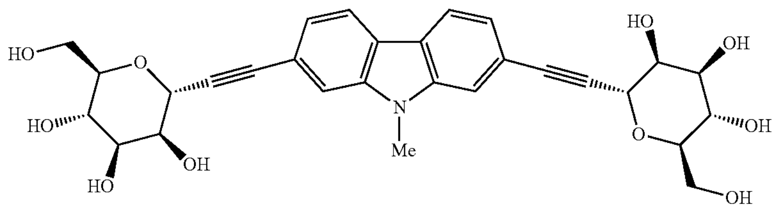 [SMILES: Cn1c2cc(C#C[C@H]3O[C@H](CO)[C@@H](O)[C@H](O)[C@@H]3O)ccc2c2ccc(C#C[C@H]3O[C@H](CO)[C@@H](O)[C@H](O)[C@@H]3O)cc21] |
| 113 | 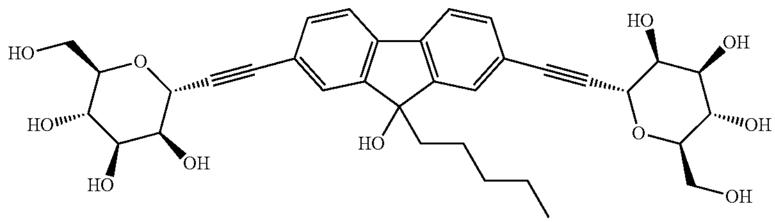 [SMILES: CCCCCC1(O)c2cc(C#C[C@H]3O[C@H](CO)[C@@H](O)[C@H](O)[C@@H]3O)ccc2-c2ccc(C#C[C@H]3O[C@H](CO)[C@@H](O)[C@H](O)[C@@H]3O)cc21] |
| 114 | 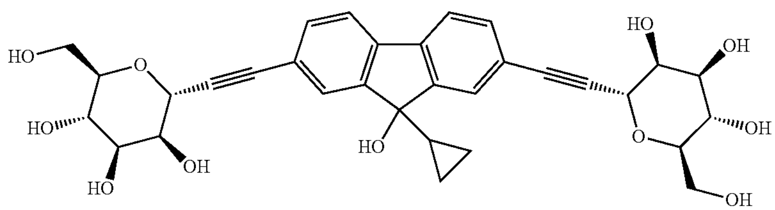 [SMILES: OC[C@H]1O[C@H](C#Cc2ccc3c(c2)C(O)(C2CC2)c2cc(C#C[C@H]4O[C@H](CO)[C@@H](O)[C@H](O)[C@@H]4O)ccc2-3)[C@@H](O)[C@@H](O)[C@@H]1O] |
| 115 | 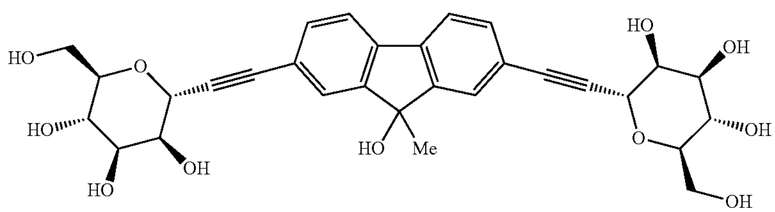 [SMILES: CC1(O)c2cc(C#C[C@H]3O[C@H](CO)[C@@H](O)[C@H](O)[C@@H]3O)ccc2-c2ccc(C#C[C@H]3O[C@H](CO)[C@@H](O)[C@H](O)[C@@H]3O)cc21] |
| 116 | 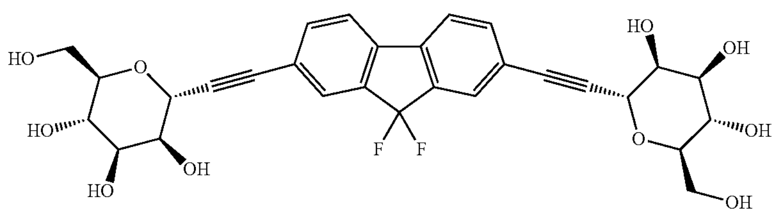 [SMILES: OC[C@H]1O[C@H](C#Cc2ccc3c(c2)C(F)(F)c2cc(C#C[C@H]4O[C@H](CO)[C@@H](O)[C@H](O)[C@@H]4O)ccc2-3)[C@@H](O)[C@@H](O)[C@@H]1O] |
| 117 | 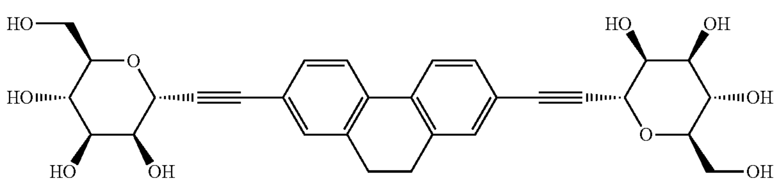 [SMILES: OC[C@H]1O[C@H](C#Cc2ccc3c(c2)CCc2cc(C#C[C@H]4O[C@H](CO)[C@@H](O)[C@H](O)[C@@H]4O)ccc2-3)[C@@H](O)[C@@H](O)[C@@H]1O] |
| 118 | 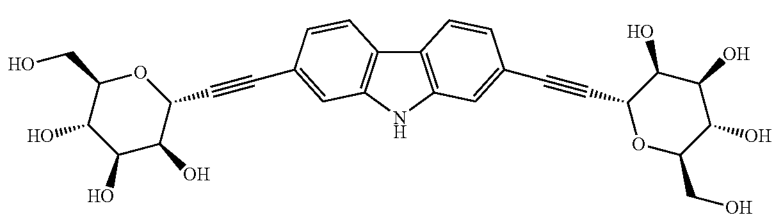 [SMILES: OC[C@H]1O[C@H](C#Cc2ccc3c(c2)[nH]c2cc(C#C[C@H]4O[C@H](CO)[C@@H](O)[C@H](O)[C@@H]4O)ccc23)[C@@H](O)[C@@H](O)[C@@H]1O] |

| # | Structure |
|---|---|
| 119 | 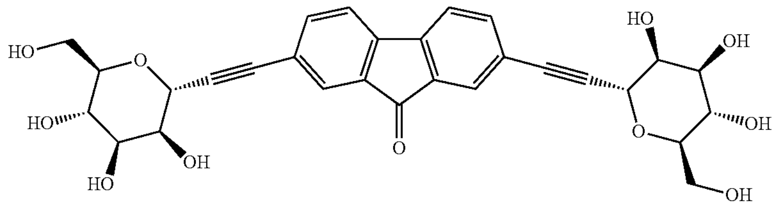 [SMILES: O=C1c2cc(C#C[C@H]3O[C@H](CO)[C@@H](O)[C@H](O)[C@@H]3O)ccc2-c2ccc(C#C[C@H]3O[C@H](CO)[C@@H](O)[C@H](O)[C@@H]3O)cc21] |
| 120 | 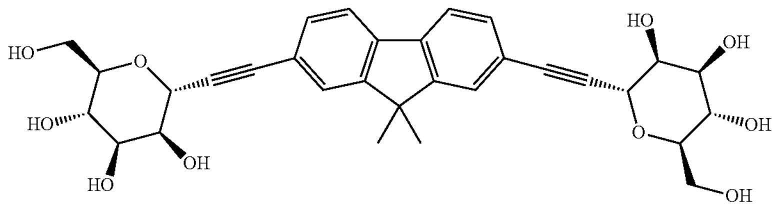 [SMILES: CC1(C)c2cc(C#C[C@H]3O[C@H](CO)[C@@H](O)[C@H](O)[C@@H]3O)ccc2-c2ccc(C#C[C@H]3O[C@H](CO)[C@@H](O)[C@H](O)[C@@H]3O)cc21] |
| 121 | 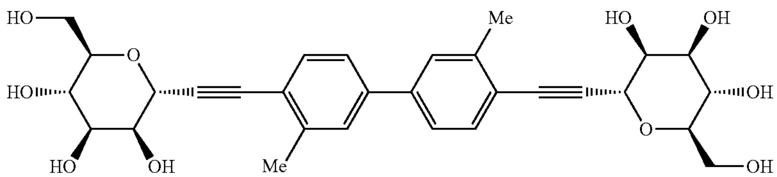 [SMILES: Cc1cc(-c2ccc(C#C[C@H]3O[C@H](CO)[C@@H](O)[C@H](O)[C@@H]3O)c(C)c2)ccc1C#C[C@H]1O[C@H](CO)[C@@H](O)[C@H](O)[C@@H]1O] |
| 122 | 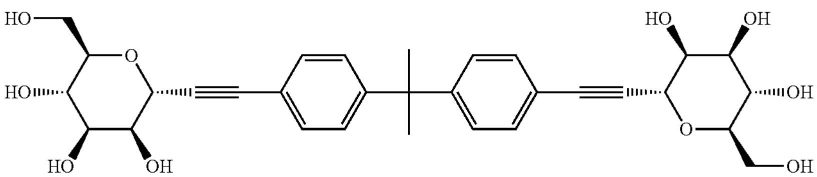 [SMILES: CC(C)(c1ccc(C#C[C@H]2O[C@H](CO)[C@@H](O)[C@H](O)[C@@H]2O)cc1)c1ccc(C#C[C@H]2O[C@H](CO)[C@@H](O)[C@H](O)[C@@H]2O)cc1] |
| 123 | 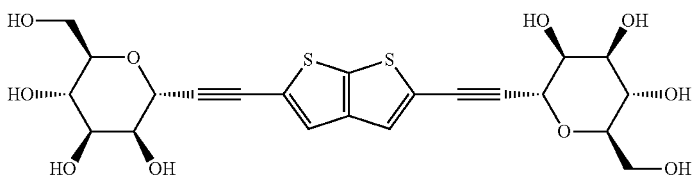 [SMILES: OC[C@H]1O[C@H](C#Cc2cc3cc(C#C[C@H]4O[C@H](CO)[C@@H](O)[C@H](O)[C@@H]4O)sc3s2)[C@@H](O)[C@@H](O)[C@@H]1O] |
| 124 | 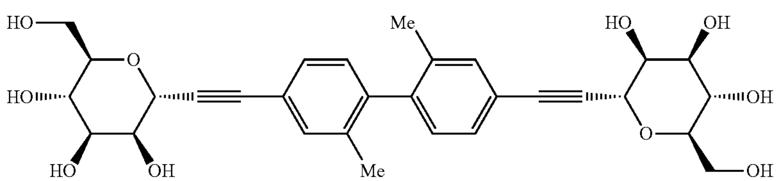 [SMILES: Cc1cc(C#C[C@H]2O[C@H](CO)[C@@H](O)[C@H](O)[C@@H]2O)ccc1-c1ccc(C#C[C@H]2O[C@H](CO)[C@@H](O)[C@H](O)[C@@H]2O)cc1C] |
| 125 | 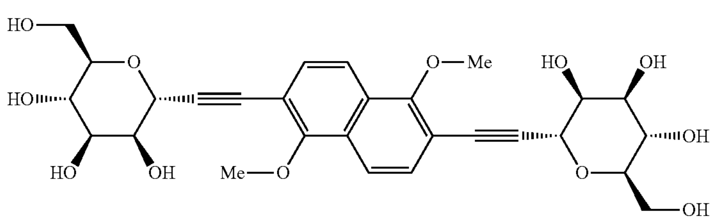 [SMILES: COc1c(C#C[C@H]2O[C@H](CO)[C@@H](O)[C@H](O)[C@@H]2O)ccc2c(OC)c(C#C[C@H]3O[C@H](CO)[C@@H](O)[C@H](O)[C@@H]3O)ccc12] |
| 126 | 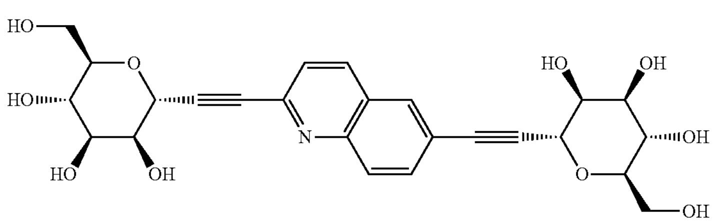 [SMILES: OC[C@H]1O[C@H](C#Cc2ccc3nc(C#C[C@H]4O[C@H](CO)[C@@H](O)[C@H](O)[C@@H]4O)ccc3c2)[C@@H](O)[C@@H](O)[C@@H]1O] |

| # | Structure |
|---|---|
| 128 | 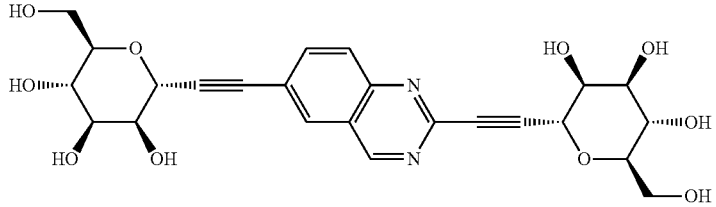 [SMILES: OC[C@H]1O[C@H](C#Cc2ccc3nc(C#C[C@H]4O[C@H](CO)[C@@H](O)[C@H](O)[C@@H]4O)ncc3c2)[C@@H](O)[C@@H](O)[C@@H]1O] |
| 129 | 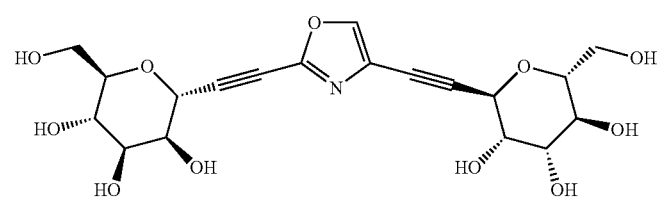 [SMILES: OC[C@H]1O[C@H](C#Cc2coc(C#C[C@H]3O[C@H](CO)[C@@H](O)[C@H](O)[C@@H]3O)n2)[C@@H](O)[C@@H](O)[C@@H]1O] |
| 130 | 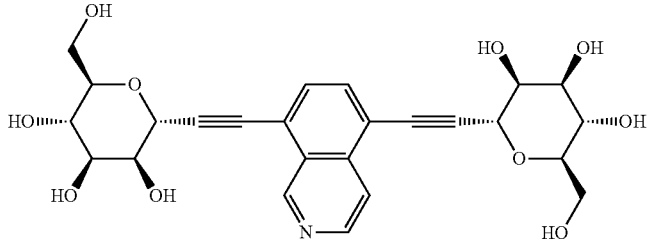 [SMILES: OC[C@H]1O[C@H](C#Cc2ccc(C#C[C@H]3O[C@H](CO)[C@@H](O)[C@H](O)[C@@H]3O)c3cnccc23)[C@@H](O)[C@@H](O)[C@@H]1O] |
| 131 | 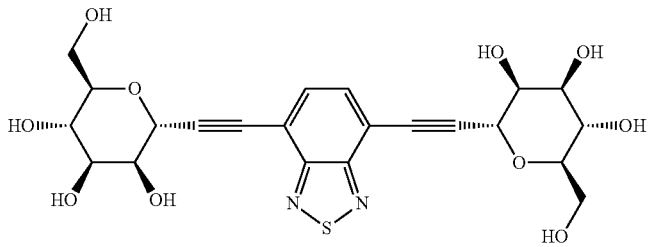 [SMILES: OC[C@H]1O[C@H](C#Cc2ccc(C#C[C@H]3O[C@H](CO)[C@@H](O)[C@H](O)[C@@H]3O)c3nsnc23)[C@@H](O)[C@@H](O)[C@@H]1O] |
| 132 | 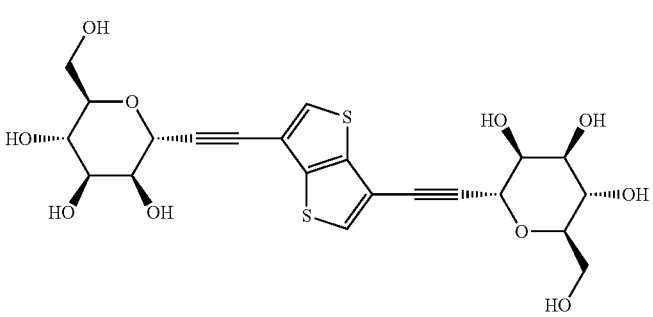 [SMILES: OC[C@H]1O[C@H](C#Cc2csc3c(C#C[C@H]4O[C@H](CO)[C@@H](O)[C@H](O)[C@@H]4O)csc23)[C@@H](O)[C@@H](O)[C@@H]1O] |
| 133 | 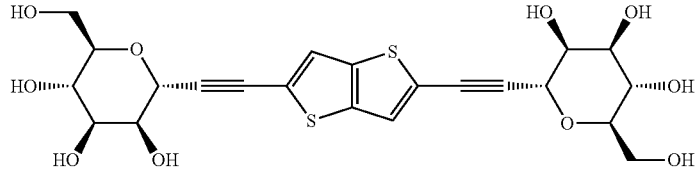 [SMILES: OC[C@H]1O[C@H](C#Cc2cc3sc(C#C[C@H]4O[C@H](CO)[C@@H](O)[C@H](O)[C@@H]4O)cc3s2)[C@@H](O)[C@@H](O)[C@@H]1O] |
| 134 | 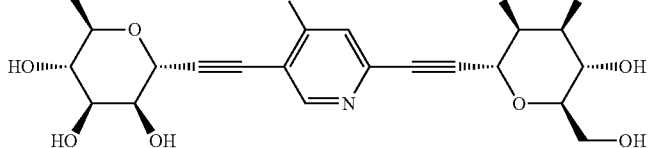 |

| # | Structure |
|---|-----------|
| 135 | 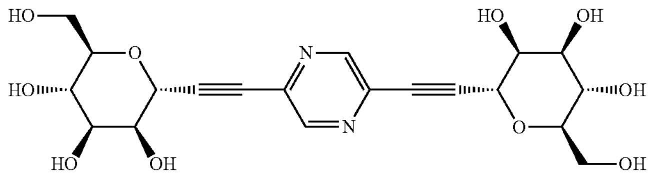 [SMILES: OC[C@H]1O[C@H](C#Cc2cnc(C#C[C@H]3O[C@H](CO)[C@@H](O)[C@H](O)[C@@H]3O)cn2)[C@@H](O)[C@@H](O)[C@@H]1O] |
| 136 | 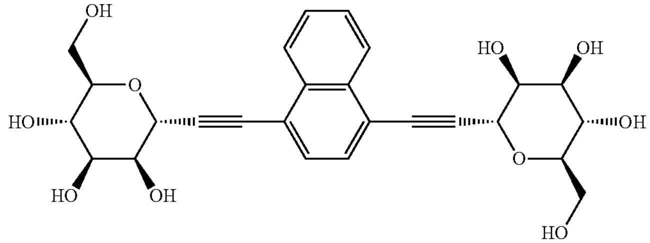 [SMILES: OC[C@H]1O[C@H](C#Cc2ccc(C#C[C@H]3O[C@H](CO)[C@@H](O)[C@H](O)[C@@H]3O)c3ccccc23)[C@@H](O)[C@@H](O)[C@@H]1O] |
| 137 | 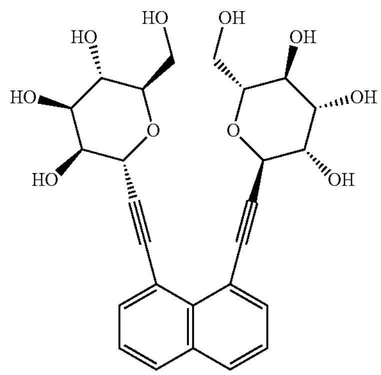 [SMILES: OC[C@H]1O[C@H](C#Cc2cccc3cccc(C#C[C@H]4O[C@H](CO)[C@@H](O)[C@H](O)[C@@H]4O)c23)[C@@H](O)[C@@H](O)[C@@H]1O] |
| 138 | 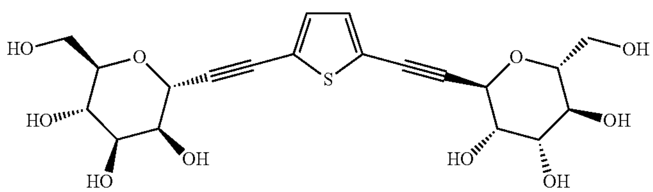 [SMILES: OC[C@H]1O[C@H](C#Cc2ccc(C#C[C@H]3O[C@H](CO)[C@@H](O)[C@H](O)[C@@H]3O)s2)[C@@H](O)[C@@H](O)[C@@H]1O] |
| 139 | 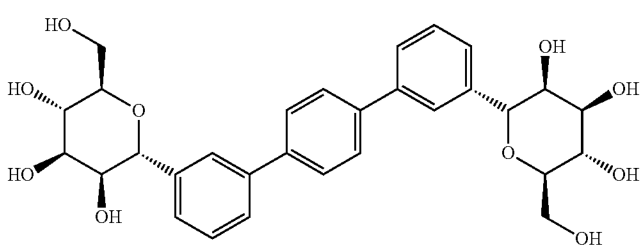 |
| 140 | 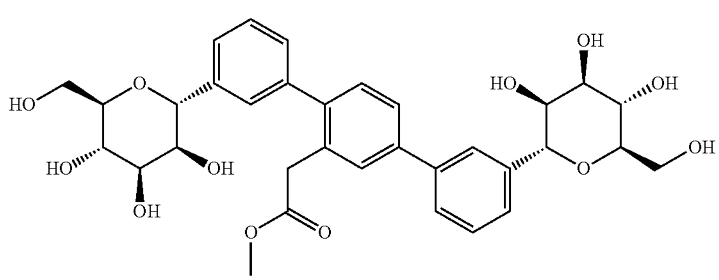 [SMILES: COC(=O)Cc1cc(-c2cccc([C@H]3O[C@H](CO)[C@@H](O)[C@H](O)[C@@H]3O)c2)ccc1-c1cccc([C@H]2O[C@H](CO)[C@@H](O)[C@H](O)[C@@H]2O)c1] |

-continued

| # | Structure |
|---|---|
| 141 | 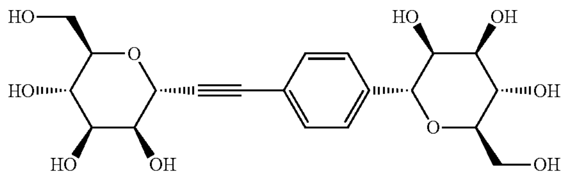 [SMILES: OC[C@H]1O[C@H](c2ccc(C#C[C@H]3O[C@H](CO)[C@@H](O)[C@H](O)[C@@H]3O)cc2)[C@@H](O)[C@@H](O)[C@@H]1O] |
| 142 | 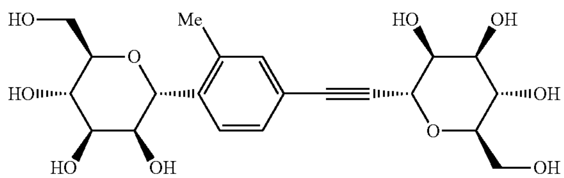 [SMILES: Cc1cc(C#C[C@H]2O[C@H](CO)[C@@H](O)[C@H](O)[C@@H]2O)ccc1[C@H]1O[C@H](CO)[C@@H](O)[C@H](O)[C@@H]1O] |
| 143 | 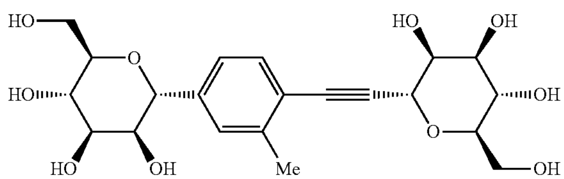 [SMILES: Cc1cc([C@H]2O[C@H](CO)[C@@H](O)[C@H](O)[C@@H]2O)ccc1C#C[C@H]1O[C@H](CO)[C@@H](O)[C@H](O)[C@@H]1O] |
| 144 | 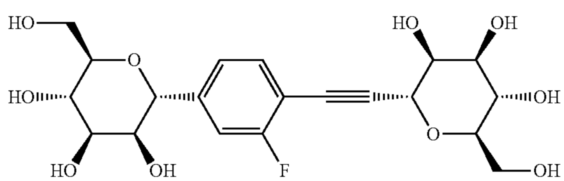 [SMILES: OC[C@H]1O[C@H](c2ccc(C#C[C@H]3O[C@H](CO)[C@@H](O)[C@H](O)[C@@H]3O)c(F)c2)[C@@H](O)[C@@H](O)[C@@H]1O] |
| 145 | 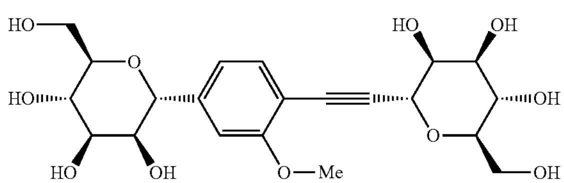 [SMILES: COc1cc([C@H]2O[C@H](CO)[C@@H](O)[C@H](O)[C@@H]2O)ccc1C#C[C@H]1O[C@H](CO)[C@@H](O)[C@H](O)[C@@H]1O] |
| 146 | 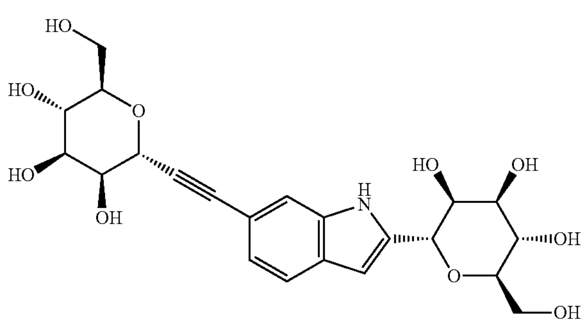 [SMILES: OC[C@H]1O[C@H](c2cc3ccc(C#C[C@H]4O[C@H](CO)[C@@H](O)[C@H](O)[C@@H]4O)cc3[nH]2)[C@@H](O)[C@@H](O)[C@@H]1O] |
| 147 | 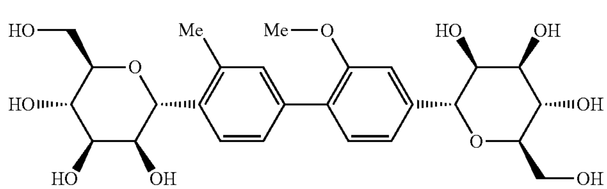 [SMILES: COc1cc([C@H]2O[C@H](CO)[C@@H](O)[C@H](O)[C@@H]2O)ccc1-c1ccc([C@H]2O[C@H](CO)[C@@H](O)[C@H](O)[C@@H]2O)c(C)c1] |

-continued

| # | Structure |
|---|---|
| 148 | 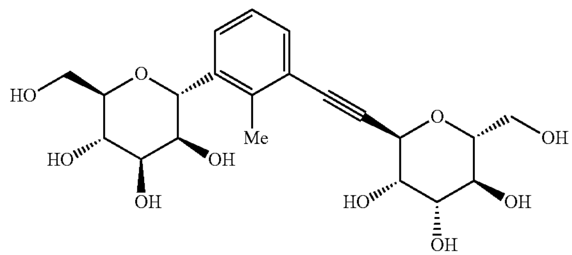 [SMILES: Cc1c(C#C[C@H]2O[C@H](CO)[C@@H](O)[C@H](O)[C@@H]2O)cccc1[C@H]1O[C@H](CO)[C@@H](O)[C@H](O)[C@@H]1O] |
| 149 | 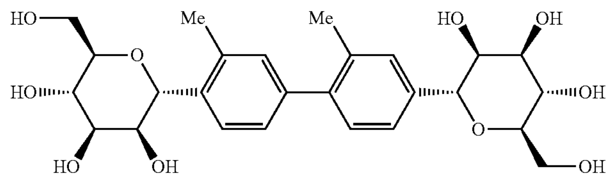 [SMILES: Cc1cc([C@H]2O[C@H](CO)[C@@H](O)[C@H](O)[C@@H]2O)ccc1-c1ccc([C@H]2O[C@H](CO)[C@@H](O)[C@H](O)[C@@H]2O)c(C)c1] |
| 150 | 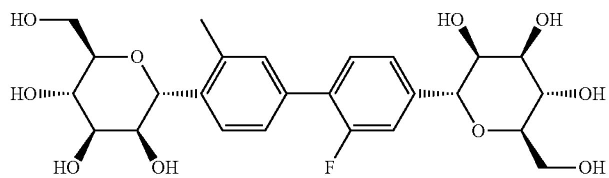 [SMILES: Cc1cc(-c2ccc([C@H]3O[C@H](CO)[C@@H](O)[C@H](O)[C@@H]3O)cc2F)ccc1[C@H]1O[C@H](CO)[C@@H](O)[C@H](O)[C@@H]1O] |
| 151 | 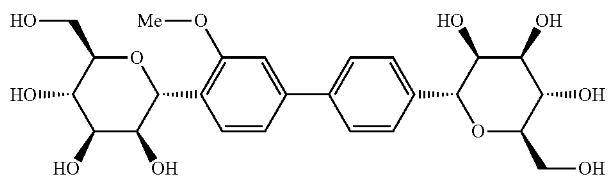 [SMILES: COc1cc(-c2ccc([C@H]3O[C@H](CO)[C@@H](O)[C@H](O)[C@@H]3O)cc2)ccc1[C@H]1O[C@H](CO)[C@@H](O)[C@H](O)[C@@H]1O] |
| 152 | 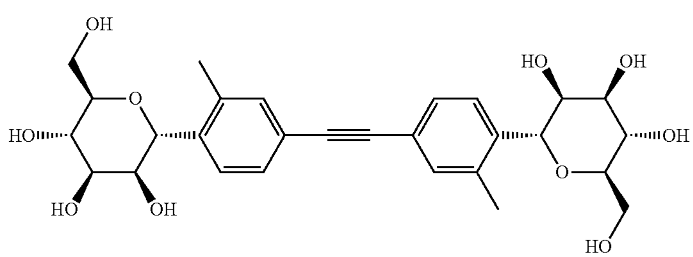 [SMILES: Cc1cc(C#Cc2ccc([C@H]3O[C@H](CO)[C@@H](O)[C@H](O)[C@@H]3O)c(C)c2)ccc1[C@H]1O[C@H](CO)[C@@H](O)[C@H](O)[C@@H]1O] |
| 153 | 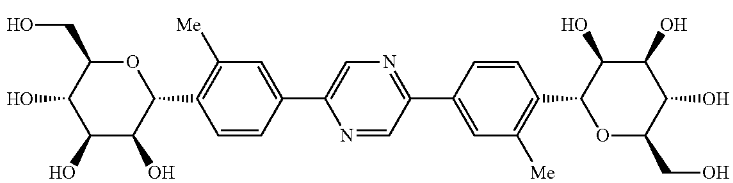 [SMILES: Cc1cc(-c2cnc(-c3ccc([C@H]4O[C@H](CO)[C@@H](O)[C@H](O)[C@@H]4O)c(C)c3)cn2)ccc1[C@H]1O[C@H](CO)[C@@H](O)[C@H](O)[C@@H]1O] |
| 154 | 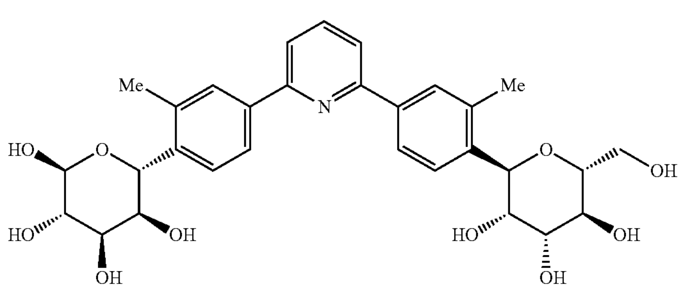 [SMILES: Cc1cc(-c2cccc(-c3ccc([C@H]4O[C@H](CO)[C@@H](O)[C@H](O)[C@@H]4O)c(C)c3)n2)ccc1[C@H]1O[C@H](O)[C@@H](O)[C@H](O)[C@@H]1O] |

| # | Structure |
|---|---|
| 155 | 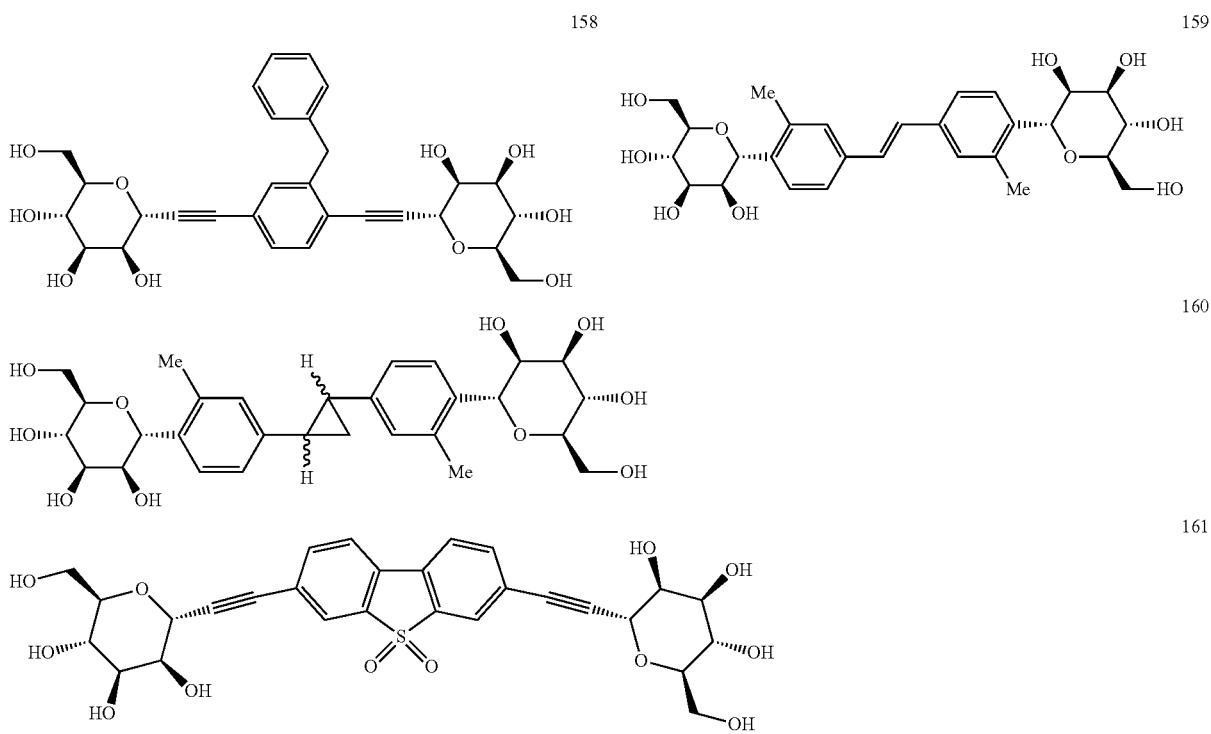 |
| 156 | 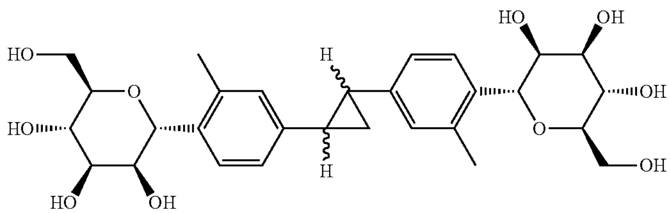 [SMILES: Cc1cc(C2CC2c2ccc([C@H]3O[C@H](CO)[C@@H](O)[C@H](O)[C@@H]3O)c(C)c2)ccc1[C@H]1O[C@H](CO)[C@@H](O)[C@H](O)[C@@H]1O] |
| 157 | 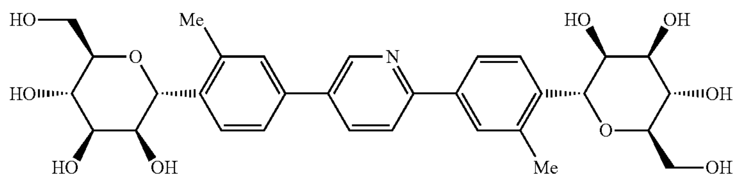 [SMILES: Cc1cc(-c2ccc(-c3ccc([C@H]4O[C@H](CO)[C@@H](O)[C@H](O)[C@@H]4O)c(C)c3)nc2)ccc1[C@H]1O[C@H](CO)[C@@H](O)[C@H](O)[C@@H]1O] |
or a pharmaceutically acceptable salt thereof.
Another embodiment provides a compound represented by a structural formula selected from the group consisting of:

-continued
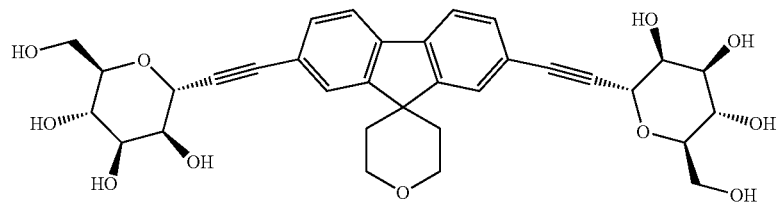
162
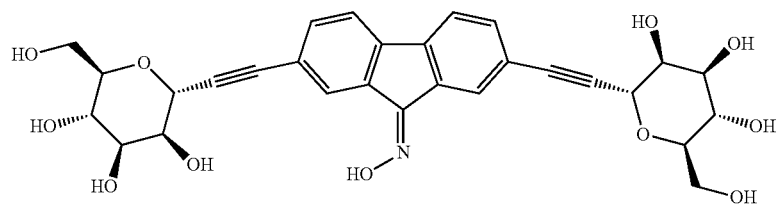
163
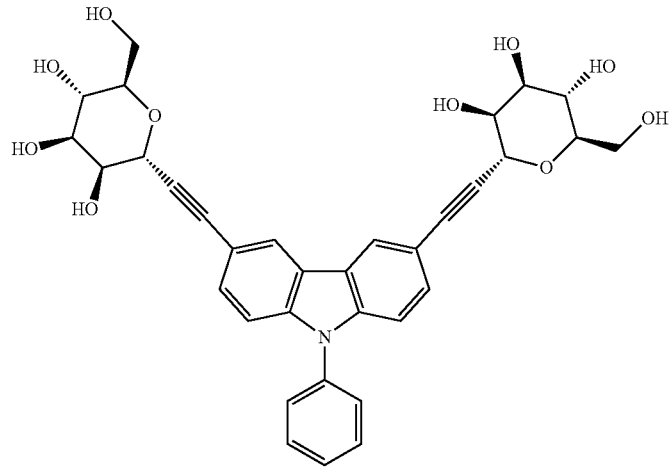
164
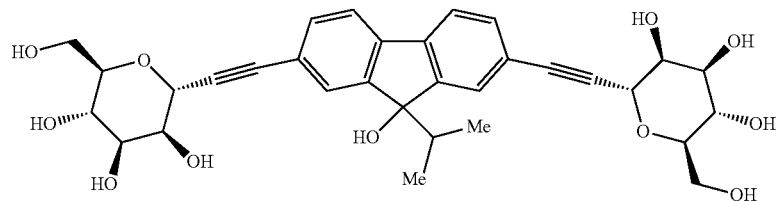
165
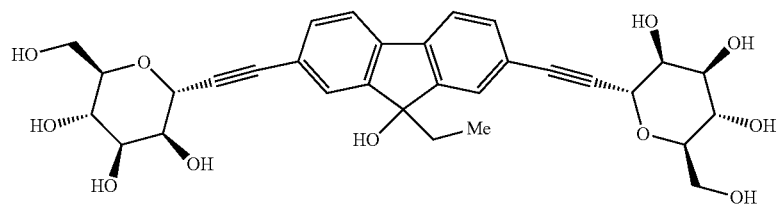
166
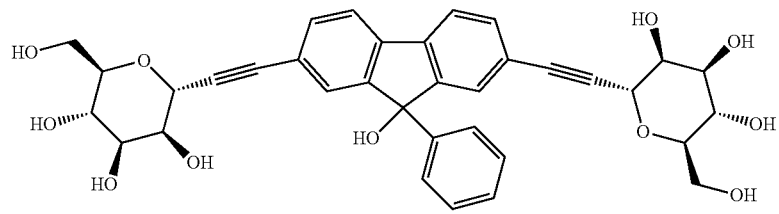
167

-continued
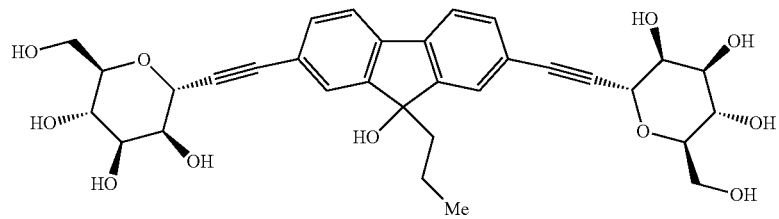
168
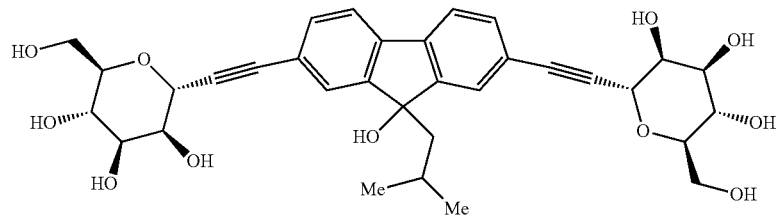
169
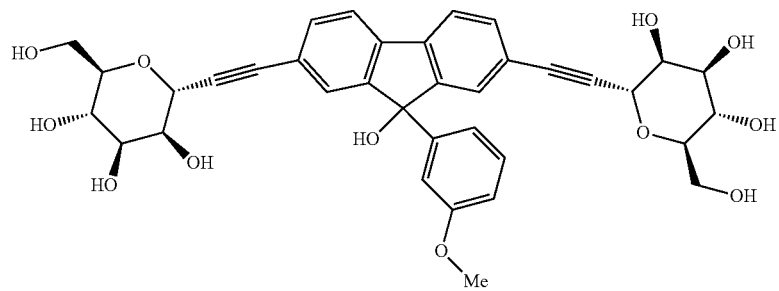
170
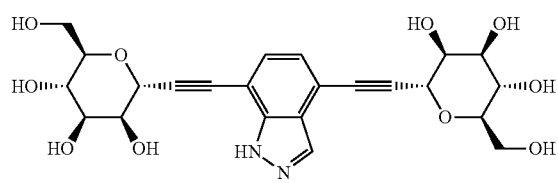
171
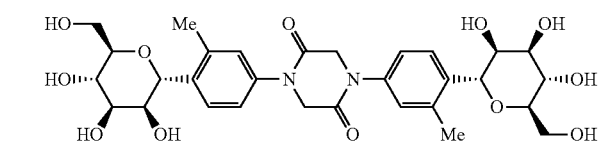
172
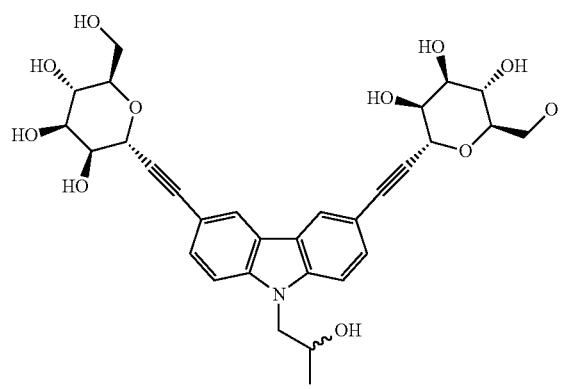
173
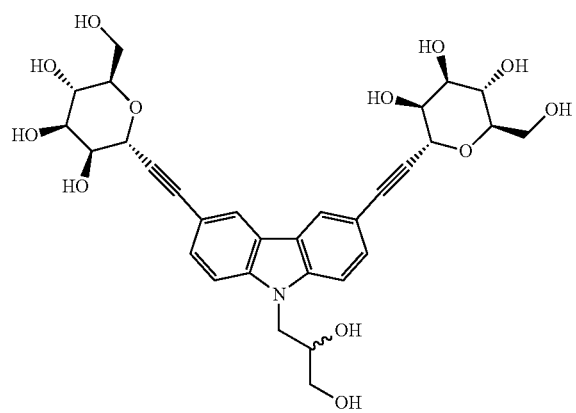
174
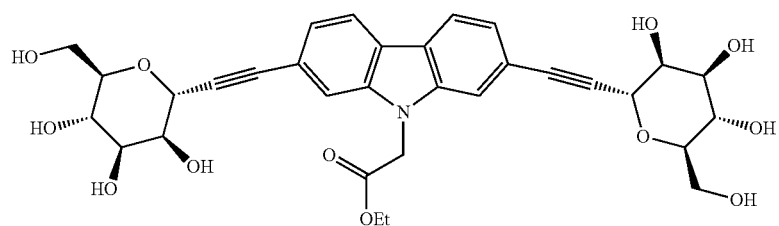
175

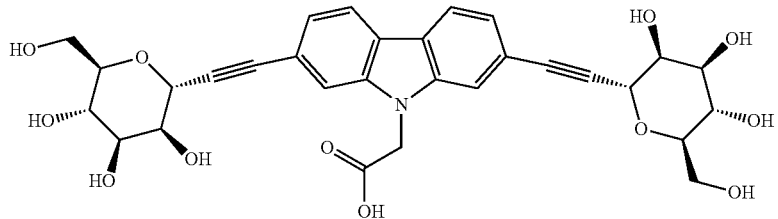
176
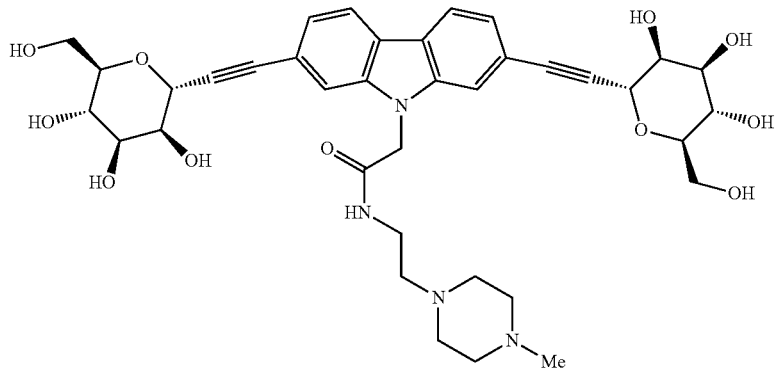
177
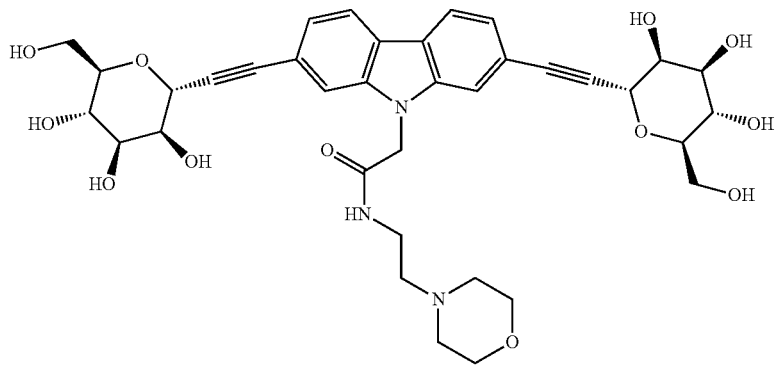
178
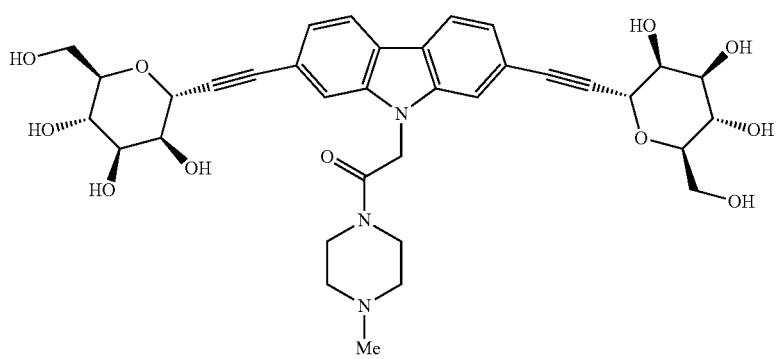
179
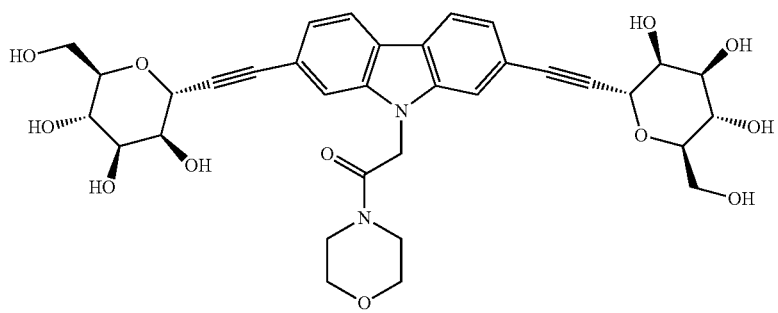
180

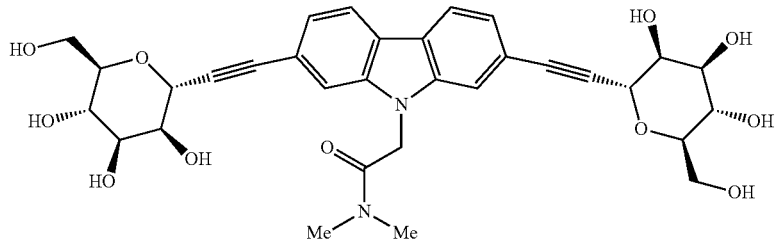
181
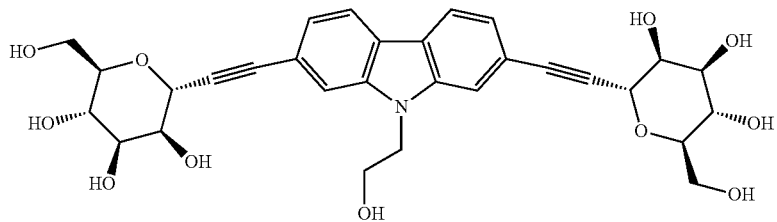
182
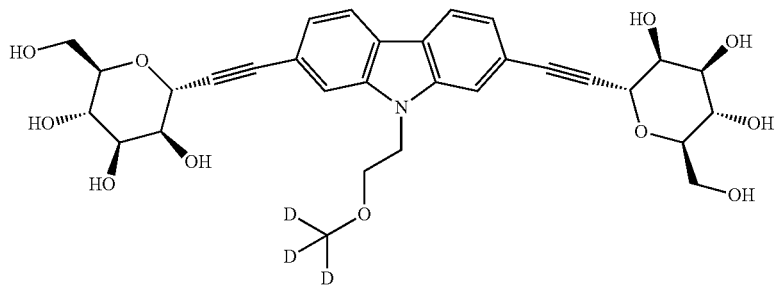
183
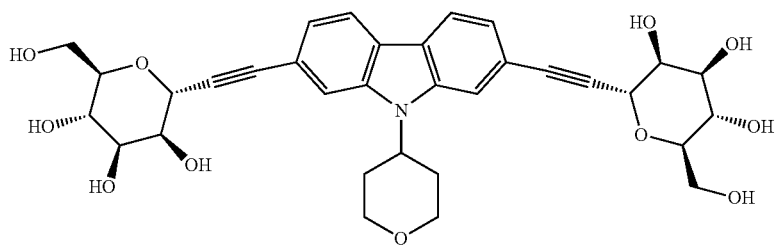
184
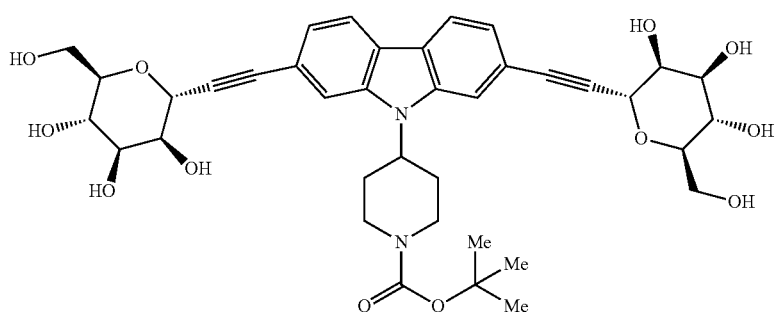
185
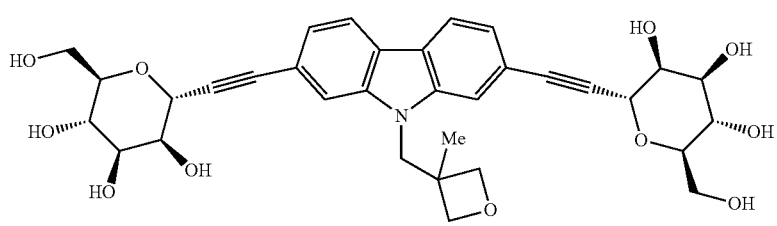
186

-continued
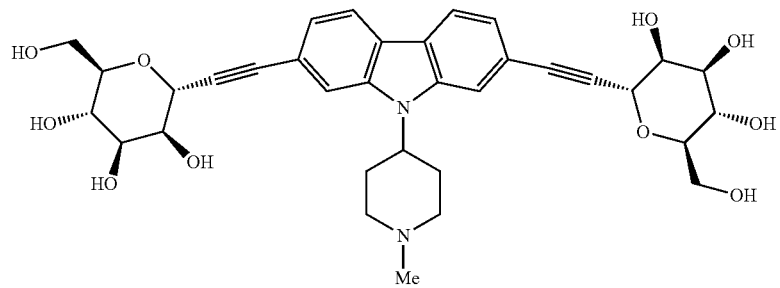 187
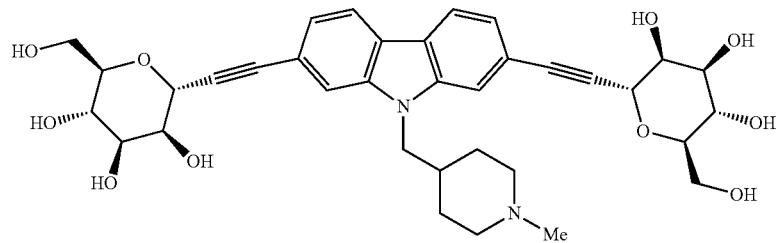 188
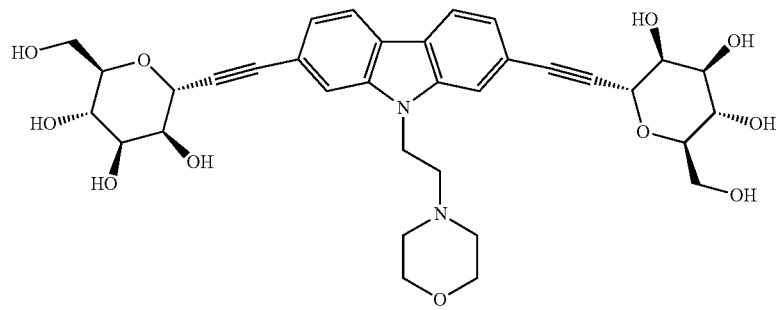 189
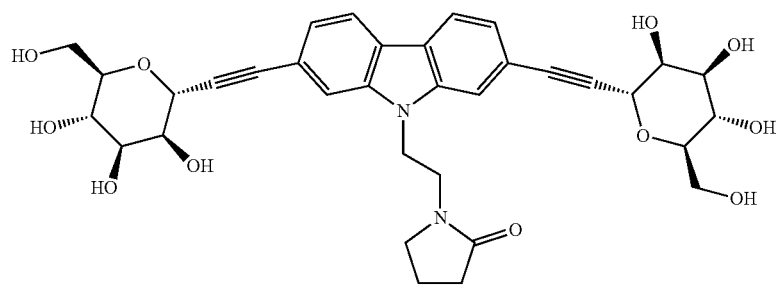 190
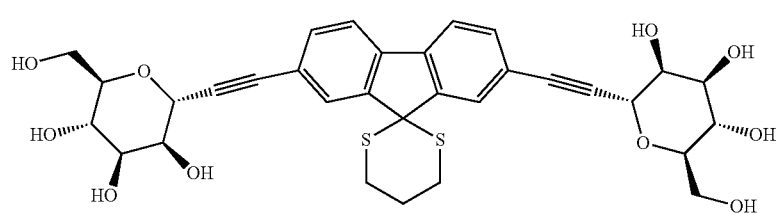 191
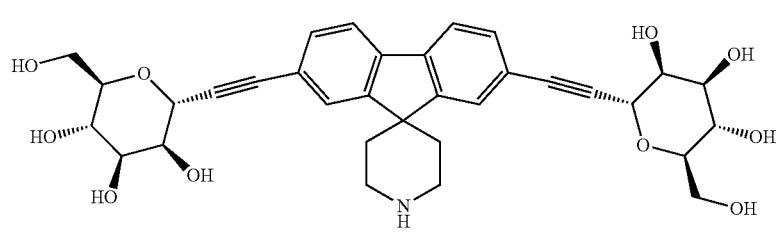 192

-continued
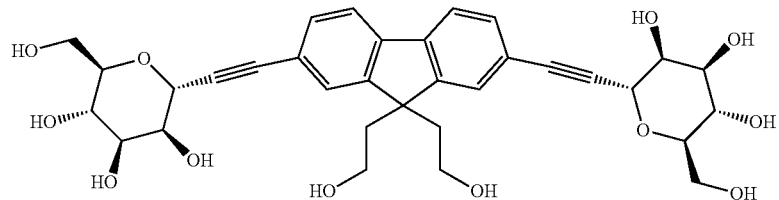 193
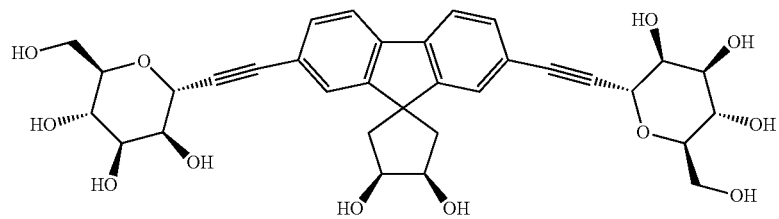 194
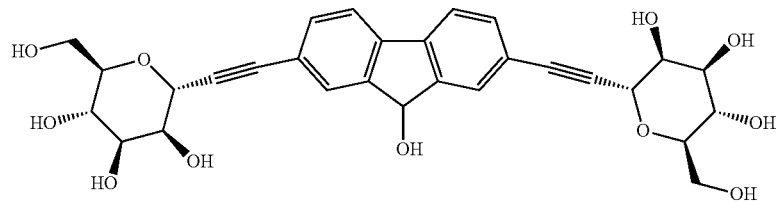 195
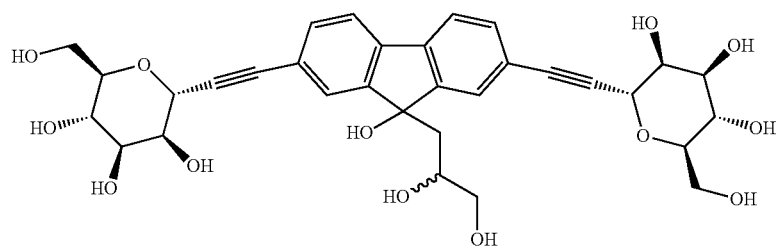 196
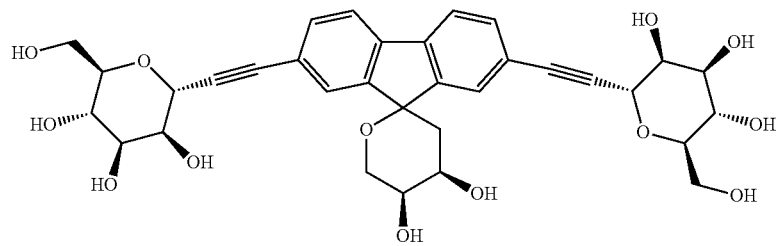 197
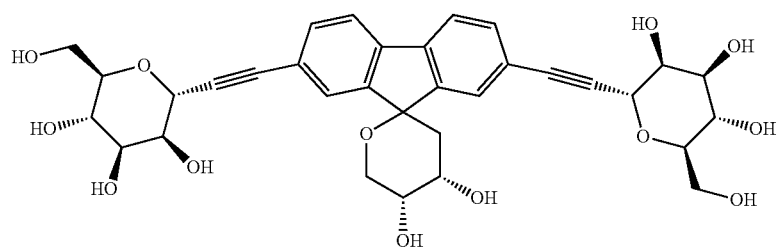

198
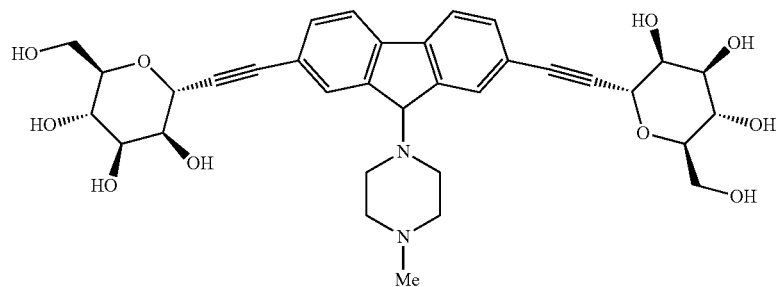
199
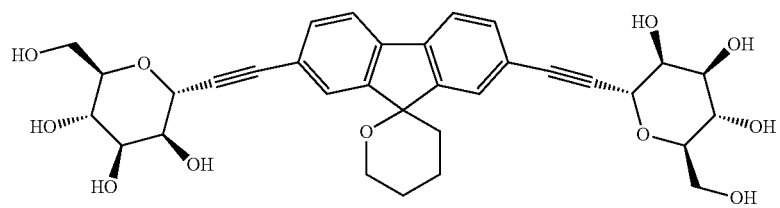
200
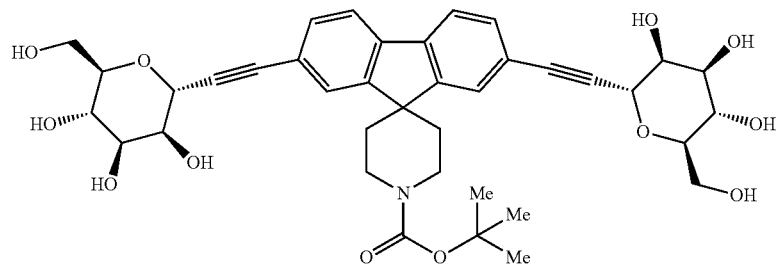
201
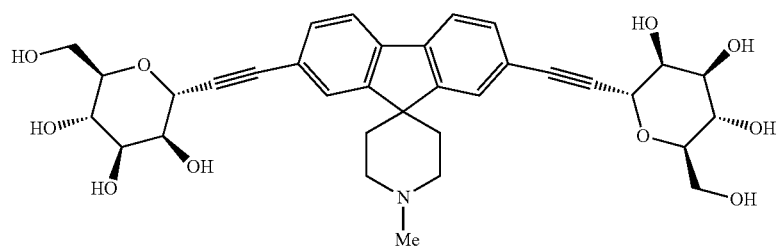
202
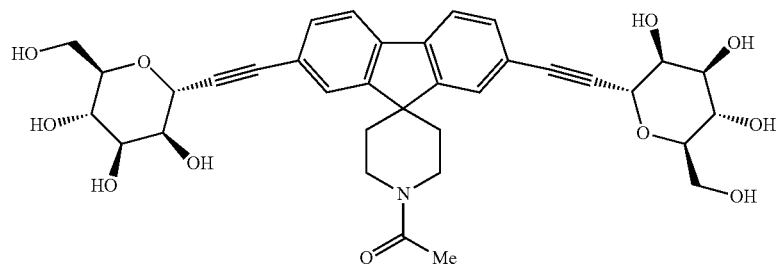
203
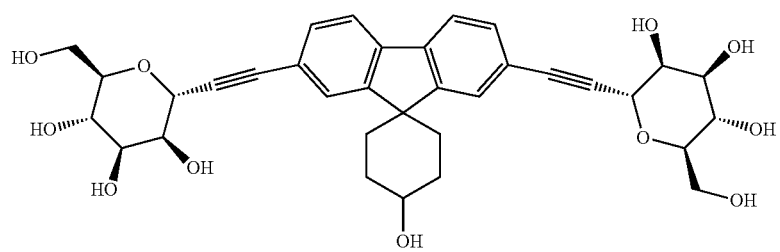

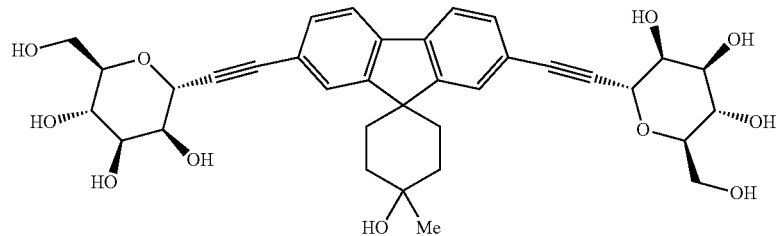
204
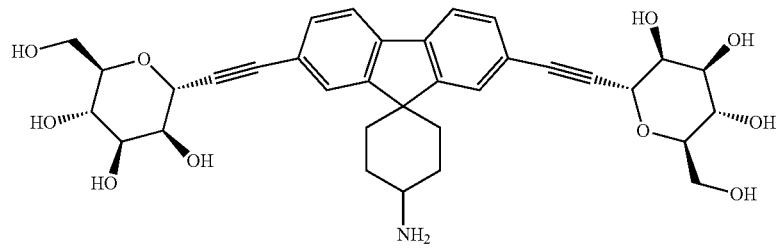
205
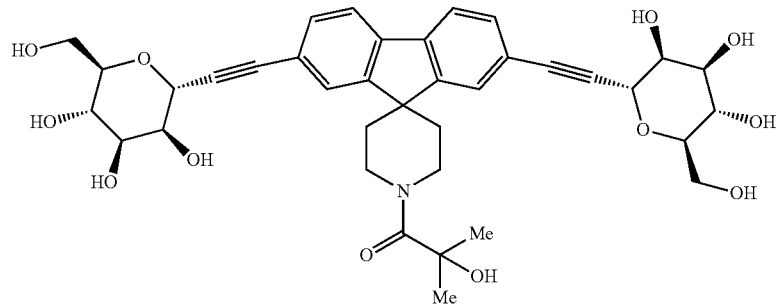
206
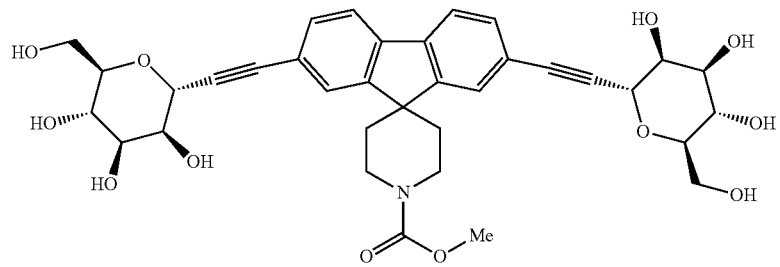
207
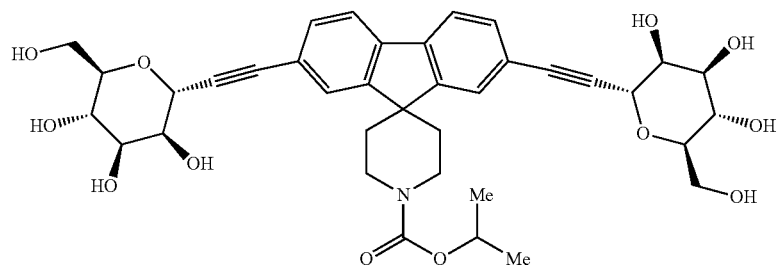
208
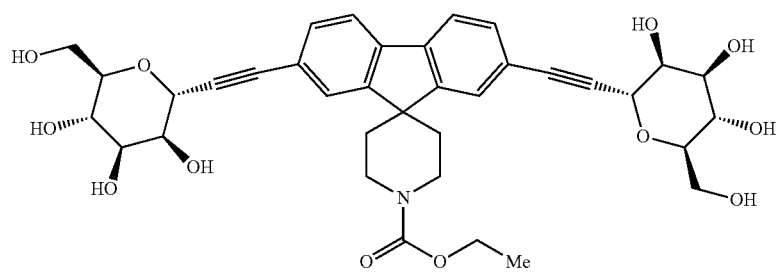
209

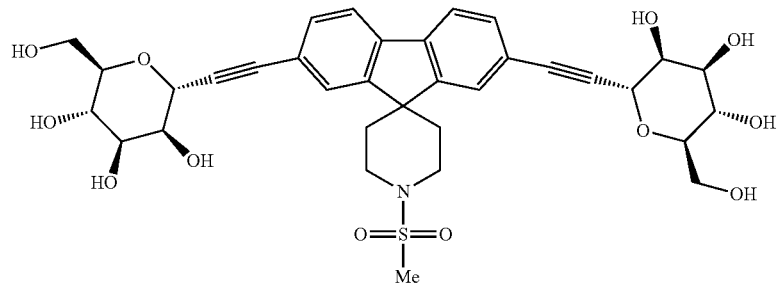
210
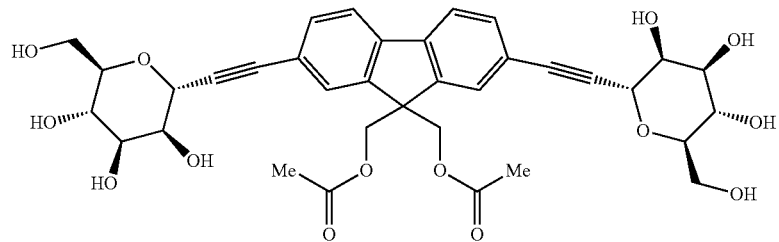
211
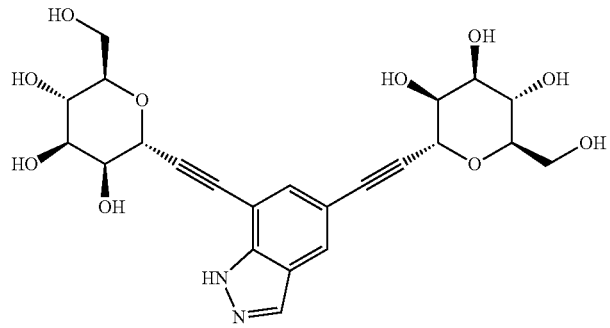
212
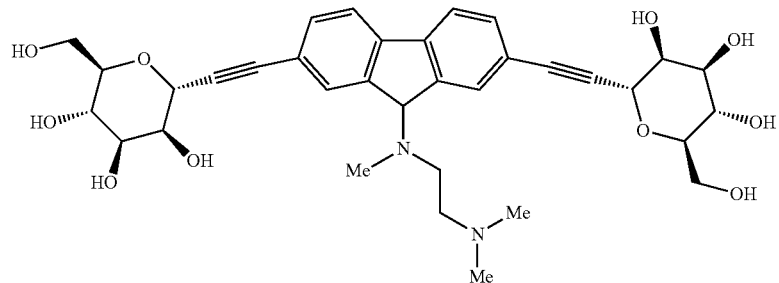
213
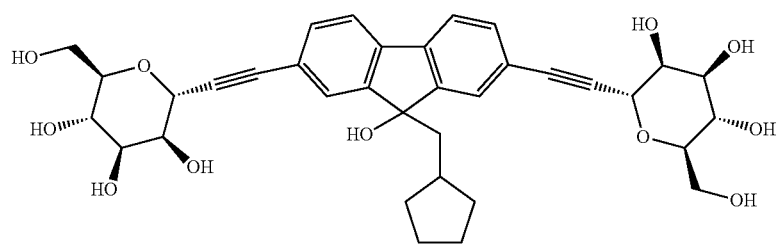
214

-continued
| | |
|---|---|
| 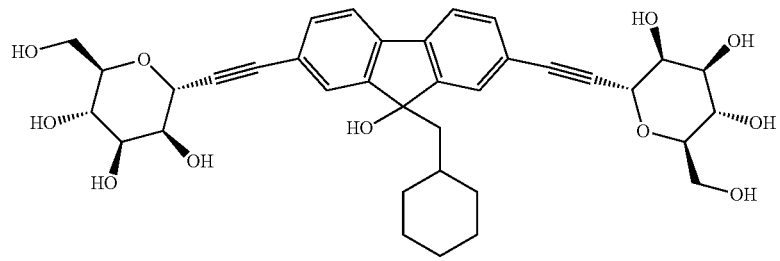 | 215 |
| 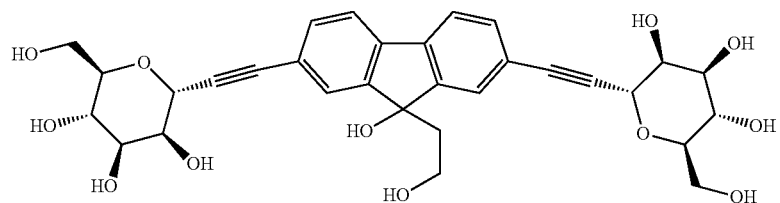 | 216 |
| 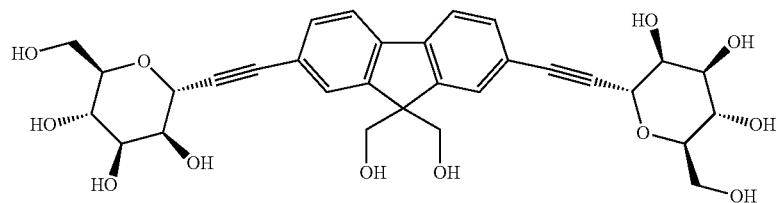 | 217 |
| 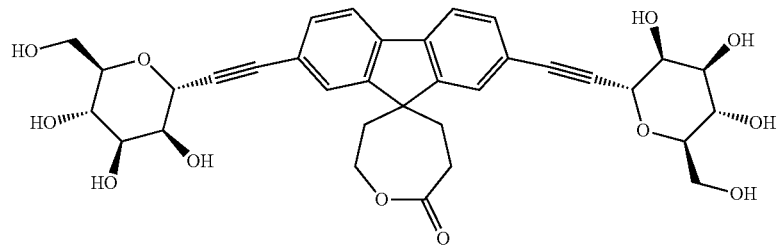 | 218 |
| 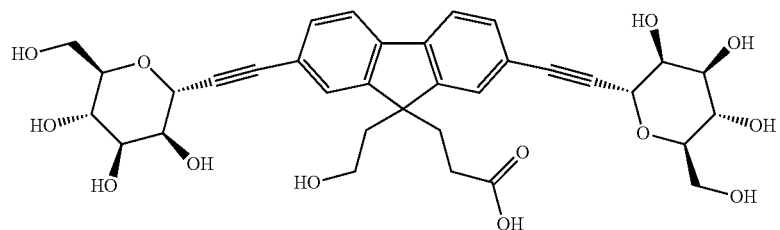 | 219 |
| 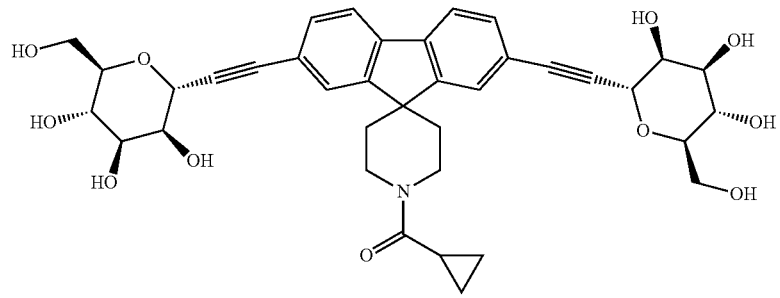 | 220 |

-continued
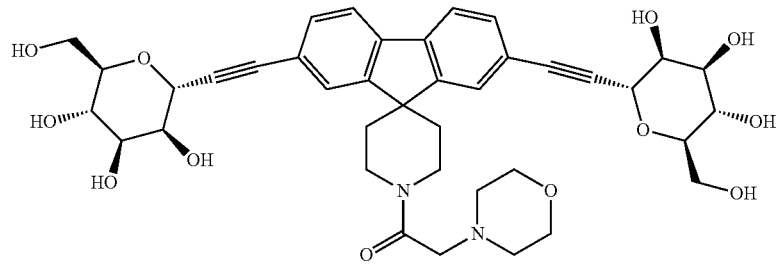 221
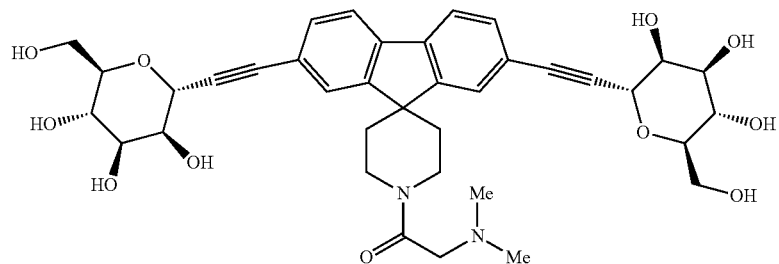 222
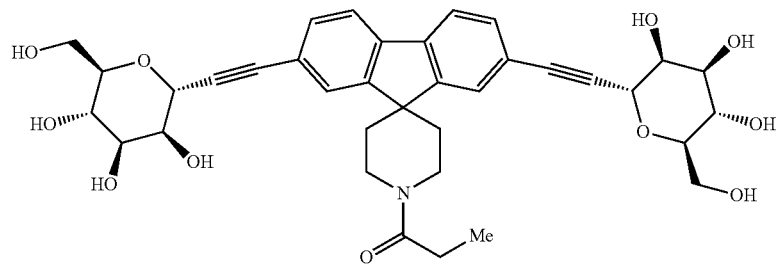 223
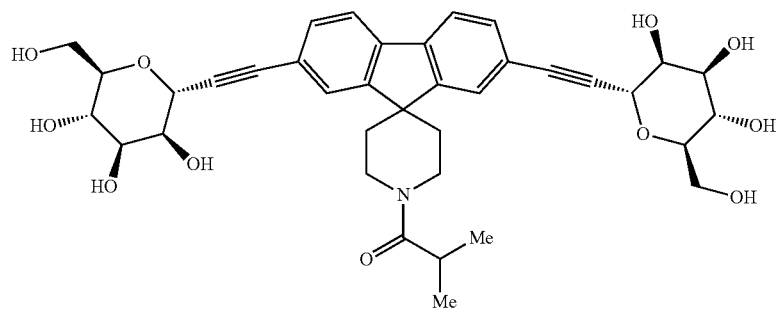 224
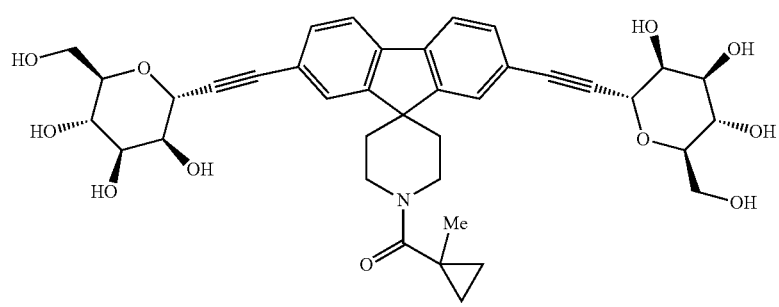 225

-continued
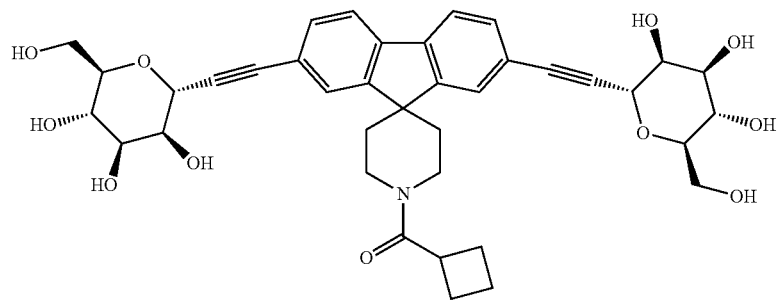
226
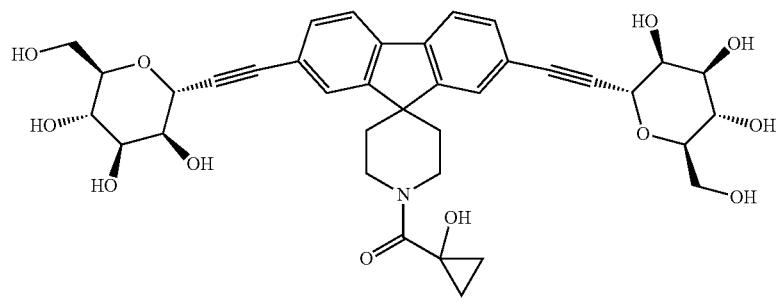
227
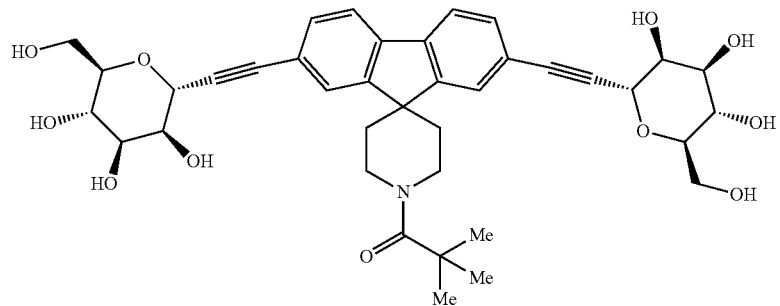
228
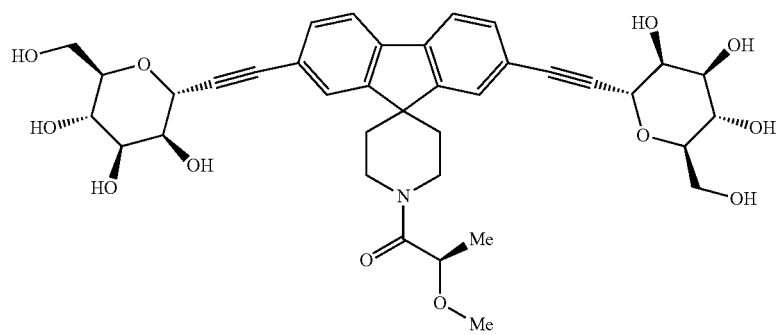
229
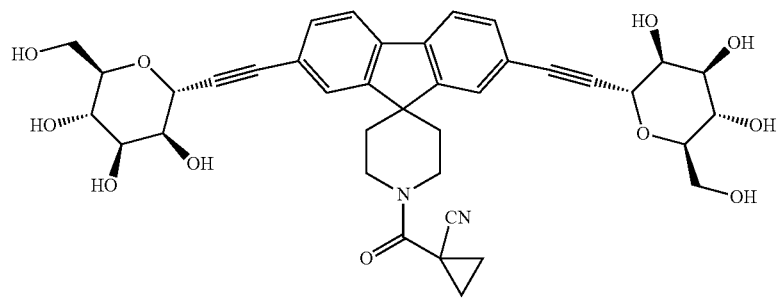
230

231
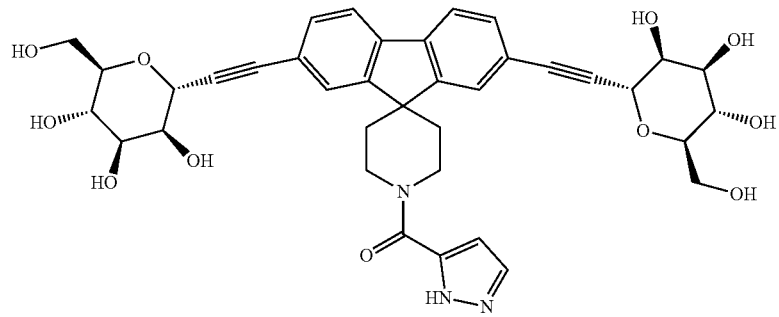
232
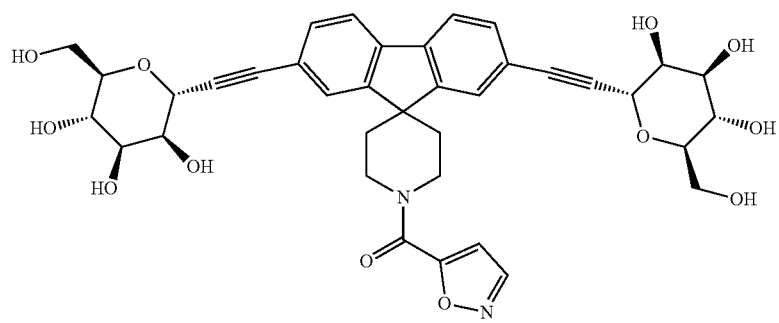
233
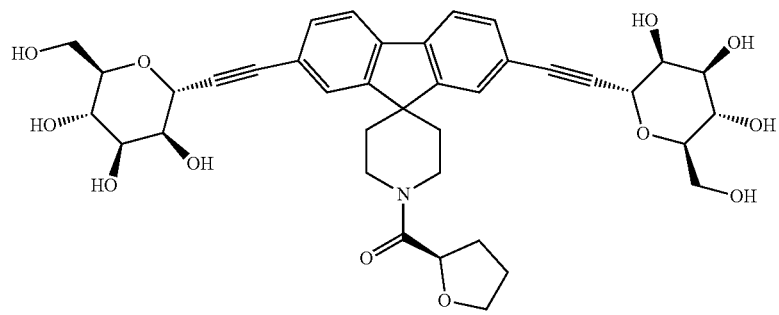
234
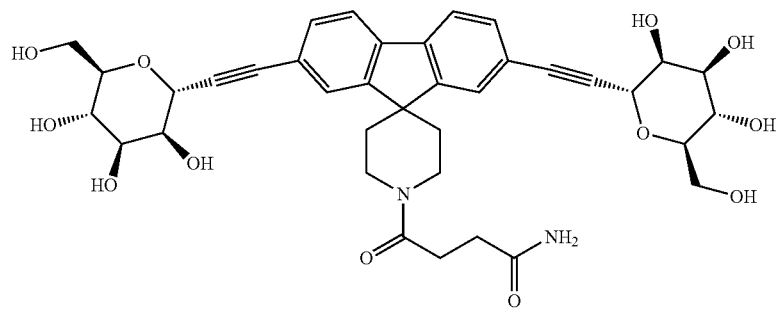
235
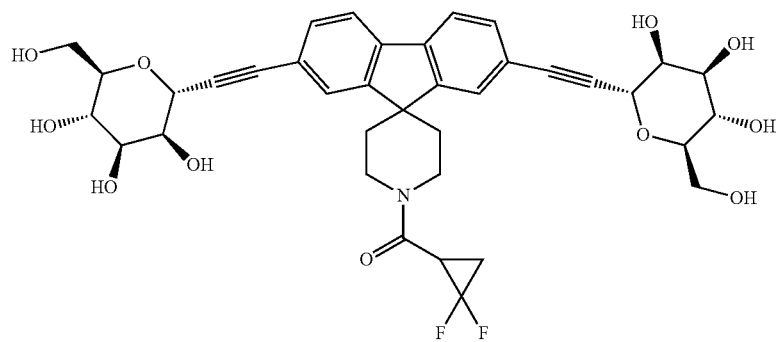

236
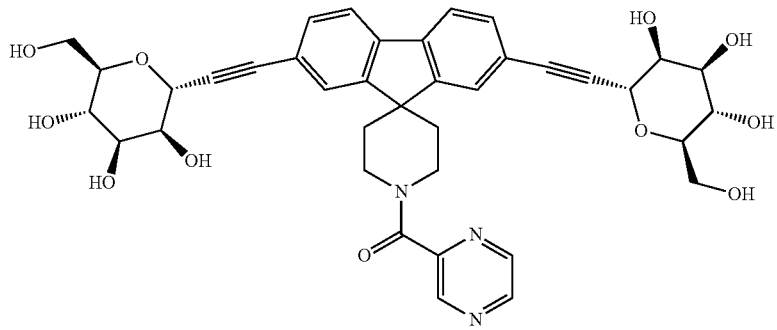
237
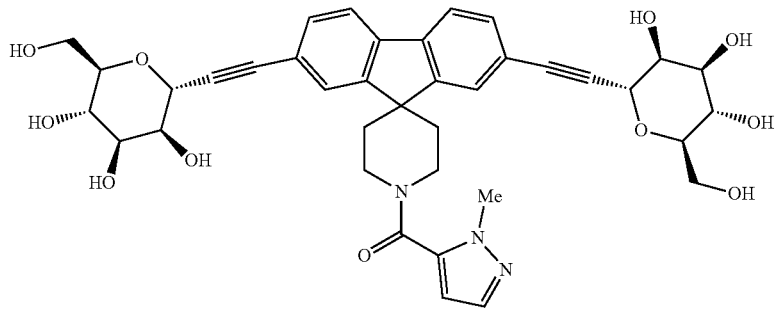
238
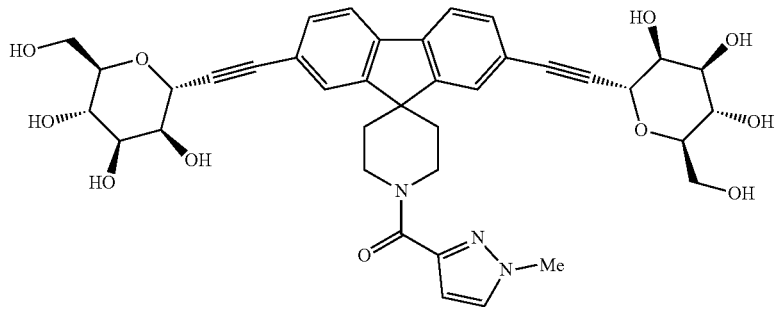
239
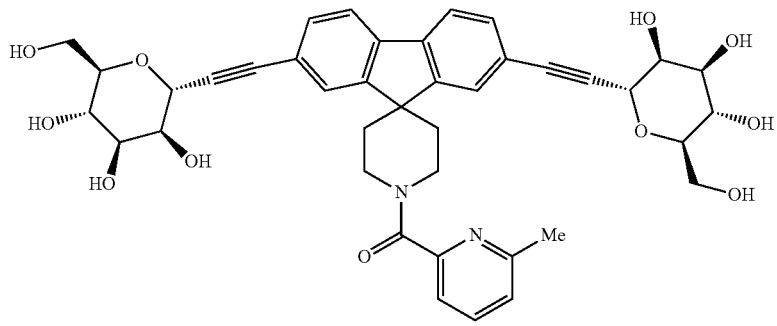
240
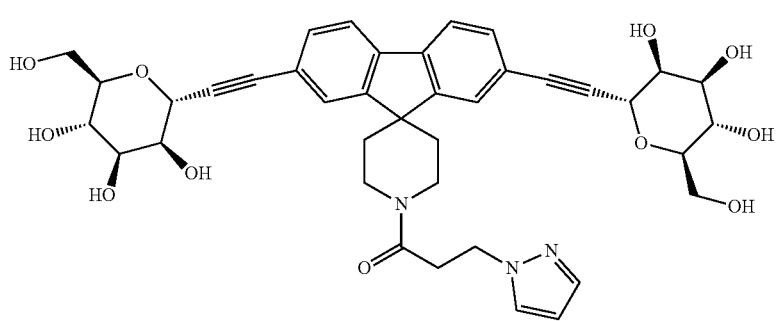

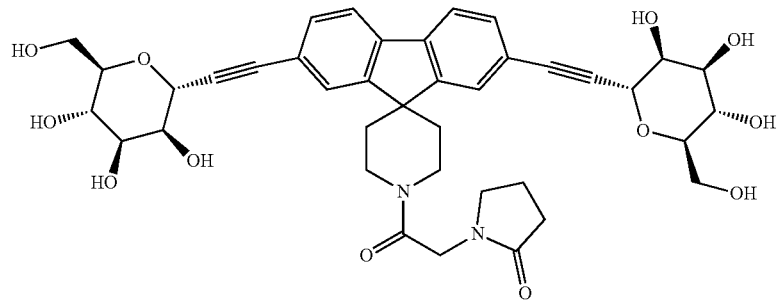
241
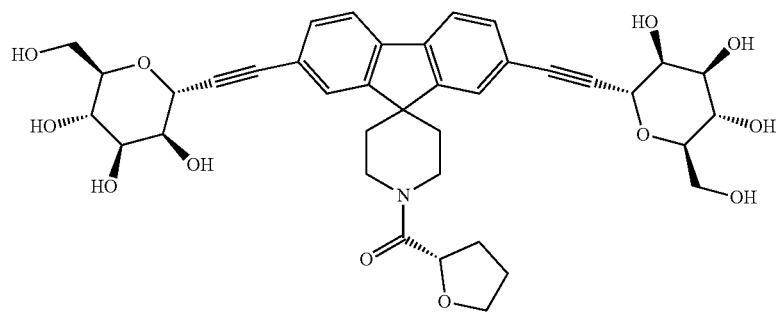
242
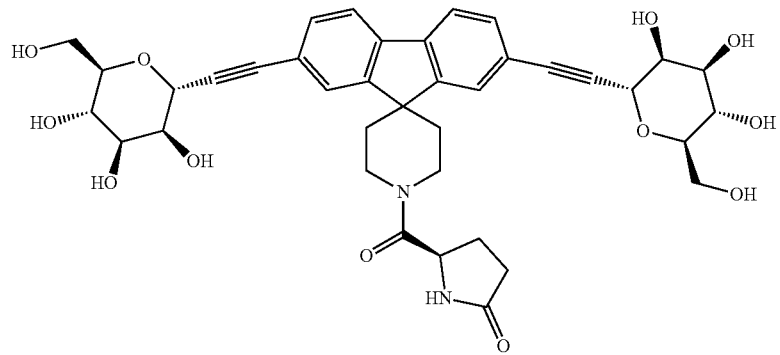
243
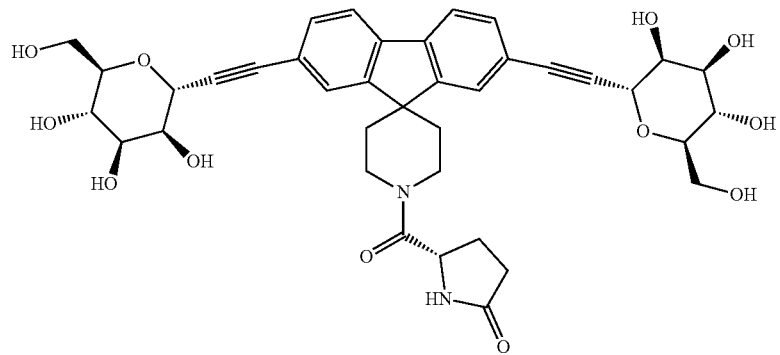
244

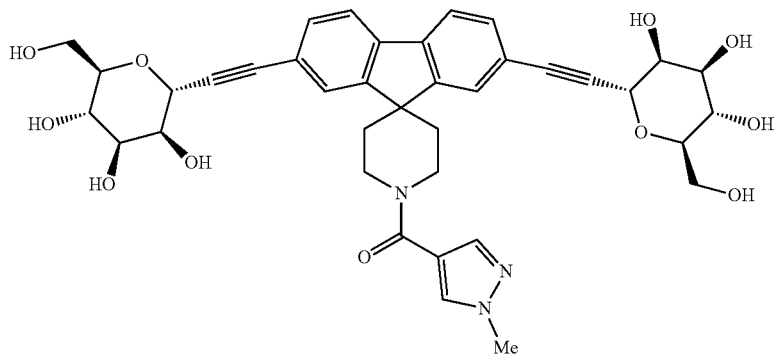
245
or a pharmaceutically acceptable salt thereof.
In some embodiments, the compound is compound 162:
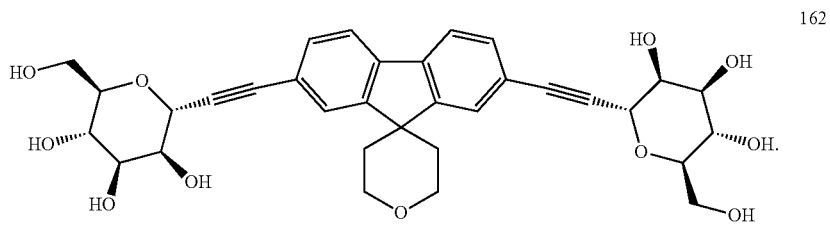 [SMILES: OC[C@H]1O[C@H](C#Cc2ccc3c(c2)C2(CCOCC2)c2cc(C#C[C@H]4O[C@H](CO)[C@@H](O)[C@H](O)[C@@H]4O)ccc2-3)[C@@H](O)[C@@H](O)[C@@H]1O]
162
In other embodiments, the compound is compound 202:
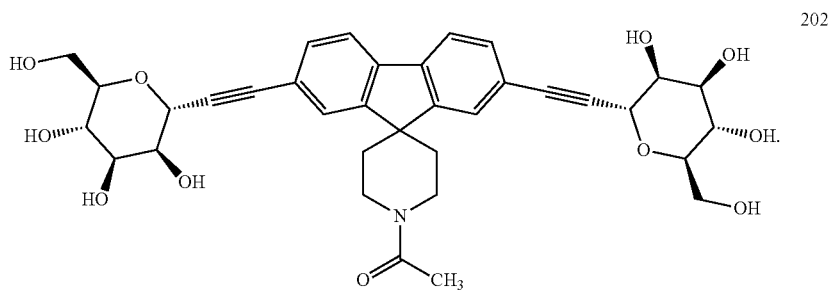 [SMILES: CC(=O)N1CCC2(CC1)c1cc(C#C[C@H]3O[C@H](CO)[C@@H](O)[C@H](O)[C@@H]3O)ccc1-c1ccc(C#C[C@H]3O[C@H](CO)[C@@H](O)[C@H](O)[C@@H]3O)cc12]
202
In other embodiments, the compound is compound 53:
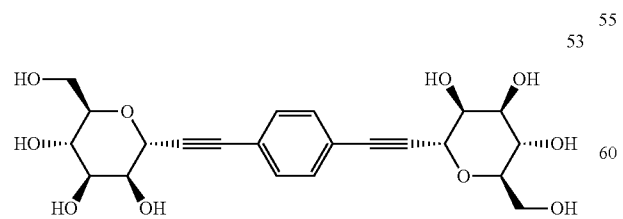
53
Another embodiment provides processes for preparing the compounds of this invention.

One embodiment provides a process for preparing a compound of formula

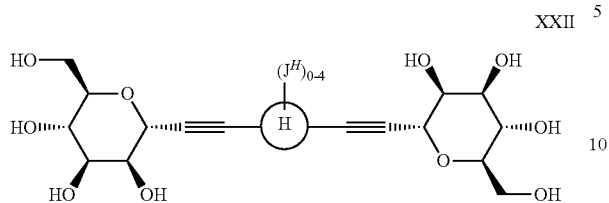
XXII wherein Ring H and $J^H$ are as defined herein; comprising reacting a compound of formula XX:

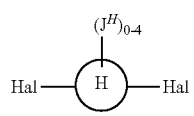
XX wherein Hal is a halogen, such as bromo or iodo; and $J^H$ is as defined herein; with Intermediate M:

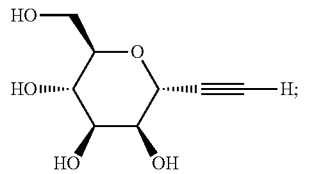
M under Sonogashira coupling conditions to form the compound of formula XXII.

Another embodiment provides a process for preparing a compound of formula

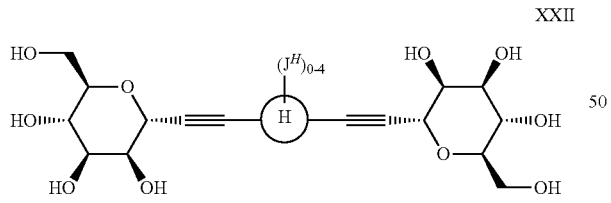
XXII wherein Ring H and $J^H$ are as defined herein; comprising
a) reacting a compound of formula XX:

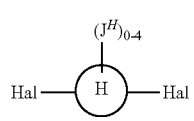
XX wherein Hal is a halogen, such as bromo or iodo; and $J^H$ is as defined herein; with Intermediate P:

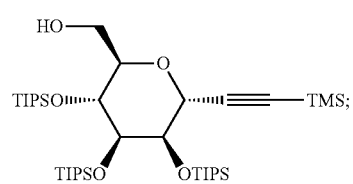
P under Sonogashira coupling conditions;

b) deprotecting Intermediate P under acidic conditions (such as TFA, THF, H₂O) or with TBAF to afford a compound of formula XXII.

Another embodiment provides a process of preparing a compound of formula IIXX comprising
a) reacting a compound of formula XXIII:

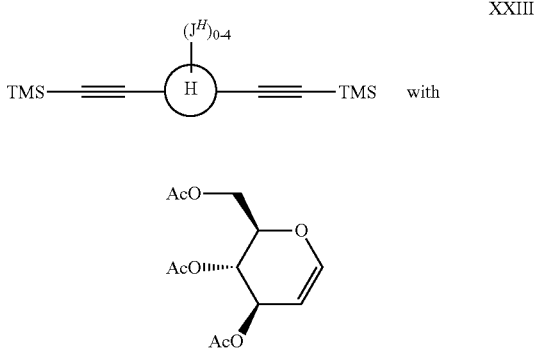
XXIII under Lewis acid catalyzed double Ferrier type alkynylation conditions to afford a compound of formula XXIV:

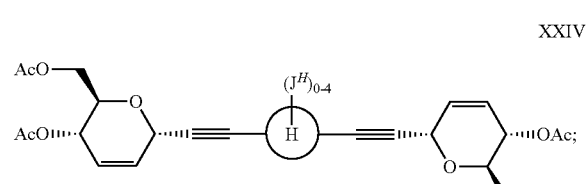
XXIV b) performing a stereospecific bis-dihydroxylation of compound XXIV followed by a saponification to form a compound of formula XXII.

In some embodiments, Ring H is unsubstituted phenyl and Hal is iodo.

Another embodiment provides a process for making compound 202:
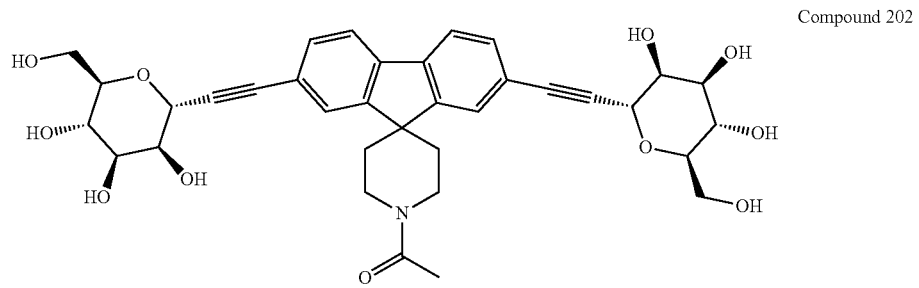 [SMILES: CC(=O)N1CCC2(CC1)c1cc(C#C[C@H]3O[C@H](CO)[C@@H](O)[C@H](O)[C@@H]3O)ccc1-c1ccc(C#C[C@H]3O[C@H](CO)[C@@H](O)[C@H](O)[C@@H]3O)cc12]
Compound 202
comprising reacting Intermediate M:
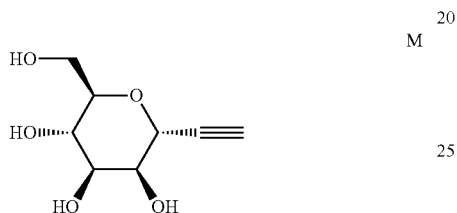
M
with Intermediate AG8:
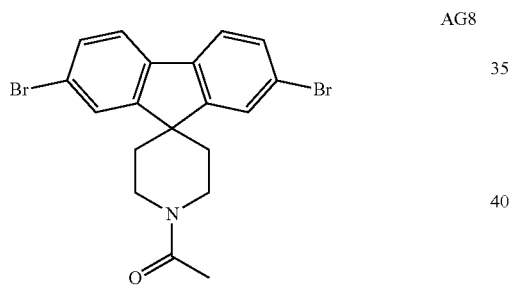
AG8
under Sonogashira coupling conditions to form Compound 202.
Another embodiment provides a process for preparing Intermediate AG8, comprising the steps of:
a) reacting
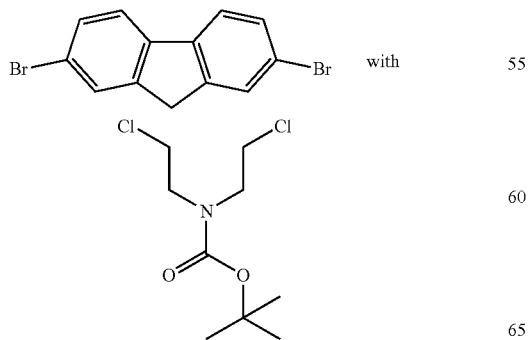
with in the presence of a suitable base, such as NaH, and a suitable solvent, such as THF; to form Intermediate AG5:

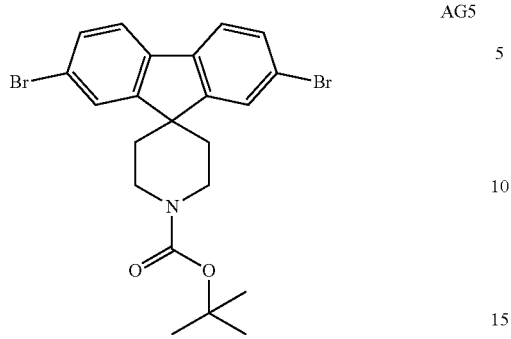

AG5 b) Reacting Intermediate AG5 under acidic conditions, such as HCl in dioxane, to form Intermediate AG4:

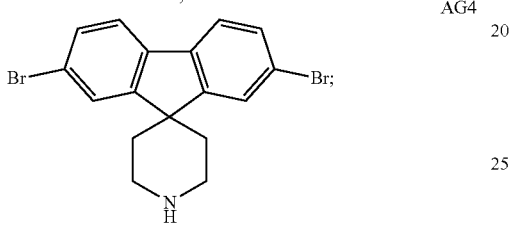

AG4 c) Reacting Intermediate AG4 with acetyl chloride, a suitable base (such as triethylamine), and a suitable solvent (such as DMF), to form Intermediate AG8.

Another embodiment provides a process for preparing Compound 162

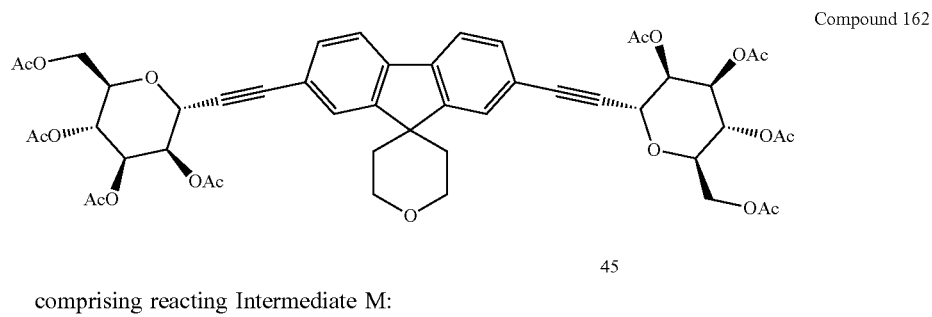

Compound 162 comprising reacting Intermediate M:

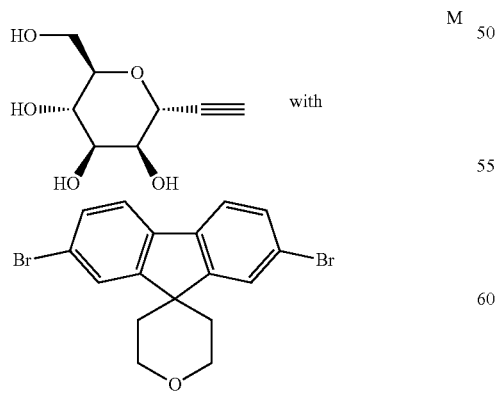

M with under Sonogashira coupling conditions to form Compound 162.

Another embodiment provides a process for purifying crude compound 162 formed by the Sonogashira coupling conditions described above comprising one or more of the following steps: acetylating Compound 162 under suitable acetylating reaction conditions to form a compound of formula 162AC:

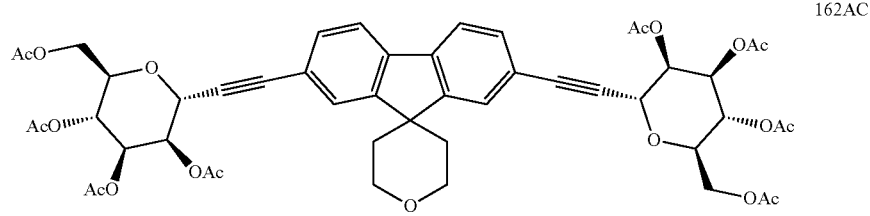 [SMILES: CC(=O)OC[C@H]1O[C@H](C#Cc2ccc3c(c2)C2(CCOCC2)c2cc(C#C[C@H]4O[C@H](COC(C)=O)[C@@H](OC(C)=O)[C@H](OC(C)=O)[C@@H]4OC(C)=O)ccc2-3)[C@@H](OC(C)=O)[C@@H](OC(C)=O)[C@@H]1OC(C)=O]

162AC

Comprising the steps of
a) purifying compound 162AC via known purification methods; and
b) reacting compound 162AC with suitable deprotection conditions to afford Compound 162. Examples of deprotection methods include, for example, column chromatography.

The present invention also provides a composition comprising the compound described herein, and a pharmaceutically acceptable carrier, adjuvant, or vehicle.

The present invention also provides a method of treating or preventing bacteria infection in a subject, comprising administering to the subject an effective amount of the compound or the composition described herein.

In an embodiment of the method, the bacteria infection is urinary tract infection or inflammatory bowel disease.

Another embodiment provides a method of treating or preventing a bacteria infection in a subject, comprising administering to the subject an effective amount of a compound described herein or a pharmaceutically acceptable salt thereof, or a composition comprising said compound. In some embodiments, the bacteria infection is urinary tract infection or inflammatory bowel disease. In some embodiments, the bacteria infection is ulcerative colitis. In other embodiments, the bacteria infection is Crohn's disease. In some embodiments, bacteria infection is the cause of Crohn's Disease or ulcerative colitis. In some embodiments, the bacteria infections are caused by AIEC (adherent-invasive *E. coli*) strains.

Another embodiment provides a method of treating or preventing inflammatory bowel disease in a subject, comprising administering to the subject an effective amount of a compound described herein or a pharmaceutically acceptable salt thereof, or a composition comprising said compound. In some embodiments, the subject is a patient. In other embodiments, the subject is a human. In some embodiments, the inflammatory bowel disease is Crohn's Disease. In other embodiments, the inflammatory bowel disease is ulcerative colitis.

Another embodiment provides a method of inhibiting FimH in bacteria from an *E. coli* bacterial strain isolated from patients with inflammatory bowel disease, comprising contacting the bacteria with an effective amount of a compound described herein, or a pharmaceutically acceptable salt thereof, or a composition comprising said compound. In some embodiments, the bacterial strain is LF-82.

Another embodiment provides a method of inhibiting FimH in a subject, comprising administering to the subject an effective amount of a compound described herein, or a pharmaceutically acceptable salt thereof, or a composition comprising said compound.

Another embodiment provides a method of inhibiting adhesion of *E. coli* in a subject, comprising administering to the subject an effective amount of a compound described herein, or a pharmaceutically acceptable salt thereof, or a composition comprising said compound. In some embodiments, the inhibition of adhesion results in the prevention of the establishment of a sub-mucosal infection.

Another embodiment provides a method of blocking the interaction between type 1 pili and CEACAM6 in a subject, comprising administering to the subject an effective amount of a compound described herein, or a pharmaceutically acceptable salt thereof, or a composition comprising said compound.

As described herein, a specified number range of atoms includes any integer therein. For example, a group having from 1-4 atoms could have 1, 2, 3, or 4 atoms. The term "stable", as used herein, refers to compounds that are not substantially altered when subjected to conditions to allow for their production, detection, recovery, storage, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched), or branched, hydrocarbon chain that is completely saturated or that contains one or more units of unsaturation but is non-aromatic.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl. Alkyl groups can also include deuterated hydrogens and include groups like $CD_3$.

The term "alkyl" as used herein means a saturated straight or branched chain hydrocarbon. The term "alkenyl" as used herein means a straight or branched chain hydrocarbon comprising one or more double bonds. The term "alkynyl" as used herein means a straight or branched chain hydrocarbon comprising one or more triple bonds. The term "cycloaliphatic" (or "carbocycle" or "carbocyclyl" or "carbocyclic") refers to a non-aromatic monocyclic carbon containing ring which can be saturated or contain one or more units of unsaturation, having three to fourteen ring carbon atoms. The term includes polycyclic fused, spiro or bridged carbocyclic ring systems. The term also includes polycyclic ring systems in which the carbocyclic ring can be fused to one or more non-aromatic carbocyclic or heterocyclic rings or one or more aromatic rings or combination thereof, wherein the radical or point of attachment is on the carbocyclic ring. Fused bicyclic ring systems comprise two rings which share two adjoining ring atoms, bridged bicyclic group comprise two rings which share three or four adjacent ring atoms, spiro bicyclic ring systems share one ring atom. Examples of cycloaliphatic groups include, but are not limited to, cycloalkyl and cycloalkenyl groups. Specific examples include, but are not limited to, cyclohexyl, cyclopropenyl, and cyclobutyl. The term "heterocycle" (or "heterocyclyl", or "heterocyclic") as used herein means refers to a non-aromatic monocyclic ring which can be saturated or contain one or more units of unsaturation, having three to fourteen ring atoms in which one or more ring carbons is replaced by a heteroatom such as, N, S, or O. The term includes polycyclic fused, spiro or bridged heterocyclic ring systems. The term also includes polycyclic ring systems in which the heterocyclic ring can be fused to one or more non-aromatic carbocyclic or heterocyclic rings or one or more aromatic rings or combination thereof, wherein the radical or point of attachment is on the heterocyclic ring. Examples of heterocycles include, but are not limited to, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydrofuranyl, tetrahydrothiophenyl, tetrahydrothiophenyl, morpholino, including, for example, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, thienothienyl, thienothiazolyl, benzothiolanyl, benzodithianyl, 3-(1-alkyl)-benzimidazol-2-onyl, and 1,3-dihydro-imidazol-2-onyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the molecule through an oxygen ("alkoxy" e.g., —O-alkyl) or sulfur ("thioalkyl" e.g., —S-alkyl) atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —$CF_3$ and —$CF_2CF_3$.

The terms "halogen", "halo", and "hal" mean F, Cl, Br, or I.

The term "aryl" used alone or as part of a larger moiety as in "aralkyl", "aralkoxy", or "aryloxyalkyl", refers to carbocyclic aromatic ring systems. The term "aryl" may be used interchangeably with the term "aryl ring".

Carbocyclic aromatic ring groups have only carbon ring atoms (typically six to fourteen) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The term "heteroaryl", "heteroaromatic", "heteroaryl ring", "heteroaryl group" and "heteroaromatic group", used alone or as part of a larger moiety as in "heteroaralkyl" or "heteroarylalkoxy", refers to heteroaromatic ring groups having five to fourteen members, including monocyclic heteroaromatic rings and polycyclic aromatic rings in which a monocyclic aromatic ring is fused to one or more other aromatic ring. Heteroaryl groups have one or more ring heteroatoms. Also included within the scope of the term "heteroaryl", as it is used herein, is a group in which an aromatic ring is fused to one or more non-aromatic rings (carbocyclic or heterocyclic), where the radical or point of attachment is on the aromatic ring. Bicyclic 6,5 heteroaromatic ring, as used herein, for example, is a six membered heteroaromatic ring fused to a second five membered ring, wherein the radical or point of attachment is on the six membered ring. Examples of heteroaryl groups include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, where indicated a methylene unit of an aliphatic chain is optionally replaced with another atom or group. Examples of such atoms or groups include, but are not limited to, —NR—, —O—, —C(O)—, —C(=N—CN)—, —C(=NR)—, —C(=NOR)—, —S—, —S(O)—, and —S(O)$_2$—. These atoms or groups can be combined to form larger groups. Examples of such larger groups include, but are not limited to, —OC(O)—, —C(O)CO—, —CO$_2$—, —C(O)NR—, —C(=N—CN), —NRC(O)—, —NRC(O)O—, —S(O)$_2$NR—, —NRSO$_2$—, —NRC(O)NR—, —OC(O)NR—, and —NRSO$_2$NR—, wherein R is defined herein.

Only those replacement and combinations of groups that result in a stable structure are contemplated. Optional replacements can occur both within the chain and/or at either end of the chain; i.e. both at the point of attachment and/or also at the terminal end. Two optional replacements can also be adjacent to each other within a chain so long as it results in a chemically stable compound. The optional replacements can also completely replace all of the carbon atoms in a chain. For example, a C$_3$ aliphatic can be optionally replaced by —NR—, —C(O)—, and —NR— to form —NRC(O) NR— (a urea).

Unless otherwise indicated, if the replacement occurs at the terminal end, the replacement atom is bound to an H on the terminal end. For example, if —CH$_2$CH$_2$CH$_3$ were optionally replaced with —O—, the resulting compound could be —OCH$_2$CH$_3$, —CH$_2$OCH$_3$, or —CH$_2$CH$_2$OH.

It shall be understood that an aliphatic chain may include bonds of unsaturation, and therefore the atom which is replacing the "methylene" unit of an aliphatic may in fact be replacing a —CH= unit, a =C=unit or a ≡C— unit. One of skill in the art would understand that the atom replacing these units would have the appropriate bond order to result in a stable structure. For example, when a methylene unit of an aliphatic chain is optionally replaced with —NR—, one of skill in the art would understand that if the aliphatic group were CH=CH—CH$_3$ and the middle methylene group, "CH" were to be replaced, it would actually be replaced with "N", not "—NR—" to result in CH=N—CH$_3$.

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

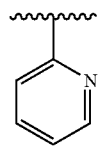

also represents

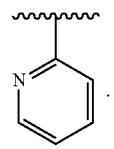 [SMILES: *c1ccccn1]

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays. These compounds are also useful in the treatment of bacteria infections (see e.g., compound 183).

As described herein, where indicated compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position.

Only those choices and combinations of substituents that result in a stable structure are contemplated. Such choices and combinations will be apparent to those of ordinary skill in the art and may be determined without undue experimentation.

The term "ring atom" is an atom such as C, N, O or S that is in the ring of an aromatic group, cycloalkyl group or non-aromatic heterocyclic ring.

A "substitutable ring atom" in an aromatic group is a ring carbon or nitrogen atom bonded to a hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to a moiety other than hydrogen.

It shall be understood that a bond with a substituent drawn through several rings of a polycyclic molecule indicates that the substituent may be bonded at any ring of the polycyclic ring. For example, in the figure shown below:

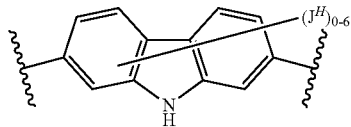

$J^H$ can be substituted on either benzo ring of the carbozolyl ring, as well as on the 5-membered ring in the center, such as at the nitrogen of the carbazolyl ring. Therefore, if $J^H$ were "CH$_3$", any of the following three would be comtemplated based on the above formula:

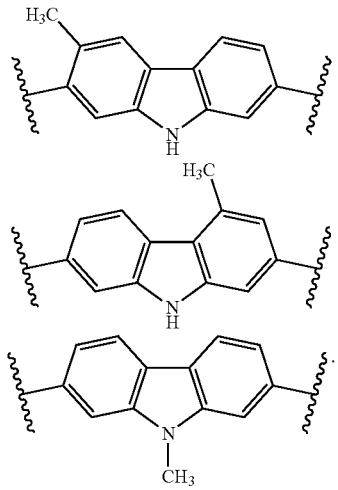

An aryl group as defined herein may contain one or more substitutable ring atoms, which may be bonded to a suitable substituent. Examples of suitable substituents on a substitutable ring carbon atom of an aryl group include R'. R' is —Ra, —Br, —Cl, —I, —F, —ORa, —SRa, —O—CORa, —CORa, —CSRa, —CN, —NO$_2$, —NCS, —SO$_3$H, —N(RaRb), —COORa, —NRcNRcCORa, —NRcNRcCO2Ra, —CHO, —CON(RaRb), —OC(O)N(RaRb), —CSN(RaRb), —NRcCORa, —NRcCOORa, —NRcCSRa, —NRcCON(RaRb), —NRcNRcC(O)N(RaRb), —NRcCSN(RaRb), —C(=NRc)-N(RaRb), —C(=S)N(RaRb), —NRd-C(=NRc)-N(RaRb), —NRcN-RaRb, —S(O)$_p$NRaRb, —NRcSO$_2$N(RaRb), —NRcS(O)$_p$Ra, —S(O)$_p$Ra, —OS(O)$_p$NRaRb or —OS(O)$_p$Ra; wherein p is 1 or 2.

Ra-Rd are each independently —H, an aliphatic group, aromatic group, non-aromatic carbocyclic or heterocyclic group or —N(RaRb), taken together, form a non-aromatic heterocyclic group. The aliphatic, aromatic and non-aromatic heterocyclic group represented by Ra-Rd and the non-aromatic heterocyclic group represented by —N(RaRb) are each optionally and independently substituted with one or more groups represented by R$^\#$. Preferably Ra-Rd are unsubstituted.

R$^\#$ is halogen, R$^+$, —OR$^+$, —SR$^+$, —NO$_2$, —CN, —N(R$^+$)$_2$, —COR$^+$, —COOR$^+$, —NHCO$_2$R$^+$, —NHC(O)R$^+$, —NHNHC(O)R$^+$, —NHC(O)N(R$^+$)$_2$, —NHNHC(O)N(R$^+$)$_2$, —NHNHCO$_2$R$^+$, —C(O)N(R$^+$)$_2$, —OC(O)R$^+$, —OC(O)N(R$^+$)$_2$, —S(O)$_2$R$^+$, —SO$_2$N(R$^+$)$_2$, —S(O)$_2$R$^+$, —NHSO$_2$N(R$^+$)$_2$, —NHSO$_2$R$^+$, —C(=S)N(R$^+$)$_2$, or —C(=NH)—N(R$^+$)$_2$.

R$^+$ is —H, a C$_1$-C$_4$ alkyl group, a monocyclic aryl group, a non-aromatic carbocyclic or heterocyclic group each optionally substituted with alkyl, haloalkyl, alkoxy, haloalkoxy, halo, —CN, —NO$_2$, amine, alkylamine or dialkylamine. Preferably R+ is unsubstituted.

An aliphatic or a non-aromatic heterocyclic or carbocyclic group as used herein may contain one or more substituents. Examples of suitable substituents for an aliphatic group or a ring carbon of a non-aromatic heterocyclic group is R". R" include those substituents listed above for R' and =O, =S, =NNHR, =NN(R)2, =NNHC(O)R, =NNHCO2(alkyl), =NNHSO2 (alkyl), =NR, spiro cycloalkyl group or fused cycloalkyl group. Each R is independently selected from hydrogen, an unsubstituted alkyl group or a substituted alkyl group. Examples of substituents on the alkyl group represented by R include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

A preferred position for substitution of a non-aromatic nitrogen-containing heterocyclic group is the nitrogen ring atom. Suitable substituents on the nitrogen of a non-aromatic heterocyclic group or heteroaryl group include —R^, —N(R^)$_2$, C(O)R^, CO$_2$R^, —C(O)C(O)R^, —SO$_2$R^, SO$_2$N(R^)$_2$, C(=S)N(R^)$_2$, C(=NH)—N(R^)$_2$, and —NR^SO$_2$R^; wherein R^ is hydrogen, an aliphatic group, a substituted aliphatic group, aryl, substituted aryl, heterocyclic or carbocyclic ring or a substituted heterocyclic or carbocyclic ring. Examples of substituents on the group represented by R^ include alkyl, haloalkoxy, haloalkyl, alkoxyalkyl, sulfonyl, alkylsulfonyl, halogen, nitro, cyano, hydroxy, aryl, carbocyclic or heterocyclic ring, oxo, amino, alkylamino, dialkylamino, aminocarbonyl, alkylaminocarbonyl, dialkylaminocarbonyloxy, alkoxy, carboxy, alkoxycarbonyl, or alkylcarbonyl. Preferably R^ is not substituted.

Non-aromatic nitrogen containing heterocyclic rings that are substituted on a ring nitrogen and attached to the remainder of the molecule at a ring carbon atom are said to be N substituted. For example, an N alkyl piperidinyl group is attached to the remainder of the molecule at the two, three or four position of the piperidinyl ring and substituted at the ring nitrogen with an alkyl group. Non-aromatic nitrogen containing heterocyclic rings such as pyrazinyl that are substituted on a ring nitrogen and attached to the remainder of the molecule at a second ring nitrogen atom are said to be N' substituted-N-heterocycles. For example, an N' acyl N-pyrazinyl group is attached to the remainder of the molecule at one ring nitrogen atom and substituted at the second ring nitrogen atom with an acyl group.

As used herein an optionally substituted aralkyl can be substituted on both the alkyl and the aryl portion. Unless otherwise indicated as used herein optionally substituted aralkyl is optionally substituted on the aryl portion.

The terms "a bond" and "absent" are used interchangeably to indicate that a group is absent.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The compounds of this invention can exist in free form for treatment, or where appropriate, as a pharmaceutically acceptable salt.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Base addition salts can be prepared by 1) reacting the purified compound in its acid form with a suitable organic or inorganic base and 2) isolating the salt thus formed. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

In addition to the compounds of this invention, pharmaceutically acceptable derivatives or prodrugs of the compounds of this invention may also be employed in compositions to treat or prevent the herein identified disorders.

As used herein and unless otherwise indicated, the term "prodrug" means a derivative of a compound that can hydrolyze, oxidize, or otherwise react under biological conditions (in vitro or in vivo) to provide a compound of this invention. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of the invention that comprise —NO, —NO$_2$, —ONO, or —ONO$_2$ moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

A "pharmaceutically acceptable derivative or prodrug" includes any pharmaceutically acceptable ester, salt of an ester or other derivative or salt thereof of a compound, of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

In one embodiment the present invention is a pharmaceutical composition comprising a compound of the present invention and a pharmaceutically acceptable carrier, diluent, adjuvant or vehicle. In one embodiment the present invention is a pharmaceutical composition comprising an effective amount of compound of the present invention and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compounds of present invention or pharmaceutical salts thereof may be formulated into pharmaceutical compositions for administration to a subject as defined herein. These pharmaceutical compositions, which comprise an amount of the compounds effective to treat or prevent a bacteria infection, such as IBD, and a pharmaceutically acceptable carrier, are another embodiment of the present invention.

In one embodiment the present invention is a method of treating or preventing a bacteria infection, such as IBD, in a subject in need thereof, comprising administering to the subject an effective amount of a compound or composition of the present invention.

As used herein, the terms "subject", "patient" and "mammal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In a preferred embodiment, the subject is a human.

As used herein, an "effective amount" refers to an amount sufficient to elicit the desired biological response. In the present invention the desired biological response is to reduce or ameliorate the severity, duration, progression, or onset of a bacteria infection, prevent the advancement of a bacteria infection, cause the regression of a bacteria infection, prevent the recurrence, development, onset or progression of a symptom associated with a bacteria infection, or enhance or improve the prophylactic or therapeutic effect(s) of another therapy. The precise amount of compound administered to a subject will depend on the mode of administration, the type and severity of the disease or condition and on the characteristics of the subject, such as general health, age, sex, body weight and tolerance to drugs. It will also depend on the degree, severity and type of bacteria infection, and the mode of administration. The skilled artisan will be able to determine appropriate dosages depending on these and other factors. When co-administered with other agents, e.g., when co-administered with a bacteria infection agent, an "effective amount" of the second agent will depend on the type of drug used. Suitable dosages are known for approved agents and can be adjusted by the skilled artisan according to the condition of the subject, the type of condition(s) being treated and the amount of a compound of the invention being used. In cases where no amount is expressly noted, an effective amount should be assumed.

As used herein, the terms "treat", "treatment" and "treating" refer to the reduction or amelioration of the progression, severity and/or duration of a bacteria infection, or the amelioration of one or more symptoms (preferably, one or more discernible symptoms) of a bacteria infection resulting from the administration of one or more therapies (e.g., one or more therapeutic agents such as a compound of the invention). In specific embodiments, the terms "treat", "treatment" and "treating" refer to the amelioration of at least one measurable physical parameter of a bacteria infection. In other embodiments the terms "treat", "treatment" and "treating" refer to the inhibition of the progression of a bacteria infection, either physically by, e.g., stabilization of a discernible symptom, physiologically by, e.g., stabilization of a physical parameter, or both. In other embodiments the terms "treat", "treatment" and "treating" refer to the reduction or stabilization of a bacteria infection.

As used herein, the terms "prevent", "prevention" and "preventing" refer to the reduction in the risk of acquiring or developing a given bacteria infection, or the reduction or inhibition of the recurrence or a bacteria infection. In one embodiment, a compound of the invention is administered as a preventative measure to a patient, preferably a human, having a genetic predisposition to any of the conditions, diseases or disorders described herein.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. The dosage regimen utilizing the compounds of present invention can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe the effective amount of the compound of present invention required to treat, for example, to prevent, inhibit (fully or partially) or arrest the progress of the disease.

Dosages of the compounds of present invention can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosings such as twice, three or four times per day.

The compounds for use in the method of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

An effective amount can be achieved in the method or pharmaceutical composition of the invention employing a compound of present invention or a pharmaceutically acceptable salt thereof alone or in combination with an additional suitable therapeutic agent, for example, a cancer-therapeutic agent. When combination therapy is employed, an effective amount can be achieved using a first amount of a compound of present invention or a pharmaceutically acceptable salt thereof and a second amount of an additional suitable therapeutic agent.

In one embodiment, the compound of present invention and the additional therapeutic agent, are each administered in an effective amount (i.e., each in an amount which would be therapeutically effective if administered alone). In another embodiment, the compound of present invention and the additional therapeutic agent, are each administered in an amount which alone does not provide a therapeutic effect (a sub-therapeutic dose). In yet another embodiment, the compound of present invention can be administered in an effective amount, while the additional therapeutic agent is administered in a sub-therapeutic dose. In still another embodiment, the compound of present invention can be administered in a sub-therapeutic dose, while the additional therapeutic agent, for example, a suitable cancer-therapeutic agent is administered in an effective amount.

As used herein, the terms "in combination" or "coadministration" can be used interchangeably to refer to the use of more than one therapies (e.g., one or more prophylactic and/or therapeutic agents). The use of the terms does not restrict the order in which therapies (e.g., prophylactic and/or therapeutic agents) are administered to a subject. Coadministration encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order.

When coadministration involves the separate administration of the first amount of a compound of present invention and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of present invention and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

It is understood that the method of coadministration of a first amount of a compound of present invention and a second amount of an additional therapeutic agent can result in an enhanced or synergistic therapeutic effect, wherein the combined effect is greater than the additive effect that would result from separate administration of the first amount of the compound of present invention and the second amount of the additional therapeutic agent.

As used herein, the term "synergistic" refers to a combination of a compound of the invention and another therapy (e.g., a prophylactic or therapeutic agent), which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

The presence of a synergistic effect can be determined using suitable methods for assessing drug interaction. Suitable methods include, for example, the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

The activity of the compounds as inhibitors of bacteria infection may be assayed in vitro or in vivo. In vitro assays include assays that determine inhibition of FimH activity, bacterial adhesion, and bacterial binding. Alternate in vitro assays quantitate the ability of the inhibitor to bind to the FimH and may be measured either by radiolabelling the inhibitor prior to binding, isolating the inhibitor complex and determining the amount of radiolabel bound, or by running a competition experiment where new inhibitors are incubated with the FimH bound to known radioligands.

Detailed conditions for assaying a compound utilized in this invention are set forth in the Examples below.

EXPERIMENTAL DETAILS

The following abbreviations are used in the examples below:
Ac acetyl
AcOH acetic acid
$Ac_2O$ acetic anhydride
$BF_3.OEt_2$ diethyloxonio-trifluoro-boron
Bn benzyl
$CH_3CN$ acetonitrile
$CD_3OD$ methanol-D4
$CDCl_3$ chloroform-D
$CH_2Cl_2$ methylene chloride or dichloromethane
conc concentrate
$Cs_2CO_3$ cesium carbonate
CuI copper(I) iodide
$CuSO_4$ copper(II) sulfate
CV column volume
DBU 1,8-diazabicyclo[5.4.0]undec-7-ene
DIPEA N-ethyl-N-isopropyl-propan-2-amine
DMAP 4-dimethylaminopyridine
DMF dimethylformamide
DMSO dimethylsulfoxide
Eq. equivalent
EtOAc ethyl acetate
HATU O-(7-azabenzotriazol-1-yl),N,N,N'',N''-tetramethyl-uroniumhexafluorophosphate
h hour(s)
Hex hexanes
M molar
MeOH methanol
MeONa sodium methoxide
min minute(s)
MTBE methyl tert-butyl ether
$NaIO_4$ sodium periodate
$Na_2SO_4$ sodium sulfate
NMO N-methylmorpholine-N-oxide
$OsO_4$ osmium tetroxide
$PdCl_2$ palladium (II)chloride
$Pd(PPh_3)_4$ palladium tetrakis triphenylphosphine
$Pd(OAc)_2$ palladium(II) acetate
$PdCl_2(dppf).CH_2Cl_2$ (1,1'-Bis-(diphenylphosphino)-ferrocene)palladium (II) dichloride dichloromethane complex
$Pd(OH)_2$ dihydroxy palladium
Piv trimethylacetyl
Py pyridine
RBF round bottom flask
RT room temperature
TBAF tetrabutylammonium fluoride
TBDMSOTf tert-butyldimethylsilyl trifluoromethane-sulfonate
TBS tert-butyldimethylsilyl
TEA triethylamine
Tf trifluoromethanesulfonyl
TFA trifluoroacetic acid
THF tetrahydrofuran
TLC thin layer chromatography
TMS trimethylsilyl
TMSI trimethylsilyl iodide
$TMSN_3$ trimethylsilyl azide
TMSOTf trimethylsilyl trifluoromethanesulfonate The compounds of this invention may be prepared in light of the specification using steps generally known to those of ordinary skill in the art. Those compounds may be analyzed by known methods, including but not limited to LC-MS (liquid chromatography mass spectrometry), HPLC (high performance liquid chromatography) and NMR (nuclear magnetic resonance). It should be understood that the specific conditions shown below are only examples, and are not meant to limit the scope of the conditions that can be used for making compounds of this invention. Instead, this invention also includes conditions that would be apparent to those skilled in that art in light of this specification for making the compounds of this invention. Unless otherwise indicated, all variables in the following Examples are as defined herein.

Mass spec. samples are analyzed on a Waters UPLC Acquity mass spectrometer operated in single MS mode with electrospray ionization. Samples are introduced into the mass spectrometer using chromatography. Mobile phase for the mass spec. analyses consisted of 0.1% formic acid and $CH_3CN$-water mixture. Column gradient conditions are 5%-85% $CH_3CN$-water over 6 minutes run time, AcquityHSS T3 1.8μ 2.1 mm ID×50 mm. Flow rate is 1.0 mL/min. As used herein, the term "Rt(min)" refers to the LC-MS retention time, in minutes, associated with the compound. Unless otherwise indicated, the LC-MS method utilized to obtain the reported retention time is as detailed above.

Purification by reverse phase HPLC is carried out under standard conditions using either Phenomenex Gemini 21.2 mm ID×250 mm column (5 m), Gemini 21.2 mm ID×75 mm column, (5 μm), 110 Å or in most cases aWaters XSELECT CSH Prep C18 (5 μm) ODB 19×100 mm column. Elution is performed using a linear gradient $CH_3CN$—$H_2O$ (with or without 0.01% TFA buffer or 0.1% HCOH) as mobile phase. Solvent system is tailored according to the polarity of the compound, Flow rate, 20 mL/min. Compounds are collected either by UV or Waters 3100 Mass Detector, ESI Positive Mode. Fractions containing the desired compound are combined, concentrated (rotary evaporator) to remove excess $CH_3CN$ and the resulting aqueous solution is lyophilized to afford the desired material in most cases as a white foam.

General Method of Synthesis

Compounds described therein are prepared from key intermediates using two key reactions; Suzuki and Sonogashira coupling.

Compounds of formula IV (Z=i) can be prepared by two distinct methods, as exemplified in Scheme 1. In Method A, a palladium catalyzed stereoselective C-glycosidation of per-acetylated glycal with aryl/heteroaryl bis-boronic of type I generates selectively bis-α-glucal of type II (Maddaford et al. Org Letters, 2001, 3 (13), 2013). A stereoselective bis-dihydroxylation of the latter ($OsO_4$, NMO) affords the aryl/heteroaryl bis-α-mannosides of type III. Removal of the acetate protective group by saponification (MeONa/MeOH) generates the desired final product of type IV (Z=i). Alternatively in Method B, the stereoselective C-glycosidation results from the double addition of aryl/heteroaryl zinc reagents derived from diiodo aryl/heteroaryl of type V on (3S,4S,5R,6R)-2-bromo-6-((pivaloyloxy)methyl)tetrahydro-2H-pyran-3,4,5-triyl tris(2,2-dimethylpropanoate) as reported by Knochel (Org Letters, 2012, 14 (6), 1480). The resulting fully pivalated bismannosides VI is deprotected under acidic condition (AcOH, THF, $H_2O$) to afford the desired material IV.

Scheme 1: Method A and B for the preparation of compounds of formula IV (Z = i)

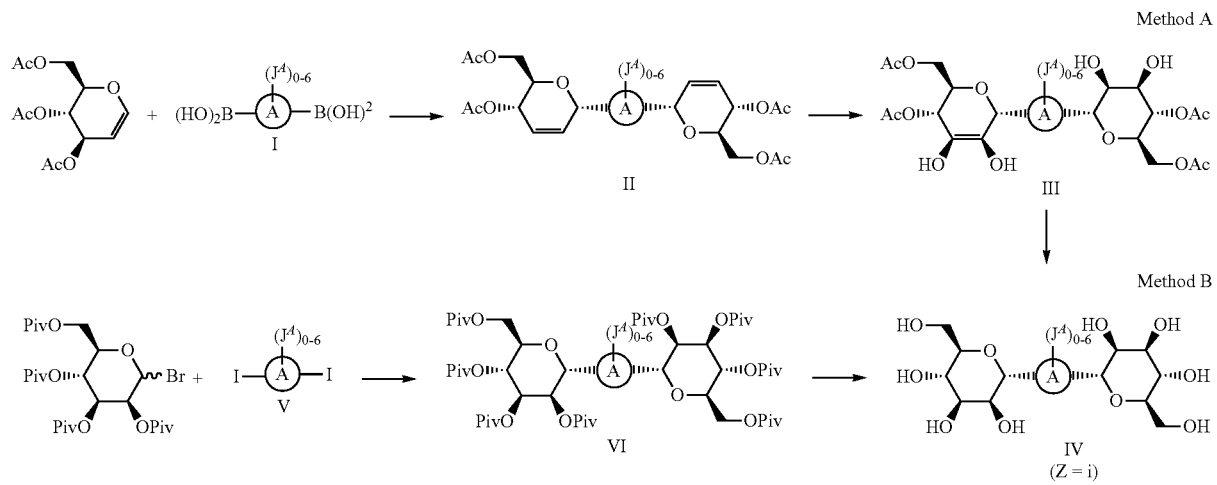

Compounds of formula XI (Z=ii), XIV (Z=iii), and XIX (Z=vii) can also be prepared using Methods A and B, as exemplified in Scheme 2. Biaryls or bis-heteroaryls of type XI can either be prepared sequentially in Method A for primarily unsymmetrical analogs (B≠C) or more promptly using Method B, pending the availability of starting material of type V. In Method A, intermediates of type IX are prepared as described previously using boronic acids of type VII. In some cases, the boronic acid VII is replaced by the corresponding pinacolo-boronate prepared from the corresponding benzyl protected bromo or iodo-phenol. After coupling with the glucal and dihydroxylation the benzyl protective group is removed by hydrogenolysis and converted to the triflate to enable palladium catalyzed cross coupling. Suzuki coupling of intermediates IX and X followed by saponification provides the desired bis-mannosides XI. Compounds of type XIV (Z=iii) can be prepared in a similar fashion from the pinacol boronate of type XII by Suzuki coupling with bis halogenated intermediates of type XIII. This approach is performed in two steps (coupling and deprotection) for symmetrical compounds (D=F) or sequentially for unsymmetrical (D≠F) analogs. In Method B, compounds of types XI, XIV and XIX are prepared as described previously from intermediates XV, XVI and XVIII respectively either commercially available or prepared by cross coupling strategies.

Scheme 2: Method A and B for the preparation of compounds of formula XX (Z = ii), XIV (Z = iii) and XIX (Z = vii)

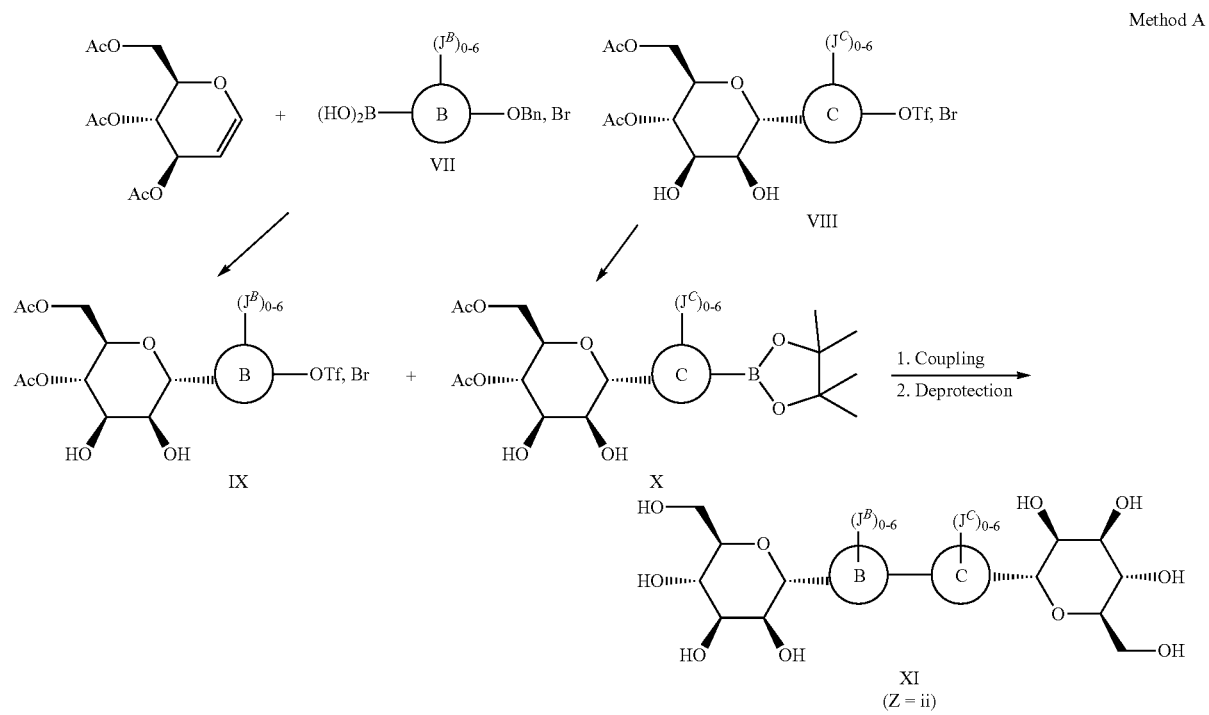

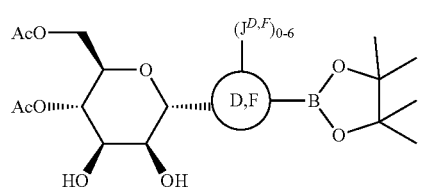
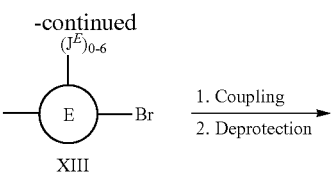
1. Coupling
2. Deprotection
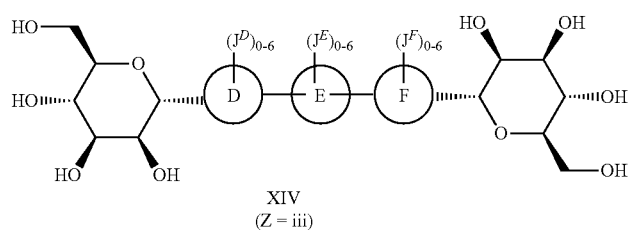
Method B
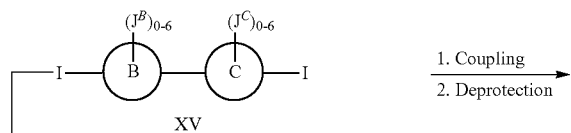
1. Coupling
2. Deprotection
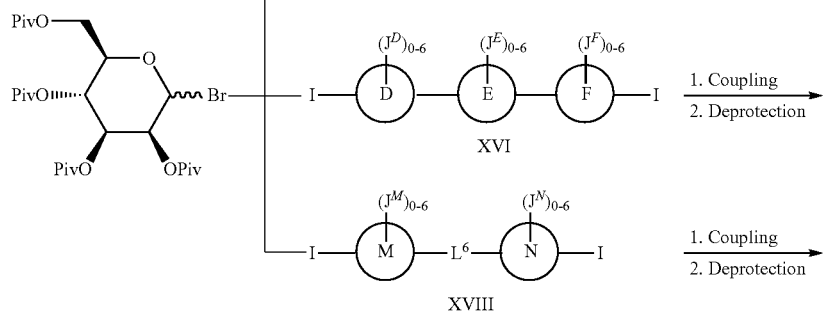
1. Coupling
2. Deprotection
1. Coupling
2. Deprotection
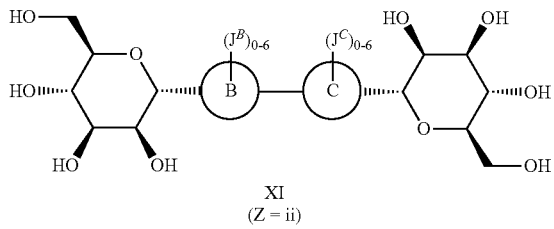
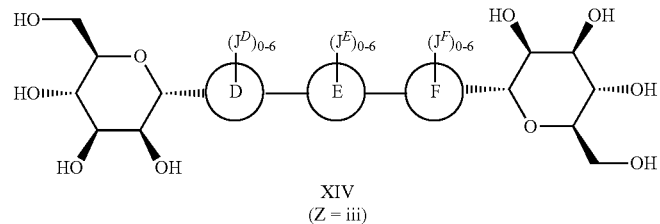
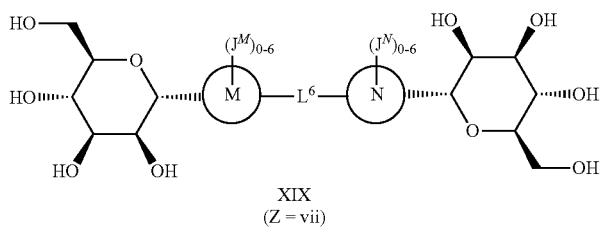

Compounds of formula XXII (Z=v) in which L2 and L3 are alkyne, can be prepared by three distinct Methods (C, D and E), as exemplified in Scheme 3. In Method C, the intermediate XXI is prepared via a Sonogashira coupling between dibromo or diiodo aryl or heteroaryl of type XX and ((2R,3R,4R,5R,6R)-6-ethynyl-3,4,5-tris((triisopropylsilyl)oxy)tetrahydro-2H-pyran-2-yl)methanol or the TMS protected analog (see Helv. Chim. Acta. 2001, 84(8), 2355-2367). Removal of the TIPS protecting groups of XVIII under acidic condition (TFA, THF, H$_2$O) or using TBAF affords the desired compound XXII. Alternatively, in Method D, the same Sonogashira coupling described in Method C is performed using the unprotected α-ethynyl mannose ((2R,3S,4R,5S,6R)-2-ethynyl-6-(hydroxymethyl)tetrahydro-2H-pyran-3,4,5-triol; Helv. Chim. Acta. 2001, 84(8), 2355-2367). Finally in Method E, a Lewis acid catalyzed double Ferrier type alkynylation between (2R,3S,4R)-2-(acetoxymethyl)-3,4-dihydro-2H-pyran-3,4-diyl diacetate and the bis-TMS-acetylene aryl of heteroaryl type XXIII compound can be performed to afford the desired intermediate XXIV (Tetrahedron Letters 2002, 43, 5437-5440. A stereospecific bis-dihydroxylation of intermediate XXIV followed by a saponification generated the desired final compound XXII.

Scheme 3: Method C, D and E for the preparation of compounds of formula III (Z = v)

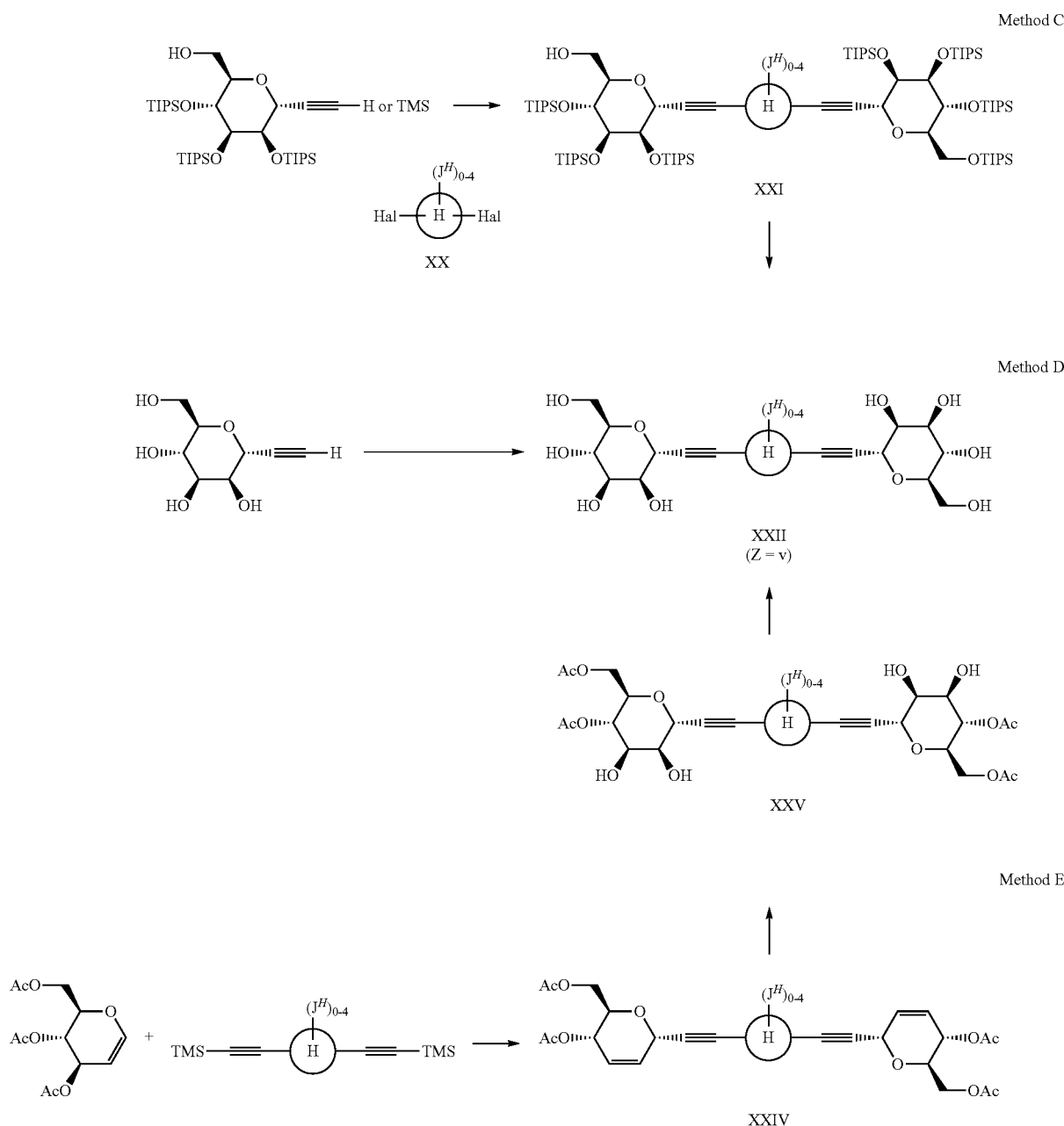

Bis-mannosides of type XXVII exhibiting α-aryl and α-alkynyl linkers to mannose are prepared by reactions previously described, according to the synthetic route of Scheme 4, Method F. Sonogashira coupling between halogenated aryls or heteroaryls of type XXVI (prepared as described for IX) and (2R,3R,4R,5R,6R)-6-ethynyl-3,4,5-tris((triisopropylsilyl)oxy)tetrahydro-2H-pyran-2-yl)methanol or the TMS protected analog can afford after sequential deprotection of acetate and TIPS groups if necessary the desired compounds of type XXVII.

Scheme 4: Method F for the preparation of compounds of formula XXIII (Z = iv)

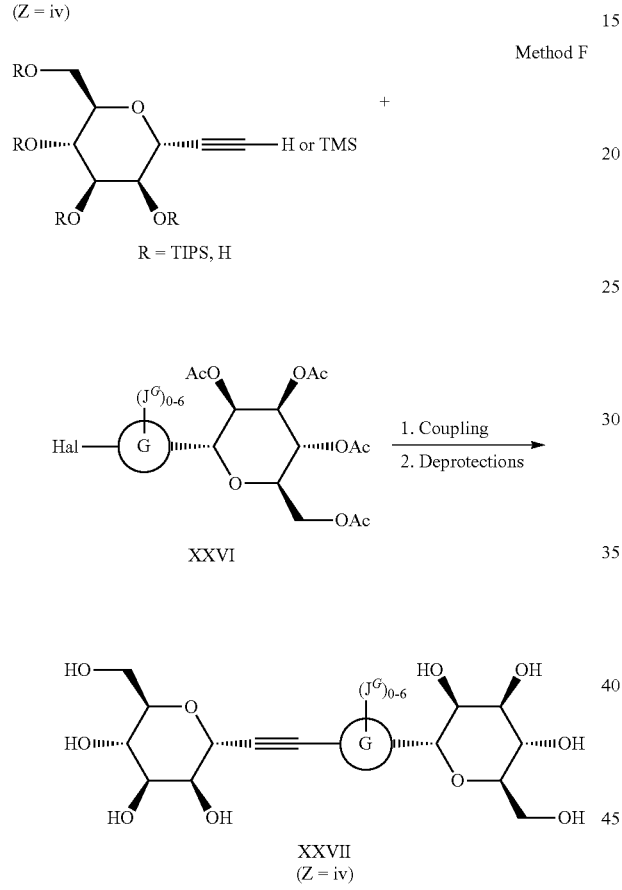

The following is a list of key intermediates which are used in the preparation of Compounds described therein

A

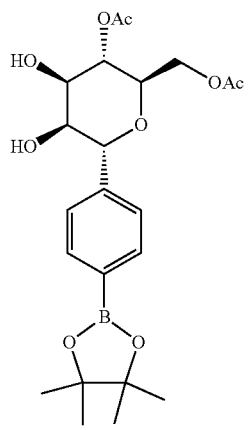

B

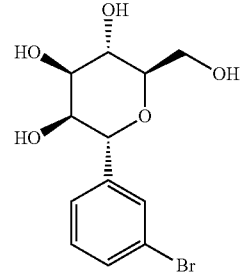

C

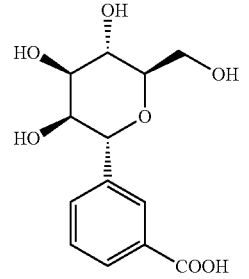

D

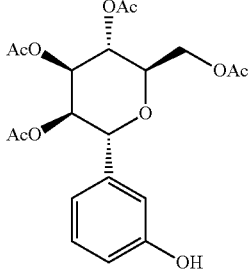

E

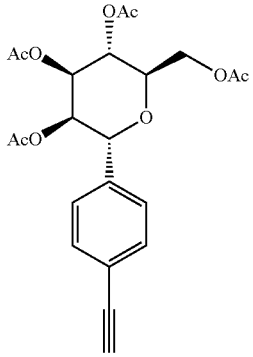

F

G
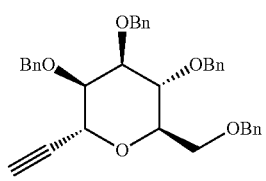
H
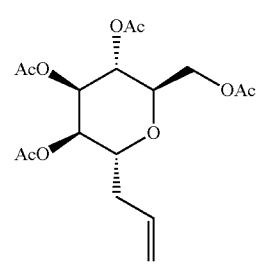
I
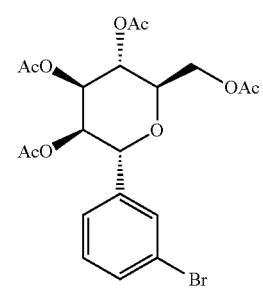
J
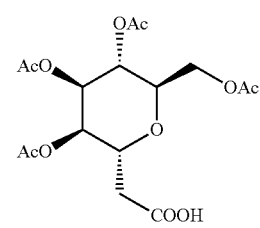
K
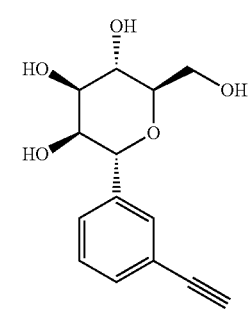
L
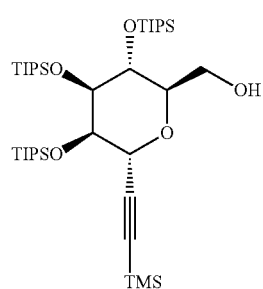
M
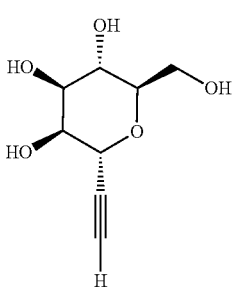
N
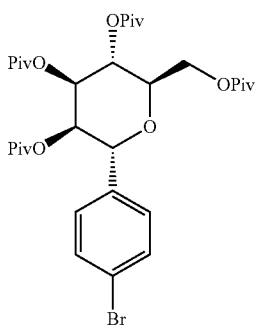
O
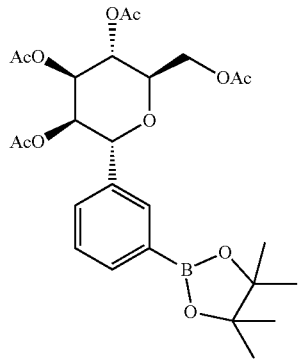
P
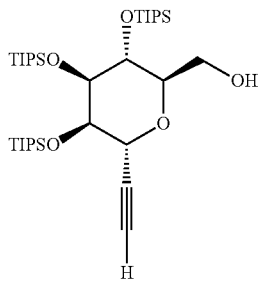
Q
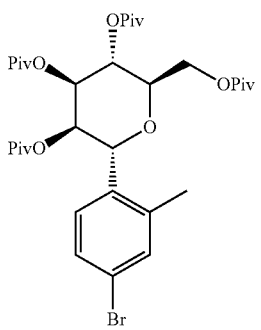

-continued

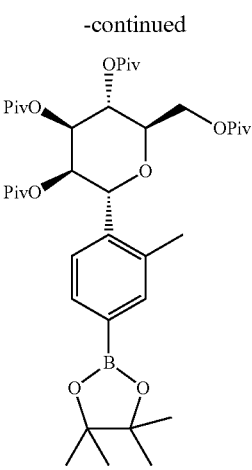

Preparation of Intermediate A ([(2R,3S,4R,5S,6R)-3-Acetoxy-4,5-dihydroxy-6-[4-(trifluoromethylsulfonyloxy)phenyl]tetrahydropyran-2-yl]methyl acetate)

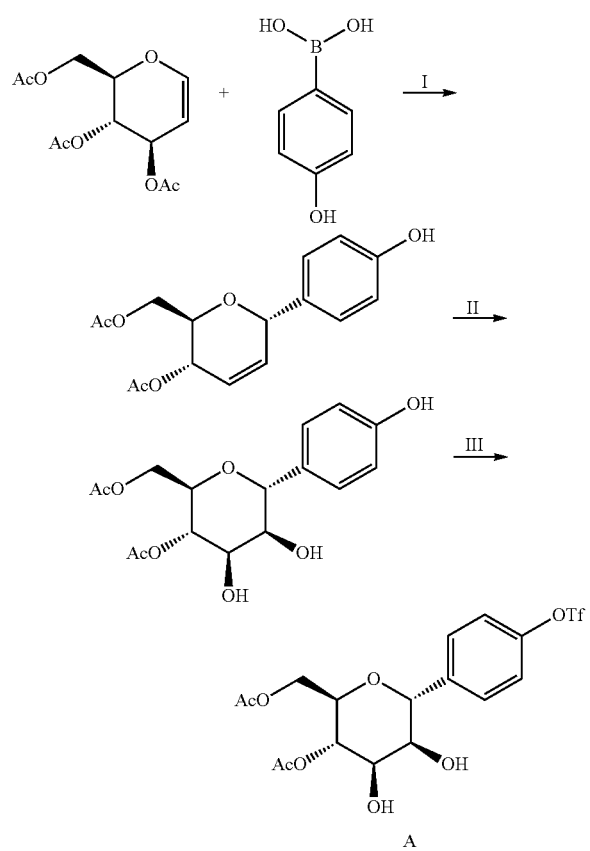

Step I: [(2R,3S,6S)-3-Acetoxy-6-(4-hydroxyphenyl)-3,6-dihydro-2H-pyran-2-yl]methyl acetate Acetonitrile (50.00 mL) is added to a mixture of [(2R, 3S,4R)-3,4-diacetoxy-3,4-dihydro-2H-pyran-2-yl]methyl acetate (9.869 g, 36.25 mmol), (4-hydroxyphenyl)boronic acid (5 g, 36.25 mmol) and Pd(OAc)$_2$ (1.221 g, 5.438 mmol) and the reaction mixture is stirred at RT overnight. An additional amount of (4-hydroxyphenyl)boronic acid (1 g) is added and the reaction mixture is stirred for a further 2 h and filtered through celite. The filtrate is evaporated and the crude product is purified on a Biotage™ SNAP 340 g silica gel cartridge with a gradient of 5%-80% EtOAc in Hex to afford title product (6.03 g).

Step II: [(2R,3S,4R,5S,6R)-3-Acetoxy-4,5-dihydroxy-6-(4-hydroxyphenyl)tetrahydropyran-2-yl]methyl acetate To a suspension of [(2R,3S,6S)-3-acetoxy-6-(4-hydroxyphenyl)-3,6-dihydro-2H-pyran-2-yl]methyl acetate (6.03 g, 19.69 mmol) in THF (36 mL)/water (24 mL) are added methanesulfonamide (2.810 g, 29.54 mmol), OsO$_4$ (6.007 g, 7.4 mL of 2.5% w/w in -t-BuOH, 0.5907 mmol) and NMO (4.613 g, 39.38 mmol). The reaction mixture is stirred at RT overnight. 1M Na$_2$S$_2$O$_3$ (40 mL) is added and the mixture is extract with EtOAc (3×40 mL). The combined organic extracts are washed with brine (15 mL) and dried over Na$_2$SO$_4$. The mixture is filtered, the solvent is evaporated and the crude product is purified on a Biotage™ SNAP 220 g silica gel cartridge with a gradient of 0%-20% MeOH in CH$_2$Cl$_2$ to afford title product (6.05 g).

LC-MS: m/z=329.3 (M+Na$^+$)

Step III: Intermediate A

To a solution of [(2R,3S,4R,5S,6R)-3-acetoxy-4,5-dihydroxy-6-(4-hydroxyphenyl)tetrahydropyran-2-yl]methyl acetate (872 mg, 2.562 mmol) in CH$_2$Cl$_2$ (22 mL) are added 1,1,1-trifluoro-N-phenyl-N-(trifluoromethylsulfonyl)methanesulfonamide (1.190 g, 3.331 mmol), NEt$_3$ (518.5 mg, 714 µL, 5.124 mmol) and the reaction mixture is stirred at RT overnight. The solvent is evaporated and the crude product is purified on a Biotage™ SNAP 100 g silica gel cartridge with a gradient of 0%-20% MeOH/CH$_2$Cl$_2$ over 15 column volume to afford the title product (1.06 g).

Preparation of Intermediate B ([(2R,3S,4R,5S,6R)-3-Acetoxy-4,5-dihydroxy-6-[4-(4,4,5,5-tetramethyl-1,3,2-dioxaborolan-2-yl)phenyl]tetrahydropyran-2-yl]methyl acetate)

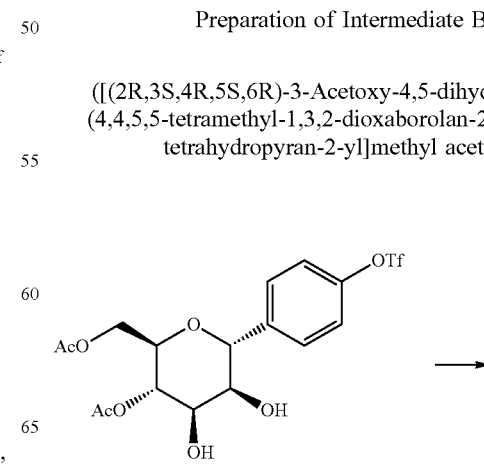

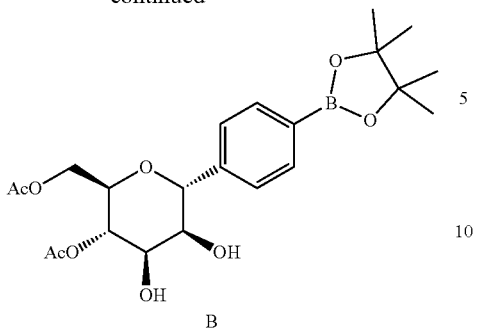

B

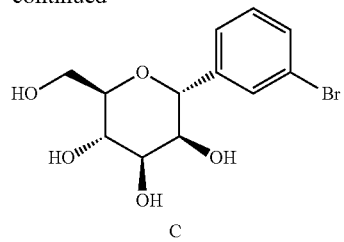

C

Step I: ((2R,3S,6S)-3-Acetoxy-6-(3-bromophenyl)-3,6-dihydro-2H-pyran-2-yl)methyl acetate A mixture of [(2R,3S,4R,5S,6R)-3-acetoxy-4,5-dihydroxy-6-[4-(trifluoromethylsulfonyloxy)phenyl]tetrahydropyran-2-yl]methyl acetate (350 mg, 0.74 mmol), 4,4,5,5-tetramethyl-2-(4,4,5,5-tetramethyl-1,3,2-dioxaborolan-2-yl)-1,3,2-dioxaborolane (225.8 mg, 0.89 mmol), PdCl$_2$ (dppf).CH$_2$Cl$_2$ (45.18 mg, 0.074 mmol) and potassium acetate (291 mg, 2.96 mmol) in DMF (3.7 mL) is degassed by bubbling N$_2$(g) through for 5 min. The reaction mixture is then heated at 80° C. for 5 h. The solvent is removed under high vacuum and the crude product is triturated with EtOAc (10 mL) and filtered. The filtrate is concentrated and purified on a Biotage™ SNAP 25 g silica gel cartridge with a gradient elution of 40%-60% EtOAc in Hex and a flow rate of 24 mL/min over 20 min to afford the title product (168 mg, 0.3731 mmol, 50.36%) as a foam. $^1$H NMR (400 MHz, CD$_3$OD) δ 7.75 (d, J=7.8 Hz, 2H), 7.45 (d, J=7.9 Hz, 2H), 4.96-4.90 (m, 1H), 4.72 (dd, J=12.1, 8.2 Hz, 1H), 4.20-4.02 (m, 2H), 3.93-3.76 (m, 2H), 3.49 (dd, J=14.4, 7.0 Hz, 1H), 2.07 (s, 3H), 2.05 (s, 3H), 1.35 (s, 12H).

LC-MS: m/z=451.3 (M+H$^+$).

Preparation of Intermediate C ((2R,3S,4R,5S,6R)-2-(3-Bromophenyl)-6-(hydroxymethyl)tetrahydro-2H-pyran-3,4,5-triol)

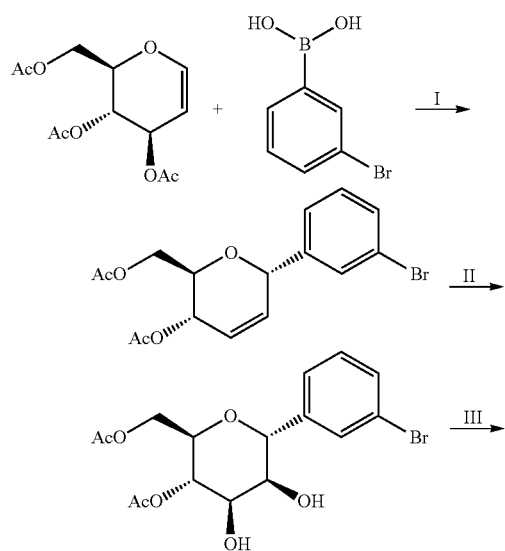

A solution of [(2R,3S,4R)-3,4-diacetoxy-3,4-dihydro-2H-pyran-2-yl]methyl acetate (3.00 g, 11.02 mmol) and (3-bromophenyl)boronic acid (4.43 g, 22.04 mmol) in CH$_3$CN (22 mL) is degassed by bubbling nitrogen gas through for 3 min. Palladium (II) acetate (371 mg, 1.65 mmol) is added and the reaction mixture is stirred at RT for 5 h then another portion of palladium (II) acetate (371 mg, 1.65 mmol) is added and stirring is continued for 18 h. The solvent is evaporated and the mixture is diluted with dichloromethane (10 mL) and saturated aqueous NaHCO$_3$ (20 mL). The mixture is filtered through a phase separator cartridge, the filtrate is evaporated and purified on a Biotage™ SNAP 50 g silica gel cartridge using a gradient elution of 5%-10% EtOAc/Hex with a flow rate of 40 mL/min over 30 min to afford title product (1.61 g, 4.36 mmol, 40%) as an oil. LC-MS: m/z=391.1, 393.1 (M+Na$^+$)

Step II: ((2R,3S,4R,5S,6R)-3-Acetoxy-6-(3-bromophenyl)-4,5-dihydroxytetrahydro-2H-pyran-2-yl)methyl acetate To a solution of [(2R,3S,6S)-3-acetoxy-6-(3-bromophenyl)-3,6-dihydro-2H-pyran-2-yl]methyl acetate (1.60 g, 4.33 mmol) in water (3 mL) and THF (19 mL) is added methanesulfonamide (618 mg, 6.50 mmol), osmium tetroxide (1.3 mL of 2.5% w/v in t-BuOH, 0.130 mmol) and N-methylmorpholine-N-oxide (2.030 g, 17.33 mmol) and the reaction mixture is stirred at RT for 2 days. Another portion of osmium tetroxide (1.3 mL of 2.5% w/v in t-BuOH, 0.130 mmol), methanesulfonamide (618 mg, 6.50 mmol) and N-methylmorpholine-N-oxide (2.030 g, 17.33 mmol) are added and the mixture is stirred for a further 24 h. The solvent is evaporated and the crude mixture is diluted with a saturated solution of sodium bisulfite (50 mL) and extracted with EtOAc (3×15 mL). The combined organic extracts are dried over Na$_2$SO$_4$ and the solvent is evaporated. The gel-like material obtained is dissolved in a minimum amount of MeOH and diluted with diethyl ether and placed in the fridge for 2 h. The mixture is filtered and washed with diethyl ether and dried under high vacuum to afford title product (1.480 g, 85%) as a solid. LC-MS: m/z=425.1, 427.1 (M+Na$^+$)

Step III: Intermediate C ((2R,3S,4R,5S,6R)-3-Acetoxy-6-(3-bromophenyl)-4,5-dihydroxytetrahydro-2H-pyran-2-yl)methyl acetate (1.48 g) is dissolved in MeOH (20 mL) and MeONa in MeOH (187 μL of 25% w/v, 0.87 mmol) is added and the reaction mixture is stirred at RT for 4 h. The reaction mixture is neutralized by the addition of Amberlite IR120H resin until the pH changed to neutral. The reaction mixture is filtered, the filtrate is evaporated and the solid is triturated with Et$_2$O (2×10 mL) to afford the title product (1.08 g, 3.046 mmol, 70.3%) as a solid. $^1$H NMR (400 MHz, CD$_3$OD) δ 7.68 (s, 1H), 7.45 (dd, J=10.6, 4.1 Hz, 2H), 7.29 (t, J=7.9 Hz, 1H), 4.91 (d, J=4.7 Hz, 1H), 4.29 (dd, J=4.6, 3.2 Hz, 1H), 3.95-3.71 (m, 3H), 3.61 (dd, J=7.4, 3.1 Hz, 1H), 3.55-3.47 (m, 1H). LC-MS: m/z=341.1, 343.1 (M+Na$^+$).

Preparation of Intermediate D 3-((2R,3S,4R,5S,6R)-3,4,5-trihydroxy-6-(hydroxymethyl)tetrahydro-2H-pyran-2-yl)benzoic acid

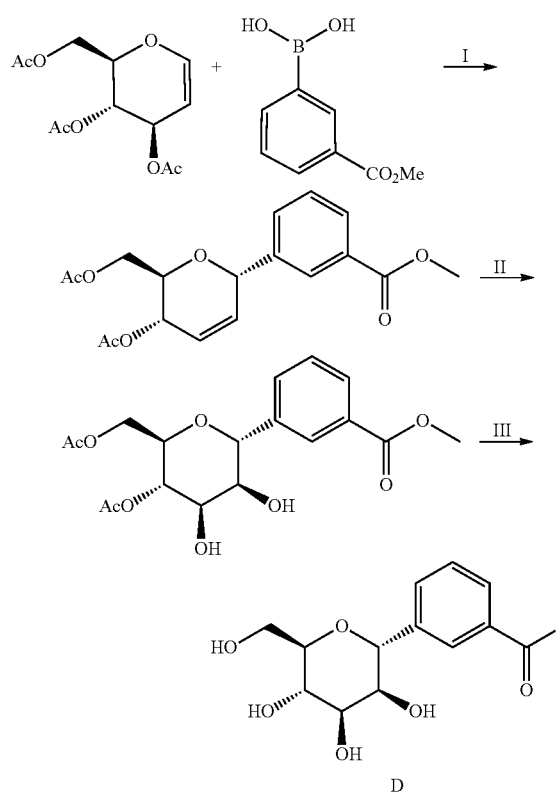

Step I: methyl 3-((2S,5S,6R)-5-acetoxy-6-(acetoxymethyl)-5,6-dihydro-2H-pyran-2-yl)benzoate Methyl 3-[(2R,3S,6S)-3-acetoxy-2-(acetoxymethyl)-3,6-dihydro-2H-pyran-6-yl]benzoate is prepared using the same procedure as described in Step I for the preparation of Intermediate C, but using (3-methoxycarbonylphenyl)boronic acid as the starting material.
LC-MS: m/z=371.2 (M+Na$^+$).

Step II: methyl 3-((2R,3S,4R,5S,6R)-5-acetoxy-6-(acetoxymethyl)-3,4-dihydroxytetrahydro-2H-pyran-2-yl)benzoate Methyl 3-[(2R,3S,4R,5S,6R)-5-acetoxy-6-(acetoxymethyl)-3,4-dihydroxy-tetrahydropyran-2-yl]benzoate is prepared using the same procedure as described in Step II for the preparation of Intermediate C. LC-MS: m/z=383.3 (M+H$^+$).

Step III: Intermediate D

A mixture of methyl 3-[(2R,3S,4R,5S,6R)-5-acetoxy-6-(acetoxymethyl)-3,4-dihydroxy-tetrahydropyran-2-yl]benzoate (2.20 g, 5.75 mmol) in MeOH (30 mL) is treated with MeONa in MeOH (341 µL of 25% w/v, 1.58 mmol) and the reaction mixture is stirred at RT for 18 h. The volatiles are evaporated, the mixture is dissolved in MeOH (30 mL), aqueous sodium hydroxide (5.1 mL of 2 M, 10.3 mmol) is added and the reaction mixture is stirred at RT for 15 h. The mixture is neutralized by the addition of Amberlite IR120H resin until the pH changed to neutral. The reaction mixture is filtered and the filtrate is evaporated to afford the title product (1.57 g, 66%) as a white solid. $^1$H NMR (400 MHz, CD$_3$OD) δ 8.15 (s, 1H), 7.96 (d, J=7.7 Hz, 1H), 7.75 (d, J=7.7 Hz, 1H), 7.51 (t, J=7.8 Hz, 1H), 4.99 (d, J=4.4 Hz, 1H), 4.42-4.36 (m, 1H), 3.93-3.74 (m, 3H), 3.63 (dd, J=7.5, 3.1 Hz, 1H), 3.54-3.49 (m, 1H). LC-MS: m/z=285.2 (M+H$^+$).

Preparation of Intermediate E ((2R,3R,4R,5R,6R)-2-(Acetoxymethyl)-6-(3-hydroxyphenyl)tetrahydro-2H-pyran-3,4,5-triyl triacetate)

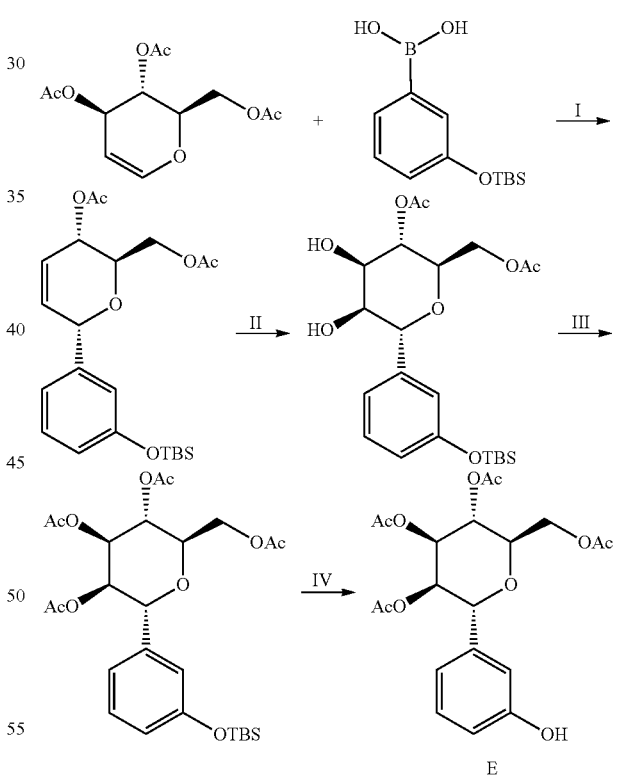

Step I: [(2R,3S,6S)-3-Acetoxy-6-[3-[tert-butyl(dimethyl)silyl]oxyphenyl]-3,6-dihydro-2H-pyran-2-yl] methyl acetate To a solution of [(2R,3S,4R)-3,4-diacetoxy-3,4-dihydro-2H-pyran-2-yl]methyl acetate (1.100 g, 4.040 mmol) in 10 mL of CH$_3$CN are added [3-(tert-butyl-dimethyl-silyl)oxyphenyl]boronic acid (2.038 g, 8.080 mmol) and Pd(OAc)$_2$ (136.1 mg, 0.6060 mmol). The mixture is stirred at RT for 5 h and then to it are added another batch of Pd(OAc)$_2$ (136 mg, 0.606 mmol) and [3-(tert-butyl-dimethyl-silyl)oxyphenyl]boronic acid (2.038 g, 8.080 mmol). It is then stirred at RT overnight. The mixture is diluted with 20 mL of CH$_2$Cl$_2$ and filtered over a pad of celite. The filtrate is concentrated and the residue is separated on Biotage™ SNAP 100 g silica gel cartridge using a gradient of EtOAc in Hex (0-20%) in 20 column volume to afford the title product (805 mg, 47%) as an oil, which solidifies upon standing. $^1$H NMR (CDCl$_3$, 400 MHz): 7.06 (m, 1H), 6.78 (m, 1H), 6.70 (m, 1H), 6.60 (m, 1H), 5.97 (m, 1H), 5.71 (m, 1H), 5.09 (m, 2H), 4.08 (m, 1H), 3.85 (m, 1H), 3.62 (m, 1H), 1.88 and 1.87 (2s, 6H), 0.78 (m, 9H), 0.00 (m, 6H).

Step II: [(2R,3S,4R,5S,6R)-3-Acetoxy-6-[3-[tert-butyl(dimethyl)silyl]oxyphenyl]-4,5-dihydroxy-tetrahydropyran-2-yl]methyl acetate To a solution of [(2R,3S,6S)-3-acetoxy-6-[3-[tert-butyl(dimethyl)silyl]oxyphenyl]-3,6-dihydro-2H-pyran-2-yl] methyl acetate (2.500 g, 5.944 mmol) in water (10 mL)/t-BuOH (10 mL) are added methanesulfonamide (848.0 mg, 8.92 mmol), 2.5% OsO$_4$/t-BuOH (1.9 mL, 0.149 mmol), NMO (1.393 g, 11.89 mmol) and lutidine (689 µL, 5.94 mmol). The mixture is stirred at RT overnight. It is then quenched with 15% sodium bisulfite (15 mL) and diluted with EtOAc (40 mL). The aqueous phase is then separated, washed with water (20 mL) and brine (20 mL) consecutively, dried over Na$_2$SO$_4$. After removal of the solvent under reduced pressure, the residue is purified on Biotage™ SNAP 100 g silica gel cartridge using a gradient of MeOH in CH$_2$Cl$_2$ (0-6%) in 20 column volume to afford the title compound (2.20 g, 81%) as an oil. $^1$H NMR (CD$_3$OD, 400 MHz): 7.06 (m, 1H), 6.78 (m, 1H), 6.70 (m, 1H), 6.58 (m, 1H), 4.85 (m, 1H), 4.64 (m, 1H), 4.46 (m, 1H), 3.96 (m, 1H), 3.85 (m, 1H), 3.62 (m, 2H), 1.86 and 1.83 (2s, 6H), 0.78 (m, 9H), 0.00 (m, 6H).

Step III: (2R,3R,4R,5R,6R)-2-(Acetoxymethyl)-6-(3-((tert-butyldimethylsilyl)oxy)phenyl)tetrahydro-2H-pyran-3,4,5-triyl triacetate To a solution of [(2R,3S,4R,5R,6R)-3-acetoxy-6-[3-[tert-butyl(dimethyl)silyl]oxyphenyl]-4,5-dihydroxy-tetrahydropyran-2-yl]methyl acetate (1.00 g, 2.20 mmol) in methylene chloride (20 mL) at 0° C., under N$_2$, is added 2,6-lutidine (872 µL, 6.60 mmol) followed by DMAP (53.8 mg, 0.44 mmol) & acetic anhydride (623 µL, 6.60 mmol). The yellow solution is stirred at 0° C. for 1.5 h. TLC (30% EtOAc/hex) showed complete consumption of starting material. The reaction is treated with KHSO$_4$ (15%, 2×6 mL) then washed with brine, dried & evaporated. The crude material is purified on Biotage™ SNAP silica gel cartridge using EtOAc-Hex (0-5%, 3 CV; 5-30%, 20 CV) as eluent to afford the title product (1.02 g) as a clear gum.

Step IV: Intermediate E

To a stirred solution of [(2R,3R,4R,5R,6R)-3,4,5-triacetoxy-6-[3-[tert-butyl(dimethyl)silyl]oxyphenyl]tetrahydropyran-2-yl]methyl acetate (1.02 g, 1.799 mmol) in THF (10 mL) are added acetic acid (162.0 mg, 153 µL, 2.698 mmol) and TBAF (5.4 mL of 1 M, 5.397 mmol). The mixture is stirred at RT for 30 min. It is then diluted with EtOAc (30 mL), washed with water (20 mL) and brine (20 mL), dried over sodium sulfate, and concentrated. The crude material is purified on Biotage™ SNAP 25 g silica gel column using EtOAc in Hex (5%, 5 CV; 5-30%, 25 CV; 30-40% 5 CV, 40-50%, 30 CV) as eluent to afford the title product (409 mg, 48.35%) as white foam. $^1$H NMR (400 MHz, CD$_3$OD) δ 7.23 (t, 1H), 6.92 (dd, 2H), 6.76 (dd, 1H), 5.86 (t, 1H), 5.24 (t, 1H), 5.10 (dd, 1H), 5.01 (d, 1H), 4.37 (dd, 1H), 4.13 (dd, 1H), 3.86-3.66 (m, 1H), 2.08 (d, 6H), 2.02 (d, 6H).

Preparation of Intermediate F ((2R,3R,4R,5R,6R)-2-(Acetoxymethyl)-6-(4-ethynylphenyl)tetrahydro-2H-pyran-3,4,5-triyl triacetate)

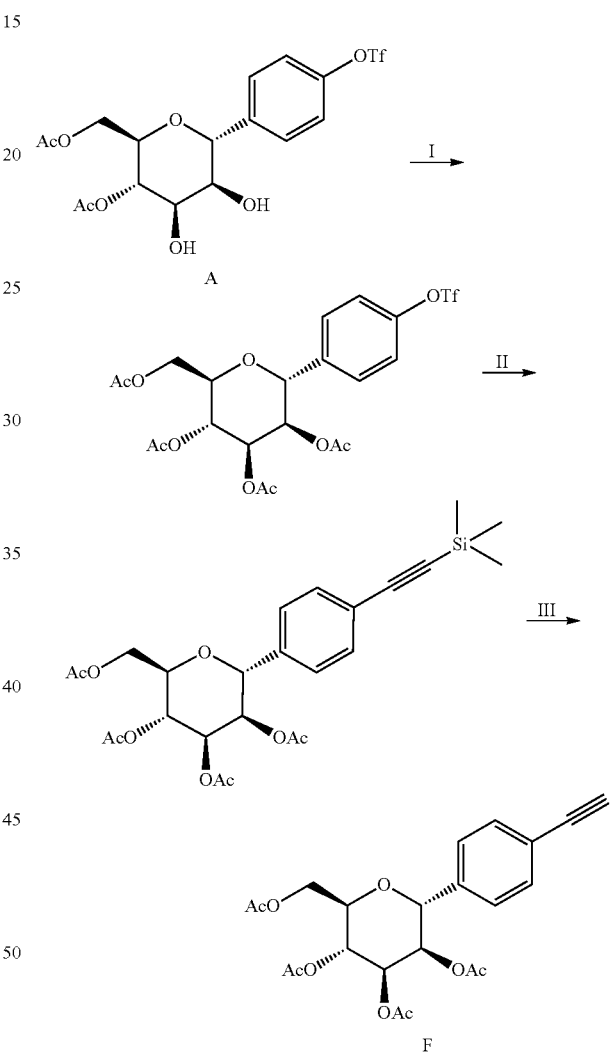

Step I: [(2R,3R,4R,5R,6R)-3,4,5-Triacetoxy-6-[4-(trifluoromethylsulfonyloxy)phenyl]tetrahydropyran-2-yl]methyl acetate To a solution of (2R,3S,4R,5S,6R)-3-acetoxy-4,5-dihydroxy-6-[4-(trifluoromethylsulfonyloxy)phenyl]tetrahydropyran-2-yl]methyl acetate (256 mg, 0.542 mmol) in 2.6 mL of CH$_2$Cl$_2$ is sequentially added pyridine (132 µL, 1.63 mmol), Ac$_2$O (128 µL, 1.36 mmol) and DMAP (6.6 mg, 0.054 mmol). The reaction mixture is stirred at RT for 2 h, diluted with water (1 mL) and the organic layer is dried over Na$_2$SO$_4$, filtered, and concentrated to dryness. The residue is purified by flash column chromatography on silica gel (10 to 80% EtOAc in Hex) to give title product (232 mg, 77%).

Step II: (2R,3R,4R,5R,6R)-2-(Acetoxymethyl)-6-(4-((trimethylsilyl)ethynyl)phenyl)tetrahydro-2H-pyran-3,4,5-triyl triacetate To a mixture of [(2R,3R,4R,5R,6R)-3,4,5-triacetoxy-6-[4-(trifluoromethylsulfonyloxy)phenyl]tetrahydropyran-2-yl]methyl acetate (1217 mg, 2.187 mmol), Pd(dppf)Cl$_2$—CH$_2$Cl$_2$ (178.6 mg, 0.2187 mmol) and CuI (83.3 mg, 0.437 mmol) in 12 mL of DMF is added Et$_3$N (1.5 mL, 11 mmol) followed by ethynyl(trimethyl)silane (1.54 mL, 10.9 mmol). The reaction mixture is heated at 70° C. in a sealed tube for 21 h, cooled to RT, and diluted with water (40 mL). The reaction mixture is extracted by EtOAc (5×20 mL), and the combined organic layer are washed with water (3×10 mL), 10 mL of brine, dried over Na$_2$SO$_4$, filtered, and concentrated to dryness. The residue is purified by flash column chromatography on silica gel (10 to 80% EtOAc in Hex) to give title product (1.0596 g, 96%).

Step III: Intermediate F

To a solution of (2R,3R,4R,5R,6R)-2-(acetoxymethyl)-6-(4-((trimethylsilyl)ethynyl)phenyl)tetrahydro-2H-pyran-3,4,5-triyl triacetate (1.054 g, 2.089 mmol) in 21 mL of THF is sequentially added AcOH (150.6 mg, 143 µL, 2.507 mmol) and TBAF 1M in THF (2.298 mL of 1 M, 2.298 mmol) under nitrogen atmosphere. The reaction mixture is stirred at RT for 2 h, and concentrated to dryness. The residue is purified by flash column chromatography on silica gel (10 to 80% EtOAc in Hex) to give the title compound (892 mg, 99%).

Preparation of Intermediate G ((2R,3R,4R,5R,6R)-3,4,5-Tribenzyloxy-2-(benzyloxymethyl)-6-ethynyl-tetrahydropyran)

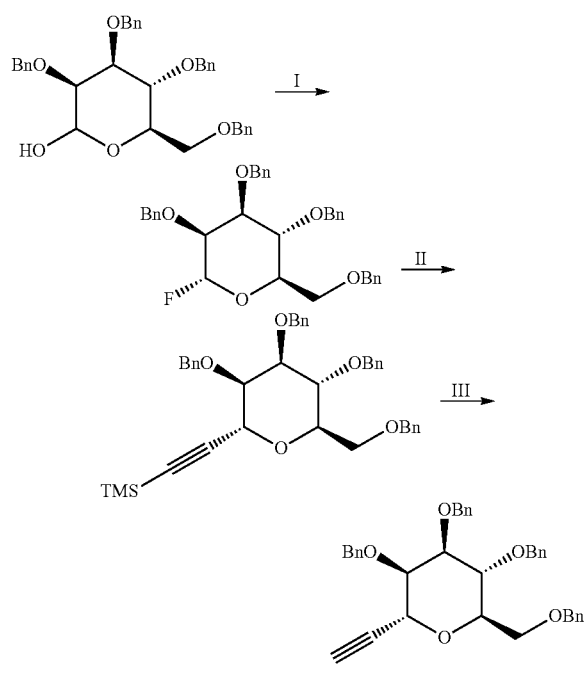

Step I: (2R,3R,4S,5S,6R)-3,4,5-tribenzyloxy-2-(benzyloxymethyl)-6-fluoro-tetrahydropyran To a solution of (3S,4S,5R,6R)-3,4,5-tribenzyloxy-6-(benzyloxymethyl)tetrahydropyran-2-ol (10.8 g, 19.98 mmol) and (diethylamino)difluorosulfonium tetrafluoroborate (7.075 g, 29.97 mmol) in 50 mL of CH$_2$Cl$_2$ is added DBU (4.8 mL, 32.1 mmol) at −15° C. and then stirred for 20 min. The reaction is quenched with saturated sodium bicarbonate solution. Then the mixture is extracted with CH$_2$Cl$_2$ (3×20 mL). The combined organic extracts are washed with water and brine consecutively, dried over sodium sulfate, filtered, and concentrated to dryness. The residue is separated on Biotage™ SNAP 100 g silica gel cartridge using a gradient of EtOAc in Hex (0-15%, 20 CV) to obtain a major fraction containing title product (6.40 g). LC-MS: m/z=565.4 (M+Na$^+$).

Step II: Trimethyl-[2-[(2R,3R,4R,5R,6R)-3,4,5-tribenzyloxy-6-(benzyloxymethyl) tetrahydropyran-2-yl]ethynyl]silane To a solution of (2R,3R,4S,5S,6R)-3,4,5-tribenzyloxy-2-(benzyloxymethyl)-6-fluoro-tetrahydropyran (1120 mg, 2.064 mmol) and trifluoro(2-trimethylsilylethynyl)boranuide (Potassium Ion (1)) (547.6 mg, 2.683 mmol) in CH$_3$CN (15 mL) is added BF$_3$.OEt$_2$ (351.6 mg, 306 µL, 2.48 mmol) at −10° C. and the mixture is stirred under nitrogen for 20 min at the same temperature. Then it is diluted with EtOAc (30 mL), quenched with saturated sodium bicarbonate solution, washed with water and brine consecutively, dried over sodium sulfate, concentrated to dryness. The residue is separated on Biotage™ SNAP 50 g silica gel cartridge using a gradient of EtOAc in Hex (0-15%, 20 CV) to obtain title product (1.06 g) as oil.

Step III: Intermediate G

To a solution of trimethyl-[2-[(2R,3R,4R,5R,6R)-3,4,5-tribenzyloxy-6-(benzyloxymethyl)tetrahydropyran-2-yl]ethynyl]silane (550 mg, 1.0 mmol) in THF (10 mL) is added 1M TBAF/THF (1.5 mL of 1 M, 1.500 mmol). The mixture is stirred at RT for 20 min. Then it is diluted with EtOAc (30 mL), washed with water and brine consecutively, dried with sodium sulfate, filtered and concentrated to dryness. The residue is separated on Biotage™ SNAP 25 g silica gel cartridge using a gradient of EtOAc in Hex 0-15% in 20 CV to obtain (2R,3R,4R,5R,6R)-3,4,5-tribenzyloxy-2-(benzyloxymethyl)-6-ethynyl-tetrahydropyran (450 mg) as an oil. $^1$H NMR (400 MHz, CDCl$_3$) δ 7.44-7.20 (m, 18H), 7.19-7.11 (m, 2H), 4.87 (d, 1H), 4.81 (t, 1H), 4.74 (d, 1H), 4.58 (m, 6H), 4.09-3.91 (m, 3H), 3.85-3.68 (m, 3H), 2.49 (d, 1H).

Preparation of Intermediate H ([(2R,3R,4R,5R,6R)-3,4,5-Triacetoxy-6-allyl-tetrahydropyran-2-yl]methyl acetate)

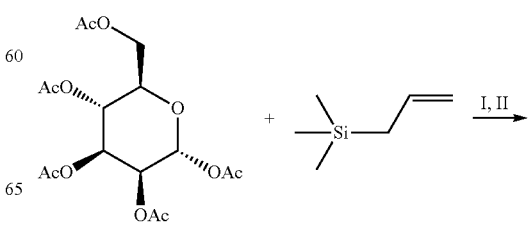

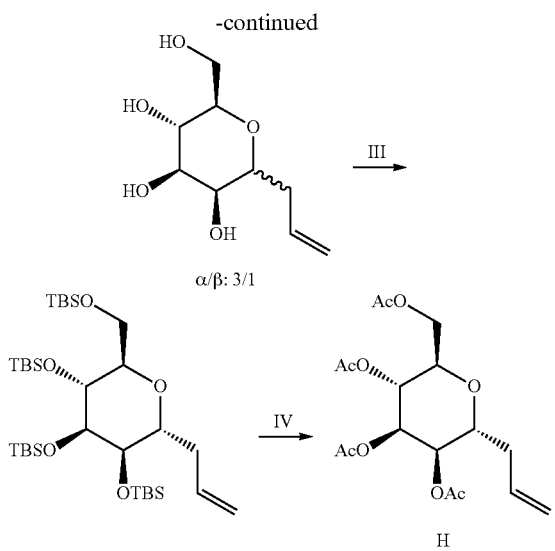

Step I: (2R,3R,4R,5R)-2-(Acetoxymethyl)-6-allyltetrahydro-2H-pyran-3,4,5-triyl triacetate To a stirred solution of [(2R,3R,4S,5S,6R)-3,4,5,6-tetraacetoxytetrahydropyran-2-yl]methyl acetate (5 g, 12.81 mmol) and allyl-trimethyl-silane (6.1 mL, 38.43 mmol) in $CH_3CN$ (30 mL) is added $BF_3.EtO_2$ (Ether (1)) (8.12 mL, 64.05 mmol) at 0° C. The mixture is stirred at RT for 2 days, poured into a saturated solution of $NaHCO_3$ and stirred till bubbling stops. It is then extracted with $CH_2Cl_2$. The combined organic extracts are washed with water and brine consecutively, dried with sodium sulfate, filtered, and concentrated to dryness. The residue is purified on Biotage™ SNAP 100 g silica gel cartridge using a gradient of EtOAc in Hex 0-50% in 20 column volume to obtain title product (2.2 g, 46%), which contains α/β~3:1. $^1H$ NMR (400 MHz, $CDCl_3$) δ 5.76 (ddt, 1H), 5.40-4.97 (m, 5H), 4.28 (ddd, 1H), 4.21-3.96 (m, 2H), 3.96-3.81 (m, 1H), 2.57-2.33 (m, 2H), 2.18-1.94 (m, 12H).

Step II: (3S,4R,5S,6R)-2-Allyl-6-(hydroxymethyl)tetrahydro-2H-pyran-3,4,5-triol To a stirred solution of (2R,3R,4R,5R)-2-(acetoxymethyl)-6-allyltetrahydro-2H-pyran-3,4,5-triyl triacetate (3.9 g, 10.47 mmol) in MeOH (22.5 mL) is added 25% wt./v MeONa in MeOH (241 µL, 1.047 mmol). The mixture is stirred at RT overnight, neutralized with resin Amberlite 120 (H). After filtration, the filtrate is concentrated to dryness and the residue separated on Biotage™ SNAP 50 g silica gel cartridge using a gradient of MeOH in $CH_2Cl_2$ (0-20%) in 24 column volume to obtain title product (1.9 g, 89%). $^1H$ NMR (400 MHz, $CD_3OD$) δ 5.95-5.69 (m, 1H), 5.08 (ddd, 2H), 3.94-3.81 (m, 1H), 3.81-3.54 (m, 5H), 3.50-3.37 (m, 1H), 2.53-2.40 (m, 1H), 2.34 (dq, 1H).

Step III: [(2R,3R,4R,5R,6R)-2-Allyl-3,5-bis[[tert-butyl(dimethyl)silyl]oxy]-6-[[tert-butyl(dimethyl)silyl]oxymethyl]tetrahydropyran-4-yl]oxy-tert-butyl-dimethyl-silane To (3S,4R,5S,6R)-2-allyl-6-(hydroxymethyl)tetrahydro-2H-pyran-3,4,5-triol (1.9 g, 9.30 mmol) in $CH_2Cl_2$ (90 mL) is added DIPEA (8.10 mL, 46.52 mmol) followed by TBDMSOTf (9.40 mL, 40.94 mmol). The reaction mixture is stirred at RT overnight, then diluted with $CH_2Cl_2$, washed with a saturated solution of $CuSO_4$, $H_2O$, and brine. The organic phase is dried over $Na_2SO_4$, filtered and dried. The crude residue is purified by Biotage™ SNAP 100 g silica gel cartridge using EtOAc in Hex 0 to 2% in 24CV to afford title product (4 g, 65%). $^1H$ NMR (400 MHz, $CDCl_3$) δ 5.89 (tt, 1H), 5.18-4.83 (m, 2H), 3.98-3.82 (m, 2H), 3.82-3.67 (m, 4H), 3.63 (t, 1H), 2.46 (dd, 1H), 2.00 (d, 1H), 1.10-0.66 (m, 36H), 0.28--0.28 (m, 24H).

Step IV: Intermediate H

To a solution of [(2R,3R,4R,5R,6R)-2-allyl-3,5-bis[[tert-butyl(dimethyl)silyl]oxy]-6-[[tert-butyl(dimethyl)silyl]oxymethyl]tetrahydropyran-4-yl]oxy-tert-butyl-dimethyl-silane (4 g, 6.05 mmol) in dry DMSO (35 mL) under $N_2$, is added TBAF (26.6 mL of 1 M in THF, 26.62 mmol) and the RM is stirred for 3 h at 60° C. The reaction is cooled down to RT, pyridine (5.38 mL, 66.54 mmol), acetic anhydride (5.7 mL, 60.49 mmol) and catalytic DMAP (36.94 mg, 0.30 mmol) are added and stirring is continued for 20 h. The reaction is slowly poured into ice/water and extracted with EtOAc. The organic layer is carefully washed with a saturated solution of $NaHCO_3$, $H_2O$, and brine. The organic phase is dried over $Na_2SO_4$, filtered and dried to afford the title compound (2.00 g, 89%). $^1H$ NMR (400 MHz, $CDCl_3$) δ 5.76 (ddt, 1H), 5.35-4.99 (m, 5H), 4.31 (dd, 1H), 4.20-3.94 (m, 2H), 3.94-3.71 (m, 1H), 2.60-2.48 (m, 1H), 2.47-2.29 (m, 1H), 2.23-1.91 (m, 12H).

Preparation of Intermediate I ([(2R,3R,4R,5R,6R)-3,4,5-Triacetoxy-6-(3-bromophenyl)tetrahydropyran-2-yl]methyl acetate)

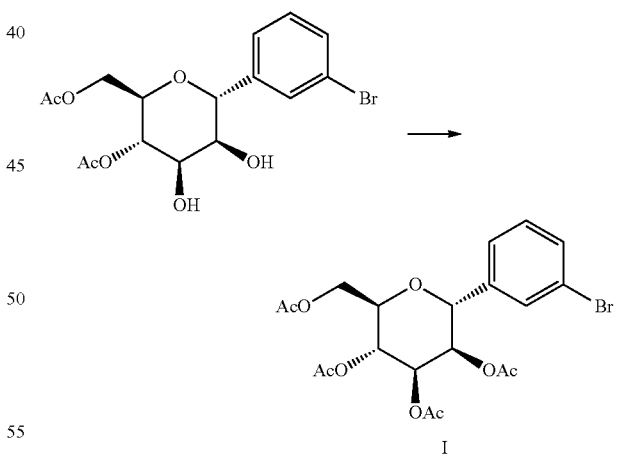

To a solution of [(2R,3S,4R,5S,6R)-3-acetoxy-6-(3-bromophenyl)-4,5-dihydroxy-tetrahydropyran-2-yl]methyl acetate (604.8 mg, 1.5 mmol) in THF (10 mL) are added DIPEA (969.3 mg, 1.31 mL, 7.50 mmol), DMAP (18.3 mg, 0.150 mmol) and $Ac_2O$ (536.0 mg, 495 L, 5.25 mmol) at 0° C. The mixture is stirred at RT overnight. Then it is quenched with saturated sodium bicarbonate solution. The mixture is extracted with $CH_2Cl_2$ (3×15 mL). The combined organic extracts are washed with water and brine consecutively, dried over sodium sulfate, filtered, and concentrated to dryness. The residue is separated on Biotage™ SNAP 25 g silica gel cartridge using a gradient of EtOAc in Hex 0-30% in 20 column volume to obtain title product (650 mg, 1.334 mmol, 88.9%). $^1$H NMR (400 MHz, CDCl$_3$) δ 7.66 (s, 1H), 7.55-7.45 (m, 1H), 7.41 (dd, 1H), 7.29 (t, 1H), 5.87 (t, 1H), 5.28 (t, 1H), 5.10 (dd, 1H), 5.04 (d, 1H), 4.36 (dd, 1H), 4.14 (dd, 1H), 3.86-3.66 (m, 1H), 2.13 (2s, 6H), 2.05 (s, 3H), 2.02 (s, 3H)

Preparation of Intermediate J (2-[(2R,3R,4R,5R,6R)-3,4,5-Triacetoxy-6-(acetoxymethyl)tetrahydropyran-2-yl]acetic acid)

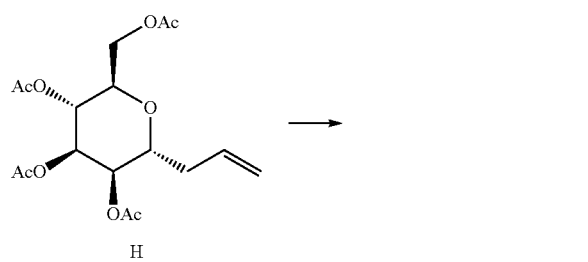

To a solution of Intermediate H (220 mg, 0.590 mmol) in a mixture of CH$_3$CN (1.1 mL)/CCl$_4$ (1.1 mL)/H$_2$O (1.9 mL) is added NaIO$_4$ (147.1 µL, 2.66 mmol) followed by Cl$_3$Ru (Water (1)) (53.27 mg, 0.234 mmol). The reaction mixture is stirred at RT for 4 h, diluted with water and CH$_2$Cl$_2$, filtered on celite, washed with CH$_2$Cl$_2$. The aqueous phase is extracted twice with CH$_2$Cl$_2$. Combined organic phases are dried over Na$_2$SO$_4$, filtered and concentrated to afford title product (110 mg, 74%) which is used in the next step without further purification. LC-MS: m/z=391.3 (M+H$^+$).

Preparation of Intermediate K ((2R,3S,4R,5S,6R)-2-(3-Ethynylphenyl)-6-(hydroxymethyl)tetrahydropyran-3,4,5-triol)

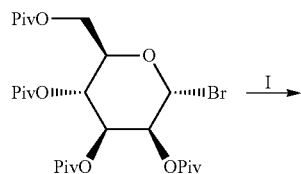

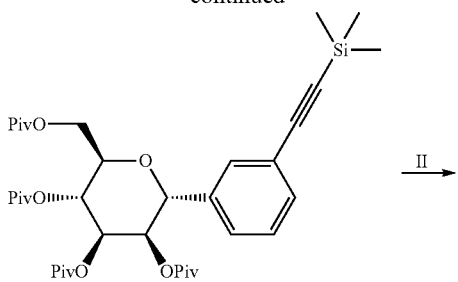

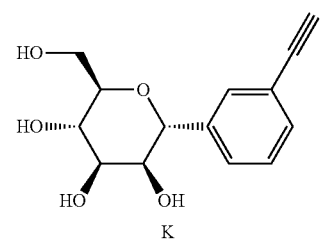

Step I: [(2R,3R,4R,5R,6R)-3,4,5-Tris(2,2-dimethylpropanoyloxy)-6-[3-(2-trimethylsilylethynyl)phenyl]tetrahydropyran-2-yl]methyl 2,2-dimethylpropanoate A solution of n-Bu$_3$MgLi (2.65 mL of 0.65 M, 1.725 mmol) in Hex-heptane-dibutylether (8:20:3) is added to 2-(3-bromophenyl)ethynyl-trimethyl-silane (1.248 g, 1.05 mL, 4.928 mmol) in toluene (2.4 mL) and dibutylether (1.4 mL) at 0° C. and stirred in cold room for 25 h. A solution of ZnBr$_2$—LiBr in dibutyl ether (2.6 mL of 1.05 M, 2.711 mmol) is added dropwise, cooling bath removed, stirred at RT for 1 h. A solution of [(2R,3R,4S,5S,6R)-6-bromo-3,4,5-tris(2,2-dimethylpropanoyloxy)tetrahydropyran-2-yl] methyl 2,2-dimethylpropanoate (2.38 g, 4.107 mmol) in toluene (4.3 mL) is added, it is placed on pre-heated oil bath at 90° C. for weekend. The reaction mixture is cooled to RT, it is poured into aqueous 1 N HCl solution (40 mL) and extracted with EtOAc (3×40 mL). The combined extracts are washed with brine, dried (Na$_2$SO$_4$), concentrated, purified on Biotage™ SNAP 100 g silica gel cartridge using EtOAc in Hex (0% to 10%, 12 CV, 10%, 5 CV) as eluent to afford title product (765 mg) as an oil.

Step II: Intermediate K

To a stirred light suspension of [(2R,3R,4R,5R,6R)-3,4,5-tris(2,2-dimethylpropanoyloxy)-6-[3-(2-trimethylsilylethynyl)phenyl]tetrahydropyran-2-yl]methyl 2,2-dimethylpropanoate (765 mg, 1.137 mmol) in MeOH (15 mL) is added MeONa (4.6 mL of 0.5 M, 2.274 mmol) and stirred at RT for 24 h. To the resultant solution is added DOWEX 50WX4-400 until pH 4-5, filtered, eluted with MeOH. The filtrate is concentrated, purified on Biotage™ SNAP 40 g silica gel cartridge using EtOAc-MeOH—H$_2$O (47.5:1.5:1 to 10:1.5:1) as eluent to afford title product (170 mg, 55%) as beige solid. LC-MS: m/z=265.28 (M+H$^+$).

Preparation of Intermediate L

[(2R,3R,4R,5R,6R)-3,4,5-tris(triisopropylsilyloxy)-6-(2-trimethylsilylethynyl)tetrahydropyran-2-yl]methanol

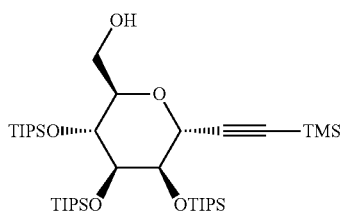

Intermediate L is prepared according to the procedure described in Jurgen Stichler-Bonaparte et. al. Helv. Chim. Acta. 2001, 84(8), 2355-2367),

Preparation of Intermediate M (2R,3S,4R,5S,6R)-2-ethynyl-6-(hydroxymethyl)tetrahydropyran-3,4,5-triol

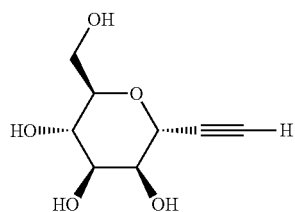 [SMILES: C#C[C@H]1O[C@H](CO)[C@@H](O)[C@H](O)[C@@H]1O]

Intermediate M is prepared according to the procedure described in Jurgen Stichler-Bonaparte et. al. Helvetica Chimica Acta, 2001, 84(8), 2355-2367

Preparation of Intermediate N

[(2R,3R,4R,5R,6R)-6-(4-bromophenyl)-3,4,5-tris(2,2-dimethylpropanoyloxy)tetrahydropyran-2-yl]methyl 2,2-dimethylpropanoate

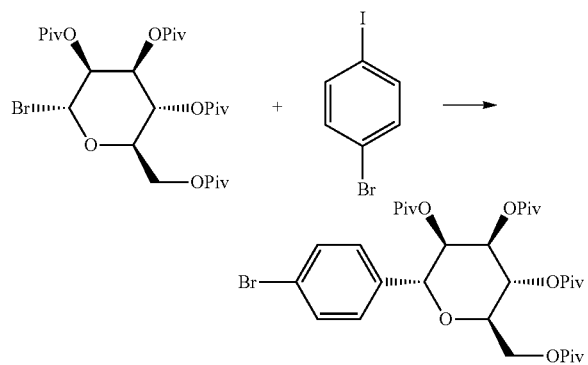

A solution of n-Bu$_3$MgLi (2.20 mL of 0.66 M, 1.45 mmol) in hexane-heptane-dibutyl ether (8:20:3) is added to 1-bromo-4-iodo-benzene (1.172 g, 4.141 mmol) in toluene (2.0 mL) and dibutyl ether (1.2 mL) at 0° C. The mixture is stirred at the same temperature for 3.5 h, then a solution of ZnBr$_2$—LiBr in dibutyl ether (2.17 mL of 1.05 M, 2.28 mmol) is added dropwise. The cooling bath is removed and the mixture is stirred at RT for 1 h then a solution of [(2R,3R,4S,5S,6R)-6-bromo-3,4,5-tris(2,2-dimethylpropanoyloxy)tetrahydropyran-2-yl]methyl 2,2-dimethylpropanoate (2.00 g, 3.45 mmol) in toluene (3.60 mL) is added. The final mixture is placed on pre-heated oil bath at 90° C. for 4 h (TLC showed lots of starting material), continued at 100° C. for 22 h. The resulting mixture is cooled to RT, poured into aqueous 1N HCl solution (40 mL), extracted with EtOAc (3×25 mL). The combined organic extracts are washed with brine, dried over Na$_2$SO$_4$, concentrated, purified on Biotage™ SNAP 100 g silica gel cartridge using EtOAc-Hex (0% to 15%, 8 CV) as eluent afforded the title compound (1.00 g, 44%). (Ref. Sebastien Lemaire et. al. Org. Letts. 2012, 14, 1480-1483)

Preparation of Intermediate O (2R,3R,4R,5R,6R)-2-(acetoxymethyl)-6-(3-(4,4,5,5-tetramethyl-1,3,2-dioxaborolan-2-yl)phenyl)tetrahydro-2H-pyran-3,4,5-triyl triacetate

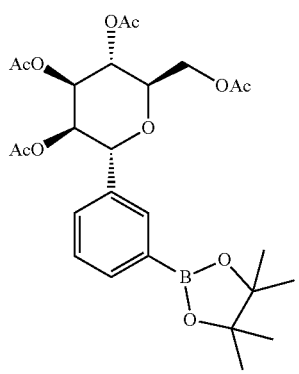 [SMILES: CC(=O)OC[C@H]1O[C@H](c2cccc(B3OC(C)(C)C(C)(C)O3)c2)[C@@H](OC(C)=O)[C@@H](OC(C)=O)[C@@H]1OC(C)=O]

Intermediate I (6.640 g, 13.63 mmol) is dissolved in DMF (100 mL) and the mixture is degassed 3 times with house vacuum and N$_2$. 4,4,5,5-tetramethyl-2-(4,4,5,5-tetramethyl-1,3,2-dioxaborolan-2-yl)-1,3,2-dioxaborolane (5.191 g, 20.44 mmol), KOAc (5.351 g, 54.52 mmol) and Pd(dppf)Cl$_2$.CH$_2$Cl$_2$ (1.113 g, 1.363 mmol) are added and the mixture is heated to 60° C. for 24 hrs. The resulting mixture is cooled down to RT and filtered on Celite. The DMF fraction is washed with Hex (3×100 mL), diluted with EtOAc (300 mL). The organic layer is washed with 100 mL of aqueous NH$_4$Cl (20%), water (2×100 mL), brine, dried over Na$_2$SO$_4$ then evaporate to dryness. The residue is purified Biotage™ SNAP 340 g silica gel cartridge using EtOAc-Hex (7 to 60%) as eluent to afford title product contaminated with dioxaborolane. The residue is triturated in heptane at 0° C. and the resulting oil is isolated by decantation and finally dried under vacuum to afford the title compounds as colorless oil (7.512 g). LC-MS: m/z=557.4 (M+Na$^+$).

Preparation of Intermediate P ((2R,3R,4R,5R,6R)-6-ethynyl-3,4,5-tris((triisopropylsilyl)oxy)tetrahydro-2H-pyran-2-yl)methanol

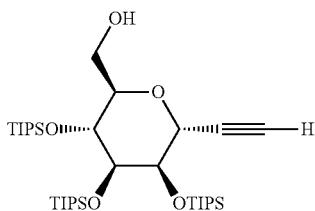

To a solution of Intermediate L (1.02 g, 1.40 mmol) in MeOH (10 mL) is added $K_2CO_3$ (386 mg, 2.80 mmol). After stirring for 1 h, the reaction is treated with prewashed Dowex 50WX4-400 resin, filtered and washed with portions of MeOH. The combined filtrates are concentrated to provide a colorless gum which is purified by flash chromatography on a Biotage™ SNAP 25 g cartridge, using a gradient of EtOAc in Hex, 0-20% as eluent. Combined fractions concentrated to provide the title compound as a colorless (878 mg, 96% yield).

Preparation of Intermediate Q (2R,3R,4R,5R,6R)-2-(4-bromo-2-methylphenyl)-6-((pivaloyloxy)methyl)tetrahydro-2H-pyran-3,4,5-triyl tris(2,2-dimethylpropanoate)

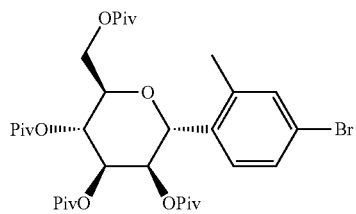

Intermediate Q is prepared according to the procedure described for Intermediate N but using 4-bromo-1-iodo-2-methyl-benzene as starting material.

Preparation of Intermediate R (2R,3R,4R,5R,6R)-2-(2-methyl-4-(4,4,5,5-tetramethyl-1,3,2-dioxaborolan-2-yl)phenyl)-6-((pivaloyloxy)methyl)tetrahydro-2H-pyran-3,4,5-triyl tris(2,2-dimethylpropanoate)

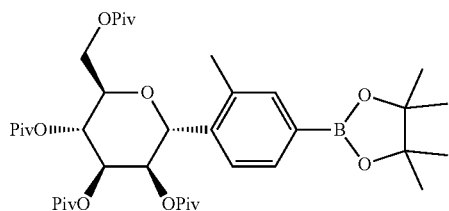

Intermediate R is prepared according to the procedure described for Intermediate O but using Intermediate Q as starting material.

The following is a list of key Intermediates which are used in the preparation of Compounds described therein:

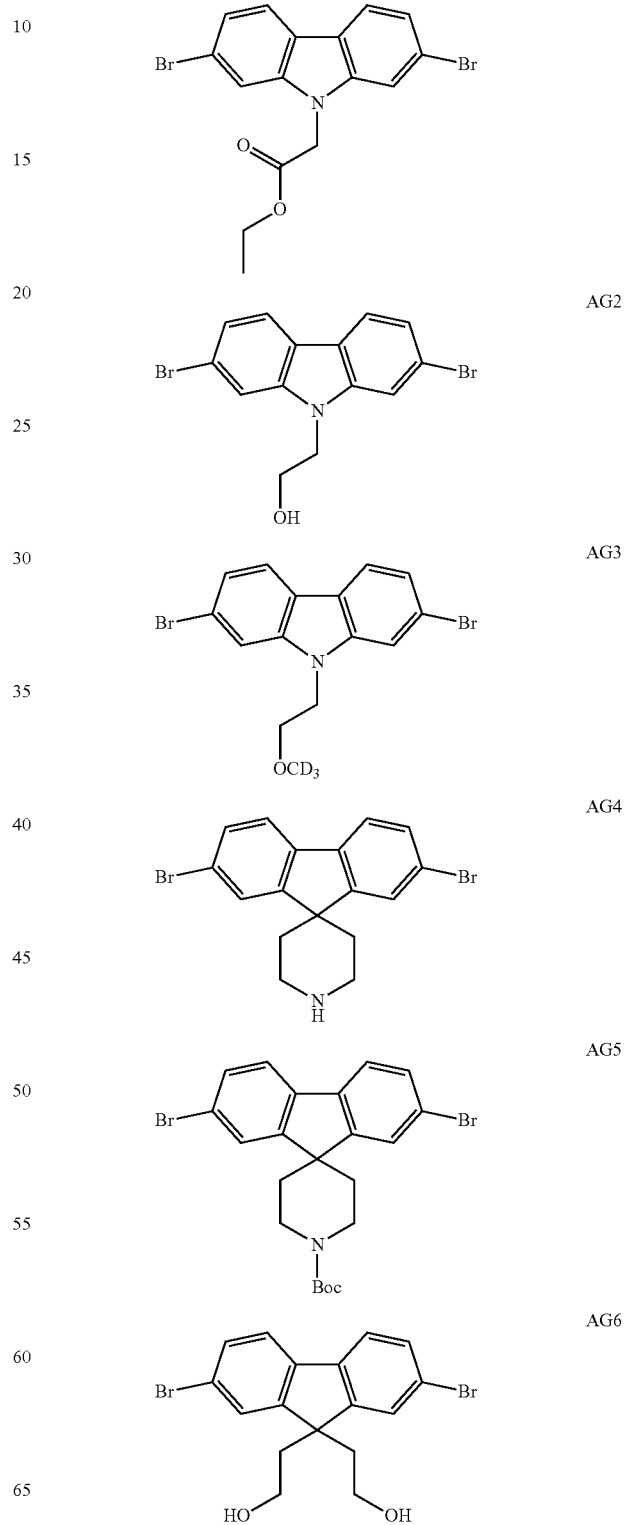

| | |
|---|---|
| AG7 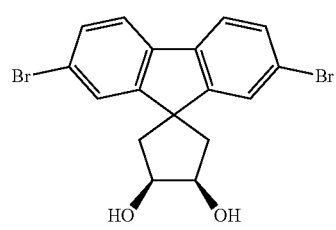 | AG13 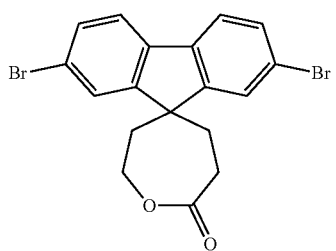 |
| AG8 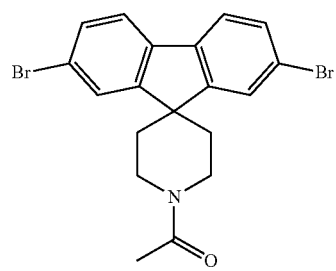 | AG14 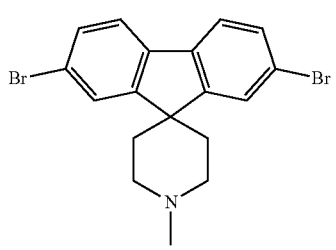 |
| AG9 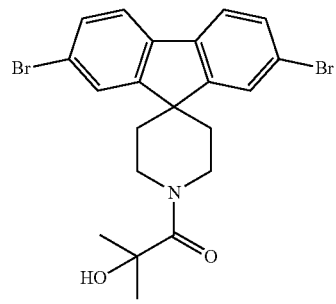 | AG15 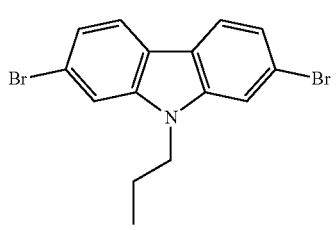 |
| AG10 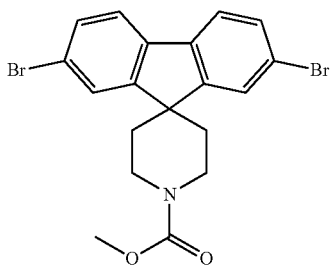 | AG16 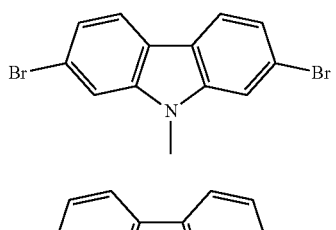 |
| AG11 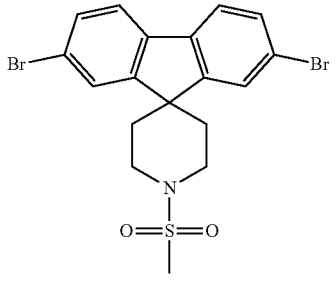 | AG17 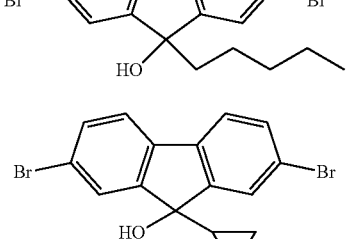 |
| | AG18 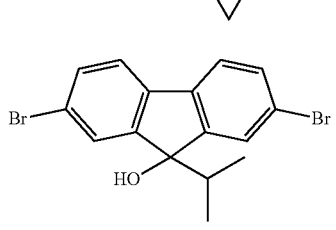 |
| | AG19 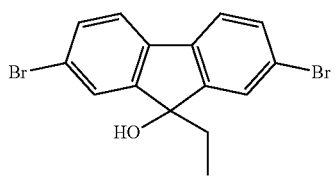 |
| AG12 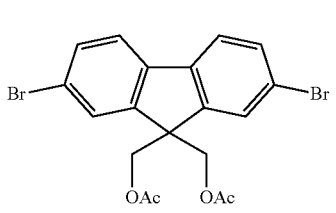 | AG20 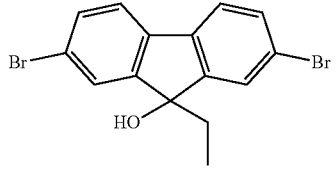 |

-continued
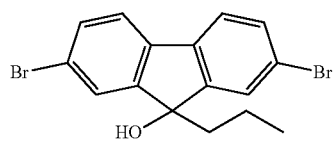 AG21
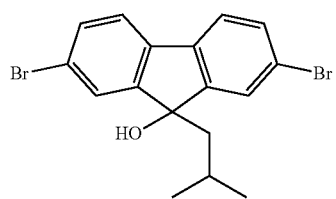 AG22
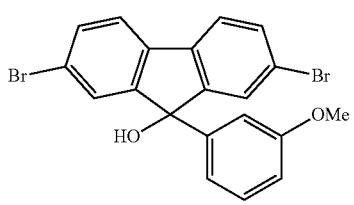 AG23
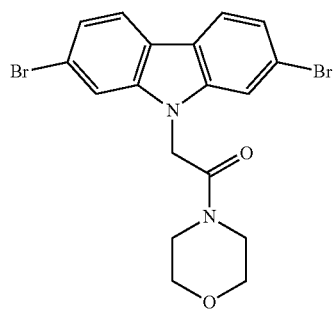 AG24
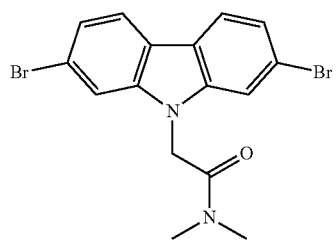 AG25
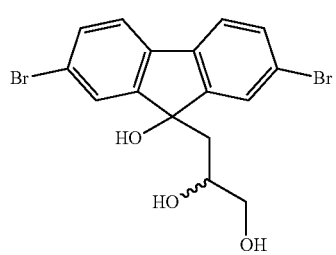 AG26
-continued
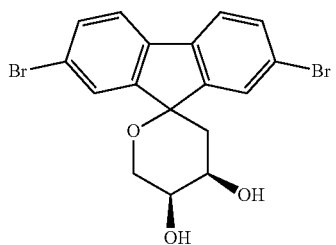 AG27
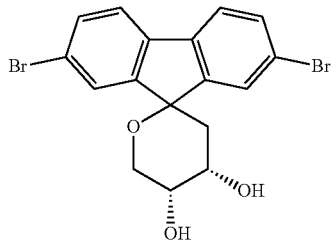
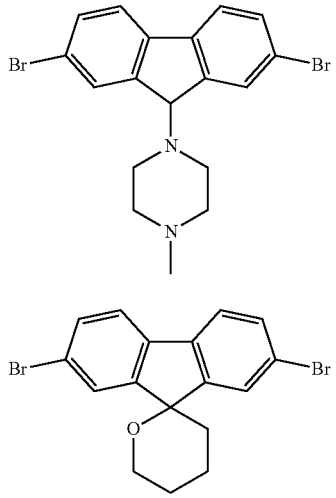 AG28
AG29
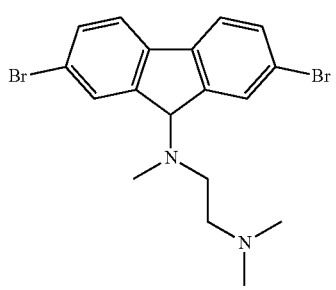 AG30
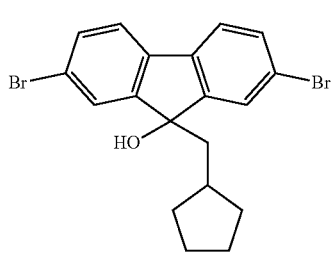 AG31

| | |
|---|---|
| 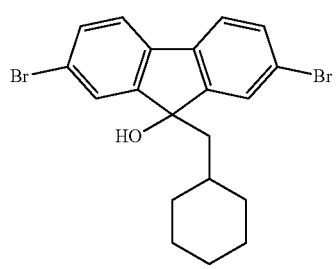 AG32 | 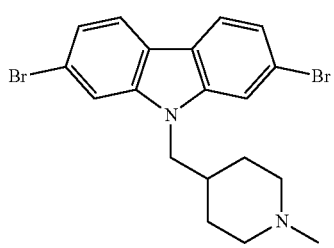 AG38 |
| 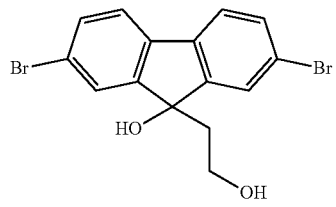 AG33 | 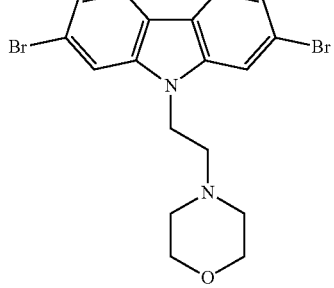 AG39 |
| 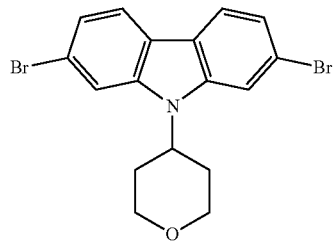 AG34 | 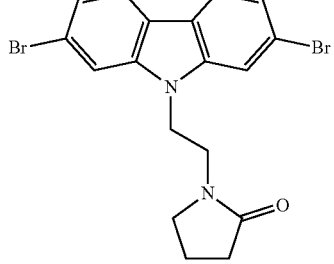 AG40 |
| 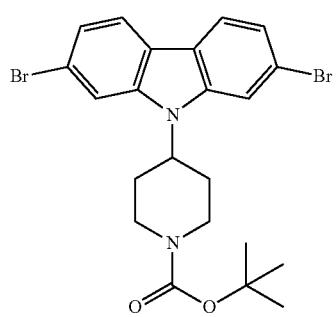 AG35 | 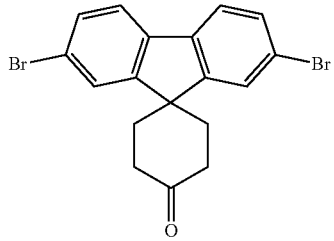 AG41 |
| 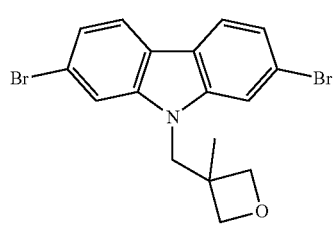 AG36 | 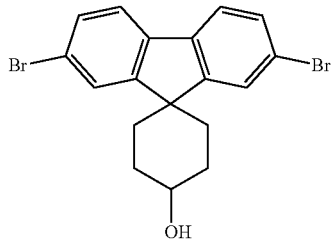 AG42 |
| 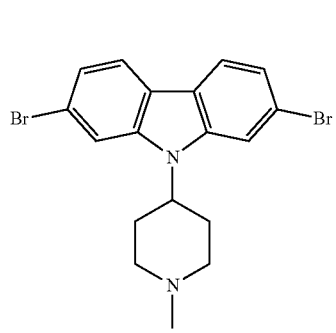 AG37 | 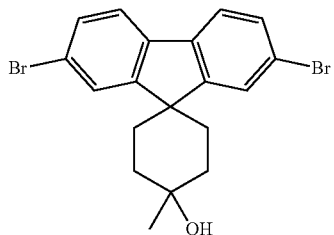 AG43 |

-continued

AG44

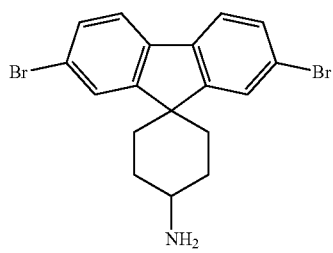

Preparation of Intermediate AG1

Ethyl 2-(2,7-dibromocarbazol-9-yl)acetate

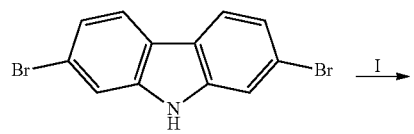

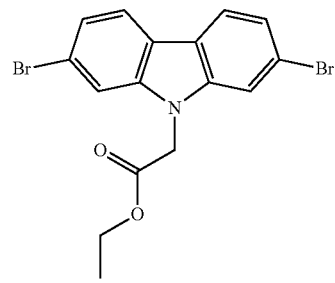

AG1

To a solution of 2,7-dibromo-9H-carbazole (3.00 g, 9.23 mmol) in $CH_3CN$ (30 mL) are added ethyl 2-iodoacetate (5.926 g, 3.274 mL, 27.69 mmol) and $Cs_2CO_3$ (3.008 g, 9.231 mmol). The reaction mixture is heated to reflux for 4 h, cooled to RT, diluted with EtOAc (50 mL), filtered through sintered funnel, solids are washed with EtOAc (20 mL) and $CH_2Cl_2$ (20 mL). The filtrate is washed with aqueous $NH_4Cl$ solution, brine, dried over $Na_2SO_4$, filtered ans concentrated to afford solid. The latter is dissolved in $CH_2Cl_2$, heptane is added, $CH_2Cl_2$ is slowly removed under vacuo and the resultant precipitate is filtered, washed with heptane to afford the title compound (1.75 g, 3.97 mmol, 43%) as light yellow solid. ESI-MS m/z calc. 410.16, found 410.16 $(M+1)^+$

Preparation of Intermediate AG2

(2R,3S,4R,5S,6R)-2-Ethynyl-6-(hydroxymethyl)tetrahydropyran-3,4,5-triol

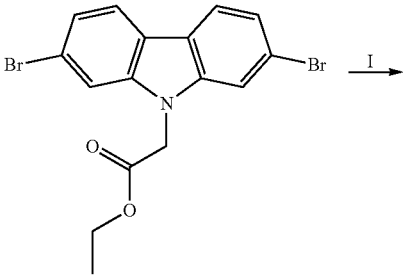

AG1

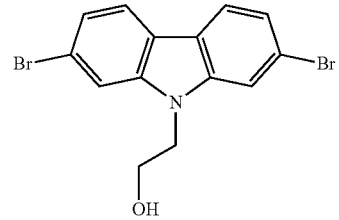

AG2

To a mixture of ethyl 2-(2,7-dibromocarbazol-9-yl)acetate (500 mg, 1.216 mmol) in THF (3.0 mL) is added borane (1.58 mL of 1 M, 1.58 mmol) in THF at RT. The reaction mixture is stirred at RT for 5.5 h (LC-MS showed 80% of the SM), Reaction mixture is continued for 88 h. It is carefully quenched with THF:Water (1:1, 4 mL) mixture, basified with solid $K_2CO_3$, extracted with EtOAc (2×10 mL), combined extracts are washed with brine, dried, concentrated to afford the title compound (440 mg, 88.19%) as white solid. $^1H$ NMR (400 MHz, $CDCl_3$) δ 7.87 (d, J=8.3 Hz, 2H), 7.60 (d, J=1.4 Hz, 2H), 7.34 (dd, J=8.3, 1.5 Hz, 2H), 4.37 (t, J=5.4 Hz, 2H), 4.09-4.01 (m, 2H). ESI-MS m/z found 368.18 $(M+1)^+$.

Preparation of Intermediate AG3

2,7-Dibromo-9-[2-(trideuteriomethoxy)ethyl]carbazole

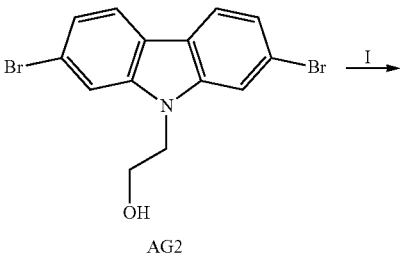

AG2

-continued

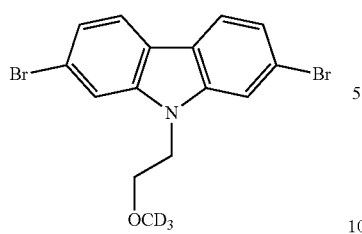

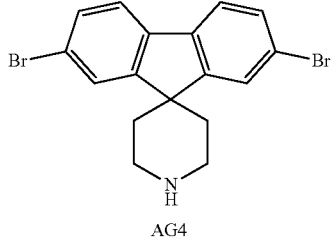

AG4

To a cold (0° C.) stirred suspension of 60% NaH in oil (51 mg, 1.27 mmol) (prewashed with toluene) in DMF (1 mL) is added a solution of Intermediate AG3, (260 mg, 0.634 mmol) in DMF (1 mL). The reaction mixture is stirred at 0° C. 45 min, treated with trideuterio(iodo)methane (118 µL, 1.90 mmol), stirred for 20 min. The cooling bath is removed, and the mixture is stirred 45 min, quenched with aqueous NH$_4$Cl solution. The resulting precipitate is filtered, washed with water, dried under high vacuum to afford the title compound (235 mg, 78%) as white solid. $^1$H NMR (400 MHz, CDCl$_3$) δ 7.87 (d, J=8.3 Hz, 2H), 7.58 (d, J=1.5 Hz, 2H), 7.33 (dd, J=8.3, 1.6 Hz, 2H), 4.37 (t, J=5.7 Hz, 2H), 3.74 (t, J=5.7 Hz, 2H).

Preparation of Intermediate AG4

2,7-Dibromospiro[fluorene-9,4'-piperidine]

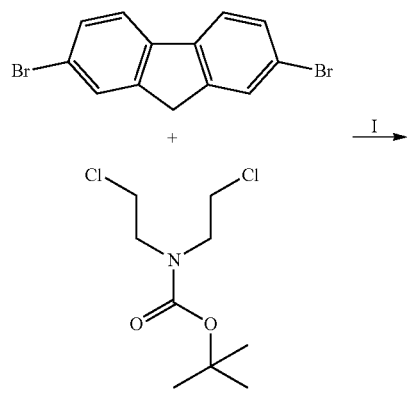

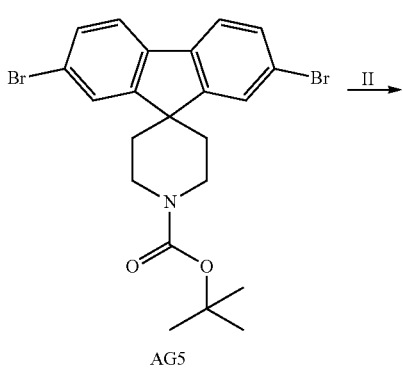

AG5

Step I: tert-Butyl 2,7-dibromospiro[fluorene-9,4'-piperidine]-1'-carboxylate. Intermediate AG5

To a cold (0° C.) stirred solution of 2,7-dibromo-9H-fluorene (7.500 g, 23.15 mmol) in THF (38 mL) is added NaH in oil (3.7 g, 146.5 mmol) in portions. Cooling bath is removed, mixture stirred at RT for 30 min (rapid evolution of hydrogen gas observed) cooled back to 0° C. A solution of tert-butyl N,N-bis(2-chloroethyl)carbamate (4.00 g, 16.52 mmol) in THF (6.0 mL) is then added. The reaction mixture is slowly warmed to reflux and stirred for 4 h (bath temp. 75° C.). The final reaction mixture is cooled to RT, quenched slowly by pouring onto crushed ice, extracted with Et$_2$O (2×100 mL). The combined organic extracts are washed with brine, dried over Na$_2$SO$_4$ and concentrated. The residue is purified on Biotage™ Snap silica gel cartridge (340 g) using a gradient of EtOAc in Hex (0% to 10%, 6 CV and 10%) as eluent to afford the title compound (5.00 g, 61%) as an orange solid. $^1$H NMR (400 MHz, CDCl$_3$) δ 7.71 (d, J=1.7 Hz, 2H), 7.56 (d, J=8.1 Hz, 2H), 7.49 (dd, J=7.9, 1.5 Hz, 2H), 3.92-3.72 (m, 4H), 1.94-1.74 (m, 4H), 1.53 (s, 9H).

Step II: Intermediate AG4

To solution of HCl in dioxane (39.0 mL of 4 M, 156 mmol) is added Intermediate AG5, (4.50 g, 9.12 mmol) at RT. The mixture is stirred at RT for 45 min (product precipitated within 5 min), diluted with anhydrous Et$_2$O (80 mL), cooled to −4° C. and filtered. The precipitate is washed with Et$_2$O (40 mL) and dried to afford the title compound (3.567 g, 84%) as a white solid. $^1$H NMR (400 MHz, DMSO-D$_6$) δ 8.95 (brs, 2H), 7.91 (d, J=1.5 Hz, 2H), 7.88 (d, J=8.2 Hz, 2H), 7.62 (dd, J=8.1, 1.6 Hz, 2H), 3.50-3.38 (m, 4H), 2.08-1.97 (m, 4H). ESI-MS m/z calc. 390.95712, found 394.19 (M+1)$^+$.

Preparation of Intermediate AG6

2-[2,7-Dibromo-9-(2-hydroxyethyl)fluoren-9-yl]ethanol

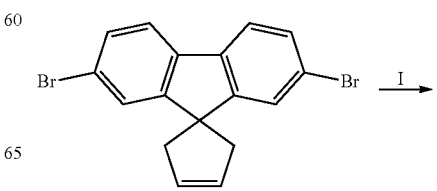

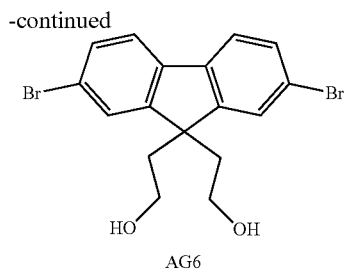

AG6

Step I: 2-[2,7-dibromo-9-(2-oxoethyl)fluoren-9-yl]acetaldehyde

To a stirred solution of 2',7'-dibromospiro[cyclopentene-4,9'-fluorene] (500 mg, 1.33 mmol) in $CH_2Cl_2$ (10 mL) is added MeOH (100 µL, 2.47 mmol) and cooled to −78° C. A stream of $O_3/O_2$ mixture is bubbled through the solution until blue color persist (10 min), and then excess ozone is flushed off with nitrogen gas until the solution is clear. The reaction mixture is quenched with methyl sulfide (0.38 mL, 6.85 mmol), stirred for 1 h, the cooling bath removed, stirred for 1 h, concentrated to afford the title compound. The latter is used without purification in the next step.

Step II: Intermediate AG6

To a cold (0° C.) stirred solution of 2-[2,7-dibromo-9-(2-oxoethyl)fluoren-9-yl]acetaldehyde from Step I (0.66 mmol) in a mixture of MeOH (2 mL) and THF (2 mL) is added $NaBH_4$ (100 mg, 2.64 mmol) in one portion, after stirring for 1.5 h, the reaction mixture is quenched with water (5 mL) and aqueous 1N HCl (5 mL). The mixture is concentrated and the resulting aqueous phase is extracted with EtoAc (2×15 mL). The combined extracts are washed with brine, dried over $Na_2SO_4$, and concentrated. The residue is purified on Biotage™ SNAP silica gel cartridge (25 g) using EtOAc in Hex (20% to 75%) as eluent to afford the title compound (230 mg, 84%) as white solid. $^1$H NMR (400 MHz, $CD_3OD$) δ 7.67 (d, J=1.7 Hz, 2H), 7.65 (d, J=8.1 Hz, 2H), 7.50 (dd, J=8.1, 1.7 Hz, 2H), 2.84-2.75 (m, 4H), 2.36-2.27 (m, 4H).

Preparation of Intermediate AG7

(1R,2S)-2',7'-Dibromospiro[cyclopentane-4,9'-fluorene]-1,2-diol

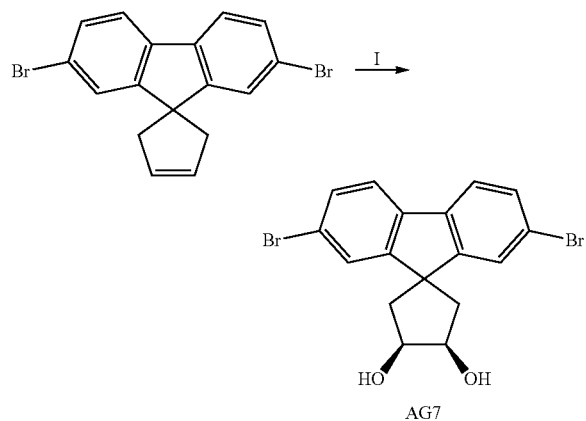

AG7

A 100 mL flask is charged with potassium carbonate (880 mg, 6.367 mmol), hexacyanoiron(3-) (Potassium Ion (3)) (2.1 g, 6.378 mmol), 1,4-bis[(S)-[(2R,4S,5R)-5-ethylquinuclidin-2-yl]-(6-methoxy-4-quinolyl)methoxy]phthalazine (17 mg, 0.022 mmol)[(DHQD)$_2$PHAL] and dipotassium dioxido-dioxo-osmium dihydrate (2 mg, 0.005 mmol), to this is added water (5.0 mL) and t-Butanol (4.0 mL), stirred for 15 min, methanesulfonamide (304 mg, 3.196 mmol) is added, stirred for 15 min. To the yellow-orange mixture is added a warm solution of 2',7'-dibromospiro[cyclopentene-4,9'-fluorene](200 mg, 0.5318 mmol) in EtOAc (1.0 mL) and stirred vigorously for 15 h. The reaction mixture is quenched with sodium sulfite (1.4 g, 13.59 mmol), stirred for 1 h, filtered through Celite cartridge, flask is rinsed with EtOAc (4×5 mL), combined filtrate is dried ($Na_2SO_4$), and concentrated. The residue is purified on Biotage™ SNAP silica gel cartridge (25 g) eluting with a gradient of EtOAc in hexanes (10% to 50%) to afford the title compound (200 mg, 91.7%) as white solid. $^1$H NMR (400 MHz, $CD_3OD$) δ 8.04 (d, J=1.8 Hz, 1H), 7.64-7.53 (m, 3H), 7.49-7.38 (m, 2H), 4.45 (t, J=4.5 Hz, 2H), 2.31-2.12 (m, 4H). ESI-MS m/z calc. 407.93607, found 408.06 (M+1)$^+$.

Preparation of Intermediate AG8

1-(2,7-Dibromospiro[fluorene-9,4'-piperidine]-1'-yl)ethanone

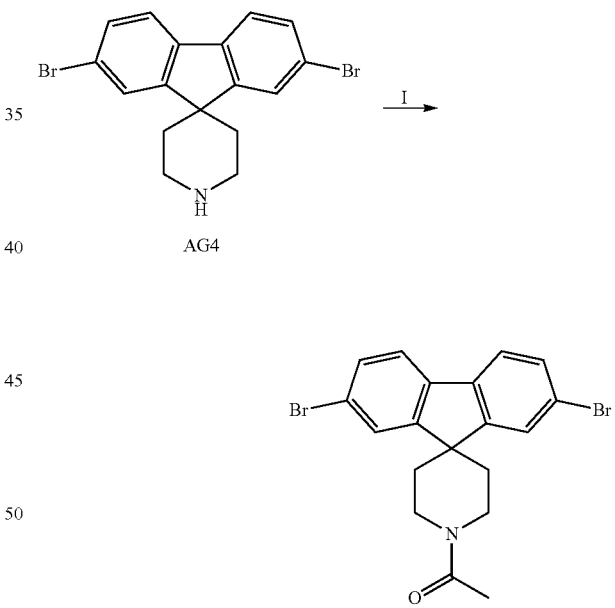

To a stirred mixture of 2,7-dibromospiro[fluorene-9,4'-piperidine] (Hydrochloric Acid (1)), AG4, (1000 mg, 2.142 mmol) in DMF (10 mL) is added $Et_3N$ (900 µL, 6.457 mmol), to the resultant clear solution is added drop wise acetyl chloride (180 µL, 2.532 mmol) at RT (exotherm). The resultant reaction mixture is stirred for 1 h, diluted with water (~20 mL)), stirred for 20 min, resultant precipitate is filtered, washed with water (10 mL), heptane (6 mL), and dried under high vacuum to afford the title compound (885 mg, 94.4%) as white solid. $^1$H NMR (400 MHz, DMSO-$D_6$)

δ 7.99 (brs, 2H), 7.84 (d, J=8.1 Hz, 2H), 7.57 (brd, J=8.1 Hz, 2H), 3.88-3.71 (m, 4H), 2.08 (s, 3H), 1.88-1.78 (m, 2H), 1.76-1.65 (m, 2H).

ESI-MS m/z calc. 432.96768, found 434.2 (M+1)⁺.

Preparation of Intermediate AG9

1-(2,7-Dibromospiro[fluorene-9,4'-piperidine]-1'-yl)-2-hydroxy-2-methyl-propan-1-one

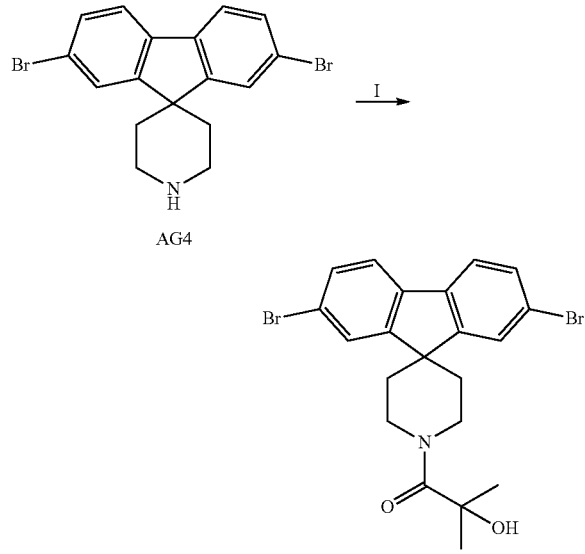

To a stirred mixture of 2,7-dibromospiro[fluorene-9,4'-piperidine] (Hydrochloric Acid (1)), AG4, (60 mg, 0.1397 mmol) and HATU (64 mg, 0.1683 mmol) in DMF (1 mL) is added sequentially 2-hydroxy-2-methyl-propanoic acid (17.5 mg, 0.168 mmol) and Et₃N (60 μL, 0.4305 mmol) at RT, stirred for 2 h, diluted with water (~3 mL), resultant precipitate is filtered, washed with water, heptane (1 mL), and dried under high vacuum to afford the title compound (52 mg, 68.1%) as white solid. ¹H NMR (400 MHz, CDCl₃) δ 7.71 (brs, J=1.5 Hz, 2H), 7.58 (d, J=8.1 Hz, 2H), 7.52 (d, J=8.1 Hz, 2H), 4.37 (s, 1H), 4.12-4.01 (m, 4H), 1.94-1.84 (m, 4H), 1.60 (s, 6H).

Preparation of Intermediate A10

Methyl 2,7-dibromospiro[fluorene-9,4'-piperidine]-1'-carboxylate

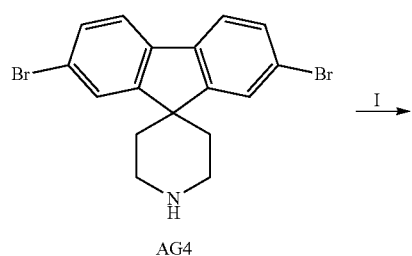

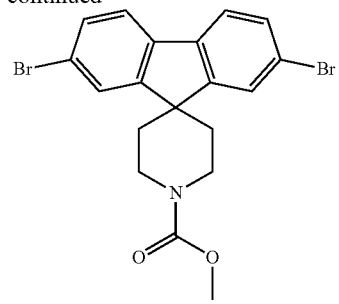

To a cold (0° C.) stirred mixture of 2,7-dibromospiro[fluorene-9,4'-piperidine](Hydrochloric Acid (1)), AG4, (60 mg, 0.1397 mmol) in CH₂Cl₂ (1 mL) is added methyl chloroformate (16 μL, 0.207 mmol) followed by Et₃N (58 μL, 0.419 mmol), stirred for 1.5 h. Reaction mixture is quenched with aqueous 1N HCl (1.5 mL), extracted with methylene chloride (3×2 mL). The combined filtrate is passed through phase separator, and concentrated to afford the title compound (59 mg, 88.74%) as white solid. ¹H NMR (400 MHz, CDCl₃) δ 7.71 (d, J=1.3 Hz, 2H), 7.57 (d, J=8.1 Hz, 2H), 7.50 (dd, J=8.1, 1.5 Hz, 2H), 3.87 (s, 4H), 3.78 (s, 3H), 1.84 (s, 4H).

Preparation of Intermediate A11

2,7-Dibromo-1'-methylsulfonyl-spiro[fluorene-9,4'-piperidine]

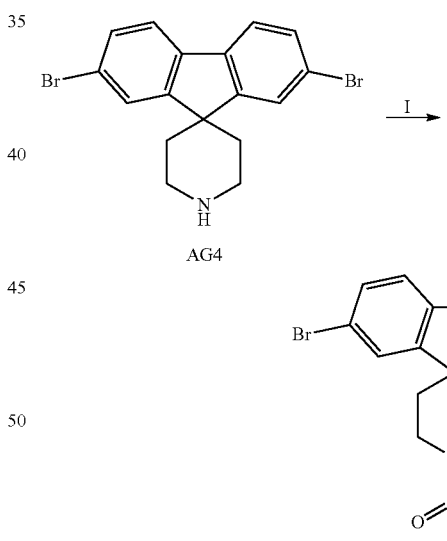

To a cold (0° C.) stirred mixture of 2,7-dibromospiro[fluorene-9,4'-piperidine](Hydrochloric Acid (1)), AG4, (60 mg, 0.1397 mmol) in CH₂Cl₂ (1 mL) is added methane sulfonyl chloride (16 μL, 0.2096 mmol) followed by Et₃N (58 μL, 0.4191 mmol), stirred for 1.5 hr (LC-MS showed complete conversion). The reaction mixture is quenched with aqueous 1N HCl (1.5 mL), extracted with methylene chloride (3×2 mL). The combined filtrate is passed through phase separator, and concentrated to afford the title compound (62 mg, 0.1240 mmol, 88.74%) as white solid. ¹H NMR (400 MHz, CDCl₃) δ 7.69 (d, J=1.5 Hz, 2H), 7.58 (d, J=8.1 Hz, 2H), 7.52 (dd, J=8.1, 1.6 Hz, 2H), 3.71-3.63 (m, 4H), 2.99 (s, 3H), 2.04-1.95 (m, 4H).

Preparation of Intermediate AG12

[9-(Acetoxymethyl)-2,7-dibromo-fluoren-9-yl] methyl acetate

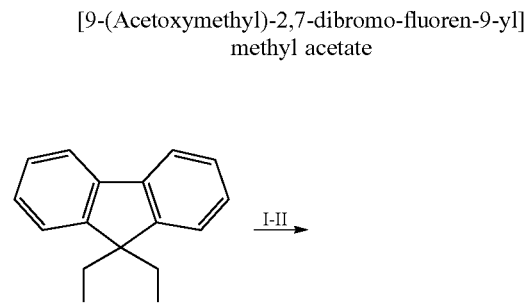

Step I: [2,7-dibromo-9-(hydroxymethyl)fluoren-9-yl]methanol

To a mixture of [9-(hydroxymethyl)fluoren-9-yl]methanol (1.584 g, 7 mmol) in water (5.5 mL) is added conc. $H_2SO_4$ (3 drops) and heated at 50° C. for 4.5 h, cooled to RT, quenched with aqueous sodium thiosulfate, diluted with water (30 mL), filtered, precipitate is washed with water (15 mL), and dried under high vacuum to afford the title compound (2.5 g, 70.3%) as white solid. The product contains ~15% of unknown impurity and it has been used as such in the next step without further purification. In LC-MS, major peak appeared at 349 $(M–2×H_2O)^+$

Step II

To a stirred mixture of [2,7-dibromo-9-(hydroxymethyl)fluoren-9-yl]methanol (250 mg, 0.492 mmol) in $CH_2Cl_2$ (5 mL) and pyridine (1 mL) is added 4-dimethylaminopyridine (25 mg, 0.205 mmol) and acetic anhydride (1 mL, 10.6 mmol) at RT, after 1.5 h, quenched with aqueous 1 N HCl (3 mL), stirred for 30 min, extracted with methylene chloride (3×5 mL), combined extracts are washed with aqueous 1 N HCl (2×4 mL), passed through phase separator, dried ($Na_2SO_4$), and concentrated. The residue is purified on Biotage™) SNAP silica gel cartridge (50 g) eluting with a gradient of EtOAc in Hex (10% to 40%, 8 CV) to afford the title compound (120 mg, 52.11%) as white solid. A peak at 349 appeared in the LC-MS (M–2×OAc). $^1$H NMR (400 MHz, $CDCl_3$) δ 7.71-7.67 (m, 2H), 7.58-7.55 (m, 4H), 4.29 (s, 4H), 2.10 (s, 6H).

Preparation of Intermediate AG13

2,7-Dibromospiro[fluorene-9,5'-oxepane]-2'-one

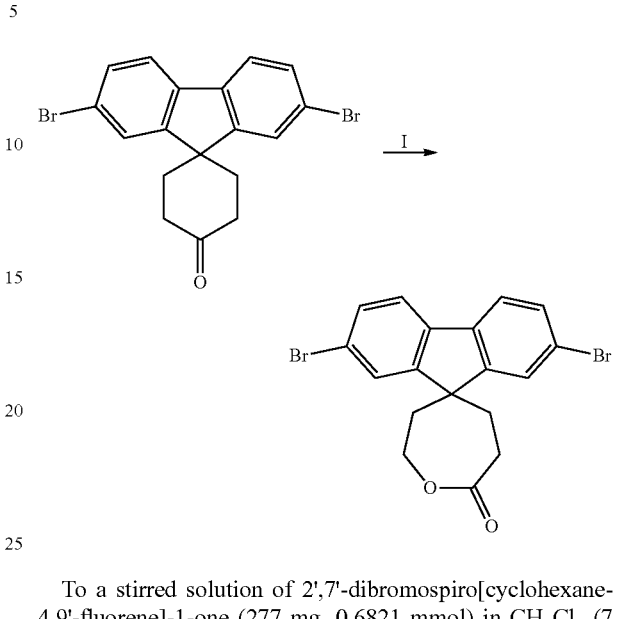

To a stirred solution of 2',7'-dibromospiro[cyclohexane-4,9'-fluorene]-1-one (277 mg, 0.6821 mmol) in $CH_2Cl_2$ (7 mL) is added m-CPBA (155 mg, 0.8982 mmol). The reaction mixture is stirred at RT for 18 h, aqueous saturated $NaHCO_3$ is added, extracted with $CH_2Cl_2$. The organic phases are combined, dried over $MgSO_4$, filtered, and concentrated. The residue is purified on Biotage™ SNAP silica gel cartridge with a gradient of EtOAc in Hex (0-20%, 20 CV) to afford the title compound (205 mg, 71.2%) as a white solid.

Preparation of Intermediate AG14

2,7-Dibromo-1'-methyl-spiro[fluorene-9,4'-piperidine]

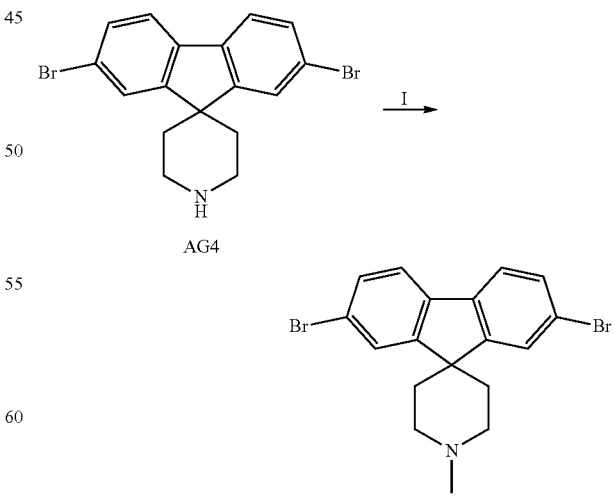

To a stirred mixture of 2,7-dibromospiro[fluorene-9,4'-piperidine] (Hydrochloric Acid (1)), AG4, (100 mg, 0.233 mmol) in 1,2-dichloroethane (2 mL) is added aqueous formaldehyde (38 μL of 37% w/v, 0.4683 mmol) followed by triacetoxyboranuide (sodium ion (1)) (148.0 mg, 0.698 mmol) in one portion at RT. Reaction mixture is stirred at RT for 1 h (LC-Ms showed the presence of clean product). It is quenched with aqueous 10% NaOH until pH 6-7, extracted with methylene chloride (4×5 mL), combined extracts are dried (Na$_2$SO$_4$) and concentrated to afford the title compound (91 mg, 93.9%). $^1$H NMR (400 MHz, CDCl$_3$) δ 7.79 (d, J=1.3 Hz, 2H), 7.54 (d, J=8.1 Hz, 2H), 7.48 (dd, J=8.1, 1.7 Hz, 2H), 2.91-2.79 (m, 4H), 2.54 (s, 3H), 2.02-1.89 (m, 4H). ESI-MS m/z calc. 404.97278, found 406.28 (M+1)$^+$.

Preparation of Intermediate AG15

2,7-dibromo-9-propyl-carbazole

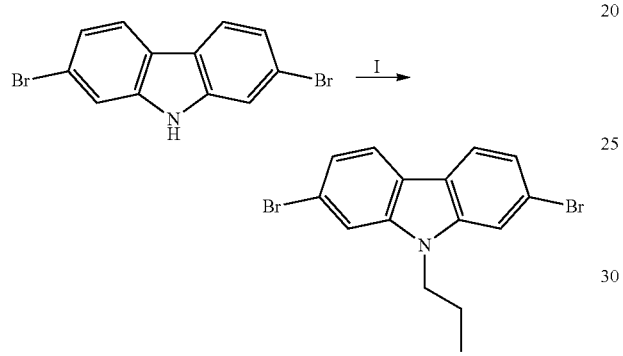

To a solution of 2,7-dibromo-9H-carbazole (150 mg, 0.462 mmol) in MeCN (9 mL) is added 1-iodopropane (135 μL, 1.38 mmol) and Cs$_2$CO$_3$ (752 mg, 2.31 mmol). The reaction is stirred for 18 h at reflux. The resulting mixture is cooled to RT, filtered and diluted with EA. The organic phase is washed with saturated aqueous NH$_4$Cl, dried over MgSO$_4$, and concentrated. The residue is purified on Biotage™ SNAP silica gel cartridge (0-5% EA/Hex) to give 2,7-dibromo-9-propyl-carbazole (145 mg, 86%) as a white solid.

Intermediates AG16, AG24, AG25 are prepared according to the procedure described for Intermediate AG15 using the appropriated alkylating reagent.

Intermediate AG16

2,7-Dibromo-9-methyl-carbazole

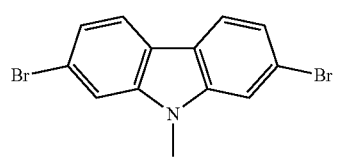 [SMILES: Cn1c2cc(Br)ccc2c2ccc(Br)cc21]

$^1$H NMR (400 MHz, Chloroform-d) δ 7.88 (d, J=8.3 Hz, 2H), 7.53 (d, J=1.6 Hz, 2H), 7.33 (dd, J=8.3, 1.7 Hz, 2H), 3.77 (s, 3H).

Intermediate AG24

2-(2,7-Dibromocarbazol-9-yl)-1-morpholino-ethanone

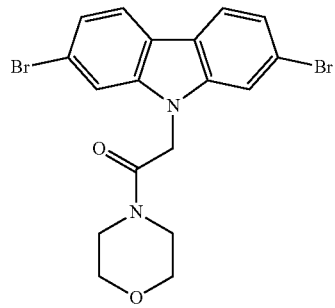 [SMILES: O=C(Cn1c2cc(Br)ccc2c2ccc(Br)cc21)N1CCOCC1]

$^1$H NMR (400 MHz, Chloroform-d) δ 7.88 (d, J=8.3 Hz, 2H), 7.40 (s, 2H), 7.35 (dd, J=8.3, 1.4 Hz, 2H), 4.96 (s, 2H), 3.77-3.49 (m, 8H).

Intermediate AG25

2-(2,7-Dibromocarbazol-9-yl)-N,N-dimethyl-acetamide

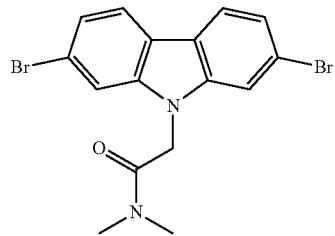 [SMILES: CN(C)C(=O)Cn1c2cc(Br)ccc2c2ccc(Br)cc21]

$^1$H NMR (400 MHz, Chloroform-d) δ 7.88 (d, J=8.3 Hz, 2H), 7.41 (s, 2H), 7.34 (d, J=8.3 Hz, 2H), 4.96 (s, 2H), 3.17 (s, 3H), 3.02 (s, 3H).

Preparation of Intermediate AG17

2,7-dibromo-9-pentyl-fluoren-9-ol

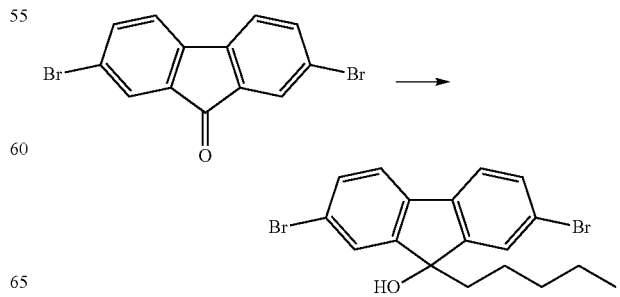

A solution of 2,7-dibromofluoren-9-one (200 mg, 0.592 mmol) in THF (2 mL) is added to a solution of n-pentyl magnesium bromide in Et$_2$O (355 µL of 2.0 M, 0.710 mmol) diluted with Et$_2$O (4 mL) at 0° C. The reaction is stirred 18 h at RT and quenched with 1N Na$_2$CO$_3$. The organic phase is separated, washed with brine, dried over MgSO$_4$, filtered and concentrated. The residue is purified on Biotage™ SNAP silica gel cartridge (0-8% EA/hex) to give 2,7-dibromo-9-pentyl-fluoren-9-ol (150 mg, 62%) as a white solid.

Intermediates AG18, AG19, AG20, AG21, AG22, and AG23 are prepared according to the procedure described for Intermediate AG17 using the appropriated Grignard reagent.

| Intermediate | Name/Structure | $^1$HNMR |
|---|---|---|
| AG18 | 2,7-Dibromo-9-cyclopropyl-fluoren-9-ol | (400 MHz, Chloroform-d) δ 7.65 (d, J = 8.0 Hz, 2H), 7.52-7.39 (m, 4H), 1.90 (s, 1H), 1.15-1.00 (m, 1H), 0.79-0.66 (m, 2H), 0.51 (dd, J = 10.2, 4.2 Hz, 2H). |
| AG19 | 2,7-Dibromo-9-isopropyl-fluoren-9-ol | (400 MHz, Chloroform-d) δ 7.62 (d, J = 1.5 Hz, 2H), 7.48 (dd, J = 8.0, 1.7 Hz, 2H), 7.43 (d, J = 8.1 Hz, 2H), 2.43 (p, J = 6.9 Hz, 1H), 2.03 (s, 1H), 0.81 (d, J = 6.8 Hz, 6H). |
| AG20 | 2,7-Dibromo-9-ethyl-fluoren-9-ol | (400 MHz, Chloroform-d) δ 7.61 (d, J = 1.7 Hz, 2H), 7.48 (dd, J = 8.0, 1.7 Hz, 2H), 7.44 (d, J = 8.1 Hz, 2H), 2.14 (q, J = 7.5 Hz, 2H), 2.02 (s, 1H), 0.54 (t, J = 7.5 Hz, 3H). |
| AG21 | 2,7-Dibromo-9-propyl-fluoren-9-ol | (400 MHz, Chloroform-d) δ 7.62 (d, J = 1.7 Hz, 2H), 7.48 (dd, J = 8.0, 1.7 Hz, 2H), 7.43 (d, J = 8.0 Hz, 2H), 2.11-2.03 (m, 2H), 2.01 (s, 1H), 0.97-0.84 (m, 2H), 0.78 (t, J = 7.0 Hz, 3H). |
| AG22 | 2,7-Dibromo-9-isobutyl-fluoren-9-ol | (400 MHz, Chloroform-d) δ 7.62 (d, J = 1.7 Hz, 2H), 7.49 (dd, J = 8.1, 1.8 Hz, 2H), 7.44 (d, J = 8.0 Hz, 2H), 2.10 (d, J = 6.3 Hz, 2H), 1.95 (s, 1H), 1.53 (s, 2H), 1.17 (dt, J = 13.0, 6.2 Hz, 1H), 0.59 (d, J = 6.7 Hz, 6H). |
| AG23 | 2,7-Dibromo-9-(3-methoxyphenyl)fluoren-9-ol | (400 MHz, Chloroform-d) δ 7.48 (d, J = 1.0 Hz, 4H), 7.45-7.41 (m, 2H), 7.19 (t, J = 8.0 Hz, 1H), 7.00-6.96 (m, 1H), 6.84-6.77 (m, 2H), 3.77 (s, 3H), 2.42 (s, 1H). |

Preparation of Intermediate AG26

3-(2,7-dibromo-9-hydroxy-fluoren-9-yl)propane-1,2-diol

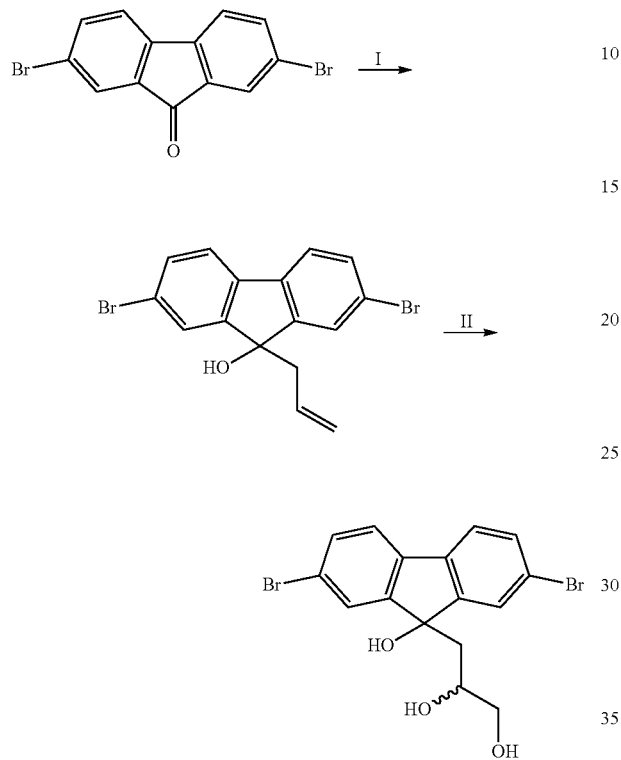

Step I: 9-Allyl-2,7-dibromo-fluoren-9-ol

The title compound is prepared according to the procedure described for Intermediate AG17 using ally magnesium bromide. $^1$H NMR (400 MHz, Chloroform-d) δ 7.64 (d, J=1.7 Hz, 2H), 7.51-7.40 (m, 4H), 5.62-5.48 (m, 1H), 5.05-4.95 (m, 2H), 2.77 (d, J=7.3 Hz, 2H), 2.18 (s, 1H).

Step II: Intermediate AG26

To a solution of 9-allyl-2,7-dibromo-fluoren-9-ol from Step I (250 mg, 0.658 mmol) in acetone/H$_2$O 4:1 (6.6 mL) were added 4-methyl-4-oxido-morpholin-4-ium (193 mg, 1.65 mmol) and OsO$_4$ 2.5% in tBuOH (401 μL of 2.5% w/v, 0.03943 mmol). The mixture is stirred at RT for 18 h. The reaction is quenched with the addition of saturated aqueous NH$_4$Cl. The mixture is extracted with EtOAc. The organic phase is washed with saturated aqueous NH$_4$Cl, dried over MgSO$_4$, filtered and concentrated. The residue is purified over Biotage™ SNAP silica gel cartridge (30-100% EA/hex 20 CV) to give the title compound (174 mg, 64%) as a white solid. $^1$H NMR (400 MHz, Chloroform-d) δ 7.82 (s, 1H), 7.67 (s, 1H), 7.54-7.40 (m, 4H), 4.26-4.13 (m, 1H), 3.76-3.67 (m, 1H), 3.66-3.55 (m, 1H), 3.52-3.37 (m, 2H), 2.49-2.37 (m, 1H), 1.86 (d, J=5.4 Hz, 2H), 1.59 (dd, J=8.1, 3.5 Hz, 1H).

Preparation of Intermediates AG27

(3'S,4'R)-2,7-Dibromospiro[fluorene-9,6'-tetrahydropyran]-3',4'-diol and (3'R,4'S)-2,7-dibromospiro[fluorene-9,6'-tetrahydropyran]-3',4'-diol

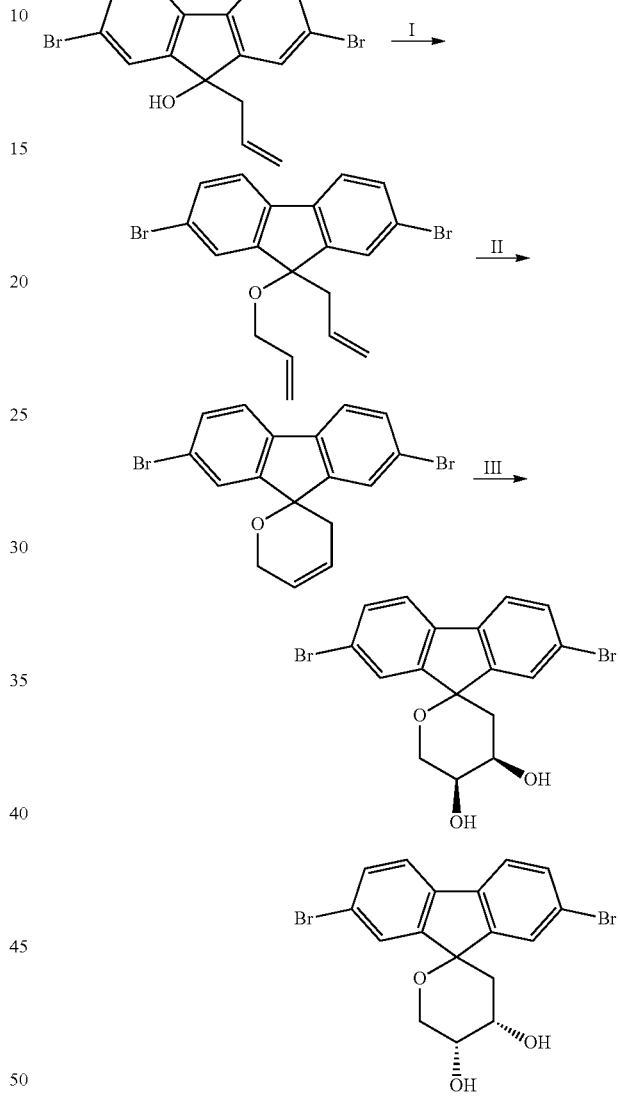

Step I: 9-Allyl-9-allyloxy-2,7-dibromo-fluorene

To a suspension of NaH (60% suspended in oil, 526 mg, 13.15 mmol) in DMF (15 mL) at 0° C. was added a solution of 9-allyl-2,7-dibromo-fluoren-9-ol from Intermediate AG26 Step I (1.00 g, 2.63 mmol) in DMF (7.5 mL). The reaction is warmed to RT for 1 h, cooled to 0° C. and allyl bromide (797 μL, 9.210 mmol) is added. The reaction mixture is stirred at RT for 18 h. The resulting mixture is diluted with EtOAc and quenched with saturated aqueous NH$_4$Cl. The organic phase is separated, dried over MgSO$_4$, filtered and concentrated. The residue is purified on Biotage™ SNAP silica gel cartridge (0-8% EA/hex 20 CV) to give the title compound (1.04 g, 94%) as a yellow solid.

¹H NMR (400 MHz, Chloroform-d) δ 7.60 (d, J=1.7 Hz, 2H), 7.49 (dd, J=8.1, 1.8 Hz, 2H), 7.45 (d, J=8.0 Hz, 2H), 5.74 (ddt, J=17.1, 10.6, 5.4 Hz, 1H), 5.45 (ddt, J=17.4, 10.3, 7.2 Hz, 1H), 5.16 (dq, J=17.2, 1.7 Hz, 1H), 5.05 (dq, J=10.5, 1.4 Hz, 1H), 4.91-4.81 (m, 2H), 3.36 (dt, J=5.4, 1.5 Hz, 2H), 2.78 (d, J=7.2 Hz, 2H).

Step II: 2',7'-Dibromospiro[2,5-dihydropyran-6,9'-fluorene]

To a solution of 9-allyl-9-allyloxy-2,7-dibromo-fluorene from Step I (1.04 g, 2.48 mmol) in CH₂Cl₂ (200 mL) at RT is added Grubbs 2ⁿᵈ gen. catalyst (105 mg, 0.124 mmol). The reaction mixture is stirred at RT for 18 h. The resulting mixture is concentrated and the residue is purified on Biotage™ SNAP silica gel cartridge (0-8% EA/hex 20 CV) to give the title compound (853 mg, 88%) as a white solid. ¹H NMR (400 MHz, Chloroform-d) δ 7.68 (d, J=1.4 Hz, 2H), 7.53-7.44 (m, 4H), 6.18-6.02 (m, 1H), 4.54-4.41 (m, 2H), 2.53 (s, 2H).

Step III: Intermediates AG27

The title compounds are prepared using 2',7'-Dibromo-spiro[2,5-dihydropyran-6,9'-fluorene] from Step II (250 mg, 0.6376 mmol) as starting material according to the procedure described in Compound 196 Step II to give the title racemic mixture of diastereoisomers as a white solid (201 mg, 74% yield). ¹H NMR (400 MHz, Chloroform-d) δ 7.83 (s, 1H), 7.68 (s, 1H), 7.57-7.41 (m, 4H), 4.54-4.43 (m, 1H), 4.20 (d, J=13.3 Hz, 1H), 4.13 (d, J=8.6 Hz, 2H), 2.46-2.33 (m, 2H), 2.27 (dd, J=7.1, 1.8 Hz, 1H), 2.00-1.91 (m, 1H).

Preparation of Intermediate AG28

1-(2,7-Dibromo-9H-fluoren-9-yl)-4-methyl-piperazine

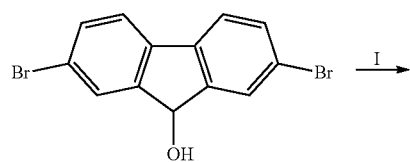

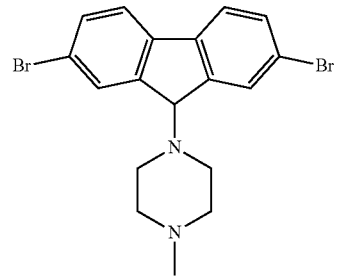

To a solution of 2,7-dibromo-9H-fluoren-9-ol (250 mg, 0.735 mmol) in CH₂Cl₂ (3 mL) and THF (1 mL) is added thionyl chloride (120 μL, 1.65 mmol). The mixture is stirred at RT for 1 h. The resulting mixture is concentrated to dryness. MeCN (3 mL) is added then 1-methylpiperazine (408 μL, 3.67 mmol) is added and the mixture is stirred at 82° C. for 18 h. The reaction mixture is quenched by addition of saturated aqueous NH₄Cl and diluted with EtOAc. The organic phase is separated, washed with saturated aqueous NH₄Cl, dried over MgSO₄, filtered and concentrated. The residue is purified over Biotage™ SNAP silica gel cartridge (30-100% EA/hex+1% Et₃N buffer 20 CV) to give the title compound (200 mg, 64% yield) as a yellow solid. ¹H NMR (400 MHz, Chloroform-d) δ 7.75 (s, 2H), 7.47 (s, 4H), 4.77 (s, 1H), 2.64 (t, J=4.1 Hz, 4H), 2.40 (s, 4H), 2.26 (s, 3H).

Preparation of Intermediate AG29

2,7-Dibromospiro[fluorene-9,2'-tetrahydropyran]

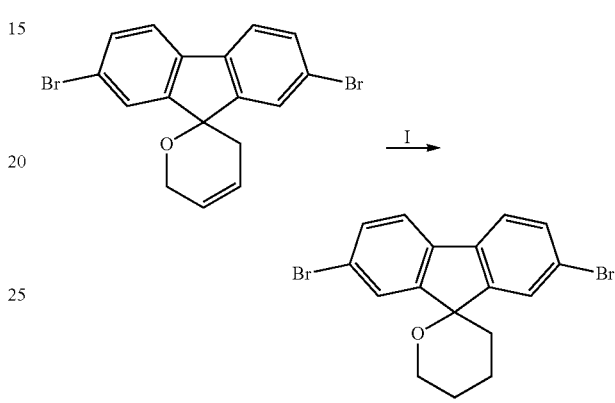

To a solution of 2',7'-dibromospiro[2,5-dihydropyran-6,9'-fluorene] from Intermediate AG27 Step II (200 mg, 0.510 mmol) in EtOAc (7 mL) is added SiliaCat Pd⁰ (26 mg, 0.0013 mmol). H₂ is then bubbled for 5 minutes and the reaction is stirred under H₂ atmosphere for 1 week. The resulting mixture is filtered and concentrated. The residue is purified on Biotage™ SNAP silica gel cartridge (0-8% EA/hex 17 CV) to give the title compound (120 mg, 60%) as a pale yellow solid. ¹H NMR (400 MHz, Chloroform-d) δ 7.82 (d, J=1.6 Hz, 2H), 7.51-7.46 (m, 4H), 4.18-4.00 (m, 2H), 2.11-2.03 (m, 2H), 1.93 (dt, J=13.3, 6.4 Hz, 4H).

Preparation of Intermediate AG30

N'-(2,7-Dibromo-9H-fluoren-9-yl)-N,N,N'-trimethyl-ethane-1,2-diamine

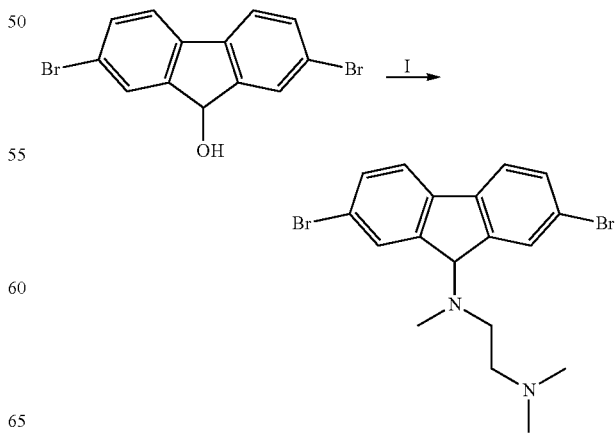

The title compound is prepared according to the procedure described for Intermediate A28 but using N1,N1,N2-trimethylethane-1,2-diamine as starting material. ¹H NMR (400 MHz, Chloroform-d) δ 7.73 (s, 2H), 7.48 (s, 4H), 4.87 (s, 1H), 2.74 (t, J=6.3 Hz, 2H), 2.59 (t, J=6.2 Hz, 2H), 2.37 (s, 6H), 2.26 (s, 3H).

Preparation of Intermediate AG31

2,7-Dibromo-9-(cyclopentylmethyl)fluoren-9-ol

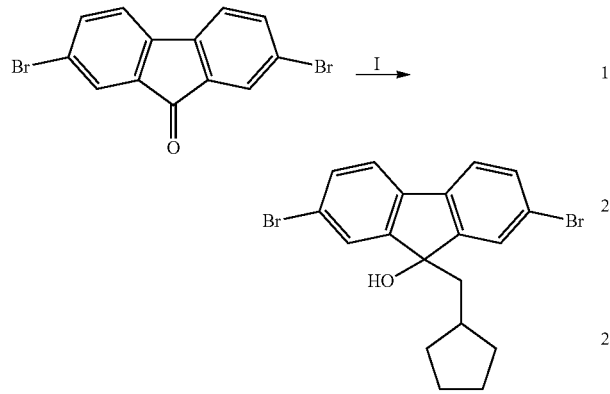

A Et₂O washed sealed tube under N₂ flow is charged with iodomethylcyclopentane (145 µL) in Et₂O (1 mL) at RT. Magnesium (27 mg, 1.111 mmol) and iodine (0.30 mg, 0.0012 mmol) are added and the mixture is stirred at reflux for 2 h (or until all magnesium was consumed). The resulting mixture is cooled down to 0° C. and a solution of 2,7-dibromofluoren-9-one (250 mg, 0.740 mmol) in THF (2 mL) is added. The reaction is stirred at RT for 18 h. The resultant mixture is quenched with saturated aqueous NaHCO₃, the organic phase is separated, washed with brine, dried over MgSO₄, filtered and concentrated. The residue is purified Biotage™ SNAP silica gel cartridge (0-10% EA/hex 20 CV) to give the title compound (62 mg, 13%) as a yellow solid. ¹H NMR (400 MHz, Chloroform-d) δ 7.61 (d, J=1.8 Hz, 2H), 7.53-7.40 (m, 4H), 2.26 (d, J=5.9 Hz, 2H), 1.98 (s, 1H), 1.41 (s, 2H), 1.27-1.14 (m, 5H), 0.82 (s, 2H).

Preparation of Intermediate AG32

2,7-Dibromo-9-(cyclohexylmethyl)fluoren-9-ol

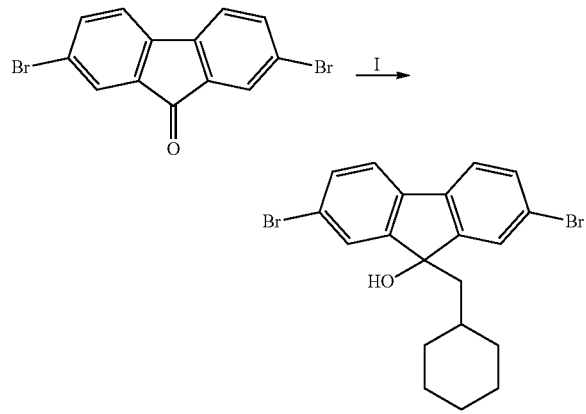

The tile compound is prepared according to the procedure described for Intermediate AG32 but using iodomethylcyclohexane as starting material. ¹H NMR (400 MHz, Chloroform-d) δ 7.61 (d, J=1.7 Hz, 2H), 7.48 (dd, J=8.0, 1.8 Hz, 2H), 7.43 (d, J=8.0 Hz, 2H), 2.07 (d, J=5.4 Hz, 2H), 1.94 (s, 1H), 1.46 (dd, J=9.0, 3.2 Hz, 3H), 1.22 (d, J=11.8 Hz, 2H), 1.05-0.69 (m, 6H).

Preparation of Intermediate A33

2,7-Dibromo-9-(2-hydroxyethyl)fluoren-9-ol

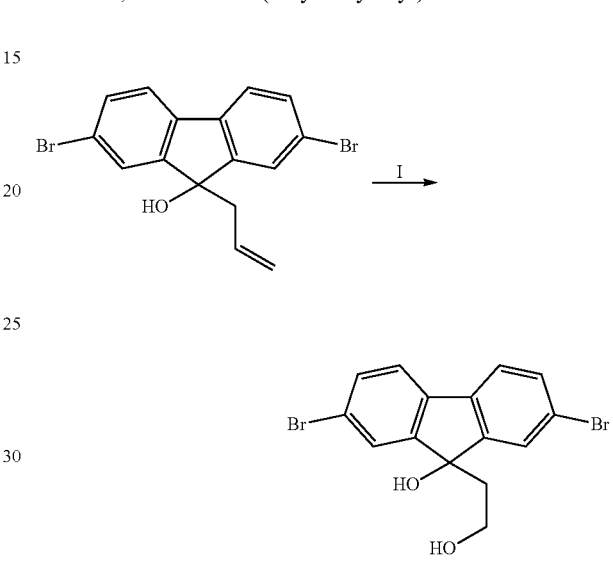

To a solution of 9-allyl-2,7-dibromo-fluoren-9-ol from Intermediate AG26 Step I (1.00 g, 2.63 mmol) in CH₂Cl₂ (13 mL) at −78° C. is bubbled 03 until the solution became blue. Nitrogen is then bubbled for 10 minutes to remove excess of 03. The reaction is allowed to warm at 0° C. and NaBH₄ (597 mg, 15.8 mmol) is added and the mixture is stirred 1. The reaction mixture is quenched by adding saturated aqueous NH₄Cl. The organic phase is separated, washed with saturated aqueous NH₄Cl, dried over MgSO₄, filtered and concentrated. The residue is purified on Biotage™ SNAP silica gel cartridge (0-20% EA/hex 20 CV) to give the title compound (443 mg, 44%) as a white solid. ¹H NMR (400 MHz, Chloroform-d) δ 7.72 (dd, J=2.6, 1.5 Hz, 2H), 7.50 (ddd, J=8.1, 3.0, 1.6 Hz, 2H), 7.47-7.42 (m, 2H), 3.84 (d, J=3.9 Hz, 2H), 3.27 (s, 1H), 2.21 (td, J=5.9, 3.0 Hz, 2H), 2.13 (td, J=4.9, 2.4 Hz, 1H).

Preparation of Intermediate AG34

2,7-dibromo-9-(tetrahydro-2H-pyran-4-yl)-9H-carbazole

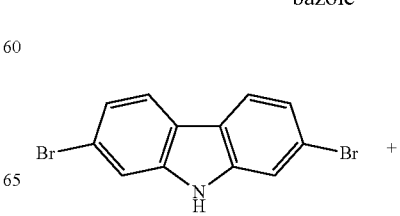

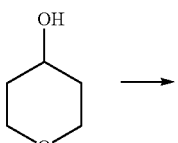 → 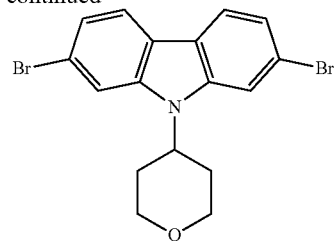

To a solution of 2,7-dibromo-9H-carbazole (250 mg, 0.77 mmol) and tetrahydropyran-4-ol (146 μL, 1.54 mmol) in Toluene 2.5 mL is added 2-tributylphosphoranylideneacetonitrile (1.54 mL of 1 M, 1.54 mmol). The reaction mixture is stirred at 110° C. for 4 h, cooled down to RT and partitioned between EtOAc and water. The organic layer is dried over $Na_2SO_4$, filtered, concentrated and purified Biotage™ SNAP silica gel cartridge (24 g) eluting with 0-50% EtOAC in Hex to afford the tittle compound (95 mg, 30%). $^1$H NMR (400 MHz, Chloroform-d) δ 7.89 (d, J=8.3 Hz, 2H), 7.70 (d, J=1.6 Hz, 2H), 7.34 (dd, J=8.3, 1.6 Hz, 2H), 4.58 (ddt, J=12.5, 8.8, 4.4 Hz, 1H), 4.24 (dd, J=11.7, 4.8 Hz, 2H), 3.64 (td, J=12.1, 2.0 Hz, 2H), 2.69 (qd, J=12.5, 4.7 Hz, 2H), 1.84 (ddd, J=12.9, 4.3, 1.8 Hz, 2H).

Intermediates AG35-40 are prepared according to the procedure described in Intermediate AG34

| Intermediate | Name/Structure | $^1$HNMR |
|---|---|---|
| AG35 | tert-butyl 4-(2,7-dibromo-9H-carbazol-9-yl)piperidine-1-carboxylate | (400 MHz, Chloroform-d) δ 7.89 (d, J = 8.3 Hz, 2H), 7.62 (d, J = 1.6 Hz, 2H), 7.33 (dd, J = 8.3, 1.6 Hz, 2H), 4.48 (tt, J = 12.6, 4.2 Hz, 1H), 4.40 (m, 2H), 2.93 (t, J = 12.8 Hz, 2H), 2.49 (qd, J = 12.5, 4.6 Hz, 2H), 1.88 (d, J = 12.4 Hz, 2H), 1.54 (s, 9H). |
| AG36 | 2,7-dibromo-9-((3-methyloxetan-3-yl)methyl)-9H-carbazole | (400 MHz, Chloroform-d) δ 7.97-7.82 (m, 2H), 7.52 (d, J = 1.6 Hz, 2H), 7.36 (dd, J = 8.3, 1.6 Hz, 2H), 4.71 (d, J = 6.1 Hz, 2H), 4.47-4.27 (m, 4H), 1.44 (s, 3H). |
| AG37 | 2,7-dibromo-9-(1-methylpiperidin-4-yl)-9H-carbazole | (400 MHz, $CD_3OD$) δ 8.02-7.77 (m, 4H), 7.29 (dd, J = 8.4, 1.6 Hz, 2H), 4.61 (tt, J = 11.2, 4.0 Hz, 1H), 3.06 (d, J = 11.8 Hz, 2H), 2.66 (qd, J = 12.7, 4.1 Hz, 2H), 2.39 (s, 3H), 2.34 (dd, J = 12.3, 2.5 Hz, 2H), 1.81 (ddd, J = 12.6, 4.9, 2.2 Hz, 2H). |

-continued

| Intermediate | Name/Structure | ¹HNMR |
|---|---|---|
| AG38 | 2,7-dibromo-9-((1-methylpiperidin-4-yl)methyl)-9H-carbazole | (400 MHz, Chloroform-d) δ 7.87 (dd, J = 8.3, 0.5 Hz, 2H), 7.49 (d, J = 1.6 Hz, 2H), 7.32 (dd, J = 8.3, 1.6 Hz, 2H), 4.18 (ddd, J = 7.9, 6.9, 1.3 Hz, 2H), 2.77-2.67 (m, 1H), 2.55 (ddd, J = 9.2, 7.7, 6.1 Hz, 1H), 2.47 (td, J = 8.8, 5.7 Hz, 1H), 2.25 (s, 3H), 2.17 (td, J = 6.2, 4.2 Hz, 2H), 2.00-1.77 (m, 2H), 1.45 (ddt, J = 12.0, 8.1, 5.7 Hz, 1H). |
| AG39 | 4-(2-(2,7-dibromo-9H-carbazol-9-yl)ethyl)morpholine | (400 MHz, Chloroform-d) δ 7.87 (dd, J = 8.3, 3.0 Hz, 2H), 7.61-7.49 (m, 2H), 7.33 (dt, J = 8.3, 1.7 Hz, 2H), 4.31 (td, J = 7.8, 7.3, 3.4 Hz, 2H), 3.68 (t, J = 4.6 Hz, 4H), 2.72 (td, J = 7.1, 2.4 Hz, 2H), 2.61-2.42 (m, 4H). |
| AG40 | 1-(2-(2,7-dibromo-9H-carbazol-9-yl)ethyl)pyrrolidin-2-one | (400 MHz, Chloroform-d) δ 7.88 (d, J = 8.2 Hz, 2H), 7.57 (d, J = 1.6 Hz, 2H), 7.35 (dd, J = 8.3, 1.6 Hz, 2H), 4.47 (t, J = 5.7 Hz, 2H), 3.64 (t, J = 5.7 Hz, 2H), 2.64 (t, J = 7.0 Hz, 2H), 2.27 (t, J = 8.1 Hz, 2H), 1.57 (t, J = 8.1 Hz, 2H). |

Preparation of Intermediate AG41

2',7'-dibromospiro[cyclohexane-1,9'-fluoren]-4-one

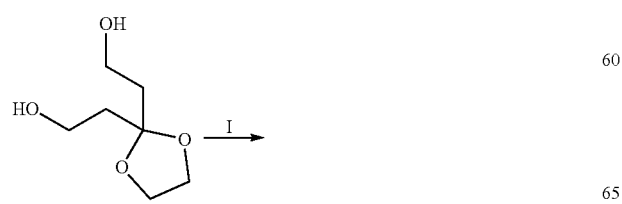

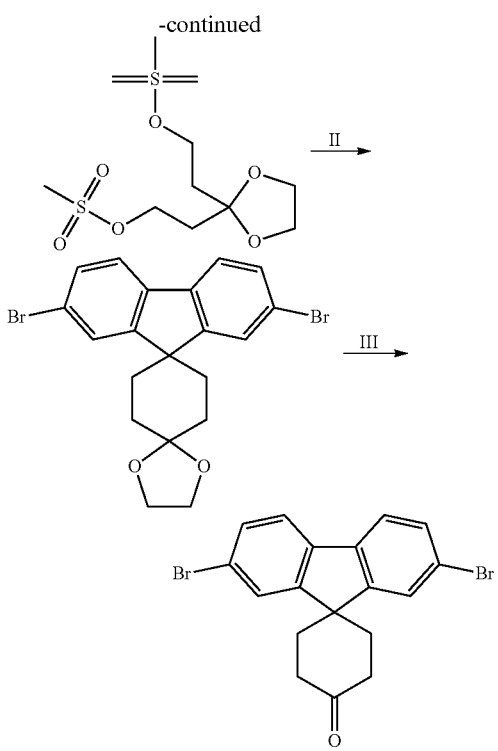

Step I: (1,3-dioxolane-2,2-diyl)bis(ethane-2,1-diyl) dimethanesulfonate

To a cold (0° C.) solution of 2-[2-(2-hydroxyethyl)-1,3-dioxolan-2-yl]ethanol (1000 mg, 6.200 mmol) in CH$_2$Cl$_2$ (10.0 mL) is added Et$_3$N (2.15 mL, 15.4 mmol) and methanesulfonyl chloride (1.00 mL, 12.9 mmol) dropwise over 10 min. The reaction mixture is stirred 45 min at 0° C., quenched with water (20 mL). The organic phase is washed with saturated aqueous NaHCO$_3$, dried over Na$_2$SO$_4$, filtered and concentrated to afford the title compound (1750 mg, 89%) as white solid.

Step II: 2,7-dibromodispiro[fluorene-9,1'-cyclohexane-4',2'''-[1,3]dioxolane]

To a cold (0° C.) of 2,7-dibromo-9H-fluorene (1.020 g, 3.100 mmol) in THF (7.0 mL) is added NaH (60%) in oil (814 mg, 20.4 mmol) in 3 portions. The reaction mixture is stirred at RT for 30 min, cooled back to 0° C. and a solution of (1,3-dioxolane-2,2-diyl)bis(ethane-2,1-diyl) dimethanesulfonate from Step I (700 mg, 2.2 mmol) in THF (3.5 mL) is added. The reaction mixture is stirred at 75° C. for 4 h, cooled to RT, quenched with ice-water, extracted with EtOAc (3×10 mL). The combined extracts are washed with brine, dried over Na$_2$SO$_4$ and concentrated. Purification of the residue on Biotage™ SNAP silica gel cartridge (24 g) using an isocratic 50% CH$_2$Cl$_2$/Hexane as eluent to afford the tittle compound (750 mg, 76%). $^1$H NMR (400 MHz, Chloroform-d) δ 7.75 (d, J=1.7 Hz, 2H), 7.54 (d, J=8.1 Hz, 2H), 7.47 (dd, J=8.1, 1.7 Hz, 2H), 4.11-4.05 (s, 4H), 2.06 (m, 4H), 1.98-1.90 (m, 4H).

Step III: Intermediate AG41

To a solution of 2,7-dibromodispiro[fluorene-9,1'-cyclohexane-4',2'''-[1,3]dioxolane](1400 mg, 3.11 mmol) in THF (7.0 mL) is added HCl (5.2 mL of 3 M, 15.6 mmol). The reaction mixture is stirred at 45° C. for 16 h, cooled down to RT, diluted with water and extracted with EtOAc. The organic phase is separated, dried over Na$_2$SO$_4$, filtered and concentrated. The residue is purified on Biotage™ SNAP silica gel cartridge (24 g) eluting with Hex/EtOAc (0-50%, 15 CV) to afford the title compound (923 mg, 73%). $^1$H NMR (400 MHz, Chloroform-d) δ 7.68 (dd, J=1.7, 0.5 Hz, 2H), 7.60 (dd, J=8.1, 0.5 Hz, 2H), 7.53 (dd, J=8.1, 1.7 Hz, 2H), 2.80 (t, J=7.0 Hz, 4H), 2.18 (dd, J=7.4, 6.5 Hz, 4H).

Preparation of Intermediate AG42

2',7'-dibromospiro[cyclohexane-1,9'-fluoren]-4-ol

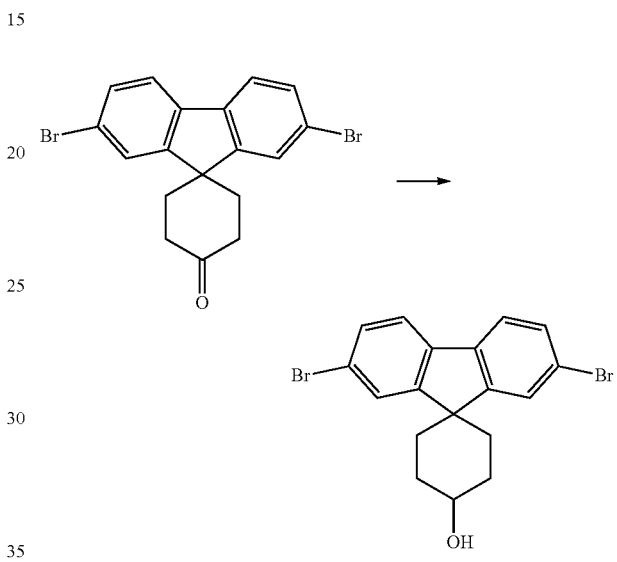

To a cold solution (−40° C.) of Intermediate AG41 (75 mg, 0.18 mmol) in THF (1.5 mL) is added NaBH$_4$ (10.0 mg, 0.260 mmol). The reaction mixture is stirred 1 h at −40° C. and 2 h at RT. The reception is quenched with water and extracted with EtOAc. The organic phase is separated, dried over Na$_2$SO$_4$, filtered and concentrated. The residue is purified on Biotage™ SNAP silica gel cartridge (12 g) eluting with Hex/EtOAc (0-50%, 15 CV) to afford the title compound (55 mg, 73%). $^1$H NMR (400 MHz, Chloroform-d) δ 7.96-7.81 (m, 1H), 7.61-7.51 (m, 3H), 7.48 (ddd, J=12.1, 8.1, 1.7 Hz, 2H), 4.19-4.00 (m, 1H), 2.13 (dq, J=13.9, 4.7 Hz, 2H), 2.01-1.88 (m, 2H), 1.83 (dt, J=9.9, 4.7 Hz, 4H).

Preparation of Intermediate AG43

2',7'-dibromo-4-methylspiro[cyclohexane-1,9'-fluoren]-4-ol

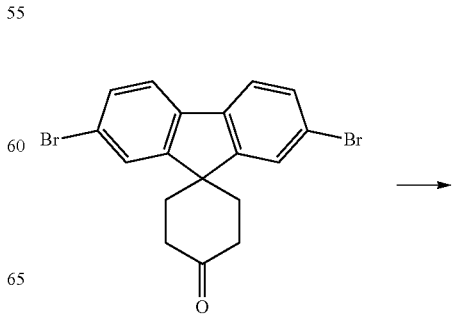

-continued

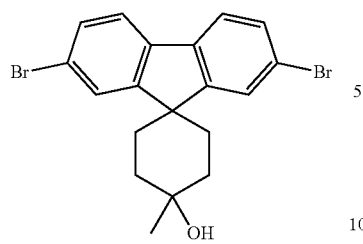

To a cold solution (−40° C.) of Intermediate AG41 (75 mg, 0.18 mmol) in THF (7.5 mL) is added methyllithium (140 μL of 1.6 M, 0.22 mmol). The reaction mixture is stirred 1 h at −40° C. and 2 h at RT, quenched with water and extracted with EtOAc. The organic phase is separated, dried over $Na_2SO_4$, filtered and concentrated. The residue is purified on Biotage™ SNAP silica gel cartridge (12 g) eluting with Hex/EtOAc (0-50%, 15 CV) to afford the title compound (25 mg, 32%). $^1$H NMR (400 MHz, Chloroform-d) δ 7.68 (dd, J=9.5, 1.8 Hz, 2H), 7.61-7.39 (m, 4H), 2.29-2.12 (m, 2H), 2.06-1.93 (m, 2H), 1.93-1.80 (m, 2H), 1.47 (s, 3H).

Preparation of Intermediate AG44

2',7'-dibromospiro[cyclohexane-1,9'-fluoren]-4-amine

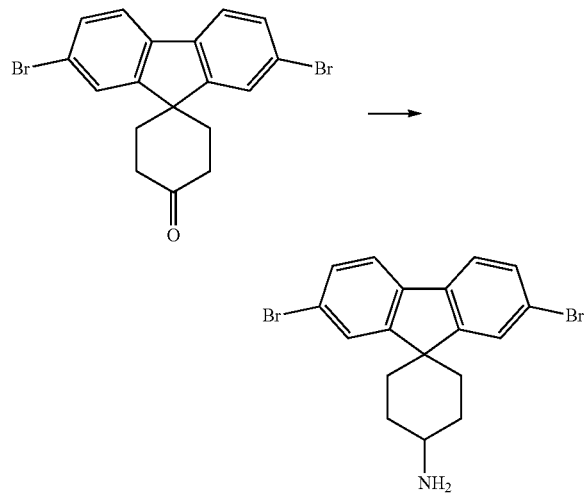

To a stirred solution of Intermediate AG41 (200 mg, 0.490 mmol) and ammonium acetate (380 mg, 4.90 mmol) in MeOH (2.0 mL) is added $NaBH_3CN$ (22 mg, 0.34 mmol). The reaction mixture is stirred at RT for 16 h, quenched with 1N NaOH (1 mL), extracted with $CH_2Cl_2$, dried over $Na_2SO_4$, filtered and concentrated. The residue is purified on Biotage™ SNAP silica gel cartridge (10 g) eluting with $CH_2CL_2$/MeOH (0-10%) to afford the title compound (80 mg, 40%). $^1$H NMR (400 MHz, Chloroform-d) δ 7.93 (d, J=1.7 Hz, 1H), 7.63-7.37 (m, 5H), 3.16-2.97 (m, 1H), 2.09-1.89 (m, 4H), 1.86-1.71 (m, 2H), 1.62 (d, J=13.4 Hz, 2H).

Example 1: Preparation of Compound 1 (Method A)

((2R,3S,4R,5S,6R)-2-(Hydroxymethyl)-6-[4-[(2R,3S,4R,5S,6R)-3,4,5-trihydroxy-6 (hydroxymethyl) tetrahydropyran-2-yl]phenyl]tetrahydropyran-3,4,5-triol)

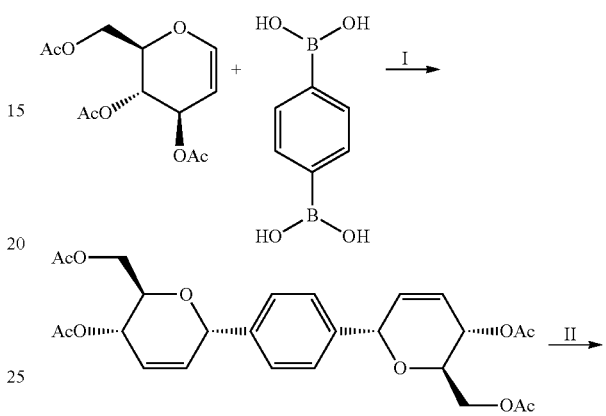

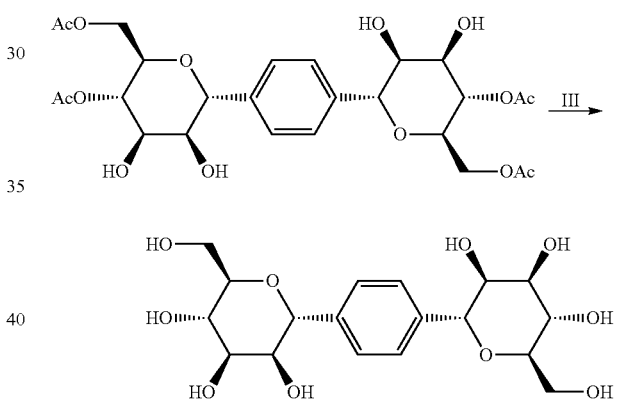

Step I: [(2R,3S,6S)-3-Acetoxy-6-[4-[(2R,3S,6S)-3-acetoxy-2-(acetoxymethyl)-3,6-dihydro-2H-pyran-6-yl]phenyl]-3,6-dihydro-2H-pyran-2-yl]methyl acetate A solution of [(2R,3S,4R)-3,4-diacetoxy-3,4-dihydro-2H-pyran-2-yl]methyl acetate (1.642 g, 6.033 mmol) and (4-boronophenyl)boronic acid (1.0 g, 6.03 mmol) in $CH_3CN$ (30 mL) is degassed by bubbling $N_2$ (g) for 5 min. $Pd(OAc)_2$ (338.6 mg, 1.50 mmol) is added and the reaction mixture is stirred at 40° C. for 5 h. Another portion of $Pd(OAc)_2$ (338.6 mg, 1.50 mmol) is added and heating is continued for a further 15 h. The solvent is evaporated and the mixture is diluted with EtOAc (25 mL) and filtered through celite. The filtrate is washed with sat $NaHCO_3$ (2×25 mL), dried over $Na_2SO_4$ and the solvent is evaporated. The crude product is purified on Biotage™ SNAP 50 g silica gel cartridge with a gradient elution of 10%-30% EtOAc in Hex and a flow rate of 40 mL/min over 35 min to afford the title compound (550 mg, 18.14%) as an oil. LC-MS: m/z=525.0 (M+Na).

Step II: [(2R,3S,4R,5S,6R)-3-Acetoxy-6-[4-[(2R,3S,4R,5S,6R)-5-acetoxy-6-(acetoxymethyl)-3,4-dihydroxy-tetrahydropyran-2-yl]phenyl]-4,5-dihydroxy-tetrahydropyran-2-yl]methyl acetate To a solution of [(2R,3S,6S)-3-acetoxy-6-[4-[(2R,3S,6S)-3-acetoxy-2-(acetoxymethyl)-3,6-dihydro-2H-pyran-6-yl]phenyl]-3,6-dihydro-2H-pyran-2-yl]methyl acetate (550 mg, 1.095 mmol) in water (1.6 mL)/THF (9.4 mL) is added methanesulfonamide (312.5 mg, 3.285 mmol), OsO$_4$ (1.1 mL of 2.5% w/v in t-BuOH, 0.1095 mmol) and NMO (1.283 g, 10.95 mmol) and the reaction mixture is stirred at RT for 5 days. The solvent is evaporated and the crude mixture is diluted with a dilute solution of sodium bisulfite (50 mL) and after 15 min it is extracted with EtOAc (3×25 mL). The combined organic extracts are dried over Na$_2$SO$_4$ and the solvent is evaporated. The crude product is purified on Biotage™ SNAP 25 g silica gel cartridge with a gradient of 5%-10% MeOH in CH$_2$Cl$_2$ as the eluent and a flow rate of 24 mL/min over 20 min. The isolated product is dissolved in a minimum amount of MeOH and diluted with Et$_2$O to precipitate the product. The mixture is filtered and washed with diethyl ether to afford title compound (145 mg, 23.21%) as a white solid. LC-MS: m/z=571.4 (M+H$^+$)

Step III: Compound 1

[(2R,3S,4R,5S,6R)-3-acetoxy-6-[4-[(2R,3S,4R,5S,6R)-5-acetoxy-6-(acetoxymethyl)-3,4-dihydroxy-tetrahydropyran-2-yl]phenyl]-4,5-dihydroxy-tetrahydropyran-2-yl]methyl acetate (145 mg, 0.2541 mmol) is dissolved in MeOH (3 mL) and MeONa in MeOH (47 µL of 25% w/v, 0.22 mmol) is added and the reaction mixture is stirred at RT for 6 h. The reaction is neutralized by the addition of Amberlite IR120H resin until the pH changed to neutral. The reaction mixture is filtered and the filtrate is evaporated to afford the title product (108 mg, 0.258 mmol, 24%) as a white solid. $^1$H NMR (400 MHz, CD$_3$OD) δ 7.51 (s, 4H), 4.98 (d, J=3.4 Hz, 2H), 4.44 (t, J=3.3 Hz, 2H), 3.81 (t, J=8.4 Hz, 4H), 3.74 (t, J=8.1 Hz, 2H), 3.57 (dd, J=8.1, 3.1 Hz, 2H), 3.50-3.41 (m, 2H). LC-MS: m/z=403.2 (M+H$^+$).

Example 2. Preparation of Compounds 2-4

Compounds 2-4 are prepared as described in Method A using the appropriate bis-boronic acids using a similar procedure as described in Example 1.

| Compound | IUPAC name | $^1$H-NMR | LC-MS: m/z (M+H$^+$) |
|---|---|---|---|
| 2 | (2R, 3S, 4R, 5S, 6R)-2-(Hydroxymethyl)-6-[3-[(2R, 3S, 4R, 5S, 6R)-3, 4, 5-trihydroxy-6-(hydroxymethyl)tetrahydropyran-2-yl]phenyl]tetrahydropyran-3, 4, 5-triol | (400 MHz, CD$_3$OD) δ 7.59 (d, J = 17.3 Hz, 1H), 7.46-7.38 (m, 3H), 4.99 (d, J = 3.5 Hz, 2H), 4.47 (t, J = 3.3 Hz, 2H), 3.86-3.82 (m, 4H), 3.74 (t, J = 8.1 Hz, 2H), 3.59 (dd, J = 8.1, 3.1 Hz, 2H), 3.46 (ddd, J = 8.2, 5.7, 3.9 Hz, 2H). | 403.3 |
| 3 | (2R, 3S, 4R, 5S, 6R)-2-(Hydroxymethyl)-6-[3-(trifluoromethyl)-5-[(2R, 3S, 4R, 5S, 6R)-3, 4, 5-trihydroxy-6-(hydroxymethyl)tetrahydropyran-2-yl]phenyl]tetrahydropyran-3, 4, 5-triol | (400 MHz, CD$_3$OD) δ 7.86 (s, 1H), 7.76 (s, 2H), 4.98 (d, J = 5.2 Hz, 2H), 4.30 (dd, J = 5.2, 3.1 Hz, 2H), 3.94 (dd, J = 12.0, 7.4 Hz, 2H), 3.84-3.76 (m, 4H), 3.66 (dd, J = 6.9, 3.1 Hz, 2H), 3.57 (td, J = 7.1, 3.1 Hz, 2H). | 471.3 |
| 4 | (2R, 3S, 4R, 5S, 6R)-2-(Hydroxymethyl)-6-[4-isopropoxy-3-[(2R, 3S, 4R, 5S, 6R)-3, 4, 5-trihydroxy-6-(hydroxymethyl)tetrahydropyran-2-yl]phenyl]tetrahydropyran-3, 4, 5-triol | (400 MHz, CDCl$_3$) δ 7.61 (d, J = 1.9 Hz, 1H), 7.37 (dd, J = 8.6, 1.8 Hz, 1H), 7.02 (d, J = 8.7 Hz, 1H), 5.22 (d, J = 5.5 Hz, 1H), 4.94 (d, J = 3.5 Hz, 1H), 4.71-4.61 (m, 1H), 4.49 (dd, J = 5.5, 3.1 Hz, 1H), 4.44 (t, J = 3.3 Hz, 1H), 3.95 (dd, J = 11.7, 6.6 Hz, 1H), 3.89-3.69 (m, 7H), 3.64 (dd, J = 8.1, 3.0 Hz, 1H), 3.53-3.42 (m, 1H), 1.36 (dd, J = 10.9, 6.0 Hz, 6H). | 461.4 |

Example 3: Preparation of Compound 5 (Method A)

(2R,2'R,3S,3'S,4R,4'R,5S,5'S,6R,6'R)-6,6'-([1,1'-Biphenyl]-3,4'-diyl)bis(2-(hydroxymethyl)tetrahydro-2H-pyran-3,4,5-triol)

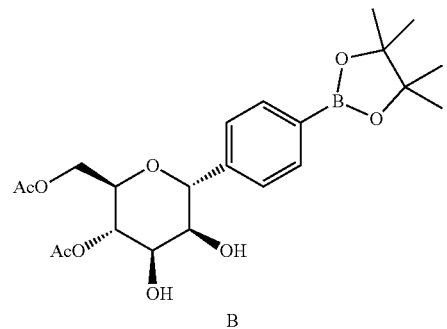

B

+

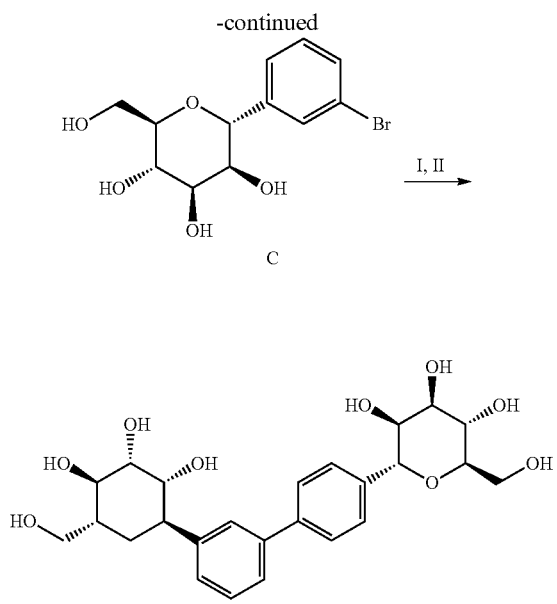

Step I: ((2R,3S,4R,5S,6R)-3-Acetoxy-4,5-dihydroxy-6-(3'-((2R,3S,4R,5S,6R)-3,4,5-trihydroxy-6-(hydroxymethyl)tetrahydro-2H-pyran-2-yl)-[1,1'-biphenyl]-4-yl)tetrahydro-2H-pyran-2-yl)methyl acetate A mixture of Intermediate B (30 mg, 0.066 mmol), (2R,3S,4R,5S,6R)-2-(3-bromophenyl)-6-(hydroxymethyl)tetrahydro-2H-pyran-3,4,5-triol (C, 30.71 mg, 0.087 mmol), PdCl$_2$(dppf).CH$_2$Cl$_2$ (4.1 mg, 0.005 mmol) and potassium phosphate (35.7 mg, 0.167 mmol) in degassed DMF is heated in a 4 mL sealed vial at 90° C. for 4 h. The mixture is filtered through a pad of celite and purified directly by reverse phase HPLC on Phenomenex C18 Gemini AXIA 5μ 110 A 21.2×75 mm 0% ACN/H$_2$O+0.01% TFA-To 50% ACN+0.01% TFA in 20 min-To 100% ACN in 5 min-Hold 5 min at 100% ACN. Total Run Time: 30 min to afford the title product.

Step II: Compound 5

((2R,3S,4R,5S,6R)-3-acetoxy-4,5-dihydroxy-6-(3'-((2R,3S,4R,5S,6R)-3,4,5-trihydroxy-6-(hydroxymethyl)tetrahydro-2H-pyran-2-yl)-[1,1'-biphenyl]-4-yl)tetrahydro-2H-pyran-2-yl)methyl acetate from Step I is dissolved in MeOH (0.5 mL) and MeONa in MeOH (5 μL of 25% w/v, 0.023 mmol) is added and the reaction mixture is stirred at RT for 15 h. The reaction is neutralized by the addition of Amberlite IR120H resin until the pH changed to neutral. The reaction mixture is filtered and the filtrate is evaporated to afford the title compound as a white solid (10.5 mg). $^1$H NMR (400 MHz, CD$_3$OD) δ 7.78 (s, 1H), 7.66 (d, J=8.4 Hz, 2H), 7.55 (d, J=8.0 Hz, 3H), 7.44 (d, J=4.9 Hz, 2H), 5.02 (2d, J=3.5 Hz, 2H), 4.47 (dd, J=6.2, 3.1 Hz, 2H), 3.88-3.79 (m, 4H), 3.74 (td, J=8.0, 2.8 Hz, 2H), 3.61 (td, J=7.9, 3.1 Hz, 2H), 3.56-3.43 (m, 2H). LC-MS: m/z=479.4 (M+H$^+$)

Example 4. Preparation of Compound 6 (Method A)

(2R,2'R,3S,3'S,4R,4'R,5S,5'S,6R,6'R)-6,6'-([1,1'-Biphenyl]-4,4'-diyl)bis(2-(hydroxymethyl)tetrahydro-2H-pyran-3,4,5-triol)

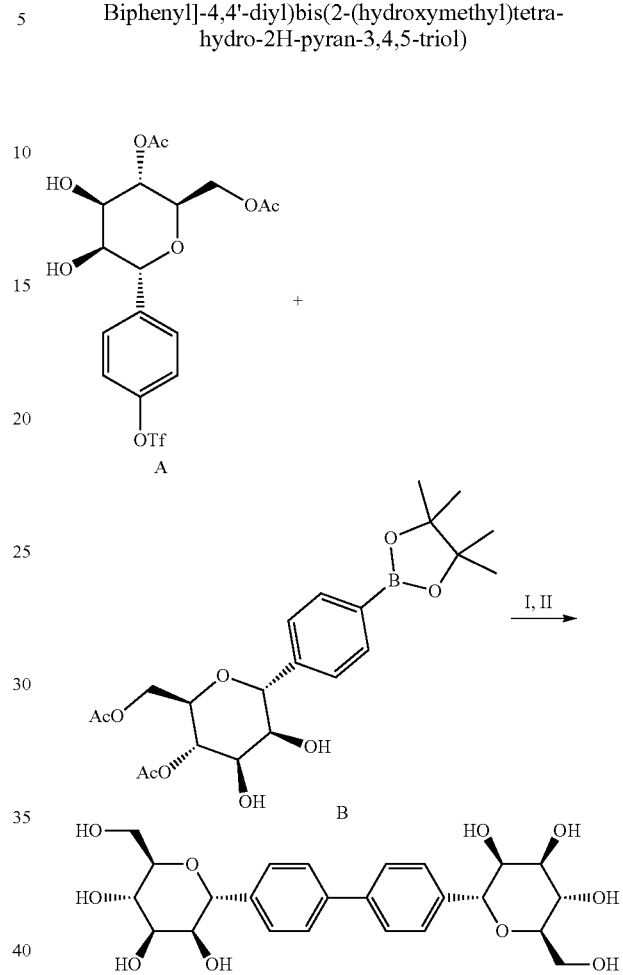

The title compound is prepared using a similar procedure as described for Example 3, Compound 5 but using Intermediate A and Intermediate B as starting materials. $^1$H NMR (400 MHz, CD$_3$OD) δ 7.64 (t, J=10.1 Hz, 4H), 7.56 (d, J=8.2 Hz, 4H), 5.03 (d, J=3.3 Hz, 2H), 4.48 (t, J=3.3 Hz, 2H), 3.89-3.81 (m, 4H), 3.76 (t, J=8.1 Hz, 2H), 3.62 (dd, J=8.1, 3.0 Hz, 2H), 3.56-3.46 (m, 2H). LC-MS: m/z=479.5 (M+H$^+$).

Alternative Synthesis of Compound 6 (Method B)

(2R,2'R,3S,3'S,4R,4'R,5S,5'S,6R,6'R)-6,6'-([1,1'-Biphenyl]-4,4'-diyl)bis(2-(hydroxymethyl)tetrahydro-2H-pyran-3,4,5-triol)

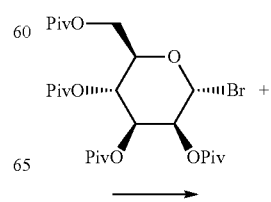

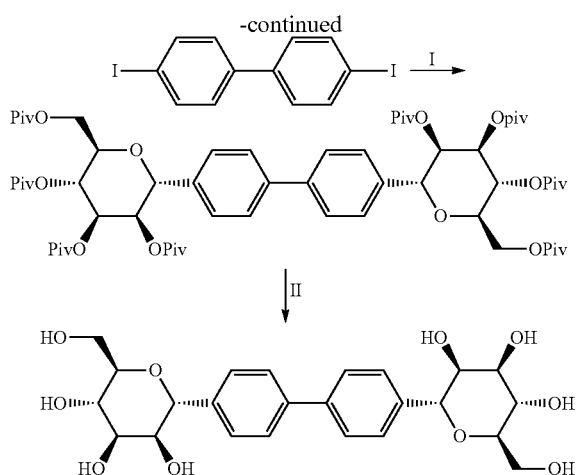

Step I: [(2R,3R,4R,5R,6R)-3,4,5-Tris(2,2-dimethyl-propanoyloxy)-6-[4-[4-[(2R,3R,4R,5R,6R)-3,4,5-tris(2,2-dimethylpropanoyloxy)-6-(2,2-dimethylpropanoyloxymethyl)tetrahydropyran-2-yl]phenyl]phenyl]tetrahydropyran-2-yl]methyl 2,2-dimethylpropanoate A solution of n-Bu$_3$MgLi (2.195 mL of 0.66 M, 1.449 mmol) in hexane-heptane-dibutylether (8:20:3) is added to heterogeneous mixture of 1-iodo-4-(4-iodophenyl)benzene (701 mg, 1.726 mmol) in toluene (4.0 mL) and dibutylether (2.4 mL) at 0° C. and stirred at the same temperature for 3.5 h. A solution of ZnBr$_2$—LiBr in dibutyl ether (2.17 mL of 1.05 M, 2.28 mmol) is added dropwise, cooling bath removed and stirred at RT for 1 h. A solution of [(2R,3R,4S,5S,6R)-6-bromo-3,4,5-tris(2,2-dimethylpropanoyloxy)tetrahydropyran-2-yl]methyl 2,2-dimethylpropanoate (2 g, 3.451 mmol, Ref. Sebastien Lemaire et. al. Org. Letts. 2012, 14, 1480-1483) in toluene (3.6 mL) is added, it is placed on pre-heated oil bath at 100° C. and stirred for 30 h. The reaction mixture is cooled to RT and poured into aqueous 1N HCl solution (40 mL), extracted with EtOAc (3×25 mL), combined extracts are washed with brine, dried (Na$_2$SO$_4$) and concentrated. The residue is purified on Biotage™ SNAP 100 g silica gel cartridge using EtOAc in Hex (0% to 15%, 8 CV) as eluent to afford the title compound (400 mg, 0.347 mmol, 20%) as light yellow solid. $^1$H NMR (400 MHz, CDCl$_3$) δ 7.67 (d, J=8.5 Hz, 4H), 7.63 (d, J=8.4 Hz, 4H), 6.07 (t, J=2.8 Hz, 2H), 5.54 (t, J=9.2 Hz, 2H), 5.19 (dd, J=9.4, 2.9 Hz, 2H), 5.13 (d, J=2.6 Hz, 2H), 4.32 (dd, J=12.2, 5.6 Hz, 2H), 4.19 (dd, J=12.2, 1.9 Hz, 2H), 3.87-3.79 (m, 2H), 1.28 (s, 36H), 1.19 (s, 18H), 1.15 (s, 18H).

Step II, Compound 6

To a stirred suspension of [(2R,3R,4R,5R,6R)-3,4,5-tris(2,2-dimethylpropanoyloxy)-6-[4-[4-[(2R,3R,4R,5R,6R)-3,4,5-tris(2,2-dimethylpropanoyloxy)-6-(2,2-dimethylpropanoyloxymethyl)tetrahydropyran-2-yl]phenyl]phenyl]tetrahydropyran-2-yl]methyl 2,2-dimethylpropanoate (165 mg, 0.1433 mmol) in MeOH (1.8 mL) is added MeONa in MeOH (57.0 μL of 0.5 M, 0.287 mmol), stirred at RT for 66 h and quenched with acetic acid (50 μL, 0.8792 mmol). The reaction mixture is concentrated and directly loaded onto 3 g C18 samplet using DMSO-CH$_2$Cl$_2$, dried under house vacuum, purified on Biotage™ SNAP 25 g C18 silica gel cartridge using CH$_3$CN in water (0% to 50%, 12 CV) as eluent to afford title compound (30 mg, 0.0613 mmol, 43%) as white solid. $^1$H NMR (400 MHz, CD$_3$OD) δ 7.64 (d, J=8.4 Hz, 4H), 7.55 (d, J=8.2 Hz, 4H), 5.01 (d, J=3.5 Hz, 2H), 4.46 (t, J=3.3 Hz, 2H), 3.83 (d, J=4.7 Hz, 4H), 3.74 (t, J=8.1 Hz, 2H), 3.60 (dd, J=8.1, 3.1 Hz, 2H), 3.53-3.46 (m, 2H)

Example 5. Preparation of Compound 7

(3-[(2R,3S,4R,5S,6R)-3,4,5-Trihydroxy-6-(hydroxymethyl)tetrahydropyran-2-yl]-N-[4-[[3-[(2R,3S,4R,5S,6R)-3,4,5-trihydroxy-6-(hydroxymethyl)tetrahydropyran-2-yl]benzoyl]amino]phenyl]benzamide)

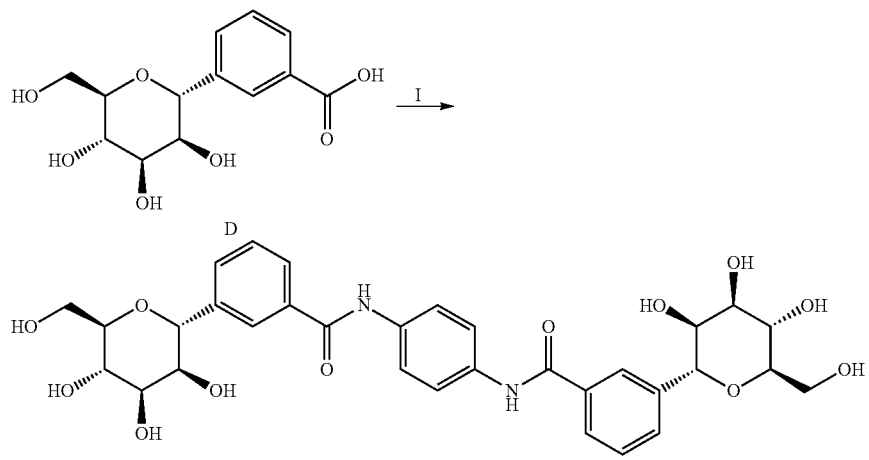

To a solution of Intermediate D (40 mg, 0.14 mmol), benzene-1,4-diamine (7.6 mg, 0.07 mmol) and HATU (69.20 mg, 0.18 mmol) in DMF (350 μL) is added triethylamine (29 μL, 0.21 mmol) and the reaction mixture is stirred at RT for 18 h. The mixture is purified directly by reverse phase HPLC on Phenomenex C18 Gemini AXIA Pack 5μ 110 A 21.2×250 mm (Hold 10 min at 10%) 10% ACN/H$_2$O+ 0.01% TFA-To 60% ACN+0.01% TFA in 20 min-To 100% ACN in 5 min-Hold 5 min at 100% ACN. Total Run Time:

40 min to afford the title product (27.1 mg, 0.04 mmol, 57.22%) as a white solid. ¹H NMR (400 MHz, CD₃OD) δ 8.06 (s, 2H), 7.86 (d, J=7.8 Hz, 2H), 7.72 (d, J=7.0 Hz, 6H), 7.53 (t, J=7.8 Hz, 2H), 5.02 (d, J=4.4 Hz, 2H), 4.46-4.39 (m, 2H), 3.97-3.75 (m, 6H), 3.68 (dd, J=7.4, 3.0 Hz, 2H), 3.57 (td, J=6.9, 3.0 Hz, 2H). LC-MS: m/z=641.4 (M+H⁺).

Example 6. Preparation of Compounds 8-16

Compounds 8-16 are prepared starting from the appropriate diamine and Intermediate D using a similar procedure as described in Example 5.

| Compound No. | Structure and IUPAC name | LC-MS m/z (M + H⁺) |
|---|---|---|
| 8 | (R,R,S,R,S)-N,N'-(Ethane-1,2-diyl)bis(3-((2R,3S,4R,5S,6R)-3,4,5-trihydroxy-6-(hydroxymethyl)tetrahydro-2H-pyran-2-yl)benzamide) | 593.4 |
| 9 | (R,R,S,R,S)-N,N'-(Propane-1,3-diyl)bis(3-((2R,3S,4R,5S,6R)-3,4,5-trihydroxy-6-(hydroxymethyl)tetrahydro-2H-pyran-2-yl)benzamide) | 607.4 |
| 10 | (R,R,S,R,S)-N,N'-(Butane-1,4-diyl)bis(3-((2R,3S,4R,5S,6R)-3,4,5-trihydroxy-6-(hydroxymethyl)tetrahydro-2H-pyran-2-yl)benzamide) | 621.4 |
| 11 | (R,R,S,R,S)-N,N'-(Pentane-1,5-diyl)bis(3-((2R,3S,4R,5S,6R)-3,4,5-trihydroxy-6-(hydroxymethyl)tetrahydro-2H-pyran-2-yl)benzamide) | 635.5 |
| 12 | (R,R,S,R,S)-N,N'-(Hexane-1,6-diyl)bis(3-((2R,3S,4R,5S,6R)-3,4,5-trihydroxy-6-(hydroxymethyl)tetrahydro-2H-pyran-2-yl)benzamide) | 649.6 |
| 13 | (R,R,S,R,S)-N,N'-(Heptane-1,7-diyl)bis(3-((2R,3S,4R,5S,6R)-3,4,5-trihydroxy-6-(hydroxymethyl)tetrahydro-2H-pyran-2-yl)benzamide) | 663.5 |
| 14 | (R,R,S,R,S)-N,N'-(Octane-1,8-diyl)bis(3-((2R,3S,4R,5S,6R)-3,4,5-trihydroxy-6-(hydroxymethyl)tetrahydro-2H-pyran-2-yl)benzamide) | 667.5 |
| 15 | (R,R,S,R,S)-N,N'-((Ethane-1,2-diylbis(oxy))bis(ethane-2,1-diyl))bis(3-((2R,3S,4R,5S,6R)-3,4,5-trihydroxy-6-(hydroxymethyl)tetrahydro-2H-pyran-2-yl)benzamide) | 681.5 |
| 16 | ((R,R,S,R,S)-N,N'-(Methylenebis(4,1-phenylene))bis(3-((2R,3S,4R,5S,6R)-3,4,5-trihydroxy-6-(hydroxymethyl)tetrahydro-2H-pyran-2-yl)benzamide) | 731.5 |

Example 7. Preparation of Compound 17

((2R,3S,4R,5S,6R)-2-(Hydroxymethyl)-6-[3-[(2R,3S,4S,5S,6R)-3,4,5-trihydroxy-6-(hydroxymethyl)tetrahydropyran-2-yl]oxyphenyl]tetrahydropyran-3,4,5-triol)

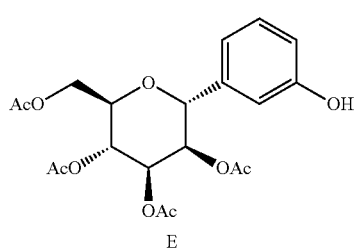

E

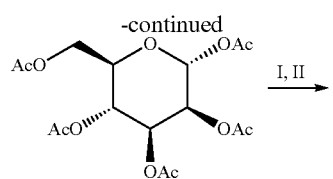

I, II →

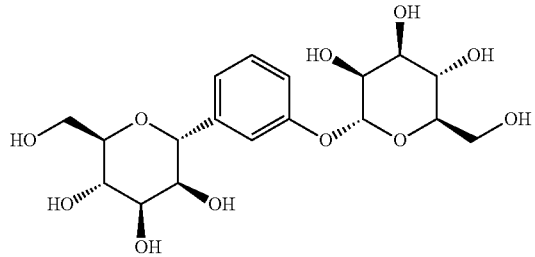

Step I: [(2R,3R,4R,5R,6R)-3,4,5-Triacetoxy-6-[3-[(2R,3S,4S,5R,6R)-3,4,5-triacetoxy-6-(acetoxymethyl)tetrahydropyran-2-yl]oxyphenyl]tetrahydropyran-2-yl]methyl acetate To a cold (0° C.) stirred solution of (2R,3R,4R,5R,6R)-2-(acetoxymethyl)-6-(3-hydroxyphenyl)tetrahydro-2H-pyran-3,4,5-triyl triacetate (100 mg, 0.2356 mmol) and [(2R,3R,4S,5S,6R)-3,4,5,6-tetraacetoxytetrahydropyran-2-yl]methyl acetate (92 mg, 0.2356 mmol) in CH₂Cl₂ (1.379 mL) is added neat BF₃.OEt₂ (100 mg, 0.7068 mmol). The cooling bath is removed, stirred at RT for 15 min and then it is heated at 40° C. for 18 h. It is cooled to RT and poured into aqueous NaHCO₃ solution (4 mL), stirred for 30 min, aqueous solution is extracted with methylene chloride (2×4 mL). The combined extracts are dried and concentrated, and purified on Biotage™ SNAP 25 g silica gel cartridge using EtOAc in Hex (30% to 70%, 8 CV, 70% 6 CV) as eluent to afford the title compound (130 mg, 0.1723 mmol, 73.12%) as half-white solid. ¹H NMR (400 MHz, CDCl₃) δ 7.41-7.33 (m, 1H), 7.23 (s, 1H), 7.19 (d, J=7.7 Hz, 1H), 7.10 (dd, J=8.2, 2.4 Hz, 1H), 5.92 (t, J=3.2 Hz, 1H), 5.59-5.52 (m, 2H), 5.45 (dd, J=3.5, 1.8 Hz, 1H), 5.39 (t, J=10.1 Hz, 1H), 5.32 (t, J=8.7 Hz, 1H), 5.13 (dd, J=8.9, 3.1 Hz, 1H), 5.07 (d, J=3.1 Hz, 1H), 4.43-4.35 (m, 1H), 4.34-4.26 (m, 1H), 4.21-4.04 (m, 3H), 3.88-3.75 (m, 1H), 2.21 (s, 3H), 2.165 (s, 3H), 2.153 (s, 3H), 2.064 (s, 3H), 2.06 (s, 3H), 2.049 (s, 3H), 2.04 (s, 3H), 2.037 (s, 3H)

Step II: Compound 17

To a stirred solution of [(2R,3R,4R,5R,6R)-3,4,5-triacetoxy-6-[3-[(2R,3S,4S,5R,6R)-3,4,5-triacetoxy-6-(acetoxymethyl)tetrahydropyran-2-yl]oxyphenyl]tetrahydropyran-2-yl]methyl acetate (118 mg, 0.1564 mmol) in MeOH (7 mL) is added MeONa (313 μL of 0.5 M, 0.1564 mmol) and the reaction mixture is stirred at RT overnight. Dowex 50 WX4-400 ion-exchange resin (H⁺)[washed several times with MeOH until colorless, dried] is added until pH 5-6, filtered off the resin and filtrate is concentrated. The residue is dissolved in CH₃CN-water, freeze dried to the title compound (55 mg, 79%) as white solid. ¹H NMR (400 MHz, CD₃OD) δ 7.21 (t, J=8.0 Hz, 1H), 7.17 (s, 1H), 7.03 (d, J=7.2 Hz, 1H), 6.94 (dd, J=8.2, 2.4 Hz, 1H), 5.40 (d, J=1.7

Hz, 1H), 4.85 (d, J=3.3 Hz, 1H), 4.32 (t, J=3.3 Hz, 1H), 3.90 (dd, J=3.4, 1.8 Hz, 1H), 3.85-3.44 (m, 9H), 3.43-3.30 (m, 1H).
LC-MS: m/z=491.2 (M+H$^+$).

Example 8. Preparation of Compound 18

((2R,3S,4S,5S,6S)-2-(Hydroxymethyl)-6-[4-[4-[1-[(2S,3S,4S,5S,6R)-3,4,5-trihydroxy-6-(hydroxymethyl)tetrahydropyran-2-yl]triazol-4-yl]phenyl]triazol-1-yl]tetrahydropyran-3,4,5-triol)

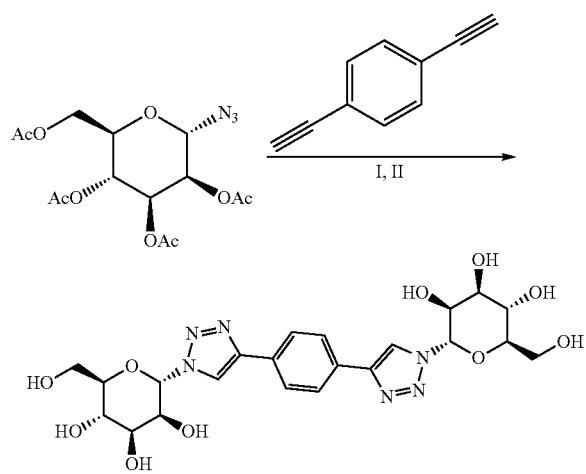

Step I: [(2R,3R,4S,5S,6S)-3,4,5-Triacetoxy-6-[4-[4-[1-[(2S,3S,4S,5R,6R)-3,4,5-triacetoxy-6-(acetoxymethyl)tetrahydropyran-2-yl]triazol-4-yl]phenyl]triazol-1-yl]tetrahydropyran-2-yl]methyl acetate To a stirred solution of [(2R,3R,4S,5S,6S)-3,4,5-triacetoxy-6-azido-tetrahydropyran-2-yl]methyl acetate (50 mg, 0.1339 mmol) in DMF (5 mL) are added, copper iodide (5.10 mg, 0.02678 mmol) and DIPEA (25.95 mg, 35 µL, 0.201 mmol) and it is purged with nitrogen gas. The reaction mixture is stirred at 80° C. for 5 h. It is cooled to RT, poured into water, extracted with EtOAc, combined extracts are washed with brine, dried (Na$_2$SO$_4$), concentrated. The residue is purified on Biotage™ SNAP 12 g silica gel cartridge using EtOAc in Hex (15% to 80%) as eluent to afford the title compound (20 mg, 34.2%) as light yellow solid. LC-MS: m/z=873.57 (M+H$^+$)

Step II: Compound 18

To a stirred suspension of [(2R,3R,4S,5S,6S)-3,4,5-triacetoxy-6-[4-[4-[1-[(2S,3S,4S,5R,6R)-3,4,5-triacetoxy-6-(acetoxymethyl)tetrahydropyran-2-yl]triazol-4-yl]phenyl]triazol-1-yl]tetrahydropyran-2-yl]methyl acetate (20 mg, 0.02292 mmol) in MeOH (1.000 mL) is added MeONa (45.84 µL of 0.5 M, 0.02292 mmol), suspension became clear and the product started crashing out. The reaction mixture is stirred at RT overnight, acetic acid is added, concentrated, suspended in 0.5 mL MeOH, and filtered to give an off white solid. The precipitate is washed with MeOH (0.5 mL), dried to the title compound (10.5 mg, 79.4%) as white solid. $^1$H NMR (400 MHz, DMSO-D$_6$) δ 8.66 (s, 2H), 7.95 (s, 4H), 6.04 (s, 2H), 5.32 (d, J=5.0 Hz, 2H), 5.08-4.96 (m, 4H), 4.58 (t, J=5.9 Hz, 2H), 3.95-3.86 (m, 2H), 3.75 (dd, J=10.9, 5.5 Hz, 2H), 3.65-3.56 (m, 2H), 3.55-3.36 (m, 6H). LC-MS: m/z=537.42 (M+H$^+$).

Example 9. Preparation of Compound 19

((2R,3S,4S,5S,6S)-2-(Hydroxymethyl)-6-[4-[3-[1-[(2S,3S,4S,5S,6R)-3,4,5-trihydroxy-6-(hydroxymethyl)tetrahydropyran-2-yl]triazol-4-yl]phenyl]triazol-1-yl]tetrahydropyran-3,4,5-triol)

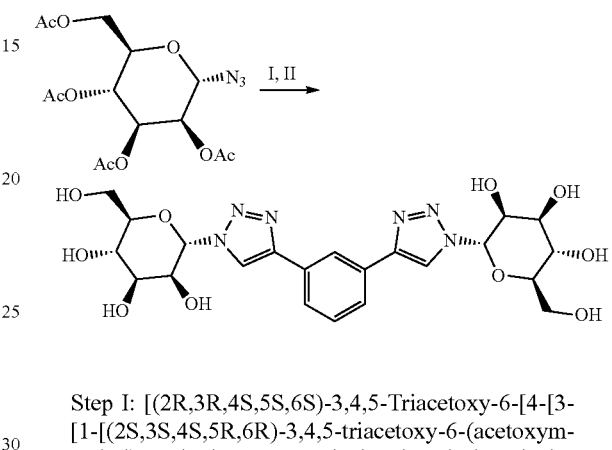

Step I: [(2R,3R,4S,5S,6S)-3,4,5-Triacetoxy-6-[4-[3-[1-[(2S,3S,4S,5R,6R)-3,4,5-triacetoxy-6-(acetoxymethyl)tetrahydropyran-2-yl]triazol-4-yl]phenyl]triazol-1-yl]tetrahydropyran-2-yl]methyl acetate To a stirred solution of [(2R,3R,4S,5S,6S)-4,5-diacetoxy-2-(acetoxymethyl)-6-azido-tetrahydropyran-3-yl] acetate (96.6 mg, 0.259 mmol) and 1,3-diethynylbenzene (11 mg, 0.087 mmol) in EtOH (1.1 mL) and water (275 µL) is added sequentially CuSO$_4$ (5.6 mg, 0.035 mmol) and sodium ascorbate (12.3 mg, 0.07 mmol) at RT. The reaction mixture is stirred at RT over weekend, it is diluted with methylene chloride, filtered through phase separator, and aqueous solution is extracted with methylene chloride. The combined extracts (35% to 75%, 15 CV; 75%, 9 CV) as eluent to afford the title compound (69 mg, 90.7%) as white solid. $^1$H NMR (400 MHz, CDCl$_3$) δ 8.34 (t, J=1.5 Hz, 1H), 8.07 (s, 2H), 7.89 (dd, J=7.8, 1.7 Hz, 2H), 7.55 (t, J=7.8 Hz, 1H), 6.10 (d, J=2.9 Hz, 2H), 6.06-6.02 (m, 2H), 5.97 (dd, J=8.8, 3.7 Hz, 2H), 5.40 (t, J=8.8 Hz, 2H), 4.42 (dd, J=12.5, 5.5 Hz, 2H), 4.13-4.05 (m, 2H), 3.99-3.92 (m, 2H), 2.20 (s, 6H), 2.11 (s, 6H), 2.09 (s, 6H), 2.08 (s, 6H).

Step II: Compound 19

To a stirred solution of [(2R,3R,4S,5S,6S)-3,4,5-triacetoxy-6-[4-[3-[1-[(2S,3S,4S,5R,6R)-3,4,5-triacetoxy-6-(acetoxymethyl)tetrahydropyran-2-yl]triazol-4-yl]phenyl]triazol-1-yl]tetrahydropyran-2-yl]methyl acetate (68 mg, 0.07791 mmol) in MeOH (3.4 mL) is added MeONa (156 µL of 0.5 M, 0.078 mmol) in MeOH. A white precipitate is started forming within an h. Reaction mixture is stirred at RT overnight. It is filtered off the fine white precipitate, washed with dry MeOH (2 mL), dried in vacuum to afford the title compound as white solid. $^1$H NMR (400 MHz, DMSO-D$_6$) δ 8.80 (s, 2H), 8.41 (s, 1H), 7.85 (dd, J=7.7, 1.6 Hz, 2H), 7.53 (t, J=7.8 Hz, 1H), 5.93 (d, J=4.5 Hz, 2H), 5.31 (d, J=5.4 Hz, 2H), 5.10 (d, J=5.2 Hz, 2H), 5.02 (d, J=5.4 Hz, 2H), 4.61

(t, J=5.8 Hz, 2H), 4.46 (dd, J=8.3, 4.8 Hz, 2H), 3.85 (dd, J=8.5, 6.5 Hz, 2H), 3.70-3.51 (m, 6H), 3.40 (td, J=6.8, 3.0 Hz, 2H).

$^1$H NMR (400 MHz, DMSO-D$_6$+D$_2$O) δ 8.68 (s, 2H), 8.33 (s, 1H), 7.82 (dd, J=7.7, 1.5 Hz, 2H), 7.53 (t, J=7.8 Hz, 1H), 5.93 (d, J=4.1 Hz, 2H), 4.46 (t, J=3.7 Hz, 2H), 3.84 (dd, J=7.2, 3.3 Hz, 2H), 3.65-3.51 (m, 6H), 3.37-3.27 (m, 2H). LC-MS: m/z=537.45 (M+H$^+$).

Example 10. Preparation of Compound 20

((2R,2'R,3S,3'S,4S,4'S,5S,5'S,6S,6'S)-6,6'-(4,4'-((Prop-2-yn-1-ylazanediyl)bis(methylene))bis(1H-1,2,3-triazole-4,1-diyl))bis(2-(hydroxymethyl)tetrahydro-2H-pyran-3,4,5-triol)

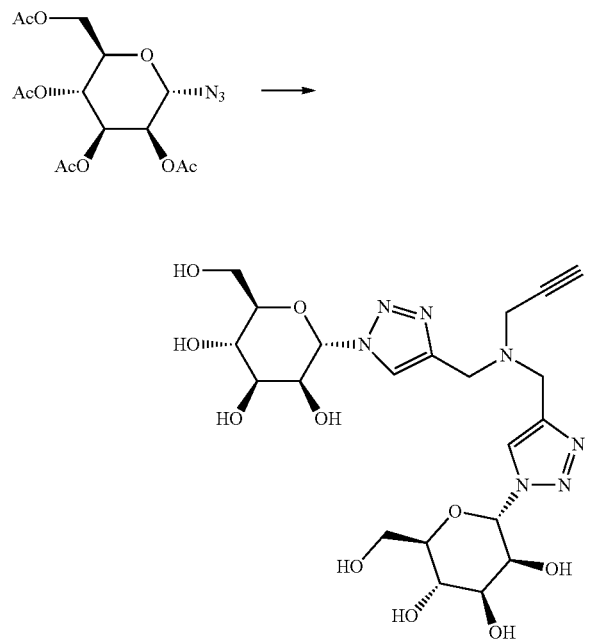

To a solution of [(2R,3R,4S,5S,6S)-4,5-diacetoxy-2-(acetoxymethyl)-6-azido-tetrahydropyran-3-yl] acetate (96.6 mg, 0.259 mmol) and N,N-bis(prop-2-ynyl)prop-2-yn-1-amine (10.3 mg, 11 μL, 0.0784 mmol) in EtOH (966 μL) and water (242 μL) is sequentially added CuSO$_4$ (5.0 mg, 0.031 mmol) and sodium ascorbate (11.1 mg, 0.0627 mmol). The reaction mixture is stirred at RT for 20 h and evaporated to dryness. The residue is purified by flash column chromatography on silica gel (2 to 20% MeOH in CH$_2$Cl$_2$) to give 73 mg of a mixture of the desired product that is used as is for the next step.

To a solution of the material obtained in the previous step in MeOH (2 mL) is added and MeONa (29 μL of 0.5 M, 0.0146 mmol) in MeOH. The mixture is stirred at RT overnight, AcOH (1 μL, 0.015 mmol) is added and the mixture is evaporated to dryness. The residue is purified by reverse phase HPLC to give 7 mg of the title compound. $^1$H NMR (400 MHz, CD$_3$OD) δ 8.23 (s, 2H), 5.96 (s, 2H), 4.60 (s, 2H), 4.30 (s, 4H), 3.95 (dd, J=8.1, 3.2 Hz, 2H), 3.82 (s, 2H), 3.69 (m, 6H), 3.25 (m, 2H), 3.13 (s, 1H).

Example 11. Preparation of Compound 21

((2R,3S,4R,5S,6R)-2-(Hydroxymethyl)-6-(4-(1-((2S,3S,4S,5S,6R)-3,4,5-trihydroxy-6-(hydroxymethyl) tetrahydro-2H-pyran-2-yl)-1H-1,2,3-triazol-4-yl) phenyl)tetrahydro-2H-pyran-3,4,5-triol)

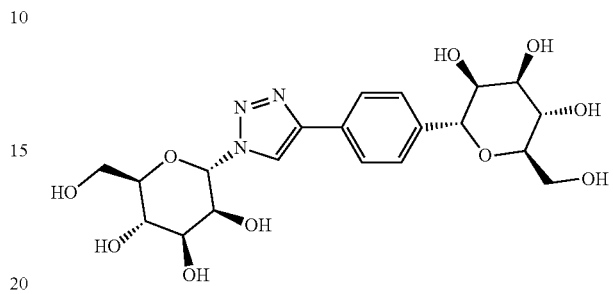

This compound is prepared from Intermediate F and [(2R,3R,4S,5S,6S)-4,5-diacetoxy-2-(acetoxymethyl)-6-azido-tetrahydropyran-3-yl] acetate using a similar procedure as described in Example 10. $^1$H NMR (400 MHz, DMSO-D$_6$) δ 8.66 (s, 1H), 7.80 (d, J=8.3 Hz, 2H), 7.44 (d, J=8.3 Hz, 2H), 5.88 (d, J=4.4 Hz, 1H), 4.68 (d, J=5.3 Hz, 1H), 4.41 (m, 1H), 4.03 (dd, J=5.3, 3.1 Hz, 1H), 3.81 (dd, J=6.7, 3.2 Hz, 1H), 3.66-3.46 (m, 6H), 3.46-3.28 (m, 3H). LC-MS: m/z=470.36 (M+H$^+$)

Example 12. Preparation of Compound 22 and Compound 23 (Modified Method D)

((2R,3S,4R,5S,6R)-2-(Hydroxymethyl)-6-[2-[4-[2-[(2R,3S,4R,5S,6R)-3,4,5-trihydroxy-6-(hydroxymethyl)tetrahydropyran-2-yl]ethyl]phenyl]ethyl]tetrahydropyran-3,4,5-triol) and (2R,3S,4R,5S,6R)-2-(Hydroxymethyl)-6-[4-[(2R,3S,4R,5S,6R)-3,4,5-trihydroxy-6-(hydroxymethyl)tetrahydropyran-2-yl] butyl]tetrahydropyran-3,4,5-triol)

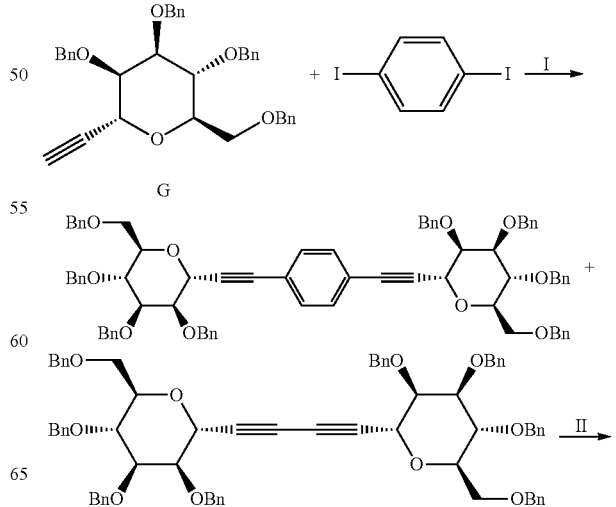

-continued

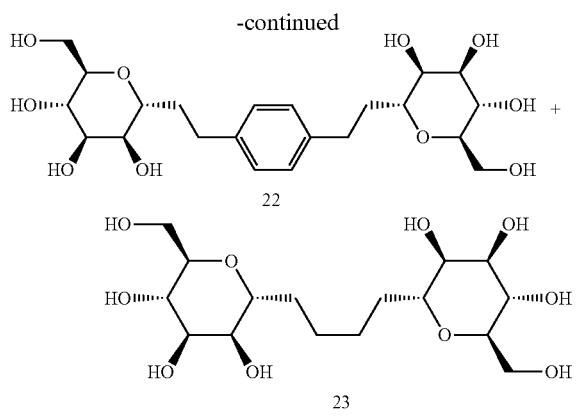

Step I

To a solution of Intermediate G (104 mg, 0.1895 mmol) in THF (4 mL) are added 1,4-diiodobenzene (27.8 mg, 0.0842 mmol), PdCl$_2$(dppf)-CH$_2$Cl$_2$ (3.5 mg, 0.0043 mmol), CuI (3.2 mg, 0.0168 mmol) and DIPEA (37 μL, 0.2106 mmol). The mixture is stirred at 50° C. overnight under nitrogen. After removal of the solvent under reduced pressure, the residue is separated on Biotage™ SNAP 25 g silica gel cartridge using a gradient of EtOAc in Hex 0-15% in 20 column volume to obtain an inseparable ~2:1 mixture (92 mg) of (2R,3R,4R,5R,6R)-3,4,5-tribenzyloxy-2-(benzyloxymethyl)-6-[2-[4-[2-[(2R,3R,4R,5R,6R)-3,4,5-tribenzyloxy-6-(benzyloxymethyl)tetrahydropyran-2-yl]ethynyl]phenyl]ethynyl]tetrahydropyran and (2R,3R,4R,5R,6R)-3,4,5-tribenzyloxy-2-(benzyloxymethyl)-6-[4-[(2R,3R,4R,5R,6R)-3,4,5-tribenzyloxy-6-(benzyloxymethyl)tetrahydropyran-2-yl]buta-1,3-diynyl]tetrahydropyran, respectively, which is used directly in the next step without further purification.

LC-MS: m/z=1193.9 (M+Na$^+$). LC-MS: m/z=1118.9 (M+Na$^+$).

Step II: Compound 22 and Compound 23

To a solution of the ~2:1 mixture from Step I (92 mg) in MeOH (5 mL) are added a catalytic amount of 20% Pd(OH)$_2$/C and a drop of acetic acid. The mixture is hydrogenated using a hydrogen balloon and stirred at RT overnight. After filtration, the solvent is removed and the residue is purified using reverse phase HPLC to obtain Compound 22 (11 mg) and Compound 23 (9 mg), both as white solid. Compound 22: $^1$H NMR (400 MHz, CD$_3$OD) δ 7.13 (s, 4H), 3.81 (m, 4H), 3.75-3.53 (m, 8H), 3.45 (m, 2H), 2.75 (m, 2H), 2.66-2.50 (m, 2H), 2.02 (m, 2H), 1.70 (m, 2H). LC-MS: m/z=459.4 (M+H$^+$). Compound 23: $^1$H NMR (400 MHz, CD$_3$OD) δ 3.83 (d, 2H), 3.77 (m, 2H), 3.72-3.61 (m, 6H), 3.58 (m, 2H), 3.39 (n, 2H), 1.76 (m, 2H), 1.45 (m, 6H). LC-MS: m/z=383.3 (M+H$^+$).

Example 13. Preparation of Compound 24

((2R,3S,4R,5S,6R)-2-(Hydroxymethyl)-6-[(E)-3-[4-[(E)-3-[(2R,3S,4R,5S,6R)-3,4,5-trihydroxy-6-(hydroxymethyl)tetrahydropyran-2-yl]prop-1-enyl]phenyl]allyl]tetrahydropyran-3,4,5-triol)

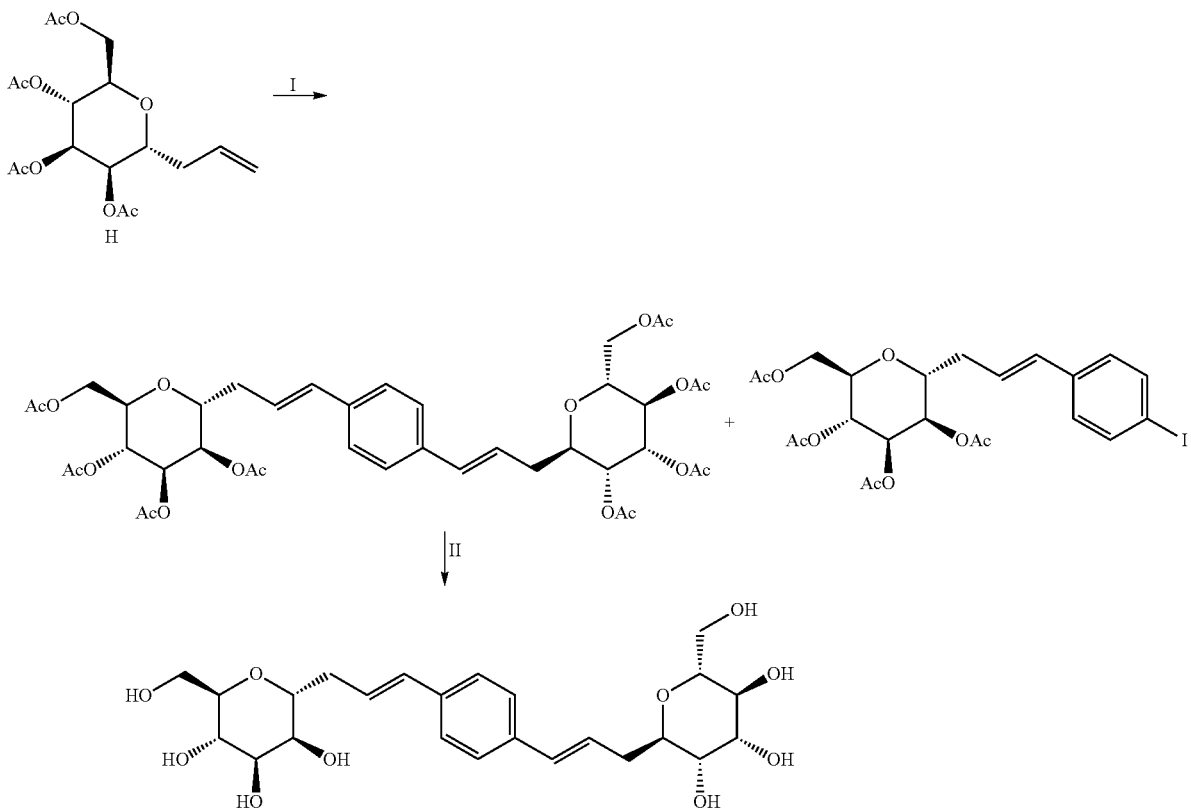

Step I: [(2R,3R,4R,5R,6R)-3,4,5-Triacetoxy-6-[(E)-3-[4-[(E)-3-[(2R,3R,4R,5R,6R)-3,4,5-triacetoxy-6-(acetoxymethyl)tetrahydropyran-2-yl]prop-1-enyl]phenyl]allyl]tetrahydropyran-2-yl]methyl acetate To a solution of Intermediate H (112.9 mg, 0.303 mmol) in DMF (1.5 mL) are added 1,4-diiodobenzene (50 mg, 0.152 mmol), palladium acetate (3.4 mg, 0.0152 mmol), tetrabutylammonium bromide (48.9 mg, 0.152 mmol) and sodium bicarbonate (38.2 mg, 0.455 mmol). The reaction mixture is heated at 85° C. overnight under $N_2$, concentrated and purified on Biotage™ SNAP (10 g silica gel cartridge) using EtOAc in Hex 0 to 70% as eluent in 20 column volume to afford title compound (71 mg, 57% yield). LC-MS: m/z=819.5 (M+H$^+$).

In addition, (2R,3R,4R,5R,6R)-2-(acetoxymethyl)-6-((E)-3-(4-iodophenyl)allyl)tetrahydro-2H-pyran-3,4,5-triyl triacetate (33 mg, 20% yield) is isolated as a minor compound. LC-MS: m/z=575.3 (M+H$^+$).

Step II: Compound 24

To a stirred solution of [(2R,3R,4R,5R,6R)-3,4,5-triacetoxy-6-[(E)-3-[4-[(E)-3-[(2R,3R,4R,5R,6R)-3,4,5-triacetoxy-6-(acetoxymethyl)tetrahydropyran-2-yl]prop-1-enyl]phenyl]allyl]tetrahydropyran-2-yl]methyl acetate (70 mg, 0.0855 mmol) in MeOH (1.1 mL) is added 2 drops of a 25% wt/v MeONa in MeOH. The reaction mixture is stirred at RT for 3 h. The mixture is diluted with MeOH and neutralized with resin Amberlite 120 (H). After filtration the resin is washed with MeOH, MeOH/H$_2$O (2:1, v/v) then a mixture dioxane/MeOH (1:1, v/v). The beige residue is triturated with MeOH to afford 19 mg of expected compound which is repurified by preparative HPLC to afford (2R,3S,4R,5S,6R)-2-(hydroxymethyl)-6-[(E)-3-[4-[(E)-3-[(2R,3S,4R,5S,6R)-3,4,5-trihydroxy-6-(hydroxymethyl)tetrahydropyran-2-yl]prop-1-enyl]phenyl]allyl]tetrahydropyran-3,4,5-triol (12.9 mg, 31% yield). $^1$H NMR (400 MHz, CD$_3$OD) δ 7.21 (s, 4H), 6.38 (d, 2H), 6.28-6.10 (m, 2H), 3.88 (dd, 2H), 3.76-3.59 (m, 8H), 3.55 (t, 2H), 3.43 (ddd, 2H), 2.62-2.46 (m, 2H), 2.48-2.30 (m, 2H). LC-MS: m/z=483.4 (M+H$^+$)

Example 14. Preparation of Compound 25

((2R,3S,4R,5S,6R)-2-(Hydroxymethyl)-6-[(E)-3-[3-[(E)-3-[(2R,3S,4R,5S,6R)-3,4,5-trihydroxy-6-(hydroxymethyl)tetrahydropyran-2-yl]prop-1-enyl]phenyl]allyl]tetrahydropyran-3,4,5-triol)

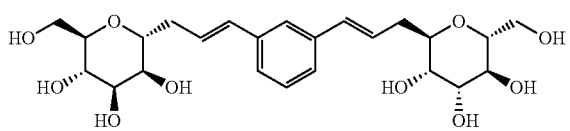 [SMILES: OC[C@H]1O[C@H](C/C=C/c2cccc(/C=C/C[C@H]3O[C@H](CO)[C@@H](O)[C@H](O)[C@@H]3O)c2)[C@@H](O)[C@@H](O)[C@@H]1O]

Compound 25 is prepared according to a similar procedure as described in Example 13, Compound 24 using 1,3-diiodobenzene instead of 1,4-diiodobenzene as starting material.

$^1$H NMR (400 MHz, CD$_3$OD) δ 7.30 (s, 1H), 7.12 (d, 3H), 6.40 (d, 2H), 6.30-6.10 (m, 2H), 3.90 (s, 2H), 3.79-3.33 (m, 12H), 2.55 (d, 2H), 2.42 (dd, 2H).

LC-MS: m/z=483.4 (M+H$^+$).

Example 15. Preparation of Compounds 26-33

Compounds 26-33 are prepared from Intermediate H and appropriate 1,4-diiodobenzene derivatives using a similar procedure as described in Example 14.

| Compound | IUPAC name | $^1$H-NMR | LC-MS m/z (M + H$^+$) |
|---|---|---|---|
| 26 | (Methyl 2,5-bis[(E)-3-[(2R,3S,4R,5S,6R)-3,4,5-trihydroxy-6-(hydroxymethyl)tetrahydropyran-2-yl]prop-1-enyl]benzoate) | (400 MHz, CD$_3$OD) δ 7.70 (d, 1H), 7.47 (dd, 2H), 7.06 (d, 1H), 6.42 (d, 1H), 6.35-6.20 (m, 1H), 6.20-6.04 (m, 1H), 3.91 (d, 2H), 3.79 (s, 3H), 3.75-3.6 (m, 8H), 3.55 (td, 2H), 3.50-3.40 (m, 2H), 2.57 (dd, 2H), 2.42 (m, 2H). | 541.4 |
| 27 | ((2R,3S,4R,5S,6R)-2-(Hydroxymethyl)-6-[(E)-3-[3-methyl-4-[(E)-3-[(2R,3S,4R,5S,6R)-3,4,5-trihydroxy-6-(hydroxymethyl)tetrahydropyran-2-yl]prop-1-enyl]phenyl]allyl]tetrahydropyran-3,4,5-triol) | (400 MHz, CD$_3$OD) δ 7.37 (d, 1H), 7.20-7.04 (m, 2H), 6.68 (d, 1H), 6.42 (d, 1H), 6.33-6.19 (m, 1H), 6.19-6.06 (m, 1H), 3.97 (m, 2H), 3.80 (m, 3H), 3.78-3.67 (m, 5H), 3.63 (td, 2H), 3.57-3.47 (m, 2H), 2.71-2.56 (m, 2H), 2.50 (dt, 2H), 2.29 (s, 3H | 497.5 |
| 28 | ((2R,3S,4R,5S,6R)-2-[(E)-3-[3-Fluoro-4-[(E)-3-[(2R,3S,4R,5S,6R)-3,4,5-trihydroxy-6-(hydroxymethyl)tetrahydropyran-2-yl]prop-1-enyl]phenyl]allyl]-6-(hydroxymethyl)tetrahydropyran-3,4,5-triol) | (400 MHz, CD$_3$OD) δ 7.36 (t, 1H), 7.02 (dd, 2H), 6.51 (d, 1H), 6.37 (d, 1H), 6.33-6.11 (m, 2H), 3.89 (td, 2H), 3.76-3.59 (m, 8H), 3.55 (td, 2H), 3.44 (ddd, 2H), 2.63-2.49 (m, 2H), 2.49-2.35 (m, 2H). | 501.5 |
| 29 | ((2R,3S,4R,5S,6R)-2-[(E)-3-[3-Chloro-4-[(E)-3-[(2R,3S,4R,5S,6R)-3,4,5-trihydroxy-6-(hydroxymethyl)tetrahydropyran- | (400 MHz, CD$_3$OD) δ 7.54 (d, 1H), 7.36 (d, 1H), 7.27 (d, 1H), 6.82 (d, 1H), 6.44 (d, 1H), 6.32 (dt, 2H), 3.98 (d, 2H), 3.75 (tdt, 8H), 3.63 (q, 2H), 3.58-3.45 | 517.4 |

| Compound | IUPAC name | ¹H-NMR | LC-MS m/z (M + H⁺) |
|---|---|---|---|
| | 2-yl]prop-1-enyl]phenyl]allyl]-6-(hydroxymethyl)tetrahydropyran-3,4,5-triol) | (m, 2H), 2.74-2.58 (m, 2H), 2.58-2.41 (m, 2H). | |
| 30 | ((2R,3S,4R,5S,6R)-2-[(E)-3-[2,5-Dimethoxy-4-[(E)-3-[(2R,3S,4R,5S,6R)-3,4,5-trihydroxy-6-(hydroxymethyl)tetrahydropyran-2-yl]prop-1-enyl]phenyl]allyl]-6-(hydroxymethyl)tetrahydropyran-3,4,5-triol) | (400 MHz, DMSO) δ 7.01 (s, 2H), 6.61 (d, 2H), 6.39-6.21 (m, 2H), 3.82-3.65 (m, 8H), 3.62-3.25 (m, 12H), 2.73 (m, 4H). | 543.5 |
| 31 | ((2R,3S,4R,5S,6R)-2-[(E)-3-[3,5-Dimethyl-4-[(E)-3-[(2R,3S,4R,5S,6R)-3,4,5-trihydroxy-6-(hydroxymethyl)tetrahydropyran-2-yl]prop-1-enyl]phenyl]allyl]-6-(hydroxymethyl)tetrahydropyran-3,4,5-triol) | (400 MHz, CD₃OD) δ 7.02 (s, 2H), 6.38 (d, 1H), 6.30-6.10 (m, 1H), 5.90 (ddd, 1H), 5.32 (dd, 1H), 4.36 (d, 1H), 3.95 (dd, 1H), 3.85-3.35 (m, 14H), 2.68-2.52 (m, 1H), 2.54-2.38 (m, 1H), 2.25 (s, 6H). | 511.5 |
| 32 | ((2R,3S,4R,5S,6R)-2-(Hydroxymethyl)-6-[(E)-3-[3-nitro-4-[(E)-3-[(2R,3S,4R,5S,6R)-3,4,5-trihydroxy-6-(hydroxymethyl)tetrahydropyran-2-yl]prop-1-enyl]phenyl]allyl]tetrahydropyran-3,4,5-triol) | (400 MHz, CD₃OD) δ 7.76 (d, 1H), 7.56 (q, 2H), 6.73 (d, 1H), 6.54-6.21 (m, 3H), 3.91 (s, 2H), 3.77-3.60 (m, 8H), 3.55 (q, 2H), 3.49-3.34 (m, 2H), 2.59 (dd, 2H), 2.45 (s, 2H). | 528.5 |
| 33 | (2,5-Bis[(E)-3-[(R2R,3S,4R,5S,6R)-3,4,5-trihydroxy-6-(hydroxymethyl)tetrahydropyran-2-yl]prop-1-enyl]benzonitrile) | (400 MHz, CD₃OD) δ 7.74-7.35 (m, 3H), 6.70 (d, 1H), 6.59-6.24 (m, 3H), 3.91 (d, 2H), 3.77-3.60 (m, 8H), 3.55 (dt, 2H), 3.45 (dt, 2H), 2.77-2.31 (m, 4H). | 508.5 |

Example 16. Preparation of Compound 34

((2R,3S,4R,5S,6R)-2-(Hydroxymethyl)-6-[(E)-3-[4-[2-[4-[(2R,3S,4R,5S,6R)-3,4,5-trihydroxy-6-(hydroxymethyl)tetrahydropyran-2-yl]phenyl]ethynyl]phenyl]allyl]tetrahydropyran-3,4,5-triol)

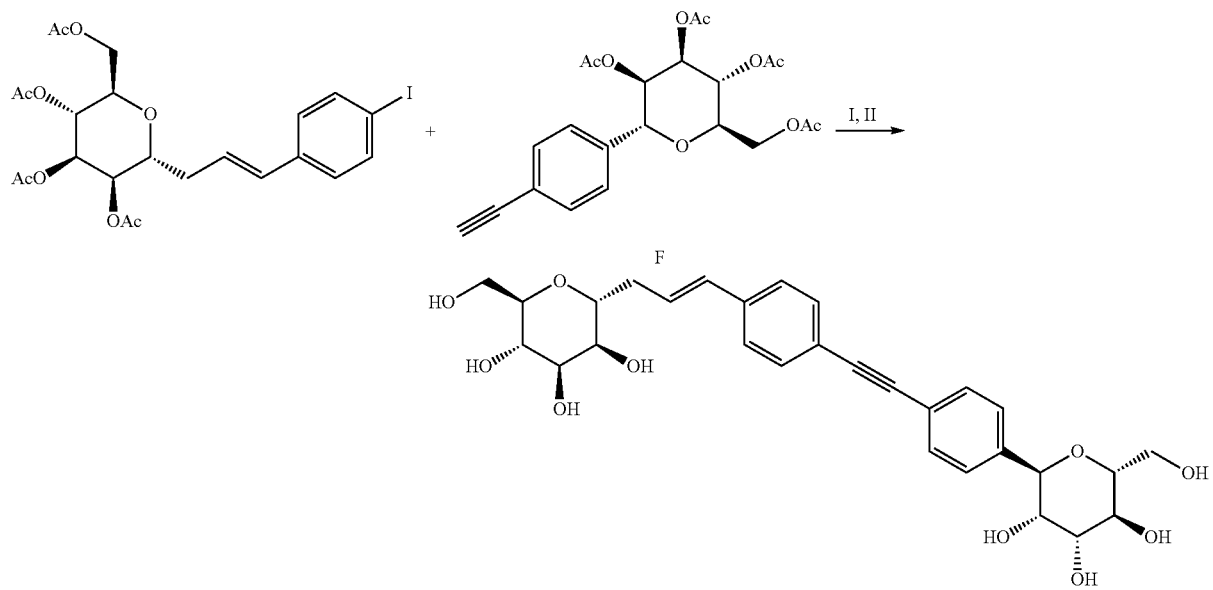

Step I: [(2R,3R,4R,5R,6R)-3,4,5-Triacetoxy-6-[(E)-3-[4-[2-[4-[(2R,3R,4R,5R,6R)-3,4,5-triacetoxy-6-(acetoxymethyl)tetrahydropyran-2-yl]phenyl]ethynyl]phenyl]allyl]tetrahydropyran-2-yl]methyl acetate To a mixture of (2R,3R,4R,5R,6R)-2-(acetoxymethyl)-6-((E)-3-(4-iodophenyl)allyl)tetrahydro-2H-pyran-3,4,5-triyl triacetate (33 mg, 0.057 mmol), Intermediate F (24.9 mg, 0.057 mmol), Pd(dppf) (4.7 mg, 0.0057 mmol), CuI (2.2 mg, 0.0115 mmol) in DMF (660 μL) is added NEt₃ (24 μL, 0.173 mmol). The system is flushed with nitrogen and the mixture is heated to 70° C. overnight under N₂. The RM is diluted with EtOAc and H₂O, filtered on celite. The organic phase is washed with brine, dried over Na₂SO₄, filtered, concentrated and purified on a Biotage™ SNAP (10 g silica gel cartridge) using a gradient of EtOAc in Hex (10-80%) in 25 column volume to afford title compound (22 mg, 43.5%). LC-MS: m/z=879.6 (M+H⁺).

Step II: Compound 34

To the residue from step I (22 mg, 0.025 mmol) in MeOH (660 μL) is added 2 drops of 25% w/v MeONa in MeOH. The reaction mixture is stirred at RT for 2 h, neutralized with resin Amberlite 120 (H). After filtration, the resin is washed with MeOH and the filtrate concentrated to dryness. The residue is purified by reverse phase HPLC to afford the title compound (2.6 mg, 20%). ¹H NMR (400 MHz, CD₃OD) δ 7.49-7.37 (m, 4H), 7.32 (m, 4H), 6.43 (d, 1H), 6.36-6.21 (m, 1H), 5.39 (s, 2H), 4.30 (t, 1H), 3.90 (t, 1H), 3.82-3.31 (m, 10H), 2.57 (dd, 1H), 2.44 (dd, 1H). LC-MS: m/z=543.4 (M+H⁺).

Example 17. Preparation of Compound 35 (Method F)

((2R,3S,4R,5S,6R)-2-(Hydroxymethyl)-6-[2-[3-[(2R,3S,4R,5S,6R)-3,4,5-trihydroxy-6-(hydroxymethyl)tetrahydropyran-2-yl]phenyl]ethynyl]tetrahydropyran-3,4,5-triol)

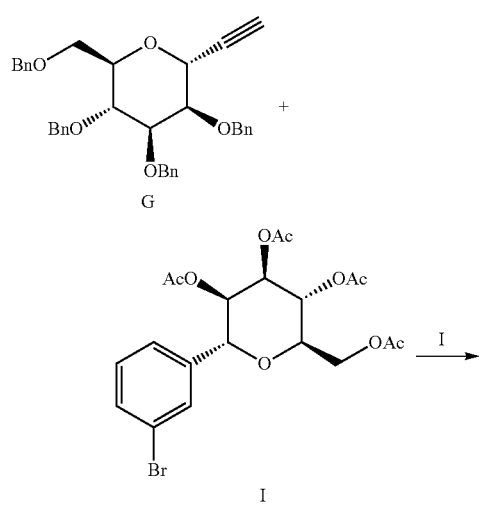

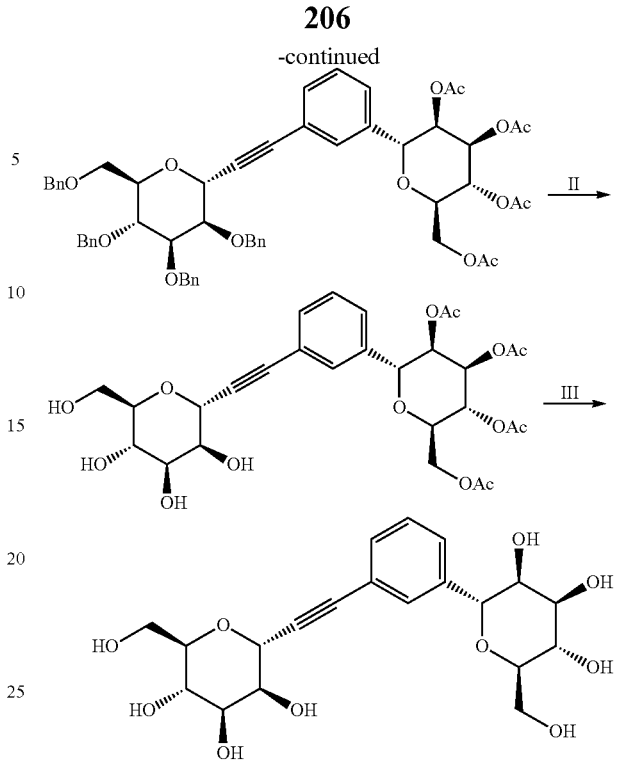

Step I: [(2R,3R,4R,5R,6R)-3,4,5-Triacetoxy-6-[3-[2-[(2R,3R,4R,5R,6R)-3,4,5-tribenzyloxy-6-(benzyloxymethyl)tetrahydropyran-2-yl]ethynyl]phenyl]tetrahydropyran-2-yl]methyl acetate To a solution of Intermediate G (160 mg, 0.2916 mmol) in DMF (4 mL) are added Intermediate I (113.7 mg, 0.2333 mmol), PdCl₂(dppf)-CH₂Cl₂ (9.5 mg, 0.0117 mmol), CuI (8.9 mg, 0.0467 mmol) and DIPEA (102 μL, 0.5832 mmol). The mixture is stirred at 80° C. overnight under nitrogen. After removal of the solvent under reduced pressure, the residue is separated on Biotage™ SNAP 25 g silica gel cartridge using a gradient of EtOAc in Hex 0-15% in 20 CV to obtain the title compound (65 mg). LC-MS: m/z=955.5 (M+H⁺).

Step II: (2R,3R,4R,5R,6R)-2-(acetoxymethyl)-6-(3-(((2R,3S,4R,5S,6R)-3,4,5-trihydroxy-6-(hydroxymethyl)tetrahydro-2H-pyran-2-yl)ethynyl)phenyl)tetrahydro-2H-pyran-3,4,5-triyl triacetate To a solution of [(2R,3R,4R,5R,6R)-3,4,5-triacetoxy-6-[3-[2-[(2R,3R,4R,5R,6R)-3,4,5-tribenzyloxy-6-(benzyloxymethyl)tetrahydropyran-2-yl]ethynyl]phenyl]tetrahydropyran-2-yl]methyl acetate from Step I (20 mg, 0.0209 mmol) in CH₃CN (2 mL) is added TMSI (41.90 mg, 29.80 μL, 0.2094 mmol) in a sealed vessel. The mixture is stirred at RT overnight. It is then quenched with drops of water. After removal of the solvent under reduced pressure, the residue is used directly in the next step without purification.

Step III: Compound 35

To the mixture from step II in MeOH (2 mL) is added a drop of 25% MeONa in MeOH. The mixture is stirred at RT for 20 min, then neutralized with resin Amberlite IR 120 (H) and filtered. The filtrate is concentrated to dryness and the

207 residue is purified using prep-HPLC to provide (2R,3S,4R,5S,6R)-2-(hydroxymethyl)-6-[2-[3-[(2R,3S,4R,5S,6R)-3,4,5-trihydroxy-6-(hydroxymethyl)tetrahydropyran-2-yl]phenyl]ethynyl]tetrahydropyran-3,4,5-triol (1.5 mg) as a white solid. ¹H NMR (400 MHz, CD$_3$OD) δ 7.51 (s, 1H), 7.45-7.35 (m, 1H), 7.28 (m, 2H), 4.82 (d, 1H), 4.76 (d, 1H), 4.24 (m, 1H), 3.91 (m, 1H), 3.84 (m, 1H), 3.80-3.75 (m, 2H), 3.74-3.69 (m, 2H), 3.67-3.60 (m, 2H), 3.58-3.46 (m, 2H), 3.41 (m, 1H).

LC-MS: m/z=427.3 (M+H$^+$).

Example 18. Preparation of Compound 36

((2R,3S,4R,5S,6R)-2-(Hydroxymethyl)-6-[4-[4-[(2R,3S,4R,5S,6R)-3,4,5-trihydroxy-6-(hydroxymethyl)tetrahydropyran-2-yl]triazol-1-yl]phenyl]tetrahydropyran-3,4,5-triol)

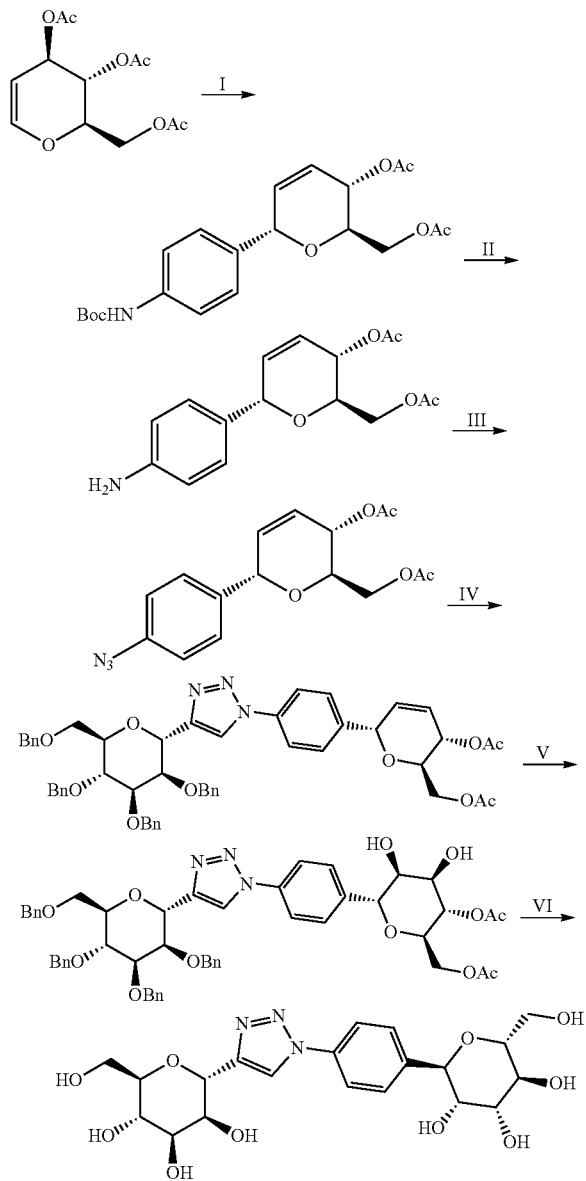

208

Step I: [(2R,3S,6S)-3-Acetoxy-6-[4-(tert-butoxycarbonylamino)phenyl]-3,6-dihydro-2H-pyran-2-yl] methyl acetate To a solution of [(2R,3S,4R)-3,4-diacetoxy-3,4-dihydro-2H-pyran-2-yl]methyl acetate (4 g, 14.69 mmol) in CH$_3$CN (35 mL) are added [4-(tert-butoxycarbonylamino)phenyl]boronic acid (6.965 g, 29.38 mmol) and Pd(OAc)$_2$ (494.6 mg, 2.203 mmol). The mixture is stirred at RT overnight and then added another batch of [4-(tert-butoxycarbonylamino)phenyl]boronic acid (6.965 g, 29.38 mmol) and Pd(OAc)$_2$ (495 mg, 2.203 mmol). After stirring at RT overnight, the mixture is diluted with CH$_2$Cl$_2$ (35 mL), filtered on a pad of celite. The filtrate is concentrated to dryness under reduced pressure and the residue is purified on Biotage™ SNAP 100 g silica gel cartridge using a gradient of EtOAc in Hex (0-15%, 20 CV) to obtain the title compound (660 mg) as a glassy solid.

Step II: ((2R,3S,6S)-3-acetoxy-6-(4-aminophenyl)-3,6-dihydro-2H-pyran-2-yl)methyl acetate To a solution of [(2R,3S,6S)-3-acetoxy-6-[4-(tert-butoxycarbonylamino)phenyl]-3,6-dihydro-2H-pyran-2-yl]methyl acetate (303 mg, 0.7473 mmol) in 1 mL of CH$_2$Cl$_2$ is added TFA (1 mL, 12.98 mmol). The mixture is stirred at RT for 20 min. After removal of the solvent under reduced pressure, the residue is dissolved in 10 mL of CH$_2$Cl$_2$, washed with 10% sodium bicarbonate (2 mL) and brine (5 mL) consecutively, dried over sodium sulfate, filtered, and concentrated to dryness. The residue is used in the next step without further purification. LC-MS of the mixture shows two products with the same desired mass. LC-MS: m/z=306.4 (M+H$^+$).

Step III: [(2R,3S,6S)-3-Acetoxy-6-(4-azidophenyl)-3,6-dihydro-2H-pyran-2-yl]methyl acetate To a solution of the mixture from Step II in 2 mL of ACN are added t-BuONO (133 μL, 1.121 mmol) and TMSN$_3$ (119 μL, 0.8968 mmol) at 0° C. and then stirred at RT for 1 h. After removal of the solvent under reduced pressure, the mixture is purified on Biotage™ SNAP 25 g silica gel cartridge using a gradient of EtOAc in Hex 0-15% in 20 CV to obtain a mixture (190 mg), containing title compound as oil, which is used directly in the next step without further purification. LC-MS: m/z=356.5 (M+Na$^+$).

Step IV: ((2R,3S,6S)-3-acetoxy-6-(4-(4-((2R,3R,4R,5R,6R)-3,4,5-tris(benzyloxy)-6-((benzyloxy)methyl)tetrahydro-2H-pyran-2-yl)-1H-1,2,3-triazol-1-yl)phenyl)-3,6-dihydro-2H-pyran-2-yl)methyl acetate To a solution of [(2R,3S,6S)-3-acetoxy-6-(4-azidophenyl)-3,6-dihydro-2H-pyran-2-yl]methyl acetate (60 mg, 0.1811 mmol) in THF (5 mL) are added (2R,3R,4R,5R,6R)-3,4,5-tribenzyloxy-2-(benzyloxymethyl)-6-ethynyl-tetrahydropyran (99.4 mg, 0.1811 mmol), CuI (6.9 mg, 0.0362 mmol) and DIPEA (24 mg, 32 μL, 0.1811 mmol). The mixture is stirred at 45° C. overnight under nitrogen. After removal of the solvent under reduced pressure, the residue is separated on Biotage™ SNAP 25 g silica gel cartridge using a gradient of EtOAc in Hex 0-45% in 20 CV to obtain a mixture (142 mg) containing[(2R,3S,6S)-3-acetoxy-6-[4-[4-[(2R,3R,4R,5R,6R)-3,4,5-tribenzyloxy-6-(benzyloxymethyl)tetrahydropyran-2-yl]triazol-1-yl]phenyl]-3,6-dihydro-2H-pyran-2-yl]methyl acetate. LC-MS: m/z=880.7 (M+H⁺).

Step V: ((2R,3S,4R,5S,6R)-3-acetoxy-4,5-dihydroxy-6-(4-(4-((2R,3R,4R,5R,6R)-3,4,5-tris(benzyloxy)-6-((benzyloxy)methyl)tetrahydro-2H-pyran-2-yl)-1H-1,2,3-triazol-1-yl)phenyl)tetrahydro-2H-pyran-2-yl)methyl acetate To a solution of [(2R,3S,6S)-3-acetoxy-6-[4-[4-[(2R,3R,4R,5R,6R)-3,4,5-tribenzyloxy-6-(benzyloxymethyl)tetrahydropyran-2-yl]triazol-1-yl]phenyl]-3,6-dihydro-2H-pyran-2-yl]methyl acetate (160 mg, 0.1818 mmol) in water (2 mL)/t-BuOH (4 mL) are added NMO (42.6 mg, 38 µL, 0.3636 mmol), 2.5% OsO₄/t-BuOH (184.9 mg, 973 µL, 0.0182 mmol), methanesulfonamide (25.9 mg, 0.2727 mmol) and 2,6-lutidine (19.48 mg, 21 µL, 0.1818 mmol). The mixture is stirred at RT for 5 days. Then it is diluted with CH₂Cl₂ (10 mL), quenched with 10% sodium bisulfite solution (5 mL), extracted with CH₂Cl₂ (3×10 mL). The combined organic extracts are dried over sodium sulfate, filtered, and concentrated to dryness. The residue is purified on Biotage™ SNAP 25 g silica gel cartridge using a gradient of MeOH in CH₂Cl₂ 0-5% in 20 CV to obtain a mixture (150 mg) as oil. LC-MS: m/z=914.7 (M+H⁺).

Step VI: Compound 36

To a solution of the mixture from Step V, containing [(2R,3S,4R,5S,6R)-3-acetoxy-4,5-dihydroxy-6-[4-[4-[(2R,3R,4R,5R,6R)-3,4,5-tribenzyloxy-6-(benzyloxymethyl)tetrahydropyran-2-yl]triazol-1-yl]phenyl]tetrahydropyran-2-yl]methyl acetate (60 mg, 0.0657 mmol) in MeOH (2 mL) is added one drop of 25% MeONa/MeOH. The mixture is stirred at RT for 30 min. It is then neutralized with resin Amberlite IR 120 (H), filtered and concentrated to dryness. The residue is not purified and dissolved in MeOH (2 mL). Then to it are added a catalytic amount of 20% Pd(OH)₂ and a drop of AcOH. The mixture is hydrogenated using a hydrogen balloon and stirred at RT overnight. After filtration, the solvent is removed under reduced pressure and the residue is purified on reverse phase HPLC to provide the title compound (11 mg) as a white solid. ¹H NMR (400 MHz, CD₃OD) δ 8.47 (s, 1H), 7.78 (d, 2H), 7.62 (d, 2H), 5.10 (d, 1H), 4.91 (d, 1H), 4.45 (t, 1H), 4.28 (m, 1H), 3.91-3.58 (m, 7H), 3.55 (m, 1H), 3.47 (m, 1H), 3.41-3.33 (m, 1H). LC-MS: m/z=470.4 (M+H⁺).

Example 19. Preparation of Compound 37

((2R,3S,4R,5S,6R)-2-(Hydroxymethyl)-6-[2-[3-[(2R,3S,4R,5S,6R)-3,4,5-trihydroxy-6-(hydroxymethyl)tetrahydropyran-2-yl]phenyl]ethyl]tetrahydropyran-3,4,5-triol)

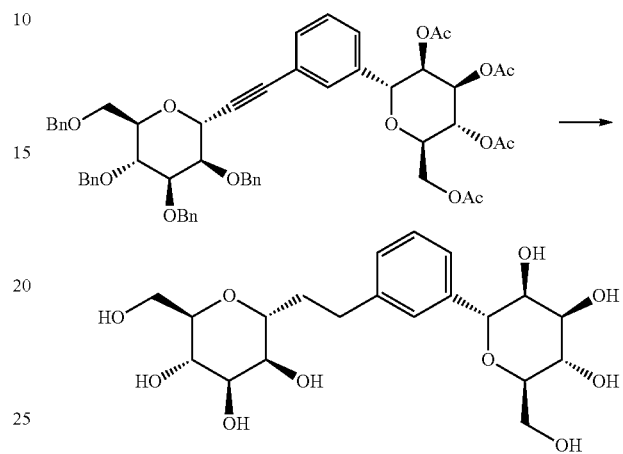

To a solution of [(2R,3R,4R,5R,6R)-3,4,5-triacetoxy-6-[3-[2-[(2R,3R,4R,5R,6R)-3,4,5-tribenzyloxy-6-(benzyloxymethyl)tetrahydropyran-2-yl]ethynyl]phenyl]tetrahydropyran-2-yl]methyl acetate (Example 17, step I) (32 mg, 0.0335 mmol) in MeOH (2 mL) is added a drop of 25% MeONa/MeOH. The mixture is stirred at RT for 30 min. Then it is neutralized with resin Amberlite IR 120 (H), and filtered. The filtrate is concentrated to dryness and the residue is dissolved in MeOH (2 mL). Then to it are added 20% Pd(OH)₂/C and drop of acetic acid. The mixture is hydrogenated using a hydrogen balloon and stirred at RT overnight. After filtration, it is concentrated to dryness and the residue is separated using reverse phase prep-HPLC to obtain the title compound (11 mg) as a white solid. ¹H NMR (400 MHz, CD₃OD) δ 7.38 (s, 1H), 7.27 (d, 2H), 7.21-7.09 (m, 1H), 4.95 (d, 1H), 4.44 (t, 1H), 3.94-3.74 (m, 4H), 3.74-3.52 (m, 6H), 3.45 (m, 2H), 2.80 (m, 1H), 2.73-2.57 (m, 1H), 2.17-1.95 (m, 1H), 1.82-1.65 (m, 1H). LC-MS: m/z=431.4 (M+H⁺).

Example 20. Preparation of Compound 38

(2R,3S,4R,5S,6R)-2-(hydroxymethyl)-6-[3-[4-[3-[(2R,3S,4R,5S,6R)-3,4,5-trihydroxy-6-(hydroxymethyl)tetrahydropyran-2-yl]propyl]phenyl]propyl]tetrahydropyran-3,4,5-triol

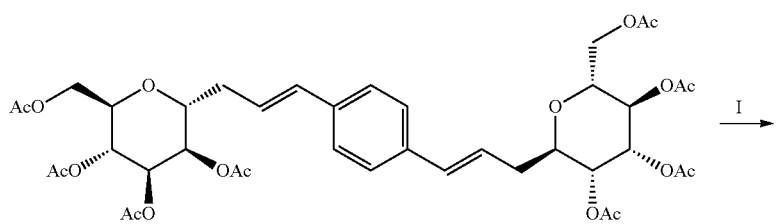

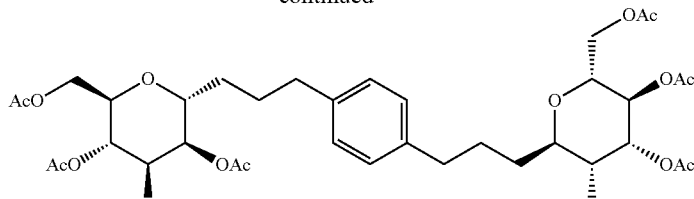

↓ II

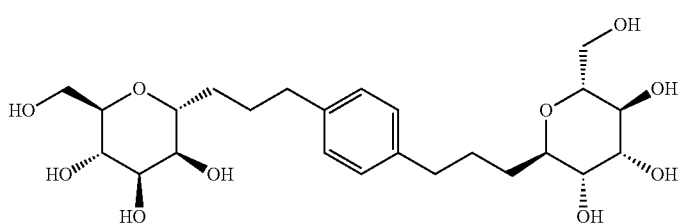

Step I: [(2R,3R,4R,5R,6R)-3,4,5-Triacetoxy-6-[3-[4-[3-[(2R,3R,4R,5R,6R)-3,4,5-triacetoxy-6-(acetoxymethyl)tetrahydropyran-2-yl]propyl]phenyl]propyl]tetrahydropyran-2-yl]methyl acetate To [(2R,3R,4R,5R,6R)-3,4,5-triacetoxy-6-[(E)-3-[4-[(E)-3-[(2R,3R,4R,5R,6R)-3,4,5-triacetoxy-6-(acetoxymethyl)tetrahydropyran-2-yl]prop-1-enyl]phenyl]allyl]tetrahydropyran-2-yl]methyl acetate (Example 13, Step I) (80 mg, 0.097 mmol) in MeOH (2.4 mL) is added Pd(OH)$_2$ (13.7 mg, 0.097 mmol) and 1 drop AcOH. The reaction mixture is hydrogenated under 1 atmosphere of H$_2$ overnight. The reaction mixture is filtered on celite, washed with MeOH. The filtrate is concentrated and purified on Biotage™ SNAP 10 g silica gel cartridge using EtOAc in Hex (15 to 100%) to provide the title compound (36 mg, 44.8%). LC-MS: m/z=823.7 (M+H$^+$).

Step II: Compound 38

To a solution of [(2R,3R,4R,5R,6R)-3,4,5-triacetoxy-6-[3-[4-[3-[(2R,3R,4R,5R,6R)-3,4,5-triacetoxy-6-(acetoxymethyl)tetrahydropyran-2-yl]propyl]phenyl]propyl]tetrahydropyran-2-yl]methyl acetate (36 mg, 0.097 mmol) in MeOH (1.6 mL) is added catalytic MeONa (2 μL of 25% w/v, 0.0097 mmol). The reaction mixture is stirred at RT for 1 h, neutralized with Amberlite IR120(H). After filtration, the solvent is removed under reduced pressure and the residue purified by reverse phase HPLC to afford the title compound (6.9 mg, 14%). $^1$H NMR (400 MHz, CD$_3$OD) δ 7.00 (s, 4H), 3.80-3.72 (m, 2H), 3.67 (dd, 2H), 3.63-3.54 (m, 4H), 3.55-3.46 (m, 4H), 3.31-3.22 (m, 2H), 2.60-2.40 (m, 4H), 1.64 (ddd, 6H), 1.48-1.25 (m, 2H). LC-MS: m/z=487.4 (M+H$^+$).

Example 21 Preparation of Compound 39

(3-[(2R,3S,4R,5S,6R)-3,4,5-Trihydroxy-6-(hydroxymethyl)tetrahydropyran-2-yl]-N-[4-[(2R,3S,4R,5S,6R)-3,4,5-trihydroxy-6-(hydroxymethyl)tetrahydropyran-2-yl]phenyl]benzamide)

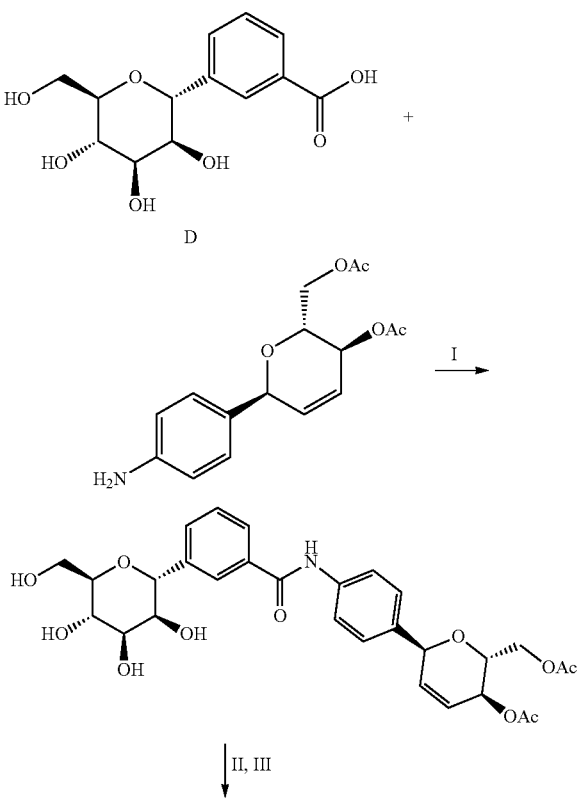

↓ II, III

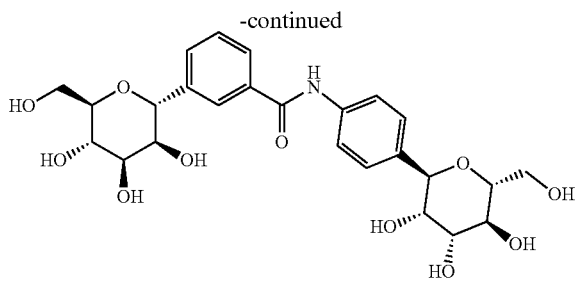

Step I: [(2R,3S,6S)-3-Acetoxy-6-[4-[[3-[(2R,3S,4R,5S,6R)-3,4,5-trihydroxy-6-(hydroxymethyl)tetrahydropyran-2-yl]benzoyl]amino]phenyl]-3,6-dihydro-2H-pyran-2-yl]methyl acetate To a mixture of Intermediate D (40.4 mg, 0.142 mmol) and [(2R,3S,6S)-3-acetoxy-6-(4-aminophenyl)-3,6-dihydro-2H-pyran-2-yl]methyl acetate (from Step II of Example 18, 43.4 mg, 0.142 mmol) in DMF (2.7 mL) is added 2,6-lutidine (49 µL, 0.426 mmol) followed by HATU (59.4 mg, 0.156 mmol) at 0° C. The reaction mixture is stirred at RT overnight, diluted with EtOAc, washed with $H_2O$, brine. The organic phase is dried over $Na_2SO_4$, filtered and concentrated. The residue is purified by Biotage™ SNAP 10 g silica gel cartridge using MeOH/$CH_2Cl_2$ (0 to 20%) to afford the title compound (45 mg, 55% yield), which is used in the next step without further purification. LC-MS: m/z=572.4 (M+H$^+$).

Step II: [(2R,3S,4R,5S,6R)-3-Acetoxy-4,5-dihydroxy-6-[4-[[3-[(2R,3S,4R,5S,6R)-3,4,5-trihydroxy-6-(hydroxymethyl)tetrahydropyran-2-yl]benzoyl]amino]phenyl]tetrahydropyran-2-yl]methyl acetate To a solution of [(2R,3S,6S)-3-acetoxy-6-[4-[[3-[(2R,3S,4R,5S,6R)-3,4,5-trihydroxy-6-(hydroxymethyl)tetrahydropyran-2-yl]benzoyl]amino]phenyl]-3,6-dihydro-2H-pyran-2-yl]methyl acetate (45 mg, 0.0788 mmol) in a mixture of water (0.45 mL)/t-BuOH (0.45 mL) are added methanesulfonamide (22.5 mg, 0.236 mmol), 2.5% OsO$_4$/t-BuOH (148.3, 0.012 mmol), NMO (37 mg, 0.315 mmol) and 2,6-lutidine (18 µL, 0.157 mmol). The mixture is stirred at RT for 2 days, quenched with 15% sodium bisulfite and diluted with EtOAc. The aqueous phase is separated, the organic phase is washed with water, brine and dried over sodium sulfate. The solvent is removed under reduced pressure to afford the title compound (29 mg, 36% yield). LC-MS: m/z=606.4 (M+H$^+$).

Step III: Compound 39

To a solution of [(2R,3S,4R,5S,6R)-3-acetoxy-4,5-dihydroxy-6-[4-[[3-[(2R,3S,4R,5S,6R)-3,4,5-trihydroxy-6-(hydroxymethyl)tetrahydropyran-2-yl]benzoyl]amino]phenyl]tetrahydropyran-2-yl]methyl acetate (29 mg, 0.048 mmol) in MeOH (0.45 mL) is added 2 drops MeONa 25% w/v in MeOH. The reaction mixture is stirred at RT for 1 h, diluted with MeOH, neutralized with resin Amberlite 120 (H), filtered and dried. The residue is purified by reverse phase HPLC to provide the title compound (2.7 mg).

$^1$H NMR (400 MHz, CD$_3$OD) δ 7.96 (s, 1H), 7.77 (d, 1H), 7.64 (d, 2H), 7.58 (d, 1H), 7.49-7.31 (m, 3H), 4.9 (m, 2H), 4.36 (dd, 2H), 3.88-3.30 (m, 10H). LC-MS: m/z=522.4 (M+H$^+$).

Example 22. Preparation of Compound 40

((2R,3S,4R,5S,6R)-2-(Hydroxymethyl)-6-[(E)-3-[3-[2-[(2R,3S,4R,5S,6R)-3,4,5-trihydroxy-6-(hydroxymethyl)tetrahydropyran-2-yl]ethynyl]phenyl]allyl]tetrahydropyran-3,4,5-triol)

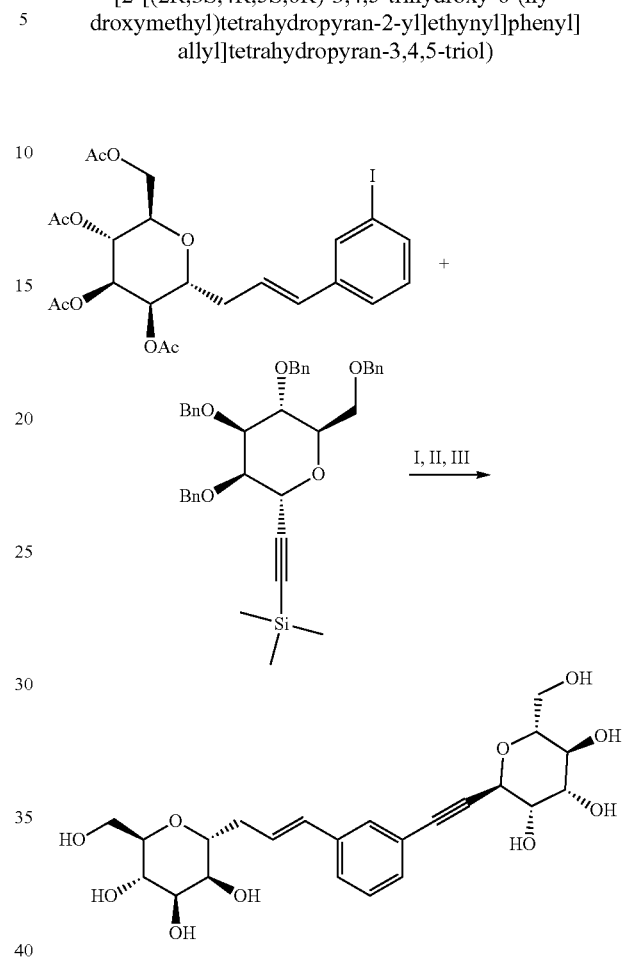

(2R,3R,4R,5R,6R)-2-(acetoxymethyl)-6-((E)-3-(3-iodophenyl)allyl)tetrahydro-2H-pyran-3,4,5-triyl triacetate is prepared according to the same procedure as described in Example 13 using 1,3-diiodobenzene instead of 1,4-diiodobenzene.

Step I: (2R,3R,4R,5R,6R)-2-(acetoxymethyl)-6-((E)-3-(3-(((2R,3R,4R,5R,6R)-3,4,5-tris(benzyloxy)-6-((benzyloxy)methyl)tetrahydro-2H-pyran-2-yl)ethynyl)phenyl)allyl)tetrahydro-2H-pyran-3,4,5-triyl triacetate To (2R,3R,4R,5R,6R)-2-(acetoxymethyl)-6-((E)-3-(3-iodophenyl)allyl)tetrahydro-2H-pyran-3,4,5-triyl triacetate (53 mg, 0.0923 mmol), trimethyl-[2-[(2R,3R,4R,5R,6R)-3,4,5-tribenzyloxy-6-(benzyloxymethyl)tetrahydropyran-2-yl]ethynyl]silane (Step II of Intermediate G, 57.3 mg, 0.0923 mmol), PdCl$_2$(dppf)-CH$_2$Cl$_2$ (7.5 mg, 0.0092 mmol) and CuI (3.5 mg, 0.0185 mmol) in DMF (1.1 mL) are added H$_2$O (16.6 al, 0.923 mmol) and DBU (140.5 mg, 0.923 mmol). The system is flushed with nitrogen and the mixture is heated to 70° C. overnight under N$_2$. The reaction mixture is diluted with EtOAc and H$_2$O, filtered on celite. The organic phase is washed with brine, dried over Na$_2$SO$_4$, filtered and concentrated to be used in the next step without further purification.

215

Step II: (2R,3S,4R,5S,6R)-2-(Hydroxymethyl)-6-[(E)-3-[3-[2-[(2R,3R,4R,5R,6R)-3,4,5-tribenzyloxy-6-(benzyloxymethyl)tetrahydropyran-2-yl]ethynyl]phenyl]allyl]tetrahydropyran-3,4,5-triol To the residue from Step I (90 mg) in 2 mL of MeOH are added 2 drops of MeONa (25% wt/v in MeOH). After 2 h at RT, the filtrate is neutralized with resin Amberlite 120 (H), filtered and concentrated to dryness. The residue is purified on Biotage™ SNAP 10 g silica gel cartridge using MeOH/CH$_2$Cl$_2$ (0 to 20%) in 20 column volume to afford title compound (44 mg, 59%). LC-MS: m/z=827.6 (M+H$^+$).

Step III: Compound 40

To (2R,3S,4R,5S,6R)-2-(hydroxymethyl)-6-[(E)-3-[3-[2-[(2R,3R,4R,5R,6R)-3,4,5-tribenzyloxy-6-(benzyloxymethyl)tetrahydropyran-2-yl]ethynyl]phenyl]allyl]tetrahydropyran-3,4,5-triol (44 mg, 0.0532 mmol) in CH$_3$CN (1.3 mL) is added TMSI (68 µL, 0.479 mmol). The reaction mixture is stirred at RT overnight, quenched with H$_2$O (2 drops) and concentrated to dryness. The residue is purified by reverse phase HPLC to provide the title compound (4.2 mg, 15.7%). $^1$H NMR (400 MHz, CD$_3$OD) δ 7.47 (s, 1H), 7.44-7.32 (m, 1H), 7.27 (dd, 2H), 6.48 (d, 1H), 6.42-6.24 (m, 1H), 4.84 (d, 1H), 4.02-3.68 (m, 10H), 3.67-3.58 (m, 2H), 3.57-3.48 (m, 1H), 2.63 (dd, 1H), 2.49 (dd, 1H). LC-MS: m/z=467.4 (M+H$^+$).

Example 23. Preparation of Compound 41

((2R,3S,4R,5S,6R)-2-(Hydroxymethyl)-6-[[4-[4-[[(2R,3S,4R,5S,6R)-3,4,5-trihydroxy-6-(hydroxymethyl)tetrahydropyran-2-yl]methyl]phenyl]phenyl]methyl]tetrahydropyran-3,4,5-triol)

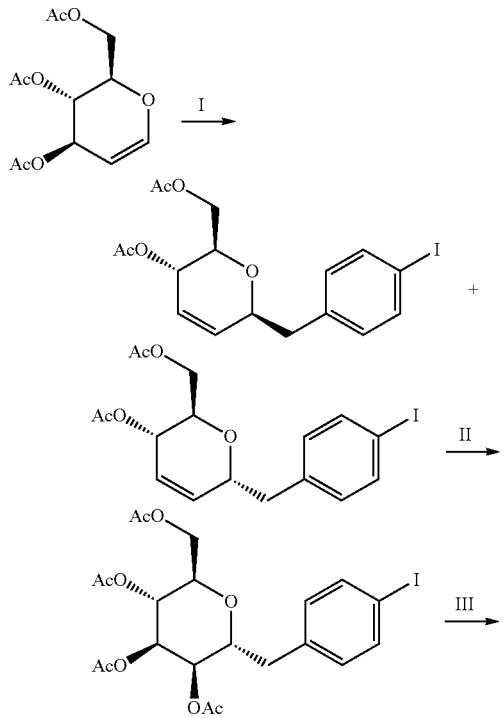

216

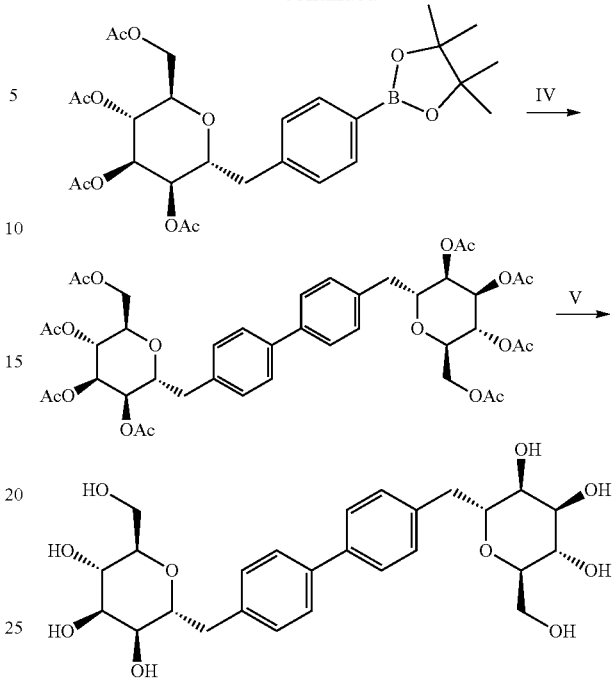

Step I: [(2R,3S,6S)-3-Acetoxy-6-[(4-iodophenyl)methyl]-3,6-dihydro-2H-pyran-2-yl]methyl acetate (β-isomer) and [(2R,3S,6R)-3-acetoxy-6-[(4-iodophenyl)methyl]-3,6-dihydro-2H-pyran-2-yl]methyl acetate (α-isomer)

To a suspension of Rieke zinc (4.80 mL of 10% w/v, 7.35 mmol) in THF at 0° C. is added dropwise a solution of 1-(bromomethyl)-4-iodo-benzene (1.091 g, 3.674 mmol) in THF (2 mL) over 20 min. The reaction mixture is stirred at 0° C. for 2 h and TLC revealed that most of the SM (benzyl bromide) is consumed. The mixture is warmed to RT, filtered under nitrogen via a frit in a separate RBF. THF is removed under a nitrogen flow while warming the solution in a warm water bath. The dark residue is dissolved/suspended in CH$_2$Cl$_2$ (8 mL), cooled to −30° C. and [(2R,3S,4R)-3,4-diacetoxy-3,4-dihydro-2H-pyran-2-yl]methyl acetate (500 mg, 1.837 mmol) is added as a solid followed by BF$_3$.OEt$_2$ (1.433 g, 1.25 mL, 10.10 mmol). The final reaction mixture is warmed to 0° C. and is stirred for 45 min. TLC showed that all the starting glucal is consumed. The mixture is diluted with CH$_2$Cl$_2$ and brine. The organic fraction is isolated in Phase Separator column, dried (Na$_2$SO$_4$), filtered and concentrated. The resulting crude mixture is purified on a Biotage™ SNAP silica gel cartridge (50 g) using EtOAc in Hex (10 to 20%) as the eluent. A second purification is performed on the mixed fraction to afford 3-isomer (187 mg) and α-isomer (282 mg). LC-MS: m/z=452.81 (M+Na$^+$) for β-isomer. LC-MS: m/z=452.77 (M+Na$^+$) for α-isomer.

Step II: [(2R,3R,4R,5R,6R)-3,4,5-Triacetoxy-6-[(4-iodophenyl)methyl]tetrahydropyran-2-yl]methyl acetate To a solution of [(2R,3S,6R)-3-acetoxy-6-[(4-iodophenyl)methyl]-3,6-dihydro-2H-pyran-2-yl]methyl acetate (α-isomer, 282 mg, 0.616 mmol) in tert-butanol (6 mL) and water (2 mL) is added in order NMO (160 mg, 1.37 mmol), methanesulfonamide (90.0 mg, 0.946 mmol), 2,6-dimethylpyridine (75.0 μL, 0.648 mmol) and finally $OsO_4$ (300 μL of 2.5% w/v, 0.0295 mmol). The reaction mixture is stirred at RT for 24 h and is monitored by LCMS. The reaction mixture is poured in 10% $NaHSO_3$ and diluted with EtOAc. The organic layer is separated, washed with water, brine, dried over $Na_2CO_3$, filtered and concentrated. The resulting crude mixture is purified on Biotage™ SNAP silica gel column (25 g) using EtOAC using Hex (10 to 60%) as the eluent. Three distinct set of fractions are isolated from which later two fractions are combined and per acetylated in pyridine/$Ac_2O$ overnight at RT. Mixture is concentrated, coevaporated with toluene twice and the resulting crude mixture is purified on a Biotage™ SNAP silica gel column (10 g) using EtOAC in Hex (10 to 50%) as the eluent o afford the title compound (204 mg, 63.1%) which contains 5% of the 2,3 alpha diastereoisomer.

Step III: [(2R,3R,4R,5R,6R)-3,4,5-Triacetoxy-6-[[4-(4,4,5,5-tetramethyl-1,3,2-dioxaborolan-2-yl)phenyl]methyl]tetrahydropyran-2-yl]methyl acetate To a solution of compound from Step II (112 mg, 0.204 mmol) in DMF (3 mL) is added 4,4,5,5-tetramethyl-2-(4,4,5,5-tetramethyl-1,3,2-dioxaborolan-2-yl)-1,3,2-dioxaborolane (73 mg, 0.288 mmol), potassium acetate (81 mg, 0.825 mmol) and Pd(dppf)$Cl_2$·$CH_2Cl_2$ (16 mg, 0.0196 mmol). The resulting suspension is degassed three times (house vacuum, then $N_2$) and stirred at 70° C. for 6 h. The resulting mixture is poured in saturated aqueous $NH_4Cl$ and extracted with $Et_2O$. The organic phase is washed with water (2×), brine, dried over $MgSO_4$, filtered and concentrated. The resulting crude mixture is purified on a Biotage™ SNAP silica gel column (10 g) using EtOAc in Hex (10 to 40%) as the eluent to afford the title compound (83 mg, 72.6%).

Step IV: [(2R,3R,4R,5R,6R)-3,4,5-Triacetoxy-6-[[4-[4-[[(2R,3R,4R,5R,6R)-3,4,5-triacetoxy-6-(acetoxymethyl)tetrahydropyran-2-yl]methyl]phenyl]phenyl]methyl]tetrahydropyran-2-yl]methyl acetate To a solution of [(2R,3R,4R,5R,6R)-3,4,5-triacetoxy-6-[(4-iodophenyl)methyl]tetrahydropyran-2-yl]methyl acetate (91 mg, 0.166 mmol) and [(2R,3R,4R,5R,6R)-3,4,5-triacetoxy-6-[[4-(4,4,5,5-tetramethyl-1,3,2-dioxaborolan-2-yl)phenyl]methyl]tetrahydropyran-2-yl]methyl acetate (83 mg, 0.148 mmol) in dioxane (5 mL) is added $K_3PO_4$ (98 mg, 0.462 mmol) and finally PdCl$_2$(dppf)·$CH_2Cl_2$ (10 mg). The reaction mixture is degassed three times (house vacuum then nitrogen), stirred at 80° C. for 5 h. Final dark brown mixture is cooled to RT, diluted with 15 mL EtOAc and filtered on a pad of silica gel. The latter is washed with EtOAc (2×15 mL). The combined fractions are concentrated and the residue is purified on a Biotage™ SNAP silica gel column (10 g) using EtOAc in Hex (10 to 80%) as the eluent to afford title compound (26 mg).

Step V: Compound 41

To a solution of [(2R,3R,4R,5R,6R)-3,4,5-triacetoxy-6-[[4-[4-[[(2R,3R,4R,5R,6R)-3,4,5-triacetoxy-6-(acetoxymethyl)tetrahydropyran-2-yl]methyl]phenyl]phenyl]methyl]tetrahydropyran-2-yl]methyl acetate (26 mg, 0.031 mmol) in MeOH (1 mL) is added MeONa (60 μL of 0.5 M, 0.030 mmol) in MeOH. The reaction mixture is stirred at RT for 12 h. Reaction mixture is quenched with acetic acid (2.0 μL, 0.035 mmol) then concentrated, and purified by reverse phase HPLC to afford the title compound (12 mg, 76.2%). $^1$H NMR (400 MHz, CD$_3$OD) δ 7.54 (d, J=8.2 Hz, 4H), 7.34 (d, J=8.2 Hz, 4H), 4.16-4.07 (m, 2H), 3.87-3.76 (m, 6H), 3.76-3.61 (m, 6H), 3.07 (dd, J=14.0, 8.3 Hz, 2H), 2.94 (dd, J=14.0, 6.8 Hz, 2H). LC-MS: m/z=507.46 (M+H$^+$).

Example 24. Preparation of Compound 42

((2R,3S,4R,5S,6R)-2-(Hydroxymethyl)-6-[1-[(2S,3S,4S,5S,6R)-3,4,5-trihydroxy-6-(hydroxymethyl)tetrahydropyran-2-yl]triazol-4-yl]tetrahydropyran-3,4,5-triol)

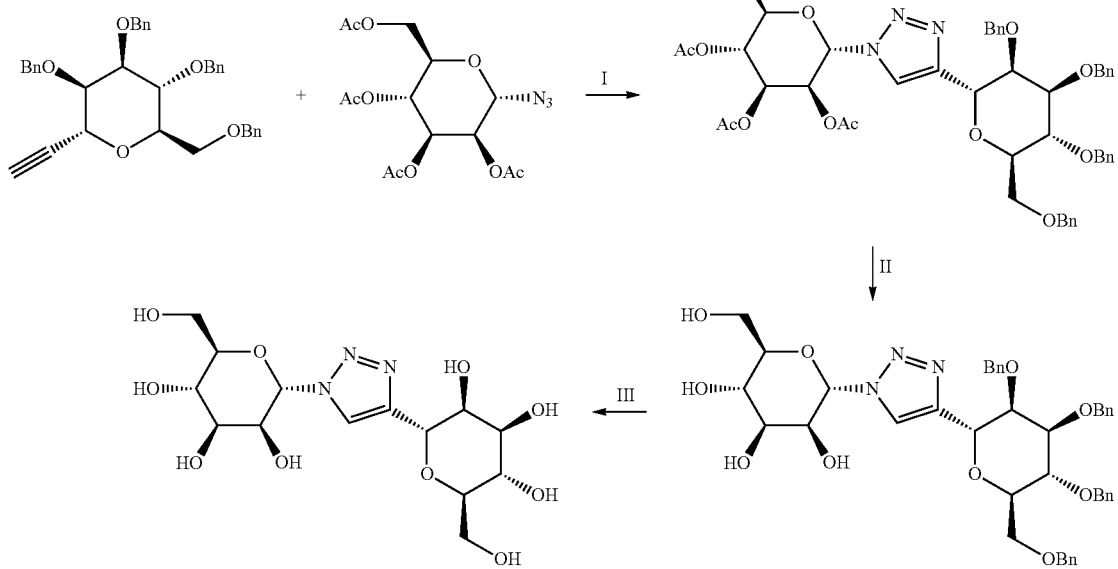

Step I: [(2R,3R,4S,5S,6S)-3,4,5-Triacetoxy-6-[4-[(2R,3R,4R,5R,6R)-3,4,5-tribenzyloxy-6-(benzyloxymethyl)tetrahydropyran-2-yl]triazol-1-yl]tetrahydropyran-2-yl]methyl acetate To a stirred mixture of the Intermediate G (76 mg, 0.1386 mmol) and [(2R,3R,4S,5S,6S)-4,5-diacetoxy-2-(acetoxymethyl)-6-azido-tetrahydropyran-3-yl] acetate (70 mg, 0.1875 mmol) in ethanol (1 mL) and water (250 μL) is added $CuSO_4$ (11 mg, 0.0689 mmol) and sodium ascorbate (22 mg, 0.1249 mmol) in one portion. Resultant reaction mixture is stirred for 30 min, additional amount of ethanol (1 mL) is added, stirred at RT for 24 h, diluted with water, extracted with methylene chloride. The combined extracts are dried, concentrated, purified on Biotage™ SNAP 12 g silica gel cartridge using EtOAc in Hex (15% to 50%) as eluent to afford the title compound (80 mg, 0.08677 mmol, 59.84%) as white solid. Rf=0.36 (50% EA in Hex). $^1$H NMR (400 MHz, $CDCl_3$) δ 7.64 (s, 1H), 7.40 (dd, J=7.7, 1.5 Hz, 2H), 7.37-7.21 (m, 16H), 7.17-7.09 (m, 2H), 5.98 (dd, J=3.6, 2.7 Hz, 1H), 5.95-5.88 (m, 2H), 5.36 (t, J=9.1 Hz, 1H), 5.32 (d, J=2.8 Hz, 1H), 4.82 (d, J=11.0 Hz, 1H), 4.77 (s, 2H), 4.69-4.53 (m, 5H), 4.48 (d, J=11.0 Hz, 1H), 4.35 (dd, J=12.5, 5.3 Hz, 1H), 4.03 (dd, J=12.5, 2.5 Hz, 1H), 3.96 (t, J=8.7 Hz, 1H), 3.86-3.77 (m, 2H), 3.76-3.71 (m, 2H), 3.69-3.62 (m, 1H), 2.19 (s, 3H), 2.07 (s, 3H), 2.05 (s, 3H), 2.05 (s, 3H).

Step II: (2R,3S,4S,5S,6S)-2-(Hydroxymethyl)-6-[4-[(2R,3R,4R,5R,6R)-3,4,5-tribenzyloxy-6-(benzyloxymethyl)tetrahydropyran-2-yl]triazol-1-yl]tetrahydropyran-3,4,5-triol To a stirred solution of [(2R,3R,4S,5S,6S)-3,4,5-triacetoxy-6-[4-[(2R,3R,4R,5R,6R)-3,4,5-tribenzyloxy-6-(benzyloxymethyl)tetrahydropyran-2-yl]triazol-1-yl]tetrahydropyran-2-yl]methyl acetate (80 mg, 0.0868 mmol) in MeOH (4 mL) is added MeONa in MeOH (185 μL of 0.5 M, 0.0925 mmol). The reaction mixture is stirred at RT overnight, neutralized with acetic acid (10 μL, 0.176 mmol), ¼ of the reaction mixture (1 mL) is concentrated, freeze dried with $CH_3CN$-water to afford the title compound (16 mg, 0.0191 mmol, 88.1%) as white solid. $^1$H NMR (400 MHz, $CD_3OD$) δ 8.05 (s, 1H), 7.37-7.11 (m, 20H), 5.97 (d, J=2.7 Hz, 1H), 5.24 (d, J=4.1 Hz, 1H), 4.73-4.45 (m, 10H), 4.42 (dd, J=4.0, 2.5 Hz, 1H), 4.04 (dd, J=8.5, 3.5 Hz, 1H), 3.98-3.89 (m, 2H), 3.81-3.63 (m, 6H). LC-MS: m/z=754.58 (M+H$^+$).

Step III: Compound 42

A solution of (2R,3S,4S,5S,6S)-2-(hydroxymethyl)-6-[4-[(2R,3R,4R,5R,6R)-3,4,5-tribenzyloxy-6-(benzyloxymethyl)tetrahydropyran-2-yl]triazol-1-yl]tetrahydropyran-3,4,5-triol in MeOH (3 mL) and acetic acid (40 μL, 0.703 mmol) is added dihydroxypalladium (50 mg, 0.0712 mmol), stirred under hydrogen at 1 atm. for 48 h, filtered through celite. The filtrate is concentrated and purified on preparative HPLC using Phenomenex C18 Gemini AXIA 5μ 110 A 21.2×75 mm 0% ACN/$H_2O$+0.01% TFA-To 30% ACN+0.01% TFA in 40 min-To 100% ACN in 1 min to afford the title compound (7.4 mg, 0.0169 mmol, 26%) as a half-white solid. $^1$H NMR (400 MHz, $CD_3OD$) δ 8.18 (s, 1H), 6.03 (d, J=2.7 Hz, 1H), 5.14 (d, J=2.3 Hz, 1H), 4.72-4.67 (m, 1H), 4.48 (t, J=2.8 Hz, 1H), 4.06 (dd, J=8.5, 3.5 Hz, 1H), 3.86-3.65 (m, 7H), 3.45-3.33 (m, 2H).

Example 25. Preparation of Compound 43

(2-[(2R,3S,4R,5S,6R)-3,4,5-Trihydroxy-6-(hydroxymethyl)tetrahydropyran-2-yl]-N-[4-[[2-[(2R,3S,4R,5S,6R)-3,4,5-trihydroxy-6-(hydroxymethyl)tetrahydropyran-2-yl]acetyl]amino]phenyl]acetamide)

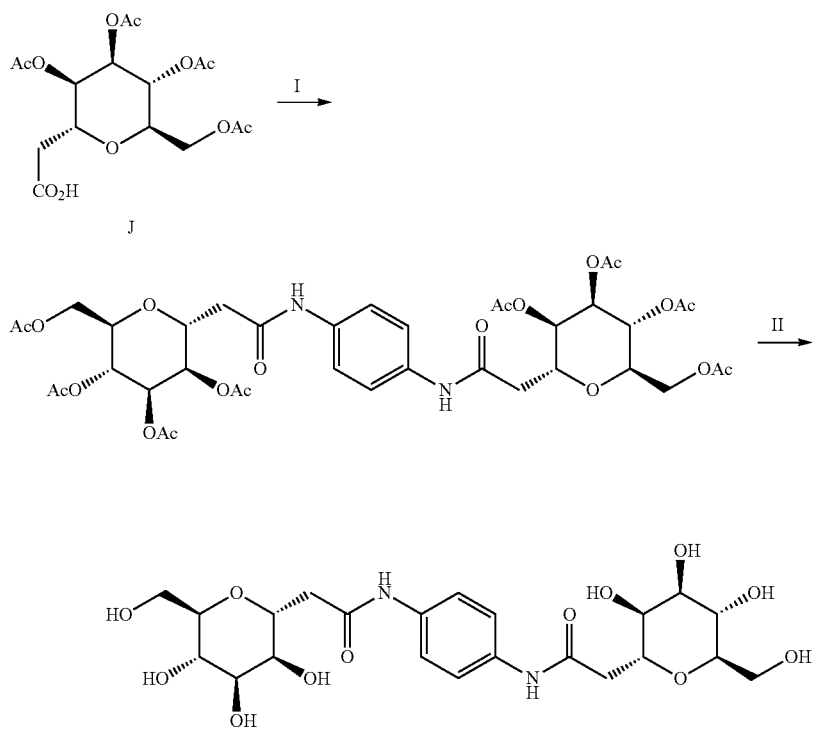

Step I: [(2R,3R,4R,5R,6R)-3,4,5-Triacetoxy-6-[2-oxo-2-[4-[[2-[(2R,3R,4R,5R,6R)-3,4,5-triacetoxy-6-(acetoxymethyl)tetrahydropyran-2-yl]acetyl]amino]anilino]ethyl]tetrahydropyran-2-yl]methyl acetate To a solution of Intermediate J (128 mg, 0.328 mmol) in 3.5 mL of DMF is sequentially added benzene-1,4-diamine (14.2 mg, 0.131 mmol), DIPEA (69 µL, 0.394 mmol) and HATU (125 mg, 0.328 mmol) under nitrogen atmosphere. The reaction mixture is stirred at RT for 20 h, and diluted with water (10 mL). The reaction mixture is extracted by EtOAc (5×10 mL), and the combined organic layer are washed with water (3×5 mL), 5 mL of brine, dried over $Na_2SO_4$, filtered, and concentrated to dryness. The residue is purified by flash column chromatography on silica gel (0 to 20% MeOH in $CH_2Cl_2$) to give the title compound (116.5 mg) that is used as is for the next step.

Step II: Compound 43

To a solution of [(2R,3R,4R,5R,6R)-3,4,5-triacetoxy-6-[2-oxo-2-[4-[[2-[(2R,3R,4R,5R,6R)-3,4,5-triacetoxy-6-(acetoxymethyl)tetrahydropyran-2-yl]acetyl]amino]anilino]ethyl]tetrahydropyran-2-yl]methyl acetate (116.5 mg) in MeOH (2.3 mL) is added MeONa (68 µL of 0.5 M, 0.034 mmol) in MeOH. The mixture is stirred at RT for 3 h. AcOH (2 µL, 0.034 mmol) is added and the mixture is evaporated to dryness. The residue is purified by preparative reverse phase HPLC to give the title compound (34.3 mg, 43% for last two steps). $^1$H NMR (400 MHz, DMSO-$D_6$) δ 9.76 (d, J=8.8 Hz, 2H), 7.43 (s, 4H), 4.77 (s, 2H), 4.64 (s, 2H), 4.54 (s, 2H), 4.29 (s, 2H), 4.09 (m, 2H), 3.50 (s, 8H), 3.43 (s, 2H), 3.36 (m, 2H), 2.51 (m, 4H).

Example 26. Preparation of Compound 44

((2R,3S,4R,5S,6R)-2-(Hydroxymethyl)-6-[3-[3-[3-[(2R,3S,4R,5S,6R)-3,4,5-trihydroxy-6-(hydroxymethyl)tetrahydropyran-2-yl]phenoxy]propoxy]phenyl]tetrahydropyran-3,4,5-triol)

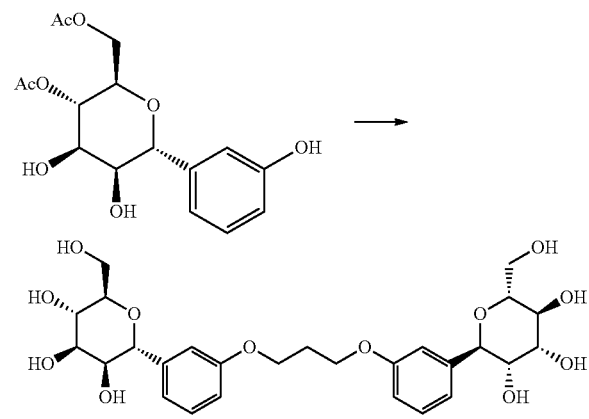

To a solution of [(2R,3S,4R,5S,6R)-3-acetoxy-4,5-dihydroxy-6-(3-hydroxyphenyl)tetrahydropyran-2-yl]methyl acetate (50 mg, 0.147 mmol) in DMF (1 mL) is added $Cs_2CO_3$ (71.81 mg, 0.22 mmol) followed by 1,3-diiodopropane (10 µL, 0.088 mmol). The reaction mixture is heated at 55° C. overnight, filtered and concentrated. To the previous residue in MeOH (1 mL) is added catalytic MeONa (8 µL of 25% w/v in MeOH, 0.037 mmol). The reaction mixture is stirred at RT for 1 h, neutralized with Amberlite IR120(H). After filtration, the solvent is removed under reduced pressure and the residue is purified by reverse phase HPLC to provide the title compound (4.8 mg, 10.8%). $^1$H NMR (400 MHz, $CD_3OD$) δ 7.17 (t, 2H), 7.01 (s, 2H), 6.92 (d, 2H), 6.76 (d, 2H), 4.84 (m, 2H), 4.32 (t, 2H), 4.09 (t, 4H), 3.82-3.66 (m, 4H), 3.61 (t, 2H), 3.48 (dd, 2H), 3.44-3.31 (m, 2H), 2.22-2.08 (m, 2H). LC-MS: m/z=553.4 (M+H$^+$).

Example 27. Preparation of Compound 45

(N-[(2R,3R,4R,5S,6R)-4,5-Dihydroxy-6-(hydroxymethyl)-2-[4-[(2R,3S,4R,5S,6R)-3,4,5-trihydroxy-6-(hydroxymethyl)tetrahydropyran-2-yl]triazol-1-yl]tetrahydropyran-3-yl]acetamide)

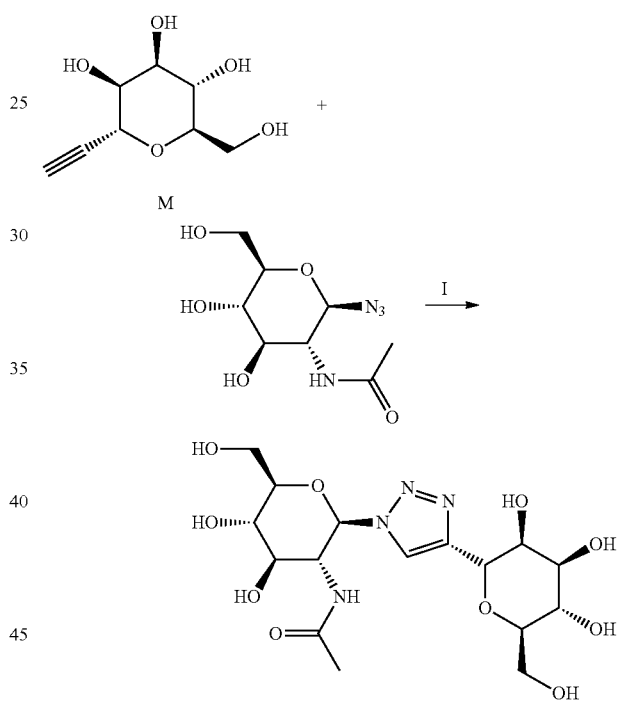

To a solution of Intermediate M (15 mg, 0.0797 mmol) and N-((2R,3R,4R,5S,6R)-2-azido-4,5-dihydroxy-6-(hydroxymethyl)tetrahydro-2H-pyran-3-yl)acetamide (20 mg, 0.0812 mmol) in ethanol (0.4 mL) and water (0.1 mL) is sequentially added $CuSO_4$ (6.0 mg, 0.0376 mmol) and sodium ascorbate (15 mg, 0.0757 mmol) at RT. The reaction mixture is stirred at RT for 24 h, diluted with water and MeOH, filtered off. The filtrate is concentrated and purified on prep. HPLC on Phenomenex C18 Gemini AXIA Pack 5µ 110 A 21.2×250 mm. 0% To 40% ACN+0.1% Formic acid in 40 min-To 100% ACN in 5 min-Hold 5 min to afford the title compound (5 mg, 14%) as white solid. $^1$H NMR (400 MHz, $CD_3OD$) δ 8.10 (s, 1H), 5.66 (d, J=9.8 Hz, 1H), 5.00 (d, J=2.1 Hz, 1H), 4.38-4.35 (m, 1H), 4.13 (t, J=10.0 Hz, 1H), 3.71-3.42 (m, 10H), 1.69 (s, 3H). LC-MS: m/z=435.32 (M+H$^+$).

Example 28. Preparation of Compound 46 and Compound 47 (Method B)

((2R,3S,4S,5S,6S)-2-(Hydroxymethyl)-6-[5-[(2S,3S,4S,5S,6R)-3,4,5-trihydroxy-6-(hydroxymethyl)tetrahydropyran-2-yl]-2-thienyl]tetrahydropyran-3,4,5-triol) and ((2R,3S,4R,5S,6R)-2-(Hydroxymethyl)-6-[5-[(2S,3S,4S,5S,6R)-3,4,5-trihydroxy-6-(hydroxymethyl)tetrahydropyran-2-yl]-3-thienyl]tetrahydropyran-3,4,5-triol)

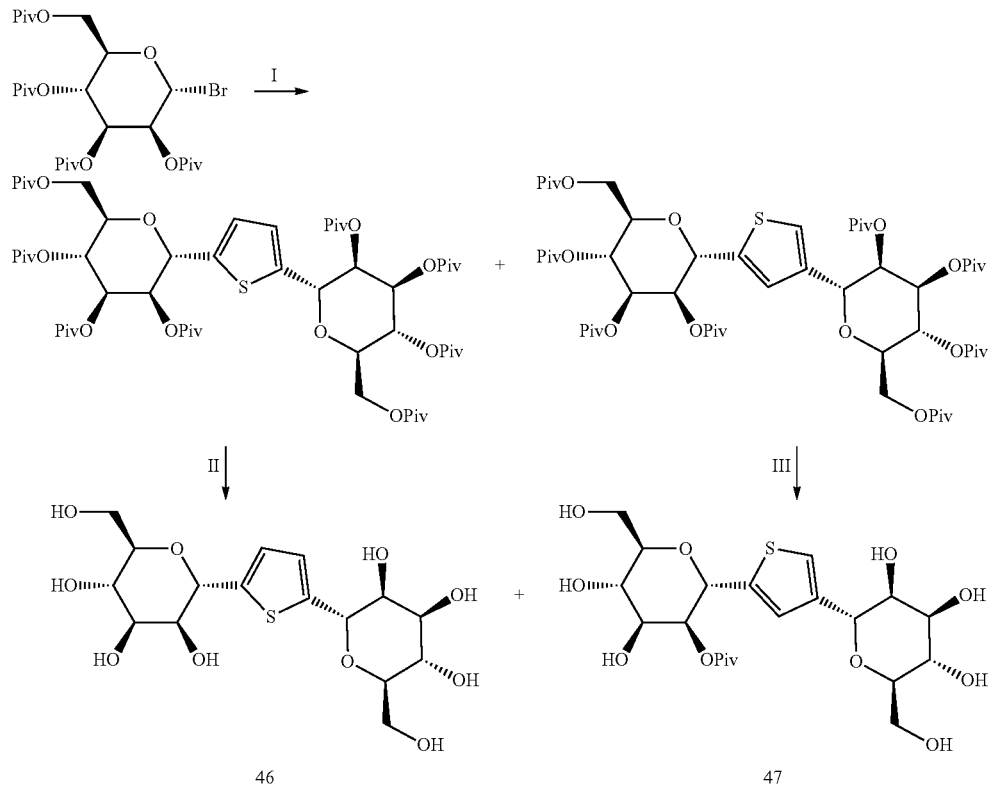

Step I: [(2R,3R,4S,5S,6S)-3,4,5-Tris(2,2-dimethylpropanoyloxy)-6-[5-[(2S,3S,4S,5R,6R)-3,4,5-tris(2,2-dimethylpropanoyloxy)-6-(2,2-dimethylpropanoyloxymethyl)tetrahydropyran-2-yl]-2-thienyl]tetrahydropyran-2-yl]methyl 2,2-dimethylpropanoate, and [(2R,3R,4R,5R,6R)-3,4,5-tris(2,2-dimethylpropanoyloxy)-6-[5-[(2S,3S,4S,5R,6R)-3,4,5-tris(2,2-dimethylpropanoyloxy)-6-(2,2-dimethylpropanoyloxymethyl)tetrahydropyran-2-yl]-3-thienyl]tetrahydropyran-2-yl]methyl 2,2-dimethylpropanoate A solution of n-Bu₃MgLi (554 μL of 0.65 M, 0.3600 mmol) in hexane-heptane-dibutylether (8:20:3) is added to 2,5-diiodothiophene (150 mg, 0.4465 mmol) in toluene (0.5 mL) at 0° C., stirred at the same temperature for 3.5 h (a thick precipitate is formed), a solution of ZnBr₂—LiBr in dibutyl ether (543 μL of 1.05 M, 0.57 mmol) is added dropwise, cooling bath removed, stirred at RT for 1 h. A solution of [(2R,3R,4S,5S,6R)-6-bromo-3,4,5-tris(2,2-dimethylpropanoyloxy)tetrahydropyran-2-yl]methyl 2,2-dimethylpropanoate (500 mg, 0.8628 mmol) in toluene (0.9 mL) is added, it is placed on pre-heated oil bath at 90° C. for 4 h. It is cooled to RT and it is poured into aqueous 1 N HCl solution (10 mL), then extracted with EtOAc (3×10 mL). The combined extracts are washed with brine, dried (Na₂SO₄), concentrated, purified on Biotage™ SNAP 50 g silica gel cartridge using EtOAc in Hex (5% to 10%, 8CV, 10%, 5CV) as eluent to afford [(2R,3R,4S,5S,6S)-3,4,5-tris(2,2-dimethylpropanoyloxy)-6-[5-[(2S,3S,4S,5R,6R)-3,4,5-tris(2,2-dimethylpropanoyloxy)-6-(2,2-dimethylpropanoyloxymethyl)tetrahydropyran-2-yl]-2-thienyl]tetrahydropyran-2-yl]methyl 2,2-dimethylpropanoate (160 mg, 0.1480 mmol, 33.1%) as white solid. Rf=0.38 (15% EA in Hex). ¹H NMR (400 MHz, CDCl₃) δ 7.23 (s, 2H), 5.87 (t, J=2.6 Hz, 2H), 5.55 (t, J=9.6 Hz, 2H), 5.25 (dd, J=9.8, 3.0 Hz, 2H), 5.19 (d, J=2.2 Hz, 2H), 4.30 (dd, J=12.4, 4.7 Hz, 2H), 4.09 (dd, J=12.4, 1.9 Hz, 2H), 3.93 (ddd, J=9.3, 4.6, 1.8 Hz, 2H), 1.28 (s, 18H), 1.26 (s, 18H), 1.16 (s, 18H), 1.15 (s, 18H) and [(2R,3R,4R,5R,6R)-3,4,5-tris(2,2-dimethylpropanoyloxy)-6-[5-[(2S,3S,4S,5R,6R)-3,4,5-tris(2,2-dimethylpropanoyloxy)-6-(2,2-dimethylpropanoyloxymethyl)tetrahydropyran-2-yl]-3-thienyl]tetrahydropyran-2-yl]methyl 2,2-dimethylpropanoate (30 mg, 6.2%). Rf=0.37 (15% EA-Hex). ¹H NMR (400 MHz, CDCl₃) δ 7.48 (s, 1H), 7.26 (s, 1H), 5.90 (t, J=2.6 Hz, 1H), 5.80 (t, J=2.6 Hz, 1H), 5.65 (t, J=9.8 Hz, 1H), 5.56 (t, J=9.8 Hz, 1H), 5.23 (s, 1H), 5.21-5.14 (m, 2H), 5.04 (s, 1H), 4.36-4.26 (m, 2H), 4.24-4.07 (m, 3H), 3.88 (d, J=9.5 Hz, 1H), 1.29 (s, 9H), 1.29 (s, 9H), 1.27 (s, 9H), 1.27 (s, 9H), 1.15 (s, 9H), 1.14 (s, 9H), 1.13 (s, 9H), 1.12 (s, 9H).

Step II: Compound 46

To a stirred suspension of [(2R,3R,4S,5S,6S)-3,4,5-tris(2,2-dimethylpropanoyloxy)-6-[5-[(2S,3S,4S,5R,6R)-3,4,5- tris(2,2-dimethylpropanoyloxy)-6-(2,2-dimethylpropanoyloxymethyl)tetrahydropyran-2-yl]-2-thienyl]tetrahydropyran-2-yl]methyl 2,2-dimethylpropanoate (92 mg, 0.0851 mmol) in MeOH (2 mL) is added MeONa (340 μL of 0.5 M, 0.1702 mmol). It is stirred at RT 48 h, to the resultant suspension is added DOWEX 50WX4-400 until pH 4-5, suspension became clear solution, filtered, concentrated, freeze dried to afford the title compound (26.5 mg, 0.0616 mmol, 72.5%) as white fluffy solid. $^1$H NMR (400 MHz, CD$_3$OD) δ6.94 (s, 2H), 5.12 (d, J=2.2 Hz, 2H), 4.31 (t, J=2.5 Hz, 2H), 3.83-3.64 (m, 8H), 3.56-3.47 (m, 2H).

Step III: Compound 47

To a stirred suspension of [(2R,3R,4R,5R,6R)-3,4,5-tris(2,2-dimethylpropanoyloxy)-6-[5-[(2S,3S,4S,5R,6R)-3,4,5-tris(2,2-dimethylpropanoyloxy)-6-(2,2-dimethylpropanoyloxymethyl)tetrahydropyran-2-yl]-3-thienyl]tetrahydropyran-2-yl]methyl 2,2-dimethylpropanoate (33 mg, 0.0305 mmol) in MeOH (600 μL) is added MeONa (122 μL of 0.5 M, 0.06104 mmol), stirred at RT 48 h. To the resultant solution is added DOWEX 50WX4-400 until pH 4-5, filtered, concentrated, freeze dried to afford the title compound (9.5 mg, 0.0221 mmol, 72.4%) as white fluffy solid. $^1$H NMR (400 MHz, CD$_3$OD) δ 7.29 (s, 1H), 7.11 (s, 1H), 5.13 (s, 1H), 4.93 (s, 1H), 4.36 (t, J=2.8 Hz, 1H), 4.32 (t, J=2.6 Hz, 1H), 3.86-3.34 (m, 10H).

Example 29. Preparation of Compound 48

(2-[(2R,3S,4R,5S,6R)-3,4,5-Trihydroxy-6-(hydroxymethyl)tetrahydropyran-2-yl]-N-[3-[[2-[(2R,3S,4R,5S,6R)-3,4,5-trihydroxy-6-(hydroxymethyl)tetrahydropyran-2-yl]acetyl]amino]phenyl]acetamide)

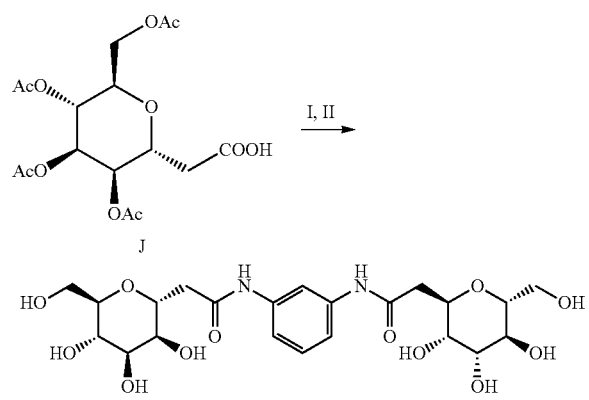

Step I: [(2R,3R,4R,5R,6R)-3,4,5-Triacetoxy-6-[2-oxo-2-[3-[[2-[(2R,3R,4R,5R,6R)-3,4,5-triacetoxy-6-(acetoxymethyl)tetrahydropyran-2-yl]acetyl]amino]anilino]ethyl]tetrahydropyran-2-yl]methyl acetate To a solution of Intermediate J (70 mg, 0.179 mmol) in DMF (1.4 mL) are added benzene-1,3-diamine (9.7 mg, 0.0896 mmol), 2,6-lutidine (62 μL, 0.538 mmol) followed by HATU (85.2 mg, 0.224 mmol) at 0° C. The RM is stirred at RT for 3 h, diluted with EtOAc, washed with H$_2$O, brine. The organic phase is dried over Na$_2$SO$_4$, filtered and concentrated. The residue is purified on Biotage™ SNAP 10 g silica gel cartridge using EtOAc in Hex (0 to 15%) in 25 column volume to afford the title compound (58 mg, 75.8%) as colorless oil. LC-MS: m/z=853.5 (M+H$^+$).

Step II: Compound 48

To a solution of [(2R,3R,4R,5R,6R)-3,4,5-triacetoxy-6-[2-oxo-2-[3-[[2-[(2R,3R,4R,5R,6R)-3,4,5-triacetoxy-6-(acetoxymethyl)tetrahydropyran-2-yl]acetyl]amino]anilino]ethyl]tetrahydropyran-2-yl]methyl acetate (58 mg, 0.068 mmol) in MeOH (1.4 mL) is added 2 drops 25% w/v MeONa in MeOH. After stirring for 1 h, the reaction mixture is neutralized with Amberlite IR120(H). After filtration, washing with MeOH, the solvent is removed under reduced pressure and the residue purified by reverse phase HPLC to provide the title compound (11 mg, 23.3%). $^1$H NMR (400 MHz, CD$_3$OD) δ 7.84 (d, 1H), 7.37-7.26 (m, 2H), 7.26-7.11 (m, 1H), 4.39-4.29 (m, 2H), 3.87 (dd, 2H), 3.79-3.64 (m, 8H), 3.64-3.55 (m, 2H), 2.71 (qd, 4H). LC-MS: m/z=517.4 (M+H$^+$).

Example 30. Preparation of Compound 49

(2-[(2R,3S,4R,5S,6R)-3,4,5-Trihydroxy-6-(hydroxymethyl)tetrahydropyran-2-yl]-N-[[4-[[[2-[(2R,3S,4R,5S,6R)-3,4,5-trihydroxy-6-(hydroxymethyl)tetrahydropyran-2-yl]acetyl]amino]methyl]phenyl]methyl]acetamide)

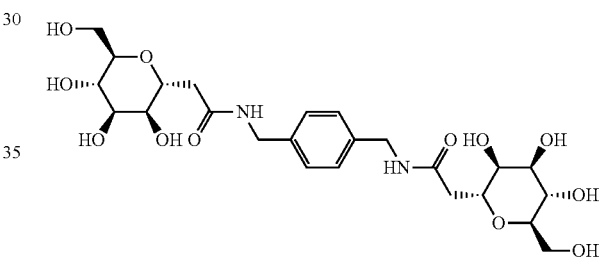

Compound 49 is prepared according to a similar procedure as described in Example 29 but using Intermediate J and [4-(aminomethyl)phenyl]methanamine instead of benzene-1,3-diamine as reagents. $^1$H NMR (400 MHz, CD$_3$OD) δ 7.24 (s, 4H), 4.46-4.15 (m, 6H), 3.81 (dt, 2H), 3.68 (ddd, 8H), 3.60-3.49 (m, 2H), 2.75-2.40 (m, 4H). LC-MS: m/z=545.4 (M+H$^+$).

Example 31. Preparation of Compound 50

((2R,3S,4R,5S,6R)-2-(Hydroxymethyl)-6-[3-[4-[3-[(2R,3S,4R,5S,6R)-3,4,5-trihydroxy-6-(hydroxymethyl)tetrahydropyran-2-yl]phenyl]buta-1,3-diynyl]phenyl]tetrahydropyran-3,4,5-triol)

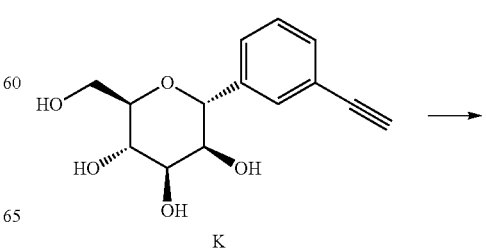

227
-continued

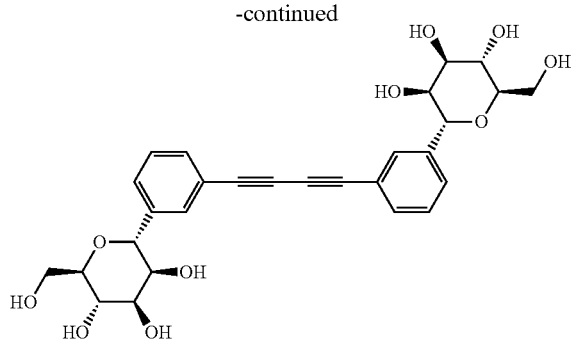

A solution of methyl 4-iodobenzoate (37 mg, 0.141 mmol), CuI (4.8 mg, 0.025 mmol) and Pd(dppf)Cl₂—CH₂Cl₂ (19 mg, 0.0233 mmol) in DMF (1.0 mL) is degassed (vacuum/N₂ flush), to this is added triethylamine (70.1 mg, 97 µL, 0.6924 mmol) and Intermediate K (35 mg, 0.115 mmol) under nitrogen atmosphere, reaction mixture is stirred at RT overnight, directly loaded onto C-18 samplet, purified on Biotage™ SNAP 25 g C18 silica gel cartridge using CH₃CN-water (5% to 50%) as eluent to afford the title compound (3.0 mg). $^1$H NMR (400 MHz, CD₃OD) δ 7.62 (s, 2H), 7.51 (d, J=7.4 Hz, 2H), 7.41 (d, J=7.7 Hz, 2H), 7.35 (t, J=7.7 Hz, 2H), 4.88 (d, J=4.5 Hz, 2H), 4.29 (dd, J=4.4, 3.2 Hz, 2H), 3.84 (dd, J=11.9, 6.9 Hz, 2H), 3.76 (dd, J=11.9, 3.1 Hz, 2H), 3.71 (t, J=7.2 Hz, 2H), 3.56 (dd, J=7.4, 3.1 Hz, 2H), 3.51-3.43 (m, 2H). LC-MS: m/z=527.51 (M+H⁺).

Example 32. Preparation of Compound 51

(1,3-Bis(3-((2R,3S,4R,5S,6R)-3,4,5-trihydroxy-6-(hydroxymethyl)tetrahydro-2H-pyran-2-yl)phenyl)urea)

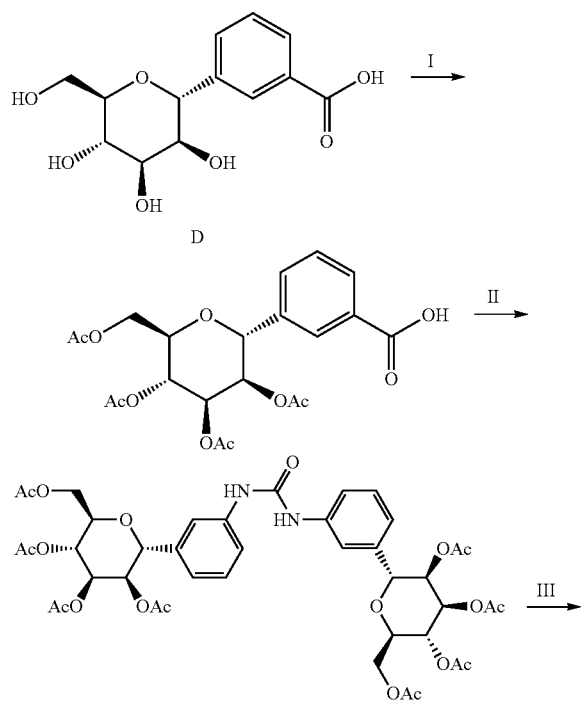

228
-continued

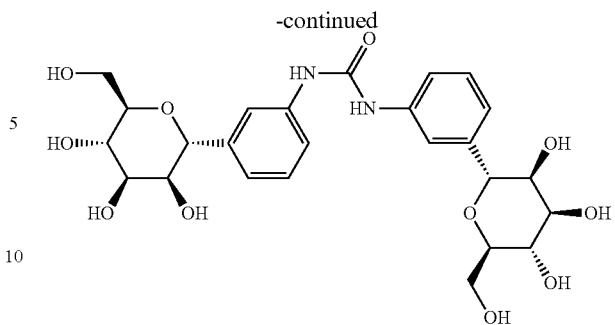

Step I: 3-((2R,3R,4R,5R,6R)-3,4,5-Triacetoxy-6-(acetoxymethyl)tetrahydro-2H-pyran-2-yl)benzoic acid To a suspension of Intermediate D (165 mg, 0.551 mmol) in 1.6 mL of CH₂Cl₂ is sequentially added pyridine (312 µL, 3.86 mmol), DMAP (6.7 mg, 0.055 mmol) and Ac₂O (312 µL, 3.31 mmol) under nitrogen atmosphere. The reaction mixture is stirred at RT for 20 h and diluted with 2M HCl (0.5 mL). The organic layer is dried over Na₂SO₄, filtered, and concentrated to dryness. The residue is purified by flash column chromatography on silica gel (0 to 20% MeOH in CH₂Cl₂) to give the raw product. The product is dissolved in 5 mL of CH₂Cl₂ and washed with 1M HCl (1 mL). The organic layer is dried over Na₂SO₄, filtered, and concentrated to dryness to give the title compound (242.2 mg, 97%).

Step II: [(2R,3R,4R,5R,6R)-3,4,5-Triacetoxy-6-[3-[[3-[(2R,3R,4R,5R,6R)-3,4,5-triacetoxy-6-(acetoxymethyl)tetrahydropyran-2-yl]phenyl]carbamoylamino]phenyl]tetrahydropyran-2-yl]methyl acetate To a solution of 3-((2R,3R,4R,5R,6R)-3,4,5-triacetoxy-6-(acetoxymethyl)tetrahydro-2H-pyran-2-yl)benzoic acid (242 mg, 0.535 mmol) in 7.3 mL of tert-butanol is sequentially added TEA (112 µL, 0.802 mmol) and diphenylphosphoryl azide (162 mg, 0.588 mmol) under nitrogen atmosphere. The reaction mixture is heated to reflux for 4 h, cooled to RT, and concentrated to dryness. The residue is purified by flash column chromatography on silica gel (2 to 20% MeOH in CH₂Cl₂) to give the title compound (113 mg, 48%).

Step III: Compound 51

To a solution of [(2R,3R,4R,5R,6R)-3,4,5-triacetoxy-6-[3-[[3-[(2R,3R,4R,5R,6R)-3,4,5-triacetoxy-6-(acetoxymethyl)tetrahydropyran-2-yl]phenyl]carbamoylamino]phenyl]tetrahydropyran-2-yl]methyl acetate in MeOH (2 mL) is added MeONa (64 µL of 0.5 M, 0.032 mmol) in MeOH. The mixture is stirred at RT overnight and filtered on a 1 g SCX-2 SPE cartridge. The filtrate is evaporated to dryness and the residue is purified by preparative HPLC to give the title compound (38 mg, 49%). $^1$H NMR (400 MHz, DMSO-D₆) δ 8.66 (s, 2H), 7.44 (s, 2H), 7.37 (d, J=8.1 Hz, 2H), 7.21 (t, J=7.9 Hz, 2H), 7.00 (d, J=7.7 Hz, 2H), 4.75 (m, 4H), 4.64 (m, 4H), 4.54 (t, J=5.8 Hz, 2H), 4.03 (m, 2H), 3.60 (m, 4H), 3.54 (m, 2H), 3.45-3.36 (m, 4H).

Example 33. Preparation of Compound 52

((2R,3S,4R,5S,6R)-2-(Hydroxymethyl)-6-[3-[4-[3-[(2R,3S,4R,5S,6R)-3,4,5-trihydroxy-6-(hydroxymethyl)tetrahydropyran-2-yl]phenyl]butyl]phenyl]tetrahydropyran-3,4,5-triol)

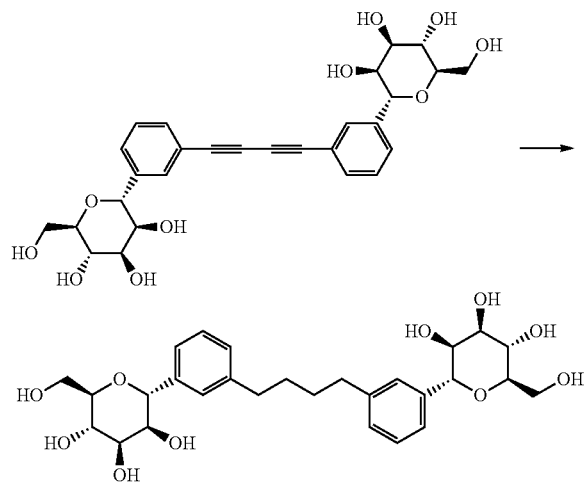 [SMILES: OC[C@H]1O[C@H](c2cccc(C#CC#Cc3cccc([C@H]4O[C@H](CO)[C@@H](O)[C@H](O)[C@@H]4O)c3)c2)[C@@H](O)[C@@H](O)[C@@H]1O ; OC[C@H]1O[C@H](c2cccc(CCCCc3cccc([C@H]4O[C@H](CO)[C@@H](O)[C@H](O)[C@@H]4O)c3)c2)[C@@H](O)[C@@H](O)[C@@H]1O]

A mixture of (2R,3S,4R,5S,6R)-2-(hydroxymethyl)-6-[3-[4-[3-[(2R,3S,4R,5S,6R)-3,4,5-trihydroxy-6-(hydroxymethyl)tetrahydropyran-2-yl]phenyl]buta-1,3-diynyl]phenyl]tetrahydropyran-3,4,5-triol (Compound 50, 5 mg, 0.009 mmol) and 10% Pd on C, wet, Degussa (10 mg, 0.0094 mmol) in MeOH (3 mL) is hydrogenated at 40 psi for 4 h, filtered off catalyst, concentrated. This material is dissolved in water-acetonitrile and freeze dried to afford title compound (4.5 mg, 86%) as white solid. $^1$H NMR (400 MHz, CD$_3$OD) δ 7.21 (s, 2H), 7.17 (d, J=4.9 Hz, 4H), 6.99 (t, J=3.7 Hz, 2H), 4.86 (d, J=3.3 Hz, 2H), 4.35 (t, J=3.3 Hz, 2H), 3.71 (d, J=4.6 Hz, 4H), 3.63 (t, J=8.2 Hz, 2H), 3.47 (dd, J=8.2, 3.1 Hz, 2H), 3.41-3.32 (m, 2H), 2.62-2.47 (m, 4H), 1.63-1.48 (m, 4H). LC-MS: m/z=535.53 (M+H$^+$).

Example 34. Preparation of Compound 53 (Method C)

(2R,3S,4R,5S,6R)-2-(Hydroxymethyl)-6-[2-[4-[2-[(2R,3S,4R,5S,6R)-3,4,5-trihydroxy-6-(hydroxymethyl)tetrahydropyran-2-yl]ethynyl]phenyl]ethynyl]tetrahydropyran-3,4,5-triol

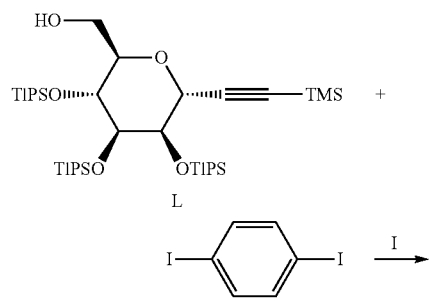

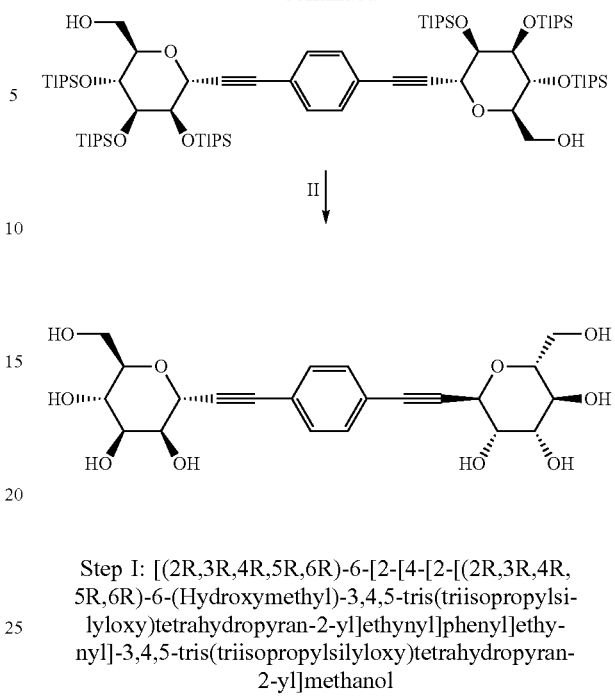

Step I: [(2R,3R,4R,5R,6R)-6-[2-[4-[2-[(2R,3R,4R,5R,6R)-6-(Hydroxymethyl)-3,4,5-tris(triisopropylsilyloxy)tetrahydropyran-2-yl]ethynyl]phenyl]ethynyl]-3,4,5-tris(triisopropylsilyloxy)tetrahydropyran-2-yl]methanol To a degassed (vacuum-nitrogen flush, 30 min) solution of Intermediate L (836 mg, 1.15 mmol), 1,4-diiodobenzene (180 mg, 0.545 mmol), PdCl$_2$(dppf). CH$_2$Cl$_2$ (44.6 mg, 0.0546 mmol) and CuI (10.4 mg, 0.0546 mmol) in DMF (8 mL) under nitrogen atmosphere are added DBU (653 μL, 4.37 mmol) and degassed water (29.5 mg, 30 μL, 1.64 mmol). The reaction mixture is slowly heated at 50° C. for 4 h, and then increased to 55° C. and heated for 16 h. Then additional amount of water (10 uL) is added, continued to heat for 6 h, cooled to rt and left it overnight. The reaction mixture is diluted with water (25 mL), extracted with EtOAc (3×25 mL), combined extracts are washed with brine, dried (Na$_2$SO$_4$) and concentrated. The residue is purified on Biotage™ SNAP 100 g silica gel cartridge using EtOAc in Hex (0% to 20%, 8 CV; 20% 3 CV) as eluent to afford title compound (511 mg, 0.368 mmol, 68%) as half-white solid. $^1$H NMR (400 MHz, CDCl$_3$) δ 7.37 (d, J=0.9 Hz, 4H), 4.90 (d, J=8.9 Hz, 2H), 4.44 (d, J=9.1 Hz, 2H), 4.20 (brs, 2H), 4.14-4.03 (m, 2H), 4.01-3.83 (m, 4H), 3.67-3.51 (m, 2H), 2.1-2.0 (m, 2H), 1.33-0.77 (m, 126H).

Step II, Compound 53

A solution of [(2R,3R,4R,5R,6R)-6-[2-[4-[2-[(2R,3R,4R,5R,6R)-6-(hydroxymethyl)-3,4,5-tris(triisopropylsilyloxy)tetrahydropyran-2-yl]ethynyl]phenyl]ethynyl]-3,4,5-tris(triisopropylsilyloxy)tetrahydropyran-2-yl]methanol (471 mg, 0.339 mmol) in THF (16.0 mL), TFA (8.0 mL) and water (8.0 mL) is heated to reflux for (bath temperature 75° C.) 30 h and concentrated. The residue is purified on Biotage™ SNAP 25 g C18 silica gel cartridge using CH$_3$CN in water (0% to 50%, 10 CV) as eluent to afford title compound (146 mg, 0.311 mmol, 88%) as half-white solid. $^1$H NMR (400 MHz, CD$_3$OD) δ 7.43 (s, 4H), 4.85 (d, J=2.1 Hz, 2H), 3.98 (dd, J=3.1, 2.2 Hz, 2H), 3.92-3.83 (m, 4H), 3.81-3.68 (m, 4H), 3.61 (t, J=9.5 Hz, 2H).

Alternate Synthesis of Compound 53 (Method C)

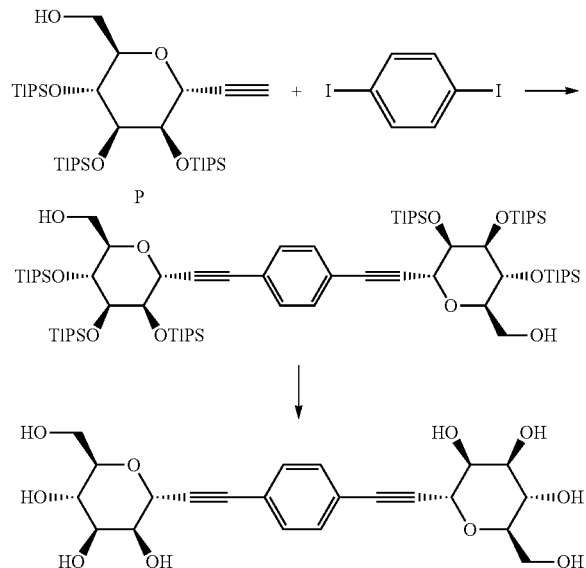

Step I: [(2R,3R,4R,5R,6R)-6-[2-[4-[2-[(2R,3R,4R,5R,6R)-6-(hydroxymethyl)-3,4,5-tris(triisopropylsilyloxy)tetrahydropyran-2-yl]ethynyl]phenyl]ethynyl]-3,4,5-tris(triisopropylsilyloxy)tetrahydropyran-2-yl]methanol Intermediate P (118 mg, 0.18 mmol) and 1,4-diiodobenzene (28 mg, 0.083 mmol) are charged in a vial, dissolved in DMF (3 mL), degassed, then CuI (7.8 mg, 0.041 mmol) and Pd(dppf)Cl$_2$—CH$_2$Cl$_2$ (8.4 mg, 0.010 mmol) are added, degassed again, then Et$_3$N (57 µL, 0.41 mmol) is added and the reaction mixture is capped and heated at 40° C. for 4 h. The reaction mixture is diluted with EtOAc (10 mL), washed sequentially with saturated NH$_4$Cl, H$_2$O, brine (5 mL each), dried over Na$_2$SO$_4$, filtered and concentrated then purified on Biotage™ SNAP 10 g silica gel cartridge using a gradient of EtOAc in Hex (0-20%). Pure fractions are combined and concentrated to afford title compound (60 mg, 0.043 mmol, 53% yield) as a colorless foam.

Step II, Compound 53

To a solution of [(2R,3R,4R,5R,6R)-6-[2-[4-[2-[(2R,3R,4R,5R,6R)-6-(hydroxymethyl)-3,4,5-tris(triisopropylsilyloxy)tetrahydropyran-2-yl]ethynyl]phenyl]ethynyl]-3,4,5-tris(triisopropylsilyloxy)-tetrahydropyran-2-yl]methanol (100 mg, 0.072 mmol) in THF (1 mL) is added a THF solution of tetrabutylammonium fluoride (575 µL of 1 M, 0.58 mmol). After stirring for 3.5 h, the reaction mixture is concentrated and purified by reverse-phase flash chromatography on Biotage™ SNAP 12 g C18 silica gel cartridge using a gradient of MeCN in H$_2$O (0-50%). The combined fractions containing desired compound are concentrated, the residue is redissolved in MeCN/H$_2$O (20% MeCN), and freeze-dried to provide 52 mg of white solid.

Alternate Synthesis of Compound 53 (Method D)

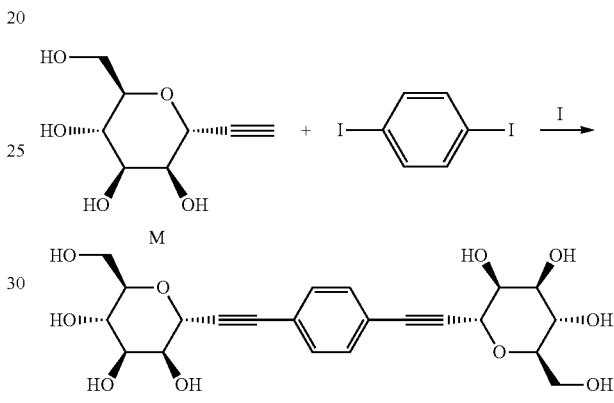

To a solution of Intermediate M (130 mg, 0.6908 mmol) in DMF (4 mL) are added 1,4-diiodobenzene (102.9 mg, 0.3119 mmol), PdCl$_2$(dppf)-CH$_2$Cl$_2$ (13.1 mg, 0.0160 mmol), CuI (11.9 mg, 0.0625 mmol) and DIPEA (163 µL, 0.936 mmol). The mixture is stirred at 60° C. for 5 h under nitrogen. After removal of the solvent under reduced pressure, the residue is purified using prep-HPLC to obtain the title compound (52 mg, 0.115 mmol, 37%) as a white solid. LC-MS: m/z=451.5 (M+H$^+$).

Alternate Synthesis of Compound 53 (Method E)

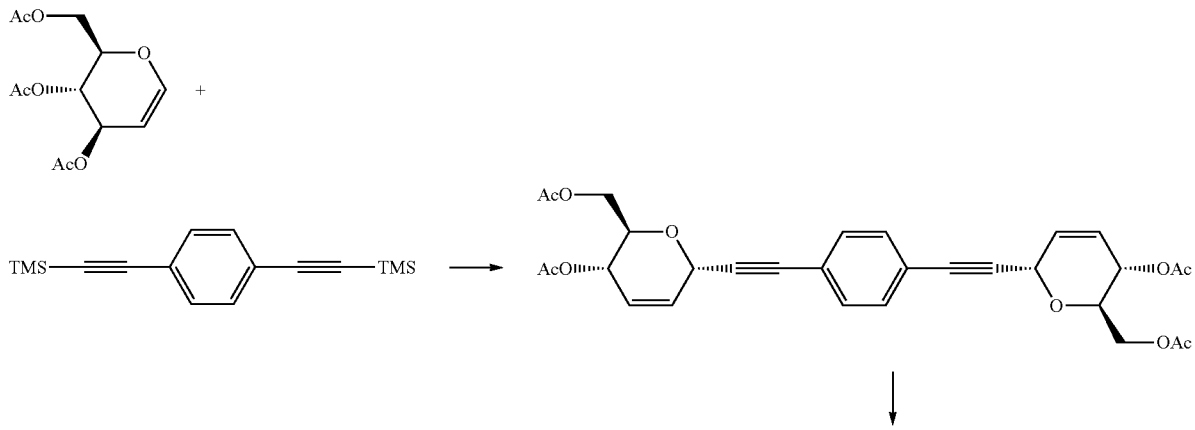

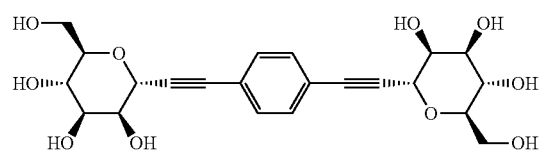 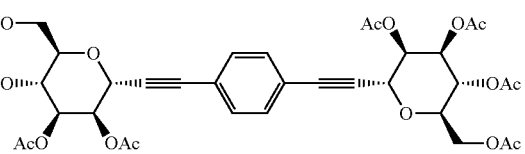

Step I: (2R,2'R,3S,3'S,6S,6'S)-(1,4-phenylenebis(ethyne-2,1-diyl))bis(2-(acetoxymethyl)-3,6-dihydro-2H-pyran-6,3-diyl) diacetate In a 1.0 L 3-neck RBF equipped with a magnetic stirrer and a thermometer is dissolved trimethyl-[2-[4-(2-trimethylsilylethynyl)phenyl]ethynyl]silane (25.00 g, 92.42 mmol) and Indium Triflate (2.597 g, 4.621 mmol) in $CH_2Cl_2$ (125 mL). The mixture is stirred at RT for 10 min then [(2R,3S,4R)-3,4-diacetoxy-3,4-dihydro-2H-pyran-2-yl]methyl acetate (100.7 g, 369.7 mmol) dissolved in 100 mL of $CH_2Cl_2$ is added dropwise over 2 h to the reaction mixture via addition funnel keeping the reaction temperature below 25° C. At the end of the addition the reaction mixture is stirred at RT for an additional 18 h. The reaction is quenched with saturated aqueous $NaHCO_3$ (250 mL) and the layers are separated. The aqueous layer is back extracted once with 150 mL of $CH_2Cl_2$ and the combined organic layers are washed with water (250 mL), dried over $MgSO_4$ and filtered. Silica gel (500 mL) is added to the organic phase and the mixture is evaporated to dryness under reduced pressure. The crude mixture is purified on a large pad of silica gel eluting with Hex/EtOAc (10 to 50%). Fractions containing the desired product are combined, concentrated to 300 mL then heptane (500 mL) and MeOH (500 mL) are added. The mixture is concentrated until a solid is formed and the latter is filtered to afford 31.0 g (58%) of the title compound.

Step II: (2R,2'R,3S,3'S,4R,4'R,5S,5'S,6R,6'R)-(1,4-phenylenebis(ethyne-2,1-diyl))bis(2-(acetoxymethyl)-4,5-dihydroxytetrahydro-2H-pyran-6,3-diyl) diacetate In a 5 L 3 necks RBF equipped with a mechanical stirrer, $N_2$ inlet and a temperature probe is charged with $K_2CO_3$ (150.6 g, 1.090 mol), methanesulfonamide (51.83 g, 544.9 mmol), $K_3[Fe(CN)_6]$ (358.9 g, 1.090 mol), 2-methylpropan-2-ol (1.000 µL) and water (1.250 L). 1,4-bis[(S)-[(5S)-5-ethylquinuclidin-2-yl]-(6-methoxy-4-quinolyl)methoxy]phthalazine (2.830 g, 3.633 mmol) is then added followed by $K_2O_4Os$ (334.6 mg, 0.9082 mmol) and the mixture is stirred at RT for 15 min. To this mixture is added [(2R,3S,6S)-3-acetoxy-6-[2-[4-[2-[(2R,3S,6S)-3-acetoxy-2-(acetoxymethyl)-3,6-dihydro-2H-pyran-6-yl]ethynyl]phenyl]ethynyl]-3,6-dihydro-2H-pyran-2-yl]methyl acetate from Step 1 (50.00 g, 90.82 mmol) dissolved in EtOAc (250.0 mL) dropwise via an addition funnel over 10 min. The resulting reaction mixture (brown-orange+quite homogeneous, no chunks) is stirred (300 rpm) at RT for 18 h. An extra amount of $K_2O_4Os$ is added (335 mg, 0.908 mmol) and the reaction mixture is stirred for 24 h. The last procedure is repeated twice for a total amount of 1.340 g of $K_2O_4Os$ and a reaction time of 96 h. The reaction mixture is quenched with $Na_2SO_3$ (233.9 g in 250 mL of water), stirred at RT for 60 min, filtered through a pad of celite. The organic layer is separated and concentrated to afford 76.74 g of crude compound as brown gum.

The crude product and DMAP (1.110 g, 9.082 mmol) are dissolved in pyridine (250.0 mL). The resulting solution is cooled in ice/water bath and $Ac_2O$ (51.4 mL, 545 mmol) is added dropwise over 10 minutes keeping temperature below 10° C. The reaction mixture is then stirred at RT for 1.5 h. After stirring at RT for 1 h, 25 mL of extra $Ac_2O$ is added and the mixture is stirred for an additional 4 h. The resulting reaction mixture is diluted with $CH_2Cl_2$ (250 mL) and water (250 mL), stirred for 15 min, then 2N HCl (2.25 µL) is added and stirred for 5 min with ice/water bath to control exotherm. The aqueous solution is separated and back-extracted with $CH_2Cl_2$ (2×250 mL) and the combined organic extracts are washed once again with 2N HCl (250 mL, added brine to help separation), dried over $Na_2SO4$ then concentrated to afford 52.3 g of crude brown foamy solid. The residue is suspended in EtOH (262 mL), stirred under reflux until complete dissolution and then slowly cooled down to RT then at 0° C. for 30 min. The resulting precipitate is filtered, washed with cold EtOH to afford after drying in vacuum oven at 35° C. for 48 hrs, 43.0 g of a beige powder (77% yield over two steps).

Step III: Compound 53

A 1 L RBF is charged [(2R,3R,4R,5R,6R)-3,4,5-triacetoxy-6-[2-[4-[2-[(2R,3R,4R,5R,6R)-3,4,5-triacetoxy-6-(acetoxymethyl)tetrahydropyran-2-yl]ethynyl]phenyl]ethynyl]tetrahydropyran-2-yl]methyl acetate from Step II (11.55 g, 14.68 mmol), EtOH (347 mL) is added and the mixture is stirred at RT for 5 minutes. MeONa (327 µL of 25% w/w, 1.47 mmol) is added and the reaction mixture is stirred at RT for 4 days. Reaction is incomplete and MeOH (120 mL) and additional MeONa (981 µL of 25% w/w, 4.41 mmol) is added. Final mixture is stirred for 2 days, filtered and the resulting solid is washed with EtOH. The mother liquors are neutralized through a 27 g Dowex 50W4 (prewash with EtOH) column. The solid is then swished for 15 min in the neutralized mother liquors. The slurry is then concentrated to dryness to afford 10 g of off-white solid. The latter is poured in EtOH (165 mL) and stirred at 70° C. for 1 h. The slurry is slowly cooled down to RT then cooled and stirred at 0° C. for 30 min. Filtration and washing twice with cold EtOH (2×10 mL) and once with Heptane (10 mL) afforded 6.70 g of an off-white solid. Drying in a vacuum oven at 50° C. for 2 days afforded the title compound as an off-white solid (6.37 g, 95%)

235

Example 35. Preparation of Compound 54

(2R,3S,4R,5S,6R)-2-(hydroxymethyl)-6-[4-[(2R,3S,4R,5S,6R)-3,4,5-trihydroxy-6-(hydroxymethyl)tetrahydropyran-2-yl]buta-1,3-diynyl]tetrahydropyran-3,4,5-triol

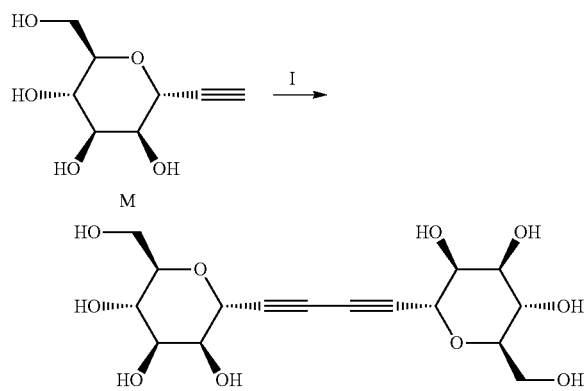

To a solution of Intermediate M (46 mg, 0.2444 mmol) in DMF (3 mL) are added PdCl$_2$(dppf)-CH$_2$Cl$_2$ (10 mg, 0.0123 mmol), CuI (9.3 mg, 0.0488 mmol) and DIPEA (85 μL, 0.488 mmol). The mixture is stirred at 50° C. overnight under nitrogen. After removal of the solvent under reduced pressure, the residue is purified on prep-HPLC to obtain the title compound (6 mg, 0.0137 mmol, 6%) as a white solid. $^1$H NMR (400 MHz, CD$_3$OD) δ 4.73 (d, 2H), 3.91-3.88 (m, 2H), 3.83 (m, 2H), 3.77-3.68 (m, 4H), 3.66-3.60 (m, 2H), 3.57 (m, 2H). LC-MS: m/z=374.5 (M+H$^+$).

Example 36. Preparation of compound 55

(2R,3S,4R,5S,6R)-2-(Hydroxymethyl)-6-[(E)-3-[4-[2-[(2R,3S,4R,5S,6R)-3,4,5-trihydroxy-6-(hydroxymethyl)tetrahydropyran-2-yl]ethynyl]phenyl]allyl]tetrahydropyran-3,4,5-triol

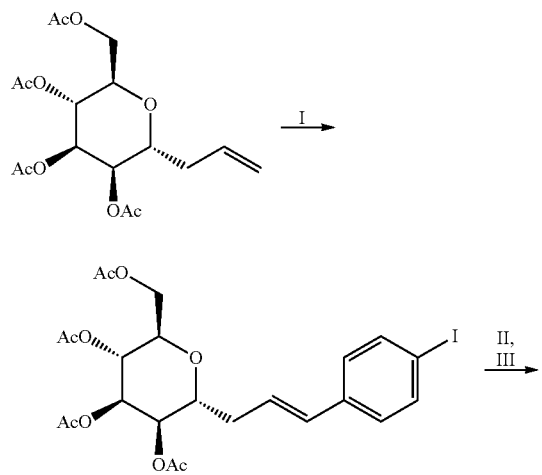

236

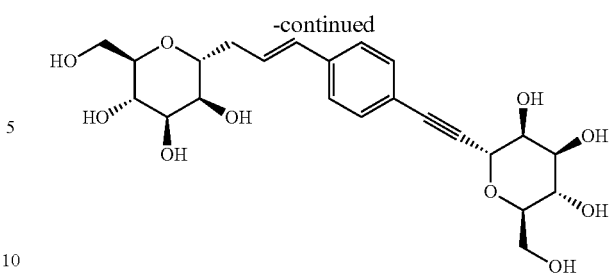

Step I: [(2R,3R,4R,5R,6R)-3,4,5-Triacetoxy-6-[(E)-3-(4-iodophenyl)allyl]tetrahydropyran-2-yl]methyl acetate To a solution of Intermediate H (300 mg, 0.8057 mmol) in DMF (8.0 mL) are added 1,4-diiodobenzene (265.8 mg, 0.806 mmol), palladium acetate (18.09 mg, 0.081 mmol), tetrabutylammonium bromide (259.7 mg, 0.81 mmol) and sodium bicarbonate (203.0 mg, 2.42 mmol). The reaction mixture is heated at 85° C. overnight under N$_2$. Water is added to reaction mixture, extracted with EtOAc (2×). Combined extracts are washed with brine/water (twice, 1:1, v/v) and dried over MgSO$_4$, filtered and concentrated under reduced pressure. The dark crude oil is purified on Biotage™ SNAP 25 g silica gel using EtOAc in Hex (0 to 45% in 20 CV; 45% in 2 CV) to afford title compound (260 mg, 0.453 mmol, 56%) as a yellowish oil. $^1$H NMR (400 MHz, CD$_3$OD) δ 7.64 (d, J=8.4 Hz, 2H), 7.18 (d, J=8.4 Hz, 2H), 6.50 (d, J=15.9 Hz, 1H), 6.32-6.22 (m, 1H), 5.35 (dd, J=8.7, 3.3 Hz, 1H), 5.24 (t, J=3.4 Hz, 1H), 5.15 (t, J=8.4 Hz, 1H), 4.40-4.31 (m, 1H), 4.15-4.00 (m, 5H), 2.78-2.53 (m, 2H), 2.10 (s, 4H), 2.07 (s, 3H), 2.01 (d, J=1.6 Hz, 5H), 1.90 (s, 3H), 1.24 (t, J=7.1 Hz, 2H). LC-MS: m/z=575.35 (M+H$^+$)

Step II: [(2R,3R,4R,5R,6R)-3,4,5-Triacetoxy-6-[(E)-3-[4-[2-[(2R,3S,4R,5S,6R)-3,4,5-trihydroxy-6-(hydroxymethyl)tetrahydropyran-2-yl]ethynyl]phenyl]allyl]tetrahydropyran-2-yl]methyl acetate A solution of [(2R,3R,4R,5R,6R)-3,4,5-triacetoxy-6-[(E)-3-(4-iodophenyl)allyl]tetrahydropyran-2-yl]methyl acetate from Step I (130 mg, 0.226 mmol), CuI (9.4 mg, 0.049 mmol) and PdCl$_2$(dppf)-CH$_2$Cl$_2$ (37.3 mg, 0.046 mmol) in DMF (4.2 mL) is degassed (vacuum/N$_2$ flush). To this are added triethylamine (137.4 mg, 189.3 μL, 1.358 mmol) and Intermediate M (42.6 mg, 0.226 mmol) under nitrogen atmosphere. The reaction mixture is stirred at RT overnight. Reaction mixture is quenched with water and extracted with EtOAc (2×). Combined organic extracts are washed with diluted NH$_4$Cl, and brine/water (twice, 1:1, v/v), and dried over MgSO$_4$, filtered and concentrated under reduced pressure to afford title compound (143 mg) and it is used as such in the next step. LC-MS: m/z=635.52 (M+H$^+$).

Step III, Compound 55

To a stirred solution of [(2R,3R,4R,5R,6R)-3,4,5-triacetoxy-6-[(E)-3-[4-[2-[(2R,3S,4R,5S,6R)-3,4,5-trihydroxy-6-(hydroxymethyl)tetrahydropyran-2-yl]ethynyl]phenyl]allyl]tetrahydropyran-2-yl]methyl acetate from step II (143 mg, 0.225 mmol) in MeOH (2.9 mL) is added MeONa in MeOH (225 μL of 0.5 M, 0.113 mmol). The reaction mixture is stirred at RT overnight. The reaction mixture is passed through ion exchange resin Isolute SCX-2 (1 g column) and washed with dry MeOH. The combined filtrate is concentrated to dryness and the residue is purified on prep. HPLC to afford the title compound (22.3 mg, 20%) as a white fluffy solid. $^1$H NMR (400 MHz, CD$_3$OD) δ 7.41 (s, 4H), 6.55 (d, J=15.9 Hz, 1H), 6.47-6.35 (m, 1H), 4.06-4.00 (m, 2H), 3.96 (dd, J=9.3, 3.3 Hz, 1H), 3.90 (dd, J=11.5, 2.1 Hz, 1H), 3.87-3.73 (m, 6H), 3.71-3.63 (m, 2H), 3.57 (ddd, J=9.0, 6.1, 3.2 Hz, 1H), 2.76-2.65 (m, 1H), 2.60-2.49 (m, 1H).

Example 37. Preparation of compound 56 (Method A)

(2R,3S,4R,5S,6R)-2-(Hydroxymethyl)-6-[2-[6-[(2R, 3S,4R,5S,6R)-3,4,5-trihydroxy-6-(hydroxymethyl) tetrahydropyran-2-yl]-2-naphthyl]ethynyl]tetrahydropyran-3,4,5-triol

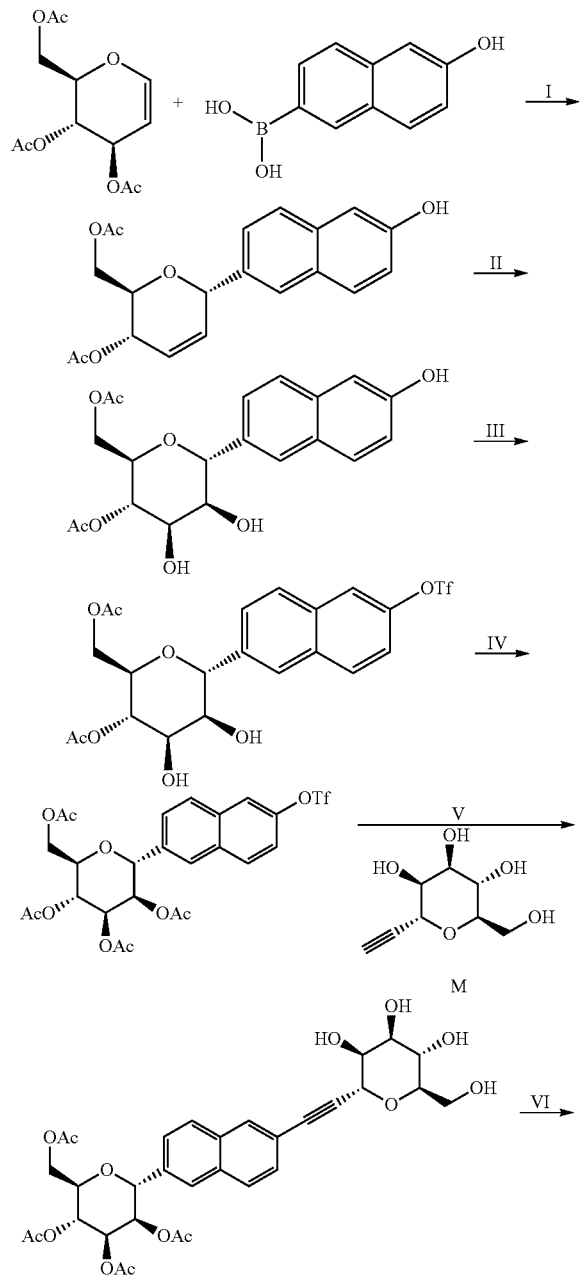

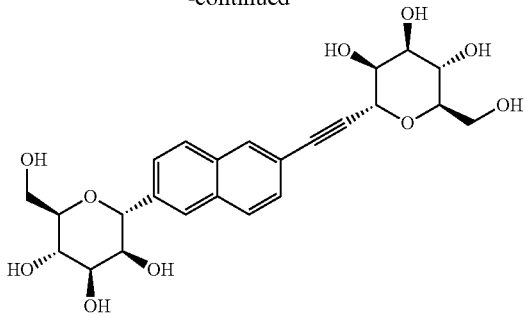

Step I: [(2R,3S,6S)-3-Acetoxy-6-(6-hydroxy-2-naphthyl)-3,6-dihydro-2H-pyran-2-yl]methyl acetate Acetonitrile (10 mL) is added to a mixture of [(2R,3S, 4R)-3,4-diacetoxy-3,4-dihydro-2H-pyran-2-yl]methyl acetate (1.49 g, 5.47 mmol), (6-hydroxy-2-naphthyl)boronic acid (1.0 g, 5.32 mmol) and diacetoxypalladium (119 mg, 0.53 mmol). The reaction mixture is stirred overnight at RT under N$_2$, then filtered through silica cartridge (5 g), and rinsed with EtOAc. Combined filtrates are concentrated, and purified on Biotage™ SNAP 50 g silica gel cartridge using a gradient of EtOAc in Hex (0-50%). Pure fractions are combined and concentrated to provide title compound (935 mg, 2.62 mmol, 49% yield) as an off-white foamy solid. $^1$H NMR (400 MHz, CDCl$_3$) δ 7.80-7.72 (m, 2H), 7.70 (d, J=8.5 Hz, 1H), 7.51 (dd, J=8.5, 1.7 Hz, 1H), 7.18-7.08 (m, 2H), 6.28 (ddd, J=10.4, 3.1, 1.6 Hz, 1H), 6.13-6.00 (m, 1H), 5.49-5.42 (m, 1H), 5.36 (ddd, J=7.4, 4.1, 2.1 Hz, 1H), 4.28 (dd, J=12.0, 5.8 Hz, 1H), 4.09 (dd, J=12.0, 3.0 Hz, 1H), 3.86 (ddd, J=7.8, 5.8, 3.0 Hz, 1H), 2.10 (s, 3H), 2.08 (s, 3H). LC-MS: m/z=357.34 (M+H$^+$).

Step II: [(2R,3S,4R,5S,6R)-3-Acetoxy-4,5-dihydroxy-6-(6-hydroxy-2-naphthyl)tetrahydropyran-2-yl]methyl acetate To a suspension of [(2R,3S,6S)-3-acetoxy-6-(6-hydroxy-2-naphthyl)-3,6-dihydro-2H-pyran-2-yl]methyl acetate (930 mg, 2.61 mmol) in THF (5.6 mL)/water (3.7 mL) are added OsO$_4$ (2.5% w/w in t-BuOH, 980 μL, 0.078 mmol) followed by 4-methyl-4-oxido-morpholin-4-ium (917 mg, 7.83 mmol). After stirring for 23 h, more OsO$_4$ solution is added (300 μL) and stirred another 18 h, then 1M aqueous Na$_2$S$_2$O$_3$ solution (6 mL), EtOAc (40 mL), and H$_2$O (10 mL) are added. Organic layer is separated, aqueous layer is extracted with EtOAc (2×20 mL). Combined organic extracts are washed with brine (20 mL), dried over Na$_2$SO$_4$, filtered and concentrated to provide crude product as a dark brown foamy solid, which is purified on Biotage™ SNAP 50 g silica gel cartridge using a gradient of $^i$PrOH in CH$_2$Cl$_2$ (0-10%). Combined pure fractions are concentrated to provide title compound (281 mg, 0.72 mmol, 27% yield) as an off-white solid. $^1$H NMR (400 MHz, CD$_3$OD) δ 7.77 (s, 1H), 7.73 (d, J=8.7 Hz, 1H), 7.67 (d, J=8.6 Hz, 1H), 7.48 (dd, J=8.6, 1.7 Hz, 1H), 7.12-7.04 (m, 2H), 5.10 (dd, J=6.3, 5.3 Hz, 1H), 5.03 (d, J=6.2 Hz, 1H), 4.74 (dd, J=12.1, 8.1 Hz, 1H), 4.31 (dd, J=6.2, 3.2 Hz, 1H), 4.12 (dd, J=12.1, 3.2 Hz, 1H), 3.95-3.84 (m, 2H), 2.09 (s, 3H), 2.06 (s, 3H). LC-MS: m/z=413.34 (M+Na$^+$).

Step III: [(2R,3S,4R,5S,6R)-3-Acetoxy-4,5-dihydroxy-6-[6-(trifluoromethylsulfonyloxy)-2-naphthyl]tetrahydropyran-2-yl]methyl acetate To a suspension of [(2R,3S,4R,5S,6R)-3-acetoxy-4,5-dihydroxy-6-(6-hydroxy-2-naphthyl)tetrahydropyran-2-yl]

methyl acetate (235 mg, 0.60 mmol) in CH$_2$Cl$_2$ (6 mL) is added Et$_3$N (168 µL, 1.21 mmol), 1,1,1-trifluoro-N-phenyl-N-(trifluoromethylsulfonyl)-methanesulfonamide (266 mg, 0.7446 mmol), and CH$_2$Cl$_2$ (4 mL). After stirring for 4 days, the reaction mixture is concentrated. Purified on Biotage™ SNAP 25 g silica gel cartridge, using a gradient of MeOH in CH$_2$Cl$_2$ (0-10%). Fractions containing product are combined, concentrated then purified again on Biotage™ SNAP 25 g silica gel cartridge, using a gradient of EtOAc in Hex (50-80%). Pure fractions are combined and concentrated to afford title compound (214 mg, 0.41 mmol, 68% yield) which is obtained as a yellowish waxy solid.
$^1$H NMR (400 MHz, CD$_3$OD) δ 8.06 (d, J=9.1 Hz, 1H), 8.02 (s, 1H), 8.00 (d, J=8.6 Hz, 1H), 7.91 (d, J=2.5 Hz, 1H), 7.74 (dd, J=8.6, 1.6 Hz, 1H), 7.47 (dd, J=9.0, 2.5 Hz, 1H), 5.15-5.00 (m, 2H), 4.24-4.07 (m, 2H), 4.02-3.97 (m, 1H), 3.95 (dd, J=5.4, 3.1 Hz, 1H), 2.12 (s, 3H), 2.03 (s, 3H). LC-MS: m/z=545.36 (M+Na$^+$).

Step IV: [(2R,3R,4R,5R,6R)-3,4,5-Triacetoxy-6-[6-(trifluoromethylsulfonyloxy)-2-naphthyl]tetrahydropyran-2-yl]methyl acetate To a solution of [(2R,3S,4R,5S,6R)-3-acetoxy-4,5-dihydroxy-6-[6-(trifluoro-methylsulfonyloxy)-2-naphthyl]tetrahydropyran-2-yl]methyl acetate (214 mg, 0.41 mmol) in CH$_2$Cl$_2$ (2.2 mL) are added pyridine (100 µL, 1.24 mmol), DMAP (2.5 mg, 0.0208 mmol) and Ac$_2$O (97 µL, 1.03 mmol). After stirring for 2 h, the reaction mixture is diluted with CH$_2$Cl$_2$ (5 mL), aqueous 1N HCl (5 mL) is added, the layers are separated. Aqueous layer is extracted with CH$_2$Cl$_2$ (2×5 mL). Combined organic extracts are concentrated, redissolved in CH$_2$Cl$_2$, treated with prewashed Dowex 50WX4-400 resin, filtered and rinsed with portions of CH$_2$Cl$_2$. Combined filtrates are concentrated to provide title compound (232 mg, 0.38 mmol, 93% yield) as an off-white foamy solid. $^1$H NMR (400 MHz, CDCl$_3$) δ 8.05 (s, 1H), 7.99 (d, J=9.0 Hz, 1H), 7.95 (d, J=8.7 Hz, 1H), 7.77 (d, J=2.4 Hz, 1H), 7.72 (dd, J=8.5, 1.5 Hz, 1H), 7.43 (dd, J=9.0, 2.5 Hz, 1H), 6.10 (t, J=3.3 Hz, 1H), 5.37 (t, J=8.6 Hz, 1H), 5.27 (d, J=3.2 Hz, 1H), 5.22 (dd, J=8.9, 3.1 Hz, 1H), 4.44 (dd, J=12.2, 6.3 Hz, 1H), 4.15 (dd, J=12.1, 2.8 Hz, 1H), 3.83-3.69 (m, 1H), 2.17 (s, 3H), 2.14 (s, 3H), 2.10 (s, 3H), 2.02 (s, 3H). LC-MS: m/z=607.41 (M+H$^+$).

Step V: [(2R,3R,4R,5R,6R)-3,4,5-Triacetoxy-6-[6-[2-[(2R,3S,4R,5S,6R)-3,4,5-trihydroxy-6-(hydroxymethyl)tetrahydropyran-2-yl]ethynyl]-2-naphthyl]tetrahydropyran-2-yl]methyl acetate To a mixture of [(2R,3R,4R,5R,6R)-3,4,5-Triacetoxy-6-[6-(trifluoromethylsulfonyloxy)-2-naphthyl]tetrahydropyran-2-yl]methyl acetate from step IV (45 mg, 0.0742 mmol), Intermediate M (25 mg, 0.13 mmol and CuI (6.3 mg, 0.033 mmol) in a microwave vial are added DMF (500 µL) and Et$_3$N (52 µL, 0.37 mmol). The reaction mixture is degassed (house-vac then N$_2$, 3×), then PdCl$_2$(dppf)-CH$_2$Cl$_2$ (8 mg, 0.0098 mmol) is added, degassed again, capped and stirred at 80° C. overnight. The reaction mixture is cooled-down to RT and diluted with EtOAc (2 mL) and H$_2$O (1 mL), filtered through celite and rinsed with EtOAc (4×0.5 mL). Filtrate is diluted with H$_2$O and brine (1 mL) and EtOAc. Layers are separated. Organic layer is washed with H$_2$O, brine, dried over Na$_2$SO$_4$, filtered and concentrated to provide crude product. Purified on Biotage™ SNAP 10 g silica gel cartridge using a gradient of MeOH in CH$_2$Cl$_2$ (0-20%). Pure fractions are combined and concentrated to provide title compound (36 mg, 0.056 mmol, 75% yield) as a beige foamy solid. $^1$H NMR (400 MHz, CD$_3$OD) δ 8.05 (s, 1H), 8.00 (s, 1H), 7.94 (d, J=8.7 Hz, 1H), 7.90 (d, J=8.6 Hz, 1H), 7.66 (dd, J=8.7, 1.6 Hz, 1H), 7.56 (dd, J=8.5, 1.5 Hz, 1H), 6.03-5.97 (m, 1H), 5.32-5.25 (m, 2H), 5.22 (dd, J=8.3, 3.1 Hz, 1H), 4.92 (d, J=2.1 Hz, 1H), 4.50 (dd, J=12.1, 6.7 Hz, 1H), 4.18 (dd, J=12.2, 3.0 Hz, 1H), 4.06 (dd, J=3.2, 2.1 Hz, 1H), 3.99 (dd, J=9.3, 3.3 Hz, 1H), 3.94-3.81 (m, 3H), 3.76 (dd, J=11.7, 5.8 Hz, 1H), 3.67 (t, J=9.6 Hz, 1H), 2.12-2.07 (m, 9H), 2.04 (s, 3H). LC-MS: m/z=645.43 (M+H$^+$).

Step VI, Compound 56

To a solution of [(2R,3R,4R,5R,6R)-3,4,5-triacetoxy-6-[6-[2-[(2R,3S,4R,5S,6R)-3,4,5-trihydroxy-6-(hydroxymethyl)tetrahydropyran-2-yl]ethynyl]-2-naphthyl]tetrahydropyran-2-yl]methyl acetate (34 mg, 0.053 mmol) in MeOH (1 mL) is added MeONa in MeOH (55 µL of 0.5 M, 0.028 mmol). The reaction mixture is stirred overnight then passed through a pre-washed SCX-2 1 g cartridge, washed with MeOH (3×1 mL). Combined filtrates are concentrated to provide a glassy solid which is redissolved in MeCN/H$_2$O mixture (20% MeCN) and freeze-dried to provide title compound (24 mg, 0.046 mmol, 88% yield) as a fluffy white solid. $^1$H NMR (400 MHz, CD$_3$OD) δ 7.91 (s, 1H), 7.84 (s, 1H), 7.77 (t, J=8.0 Hz, 2H), 7.61 (dd, J=8.7, 1.4 Hz, 1H), 7.40 (dd, J=8.5, 1.5 Hz, 1H), 5.02 (d, J=3.9 Hz, 1H), 4.81 (d, J=2.1 Hz, 1H), 4.50-4.35 (m, 1H), 3.95 (dd, J=3.2, 2.2 Hz, 1H), 3.89 (dd, J=9.3, 3.3 Hz, 1H), 3.84-3.72 (m, 4H), 3.71-3.61 (m, 2H), 3.60-3.51 (m, 2H), 3.47-3.40 (m, 1H). LC-MS: m/z=477.41 (M+H$^+$).

Example 38. Preparation of compound 57 (Method D)

(2R,3S,4R,5S,6R)-2-(Hydroxymethyl)-6-[2-[3-[2-[(2R,3S,4R,5S,6R)-3,4,5-trihydroxy-6-(hydroxymethyl)tetrahydropyran-2-yl]ethynyl]phenyl]ethynyl]tetrahydropyran-3,4,5-triol

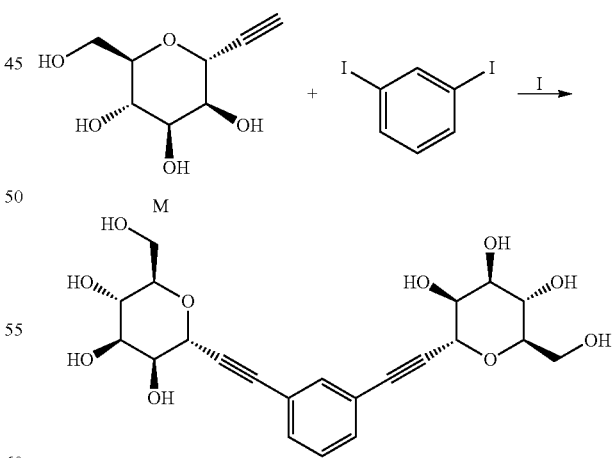

Intermediate M (108 mg, 0.57 mmol) is dissolved in DMF (2.7 mL), degassed, then added 1,3-diiodobenzene (87 mg, 0.26 mmol), followed by CuI (21 mg, 0.11 mmol) and PdCl$_2$(dppf).CH$_2$Cl$_2$ (22 mg, 0.027 mmol), degassed again, then Et$_3$N (180 µL, 1.291 mmol) is added and the reaction mixture is heated at 40° C. for 6 h. The reaction mixture is concentrated to dryness, then purified twice by reverse-phase flash chromatography on Biotage™ SNAP C18 12+M cartridge using MeCN in H$_2$O, gradient of 0-30%. Pure fractions from the second purification are concentrated to dryness, providing title compound (50 mg, 0.11 mmol, 40% yield) as a pale yellow solid. $^1$H NMR (400 MHz, dmso-d6) δ 7.51-7.38 (m, 4H), 4.95 (d, J=4.4 Hz, 2H), 4.76 (d, J=6.1 Hz, 2H), 4.73-4.68 (m, 4H), 4.47 (t, J=6.0 Hz, 2H), 3.81-3.75 (m, 2H), 3.70-3.61 (m, 4H), 3.57-3.50 (m, 2H), 3.48-3.39 (m, 2H), 3.39-3.29 (m, 6H).
LC-MS: m/z=451.49 (M+H$^+$).

Example 39. Preparation of Compound 58 (Method D)

(2R,3S,4R,5S,6R)-2-(Hydroxymethyl)-6-[2-[7-[2-[(2R,3S,4R,5S,6R)-3,4,5-trihydroxy-6-(hydroxymethyl)tetrahydropyran-2-yl]ethynyl]-2-naphthyl]ethynyl]tetrahydropyran-3,4,5-triol

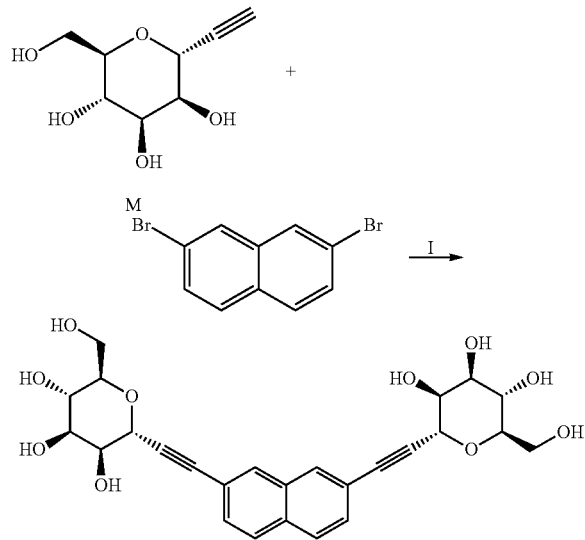

A microwave vial is charged with 2,7-dibromonaphthalene (36 mg, 0.13 mmol) and Intermediate M (54 mg, 0.29 mmol), PdCl$_2$ (dppf).CH$_2$Cl$_2$ (9.2 mg, 0.011 mmol) and CuI (14 mg, 0.074 mmol). DMF (1 mL) and Et$_3$N (88 μL, 0.6295 mmol) are added, the reaction mixture is degassed and heated in microwave for 10 min at 120° C., then concentrated to dryness and purified twice by reverse-phase flash chromatography on Biotage™ SNAP C18 12+M using MeCN in H$_2$O, gradient of 10-90% for the first purification, 10-60% for the second purification. Fractions from the second purification are concentrated to dryness and purified on prep HPLC to afford title compound (11 mg, 0.020 mmol, 16% yield) as an off-white solid. $^1$H NMR (400 MHz, DMSO-D$_6$) δ 8.11 (s, 2H), 7.96 (d, J=8.5 Hz, 2H), 7.54 (dd, J=8.5, 1.4 Hz, 2H), 5.01 (d, J=3.2 Hz, 2H), 4.84 (d, J=4.9 Hz, 2H), 4.80-4.71 (m, 4H), 4.53 (t, J=5.6 Hz, 2H), 3.85 (s, 2H), 3.71 (dd, J=18.8, 6.8 Hz, 4H), 3.65-3.55 (m, 2H), 3.52-3.20 (m, 4H).
$^1$H NMR (400 MHz, DMSO-D$_6$+D$_2$O) δ 8.09 (s, 2H), 7.95 (d, J=8.6 Hz, 2H), 7.53 (dd, J=8.5, 1.4 Hz, 2H), 4.77 (d, J=2.1 Hz, 2H), 3.86-3.81 (m, 2H), 3.73 (dd, J=9.2, 3.3 Hz, 2H), 3.69 (dd, J=11.7, 1.9 Hz, 2H), 3.64-3.56 (m, 2H), 3.56-3.43 (m, 2H), 3.39 (t, J=9.4 Hz, 2H). LC-MS: m/z=501.65 (M+H$^+$).

Preparation of Compound 59 (Method D)

(2R,3S,4R,5S,6R)-2-(Hydroxymethyl)-6-[2-[6-[2-[(2R,3S,4R,5S,6R)-3,4,5-trihydroxy-6-(hydroxymethyl)tetrahydropyran-2-yl]ethynyl]-2-naphthyl]ethynyl]tetrahydropyran-3,4,5-triol

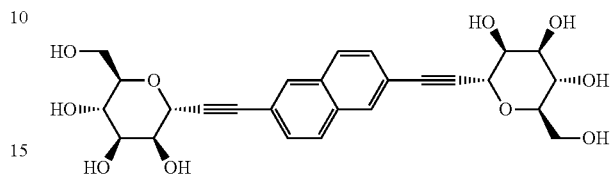

The title compound is obtained from 2,6-dibromonaphthalene using the same procedure described for compound 58 except that the reaction is carried out at 90° C. for 16 h to afford title compound (30 mg, 0.057 mmol, 42% yield) as pale yellow solid. $^1$H NMR (400 MHz, CD$_3$OD) δ 8.01 (s, 2H), 7.86 (d, J=8.6 Hz, 2H), 7.54 (dd, J=8.5, 1.4 Hz, 2H), 4.92 (d, J=2.1 Hz, 2H), 4.05 (d, J=3.1, 2.2 Hz, 2H), 3.98 (dd, J=9.4, 3.3 Hz, 2H), 3.94-3.82 (m, 4H), 3.81-3.72 (m, 2H), 3.66 (t, J=9.5 Hz, 2H).
LC-MS: m/z=501.40 (M+H$^+$).

Preparation of Compound 60 (Method D)

(2R,3S,4R,5S,6R)-2-(Hydroxymethyl)-6-[2-[5-[2-[(2R,3S,4R,5S,6R)-3,4,5-trihydroxy-6-(hydroxymethyl)tetrahydropyran-2-yl]ethynyl]-1-naphthyl]ethynyl]tetrahydropyran-3,4,5-triol

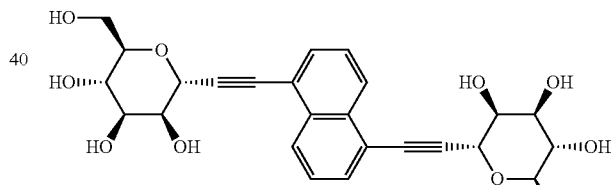

The title compound is obtained from 1,5-dibromonaphthalene using the same procedure described for compound 58 except that the reaction is carried out at 90° C. for 16 h to afford title compound (27 mg, 0.05 mmol, 24% yield) as an off-white fluffy/crystalline solid. $^1$H NMR (400 MHz, DMSO-D6) δ 8.26 (d, J=8.5 Hz, 2H), 7.81 (d, J=6.5 Hz, 2H), 7.66 (dd, J=8.2, 7.3 Hz, 2H), 5.05 (d, J=4.4 Hz, 2H), 4.91 (d, J=2.1 Hz, 2H), 4.87 (d, J=5.9 Hz, 2H), 4.82 (d, J=5.8 Hz, 2H), 4.57 (t, J=6.0 Hz, 2H), 3.97-3.88 (m, 2H), 3.83-3.61 (m, 6H), 3.54-3.37 (m, 4H). LC-MS: m/z=501.54 (M+H$^+$).

Preparation of Compounds 62-68

Compounds 62-64, 67 and 68 are prepared using Method A according to the procedure described in Compound 6 using the appropriately functionalized aryl bromide, phenol or boronic acid. Compounds 65 and 66 are prepared using Method A according to the procedure described in Compound 139 using the appropriately functionalized halogenated aryls.

| Compound | IUPAC mane | ¹H NMR | LCMS m/z (M + H⁺) |
|---|---|---|---|
| 62 | (2R,2'R,3S,3'S,4R,4'R,5S,5'S,6R,6'R)-6,6'-(2-fluoro-[1,1'-biphenyl]-4,4'-diyl)bis(2-(hydroxymethyl)tetrahydro-2H-pyran-3,4,5-triol) | (400 MHz, CD₃OD) δ 7.55 (s, 4H), 7.49 (dd, J = 11.5, 4.7 Hz, 1H), 7.34 (dd, J = 6.8, 6.3 Hz, 2H), 5.04-4.94 (m, 2H), 4.46 (d, J = 2.3 Hz, 1H), 4.36 (d, J = 2.7 Hz, 1H), 3.90-3.79 (m, 4H), 3.74 (t, J = 7.5 Hz, 2H), 3.60 (dd, J = 7.6, 2.7 Hz, 2H), 3.51 (dd, J = 10.6, 6.2 Hz, 2H) | 496.92 |
| 63 | (2R,2'R,3S,3'S,4R,4'R,5S,5'S,6R,6'R)-6,6'-(2-methyl-[1,1'-biphenyl]-4,4'-diyl)bis(2-(hydroxymethyl)tetrahydro-2H-pyran-3,4,5-triol) | (400 MHz, CD₃OD) δ 7.53 (d, J = 8.0 Hz, 2H), 7.38 (s, 1H), 7.31 (t, J = 8.9 Hz, 3H), 7.17 (d, J = 7.9 Hz, 1H), 5.00 (dd, J = 15.0, 2.7 Hz, 2H), 4.48 (d, J = 3.6 Hz, 2H), 3.84 (d, J = 4.1 Hz, 4H), 3.78-3.71 (m, 2H), 3.65-3.59 (m, 2H), 3.55-3.47 (m, 2H), 2.24 (s, 3H). | 493.35 |
| 64 | (2R,2'R,3S,3'S,4R,4'R,5S,5'S,6R,6'R)-6,6'-(3-methyl-[1,1'-biphenyl]-4,4'-diyl)bis(2-(hydroxymethyl)tetrahydro-2H-pyran-3,4,5-triol) | ¹H NMR (400 MHz, CD₃OD) δ 7.61 (d, J = 6.6 Hz, 2H), 7.55-7.47 (m, 3H), 7.43 (s, 2H), 5.13 (d, J = 6.1 Hz, 1H), 5.00 (s, 1H), 4.46 (d, J = 2.5 Hz, 1H), 4.30-4.24 (m, 1H), 4.02-3.93 (m, 2H), 3.83 (s, 3H), 3.78-3.71 (m, 2H), 3.60 (dd, J = 8.0, 2.7 Hz, 1H), 3.56-3.45 (m, 2H), 2.50 (s, 3H) | 493.63 |
| 65 | (2R,2'R,3S,3'S,4R,4'R,5S,5'S,6R,6'R)-6,6'-([1,1':4',1''-terphenyl]-4,4''-diyl)bis(2-(hydroxymethyl)tetrahydro-2H-pyran-3,4,5-triol) | (400 MHz, CD₃OD) δ 7.75-7.68 (m, 8H), 7.59 (d, J = 8.2 Hz, 4H), 5.05 (d, J = 3.4 Hz, 2H), 4.50 (t, J = 3.3 Hz, 2H), 3.86 (d, J = 4.7 Hz, 4H), 3.77 (t, J = 8.1 Hz, 2H), 3.64 (dd, J = 8.1, 3.1 Hz, 2H), 3.53 (dt, J = 8.3, 4.7 Hz, 2H), 3.52 (dt, J = 18.3, 6.9 Hz, 2H). | N/A |
| 66 | (2R,2'R,3S,3'S,4R,4'R,5S,5'S,6R,6'R)-6,6'-([1,1':3',1''-terphenyl]-4,4''-diyl)bis(2-(hydroxymethyl)tetrahydro-2H-pyran-3,4,5-triol) | (400 MHz, CD₃OD) δ 7.83 (t, J = 1.6 Hz, 1H), 7.70 (d, J = 8.4 Hz, 4H), 7.63-7.54 (m, 6H), 7.50 (dd, J = 8.4, 6.9 Hz, 1H), 5.03 (d, J = 3.5 Hz, 2H), 4.48 (t, J = 3.3 Hz, 2H), 3.84 (d, J = 4.7 Hz, 4H), 3.75 (t, J = 8.1 Hz, 2H), 3.61 (dd, J = 8.1, 3.1 Hz, 2H), 3.51 (dt, J = 8.2, 4.7 Hz, 2H). | N/A |
| 67 | (2R,2'R,3S,3'S,4R,4'R,5S,5'S,6R,6'R)-6,6'-(2-methoxy-[1,1'-biphenyl]-4,4'-diyl)bis(2-(hydroxymethyl)tetrahydro-2H-pyran-3,4,5-triol) | (400 MHz, CD₃OD) δ 7.48 (s, 4H), 7.30-7.21 (m, 2H), 7.06 (d, J = 7.8 Hz, 1H), 5.05-4.97 (m, 2H), 4.51-4.43 (m, 2H), 3.89-3.80 (m, 4H), 3.77-3.67 (m, 2H), 3.61 (dt, J = 8.1, 2.6 Hz, 2H), 3.57-3.46 (m, 2H), 3.33 (s, 3H). | N/A |
| 68 | (2R,2'R,3S,3'S,4R,4'R,5S,5'S,6R,6'R)-6,6'-(3,3'-dimethyl-[1,1'-biphenyl]-4,4'-diyl)bis(2-(hydroxymethyl)tetrahydro-2H-pyran-3,4,5-triol) | (400 MHz, CD₃OD) δ 7.50 (d, J = 8.6 Hz, 2H), 7.43 (d, J = 5.9 Hz, 4H), 5.13 (d, J = 6.3 Hz, 2H), 4.30-4.23 (m, 2H), 4.03-3.93 (m, 4H), 3.85-3.80 (m, 2H), 3.75 (dd, J = 11.9, 3.7 Hz, 2H), 3.57-3.50 (m, 2H), 2.50 (s, 6H). | N/A |

Preparation of Compound 69 (modified Method D)

(2R,3S,4R,5R,6R)-2-(hydroxymethyl)-6-[2-[4-[2-[(2R,3S,4R,5S,6R)-3,4,5-trihydroxy-6-(hydroxymethyl)tetrahydropyran-2-yl]ethynyl]phenyl]ethynyl]tetrahydropyran-3,4,5-triol

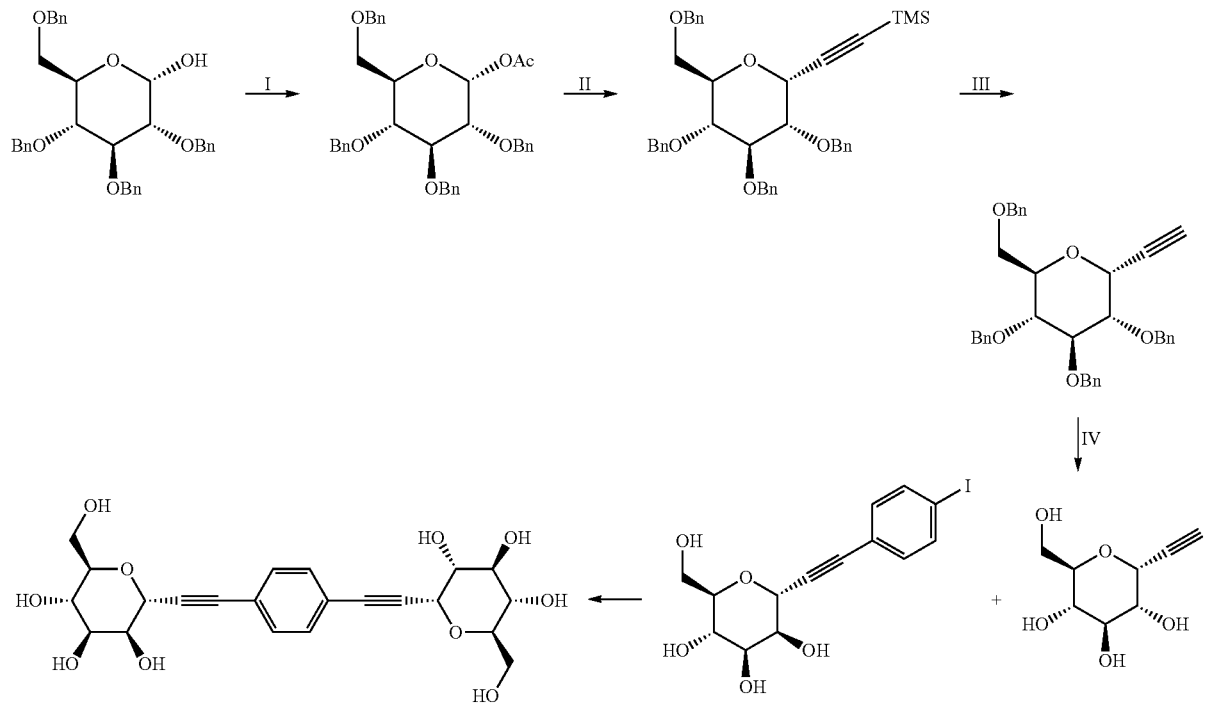

Step I: (2R,3R,4S 5R,6R)-3,4,5-tris(benzyloxy)-6-((benzyloxy)methyl)tetrahydro-2H-pyran-2-yl acetate To a solution of (2S,3R,4S,5R,6R)-3,4,5-tribenzyloxy-6-benzyloxymethyl)tetrahydropyran-2-ol (5,920 g, 10.95 mmol) in pyridine (21.90 mL) is added acetic anhydride (2.07 mL, 21.9 mmol) dropwise. The reaction is stirred for 5 h at RT then concentrated in vacuo. The crude mixture is diluted in $CH_2Cl_2$ and the resulting solution is washed with HCl 1N and brine. The organic phase is dried over $Na_2SO_4$, concentrated to give a mixture of a/13 of [(2R,3R,4S,5R,6R)-3,4,5-tribenzyloxy-6-(benzyloxymethyl)tetrahydropyran-2-yl] acetate as a colorless oil.

Step II: trimethyl-[2-[(2R,3S,4R,5R,6R)-3,4,5-tribenzyloxy-6-(benzyloxymethyl)tetrahydropyran-2-yl]ethynyl]silane A mixture of [(2R,3R,4S,5R,6R)-3,4,5-tribenzyloxy-6-(benzyloxymethyl)tetrahydropyran-2-yl] acetate (1000 mg, 1.716 mmol), trimethyl-(2-tributylstannylethynyl)silane (1.329 g, 1.260 mL, 3.432 mmol) and activated 4 Å molecular sieve (1 g) in $CH_2Cl_2$ (8.6 mL) is stirred for 15 min then TMSOTf (620 μL, 3.43 mmol) is added dropwise at RT. The reaction is stirred is stirred for 1.5 h and $Et_3N$ (1.00 mL, 7.18 mmol) and $CH_2Cl_2$ (8.6 mL) were added. The resulting mixture is filtered over celite using 10% EA/hex as eluent, the filtrate is concentrated and the residue is purified over silica gel on a Biotage™ SNAP cartridge to afford the title compound (269 mg, 25%) as yellow oil contaminated with tin byproducts.

Step III: (2R,3R,4R,5S,6R)-3,4,5-tribenzyloxy-2-(benzyloxymethyl)-6-ethynyl-tetrahydropyran To a solution of trimethyl-[2-[(2R,3S,4R,5R,6R)-3,4,5-tribenzyloxy-6-(benzyloxymethyl)tetrahydropyran-2-yl]ethynyl]silane (269 mg, 0.433 mmol) in MeOH (3.6 mL) and $CH_2Cl_2$ (722 μL) is added 1N NaOH (1.30 mL of 1 M, 1.30 mmol) for a stirring of 1 h at RT. The reaction is quenched with 1N HCl and concentrated to remove volatiles. EtOAc is added and the organic phase is separated, dried over $MgSO_4$. The residue is dissolved in 20% EtOAc/Hex and purified over silica gel pad using 20% EA/hex as eluent. The filtrate is concentrated to give the title compound (83.0 mg, 35%) as a colorless oil contaminated with tin byproducts from previous step.

Step IV: (2R,3R,4R,5S,6R)-2-ethynyl-6-(hydroxymethyl)tetrahydropyran-3,4,5-triol To a solution of (2R,3R,4R,5S,6R)-3,4,5-tribenzyloxy-2-(benzyloxymethyl)-6-ethynyl-tetrahydropyran (76.0 mg, 0.139 mmol) in EtSH (1.4 mL) is added $BF_3.OEt_2$ (479 μL, 3.88 mmol) and the reaction is stirred for 22 h at RT. The reaction is quenched with the addition of MeOH and basic resin to neutralize. The mixture is filtered and the filtrate is concentrated in vacuo affording the title compound (10 mg, 38%) as a white solid.

Preparation of (2R,3S,4R,5S,6R)-2-(hydroxymethyl)-6-[2-(4-iodophenyl)ethynyl]tetrahydropyran-3,4,5-triol

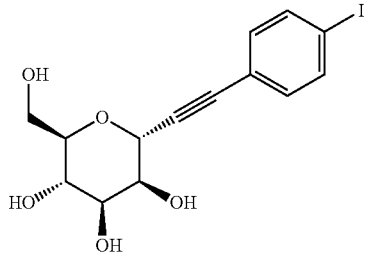 [SMILES: OC[C@H]1O[C@H](C#Cc2ccc(I)cc2)[C@@H](O)[C@@H](O)[C@@H]1O]

The title compound is prepared according to the procedure described for Compound 53 but using 1 eq. of 1,4-diiodobenzene in Step I: $^1$H NMR (400 MHz, cd3od) δ 7.66-7.59 (m, 2H), 7.15-7.08 (m, 2H), 4.75 (d, J=2.1 Hz, 1H), 3.91-3.88 (m, 1H), 3.82-3.74 (m, 2H), 3.72-3.59 (m, 2H), 3.53 (t, J=9.4 Hz, 1H). LC-MS: m/z=390.94 (M+H$^+$)

Step V: Compound 69

A solution of (2R,3R,4R,5S,6R)-2-ethynyl-6-(hydroxymethyl)tetrahydropyran-3,4,5-triol (10.0 mg, 0.053 mmol), (2R,3S,4R,5S,6R)-2-(hydroxymethyl)-6-[2-(4-iodophenyl)ethynyl]tetrahydropyran-3,4,5-triol (20.7 mg, 0.0531 mmol), PdCl$_2$(dppf). CH$_2$Cl$_2$ (8.7 mg, 0.011 mmol), CuI (2.3 mg, 0.012 mmol) in DMF (511 μL) is degassed (N$_2$) and to this is added triethylamine (44 μL, 0.32 mmol). The mixture is stirred in a sealed tube under nitrogen atmosphere at RT for 18 h. The reaction is filtered over 0.45 μm filter and purified by reverse phase HPLC to afford the title compound (5 mg, 20%) as a white solid.
$^1$H NMR (400 MHz, CD$_3$OD) δ 7.45-7.37 (m, 4H), 4.87-4.83 (m, 2H), 3.95 (s, 1H), 3.90-3.71 (m, 5H), 3.71-3.56 (m, 4H), 3.56-3.49 (m, 1H), 3.28-3.22 (m, 1H). LC-MS: m/z=451.46 (M+H$^+$)

Preparation of Compounds 70 to 76

Compound 70 is prepared according to the procedure described for Compound 53.
Compounds 71-76 are prepared according to the procedure described for Compound 59.

| Compound | IUPAC name | $^1$H-NMR | LCMS m/z (M + H)$^+$ |
|---|---|---|---|
| 70 | 2-[2,5-bis[2-[(2R,3S,4R,5S,6R)-3,4,5-trihydroxy-6-(hydroxymethyl)tetrahydropyran-2-yl]ethynyl]phenyl]-2-methyl-propanenitrile | (400 MHz, CD3OD) δ 7.58 (d, J = 8.0 Hz, 1H), 7.56 (d, J = 1.4 Hz, 1H), 7.45 (dd, J = 7.9, 1.5 Hz, 1H), 4.96 (d, J = 2.1 Hz, 1H), 4.09 (dd, J = 3.3, 2.1 Hz, 1H), 4.00 (dd, J = 3.2, 2.2 Hz, 1H), 3.97-3.57 (m, 11H), 1.87 (s, 3H), 1.86 (s, 3H). | 518.38 |
| 71 | (2R,3S,4R,5S,6R)-2-(hydroxymethyl)-6-[2-[3-methoxy-4-[2-[(2R,3S,4R,5S,6R)-3,4,5-trihydroxy-6-(hydroxymethyl)tetrahydropyran-2-yl]ethynyl]phenyl]ethynyl]tetrahydropyran-3,4,5-triol | (400 MHz, CD3OD) δ 7.35 (d, J = 7.8 Hz, 1H), 7.07 (d, J = 1.1 Hz, 1H), 7.03 (dd, J = 7.8, 1.4 Hz, 1H), 4.87 (d, J = 2.1 Hz, 1H), 4.86 (d, J = 1.6 Hz, 1H), 4.03-3.96 (m, 3H), 3.94-3.70 (m, 10H), 3.69-3.58 (m, 2H). | 481.41 |
| 72 | (2R,3S,4R,5S,6R)-2-[2-[3-butyl-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.41 (d, J = 8.0 Hz, 1H), 7.34 (d, J = 1.4 Hz, 1H), 7.26 (dd, J = 8.0, 1.6 Hz, 1H), 4.92 (d, J = 2.0 Hz, 1H), 4.87 (d, J = 2.1 Hz, 1H), 4.05-3.95 (m, 2H), 3.93 (dd, J = 3.3, 1.5 Hz, 1H), 3.91 (dd, J = 3.3, 1.5 Hz, 1H), 3.89 (dd, J = 5.4, 1.9 Hz, 1H), 3.86 (dd, J = 4.9, 1.8 Hz, 1H), 3.84-3.71 (m, 4H), 3.70-3.59 (m, 2H), 2.80-2.73 (m, 2H), 1.66-1.56 (m, 2H), 1.40 (h, J = 7.3 Hz, 2H), 0.96 (t, J = 7.3 Hz, 3H). | 507.49 |
| 73 | (2R,3S,4R,5S,6R)-2-[2-[3,5-diethyl-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.20 (s, 2H), 4.98 (d, J = 2.0 Hz, 1H), 4.90-4.83 (m, 1H), 4.04 (dd, J = 3.2, 2.1 Hz, 1H), 4.00 (dd, J = 3.2, 2.1 Hz, 1H), 3.94 (dd, J = 3.3, 1.6 Hz, 1H), 3.92 (dd, J = 3.3, 1.7 Hz, 1H), 3.89 (dd, J = 3.4, 2.2 Hz, 1H), 3.86 (dd, J = 3.3, 2.2 Hz, 1H), 3.84-3.78 (m, 2H), 3.76 (dd, J = 5.7, 2.2 Hz, 1H), 3.73 (dd, J = 5.7, 2.3 Hz, 1H), 3.70-3.59 (m, 2H), 2.80 (q, J = 7.6 Hz, 4H), 1.24 (t, J = 7.5 Hz, 6H). | 507.49 |
| 74 | (2R,3S,4R,5S,6R)-2-(hydroxymethyl)-6-[2-[3-(2-methoxyethyl)-4-[2-[(2R,3S,4R,5S,6R)-3,4,5-trihydroxy-6- | (400 MHz, CD3OD) δ 7.46-7.38 (m, 2H), 7.30 (dd, J = 8.0, 1.6 Hz, 1H), 4.92 (d, J = 2.0 Hz, 1H), 4.87 (d, J = 2.2 Hz, 1H), 4.06-3.98 (m, 2H), 3.96-3.84 (m, 4H), 3.84-3.70 (m, 4H), | 509.49 |

-continued

| Compound | IUPAC name | ¹H-NMR | LCMS m/z (M + H)⁺ |
|---|---|---|---|
|  | (hydroxymethyl)tetrahydropyran-2-yl]ethynyl]phenyl]ethynyl]tetrahydropyran-3,4,5-triol | 3.69-3.57 (m, 4H), 3.35 (s, 3H), 3.03 (t, J = 6.8 Hz, 2H). |  |
| 75 | (2R,3S,4R,5S,6R)-2-[2-[2,3-dichloro-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.49 (s, 2H), 4.93 (d, J = 1.9 Hz, 2H), 4.07-4.01 (m, 2H), 3.96 (dd, J = 9.3, 3.2 Hz, 2H), 3.92-3.79 (m, 4H), 3.74 (dd, J = 11.5, 5.6 Hz, 2H), 3.66 (t, J = 9.5 Hz, 2H). | 520.34 |
| 76 | (2R,3S,4R,5S,6R)-2-[2-[2,5-diisopropyl-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD + dmso) δ 7.36 (s, 2H), 4.94 (d, J = 2.0 Hz, 2H), 4.03 (dd, J = 3.1, 2.2 Hz, 2H), 3.95-3.84 (m, 4H), 3.84-3.70 (m, 4H), 3.65 (t, J = 9.4 Hz, 2H), 3.43-3.26 (m, 2H), 1.27 (dd, J = 6.9, 1.9 Hz, 12H). | 535.53 |

Preparation of Compound 77 (Method D)

(2R,3S,4R,5S,6R)-2-(hydroxymethyl)-6-[2-[3-phenyl-4-[2-[(2R,3S,4R,5S,6R)-3,4,5-trihydroxy-6-(hydroxymethyl)tetrahydropyran-2-yl]ethynyl]phenyl]ethynyl]tetrahydropyran-3,4,5-triol

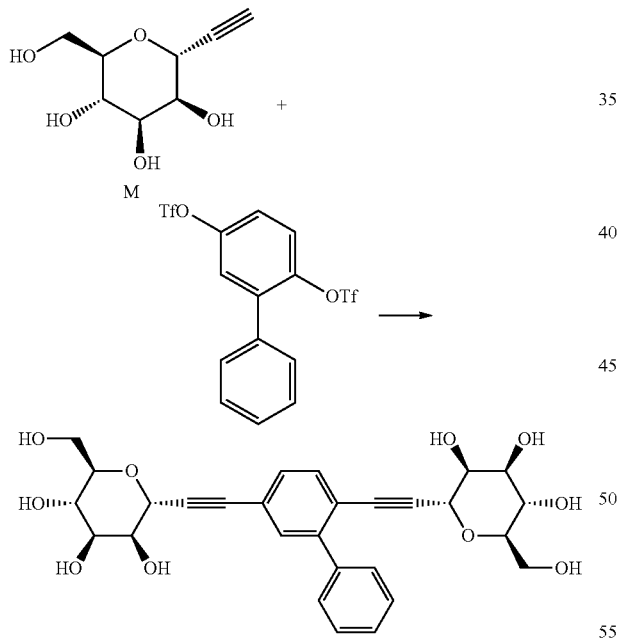

[3-phenyl-4-(trifluoromethylsulfonyloxy)phenyl]trifluoromethanesulfonate (prepared from triflation of 2-phenyl hydroquinone) (54 mg, 0.12 mmol), CuI (9.0 mg, 0.048 mmol) and Pd(dppf)Cl₂—CH₂Cl₂ (9.0 mg, 0.012 mmol) are loaded in a reaction tube. A degassed solution of Intermediate M (0.5 mL of 0.53 M, 0.27 mmol) in DMF is added, followed by DIEA (105 µL, 0.60 mmol). The tube is sealed and shaken at 90° C. overnight using a reaction block. The reaction mixture is filtered, rinsing with DMF. The resulting filtrate is purified by reverse phase HPLC and the fractions containing the desired material are combined and freeze-dried to provide the title compound (28 mg, 44% yield) as a white fluffy solid.

¹H NMR (400 MHz, CD₃OD) δ 7.56 (d, J=8.0 Hz, 1H), 7.53-7.35 (m, 7H), 4.88 (d, J=2.1 Hz, 1H), 4.74 (d, J=2.0 Hz, 1H), 4.01 (dd, J=3.2, 2.1 Hz, 1H), 3.93 (dd, J=9.4, 3.3 Hz, 1H), 3.88 (dd, J=11.5, 2.1 Hz, 1H), 3.84-3.50 (m, 9H). ESI-MS m/z calc. 526.18, found 527.44 (M+1)⁺

Preparation of Compounds 78 to 102

Compounds 78-84 and 86-89 are prepared according to the procedure described for Compound 59. Compound 85 is prepared according to the procedure described for Compound 171. Compounds 100-102 are prepared according to the procedure described for Compound 103.

| Compound | IUPAC name | ¹H-NMR | LCMS m/z (M + H)⁺ |
|---|---|---|---|
| 78 | (2R,3S,4R,5S,6R)-2-[2-[2,3-difluoro-4-[2-[(2R,3S,4R,5S,6R)-3,4,5-trihydroxy-6-(hydroxymethyl)tetrahydropyran-2- | (400 MHz, CD3OD) δ 7.38-7.24 (m, 2H), 4.92 (d, J = 2.0 Hz, 2H), 4.09-3.98 (m, 2H), 3.96-3.83 (m, 4H), 3.82-3.71 | 487.43 |

| Compound | IUPAC name | $^1$H-NMR | LCMS m/z (M + H)$^+$ |
|---|---|---|---|
| | yl]ethynyl]phenyl]ethynyl]-6-(hydroxymethyl)tetrahydropyran-3,4,5-triol | (m, 4H), 3.65 (t, J = 9.4 Hz, 2H). | |
| 79 | (2R,3S,4R,5S,6R)-2-(hydroxymethyl)-6-[2-[3-(methoxymethyl)-4-[2-[(2R,3S,4R,5S,6R)-3,4,5-trihydroxy-6-(hydroxymethyl)tetrahydropyran-2-yl]ethynyl]phenyl]ethynyl]tetrahydropyran-3,4,5-triol | (400 MHz, CD3OD) δ 7.54 (d, J = 0.9 Hz, 1H), 7.46 (d, J = 7.9 Hz, 1H), 7.38 (dd, J = 8.0, 1.6 Hz, 1H), 4.92 (d, J = 2.0 Hz, 1H), 4.88 (d, J = 2.0 Hz, 1H), 4.58 (s, 2H), 4.05-3.99 (m, 2H), 3.97-3.85 (m, 4H), 3.84-3.70 (m, 4H), 3.68-3.60 (m, 2H), 3.45 (s, 3H). | 495.51 |
| 80 | (2R,3S,4R,5S,6R)-2-[2-[3-benzyloxy-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.52-7.45 (m, 2H), 7.44-7.36 (m, 3H), 7.35-7.25 (m, 1H), 7.14 (d, J = 1.3 Hz, 1H), 7.04 (dd, J = 7.9, 1.4 Hz, 1H), 5.18 (s, 2H), 4.88 (d, J = 2.0 Hz, 1H), 4.87-4.83 (m, 1H), 4.03-3.99 (m, 2H), 3.97 (dd, J = 9.3, 3.3 Hz, 1H), 3.93-3.86 (m, 2H), 3.85-3.59 (m, 7H). | 557.51 |
| 81 | (2R,3S,4R,5S,6R)-2-[2-[2,5-diphenyl-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD + dmso) δ 7.62 (s, 2H), 7.62-7.57 (m, 4H), 7.54-7.47 (m, 4H), 7.46-7.39 (m, 2H), 4.76 (d, J = 2.1 Hz, 2H), 3.84 (dd, J = 3.2, 2.1 Hz, 2H), 3.77 (dd, J = 11.7, 1.4 Hz, 2H), 3.73-3.63 (m, 4H), 3.62-3.54 (m, 4H). | 603.49 |
| 82 | (2R,3S,4R,5S,6R)-2-[2-[2,5-dihexyl-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.26 (s, 2H), 4.89 (d, J = 2.1 Hz, 2H), 4.00 (dd, J = 3.2, 2.1 Hz, 2H), 3.91 (dd, J = 9.3, 3.3 Hz, 2H), 3.85 (dd, J = 11.2, 1.9 Hz, 2H), 3.82-3.70 (m, 4H), 3.65 (t, J = 9.4 Hz, 2H), 2.76-2.58 (m, 4H), 1.67-1.50 (m, 4H), 1.45-1.22 (m, 12H), 0.98-0.81 (m, 6H). | 619.63 |
| 83 | (2R,3S,4R,5S,6R)-2-(hydroxymethyl)-6-[2-[3-isopropoxy-4-[2-[(2R,3S,4R,5S,6R)-3,4,5-trihydroxy-6-(hydroxymethyl)tetrahydropyran-2-yl]ethynyl]phenyl]ethynyl]tetrahydropyran-3,4,5-triol | (400 MHz, CD3OD) δ 7.34 (d, J = 7.9 Hz, 1H), 7.06 (d, J = 1.2 Hz, 1H), 7.00 (dd, J = 7.9, 1.4 Hz, 1H), 4.88-4.84 (m, 2H), 4.67 (hept, J = 6.2 Hz, 1H), 4.09-3.96 (m, 3H), 3.95-3.83 (m, 4H), 3.77 (ddt, J = 17.4, 11.6, 5.8 Hz, 3H), 3.65 (dt, J = 19.0, 7.5 Hz, 2H), 1.36 (d, J = 6.0 Hz, 6H). | 509.45 |
| 84 | (2R,3S,4R,5S,6R)-2-(hydroxymethyl)-6-[2-[2,3,5,6-tetramethyl-4-[2-[(2R,3S,4R,5S,6R)-3,4,5-trihydroxy-6-(hydroxymethyl)tetrahydropyran-2-yl]ethynyl]phenyl]ethynyl]tetrahydropyran-3,4,5-triol | (400 MHz, CD3OD) δ 4.99 (d, J = 2.0 Hz, 2H), 4.05 (dd, J = 3.1, 2.2 Hz, 2H), 3.95 (dd, J = 9.3, 3.3 Hz, 2H), 3.91-3.79 (m, 4H), 3.74 (dd, J = 11.5, 5.6 Hz, 2H), 3.66 (t, J = 9.4 Hz, 2H), 2.42 (s, 12H). | 507.41 |
| 85 | (2R,3S,4R,5S,6R)-2-[2-[2,5-bis(hydroxymethyl)-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.59 (s, 2H), 4.93 (d, J = 2.1 Hz, 2H), 4.74 (s, 4H), 4.03 (dd, J = 3.2, 2.1 Hz, 2H), 3.93 (dd, J = 9.3, 3.3 Hz, 2H), 3.88 (dd, J = 11.5, 2.1 Hz, 2H), 3.81 (ddd, J = 9.5, 5.8, 2.0 Hz, 2H), 3.74 (dd, J = 11.5, 5.8 Hz, 2H), 3.65 (t, J = 9.5 Hz, 2H). | 511.47 |
| 86 | (2R,3S,4R,5S,6R)-2-[2-[2,5-diethyl-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.31 (s, 2H), 4.92 (d, J = 2.0 Hz, 2H), 4.02 (dd, J = 3.2, 2.1 Hz, 2H), 3.93 (dd, J = 9.3, 3.3 Hz, 2H), 3.88 (dd, J = 11.5, 2.1 Hz, 2H), 3.84-3.78 (m, 2H), 3.74 (dd, J = 11.5, 5.7 Hz, 2H), 3.65 (t, J = 9.5 Hz, 2H), 2.75 (q, J = 7.6 Hz, 4H), 1.23 (t, J = 7.6 Hz, 6H). | 507.51 |

| Compound | IUPAC name | ¹H-NMR | LCMS m/z (M + H)⁺ |
|---|---|---|---|
| 87 | (2R,3S,4R,5S,6R)-2-(hydroxymethyl)-6-[2-[3-(trifluoromethoxy)-4-[2-[(2R,3S,4R,5S,6R)-3,4,5-trihydroxy-6-(hydroxymethyl)tetrahydropyran-2-yl]ethynyl]phenyl]ethynyl]tetrahydropyran-3,4,5-triol | (400 MHz, CD3OD) δ 7.59 (d, J = 8.0 Hz, 1H), 7.50-7.42 (m, 2H), 4.92 (d, J = 2.0 Hz, 1H), 4.89 (d, J = 2.1 Hz, 1H), 4.04-3.98 (m, 2H), 3.93-3.82 (m, 4H), 3.81-3.59 (m, 6H). | 535.43 |
| 88 | (2R,3S,4R,5S,6R)-2-[2-[2,5-difluoro-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.36 (t, J = 7.4 Hz, 2H), 4.91 (d, J = 2.1 Hz, 2H), 4.01 (dd, J = 3.1, 2.2 Hz, 2H), 3.93-3.83 (m, 4H), 3.81-3.70 (m, 4H), 3.64 (t, J = 9.4 Hz, 2H). | 487.38 |
| 89 | (2R,3S,4R,5S,6R)-2-[2-[2,5-bis(methoxymethyl)-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD + dmso) δ 7.56 (s, 2H), 4.93 (d, J = 1.9 Hz, 2H), 4.58 (s, 4H), 4.06-4.00 (m, 2H), 3.96-3.85 (m, 4H), 3.85-3.69 (m, 4H), 3.64 (t, J = 9.6 Hz, 2H), 3.45 (s, 6H). | 539.53 |
| 90 | (2R,3S,4R,5S,6R)-2-[2-[2-chloro-5-methyl-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.52 (s, 1H), 7.44 (s, 1H), 4.92 (d, J = 2.1 Hz, 1H), 4.91 (d, J = 2.0 Hz, 1H), 4.08-4.01 (m, 2H), 4.00-3.70 (m, 8H), 3.69-3.59 (m, 2H), 2.40 (s, 3H). | 499.43 |
| 91 | (2R,3S,4R,5S,6R)-2-(hydroxymethyl)-6-[2-[3-(trifluoromethyl)-4-[2-[(2R,3S,4R,5S,6R)-3,4,5-trihydroxy-6-(hydroxymethyl)tetrahydropyran-2-yl]ethynyl]phenyl]ethynyl]tetrahydropyran-3,4,5-triol | (400 MHz, CD3OD) δ 7.80 (s, 1H), 7.74-7.63 (m, 2H), 4.92 (d, J = 1.7 Hz, 1H), 4.90 (d, J = 2.0 Hz, 1H), 4.05-4.00 (m, 2H), 3.96-3.58 (m, 10H). | 519.41 |
| 92 | (2R,3S,4R,5S,6R)-2-[2-[3-(difluoromethoxy)-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.52 (d, J = 8.0 Hz, 1H), 7.33 (dd, J = 8.0, 1.5 Hz, 1H), 7.31 (s, 1H), 6.92 (t, J = 73.1 Hz, 1H), 4.90 (d, J = 1.9 Hz, 1H), 4.88 (d, J = 2.0 Hz, 1H), 4.12-3.98 (m, 2H), 3.96-3.70 (m, 8H), 3.65 (dd, J = 19.5, 9.6 Hz, 2H). | 517.4 |
| 93 | (2R,3S,4R,5S,6R)-2-[2-[3,5-difluoro-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.23-7.15 (m, 2H), 4.94 (d, J = 2.0 Hz, 1H), 4.88 (d, J = 2.1 Hz, 1H), 4.08-3.97 (m, 2H), 3.95-3.83 (m, 4H), 3.82-3.57 (m, 6H). | 487.48 |
| 94 | (2R,3S,4R,5S,6R)-2-[2-[3-(2-hydroxyethyl)-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.44-7.37 (m, 2H), 7.28 (d, J = 7.8 Hz, 1H), 4.90 (s, 2H), 3.99 (d, J = 9.0 Hz, 2H), 3.92-3.82 (m, 4H), 3.82-3.68 (m, 6H), 3.61 (t, J = 9.4 Hz, 2H), 2.98 (t, J = 6.9 Hz, 2H). | 495.33 |
| 95 | (2R,3S,4R,5S,6R)-2-(hydroxymethyl)-6-[2-[3-(hydroxymethyl)-4-[2-[(2R,3S,4R,5S,6R)-3,4,5-trihydroxy-6-(hydroxymethyl)tetrahydropyran-2-yl]ethynyl]phenyl]ethynyl]tetrahydropyran-3,4,5-triol | (400 MHz, CD3OD) δ 7.62 (d, J = 0.8 Hz, 1H), 7.44 (d, J = 7.9 Hz, 1H), 7.35 (dd, J = 7.9, 1.7 Hz, 1H), 4.92 (d, J = 2.1 Hz, 1H), 4.88 (d, J = 2.1 Hz, 1H), 4.74 (s, 2H), 4.04-3.99 (m, 2H), 3.92 (ddd, J = 9.3, 3.3, 1.3 Hz, 2H), 3.88 (dt, J = 11.4, 1.7 Hz, 2H), 3.84-3.77 (m, 2H), 3.77-3.70 (m, 2H), 3.68-3.61 (m, 2H). | 481.41 |

-continued

| Compound | IUPAC name | ¹H-NMR | LCMS m/z (M + H)⁺ |
|---|---|---|---|
| 96 | (2R,3S,4R,5S,6R)-2-[2-[2,5-dimethoxy-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.01 (s, 2H), 4.98-4.74 (m, 2H), 4.08-3.96 (m, 4H), 3.91-3.79 (m, 10H), 3.74 (dd, J = 11.9, 5.9 Hz, 2H), 3.69-3.59 (m, 2H). | 511.43 |
| 97 | (2R,3S,4R,5S,6R)-2-[2-[2,5-dimethyl-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.30 (s, 2H), 4.91 (d, J = 2.0 Hz, 2H), 4.02 (dd, J = 3.0, 2.2 Hz, 2H), 3.94 (dd, J = 9.3, 3.2 Hz, 2H), 3.88 (dd, J = 11.5, 2.0 Hz, 2H), 3.82 (ddd, J = 9.4, 5.7, 2.0 Hz, 2H), 3.74 (dd, J = 11.5, 5.7 Hz, 2H), 3.64 (t, J = 9.5 Hz, 2H), 2.37 (s, 6H). | 479.45 |
| 98 | (2R,3S,4R,5S,6R)-2-[2-[3-ethyl-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.41 (d, J = 8.0 Hz, 1H), 7.36 (d, J = 1.3 Hz, 1H), 7.27 (dd, J = 7.9, 1.6 Hz, 1H), 4.92 (d, J = 2.0 Hz, 1H), 4.87 (d, J = 2.2 Hz, 1H), 4.07-3.99 (m, 2H), 3.92 (dd, J = 9.3, 3.3 Hz, 2H), 3.90-3.85 (m, 2H), 3.84-3.77 (m, 2H), 3.77-3.70 (m, 2H), 3.69-3.58 (m, 2H), 2.80 (q, J = 7.6 Hz, 2H), 1.25 (t, J = 7.6 Hz, 3H). | 479.49 |
| 99 | (2R,3S,4R,5S,6R)-2-[2-[2,3-dimethyl-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.26 (s, 2H), 4.92 (d, J = 2.1 Hz, 2H), 4.02 (dd, J = 3.2, 2.1 Hz, 2H), 3.94 (dd, J = 9.3, 3.3 Hz, 2H), 3.88 (dd, J = 11.5, 2.1 Hz, 2H), 3.81 (ddd, J = 9.5, 5.7, 2.0 Hz, 2H), 3.74 (dd, J = 11.5, 5.7 Hz, 2H), 3.65 (t, J = 9.5 Hz, 2H), 2.43 (s, 6H). | 479.4 |
| 100 | (2R,3S,4R,5S,6R)-2-[2-[3,5-dimethyl-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.19 (s, 2H), 4.98 (d, J = 2.0 Hz, 1H), 4.88-4.83 (m, 1H), 4.04 (dd, J = 3.2, 2.1 Hz, 1H), 3.99 (dd, J = 3.2, 2.1 Hz, 1H), 3.98-3.85 (m, 4H), 3.84-3.77 (m, 2H), 3.77-3.70 (m, 2H), 3.67 (d, J = 9.3 Hz, 1H), 3.62 (d, J = 9.4 Hz, 1H), 2.41 (s, 6H). | 479.4 |
| 101 | 2,5-bis[2-[(2R,3S,4R,5S,6R)-3,4,5-trihydroxy-6-(hydroxymethyl)tetrahydropyran-2-yl]ethynyl]benzonitrile | (400 MHz, CD3OD) δ 7.91 (d, J = 1.4 Hz, 1H), 7.74 (dd, J = 8.2, 1.7 Hz, 1H), 7.66 (d, J = 8.2 Hz, 1H), 4.97 (d, J = 2.1 Hz, 1H), 4.89 (d, J = 2.1 Hz, 1H), 4.07 (dd, J = 3.3, 2.1 Hz, 1H), 4.01 (dd, J = 3.2, 2.2 Hz, 1H), 3.97 (dd, J = 9.4, 3.3 Hz, 1H), 3.92-3.59 (m, 9H). | 476.32 |
| 102 | (2R,3S,4R,5S,6R)-2-[2-[3-chloro-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.59 (d, J = 1.5 Hz, 1H), 7.53 (d, J = 8.0 Hz, 1H), 7.39 (dd, J = 8.0, 1.6 Hz, 1H), 4.92 (d, J = 2.1 Hz, 1H), 4.88 (d, J = 2.1 Hz, 1H), 4.03 (dd, J = 3.2, 2.1 Hz, 1H), 4.02-3.94 (m, 2H), 3.93-3.70 (m, 7H), 3.69-3.59 (m, 2H). | 485.33 |

Preparation of Compound 103 (Method C)

(2R,3S,4R,5S,6R)-2-(hydroxymethyl)-6-[2-[3-isopropyl-4-[2-[(2R,3S,4R,5S,6R)-3,4,5-trihydroxy-6-(hydroxymethyl)tetrahydropyran-2-yl]ethynyl]phenyl]ethynyl]tetrahydropyran-3,4,5-triol

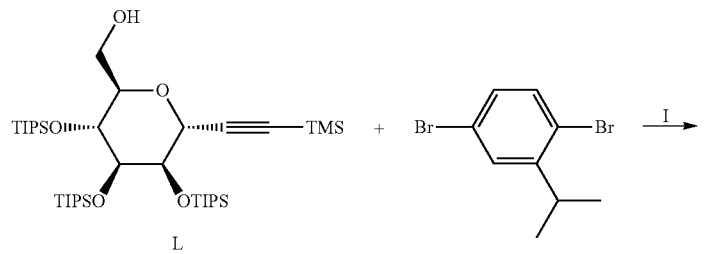

L

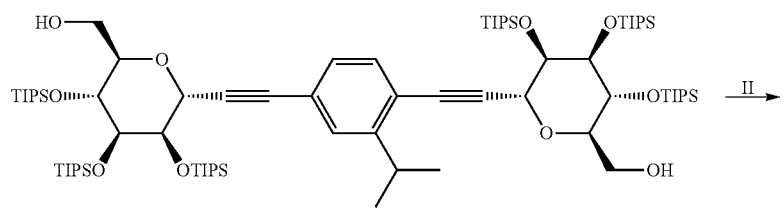

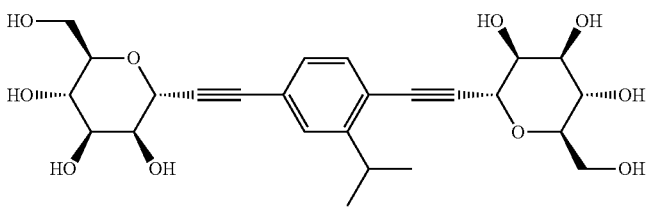

Step I: [(2R,3R,4R,5R,6R)-6-[2-[4-[2-[(2R,3R,4R,5R,6R)-6-(hydroxymethyl)-3,4,5-tris(triisopropylsilyloxy)tetrahydropyran-2-yl]ethynyl]-3-isopropyl-phenyl]ethynyl]-3,4,5-tris(triisopropylsilyloxy)tetrahydropyran-2-yl]

A glass vial is loaded with 1,4-dibromo-2-isopropylbenzene (60 mg, 0.22 mmol), iodocopper (12 mg, 0.061 mmol) and Pd(dppf)Cl$_2$—CH$_2$Cl$_2$ (20 mg, 0.028 mmol), capped and degassed (vacuum-nitrogen flush, 3 times). A degassed DMF solution of Intermediate L (1.6 mL of 0.26M, 0.41 mmol), and degassed DMF (0.9 mL) are added, followed by a degassed DBU and H$_2$O mixture (8:3 v/v, 250 µL). The vial is transferred to a preheated oil bath (90° C.) and stirred overnight. The reaction mixture is cooled to RT and partitioned between saturated NH$_4$Cl solution (5 mL) and EtOAc (10 mL). The layers are separated and the aqueous layer is back extracted with EtOAc (2×2 mL). The combined organic extracts are dried over Na$_2$SO$_4$, filtered and concentrated. The residue is purified by flash chromatography on a Biotage™ SNAP 25 g silica cartridge, using a gradient of EtOAc in Hex, 0-20% as eluent to provide the title compound (90 mg, 29% yield) as a yellowish gum.

Step II: Compound 103

A solution of [(2R,3R,4R,5R,6R)-6-[2-[4-[2-[(2R,3R,4R,5R,6R)-6-(hydroxymethyl)-3,4,5-tris(triisopropylsilyloxy)tetrahydropyran-2-yl]ethynyl]-3-isopropyl-phenyl]ethynyl]-3,4,5-tris(triisopropylsilyloxy)tetrahydropyran-2-yl]methanol (90 mg, 0.066 mmol) from Step I in a mixture of THF (810 µL), TFA (405 µL) and H$_2$O (405 µL) is heated to reflux (80° C.) for 48 h and concentrated. The residue is purified by reverse-phase flash chromatography on a Biotage™ SNAP C18-12 g cartridge, using a gradient of MeCN in H$_2$O, 0-70% as eluent. The fractions are concentrated and freeze-dried, providing the title compound (13 mg, 40% yield) as a fluffy white solid. $^1$H NMR (400 MHz, CD$_3$OD) δ 7.41 (d, J=8.0 Hz, 1H), 7.39 (d, J=1.5 Hz, 1H), 7.26 (dd, J=7.9, 1.6 Hz, 1H), 4.92 (d, J=2.1 Hz, 1H), 4.88 (d, J=2.1 Hz, 1H), 4.04-3.98 (m, 2H), 3.95-3.88 (m, 3H), 3.86 (dd, J=3.3, 2.1 Hz, 1H), 3.84-3.71 (m, 4H), 3.69-3.58 (m, 2H), 3.41 (p, J=6.9 Hz, 1H), 1.27 (d, J=6.9 Hz, 6H). ESI-MS m/z calc. 492.19955, found (M+1)$^+$ 493.36

Preparation of Compounds 104 to 109

Compounds 104 and 105 are prepared according to the procedure described for Compound 103.

Compounds 106, 108 and 109 are prepared according to the procedure described for Compound 59. Compound 107 is prepared according to the procedure described for Compound 110.

| Compound | IUPAC name | ¹H-NMR | LCMS m/z (M + H)⁺ |
|---|---|---|---|
| 104 | (2R,3S,4R,5S,6R)-2-(hydroxymethyl)-6-[2-[3-methyl-4-[2-[(2R,3S,4R,5S,6R)-3,4,5-trihydroxy-6-(hydroxymethyl)tetrahydropyran-2-yl]ethynyl]phenyl]ethynyl]tetrahydropyran-3,4,5-triol | (400 MHz, CD3OD) δ 7.40 (d, J = 8.0 Hz, 1H), 7.37 (s, 1H), 7.26 (dd, J = 7.9, 1.2 Hz, 1H), 4.92 (d, J = 2.1 Hz, 1H), 4.89-4.83 (m, 1H), 4.02 (dd, J = 3.2, 2.1 Hz, 1H), 4.00 (dd, J = 3.2, 2.1 Hz, 1H), 3.95 (d, J = 3.3 Hz, 1H), 3.92 (dd, J = 3.3, 1.4 Hz, 1H), 3.91-3.88 (m, 1H), 3.87-3.85 (m, 1H), 3.84-3.77 (m, 2H), 3.75 (d, J = 5.5 Hz, 1H), 3.72 (d, J = 5.7 Hz, 1H), 3.68-3.60 (m, 2H), 2.42 (s, 3H). | 465.35 |
| 105 | (2R,3S,4R,5S,6R)-2-[2-[3-fluoro-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol | (400 MHz, CD3OD) δ 7.52-7.42 (m, 1H), 7.28 (dd, J = 5.9, 1.1 Hz, 1H), 7.26 (dd, J = 4.1, 1.5 Hz, 1H), 4.89 (d, J = 2.1 Hz, 1H), 4.85 (d, J = 2.1 Hz, 1H), 4.05-3.95 (m, 2H), 3.93-3.82 (m, 4H), 3.81-3.67 (m, 4H), 3.66-3.55 (m, 2H). | 469.41 |
| 106 | (2R,3S,4R,5S,6R)-2-(hydroxymethyl)-6-[2-[8-[2-[(2R,3S,4R,5S,6R)-3,4,5-trihydroxy-6-(hydroxymethyl)tetrahydropyran-2-yl]ethynyl]dibenzofuran-2-yl]ethynyl]tetrahydropyran-3,4,5-triol | (400 MHz, CD3OD) δ 8.19 (s, 2H), 7.60 (s, 4H), 4.79 (s, 2H), 4.03 (d, J = 2.1 Hz, 2H), 3.98 (dd, J = 9.3, 3.2 Hz, 2H), 3.91-3.82 (m, 4H), 3.78-3.71 (m, 2H), 3.68-3.61 (m, 2H). | 541.36 |
| 107 | (2R,3S,4R,5S,6R)-2-[2-[9-ethyl-6-[2-[(2R,3S,4R,5S,6R)-3,4,5-trihydroxy-6-(hydroxymethyl)tetrahydropyran-2-yl]ethynyl]carbazol-3-yl]ethynyl]-6-(hydroxymethyl)tetrahydropyran-3,4,5-triol | (400 MHz, CD3OD) δ 8.23 (s, 2H), 7.53 (dd, J = 20.0, 8.1 Hz, 4H), 4.79 (s, 2H), 4.43 (d, J = 8.1 Hz, 2H), 4.06-3.99 (m, 4H), 3.88 (d, J = 9.4 Hz, 4H), 3.75 (dd, J = 11.7, 5.8 Hz, 2H), 3.70-3.61 (m, 2H), 1.39 (t, J = 7.2 Hz, 3H). | 568.4 |
| 108 | (2R,3S,4R,5S,6R)-2-(hydroxymethyl)-6-[2-[6-[2-[(2R,3S,4R,5S,6R)-3,4,5-trihydroxy-6-(hydroxymethyl)tetrahydropyran-2-yl]ethynyl]-9H-carbazol-3-yl]ethynyl]tetrahydropyran-3,4,5-triol | (400 MHz, CD3OD) δ 7.50-7.44 (m, 3H), 7.41-7.35 (m, 3H), 4.85 (s, 2H), 3.98 (s, 2H), 3.88 (dd, J = 19.1, 9.3 Hz, 4H), 3.81-3.76 (m, 2H), 3.71 (dd, J = 12.3, 5.0 Hz, 2H), 3.66-3.57 (m, 2H). | 540.38 |
| 109 | (2R,3S,4R,5S,6R)-2-(hydroxymethyl)-6-[2-[7-[2-[(2R,3S,4R,5S,6R)-3,4,5-trihydroxy-6-(hydroxymethyl)tetrahydropyran-2-yl]ethynyl]dibenzothiophen-3-yl]ethynyl]tetrahydropyran-3,4,5-triol | (400 MHz, CD3OD) δ 8.39 (s, 2H), 7.90 (d, J = 8.3 Hz, 2H), 7.57 (d, J = 8.3 Hz, 2H), 4.79 (s, 2H), 4.04 (dd, J = 3.0, 2.2 Hz, 2H), 3.99 (dd, J = 9.3, 3.4 Hz, 2H), 3.92-3.85 (m, 4H), 3.75 (dd, J = 11.5, 5.5 Hz, 2H), 3.69-3.62 (m, 2H). | 557.31 |

Preparation of Compound 110 (Method D)

(2R,3S,4R,5S,6R)-2-(hydroxymethyl)-6-[2-[9-propyl-7-[2-[(2R,3S,4R,5S,6R)-3,4,5-trihydroxy-6-(hydroxymethyl)tetrahydropyran-2-yl]ethynyl]carbazol-2-yl]ethynyl]tetrahydropyran-3,4,5-triol

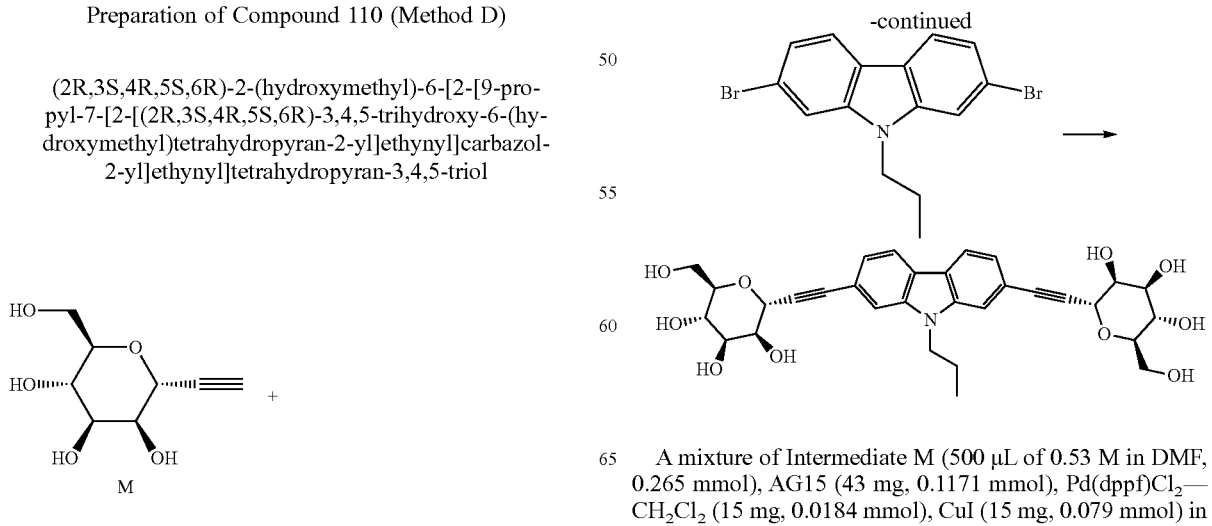

A mixture of Intermediate M (500 µL of 0.53 M in DMF, 0.265 mmol), AG15 (43 mg, 0.1171 mmol), Pd(dppf)Cl₂—CH₂Cl₂ (15 mg, 0.0184 mmol), CuI (15 mg, 0.079 mmol) in DMF (200 µL) is degassed (N₂). To the resulting mixture is added N-ethyl-N-isopropyl-propan-2-amine (180 µL, 1.03 mmol). The final mixture is stirred in a sealed tube under nitrogen atmosphere at 100° C. for 18 h. The reaction is filtered over 0.45 µM filter and concentrated in vacuo. The residue is purified by reverse phase HPLC to afford the title compound (7.9 mg, 10%) as a grey solid. ¹H NMR (400 MHz, CD₃OD) δ 8.05 (d, J=7.9 Hz, 2H), 7.63 (s, 2H), 7.29 (d, J=7.9 Hz, 2H), 4.90 (s, 2H), 4.33 (t, J=7.1 Hz, 2H), 4.04 (s, 2H), 4.03-3.96 (m, 2H), 3.88 (t, J=8.0 Hz, 4H), 3.75 (dd, J=12.1, 5.5 Hz, 2H), 3.65 (t, J=9.3 Hz, 2H), 1.87 (dd, J=14.5, 7.2 Hz, 2H), 0.93 (t, J=7.1 Hz, 3H). ESI-MS m/z calc. 581.61, found 582.44 (M+1)⁺

Preparation of Compounds 111 and 112

Compounds 111 and 112 are prepared according to the procedure described for Compound 110 using the appropriate Intermediates.

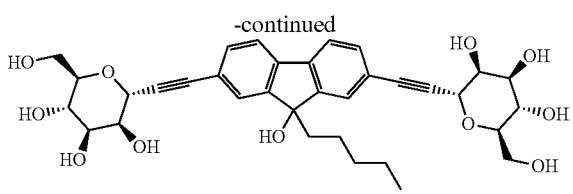

Step I 2,7-dibromo-9-pentyl-fluoren-9-ol

A solution of 2,7-dibromofluoren-9-one (200 mg, 0.592 mmol) in THF (2 mL) is added to a solution of n-pentyl magnesium bromide 2.0M in Et₂O (355 µL of 2.0 M, 0.710 mmol) diluted with Et₂O (4 mL) at 0° C. The reaction is stirred 18 h at RT and quenched with 1N Na₂CO₃. The organic phase is separated, washed with brine, dried over MgSO₄, filtered and concentrated. The residue is purified on

| Compound | IUPAC name | ¹H-NMR | LCMS m/z (M + H)⁺ |
|---|---|---|---|
| 111 | (2R,3S,4R,5S,6R)-2-[2-[9-ethyl-7-[2-[(2R,3S,4R,5S,6R)-3,4,5-trihydroxy-6-(hydroxymethyl)tetrahydropyran-2-yl]ethynyl]carbazol-2-yl]ethynyl]-6-(hydroxymethyl)tetrahydropyran-3,4,5-triol | (400 MHz, CD3OD) δ 8.05 (d, J = 8.1 Hz, 2H), 7.64 (s, 2H), 7.29 (d, J = 8.3 Hz, 2H), 4.78 (s, 2H), 4.06-4.02 (m, 2H), 4.00 (dd, J = 9.5, 3.4 Hz, 2H), 3.92-3.85 (m, 6H), 3.75 (dd, J = 12.1, 6.5 Hz, 2H), 3.69-3.62 (m, 2H), 1.38 (t, J = 7.1 Hz, 3H). | 568.53 |
| 112 | (2R,3S,4R,5S,6R)-2-(hydroxymethyl)-6-[2-[9-methyl-7-[2-[(2R,3S,4R,5S,6R)-3,4,5-trihydroxy-6-(hydroxymethyl)tetrahydropyran-2-yl]ethynyl]carbazol-2-yl]ethynyl]tetrahydropyran-3,4,5-triol | (400 MHz, CD3OD) δ 8.05 (d, J = 8.1 Hz, 2H), 7.64 (s, 2H), 7.30 (d, J = 8.5 Hz, 2H), 4.78 (s, 2H), 4.04 (d, J = 2.9 Hz, 2H), 4.03-3.97 (m, 2H), 3.93-3.84 (m, 7H), 3.79-3.74 (m, 2H), 3.65 (t, J = 9.5 Hz, 2H). | 554.39 |

Preparation of Compound 113 (Method D)

(2R,3S,4R,5S,6R)-2-(hydroxymethyl)-6-[2-[9-hydroxy-9-pentyl-7-[2-[(2R,3S,4R,5S,6R)-3,4,5-trihydroxy-6-(hydroxymethyl)tetrahydropyran-2-yl]ethynyl]fluoren-2-yl]ethynyl]tetrahydropyran-3,4,5-triol

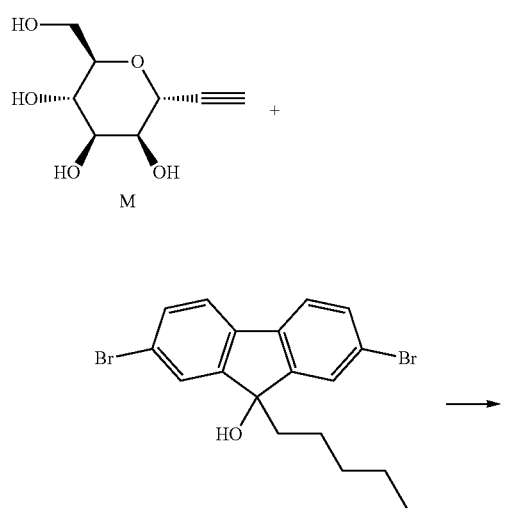

Biotage™ SNAP silica gel cartridge (0-8% EA/hex) to give 2,7-dibromo-9-pentyl-fluoren-9-ol (150 mg, 62%) as a white solid.

Step II: Compound 113

A solution of Intermediate M (500 µL of 0.53 M in DMF, 0.265 mmol), 2,7-dibromo-9-pentyl-fluoren-9-ol (50.0 mg, 0.122 mmol), Pd(dppf)Cl₂—CH₂Cl₂ (15 mg, 0.018 mmol), CuI (15 mg, 0.07876 mmol) in DMF (200 µL) is degassed (N₂). To the resulting mixture is added N-ethyl-N-isopropyl-propan-2-amine (180 µL, 1.03 mmol). The final mixture is stirred in a sealed tube under nitrogen atmosphere at 100° C. for 18 h. The reaction is filtered over 0.45 µM filter and concentrated in vacuo. The residue is purified by reverse phase HPLC to afford the title compound (9.4 mg, 11%) as a white solid. 1H NMR (400 MHz, CD3D) δ 7.68 (d, J=7.8 Hz, 2H), 7.55 (s, 2H), 7.47 (d, J=7.8 Hz, 2H), 4.80 (s, 2H), 4.01 (s, 2H), 3.98-3.92 (m, 2H), 3.91-3.80 (m, 4H), 3.73 (dd, J=11.3, 5.6 Hz, 2H), 3.63 (t, J=9.6 Hz, 2H), 2.15-2.07 (m, 2H), 1.16-1.07 (m, 4H), 0.79-0.64 (m, 5H). ESI-MS m/z calc. 624.68, found 625.47 (M+1)⁺

Preparation of Compounds 114 to 119

Compounds 114 and 115 are prepared according to the procedure described for Compound 113 using the appropriate Intermediates. Compounds 116-119 are prepared according to the procedure described for Compound 59 using commercially available starting material.

| Compound | IUPAC name | ¹H-NMR | LCMS m/z (M + H)⁺ |
|---|---|---|---|
| 114 | (2R,3S,4R,5S,6R)-2-[2-[9-cyclopropyl-9-hydroxy-7-[2-[(2R,3S,4R,5S,6R)-3,4,5-trihydroxy-6-(hydroxymethyl)tetrahydropyran-2-yl]ethynyl]fluoren-2-yl]ethynyl]-6-(hydroxymethyl)tetrahydropyran-3,4,5-triol | (400 MHz, CD3OD) δ 7.67 (d, J = 7.9 Hz, 2H), 7.59 (s, 2H), 7.47 (d, J = 8.0 Hz, 2H), 4.80 (s, 2H), 4.01 (t, J = 2.7 Hz, 2H), 3.97-3.92 (m, 2H), 3.87 (dd, J = 11.7, 2.1 Hz, 2H), 3.84-3.80 (m, 2H), 3.73 (dd, J = 11.5, 5.6 Hz, 2H), 3.63 (t, J = 9.5 Hz, 2H), 1.16-1.08 (m, 1H), 0.58 (d, J = 4.4 Hz, 2H), 0.44 (d, J = 9.3 Hz, 2H). | 595.5 |
| 115 | (2R,3S,4R,5S,6R)-2-(hydroxymethyl)-6-[2-[9-hydroxy-9-methyl-7-[2-[(2R,3S,4R,5S,6R)-3,4,5-trihydroxy-6-(hydroxymethyl)tetrahydropyran-2-yl]ethynyl]fluoren-2-yl]ethynyl]tetrahydropyran-3,4,5-triol | (400 MHz, CD3OD) δ 7.68 (d, J = 7.8 Hz, 1H), 7.61 (s, 1H), 7.46 (dd, J = 7.9, 1.4 Hz, 1H), 4.79 (s, 2H), 4.04-3.99 (m, 2H), 3.94 (dd, J = 9.4, 3.2 Hz, 2H), 3.90-3.80 (m, 4H), 3.73 (dd, J = 11.5, 5.6 Hz, 2H), 3.63 (t, J = 9.4 Hz, 2H), 1.65 (s, 3H). | 569.6 |
| 116 | (2R,3S,4R,5S,6R)-2-[2-[9,9-difluoro-7-[2-[(2R,3S,4R,5S,6R)-3,4,5-trihydroxy-6-(hydroxymethyl)tetrahydropyran-2-yl]ethynyl]fluoren-2-yl]ethynyl]-6-(hydroxymethyl)tetrahydropyran-3,4,5-triol | (400 MHz, CD3OD) δ 7.76-7.70 (m, 4H), 7.64 (d, J = 7.8 Hz, 2H), 4.78 (d, J = 3.4 Hz, 2H), 4.03-4.00 (m, 2H), 3.90 (ddd, J = 13.8, 10.4, 2.8 Hz, 4H), 3.84-3.79 (m, 2H), 3.73 (dd, J = 11.6, 5.8 Hz, 2H), 3.62 (t, J = 9.4 Hz, 2H). | 575.42 |
| 117 | (2R,3S,4R,5S,6R)-2-(hydroxymethyl)-6-[2-[7-[2-[(2R,3S,4R,5S,6R)-3,4,5-trihydroxy-6-(hydroxymethyl)tetrahydropyran-2-yl]ethynyl]-9,10-dihydrophenanthren-2-yl]ethynyl]tetrahydropyran-3,4,5-triol | (400 MHz, CD3OD) δ 7.76 (d, J = 8.1 Hz, 2H), 7.40-7.34 (m, 4H), 4.79 (s, 2H), 4.00 (dd, J = 3.3, 2.1 Hz, 2H), 3.93 (dd, J = 9.2, 3.3 Hz, 2H), 3.87 (dd, J = 11.6, 2.0 Hz, 2H), 3.81 (dd, J = 8.8, 1.8 Hz, 2H), 3.73 (dd, J = 11.1, 5.2 Hz, 2H), 3.64 (d, J = 9.4 Hz, 2H), 2.83 (s, 4H). | 552.57 |
| 118 | (2R,3S,4R,5S,6R)-2-(hydroxymethyl)-6-[2-[7-[2-[(2R,3S,4R,5S,6R)-3,4,5-trihydroxy-6-(hydroxymethyl)tetrahydropyran-2-yl]ethynyl]-9H-carbazol-2-yl]ethynyl]tetrahydropyran-3,4,5-triol | (400 MHz, CD3OD) δ 8.02 (d, J = 8.1 Hz, 2H), 7.54 (s, 2H), 7.26 (dd, J = 8.2, 1.2 Hz, 2H), 4.78 (s, 2H), 4.03 (dd, J = 3.1, 2.3 Hz, 2H), 3.98 (dd, J = 9.4, 3.1 Hz, 2H), 3.91-3.84 (m, 4H), 3.74 (dd, J = 11.5, 5.6 Hz, 2H), 3.64 (t, J = 9.5 Hz, 2H). | 540.42 |
| 119 | 2,7-bis[2-[(2R,3S,4R,5S,6R)-3,4,5-trihydroxy-6-(hydroxymethyl)tetrahydropyran-2-yl]ethynyl]fluoren-9-one | (400 MHz, CD3OD) δ 7.74-7.64 (m, 6H), 4.82 (s, 2H), 4.02-3.99 (m, 2H), 3.94-3.88 (m, 4H), 3.83-3.77 (m, 2H), 3.72 (dd, J = 11.5, 6.0 Hz, 2H), 3.62 (t, J = 9.6 Hz, 2H). | 553.52 |

Preparation of Compound 120 (Method D)

(2R,3S,4R,5S,6R)-2-[2-[9,9-dimethyl-7-[2-[(2R,3S,4R,5S,6R)-3,4,5-trihydroxy-6-(hydroxymethyl)tetrahydropyran-2-yl]ethynyl]fluoren-2-yl]ethynyl]-6-(hydroxymethyl)tetrahydropyran-3,4,5-triol

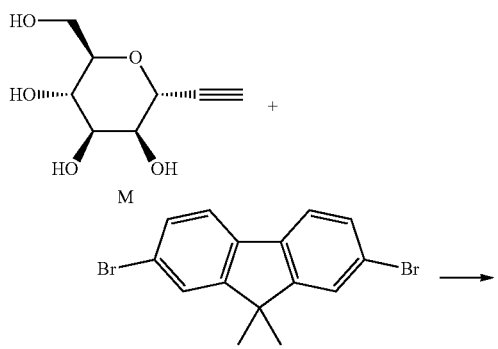

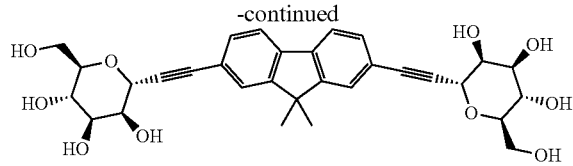

A solution of Intermediate M (1.00 g, 5.31 mmol), 2,7-dibromo-9,9-dimethyl-fluorene (870 mg, 2.47 mmol), Pd(dppf)Cl$_2$—CH$_2$Cl$_2$ (141 mg, 0.1727 mmol), CuI (141 mg, 0.7404 mmol) is degassed (N$_2$) and to the resulting mixture is added N-ethyl-N-isopropyl-propan-2-amine (3.73 mL, 21.4 mmol). The final mixture is stirred in a sealed tube under nitrogen atmosphere at 100° C. for 1 h. The reaction is poured in a round bottom flask containing Ac2O (25.0 mL, 265 mmol) and pyridine (25 mL, 309 mmol) and the resulting mixture is stirred over 18 h at RT. The reaction is then concentrated in vacuo, the residue is dissolved in EA (100 mL) and washed with NH$_4$Cl (3×125 mL). The organic phase is dried over MgSO$_4$, filtered, and concentrated. The resulting mixture is purified on Biotage™ SNAP 100 g silica gel cartridge using EtOAc (20 to 80%) to afford the per-acetylated 120 (1.36 g, 61%) as a pale yellow foamy solid. $^1$H NMR (400 MHz, CDCl$_3$) δ 7.70 (d, J=7.9 Hz, 2H), 7.57 (s, 2H), 7.52 (dd, J=7.9, 1.3 Hz, 2H), 5.60 (dd, J=10.0, 3.4 Hz, 2H), 5.48 (dd, J=3.2, 2.1 Hz, 2H), 5.36 (t, J=10.0 Hz, 2H), 5.05 (d, J=2.0 Hz, 2H), 4.37 (dd, J=12.2, 4.8 Hz, 2H), 4.31 (ddd, J=10.0, 4.7, 2.0 Hz, 2H), 4.18 (dd, J=12.2, 2.0 Hz, 2H), 2.22 (s, 6H), 2.14 (s, 6H), 2.07 (s, 6H), 2.04 (s, 6H), 1.52 (s, 6H). ESI-MS m/z calc. 902.29974, found 903.73 (M+1)$^+$.

To the per-acetylated Compound 120 namely [(2R,3R,4R,5R,6R)-3,4,5-triacetoxy-6-[2-[9,9-dimethyl-7-[2-[(2R,3R,4R,5R,6R)-3,4,5-triacetoxy-6-(acetoxymethyl)tetrahydropyran-2-yl]ethynyl]fluoren-2-yl]ethynyl]tetrahydropyran-2-yl]methyl acetate (1.36 g, 1.506 mmol) dissolved in MeOH (27 mL) (clear solution) is added MeONa in MeOH (3.00 mL of 0.5 M, 1.50 mmol). After 1 h, the reaction mixture is treated with prewashed Dowex 50WX4 (2.9 g used), filtered and concentrated. To the residual brown is added 15 mL MeOH, the suspension is sonicated then stirred at 40° C. under N$_2$ for 1.5 h. The mixture is cooled down to RT, placed in an ice bath and filtered to afford the title compound as a light beige solid (659 mg, 76% from the per-acetylated intermediate). $^1$H NMR (400 MHz, CD$_3$OD) δ 7.74 (d, J=7.8 Hz, 2H), 7.57 (s, 2H), 7.43 (d, J=7.9 Hz, 2H), 4.87 (s, 2H), 4.02 (s, 2H), 3.96 (dd, J=9.2, 3.1 Hz, 2H), 3.90-3.81 (m, 4H), 3.74 (dd, J=11.2, 5.2 Hz, 2H), 3.64 (t, J=9.2 Hz, 2H), 1.46 (s, 6H). [1], 1H NMR (400 MHz, cd3od) 7.74 (d, J=7.9 Hz, 2H), 7.57 (s, 2H), 7.44 (d, J=7.9 Hz, 2H), 4.92 (s, 2H), 4.03-4.00 (m, 2H), 3.96 (dd, J=9.4, 3.0 Hz, 2H), 3.91-3.81 (m, 4H), 3.74 (dd, J=11.2, 5.3 Hz, 2H), 3.63 (t, J=9.2 Hz, 2H), 1.46 (s, 6H). ESI-MS m/z calc. 566.60, found 567.42 (M+H)$^+$ Preparation of Compounds 121 to 138

Compounds 121-138 are prepared according to the procedure described for Compound 59 using commercially available starting material.

| Compound | IUPAC name | $^1$H-NMR | LCMS m/z (M + H)$^+$ |
|---|---|---|---|
| 121 | (2R,3S,4R,5S,6R)-2-(hydroxymethyl)-6-[2-[2-methyl-4-[3-methyl-4-[2-[(2R,3S,4R,5S,6R)-3,4,5-trihydroxy-6-(hydroxymethyl)tetrahydropyran-2-yl]ethynyl]phenyl]phenyl]ethynyl]tetrahydropyran-3,4,5-triol | (400 MHz, CD3OD + DMSO) δ 7.55 (s, 2H), 7.50 (d, J = 8.0 Hz, 2H), 7.46 (dd, J = 8.1, 1.6 Hz, 2H), 4.94 (d, J = 2.1 Hz, 2H), 4.04 (dd, J = 3.2, 2.1 Hz, 2H), 3.98 (dd, J = 9.4, 3.3 Hz, 2H), 3.92-3.81 (m, 4H), 3.75 (dd, J = 11.3, 5.5 Hz, 2H), 3.66 (t, J = 9.4 Hz, 2H), 2.51 (s, 6H). | 555.55 |
| 122 | (2R,3S,4R,5S,6R)-2-(hydroxymethyl)-6-[2-[4-[1-methyl-1-[4-[2-[(2R,3S,4R,5S,6R)-3,4,5-trihydroxy-6-(hydroxymethyl)tetrahydropyran-2-yl]ethynyl]phenyl]ethyl]phenyl]ethynyl]tetrahydropyran-3,4,5-triol | (400 MHz, CD3OD) δ 7.42-7.33 (m, 4H), 7.25-7.16 (m, 4H), 4.85 (d, J = 2.0 Hz, 2H), 3.99 (dd, J = 3.1, 2.2 Hz, 2H), 3.93 (dd, J = 9.3, 3.3 Hz, 2H), 3.87 (dd, J = 11.5, 2.0 Hz, 2H), 3.80 (ddd, J = 9.5, 5.7, 2.0 Hz, 2H), 3.73 (dd, J = 11.5, 5.7 Hz, 2H), 3.63 (t, J = 9.5 Hz, 2H), 1.66 (s, 6H). | 569.6 |
| 123 | (2R,3S,4R,5S,6R)-2-(hydroxymethyl)-6-[2-[5-[2-[(2R,3S,4R,5S,6R)-3,4,5-trihydroxy-6-(hydroxymethyl)tetrahydropyran-2-yl]ethynyl]thieno[2,3-b]thiophen-2-yl]ethynyl]tetrahydropyran-3,4,5-triol | (400 MHz, CD3OD) δ 7.41 (s, 2H), 4.89 (d, J = 2.0 Hz, 2H), 3.99 (t, J = 2.6 Hz, 2H), 3.90-3.82 (m, 4H), 3.73 (dq, J = 12.3, 6.2 Hz, 4H), 3.62 (dd, J = 11.3, 7.4 Hz, 2H). | 513.39 |
| 124 | (2R,3S,4R,5S,6R)-2-(hydroxymethyl)-6-[2-[3-methyl-4-[2-methyl-4-[2-[(2R,3S,4R,5S,6R)-3,4,5-trihydroxy-6-(hydroxymethyl)tetrahydropyran-2-yl]ethynyl]phenyl]phenyl]ethynyl]tetrahydropyran-3,4,5-triol | (400 MHz, CD3OD) δ 7.39 (s, 2H), 7.34-7.29 (m, 2H), 7.03 (d, J = 7.8 Hz, 2H), 4.86 (d, J = 2.1 Hz, 2H), 4.00 (dd, J = 3.2, 2.2 Hz, 2H), 3.94 (dd, J = 9.3, 3.3 Hz, 2H), 3.89-3.80 (m, 4H), 3.73 (dd, J = 11.4, 5.5 Hz, 2H), 3.63 (t, J = 9.4 Hz, 2H), 2.00 (s, 6H). | 555.4 |
| 125 | (2R,3S,4R,5S,6R)-2-[2-[1,5-dimethoxy-6-[2-[(2R,3S,4R,5S,6R)-3,4,5-trihydroxy-6-(hydroxymethyl)tetrahydropyran-2-yl]ethynyl]-2-naphthyl]ethynyl]-6-(hydroxymethyl)tetrahydropyran-3,4,5-triol | (400 MHz, CD3OD) δ 7.87 (d, J = 8.6 Hz, 2H), 7.50 (d, J = 8.6 Hz, 2H), 4.97 (d, J = 2.1 Hz, 2H), 4.12 (s, 6H), 4.08 (dd, J = 3.2, 2.1 Hz, 2H), 4.01 (dd, J = 9.3, 3.3 Hz, 2H), 3.95-3.84 (m, 4H), 3.76 (dd, J = 12.0, 6.1 Hz, 2H), 3.68 (t, J = 9.5 Hz, 2H). | 561.46 |
| 126 | (2R,3S,4R,5S,6R)-2-(hydroxymethyl)-6-[2-[2-[2-[(2R,3S,4R,5S,6R)-3,4,5-trihydroxy-6-(hydroxymethyl)tetrahydropyran-2-yl]ethynyl]-6-quinolyl]ethynyl]tetrahydropyran-3,4,5-triol | (400 MHz, CD3OD) δ 8.33 (d, J = 8.8 Hz, 1H), 8.09 (d, J = 8.9 Hz, 1H), 7.94 (d, J = 8.7 Hz, 1H), 7.80 (d, J = 8.3 Hz, 1H), 7.65 (d, J = 8.7 Hz, 1H), 4.96 (s, 2H), 4.11-4.02 (m, 2H), 3.99-3.92 (m, 2H), 3.91-3.81 (m, 4H), 3.75 (dd, J = 11.4, 5.5 Hz, 2H), 3.69-3.61 (m, 2H). | 502.32 |

| Compound | IUPAC name | ¹H-NMR | LCMS m/z (M + H)⁺ |
| --- | --- | --- | --- |
| 127 | (2R,3S,4R,5S,6R)-2-(hydroxymethyl)-6-[2-[2-[2-[(2R,3S,4R,5S,6R)-3,4,5-trihydroxy-6-(hydroxymethyl)tetrahydropyran-2-yl]ethynyl]quinazolin-6-yl]ethynyl]tetrahydropyran-3,4,5-triol | (400 MHz, CD3OD) δ 9.47 (s, 1H), 8.25 (d, J = 1.6 Hz, 1H), 8.04 (dd, J = 8.8, 1.8 Hz, 1H), 7.95 (d, J = 8.8 Hz, 1H), 4.96 (d, J = 2.1 Hz, 1H), 4.92 (d, J = 2.1 Hz, 1H), 4.09 (dd, J = 3.2, 2.2 Hz, 1H), 4.04 (dd, J = 3.2, 2.2 Hz, 1H), 3.98-3.91 (m, 2H), 3.89 (dd, J = 5.2, 2.9 Hz, 1H), 3.88-3.84 (m, 2H), 3.84-3.79 (m, 1H), 3.78-3.71 (m, 2H), 3.65 (dd, J = 19.3, 9.7 Hz, 2H). | 503.33 |
| 128 | (2R,3S,4R,5S,6R)-2-(hydroxymethyl)-6-[2-[5-[5-[2-[(2R,3S,4R,5S,6R)-3,4,5-trihydroxy-6-(hydroxymethyl)tetrahydropyran-2-yl]ethynyl]-2-thienyl]-2-thienyl]ethynyl]tetrahydropyran-3,4,5-triol | (400 MHz, CD3OD) δ 7.18 (dd, J = 10.4, 3.7 Hz, 4H), 4.88 (s, 2H), 3.98 (d, J = 2.0 Hz, 2H), 3.86 (dd, J = 9.4, 3.2 Hz, 4H), 3.77-3.68 (m, 4H), 3.62 (t, J = 9.4 Hz, 2H). | 539.39 |
| 129 | (2R,3S,4R,5S,6R)-2-(hydroxymethyl)-6-[2-[2-[2-[(2R,3S,4R,5S,6R)-3,4,5-trihydroxy-6-(hydroxymethyl)tetrahydropyran-2-yl]ethynyl]oxazol-4-yl]ethynyl]tetrahydropyran-3,4,5-triol | (400 MHz, CD3OD) δ 8.20 (s, 1H), 4.92 (s, 2H), 3.99 (d, J = 17.1 Hz, 2H), 3.89-3.78 (m, 4H), 3.75-3.66 (m, 4H), 3.61 (td, J = 9.1, 4.4 Hz, 2H). | 442.029 |
| 130 | (2R,3S,4R,5S,6R)-2-(hydroxymethyl)-6-[2-[8-[2-[(2R,3S,4R,5S,6R)-3,4,5-trihydroxy-6-(hydroxymethyl)tetrahydropyran-2-yl]ethynyl]-5-isoquinolyl]ethynyl]tetrahydropyran-3,4,5-triol | (400 MHz, CD3OD) δ 9.65 (s, 1H), 8.66 (s, 1H), 8.25 (s, 1H), 8.00 (d, J = 7.7 Hz, 1H), 7.88 (d, J = 7.3 Hz, 1H), 5.06 (d, J = 7.0 Hz, 2H), 4.16-4.08 (m, 2H), 3.97 (dd, J = 9.4, 3.2 Hz, 2H), 3.94-3.83 (m, 4H), 3.75 (dd, J = 11.6, 5.8 Hz, 2H), 3.67 (td, J = 9.1, 2.3 Hz, 2H). | 502.26 |
| 131 | (2R,3S,4R,5S,6R)-2-(hydroxymethyl)-6-[2-[4-[2-[(2R,3S,4R,5S,6R)-3,4,5-trihydroxy-6-(hydroxymethyl)tetrahydropyran-2-yl]ethynyl]-2,1,3-benzothiadiazol-7-yl]ethynyl]tetrahydropyran-3,4,5-triol | (400 MHz, CD3OD) δ 7.77 (s, 2H), 4.98 (d, J = 2.1 Hz, 2H), 4.11-4.08 (m, 2H), 4.05 (dd, J = 9.3, 3.3 Hz, 2H), 3.94-3.85 (m, 4H), 3.75 (dd, J = 12.0, 5.9 Hz, 2H), 3.67 (t, J = 9.5 Hz, 2H). | 509.28 |
| 132 | (2R,3S,4R,5S,6R)-2-(hydroxymethyl)-6-[2-[6-[2-[(2R,3S,4R,5S,6R)-3,4,5-trihydroxy-6-(hydroxymethyl)tetrahydropyran-2-yl]ethynyl]thieno[3,2-b]thiophen-3-yl]ethynyl]tetrahydropyran-3,4,5-triol | (400 MHz, CD3OD) δ 7.78 (s, 2H), 4.90 (d, J = 2.1 Hz, 2H), 4.04-4.00 (m, 2H), 3.93 (dd, J = 9.3, 3.3 Hz, 2H), 3.86 (dd, J = 11.5, 2.0 Hz, 2H), 3.80 (ddd, J = 9.4, 5.7, 2.0 Hz, 2H), 3.73 (dd, J = 11.5, 5.7 Hz, 2H), 3.64 (t, J = 9.4 Hz, 2H). | 513.24 |
| 133 | (2R,3S,4R,5S,6R)-2-(hydroxymethyl)-6-[2-[6-[2-[(2R,3S,4R,5S,6R)-3,4,5-trihydroxy-6-(hydroxymethyl)tetrahydropyran-2-yl]ethynyl]thieno[3,2-b]thiophen-2-yl]ethynyl]tetrahydropyran-3,4,5-triol | (400 MHz, CD3OD) δ 7.46 (d, J = 0.9 Hz, 2H), 4.90 (s, 2H), 3.99 (d, J = 2.2 Hz, 2H), 3.90-3.82 (m, 4H), 3.73 (dq, J = 11.8, 6.0 Hz, 4H), 3.66-3.58 (m, 2H). | 513.28 |
| 134 | (2R,3S,4R,5S,6R)-2-(hydroxymethyl)-6-[2-[4-methoxy-5-[2-[(2R,3S,4R,5S,6R)-3,4,5-trihydroxy-6-(hydroxymethyl)tetrahydropyran-2-yl]ethynyl]-2-pyridyl]ethynyl]tetrahydropyran-3,4,5-triol | (400 MHz, CD3OD) δ 8.16 (s, 1H), 7.55 (s, 1H), 4.89 (s, 1H), 4.01 (d, J = 2.7 Hz, 2H), 3.96 (dd, J = 9.8, 2.8 Hz, 1H), 3.92 (s, 3H), 3.91-3.79 (m, 5H), 3.73 (dt, J = 10.1, 7.1 Hz, 3H), 3.63 (q, J = 9.1 Hz, 2H). | 482.39 |

-continued

| Compound | IUPAC name | $^1$H-NMR | LCMS m/z (M + H)$^+$ |
|---|---|---|---|
| 135 | (2R,3S,4R,5S,6R)-2-(hydroxymethyl)-6-[2-[5-[2-[(2R,3S,4R,5S,6R)-3,4,5-trihydroxy-6-(hydroxymethyl)tetrahydropyran-2-yl]ethynyl]pyrazin-2-yl]ethynyl]tetrahydropyran-3,4,5-triol | N/A | 453.28 |
| 136 | (2R,3S,4R,5S,6R)-2-(hydroxymethyl)-6-[2-[4-[2-[(2R,3S,4R,5S,6R)-3,4,5-trihydroxy-6-(hydroxymethyl)tetrahydropyran-2-yl]ethynyl]-1-naphthyl]ethynyl]tetrahydropyran-3,4,5-triol | N/A | 501.28 |
| 137 | (2R,3S,4R,5S,6R)-2-(hydroxymethyl)-6-[2-[8-[2-[(2R,3S,4R,5S,6R)-3,4,5-trihydroxy-6-(hydroxymethyl)tetrahydropyran-2-yl]ethynyl]-1-naphthyl]ethynyl]tetrahydropyran-3,4,5-triol | N/A | 501.28 |
| 138 | (2R,3S,4R,5S,6R)-2-(hydroxymethyl)-6-[2-[5-[2-[(2R,3S,4R,5S,6R)-3,4,5-trihydroxy-6-(hydroxymethyl)tetrahydropyran-2-yl]ethynyl]-2-thienyl]ethynyl]tetrahydropyran-3,4,5-triol | N/A | 457.36 |

N/A means not available

Preparation of Compound 139 (Method A)

(2R,3S,4R,5S,6R)-2-(hydroxymethyl)-6-[3-[4-[3-[(2R,3S,4R,5S,6R)-3,4,5-trihydroxy-6-(hydroxymethyl)tetrahydropyran-2-yl]phenyl]phenyl]phenyl]tetrahydropyran-3,4,5-triol

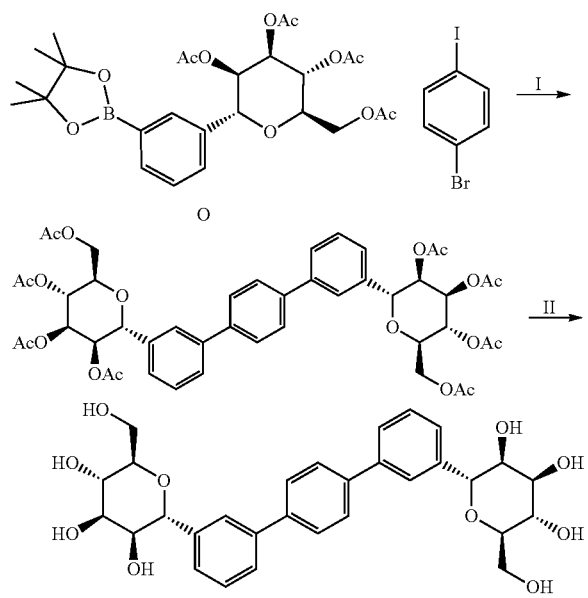

Step I: [(2R,3R,4R,5R,6R)-3,4,5-triacetoxy-6-[3-[4-3-[(2R,3R,4R,5R,6R)-3,4,5-triacetoxy-6-(acetoxymethyl)tetrahydropyran-2-yl]phenyl]phenyl]phenyl]tetrahydropyran-2-yl]methyl acetate A mixture of Intermediate O (101 mg, 0.188 mmol), 1-bromo-4-iodobenzene (86 mg, 0.304 mmol), Siliacat DPP-Pd (72 mg, 0.018 mmol), cesium carbonate (135 mg, 0.414 mmol) in CH$_3$CN (1.9 mL) in a microwave vial is microwaved for 10 minutes at 100° C. The resulting mixture is diluted with 4 mL of EtOAc, filtered on Celite and evaporated to dryness. The residue is used as is for the next step.

Step II: Compound 139

[(2R,3R,4R,5R,6R)-3,4,5-triacetoxy-6-[3-[4-[3-[(2R,3R,4R,5R,6R)-3,4,5-triacetoxy-6-(acetoxymethyl)tetrahydropyran-2-yl]phenyl]phenyl]phenyl]tetrahydropyran-2-yl]methyl acetate from Step I is deprotected as previously described using MeOH/MeONa mixture. $^1$H NMR (400 MHz, CD$_3$OD) δ 7.83 (d, J=1.5 Hz, 2H), 7.73 (s, 4H), 7.59 (ddd, J=5.7, 3.8, 2.0 Hz, 2H), 7.46 (dd, J=4.2, 1.6 Hz, 4H), 5.04 (d, J=3.7 Hz, 2H), 4.49 (t, J=3.4 Hz, 2H), 3.85 (m, 4H), 3.75 (t, J=7.8 Hz, 2H), 3.64 (dd, J=7.9, 3.1 Hz, 2H), 3.55 (ddd, J=7.8, 5.6, 4.1 Hz, 2H).

Preparation of Compound 140 (Method A)

Methyl 2-[2,5-bis[3-[(2R,3S,4R,5S,6R)-3,4,5-trihydroxy-6-(hydroxymethyl)tetrahydropyran-2-yl]phenyl]phenyl]acetate

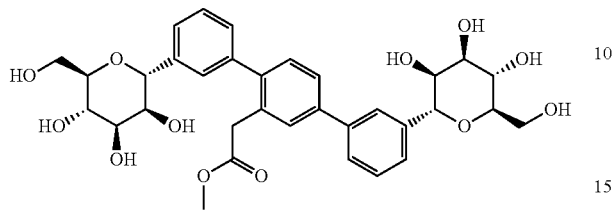

Compound 140 is prepared according to the procedure described for Compound 139 but using methyl 2-(2,5-dibromophenyl)acetate as starting material. $^1$HNMR (400 MHz, CD3OD) δ 7.82 (s, 1H), 7.63-7.56 (m, 3H), 7.50 (d, J=7.7 Hz, 1H), 7.48-7.41 (m, 4H), 7.34-7.30 (m, 1H), 7.23 (d, J=7.5 Hz, 1H), 5.04 (d, J=3.7 Hz, 1H), 5.01 (d, J=3.6 Hz, 1H), 4.49 (t, J=3.5 Hz, 1H), 4.45 (t, J=3.4 Hz, 1H), 3.87-3.81 (m, 4H), 3.78-3.73 (m, 2H), 3.70 (s, 2H), 3.66-3.60 (m, 2H), 3.58 (s, 3H), 3.57-3.49 (m, 2H). ESI-MS m/z (M+1)$^+$627.4

Preparation of Compound 141 (Method F)

(2R,3S,4R,5S,6R)-2-(hydroxymethyl)-6-[2-[4-[(2R, 3S,4R,5S,6R)-3,4,5-trihydroxy-6-(hydroxymethyl) tetrahydropyran-2-yl]phenyl]ethynyl]tetrahydropyran-3,4,5-triol

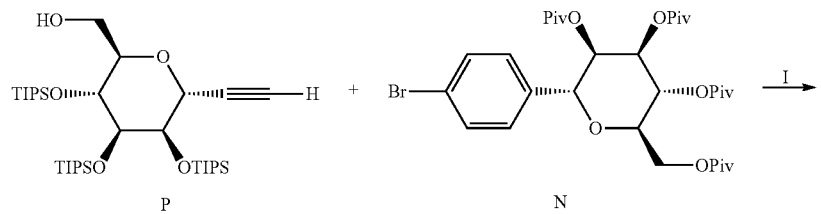

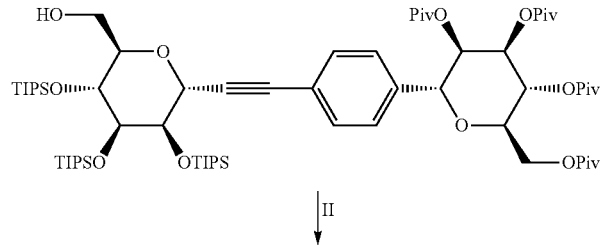

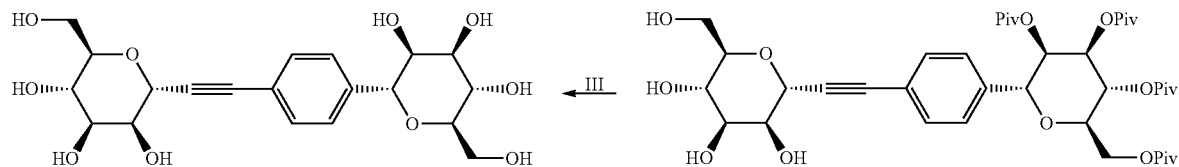

Step 1: (2R,3R,4R,5R,6R)-2-(4-(((2R,3R,4R,5R,6R)-6-(hydroxymethyl)-3,4,5-tris((triisopropylsilyl)oxy)tetrahydro-2H-pyran-2-yl)ethynyl)phenyl)-6-((pivaloyloxy)methyl)tetrahydro-2H-pyran-3,4,5-triyl tris(2,2-dimethylpropanoate)

A vial is charged with Intermediate N (100 mg, 0.153 mmol), Intermediate P (113 mg, 0.168 mmol) in DMF (2.500 mL). The resulting mixture is degassed. $PdCl_2$(dppf)$_2$-$CH_2Cl_2$ (15.8 mg, 0.0193 mmol) and CuI (8.7 mg, 0.046 mmol) are added, degassed again then $Et_3N$ (64 µL, 0.46 mmol) is added. The vial is capped and stirred at 90° C. overnight. The mixture is passed through celite and residual solvents are removed under reduced pressure. The crude mixture is used as in the next step without further purification. (201 mg, 0.163 mmol)

Step II: (2R,3R,4R,5R,6R)-2-((pivaloyloxy)methyl)-6-(4-(((2R,3S,4R,5S,6R)-3,4,5-trihydroxy-6-(hydroxymethyl)tetrahydro-2H-pyran-2-yl)ethynyl)phenyl)tetrahydro-2H-pyran-3,4,5-triyl tris(2,2-dimethylpropanoate)

To a solution of (2R,3R,4R,5R,6R)-2-(4-(((2R,3R,4R,5R,6R)-6-(hydroxymethyl)-3,4,5-tris((triisopropylsilyl)oxy)tetrahydro-2H-pyran-2-yl)ethynyl)phenyl)-6-((pivaloyloxy)methyl)tetrahydro-2H-pyran-3,4,5-triyl tris(2,2-dimethylpropanoate) from Step I (187 mg, 0.152 mmol) in THF (2.1 mL) is added TBAF (607 µL of 1 M, 0.607 mmol). The resulting suspension is stirred overnight at RT. Further diluted with THF (1.5 mL) and treated with Amberlyst $Ca^{2+}$ (500 mg) and Amberlyst A-15H (500 mg) (prewashed, $H_2O$ and THF). The suspension is stirred for 1.5 h, then filtered and washed with portions of MeOH. The solvents are removed and the crude mixture is used in the next step without purification.

Step III: Compound 141

To the crude mixture of (2R,3R,4R,5R,6R)-2-((pivaloyloxy)methyl)-6-(4-(((2R,3 S,4R,5S,6R)-3,4,5-trihydroxy-6-(hydroxymethyl)tetrahydro-2H-pyran-2-yl)ethynyl)phenyl)tetrahydro-2H-pyran-3,4,5-triyl tris(2,2-dimethylpropanoate) from Step II in MeOH (2 mL) is added MeONa (607 µL of 0.5 M, 0.304 mmol). The resulting mixture is stirred at RT overnight. AcOH (17 µL, 0.30 mmol) is added and the resulting mixture is concentrated under vacuo. The residue is purified by reverse phase HPLC to afford the title compound (7.6 mg). $^1H$ NMR (400 MHz, $CD_3OD$) δ 7.51-7.40 (m, 4H), 4.93 (d, J=4.0 Hz, 1H), 4.38-4.29 (m, 1H), 3.98 (dd, J=3.3, 2.1 Hz, 1H), 3.91 (dd, J=9.3, 3.3 Hz, 1H), 3.88-3.76 (m, 4H), 3.76-3.68 (m, J=5.6, 3.4 Hz, 2H), 3.62 (t, J=9.5 Hz, 1H), 3.56 (dd, J=7.7, 3.1 Hz, 1H), 3.47 (td, J=6.9, 3.5 Hz, 1H). ESI-MS m/z calc. 426.41, found (M+1)$^+$ 427.39

Preparation of Compounds 142-145 and 148

Compounds 142-145, 148 are prepared according to the procedure described for Compound 141

| Compound | IUPAC name | $^1$H-NMR | LCMS m/z (M + H)$^+$ |
|---|---|---|---|
| 142 | (2R,3S,4R,5S,6R)-2-(hydroxymethyl)-6-[2-[3-methyl-4-[(2R,3S,4R,5S,6R)-3,4,5-trihydroxy-6-(hydroxymethyl)tetrahydropyran-2-yl]phenyl]ethynyl]tetrahydropyran-3,4,5-triol | (400 MHz, CD3OD) δ 7.46 (d, J = 8.6 Hz, 1H), 7.27 (d, J = 6.7 Hz, 2H), 5.07 (d, J = 7.2 Hz, 1H), 4.14 (dd, J = 7.1, 3.2 Hz, 1H), 4.05-3.97 (m, 2H), 3.97-3.89 (m, 2H), 3.88-3.76 (m, 3H), 3.72 (dd, J = 11.6, 5.3 Hz, 2H), 3.65-3.57 (m, 2H), 2.41 (s, 3H). | 441.39 |
| 143 | (2R,3S,4R,5S,6R)-2-(hydroxymethyl)-6-[2-[2-methyl-4-[(2R,3S,4R,5S,6R)-3,4,5-trihydroxy-6-(hydroxymethyl)tetrahydropyran-2-yl]phenyl]ethynyl]tetrahydropyran-3,4,5-triol | (400 MHz, CD3OD) δ 7.45-7.35 (m, 2H), 7.27 (d, J = 7.9 Hz, 1H), 4.93-4.88 (m, 2H), 4.35 (t, J = 3.5 Hz, 1H), 4.03-3.98 (m, 1H), 3.94 (dd, J = 9.3, 3.3 Hz, 1H), 3.89-3.77 (m, 4H), 3.77-3.69 (m, 2H), 3.63 (t, J = 9.4 Hz, 1H), 3.55 (dd, J = 7.8, 3.0 Hz, 1H), 3.46 (dd, J = 10.3, 6.9 Hz, 1H), 2.43 (s, 3H). | 441.39 |
| 144 | (2R,3S,4R,5S,6R)-2-[2-[2-fluoro-4-[(2R,3S,4R,5S,6R)-3,4,5-trihydroxy-6-(hydroxymethyl)tetrahydropyran-2-yl]phenyl]ethynyl]-6-(hydroxymethyl)tetrahydropyran-3,4,5-triol | (400 MHz, CD3OD) δ 7.47 (t, J = 7.6 Hz, 1H), 7.30 (t, J = 9.8 Hz, 2H), 4.89 (d, J = 7.5 Hz, 2H), 4.23 (t, J = 3.6 Hz, 1H), 4.04-3.97 (m, 1H), 3.95-3.82 (m, 3H), 3.82-3.69 (m, 4H), 3.63 (t, J = 9.2 Hz, 1H), 3.58 (dd, J = 7.4, 2.7 Hz, 1H), 3.51 (s, 1H). | 445.41 |
| 145 | (2R,3S,4R,5S,6R)-2-(hydroxymethyl)-6-[2-[2-methoxy-4-[(2R,3S,4R,5S,6R)-3,4,5-trihydroxy-6-(hydroxymethyl)tetrahydropyran-2-yl]phenyl]ethynyl]tetrahydropyran-3,4,5-triol | (400 MHz, CD3OD) δ 7.35 (d, J = 7.9 Hz, 1H), 7.19 (s, 1H), 6.98 (d, J = 8.0 Hz, 1H), 4.92 (d, J = 3.9 Hz, 1H), 4.35 (t, 1H), 4.05-3.93 (m, J = 7.6, 3.2 Hz, 2H), 3.86 (s, 3H), 3.84-3.80 (m, 3H), 3.76-3.60 (m, 3H), 3.55 (dd, J = 7.8, 3.1 Hz, 1H), 3.49 (dd, J = 12.6, 4.9 Hz, 1H), 2.06 (s, 1H). | 457.36 |
| 148 | (2R,3S,4R,5S,6R)-2-(hydroxymethyl)-6-[2-[2-methyl-3-[(2R,3S,4R,5S,6R)-3,4,5-trihydroxy-6- | (400 MHz, CD3OD) δ 7.50 (m, 1H), 7.37 (dd, J = 7.7, 1.3 Hz, 1H), 7.17 (t, J = 7.8 Hz, 1H), 5.11 (d, J = 7.1 Hz, 1H), 4.89 (d, J = 2.1 Hz, 1H), 4.15 (dd, J = 7.1, 3.2 Hz, 1H), 4.01(m, | 441.35 |

| Compound IUPAC name | ¹H-NMR | LCMS m/z (M + H)⁺ |
|---|---|---|
| (hydroxymethyl)tetrahydro pyran-2-yl]phenyl]ethynyl]tetrahydropyran-3,4,5-triol | 2H), 3.94 (m, 2H), 3.84 (m, 3H), 3.73 (m, 2H), 3.64 (d, J = 9.4 Hz, 1H), 3.60 (m, 1H), 2.56 (s, 3H). | |

Preparation of Compound 146 (Method D)

(2R,3S,4R,5S,6R)-2-(hydroxymethyl)-6-[2-[2-[(2R,3S,4R,5S,6R)-3,4,5-trihydroxy-6-(hydroxymethyl)tetrahydropyran-2-yl]-1H-indol-6-yl]ethynyl]tetrahydropyran-3,4,5-triol

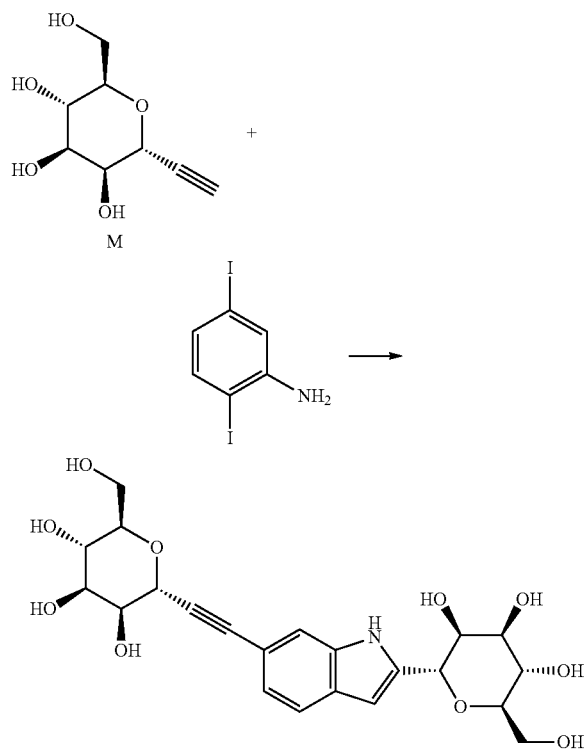

2,5-diiodoaniline (37 mg, 0.11 mmol) and Pd(PPh₃)₄ (12 mg, 0.011 mmol) are charged in a glass vial, the vial is capped, degassed (vacuum then N₂, 3×) and a solution of Intermediate M (400 μL of a 0.53 M solution in DMF, 0.22 mmol) is added followed by DIPEA (300 μL, 1.72 mmol). Degassed again then transferred to a preheated oil bath (60° C.) and stirred overnight. The resulting mixture is filtered and purified by reverse phase HPLC. Fractions containing the desired material are combined and freeze-dried to afford the title compound (4.2 mg, 8% yield) as a pale yellow fluffy solid. ¹H NMR (400 MHz, CD₃OD) δ 7.49-7.42 (m, 2H), 7.09 (dd, J=8.3, 1.3 Hz, 1H), 6.42 (t, J=0.9 Hz, 1H), 5.25-5.13 (m, 1H), 4.88 (d, J=2.0 Hz, 1H), 4.50 (dd, J=3.3, 2.2 Hz, 1H), 4.07-3.96 (m, 2H), 3.93-3.84 (m, 3H), 3.83-3.71 (m, 3H), 3.71-3.60 (m, 2H), 3.35-3.23 (m, 1H). ESI-MS m/z calc. 465.16348, found (M+1)⁺ 466.47

Preparation of Compound 150 (Method A)

(2R,2'R,3S,3'S,4R,4'R,5S,5'S,6R,6'R)-6,6'-(2-fluoro-3'-methyl-1,1'-biphenyl]-4,4'-diyl)bis(2-(hydroxymethyl)tetrahydro-2H-pyran-3,4,5-triol)

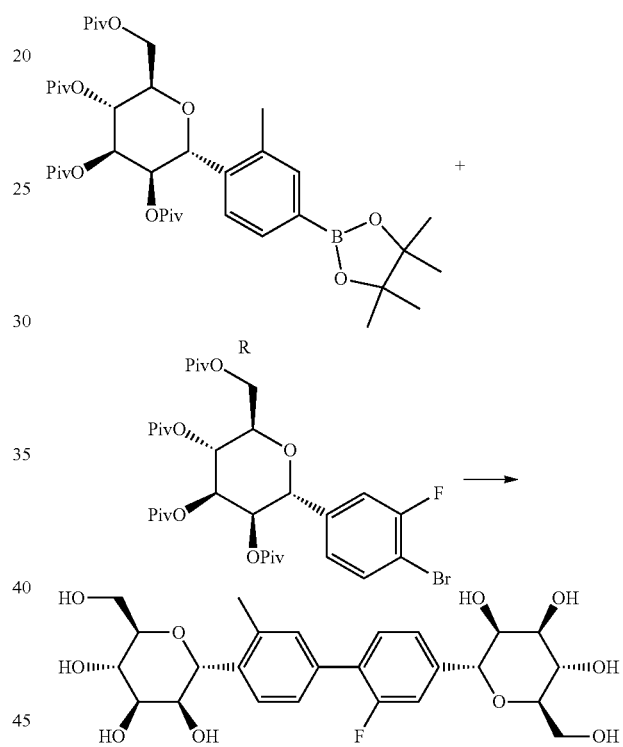

To a solution of [(2R,3R,4R,5R,6R)-6-(4-bromo-3-fluoro-phenyl)-3,4,5-tris(2,2-dimethylpropanoyloxy)tetrahydropyran-2-yl]methyl 2,2-dimethylpropanoate (90.2 mg, 0.134 mmol; prepared according to the procedure described for Intermediate N but using 1-bromo-2-fluoro-4-iodobenzene as starting material) and Intermediate R (96.0 mg, 0.134 mmol) in 2-methylTHF (2.7 mL) is sequentially added 3-(2-dicyclohexylphosphanylphenyl)-2,4-dimethoxy-benzenesulfonic acid (Sodium salt) (13.8 mg, 0.0268 mmol), Pd(OAc)₂ (3.0 mg, 0.013 mmol) (premixed in 0.25 mL of MeTHF), K₂CO₃ (335 μL of 2M, 0.669 mmol) and the mixture is stirred at 40° C. overnight. The resulting mixture is diluted with AcOEt (10 mL) and water (5 mL), layers are separated and the aqueous layer is back extracted with 10 mL of AcOEt. The combined organic layers are dried over Na₂SO₄ and concentrated to dryness. The residue is dissolved in MeOH (2 mL) and MeONa (1.0 mL of 0.5 M in MeOH, 0.5 mmol) is added and the mixture is stirred overnight at RT. AcOH (30.5 μL, 0.536 mmol) is added, the mixture is concentrated to dryness and the residue is purified by reverse phase preparative HPLC to afford the title compound (12.4 mg, 18%). ¹H NMR (400 MHz, CD₃OD) δ 7.52 (d, J=8.0 Hz, 1H), 7.46 (t, J=8.1 Hz, 1H), 7.34 (m, 4H), 5.14 (d, J=6.5 Hz, 1H), 4.97 (d, J=4.1 Hz, 1H), 4.37 (dd, J=4.1, 3.1 Hz, 1H), 4.26 (dd, J=6.4, 3.3 Hz, 1H), 3.99 (m, 2H), 3.83 (m, 3H), 3.75 (m, 2H), 3.57 (m, 3H), 2.49 (s, 3H). ESI-MS m/z calc. 510.51, found (M+1)⁺ 511.42

Preparation of Compounds 147, 149 and 151

Compounds 147, 149 and 151 are prepared according to the procedure described for Compound 150

| Compound | IUPAC name | ¹H-NMR | LCMS m/z (M + H)⁺ |
|---|---|---|---|
| 147 | (2R,3S,4R,5S,6R)-2-(hydroxymethyl)-6-[3-methoxy-4-[3-methyl-4-[(2R,3S,4R,5S,6R)-3,4,5-trihydroxy-6-(hydroxymethyl)tetrahydropyran-2-yl]phenyl]phenyl]tetrahydropyran-3,4,5-triol | (400 MHz, CD3OD) δ 7.44 (d, J = 8.0 Hz, 1H), 7.26 (m, 4H), 7.05 (dt, J = 8.0, 1.2 Hz, 1H), 5.12 (d, J = 6.0 Hz, 1H), 5.00 (d, J = 3.4 Hz, 1H), 4.46 (t, J = 3.3 Hz, 1H), 4.29 (dd, J = 6.1, 3.3 Hz, 1H), 4.01 (dd, J = 6.2, 3.3 Hz, 1H), 3.96 (dd, J = 11.9, 6.9 Hz, 1H), 3.83 (m, 2H), 3.79 (s, 3H), 3.78 (t, J = 2.0 Hz, 1H), 3.74 (m, 1H), 3.70 (d, J = 8.1 Hz, 1H), 3.61 (dd, J = 8.1, 3.1 Hz, 1H), 3.52 (ddd, J = 6.8, 5.1, 3.5 Hz, 2H), 2.46 (s, 3H). | 522.25 |
| 149 | (2R,3S,4R,5S,6R)-2-(hydroxymethyl)-6-[3-methyl-4-[3-methyl-4-[(2R,3S,4R,5S,6R)-3,4,5-trihydroxy-6-(hydroxymethyl)tetrahydropyran-2-yl]phenyl]phenyl]tetrahydropyran-3,4,5-triol | (400 MHz, CD3OD) δ 7.49 (d, J = 7.2 Hz, 1H), 7.42 (m, 1H), 7.37 (m, 1H), 7.31 (dd, J = 8.1, 1.8 Hz, 1H), 7.16 (d, J = 7.9 Hz, 1H), 7.11 (d, J = 7.8 Hz, 1H), 5.13 (dd, J = 6.3, 5.2 Hz, 1H), 4.98 (d, J = 3.4 Hz, 1H), 4.46 (t, J = 3.3 Hz, 1H), 4.28 (dt, J = 6.2, 3.6 Hz, 1H), 3.99 (m, 2H), 3.83 (m, 3H), 3.76 (m, 2H), 3.61 (dd, J = 8.2, 3.1 Hz, 1H), 3.59-3.46 (m, 2H), 2.48 (s, 3H), 2.24 (s, 3H). | N/A |
| 151 | (2R,3S,4R,5S,6R)-2-(hydroxymethyl)-6-[4-[3-methoxy-4-[(2R,3S,4R,5S,6R)-3,4,5-trihydroxy-6-(hydroxymethyl)tetrahydropyran-2-yl]phenyl]phenyl]tetrahydropyran-3,4,5-triol | (400 MHz, CD3OD) δ 7.65 (m, 3H), 7.52 (d, J = 8.1 Hz, 2H), 7.24 (dd, J = 8.1, 1.7 Hz, 1H), 7.08 (d, J = 1.7 Hz, 1H), 5.00 (d, J = 3.5 Hz, 1H), 4.46 (t, J = 3.3 Hz, 1H), 3.83 (d, J = 4.6 Hz, 2H), 3.74 (t, J = 8.1 Hz, 1H), 3.60 (dd, J = 8.2, 3.1 Hz, 1H), 3.56 (s, 3H), 3.48 (dt, J = 8.1, 4.7 Hz, 1H). | N/A |

Preparation of Compound 152 (modified Method B)

(2R,3S,4R,5S,6R)-2-(hydroxymethyl)-6-[2-methyl-4-[2-[3-methyl-4-[(2R,3S,4R,5S,6R)-3,4,5-trihydroxy-6-(hydroxymethyl)tetrahydropyran-2-yl]phenyl]ethynyl]phenyl]tetrahydropyran-3,4,5-triol

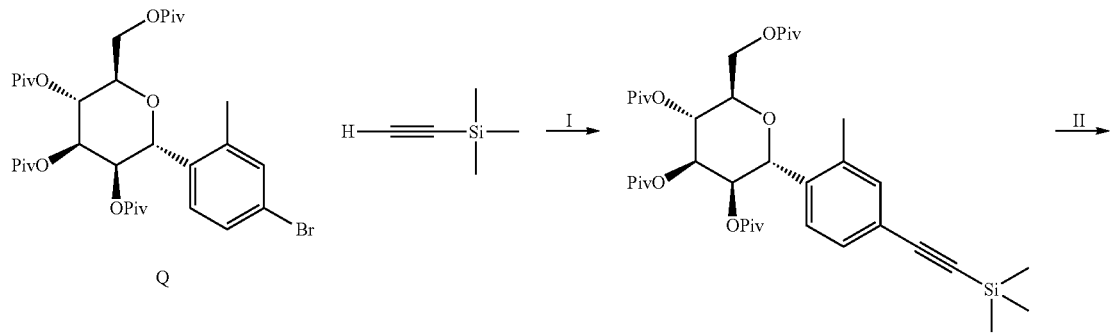

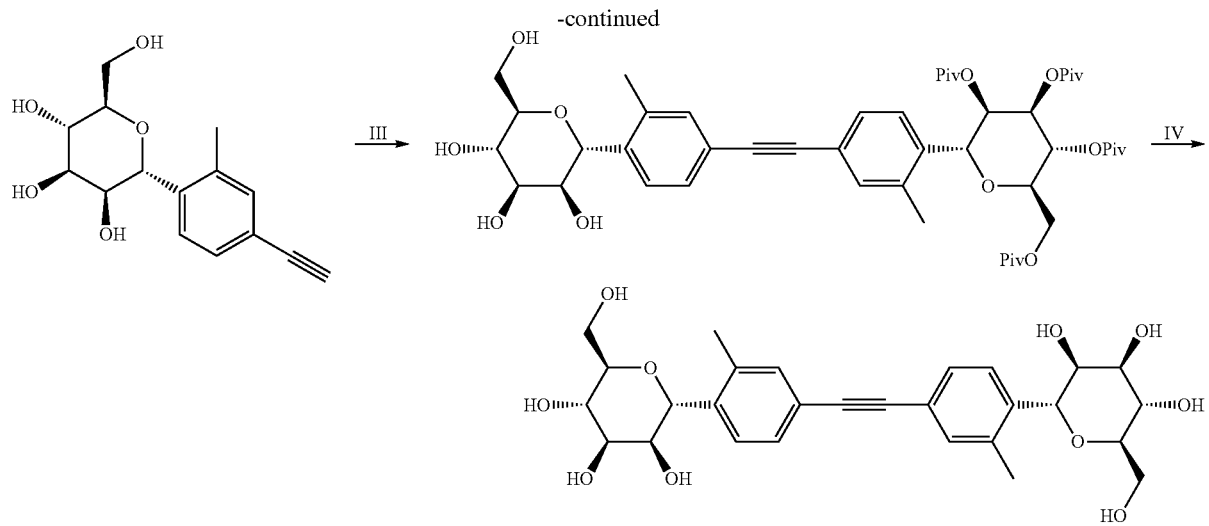

Step I: [(2R,3R,4R,5R,6R)-3,4,5-tris(2,2-dimethyl-propanoyloxy)-6-[2-methyl-4-(2-trimethylsilylethynyl)phenyl]tetrahydropyran-2-yl]methyl 2,2-dimethylpropanoate In a glass vial charged with Intermediate Q (259 mg, 0.389 mmol), Pd(dppf)Cl$_2$—CH$_2$Cl$_2$ (33 mg, 0.040 mmol) and CuI (21 mg, 0.11 mmol), capped and flushed with N$_2$ is added DMF (2.6 mL), ethynyl(trimethyl)silane (275 µL, 1.95 mmol) and Et$_3$N (270 µL, 1.94 mmol). The reaction mixture is transferred to a preheated (80° C.) oil bath and stirred overnight. The reaction mixture is cooled down to RT and diluted with EtOAc and saturated aqueous NH$_4$Cl (10 mL each). The organic layer is separated, washed with saturated aqueous NH$_4$Cl (2×5 mL), brine (5 mL), dried over Na$_2$SO$_4$ and passed through a 2 g silica cartridge, using EtOAc. The filtrate is concentrated then purified Biotage™ SNAP 10 g silica cartridge, using a gradient of EtOAc in Hex, 0-20% as eluent. The desired fractions are combined and concentrated, providing the title compound (246 mg, 93% yield) as a yellow foam.

Step II: (2R,3S,4R,5S,6R)-2-(4-ethynyl-2-methyl-phenyl)-6-(hydroxymethyl)tetrahydropyran-3,4,5-triol To a solution of [(2R,3R,4R,5R,6R)-3,4,5-tris(2,2-dimethylpropanoyloxy)-6-[2-methyl-4-(2-trimethylsilylethynyl)phenyl]tetrahydropyran-2-yl]methyl 2,2-dimethylpropanoate from Step 1 (244 mg, 0.355 mmol) in MeOH (2.5 mL) is added MeONa in MeOH (2.1 mL of 0.5 M, 1.1 mmol) and the mixture is transferred to a preheated (60° C.) oil bath. After stirring for 3 h, the reaction mixture is cooled down to RT and treated with prewashed Dowex 50WX4-400 resin, filtered and washed with portions of MeOH. The combined filtrates are concentrated and purified by flash chromatography on a bond elut 5 g silica cartridge, using a gradient of MeOH in CH$_2$Cl$_2$, 0 to 20% as eluent. Combined fractions are concentrated affording the title compound (90 mg, 91% yield) as an amber foamy solid.

Step III: [(2R,3R,4R,5R,6R)-3,4,5-tris(2,2-dimethyl-propanoyloxy)-6-[2-methyl-4-[2-[3-methyl-4-[(2R,3S,4R,5S,6R)-3,4,5-trihydroxy-6-(hydroxymethyl)tetrahydropyran-2-yl]phenyl]ethynyl]phenyl]tetrahydropyran-2-yl]methyl 2,2-dimethylpropanoate In a glass vial charged with (2R,3S,4R,5S,6R)-2-(4-ethynyl-2-methyl-phenyl)-6-(hydroxymethyl)tetrahydropyran-3,4,5-triol (35.0 mg, 0.12 mmol), Intermediate Q (70.0 mg, 0.105 mmol), CuI (10 mg, 0.053 mmol) and Pd(dppf)Cl$_2$—CH$_2$Cl$_2$ (10 mg, 0.014 mmol), capped and flushed with N$_2$ is added DMF (0.7 mL) and DIEA (55 µL, 0.32 mmol). The vial is degassed and transferred to a preheated oil bath (90° C.), and stirred for 1 h and slowly cooled to RT and left overnight. The reaction mixture is diluted with EtOAc and saturated NH$_4$Cl (10 mL each) and filtered. The layers are separated, the aqueous layer is back extracted with EtOAc (5 mL). The combined organic extracts are washed with saturated NH$_4$Cl solution (5 mL), brine (5 mL), dried over Na$_2$SO$_4$, filtered and concentrated. The crude product is purified on Biotage™ SNAP 10 g silica cartridge, using a gradient of MeOH in CH$_2$Cl$_2$, 0-20% as eluent. The combined fractions are concentrated to provide the title compound (28 mg, 31% yield) as a pinkish brown solid.

Step IV: Compound 152

Deprotection of [(2R,3R,4R,5R,6R)-3,4,5-tris(2,2-dimethylpropanoyloxy)-6-[2-methyl-4-[2-[3-methyl-4-[(2R,3S,4R,5S,6R)-3,4,5-trihydroxy-6-(hydroxymethyl)tetrahydropyran-2-yl]phenyl]ethynyl]phenyl]tetrahydropyran-2-yl]methyl 2,2-dimethylpropanoate from Step III (28 mg, 0.32 mmol) using the protocol described in step II provides the title compound (17 mg, 94% yield) as an off-white fluffy solid (after redissolving the crude product in H$_2$O/MeCN mixture (20% MeCN) and freeze-drying). $^1$H NMR (400 MHz, CD$_3$OD) δ 7.49 (d, J=8.6 Hz, 2H), 7.34 (d, J=7.2 Hz, 4H), 5.11 (d, J=7.0 Hz, 2H), 4.20 (dd, J=7.0, 3.3 Hz, 2H), 4.04 (dd, J=11.9, 7.4 Hz, 2H), 3.99 (dd, J=5.5, 3.3 Hz, 2H), 3.85 (dd, J=5.5, 4.3 Hz, 2H), 3.75 (dd, J=11.9, 3.8 Hz, 2H), 3.66-3.57 (m, 2H), 2.46 (s, 6H). ESI-MS m/z calc. 530.2152, found 531.55 (M+1)$^+$

Preparation of Compound 155 (Method A)

(2R,3S,4R,5S,6R)-2-(hydroxymethyl)-6-[2-methyl-4-[2-methyl-6-[3-methyl-4-[(2R,3S,4R,5S,6R)-3,4,5-trihydroxy-6-(hydroxymethyl)tetrahydropyran-2-yl]phenyl]-3-pyridyl]phenyl]tetrahydropyran-3,4,5-triol

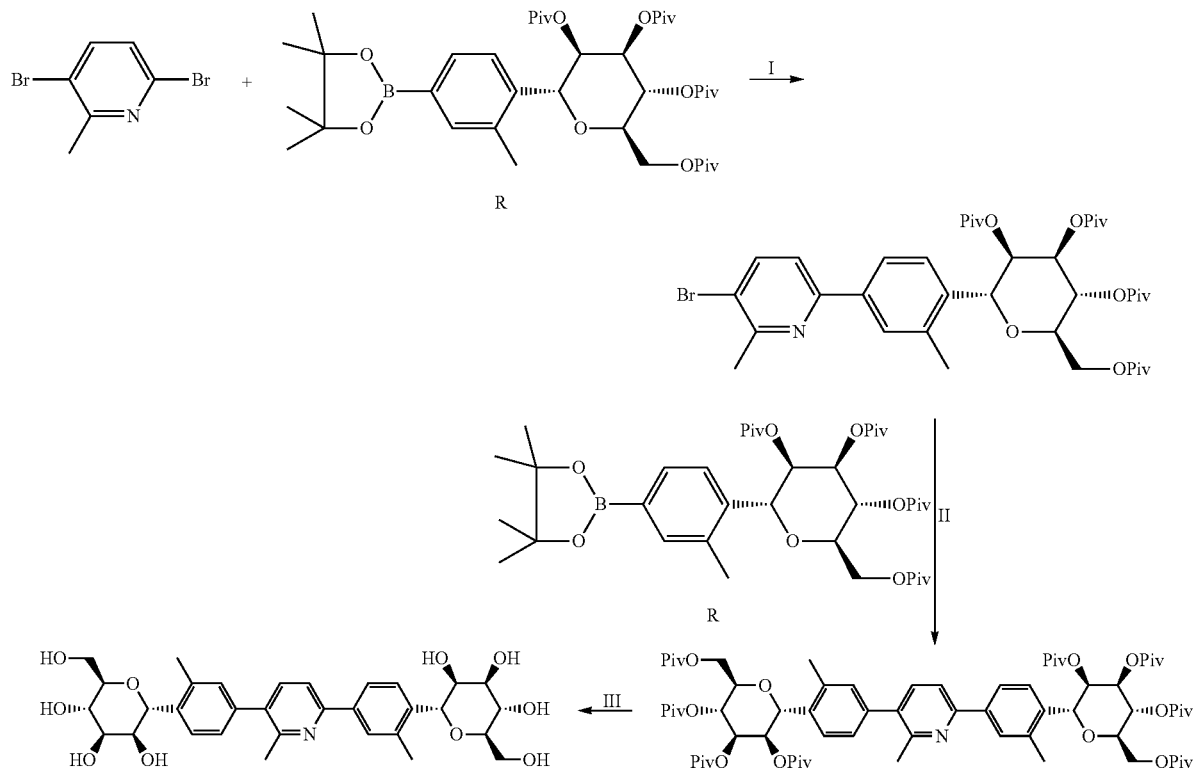

Step I: (2R,3R,4R,5R,6R)-2-(4-(5-bromo-6-methylpyridin-2-yl)-2-methylphenyl)-6-((pivaloyloxy)methyl)tetrahydro-2H-pyran-3,4,5-triyl tris(2,2-dimethylpropanoate)

A 5 ml microwave vial is charged with Intermediate R (150 mg, 0.209 mmol), 3,6-dibromo-2-methyl-pyridine (43.8 mg, 0.174 mmol), Siliacat DPP-Pd (70 mg, 0.017 mmol) and Cs$_2$CO$_3$ (171 mg, 0.523 mmol) in CH$_3$CN (2.0 mL). The vial is capped under nitrogen and irradiated at 130° C. for 30 min in the microwave. The reaction mixture is diluted with EtOAc passed on a 500 mg silica cartridge and eluted with EtOAc. The resulting mixture was concentrated under reduced pressure the residue (159 mg) is used as such in the next step.

[(2R,3R,4R,5R,6R)-3,4,5-tris(2,2-dimethylpropanoyloxy)-6-[2-methyl-4-(4,4,5,5-tetramethyl-1,3,2-dioxaborolan-2-yl)phenyl]tetrahydropyran-2-yl]methyl 2,2-dimethylpropanoate is prepared according to the procedure described for Intermediate B and N Step II A 5 ml microwave vial is charged with a crude mixture of [(2R,3R,4R,5R,6R)-6-[4-(5-bromo-6-methyl-2-pyridyl)-2-methyl-phenyl]-3,4,5-tris(2,2-dimethylpropanoyloxy)tetrahydropyran-2-yl]methyl 2,2-dimethylpropanoate (130 mg, 0.1709 mmol), Intermediate R (123 mg, 0.171 mmol), Siliacat DPP-Pd (68.4 mg, 0.0171 mmol) and Cs$_2$CO$_3$ (167.0 mg, 0.513 mmol) in CH$_3$CN (2.7 mL). The vial is capped under nitrogen and irradiated at 130° C. for 30 min in the microwave. The reaction mixture is diluted with EtOAc passed on a 500 mg silica cartridge and eluted with EtOAc. The residual mixture was concentrated under reduced pressure to afford the crude mixture of the title compound, used as such in the next step Step III: Compound 155

The residue is dissolved in MeOH (1.30 mL). MeONa (46.2 mg, 0.855 mmol) is added to the solution and the latter is allowed to stir for 48 h at RT. AcOH (58 μL, 1.03 mmol) is added to the mixture and the solvents are removed under reduced pressure. The residue is then purified by reverse-phase HPLC to afford the title compound (12.6 mg, 12%).

$^1$H NMR (400 MHz, CD3OD) δ 7.83-7.72 (m, J=8.2 Hz, 2H), 7.66 (dd, J=18.0, 8.1 Hz, 2H), 7.58 (dd, J=7.9, 5.3 Hz, 2H), 7.26-7.18 (m, 2H), 5.16 (d, J=6.7 Hz, 2H), 4.27 (dd, J=6.6, 2.8 Hz, 2H), 4.07-3.92 (m, 4H), 3.89-3.81 (m, 2H), 3.76 (dt, J=11.9, 3.5 Hz, 2H), 3.65-3.53 (m, J=11.1, 8.0, 4.0 Hz, 2H), 2.54 (s, 3H), 2.52 (s, 3H), 2.51 (s, 3H). LC-MS: m/z=598.59 (M+H$^+$).

Preparation of Compounds 153, 154 and 157

Compounds 153, 154 and 157 prepared according to the procedure described for Compound 155

| Compound | IUPAC name | ¹H-NMR | LCMS m/z (M + H)+ |
|---|---|---|---|
| 153 | (2R,3S,4R,5S,6R)-2-(hydroxymethyl)-6-[2-methyl-4-[5-[3-methyl-4-[(2R,3S,4R,5S,6R)-3,4,5-trihydroxy-6-(hydroxymethyl)tetrahydropyran-2-yl]phenyl]pyrazin-2-yl]phenyl]tetrahydropyran-3,4,5-triol | (400 MHz, CD3OD) δ 9.09 (s, 2H), 7.92 (m, 4H), 7.63 (d, J = 8.7 Hz, 2H), 5.15 (d, J = 6.8 Hz, 2H), 4.24 (dd, J = 6.8, 3.2 Hz, 2H), 4.02 (m, 4H), 3.85 (dd, J = 5.7, 4.3 Hz, 2H), 3.75 (dd, J = 11.9, 3.7 Hz, 2H), 3.61 (dt, J = 7.7, 4.0 Hz, 2H), 2.55 (s, 6H). | 585.57 |
| 154 | (2R,3S,4R,5S,6R)-2-(hydroxymethyl)-6-[2-methyl-4-[6-[3-methyl-4-[(2R,3S,4R,5S,6R)-3,4,5-trihydroxy-6-(hydroxymethyl)tetrahydropyran-2-yl]phenyl]-2-pyridyl]phenyl]tetrahydropyran-3,4,5-triol | (400 MHz, CD3OD) δ 7.95 (d, J = 7.2 Hz, 4H), 7.88 (dd, J = 8.5, 7.1 Hz, 1H), 7.77 (d, J = 7.6 Hz, 2H), 7.59 (d, J = 8.7 Hz, 2H), 5.16 (d, J = 6.5 Hz, 2H), 4.28 (dd, J = 6.4, 3.3 Hz, 2H), 4.08-3.92 (m, 4H), 3.84 (t, 2H), 3.76 (dd, J = 11.9, 3.7 Hz, 2H), 3.58 (dt, J = 8.3, 4.1 Hz, 2H), 2.56 (s, 6H). | 584.59 |
| 157 | (2R,3S,4R,5S,6R)-2-(hydroxymethyl)-6-[2-methyl-4-[6-[3-methyl-4-[(2R,3S,4R,5S,6R)-3,4,5-trihydroxy-6-(hydroxymethyl)tetrahydropyran-2-yl]phenyl]-3-pyridyl]phenyl]tetrahydropyran-3,4,5-triol | | 584.63 |

Preparation of Compound 156

2R,3S,4R,5S,6R)-2-(hydroxymethyl)-6-[4-[2-[3-methyl-4-[(2R,3S,4R,5S,6R)-3,4,5-trihydroxy-6-(hydroxymethyl)tetrahydropyran-2-yl]phenyl]cyclopropyl]phenyl]tetrahydropyran-3,4,5-triol

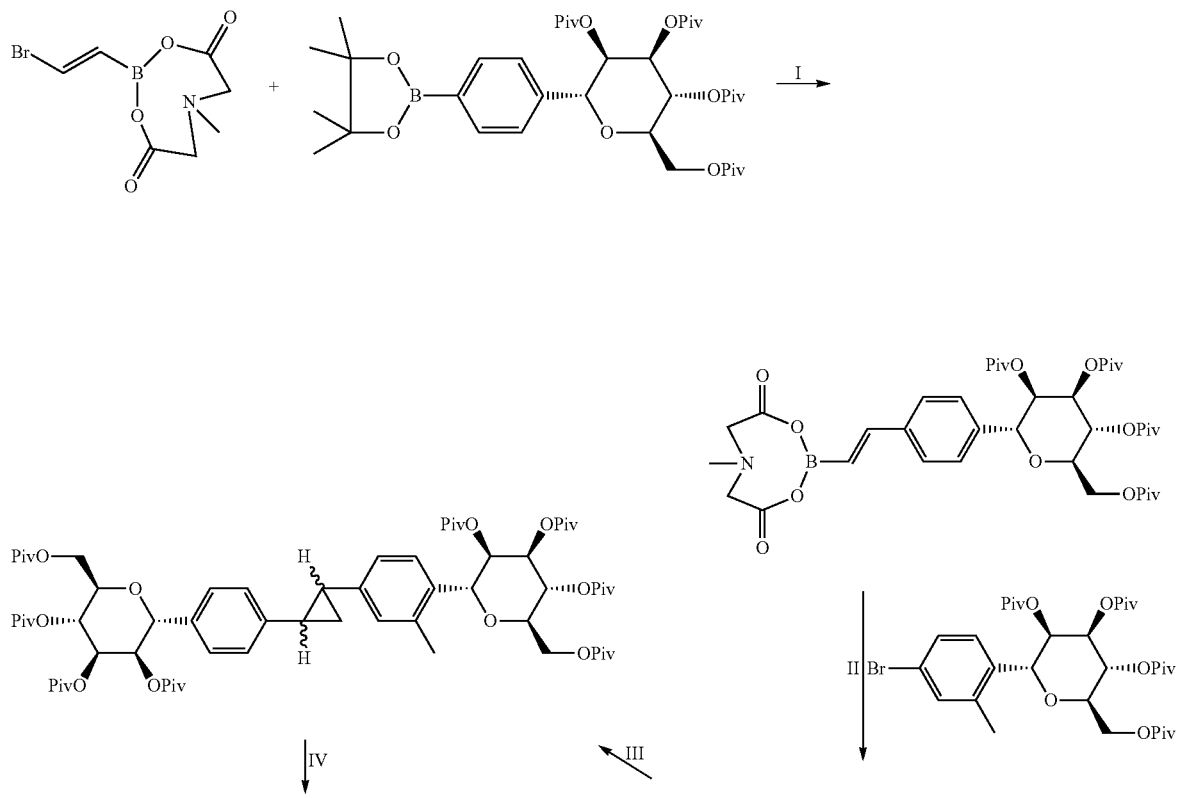

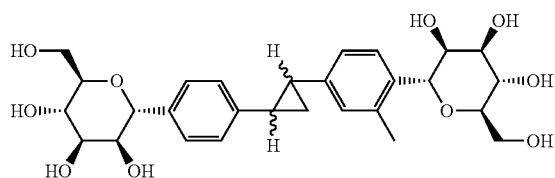 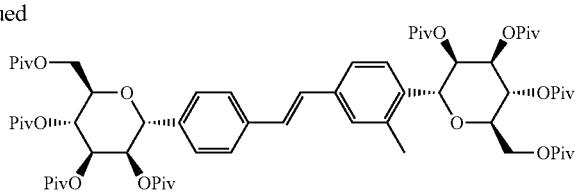

Step I: (2R,3R,4R,5R,6R)-2-(4-((E)-2-(6-methyl-4,8-dioxo-1,3,6,2-dioxazaborocan-2-yl)vinyl)phenyl)-6-((pivaloyloxy)methyl)tetrahydro-2H-pyran-3,4,5-triyl tris(2,2-dimethylpropanoate)

To a vial containing [(2R,3R,4R,5R,6R)-3,4,5-triacetoxy-6-[4-(4,4,5,5-tetramethyl-1,3,2-dioxaborolan-2-yl)phenyl]tetrahydropyran-2-yl]methyl acetate (200 mg, 0.374 mmol), 2-[(E)-2-bromovinyl]-6-methyl-1,3,6,2-dioxazaborocane-4,8-dione (118 mg, 0.449 mmol) is added under a nitrogen atmosphere $C_{34}H_{28}Cl_2FeP_2Pd$ (27.4 mg, 0.0374 mmol) and $K_3PO_4$ (238.4 mg, 1.123 mmol). $CH_3CN$ (5.5 mL) is added and the vial is sealed and allowed to stir at RT for 3 days. The mixture is passed on a silica gel pad, the solvents are removed to afford a crude mixture of the title compound (104 mg, 0.1765 mmol), used as such in the next step.

Step II: (2R,3R,4R,5R,6R)-2-(4-((E)-3-methyl-4-((2R,3R,4R,5R,6R)-3,4,5-tris(pivaloyloxy)-6-((pivaloyloxy)methyl)tetrahydro-2H-pyran-2-yl) styryl)phenyl)-6-((pivaloyloxy)methyl)tetrahydro-2H-pyran-3,4,5-triyl tris(2,2-dimethylpropanoate)

To a vial containing [(2R,3R,4R,5R,6R)-6-(4-bromo-2-methyl-phenyl)-3,4,5-tris(2,2-dimethylpropanoyloxy)tetrahydropyran-2-yl]methyl 2,2-dimethylpropanoate (119.0 mg, 0.1777 mmol), [(2R,3R,4R,5R,6R)-3,4,5-triacetoxy-6-[4-[(E)-2-(6-methyl-4,8-dioxo-1,3,6,2-dioxazaborocan-2-yl)vinyl]phenyl]tetrahydropyran-2-yl]methyl acetate (104.7 mg, 0.1777 mmol), $C_{34}H_{28}Cl_2FeP_2Pd$ (130.0 mg, 0.1777 mmol), $K_3PO_4$ (113.2 mg, 0.5331 mmol) is added under a nitrogen atmosphere in $CH_3CN$ (1.2 mL) and water (251 µL). The vial is sealed and allowed to stir at RT for 24 h. The mixture is passed on a silica pad, ($CH_2Cl_2$ and EtOAc) the solvents are removed and the residue is purified using (0-80%) EtOAc in Hex as solvents to afford the title compound (46.5 mg, 26%).

Step III: [(2R,3R,4R,5R,6R)-3,4,5-tris(2,2-dimethylpropanoyloxy)-6-[4-[(E)-2-[3-methyl-4-[(2R,3R,4R,5R,6R)-3,4,5-tris(2,2-dimethylpropanoyloxy)-6-(2,2-dimethylpropanoyloxymethyl)tetrahydropyran-2-yl]phenyl]vinyl]phenyl]tetrahydropyran-2-yl]methyl 2,2-dimethylpropan To a solution of [(2R,3R,4R,5R,6R)-3,4,5-tris(2,2-dimethylpropanoyloxy)-6-[2-methyl-4-[(E)-2-[4-[(2R,3R,4R,5R,6R)-3,4,5-triacetoxy-6-(acetoxymethyl)tetrahydropyran-2-yl]phenyl]vinyl]phenyl]tetrahydropyran-2-yl]methyl 2,2-dimethylpropanoate (46.0 mg, 0.0450 mmol) and palladium acetate (3.0 mg, 0.014 mmol) in $CH_2Cl_2$ (1.2 mL) at 0° C. is added a solution of diazomethane (9.0 mL of 0.5 M, 4.5 mmol) dropwise and the solution is stirred until complete conversion. LCMS shows complete conversion to product. The resulting mixture is filtered over celite and the filtrate is concentrated under reduced pressure to afford as a crude mixture of the title compound used as such in the next step.

Step IV: Compound 156

The residue is diluted in MeOH (1.4 mL) and MeONa (540 µL of 0.5 M, 0.270 mmol) is added. The solution is allowed to stir for 72 h at RT. AcOH (13 µL, 0.23 mmol) is added, the volatiles are removed under reduced pressure and the residue is purified by reverse-phase HPLC to afford the title compound (4.2 mg, 17%). $^1$H NMR (400 MHz, CD3OD) δ 7.34 (dd, J=18.6, 8.3 Hz, 3H), 7.14 (d, J=8.3 Hz, 2H), 7.01-6.86 (m, J=5.1 Hz, 2H), 5.06 (d, J=6.0 Hz, 1H), 4.94 (d, J=3.2 Hz, 1H), 4.42 (t, J=3.2 Hz, 1H), 4.24 (dd, J=5.8, 3.2 Hz, 1H), 4.01-3.86 (m, J=18.7, 9.0, 5.0 Hz, 2H), 3.79 (t, J=4.6 Hz, 3H), 3.77-3.67 (m, J=16.5, 5.9 Hz, 2H), 3.56 (dd, J=8.3, 3.1 Hz, 1H), 3.50-3.37 (m, 2H), 2.41 (s, 3H), 2.17-2.01 (m, J=14.5, 6.6 Hz, 2H), 1.52-1.29 (m, 2H). LC-MS: m/z=533.52 (M+H$^+$).

Preparation of Compound 158 (Method D)

(2R,3S,4R,5S,6R)-2-[2-[3-benzyl-4-[2-[(2R,3S,4R,5S,6R)-3,4,5-trihydroxy-6-(hydroxymethyl)tetrahydropyran-2-yl]ethynyl]phenyl]ethynyl]-6-(hydroxymethyl)tetrahydropyran-3,4,5-triol

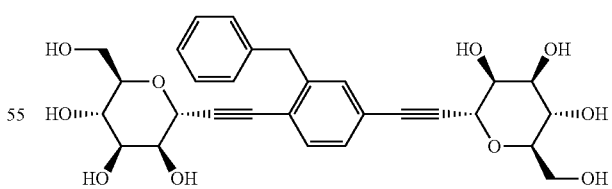

Compound 158 is prepared according to the procedure described for 59. $^1$H NMR (400 MHz, CD3OD) δ 7.46 (d, J=7.9 Hz, 1H), 7.36-7.24 (m, 4H), 7.22-7.14 (m, 3H), 4.94-4.87 (m, 1H), 4.85 (d, J=1.9 Hz, 1H), 4.14 (s, 2H), 4.00-3.97 (m, 1H), 3.97-3.94 (m, 1H), 3.92-3.68 (m, 8H), 3.65 (d, J=8.5 Hz, 1H), 3.60 (d, J=9.3 Hz, 1H). LC-MS: m/z (M+H)$^+$=541.5

287

Preparation of Compound 159 (Method B)

(2R,3S,4R,5S,6R)-2-(hydroxymethyl)-6-[2-methyl-4-[(E)-2-[3-methyl-4-[(2R,3S,4R,5S,6R)-3,4,5-trihydroxy-6-(hydroxymethyl)tetrahydropyran-2-yl]phenyl]vinyl]phenyl]tetrahydropyran-3,4,5-triol

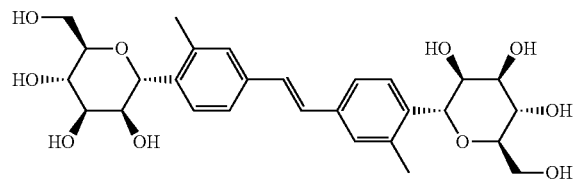 [SMILES: Cc1cc(/C=C/c2ccc([C@H]3O[C@H](CO)[C@@H](O)[C@H](O)[C@@H]3O)c(C)c2)ccc1[C@H]1O[C@H](CO)[C@@H](O)[C@H](O)[C@@H]1O]

Compound 159 is prepared according to the procedure described for 156. ¹H NMR (400 MHz, CD3OD) δ 7.43 (d, J=8.0 Hz, 2H), 7.37 (d, J=10.8 Hz, 4H), 7.11 (s, 2H), 5.09 (d, J=6.2 Hz, 2H), 4.24 (dd, J=6.2, 3.2 Hz, 2H), 4.04-3.92 (m, J=11.9, 7.5 Hz, 4H), 3.82 (t, J=5.4 Hz, 2H), 3.74 (dd, J=11.9, 3.6 Hz, 2H), 3.58-3.50 (m, 2H), 2.46 (s, 6H).

288

Preparation of Compound 160 (Method B)

(2R,3S,4R,5S,6R)-2-(hydroxymethyl)-6-[2-methyl-4-[2-[3-methyl-4-[(2R,3S,4R,5S,6R)-3,4,5-trihydroxy-6-(hydroxymethyl)tetrahydropyran-2-yl]phenyl]cyclopropyl]phenyl]tetrahydropyran-3,4,5-triol

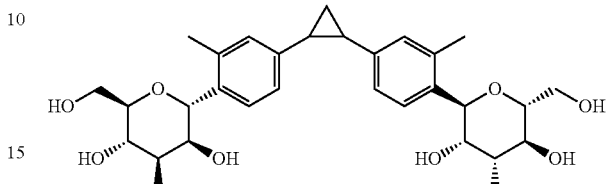

Compound 160 is prepared according to the procedure described for 156. (400 MHz, CD3OD) δ 7.37-7.27 (m, J=8.6 Hz, 2H), 6.99-6.89 (m, J=4.7 Hz, 4H), 5.06 (d, J=5.9 Hz, 2H), 4.24 (dd, J=5.8, 3.3 Hz, 2H), 4.01-3.87 (m, J=18.7, 9.0, 5.1 Hz, 4H), 3.79 (t, J=5.8 Hz, 2H), 3.73 (dd, J=11.8, 3.6 Hz, 2H), 3.49-3.41 (m, 2H), 2.41 (s, 6H), 2.12-2.02 (m, J=7.3 Hz, 2H), 1.44-1.34 (m, 2H).

Preparation of Compound 162 (Method D)

(2R,2'R,3S,3'S,4R,4'R,5S,5'S,6R,6'R)-6,6'-((2',3',5',6'-tetrahydrospiro[fluorene-9,4'-pyran]-2,7-diyl)bis(ethyne-2,1-diyl))bis(2-(hydroxymethyl)tetrahydro-2H-pyran-3,4,5-triol)

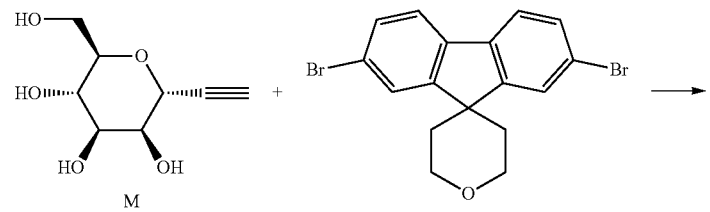

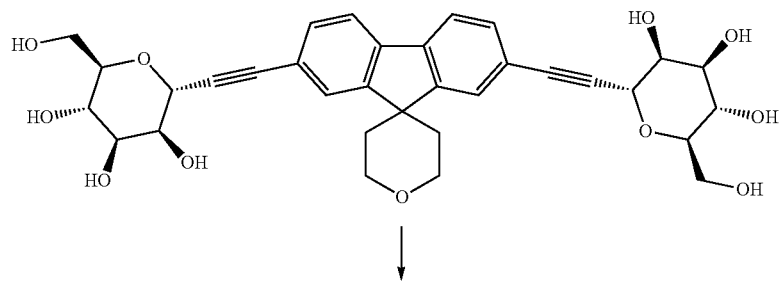

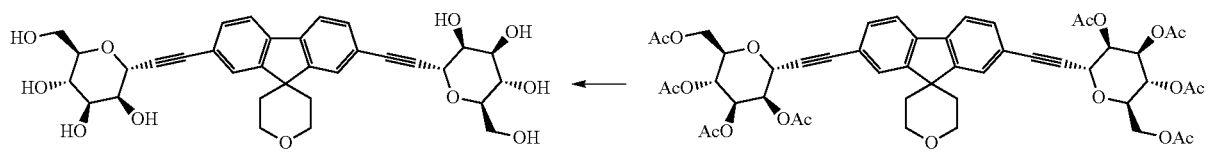

Step I: Compound 162 Crude

A mixture of 2,7-dibromospiro[fluorene-9,4'-tetrahydropyran] (12.00 g, 30.45 mmol) and Intermediate M (16.02 g, 85.14 mmol) in DMF (168.0 mL) is degassed for 5 minutes by bubbling nitrogen in the reaction mixture. $Pd(dppf)Cl_2$—$CH_2Cl_2$ (1.680 g, 2.296 mmol) and CuI (1.685 g, 8.849 mmol are added and nitrogen is bubbled one more time in the reaction mixtures for 5 minutes. Diisopropyl ethyl amine (42.0 mL, 241 mmol) is then added and the final mixture is stirred under nitrogen atmosphere at 100° C. for 1 h. The resulting reaction mixture is cooled to 35° C. and water (336.0 mL) is added dropwise. The resulting deep red mixture is stirred overnight at RT and the resulting precipitate is filtered (ML1), washed with 100 ml of water. The resulting crude orange solid is transferred in a 250 ml RBF and triturated in 60 ml of ethanol for 30 minutes. The resulting solid is isolated by filtration and dried in a vacuum oven overnight at 45° C. To further purify the title compound, the latter is per-acetylated (Step 2), submitted to flash chromatography and de-acetylated (Step 3).

Step II: [(2R,3R,4R,5R,6R)-3,4,5-triacetoxy-6-[2-[7-[2-[(2R,3R,4R,5R,6R)-3,4,5-triacetoxy-6-(acetoxymethyl)tetrahydropyran-2-yl]ethynyl]spiro[fluorene-9,4'-tetrahydropyran]-2-yl]ethynyl]tetrahydropyran-2-yl]methyl acetate To the crude solid from Step 1 (13.77 g) is added DMAP (276 mg, 2.26 mmol) and pyridine (69 mL). The resulting mixture (brown suspension) is cooled to 0° C. in an ice/water bath and $Ac_2O$ (25.6 mL, 271 mmol) is added dropwise over 10 minutes keeping temperature below 20° C. The reaction mixture is then stirred at RT for one h. The resulting dark brown solution is diluted with $CH_2Cl_2$ (100 mL) and water (75 mL), stirred for 15 min, then 2N HCl (~475 mL) is added and stirred for 5 min with ice/water bath to control exotherm. The aqueous solution is separated, back-extracted with $CH_2Cl_2$ (2×75 mL) and the combined organic extracts are washed once again with 2N HCl (75 mL, added brine to help separation), dried over $Na_2SO_4$, filtered and concentrated to afford 20.78 g of an orange glassy solid. The solid is dissolved in a minimum amount of $CH_2Cl_2$, adsorbed on 75 ml of silica gel and purified using Biotage™ SNAP 340 g silica cartridge, using a gradient of Hex/EtOAC (100% Hex 1 CV, 0-85% EA/hex 16 CV, 85% EA/hex 4 CV). The fractions containing the desired compound are combined and treated with 4.5 g of SiliaMet® Thiol overnight at RT to remove traces of palladium. The resulting mixture is the filtered and concentrated to dryness to yield 16.87 g of the title compound.

Step III: Compound 162

[(2R,3R,4R,5R,6R)-3,4,5-triacetoxy-6-[2-[7-[2-[(2R,3R,4R,5R,6R)-3,4,5-triacetoxy-6-(acetoxymethyl)tetrahydropyran-2-yl]ethynyl]spiro[fluorene-9,4'-tetrahydropyran]-2-yl]ethynyl]tetrahydropyran-2-yl]methyl acetate. From Step II (15.37 g, 16.27 mmol) is dissolved in MeOH (344 mL) and MeONa (290 µL of 25% w/w, 1.30 mmol in MeOH) is added. Final pH reached is 9. The reaction is stirred at RT for 18 h. The resulting suspension (white solid) is filtered and the solid washed with 8 volumes of MeOH. The white solid is dried in a vacuum oven at 40° C. overnight to afford the title compound as a beige solid (9.38 g, 15.03 mmol) containing 1.6% of a mono-acetate impurity. $^1$H NMR (400 MHz, DMSO) δ 7.94 (d, J=7.9 Hz, 2H), 7.88 (d, J=1.4 Hz, 2H), 7.50 (dd, J=7.8, 1.3 Hz, 2H), 4.98 (d, J=4.3 Hz, 2H), 4.81 (d, J=5.9 Hz, 2H), 4.78-4.67 (m, 4H), 4.50 (t, J=6.0 Hz, 2H), 4.09 (q, J=5.2 Hz, OH), 4.00 (dd, J=7.1, 3.8 Hz, 4H), 3.89-3.80 (m, 2H), 3.80-3.65 (m, 4H), 3.60 (ddd, J=8.8, 6.3, 2.0 Hz, 2H), 3.48 (dt, J=12.0, 6.2 Hz, 2H), 3.40 (td, J=9.3, 5.9 Hz, 2H), 3.16 (d, J=5.3 Hz, OH), 2.03 (s, OH), 1.81 (dd, J=7.3, 3.8 Hz, 4H). LC-MS: m/z=609.57 (M+H)$^+$

Preparation of Compounds 161, 162 and 164

Compounds 161, 162 and 164 are prepared according to the procedure described for 120 using commercially available dibromo fluorene derivatives

| Compound | IUPAC name | $^1$H-NMR | LCMS m/z (M + H)$^+$ |
|---|---|---|---|
| 161 | (2R,3S,4R,5S,6R)-2-[2-[5,5-dioxo-7-[2-[(2R,3S,4R,5S,6R)-3,4,5-trihydroxy-6-(hydroxymethyl)tetrahydropyran-2-yl]ethynyl]dibenzothiophen-3-yl]ethynyl]-6-(hydroxymethyl)tetrahydropyran-3,4,5-triol | N/A | 589.16 |
| 163 | 2,7-bis[2-[(2R,3S,4R,5S,6R)-3,4,5-trihydroxy-6-(hydroxymethyl)tetrahydropyran-2-yl]ethynyl]fluoren-9-one oxime | (400 MHz, CD3OD) δ 8.48 (d, J = 33.2 Hz, 1H), 7.84-7.66 (m, 3H), 7.52 (dd, J = 27.9, 7.7 Hz, 2H), 4.87 (s, 2H), 4.05-4.00 (m, 2H), 3.98-3.92 (m, 2H), 3.91-3.80 (m, 4H), 3.73 (dd, J = 11.5, 5.7 Hz, 2H), 3.63 (t, J = 9.4 Hz, 2H). | 568.43 |
| 164 | (2R,3S,4R,5S,6R)-2-(hydroxymethyl)-6-[2-[9-phenyl-6-[2-[(2R,3S,4R,5S,6R)-3,4,5-trihydroxy-6-(hydroxymethyl)tetrahydropyran-2-yl]ethynyl]carbazol-3-yl]ethynyl]tetrahydropyran-3,4,5-triol | (400 MHz, CD3OD) δ 8.31 (s, 2H), 7.71-7.64 (m, 2H), 7.59-7.48 (m, 5H), 7.31 (d, J = 8.6 Hz, 2H), 4.87 (s, 2H), 4.07-3.97 (m, 4H), 3.88 (d, J = 9.9 Hz, 4H), 3.75 (dd, J = 11.9, 6.2 Hz, 2H), 3.70-3.61 (m, 2H). | 616.43 |

Preparation of Compounds 165 to 170

Compounds 165 to 170 are prepared according to the procedure described for 113 using the appropriate Intermediates.

| Compound/ Intermediate | IUPAC name | ¹H-NMR | LCMS m/z (M + H)⁺ |
|---|---|---|---|
| 165 | (2R,3S,4R,5S,6R)-2-[2-[9-hydroxy-9-isopropyl-7-[2-[(2R,3S,4R,5S,6R)-3,4,5-trihydroxy-6-(hydroxymethyl)tetrahydropyran-2-yl]ethynyl]fluoren-2-yl]ethynyl]-6-(hydroxymethyl)tetrahydropyran-3,4,5-triol | (400 MHz, CD3OD) δ 7.67 (d, J = 7.6 Hz, 2H), 7.55 (s, 2H), 7.47 (d, J = 7.7 Hz, 2H), 4.59 (s, 2H), 4.01 (s, 2H), 3.95 (d, J = 9.1 Hz, 2H), 3.90-3.79 (m, 4H), 3.73 (dd, J = 11.7, 5.6 Hz, 2H), 3.63 (t, J = 9.5 Hz, 2H), 2.41 (dt, J = 13.7, 6.8 Hz, 1H), 0.76 (d, J = 6.7 Hz, 6H). | 597.32 |
| 166 | (2R,3S,4R,5S,6R)-2-[2-[9-ethyl-9-hydroxy-7-[2-[(2R,3S,4R,5S,6R)-3,4,5-trihydroxy-6-(hydroxymethyl)tetrahydropyran-2-yl]ethynyl]fluoren-2-yl]ethynyl]-6-(hydroxymethyl)tetrahydropyran-3,4,5-triol | (400 MHz, CD3OD) δ 7.68 (d, J = 7.7 Hz, 2H), 7.55 (s, 2H), 7.47 (d, J = 7.8 Hz, 2H), 4.59 (s, 2H), 4.05-3.99 (m, 2H), 3.95 (dd, J = 9.3, 3.2 Hz, 2H), 3.91-3.79 (m, 4H), 3.73 (dd, J = 11.6, 5.7 Hz, 2H), 3.63 (t, J = 9.4 Hz, 2H), 2.15 (dd, J = 15.3, 7.9 Hz, 2H), 0.42 (t, J = 7.3 Hz, 3H). | 583.31 |
| 167 | (2R,3S,4R,5S,6R)-2-(hydroxymethyl)-6-[2-[9-hydroxy-9-phenyl-7-[2-[(2R,3S,4R,5S,6R)-3,4,5-trihydroxy-6-(hydroxymethyl)tetrahydropyran-2-yl]ethynyl]fluoren-2-yl]ethynyl]tetrahydropyran-3,4,5-triol | (400 MHz, CD3OD) δ 7.75 (d, J = 7.9 Hz, 2H), 7.47 (d, J = 7.9 Hz, 2H), 7.32-7.18 (m, 7H), 4.82 (d, J = 2.0 Hz, 2H), 3.98-3.94 (m, 2H), 3.91-3.80 (m, 4H), 3.79-3.73 (m, 2H), 3.69 (dd, J = 11.5, 6.0 Hz, 2H), 3.58 (t, J = 9.4 Hz, 2H). | 631.19 |
| 168 | (2R,3S,4R,5S,6R)-2-(hydroxymethyl)-6-[2-[9-hydroxy-9-propyl-7-[2-[(2R,3S,4R,5S,6R)-3,4,5-trihydroxy-6-(hydroxymethyl)tetrahydropyran-2-yl]ethynyl]fluoren-2-yl]ethynyl]tetrahydropyran-3,4,5-triol | (400 MHz, CD3OD) δ 7.67 (d, J = 7.8 Hz, 2H), 7.55 (s, 2H), 7.47 (d, J = 8.0 Hz, 2H), 4.59 (s, 2H), 4.02 (d, J = 2.6 Hz, 2H), 3.95 (d, J = 9.0 Hz, 2H), 3.90-3.80 (m, 4H), 3.73 (dd, J = 11.6, 5.7 Hz, 2H), 3.63 (t, J = 9.4 Hz, 2H), 2.13-2.05 (m, 2H), 0.74 (s, 5H). | 597.32 |
| 169 | (2R,3S,4R,5S,6R)-2-[2-[9-hydroxy-9-isobutyl-7-[2-[(2R,3S,4R,5S,6R)-3,4,5-trihydroxy-6-(hydroxymethyl)tetrahydropyran-2-yl]ethynyl]fluoren-2-yl]ethynyl]-6-(hydroxymethyl)tetrahydropyran-3,4,5-triol | (400 MHz, CD3OD) δ 7.68 (d, J = 7.9 Hz, 2H), 7.56 (s, 2H), 7.48 (dd, J = 7.9, 1.4 Hz, 2H), 4.88 (s, 2H), 4.02 (t, J = 2.6 Hz, 2H), 3.95 (dt, J = 9.3, 3.3 Hz, 2H), 3.90-3.80 (m, 4H), 3.73 (dd, J = 11.5, 5.6 Hz, 2H), 3.63 (t, J = 9.5 Hz, 2H), 2.12 (d, J = 6.0 Hz, 2H), 0.95 (td, J = 13.0, 6.6 Hz, 1H), 0.51 (d, J = 6.7 Hz, 6H). | 611.4 |
| 170 | (2R,3S,4R,5S,6R)-2-[2-[9-hydroxy-9-(3-methoxyphenyl)-7-[2-[(2R,3S,4R,5S,6R)-3,4,5-trihydroxy-6-(hydroxymethyl)tetrahydropyran-2-yl]ethynyl]fluoren-2-yl]ethynyl]-6-(hydroxymethyl)tetrahydropyran-3,4,5-triol | (400 MHz, CD3OD) δ 7.74 (d, J = 7.9 Hz, 2H), 7.47 (d, J = 7.9 Hz, 2H), 7.30 (s, 2H), 7.13 (t, J = 8.1 Hz, 1H), 6.96 (d, J = 1.5 Hz, 1H), 6.78 (dd, J = 8.0, 2.2 Hz, 1H), 6.67 (d, J = 7.8 Hz, 1H), 4.83 (s, 2H), 3.99-3.94 (m, 2H), 3.92-3.80 (m, 4H), 3.79-3.65 (m, 7H), 3.58 (t, J = 9.5 Hz, 2H). | 661.19 |

293

Preparation of Compound 171 (Method D)

(2R,3S,4R,5S,6R)-2-(hydroxymethyl)-6-[2-[7-[2-[(2R,3S,4R,5S,6R)-3,4,5-trihydroxy-6-(hydroxymethyl)tetrahydropyran-2-yl]ethynyl]-1H-indazol-4-yl]ethynyl]tetrahydropyran-3,4,5-triol

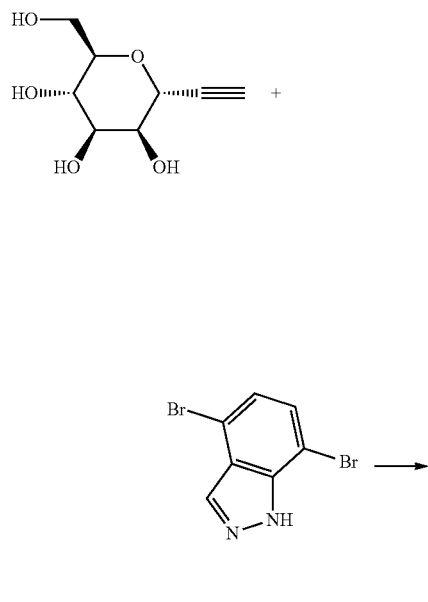

To a reaction tube charged with commercially available 4,7-dibromo-1H-indazole (35.0 mg, 0.127 mmol) and Pd(PPh$_3$)$_4$ (18.0 mg, 0.0156 mmol), capped and degassed (vacuum then nitrogen flush, twice) is added Intermediate M as a solution in DMF (500 µL of 0.53 M, 0.265 mmol and DIPEA (500 µL). The reaction tube is degassed again, transferred to a preheated (80° C.) oil bath and stirred for 48 h. After cooling down to RT, the reaction mixture is passed through a 200 mg Si-DMT cartridge, rinsed with portions of MeOH and purified by reverse phase HPLC. The fraction is freeze-dried, providing the title compound (12.6 mg, 20% yield) as a fluffy white solid. $^1$H NMR (400 MHz, CD3OD) δ 8.21 (s, 1H), 7.50 (d, J=7.5 Hz, 1H), 7.28 (d, J=7.5 Hz, 1H), 5.02 (d, J=2.1 Hz, 1H), 5.00 (d, J=2.0 Hz, 1H), 4.16-4.08 (m, 2H), 4.04-3.83 (m, 6H), 3.82-3.72 (m, 2H), 3.71-3.59 (m, 2H). ESI-MS m/z: 491.44 (M+1)$^+$

294

Preparation of Compound 172

1,4-bis[3-methyl-4-[(2R,3 S,4R,5S,6R)-3,4,5-trihydroxy-6-(hydroxymethyl)tetrahydropyran-2-yl]phenyl]piperazine-2,5-dione

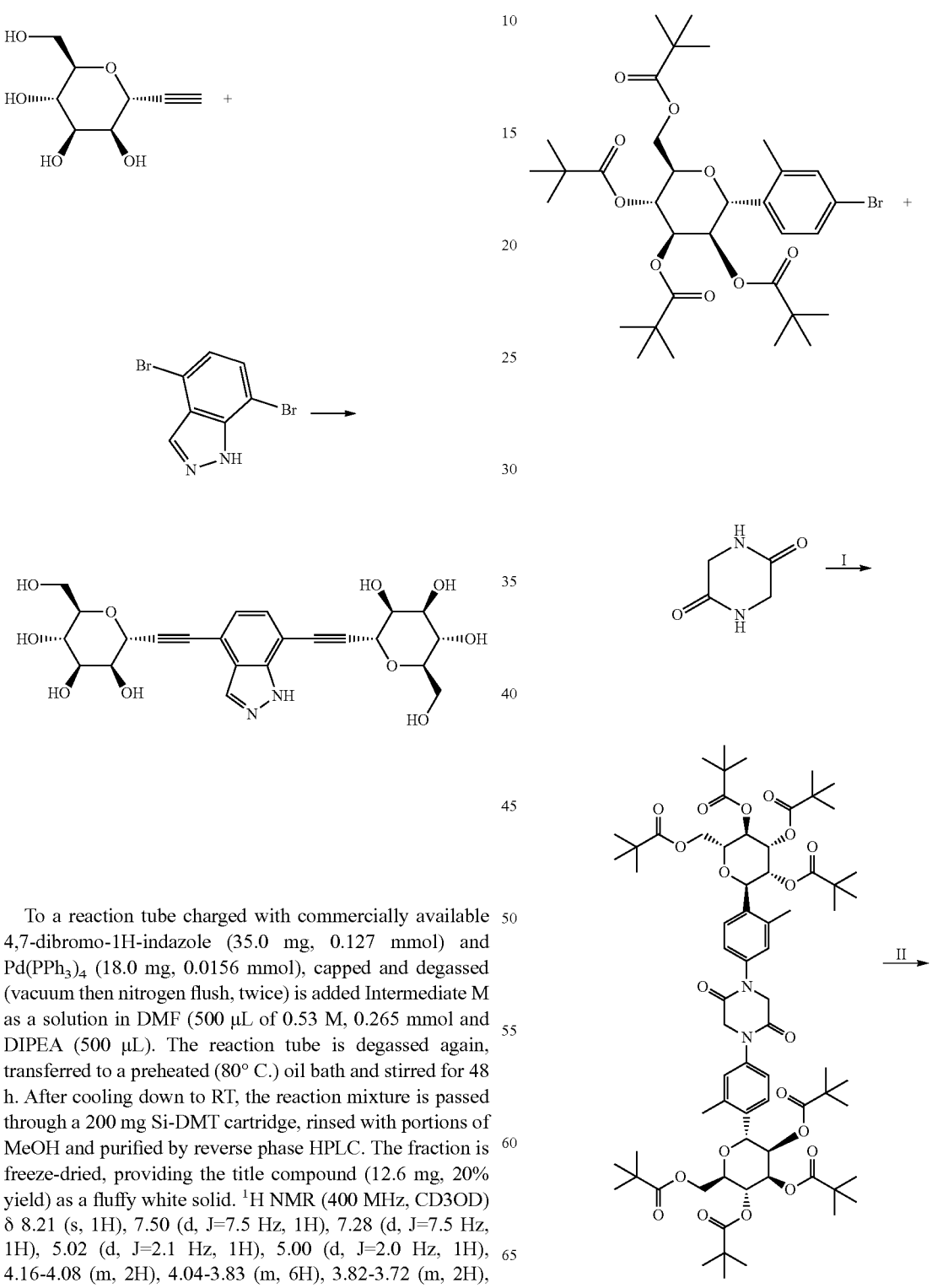

-continued

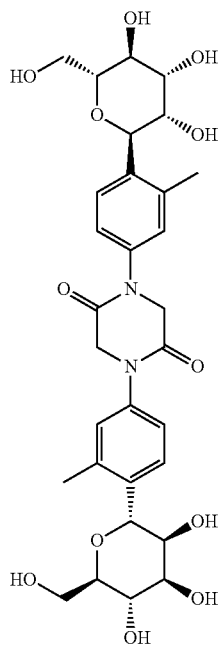 [SMILES: Cc1cc(N2CC(=O)N(c3ccc([C@H]4O[C@H](CO)[C@@H](O)[C@H](O)[C@@H]4O)c(C)c3)CC2=O)ccc1[C@H]1O[C@H](CO)[C@@H](O)[C@H](O)[C@@H]1O]

Step I: [(2R,3R,4R,5R,6R)-3,4,5-tris(2,2-dimethyl-propanoyloxy)-6-[2-methyl-4-[4-[3-methyl-4-[(2R,3R,4R,5R,6R)-3,4,5-tris(2,2-dimethylpropanoyloxy)-6-(2,2-dimethylpropanoyloxymethyl)tetrahydropyran-2-yl]phenyl]-2,5-dioxo-piperazin-1-yl]phenyl]tetrahydropyran-2-yl]

To a reaction tube loaded with Intermediate Q (213 mg, 0.318 mmol), piperazine-2,5-dione (12.6 mg, 0.110 mmol), CuI (7.8 mg, 0.0410 mmol) and $K_2CO_3$ (50.0 mg, 0.362 mmol), capped and degassed (vacuum then nitrogen flush, 3×) is added degassed DMF (1 mL) followed by N,N'-dimethylethane-1,2-diamine (8.0 µL, 0.075 mmol). The reaction tube is degassed again and transferred to a preheated (110° C.) oil bath and stirred overnight. The reaction mixture is cooled down to RT, diluted with EtOAc (5 mL), and washed sequentially with saturated aqueous $NH_4Cl$ solution (2×5 mL), $H_2O$ (2 mL), brine (2 mL), dried over $Na_2SO_4$ and passed through a 500 mg silica cartridge using EtOAc. The filtrate is concentrated then purified by flash chromatography on a Biotage™ SNAP 10 g silica cartridge, using a gradient of EtOAc in Hex, 0-100% as eluent. The fractions are combined and concentrated to provide the title compound (40 mg, 28% yield) as a white crystalline solid.

Step II: Compound 172

To a solution of the intermediate from Step I above (38.0 mg, 0.0294 mmol) in MeOH (1.4 mL) is added a solution of MeONa in MeOH (90 µL of 0.5 M, 0.0450 mmol). The reaction mixture is stirred at 60° C. for 4 h, then passed through a prewashed (MeOH) 1 g SCX-2 cartridge, washing with portions of MeOH (3×1 mL). The combined filtrates are concentrated, redissolved in a $H_2O$/MeCN mixture (20% MeCN) and freeze-dried, affording the title compound (19 mg, 96% yield) as a fluffy white solid. $^1$H NMR (400 MHz, CD3OD) δ 7.60 (d, J=9.1 Hz, 2H), 7.30-7.21 (m, 4H), 5.12 (d, J=7.0 Hz, 2H), 4.52 (s, 4H), 4.20 (dd, J=7.0, 3.2 Hz, 2H), 4.05 (dd, J=11.9, 7.4 Hz, 2H), 4.00 (dd, J=5.4, 3.3 Hz, 2H), 3.88-3.81 (m, 2H), 3.75 (dd, J=11.9, 3.8 Hz, 2H), 3.63 (dt, J=7.6, 3.9 Hz, 2H), 2.50 (s, 6H). ESI-MS m/z: 619.6 (M+1)$^+$ Preparation of Compounds 173 and 174

Compounds 173 and 174 are prepared according to the procedure described for 59 using commercially available starting material. Reaction mixtures are stirred 1 h at 100° C.

| Compound | IUPAC name | $^1$H-NMR | LCMS m/z (M + H)$^+$ |
|---|---|---|---|
| 173 | (2R,3S,4R,5S,6R)-2-[2-[9-[3-(dimethylamino)-2-hydroxy-propyl]-6-[2-[(2R,3S,4R,5S,6R)-3,4,5-trihydroxy-6-(hydroxymethyl)tetrahydropyran-2-yl]ethynyl]carbazol-3-yl]ethynyl]-6-(hydroxymethyl)tetrahydropyran-3,4,5-triol | (400 MHz, CD3OD) δ 8.24 (s, 2H), 7.63-7.53 (m, 4H), 4.89 (s, 2H), 4.44-4.34 (m, 3H), 4.01 (ddd, J = 12.5, 6.2, 2.7 Hz, 4H), 3.88 (ddd, J = 9.4, 4.3, 2.1 Hz, 4H), 3.75 (dd, J = 12.2, 6.3 Hz, 2H), 3.65 (t, J = 9.3 Hz, 2H), 2.72 (s, 6H). | 641.36 |
| 174 | (2R,3S,4R,5S,6R)-2-[2-[9-(2,3-dihydroxypropyl)-6-[2-(2R,3S,4R,5S,6R)-3,4,5-trihydroxy-6-(hydroxymethyl)tetrahydropyran-2-yl]ethynyl]carbazol-3-yl]ethynyl]-6-(hydroxymethyl)tetrahydropyran-3,4,5-triol | (400 MHz, CD3OD) δ 8.22 (d, J = 1.2 Hz, 2H), 7.55 (dt, J = 8.5, 4.9 Hz, 4H), 4.88 (s, 2H), 4.42 (ddd, J = 22.6, 14.6, 5.8 Hz, 1H), 4.05-3.99 (m, 5H), 3.89 (ddd, J = 9.1, 5.5, 2.2 Hz, 4H), 3.75 (dd, J = 12.3, 6.3 Hz, 2H), 3.65 (t, J = 9.2 Hz, 2H), 3.57 (dd, J = 5.5, 2.1 Hz, 2H), 3.46 (dt, J = 3.2, 1.5 Hz, 1H). | 614.32 |

Preparation of Compound 175 (Method D)

Ethyl 2-[2,7-bis[2-[(2R,3S,4R,5S,6R)-3,4,5-trihydroxy-6-(hydroxymethyl)tetrahydropyran-2-yl]ethynyl]carbazol-9-yl]acetate

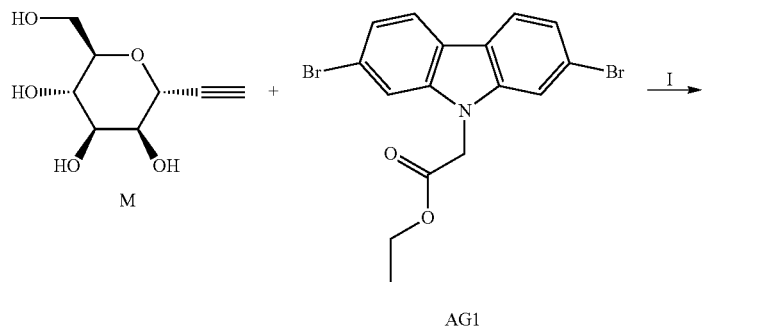

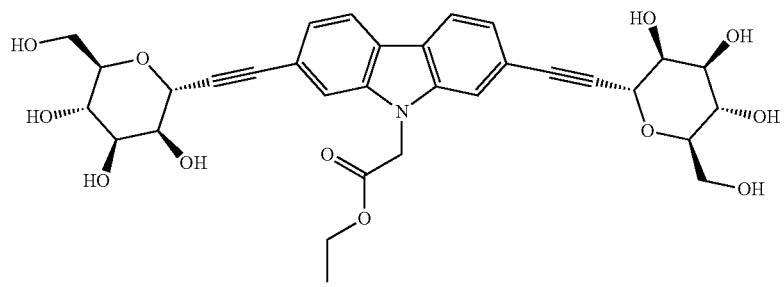

Step I: Compound 175

To a mixture of Intermediates AG1 (200 mg, 0.49 mmol) and M (1.96 mL of 0.53 M, 1.036 mmol), Pd(dppf)Cl$_2$—CH$_2$Cl$_2$ (26.2 mg, 0.032 mmol), CuI (27.8 mg, 0.146 mmol) in DMF (800.0 µL) is degassed (vacuum/N$_2$). To the resulting mixture is added DIPEA (678 µL, 3.89 mmol), degassed. The reaction mixture is heated at 100° C. for 2 h 45 min under N$_2$, concentrated under high vacuum, dissolved in DMSO (1.5 mL), loaded onto C18 Samplet, The residue is purified on 50 g C-18 silica gel cartridge on Isolera™ purification system with a gradient of CH$_3$CN in water (10%-45%, 12.5 CV) as eluent to afford after concentrating the title compound (140 mg, 42%) as light yellow solid. $^1$H NMR (400 MHz, CD$_3$OD) δ 8.06 (d, J=8.1 Hz, 2H), 7.57 (s, 2H), 7.32 (dd, J=8.1, 1.2 Hz, 2H), 5.20 (s, 2H), 4.89 (d, J=2.1 Hz, 2H), 4.20 (q, J=7.1 Hz, 2H), 4.03 (dd, J=3.2, 2.2 Hz, 2H), 3.98 (dd, J=9.3, 3.3 Hz, 2H), 3.91-3.84 (m, 4H), 3.78-3.71 (m, 2H), 3.64 (t, J=9.5 Hz, 2H), 1.24 (t, J=7.1 Hz, 3H). ESI-MS m/z calc. 625.21594, found 626.56 (M+1)$^+$.

Preparation of Compound 176 (Method D)

2-[2,7-Bis[2-[(2R,3S,4R,5S,6R)-3,4,5-trihydroxy-6-(hydroxymethyl)tetrahydropyran-2-yl]ethynyl]carbazol-9-yl]acetic acid

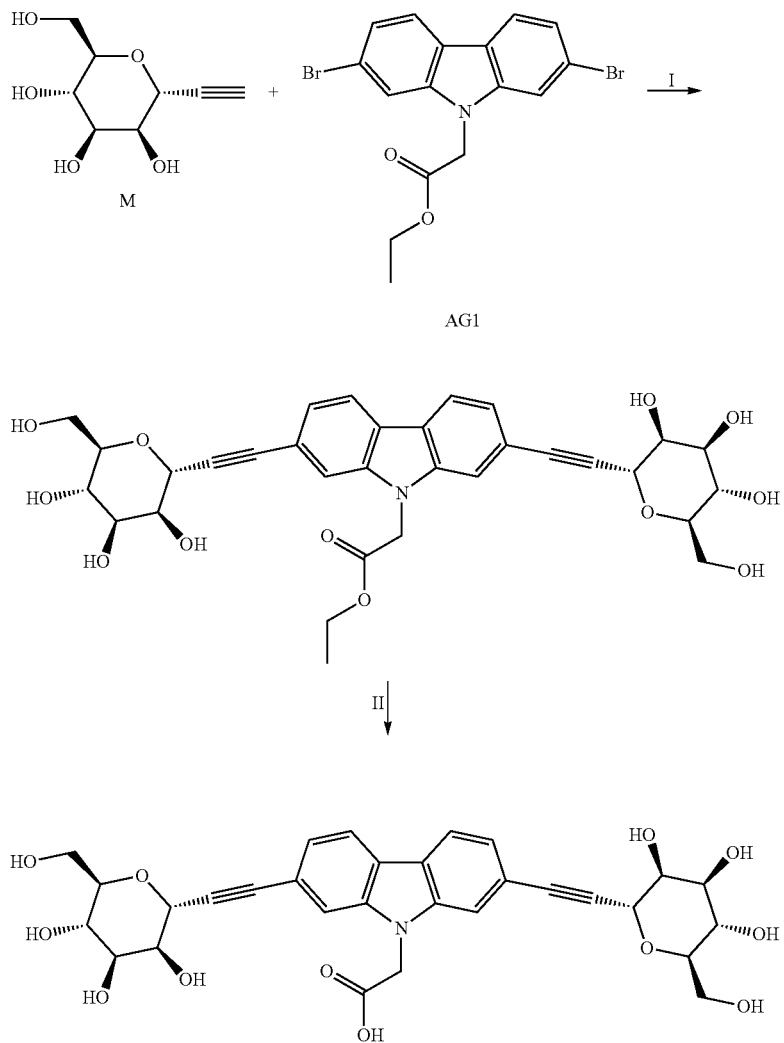

Step I: Compound 176

To mixture of ethyl 2-[2,7-bis[2-[(2R,3S,4R,5S,6R)-3,4,5-trihydroxy-6-(hydroxymethyl)tetrahydropyran-2-yl]ethynyl]carbazol-9-yl]acetate (Compound 175, 140 mg, 0.205 mmol) in EtOH (2 mL) and $H_2O$ (1.5 mL) is added aqueous NaOH (250 μL of 10% w/v, 0.6250 mmol). The final mixture is heated in a sealed tube at 80° C. for 1 h (LC-MS showed clean product). Reaction mixture is quenched with DOWEX 50WX4 hydrogen form resin until pH 4-5, it formed the gel, diluted with water-methanol (10 mL) until the gel is dissolved, filtered off, concentrated, dissolved in water and $CH_3CN$, lyophilized to afford the title compound (112 mg, 88.7%) as light yellow solid. $^1H$ NMR (400 MHz, $CD_3OD$) δ 8.04 (d, J=8.1 Hz, 2H), 7.56 (s, 2H), 7.29 (d, J=8.1 Hz, 2H), 4.06-3.96 (m, 4H), 3.92-3.82 (m, 4H), 3.80-3.70 (m, 2H), 3.64 (t, J=9.3 Hz, 2H), 2.64 (s, 4H). (C1-H protons are underneath of water peak). ESI-MS m/z calc. 597.18463, found 598.59 $(M+1)^+$.

Preparation of Compound 177 (Method D)

2-[2,7-bis[2-[(2R,3S,4R,5S,6R)-3,4,5-trihydroxy-6-(hydroxymethyl)tetrahydropyran-2-yl]ethynyl]carbazol-9-yl]-N-[2-(4-methylpiperazin-1-yl)ethyl]acetamide

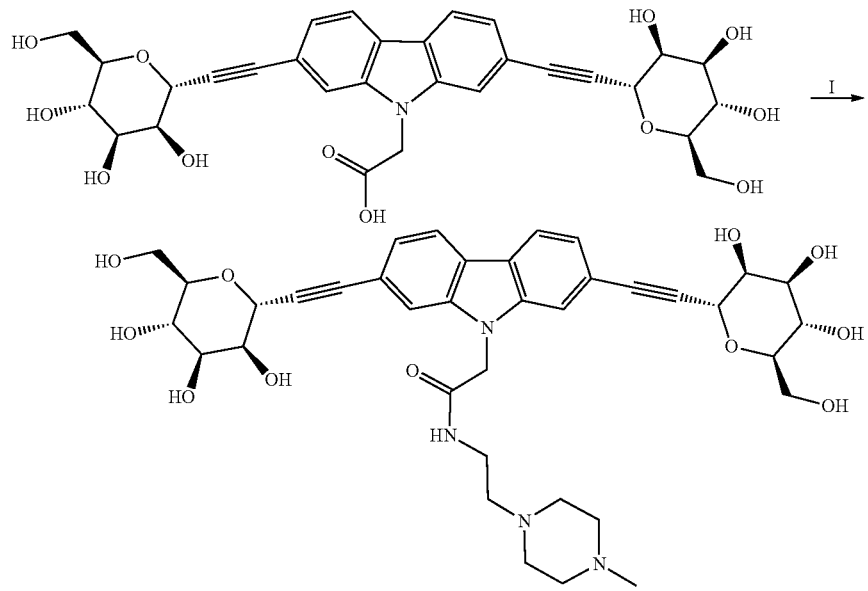

To a stirred solution of 2-(4-methylpiperazin-1-yl)ethanamine (7.7 mg, 0.054 mmol) and Et$_3$N (20 µL) in DMF (0.3 mL) is added a premixed solution of Compound 176 and HATU (23 mg, 0.061 mmol) in DMF (0.4 mL). Reaction mixture is stirred at RT for 3 h and the mixture is purified directly by reverse phase HPLC to afford the title compound (16 mg, 40% yield). $^1$H NMR (400 MHz, CD$_3$OD) δ 8.38 (brs, 1H), 8.11 (d, J=8.1 Hz, 2H), 7.63 (s, 2H), 7.36 (dd, J=8.1, 1.2 Hz, 2H), 5.04 (s, 2H), 4.90 (d, J=2.1 Hz, 2H), 4.03 (dd, J=3.2, 2.2 Hz, 2H), 3.96 (dd, J=9.3, 3.3 Hz, 2H), 3.91-3.81 (m, 4H), 3.73 (dd, J=11.3, 5.8 Hz, 2H), 3.63 (t, J=9.4 Hz, 2H), 2.64 (s, 3H), 2.46 (t, J=6.0 Hz, 2H). $^1$H NMR (400 MHz, DMSO-D$_6$) δ 8.17 (d, J=8.1 Hz, 2H), 8.08 (t, J=5.6 Hz, 1H), 7.64 (s, 2H), 7.30-7.25 (m, 2H), 5.06 (s, 2H), 4.76 (d, J=2.0 Hz, 2H), 3.83 (s, 2H), 3.77-3.65 (m, 4H), 3.63-3.55 (m, 2H), 3.46 (dd, J=11.7, 6.2 Hz, 2H), 3.39 (t, J=9.3 Hz, 2H), 3.16 (dd, J=12.1, 6.2 Hz, 2H), 2.40-2.16 (m, 10H), 2.11 (s, 3H). ESI-MS m/z calc. 722.3163, found 723.71 (M+1)$^+$.

Preparation of Compounds 178 to 181

Compounds 178 to 181 are prepared according to the procedure described for 177 using appropriate commercially available starting material.

| Compound | IUPAC name | $^1$H-NMR | LCMS m/z (M + H)$^+$ |
|---|---|---|---|
| 178 | 2-[2,7-bis[2-[(2R,3S,4R,5S,6R)-3,4,5-trihydroxy-6-(hydroxymethyl)tetrahydropyran-2-yl]ethynyl]carbazol-9-yl]-N-(2-morpholinoethyl)acetamide | (400 MHz, CD$_3$OD) δ 8.10 (d, J = 8.1 Hz, 2H), 7.60 (s, 2H), 7.35 (d, J = 8.1 Hz, 2H), 5.06 (s, 2H), 4.89 (d, J = 2.1 Hz, 2H), 4.05-4.00 (m, 2H), 3.96 (dd, J = 9.3, 3.2 Hz, 2H), 3.91- | 710.69 |

-continued

| Compound | IUPAC name | ¹H-NMR | LCMS m/z (M + H)⁺ |
|---|---|---|---|
|  |  | 3.82 (m, 4H), 3.74 (dd, J = 11.8, 6.0 Hz, 2H), 3.69-3.59 (m, 6H), 3.50-3.40 (m, 2H), 2.81 (s, 6H). [1] |  |
| 179 | 2-[2,7-bis[2-[(2R,3S,4R,5S,6R)-3,4,5-trihydroxy-6-(hydroxymethyl)tetrahydropyran-2-yl]ethynyl]carbazol-9-yl]-1-(4-methylpiperazin-1-yl)ethanone | (400 MHz, CD₃OD) δ 8.05 (d, J = 8.1 Hz, 2H), 7.55 (s, 2H), 7.30 (d, J = 8.1 Hz, 2H), 5.34 (s, 2H), 4.03 (dd, J = 3.2, 2.2 Hz, 2H), 3.97 (dd, J = 9.3, 3.3 Hz, 2H), 3.91-3.61 (m, 12H), 2.86-2.78 (m, 2H), 2.70 (s, 2H), 2.52 (s, 3H) and two protons under the solvent peak | 680.67 |
| 180 | 2-[2,7-bis[2-[(2R,3S,4R,5S,6R)-3,4,5-trihydroxy-6-(hydroxymethyl)tetrahydropyran-2-yl]ethynyl]carbazol-9-yl]-1-morpholino-ethanone | (400 MHz, CD₃OD) δ 8.05 (d, J = 8.1 Hz, 2H), 7.57 (s, 2H), 7.30 (d, J = 8.1 Hz, 2H), 5.35 (s, 2H), 4.89 (d, J = 2.2 Hz, 2H), 4.05-4.01 (m, 2H), 3.98 (dd, J = 9.3, 3.3 Hz, 2H), 3.87 (ddd, J = 11.6, 7.1, 2.2 Hz, 4H), 3.83-3.79 (m, 2H), 3.77-3.69 (m, 6H), 3.65 (t, J = 9.5 Hz, 2H), 3.59-3.55 (m, 2H). [1] | 667.36 |
| 181 | 2-[2,7-bis[2-[(2R,3S,4R,5S,6R)-3,4,5-trihydroxy-6-(hydroxymethyl)tetrahydropyran-2-yl]ethynyl]carbazol-9-yl]-N,N-dimethyl-acetamide | (400 MHz, CD₃OD) δ 8.05 (d, J = 8.1 Hz, 2H), 7.55 (s, 2H), 7.30 (d, J = 8.1 Hz, 2H), 5.32 (s, 2H), 4.89 (d, J = 2.1 Hz, 2H), 4.05-4.01 (m, 2H), 3.98 (dd, J = 9.3, 3.2 Hz, 2H), 3.91-3.82 (m, 4H), 3.74 (dd, J = 11.6, 5.6 Hz, 2H), 3.64 (t, J = 9.6 Hz, 2H), 3.27 (s, 3H), 2.98 (s, 3H). | 625.37 |

Preparation of Compound 182 (Method D)

(2R,3S,4R,5S,6R)-2-[2-[9-(2-Hydroxyethyl)-7-[2-[(2R,3S,4R,5S,6R)-3,4,5-trihydroxy-6-(hydroxymethyl)tetrahydropyran-2-yl]ethynyl]carbazol-2-yl]ethynyl]-6-(hydroxymethyl)tetrahydropyran-3,4,5-triol

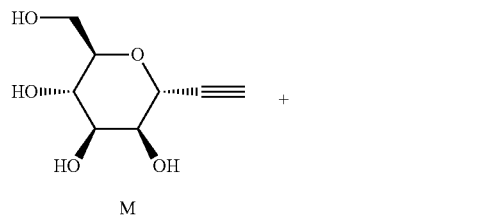

M

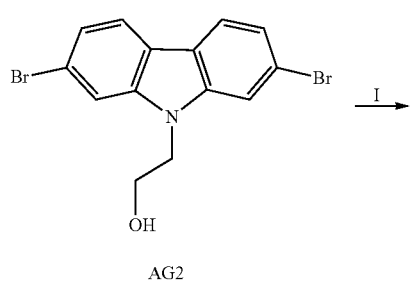

AG2

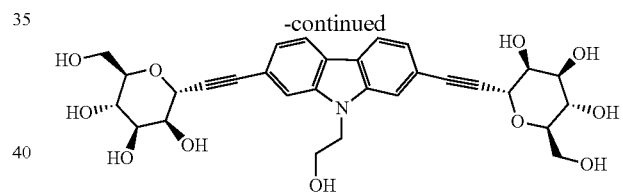

A mixture of Intermediates AG2 (60 mg, 0.15 mmol) and M (588 μL of 0.53 M, 0.311 mmol) Pd(dppf)Cl₂—CH₂Cl₂ (7.9 mg, 0.01 mmol), CuI (8.4 mg, 0.044 mmol) in DMF (215 μL) is degassed (vacuum/N₂). To the resulting mixture is added DIPEA (204 μL, 1.17 mmol), and degassed. The reaction mixture is heated at 100° C. for 2 h under N₂, passed through metal-scavenger cartridge (Si-DMT; Silicycle; SPE-R79030B-06P), washed with DMF (0.5 mL). The resulting filtrate is concentrated under high vacuum, dissolved in DMSO, purified by reverse phase HPLC to afford the title compound (24 mg, 28%) as light yellow solid. ¹H NMR (400 MHz, CD₃OD) δ 8.05 (d, J=8.1 Hz, 2H), 7.68 (s, 2H), 7.29 (d, J=8.1 Hz, 2H), 4.91-4.89 (m, 2H), 4.45 (t, J=5.4 Hz, 2H), 4.06-4.02 (m, 2H), 3.99 (dd, J=9.3, 3.3 Hz, 2H), 3.94-3.84 (m, 6H), 3.79-3.71 (m, 2H), 3.65 (t, J=9.4 Hz, 2H). ESI-MS m/z calc. 583.2054, found 584.54 (M+1)⁺.

305

Preparation of Compound 183 (Method D)

(2R,3S,4R,5S,6R)-2-(Hydroxymethyl)-6-[2-[9-[2-(trideuteriomethoxy)ethyl]-7-[2-[(2R,3S,4R,5S,6R)-3,4,5-trihydroxy-6-(hydroxymethyl)tetrahydropyran-2-yl]ethynyl]carbazol-2-yl]ethynyl]tetrahydropyran-3,4,5-triol

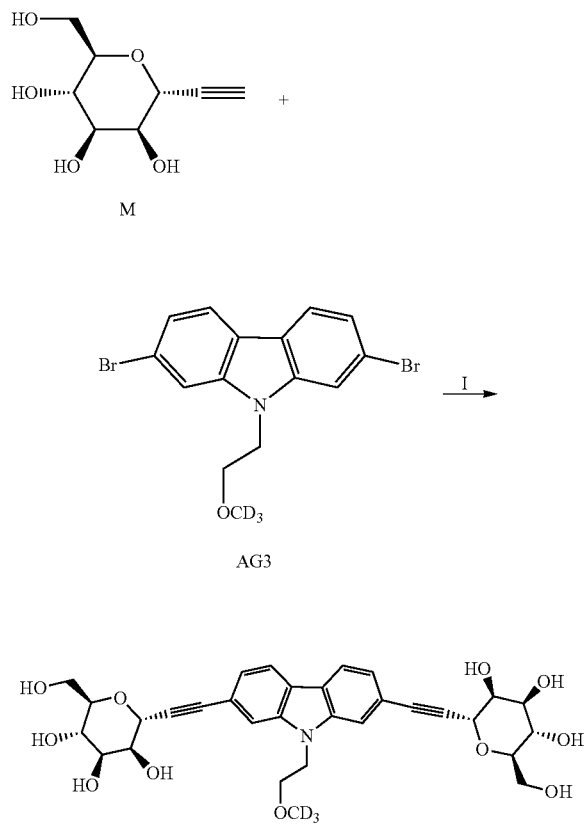

Compound 183 is prepared according to the procedure described for Compound 182 but using Intermediates AG3 (63 mg, 0.15 mmol) and M (590.0 μL of 0.53 M, 0.313 mmol). The title compound is isolated as white solid by filtration after purification by reverse phase HPLC as it precipitated out of solution (16.7 mg, 19%). $^1$H NMR (400 MHz, DMSO-D$_6$) δ 8.15 (d, J=8.1 Hz, 2H), 7.72 (s, 2H), 7.26 (d, J=8.1 Hz, 2H), 4.96 (d, J=4.3 Hz, 2H), 4.82 (d, J=5.7 Hz, 2H), 4.76 (s, 2H), 4.72 (d, J=5.9 Hz, 2H), 4.58 (s, 2H), 4.50 (t, J=5.9 Hz, 2H), 3.84 (s, 2H), 3.79-3.55 (m, 8H), 3.52-3.34 (m, 4H). ESI-MS m/z calc. 600.23987, found (M+1)$^+$ 601.58.

306

Preparation of Compound 184 (Method D)

(2R,3S,4R,5S,6R)-2-(hydroxymethyl)-6-[2-[9-tetrahydropyran-4-yl-7-[2-[(2R,3S,4R,5S,6R)-3,4,5-trihydroxy-6-(hydroxymethyl)tetrahydropyran-2-yl]ethynyl]carbazol-2-yl]ethynyl]tetrahydropyran-3,4,5-triol A solution of Intermediates M (889 μL of 0.53 M in DMF, 0.47 mmol) and AG34 (90 mg, 0.22 mmol), Pd(dppf)Cl$_2$—CH$_2$Cl$_2$ (13 mg, 0.016 mmol), CuI (13 mg, 0.068 mmol) is degassed (vacuum/N$_2$). To the resulting mixture is added DIPEA (320 μL, 1.84 mmol). The final mixture is stirred in a sealed tube under N$_2$ atmosphere at 100° C. for 2 h. The reaction is cooled down, filtered over SiliCycle SiliaPrep DMT 200 mg 3 mL SPE cartridge and concentrated in vacuo. The residue is purified by reverse phase HPLC to afford the title compound (15 mg, 11%) as a solid. $^1$H NMR (400 MHz, CD$_3$OD) δ 8.06 (d, J=8.1 Hz, 2H), 7.79 (s, 2H), 7.30 (dd, J=8.0, 1.1 Hz, 2H), 4.91 (d, J=2.1 Hz, 2H), 4.22-4.10 (m, 2H), 4.05 (dd, J=3.2, 2.1 Hz, 2H), 3.99 (dd, J=9.3, 3.3 Hz, 2H), 3.93-3.82 (m, 4H), 3.81-3.60 (m, 7H), 2.68 (qd, J=12.6, 4.7 Hz, 2H), 1.83 (dd, J=11.8, 3.6 Hz, 2H). ESI-MS m/z calc. 623.65, found 624.56 (M+1)$^+$

Preparation of Compounds 185 to 190

Compounds 185 to 190 are prepared according to the procedure described for 184 using Intermediates AG35 to AG40

| Compound | IUPAC name | $^1$H-NMR | LCMS m/z (M + H)$^+$ |
|---|---|---|---|
| 185 | tert-butyl 4-[2,7-bis[2-(2R,3S,4R,5S,6R)-3,4,5-trihydroxy-6-(hydroxymethyl)tetrahydropyran- | (400 MHz, CD$_3$OD) δ 8.06 (d, J = 8.0 Hz, 2H), 7.72 (s, 2H), 7.30 (dd, J = 8.1, 1.2 Hz, 2H), 4.87 (s, 2H), 4.78 (s, 1H), 4.60 (s, 1H), | 722.14 |

| Compound | IUPAC name | ¹H-NMR | LCMS m/z (M + H)⁺ |
|---|---|---|---|
| | 2-yl]ethynyl]carbazol-9-yl]piperidine-1-carboxylate | 4.32 (s, 2H), 4.03 (dd, J = 3.3, 2.2 Hz, 2H), 3.98 (dd, J = 9.3, 3.3 Hz, 2H), 3.92-3.82 (m, 4H), 3.79-3.71 (m, 2H), 3.65 (t, J = 9.5 Hz, 2H), 3.24-3.17 (m, 2H), 1.54 (s, 9H). Three proton under solvent peaks | |
| 186 | (2R,3S,4R,5S,6R)-2-(hydroxymethyl)-6-[2-[9-[(3-methyloxetan-3-yl)methyl]-7-[2-(2R,3S,4R,5S,6R)-3,4,5-trihydroxy-6-(hydroxymethyl)tetrahydropyran-2-yl]ethynyl]carbazol-2-yl]ethynyl]tetrahydropyran-3,4,5-triol | (400 MHz, CD₃OD) δ 8.09 (d, J = 8.1 Hz, 2H), 7.67 (s, 2H), 7.33 (d, J = 8.1 Hz, 2H), 4.90 (d, J = 2.1 Hz, 2H), 4.79-4.68 (m, 2H), 4.49 (s, 2H), 4.30 (d, J = 6.0 Hz, 2H), 4.04 (t, J = 2.7 Hz, 2H), 3.98 (dd, J = 9.3, 3.4 Hz, 2H), 3.92-3.81 (m, 4H), 3.74 (dd, J = 11.7, 5.8 Hz, 2H), 3.65 (t, J = 9.6 Hz, 2H), 1.43 (s, 3H). | 625.58 |
| 187 | (2R,3S,4R,5S,6R)-2-(hydroxymethyl)-6-[2-[9-(1-methyl-4-piperidyl)-7-[2-[(2R,3S,4R,5S,6R)-3,4,5-trihydroxy-6-(hydroxymethyl)tetrahydropyran-2-yl]ethynyl]carbazol-2-yl]ethynyl]tetrahydropyran-3,4,5-triol | N/A | 638.2 |
| 188 | (2R,3S,4R,5S,6R)-2-(hydroxymethyl)-6-[2-[9-[(1-methyl-4-piperidyl)methyl]-7-[2-[(2R,3S,4R,5S,6R)-3,4,5-trihydroxy-6-(hydroxymethyl)tetrahydropyran-2-yl]ethynyl]carbazol-2-yl]ethynyl]tetrahydropyran-3,4,5-triol | (400 MHz, CD₃OD) δ 8.07 (d, J = 8.1 Hz, 2H), 7.68 (d, J = 1.2 Hz, 2H), 7.31 (dd, J = 8.1, 1.2 Hz, 2H), 4.90 (d, J = 2.1 Hz, 2H), 4.45 (t, J = 7.1 Hz, 2H), 4.03 (dd, J = 3.3, 2.1 Hz, 2H), 3.97 (dd, J = 9.3, 3.3 Hz, 2H), 3.87 (ddt, J = 10.0, 7.7, 2.3 Hz, 4H), 3.78-3.71 (m, 2H), 3.65 (t, J = 9.6 Hz, 2H), 3.31 (s, 1H), 3.25 (s, 2H), 2.90 (s, 1H), 2.79 (s, 3H), 2.41 (s, 1H), 2.20 (s, 1H), 2.03 (dd, J = 11.6, 6.8 Hz, 2H), 1.72 (m, 1H). | 652.6 |
| 189 | (2R,3S,4R,5S,6R)-2-(hydroxymethyl)-6-[2-[9-(2-morpholinoethyl)-7-[2-[(2R,3S,4R,5S,6R)-3,4,5-trihydroxy-6-(hydroxymethyl)tetrahydropyran-2-yl]ethynyl]carbazol-2-yl]ethynyl]tetrahydropyran-3,4,5-triol | (400 MHz, CD₃OD) δ 8.05 (dd, J = 8.0, 0.7 Hz, 2H), 7.68 (dd, J = 1.3, 0.7 Hz, 2H), 7.30 (dd, J = 8.1, 1.2 Hz, 2H), 4.90 (d, J = 2.1 Hz, 2H), 4.51 (t, J = 6.7 Hz, 2H), 4.04 (dd, J = 3.3, 2.1 Hz, 2H), 3.99 (dd, J = 9.3, 3.3 Hz, 2H), 3.93-3.82 (m, 4H), 3.81-3.70 (m, 2H), 3.70-3.57 (m, 6H), 2.78 (t, J = 6.7 Hz, 2H), 2.56 (t, J = 4.5 Hz, 4H). | 654.56 |
| 190 | 1-[2-[2,7-bis[2-[(2R,3S,4R,5S,6R)-3,4,5-trihydroxy-6-(hydroxymethyl)tetrahydropyran-2-yl]ethynyl]carbazol-9-yl]ethyl]pyrrolidin-2-one | (400 MHz, CD₃OD) δ 8.07 (d, J = 8.1 Hz, 2H), 7.67 (s, 2H), 7.31 (d, J = 8.1 Hz, 2H), 4.90 (d, J = 2.1 Hz, 2H), 4.59 (t, J = 5.7 Hz, 2H), 4.12-3.95 (m, 4H), 3.88 (ddd, J = 11.8, 7.1, 2.3 Hz, 4H), 3.75 (dd, J = 11.7, 5.8 Hz, 2H), 3.70-3.54 (m, 4H), 2.86 (t, J = 7.1 Hz, 2H), 2.12 (t, J = 8.1 Hz, 2H), 1.60 (q, J = 7.6 Hz, 2H). | 651.6 |

309
Preparation of Compound 191 (Method D)

(2R,3S,4R,5S,6R)-2-(hydroxymethyl)-6-[2-[7'-[2-[(2R,3S,4R,5S,6R)-3,4,5-trihydroxy-6-(hydroxymethyl)tetrahydropyran-2-yl]ethynyl]spiro[1,3-dithiane-2,9'-fluorene]-2'-yl]ethynyl]tetrahydropyran-3,4,5-triol

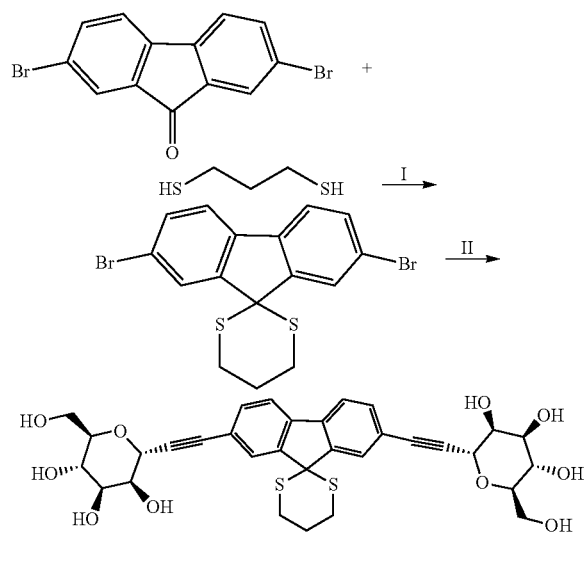

Step I: 2',7'-dibromospiro[1,3-dithiane-2,9'-fluorene]

To a solution of 2,7-dibromofluoren-9-one (1000 mg, 2.959 mmol) in CH$_2$Cl$_2$ (9.863 mL) at RT under argon is added propane-1,3-dithiol (446 µL, 4.44 mmol) followed by BF$_3$.OEt$_2$ (548 µL, 4.44 mmol). The resulting mixture is stirred at RT for 1 h and then warmed to 60° C. overnight. The reaction mixture is quenched by pouring into saturated aqueous Na$_2$CO$_3$, and extracted with EtOAc. The combined organic extracts are dried over Na$_2$SO$_4$, filtered and concentrated. During the concentration process a precipitate is formed and it is isolate by filtration to afford the title compound (0.937 g, 2.188 mmol, 73.95%). LC-MS: m/z=428.13 (M+H$^+$).

Step II: Compound 191

To a degassed mixture of intermediate M (925 µL of 0.53 M, 0.490 mmol), 2',7'-dibromospiro[1,3-dithiane-2,9'-fluorene] from Step I (100 mg, 0.2335 mmol), Pd(dppf)Cl$_2$—CH$_2$Cl$_2$ (19.07 mg, 0.02335 mmol), CuI (13.34 mg, 0.07005 mmol) in DMF (778.3 µL) is added DIPEA (122 µL, 0.701 mmol). The mixture is stirred in a sealed tube under nitrogen atmosphere at 90° C. overnight. The reaction mixture is filtered over celite cartridge and concentrated in vacuo. Purification by reverse phase HPLC afford the title compound (37.2 mg, 25%). $^1$H NMR (400 MHz, CD$_3$OD) δ 7.95 (s, 2H), 7.78 (d, J=7.9 Hz, 2H), 7.53 (dd, J=7.9 Hz, 2H), 4.90 (d, J=1.9 Hz, 3H), 4.04 (t, 2H), 3.96 (dd, J=9.4, 3.2 Hz, 2H), 3.90 (d, J=2.0 Hz, 1H), 3.89-3.80 (m, 3H), 3.74 (dd, J=11.4, 5.6 Hz, 2H), 3.63 (t, J=9.4 Hz, 2H), 2.38-2.28 (m, 2H). LC-MS: m/z=643.51 (M+H$^+$).

310
Preparation of Compound 192 (Method D)

(2R,3S,4R,5S,6R)-2-(Hydroxymethyl)-6-[2-[7-[2-[(2R,3S,4R,5S,6R)-3,4,5-trihydroxy-6-(hydroxymethyl)tetrahydropyran-2-yl]ethynyl]spiro[fluorene-9,4'-piperidine]-2'-yl]ethynyl]tetrahydropyran-3,4,5-triol

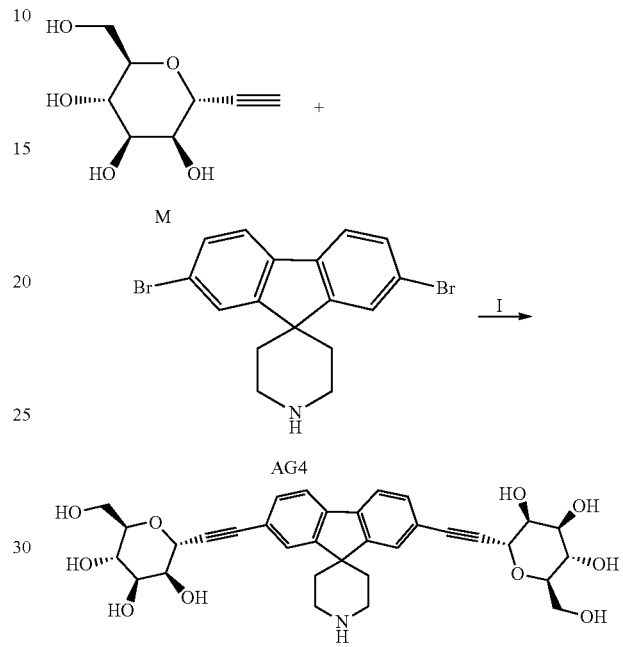

Compound 192 is prepared according to the procedure described for Compound 182 but using Intermediates AG4 (45 mg, 0.08940 mmol) and M (360 µL of 0.53 M, 0.1908 mmol). Half of the resulting crude mixture is dissolved in DMSO (1 mL), purified by reverse phase HPLC. Two drops of ammonia is added to the combined fractions (pH 6-7), followed by lyophilisation (twice) to afford the title compound (11.8 mg, 43%) as light yellow solid.
$^1$H NMR (400 MHz, CD$_3$OD) δ 7.85 (d, J=7.9 Hz, 2H), 7.82 (s, 2H), 7.55 (d, J=7.9 Hz, 2H), 4.89 (d, J=2.1 Hz, 2H), 4.05-3.98 (m, 2H), 3.93 (dd, J=9.3, 3.3 Hz, 2H), 3.89-3.79 (m, 4H), 3.74 (dd, J=11.4, 5.8 Hz, 2H), 3.67-3.57 (m, 6H), 2.11-2.03 (m, 4H). ESI-MS m/z calc. 607.24176, found 608.58 (M+1)$^+$.

Preparation of Compound 193 (Method D)

(2R,3S,4R,5S,6R)-2-[2-[9,9-Bis(2-hydroxyethyl)-7-[2-[(2R,3S,4R,5S,6R)-3,4,5-trihydroxy-6-(hydroxymethyl)tetrahydropyran-2-yl]ethynyl]fluoren-2-yl]ethynyl]-6-(hydroxymethyl)tetrahydropyran-3,4,5-triol

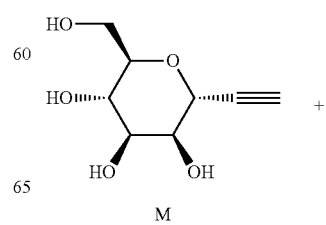

M

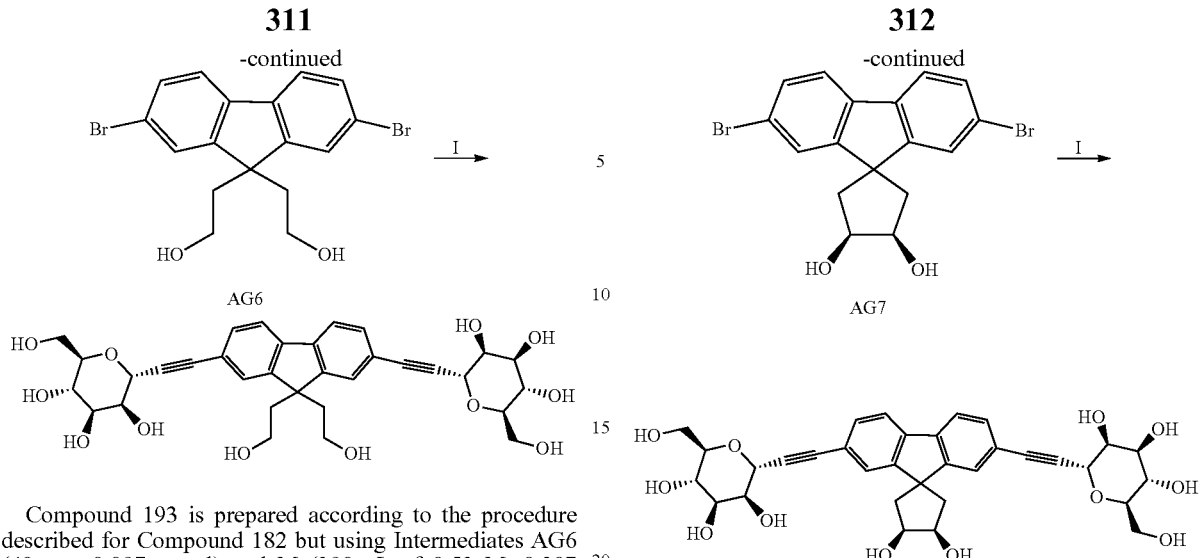

AG6

Compound 193 is prepared according to the procedure described for Compound 182 but using Intermediates AG6 (40 mg, 0.097 mmol) and M (390 µL of 0.53 M, 0.207 mmol). The title compound is obtained (24 mg, 40%) as white solid after lyophilisation. $^1$H NMR (400 MHz, CD$_3$OD) δ 7.75 (d, J=7.9 Hz, 2H), 7.60 (d, J=0.7 Hz, 2H), 7.47 (dd, J=7.9, 1.4 Hz, 2H), 4.88 (d, J=2.3 Hz, 2H), 4.02 (dd, J=3.2, 2.2 Hz, 2H), 3.95 (dd, J=9.3, 3.3 Hz, 2H), 3.91-3.80 (m, 4H), 3.74 (dd, J=11.4, 5.5 Hz, 2H), 3.63 (t, J=9.4 Hz, 2H), 2.82-2.70 (m, 4H), 2.39-2.29 (m, 4H). ESI-MS m/z calc. 626.2363, found 627.54 (M+1)$^+$.

Preparation of Compound 194 (Method D)

(2R,3S,4R,5S,6R)-2-[2-[(3R,4S)-3,4-Dihydroxy-7'-[2-[(2R,3S,4R,5S,6R)-3,4,5-trihydroxy-6-(hydroxymethyl)tetrahydropyran-2-yl]ethynyl]spiro[cyclopentane-1,9'-fluorene]-2'-yl]ethynyl]-6-(hydroxymethyl)tetrahydropyran-3,4,5-triol

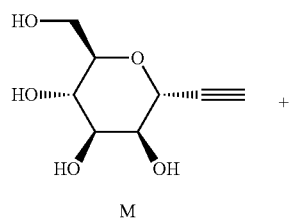

M

Compound 194 is prepared according to the procedure described for Compound 182 but using Intermediates AG7 (41 mg, 0.01 mmol) and M (400 µL of 0.53 M, 0.213 mmol). Purification by reverse phase HPLC followed by lyophilisation afforded the title compound (31 mg, 50%) as a whit solid. $^1$H NMR (400 MHz, CD$_3$OD) δ 7.95 (s, 1H), 7.72-7.64 (m, 2H), 7.52 (s, 1H), 7.46-7.38 (m, 2H), 4.53-4.41 (m, 2H), 4.06-3.98 (m, 2H), 3.99-3.92 (m, 2H), 3.91-3.78 (m, 4H), 3.74 (dd, J=11.3, 5.3 Hz, 2H), 3.63 (t, J=9.4 Hz, 2H), 2.32-2.11 (m, 4H). [Two protons for C-1 sugar overlapped with solvent peak). ESI-MS m/z calc. 624.2207, found 625.53 (M+1)$^+$.

Preparation of Compounds 195 to 199

Compounds 195-199 are prepared according to the procedure described for Compound 182 but using the appropriate commercially available starting material (for Compound 195) and Intermediates AG27 to AG29 (for Compound 196 to 199 respectively)

| Compound | IUPAC name | $^1$H-NMR | LCMS m/z (M + H)$^+$ |
|---|---|---|---|
| 195 | (2R,3S,4R,5S,6R)-2-(hydroxymethyl)-6-[2-[9-hydroxy-7-[2-[(2R,3S,4R,5S,6R)-3,4,5-trihydroxy-6-(hydroxymethyl)tetrahydropyran-2-yl]ethynyl]-9H-fluoren-2-yl]ethynyl]tetrahydropyran-3,4,5-triol | (400 MHz, CD$_3$OD) δ 7.74-7.66 (m, 2H), 7.49 (d, J = 7.8 Hz, 1H), 7.46-7.42 (m, 1H), 7.36-7.31 (m, 2H), 4.84 (d, J = 2.3 Hz, 2H), 4.79 (s, 1H), 4.03-3.97 (m, 2H), 3.93 (td, J = 9.5, 3.1 Hz, 2H), 3.89-3.77 (m, 4H), 3.77-3.69 (m, 2H), 3.62 (td, J = 9.5, 5.0 Hz, 2H). | 555.3 |
| 196 | (2R,3S,4R,5S,6R)-2-[2-[9-(2,3-dihydroxypropyl)-9-hydroxy-7-[2-[(2R,3S,4R,5S,6R)-3,4,5-trihydroxy-6-(hydroxymethyl)tetrahydropyran-2-yl]ethynyl]fluoren-2-yl]ethynyl]-6-(hydroxymethyl)tetrahydropyran-3,4,5-triol | (400 MHz, CD$_3$OD) δ 7.65 (dd, J = 29.2, 5.5 Hz, 4H), 7.47 (d, J = 7.4 Hz, 2H), 4.79 (s, 2H), 4.59 (s, 1H), 4.00 (s, 2H), 3.94 (d, J = 10.8 Hz, 3H), 3.84 (dd, J = 22.1, 9.9 Hz, 5H), 3.73 (dd, J = 11.1, 5.0 Hz, 2H), 3.67-3.58 (m, 2H), 2.31-2.21 (m, 1H), 2.09 (dd, J = 14.1, 3.3 Hz, 1H). | 629.3 |

-continued

| Compound | IUPAC name | ¹H-NMR | LCMS m/z (M + H)⁺ |
|---|---|---|---|
| 197 | (2R,3S,4R,5S,6R)-2-[2-[(4'R,5'S)-4',5'-dihydroxy-7-[2-[(2R,3S,4R,5S,6R)-3,4,5-trihydroxy-6-(hydroxymethyl)tetrahydropyran-2-yl]ethynyl]spiro[fluorene-9,2'-tetrahydropyran]-2-yl]ethynyl]-6-(hydroxymethyl)tetrahydropyran-3,4,5-triol (2R,3S,4R,5S,6R)-2-[2-[(4'S,5'R)-4',5'-dihydroxy-7-[2-[(2R,3S,4R,5S,6R)-3,4,5-trihydroxy-6-(hydroxymethyl)tetrahydropyran-2-yl]ethynyl]spiro[fluorene-9,2'-tetrahydropyran]-2-yl]ethynyl]-6-(hydroxymethyl)tetrahydropyran-3,4,5-triol | (400 MHz, CD₃OD) δ 7.92 (s, 1H), 7.82 (s, 1H), 7.73 (d, J = 7.8 Hz, 1H), 7.67 (d, J = 7.8 Hz, 1H), 7.50 (dd, J = 16.5, 7.8 Hz, 2H), 4.79 (d, J = 0.9 Hz, 2H), 4.49-4.42 (m, 1H), 4.25-4.18 (m, 1H), 4.02 (dd, J = 3.0, 2.1 Hz, 2H), 3.97-3.92 (m, 2H), 3.90-3.80 (m, 4H), 3.73 (ddd, J = 11.6, 5.5, 1.5 Hz, 2H), 3.63 (t, J = 9.4 Hz, 2H), 2.47 (dd, J = 13.2, 10.9 Hz, 1H), 1.74 (dd, J = 13.5, 5.1 Hz, 1H). | 641.3 |
| 198 | (2R,3S,4R,5S,6R)-2-(hydroxymethyl)-6-[2-[9-(4-methylpiperazin-1-yl)-7-[2-[(2R,3S,4R,5S,6R)-3,4,5-trihydroxy-6-(hydroxymethyl)tetrahydropyran-2-yl]ethynyl]-9H-fluoren-2-yl]ethynyl]tetrahydropyran-3,4,5-triol | (400 MHz, CD₃OD) δ 7.80-7.71 (m, 4H), 7.52 (d, J = 7.9 Hz, 2H), 5.00 (s, 1H), 4.84 (s, 2H), 4.02-3.98 (m, 2H), 3.92 (ddd, J = 9.4, 3.0, 1.7 Hz, 2H), 3.87 (d, J = 11.8 Hz, 2H), 3.84-3.78 (m, 2H), 3.74 (dd, J = 11.4, 5.7 Hz, 2H), 3.64 (t, J = 9.4 Hz, 2H), 2.92 (s, 3H), 2.76 (s, 4H), 2.58 (s, 4H). | 637.33 |
| 199 | (2R,3S,4R,5S,6R)-2-(hydroxymethyl)-6-[2-[7-[2-[(2R,3S,4R,5S,6R)-3,4,5-trihydroxy-6-(hydroxymethyl)tetrahydropyran-2-yl]ethynyl]spiro[fluorene-9,2'-tetrahydropyran]-2-yl]ethynyl]tetrahydropyran-3,4,5-triol | (400 MHz, CD₃OD) δ 7.82 (s, 2H), 7.71 (dd, J = 7.8, 3.1 Hz, 2H), 7.50 (d, J = 7.8 Hz, 2H), 4.78 (s, 2H), 4.10-4.05 (m, 2H), 4.05-3.99 (m, 2H), 3.95 (dd, J = 9.3, 3.3 Hz, 2H), 3.91-3.80 (m, 4H), 3.73 (ddd, J = 11.5, 5.8, 3.3 Hz, 2H), 3.63 (td, J = 9.5, 3.0 Hz, 2H), 2.15-2.07 (m, 2H), 1.99-1.89 (m, 4H). | 609.32 |

Preparation of Compound 200 (Method D)

tert-Butyl 2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-carboxylate

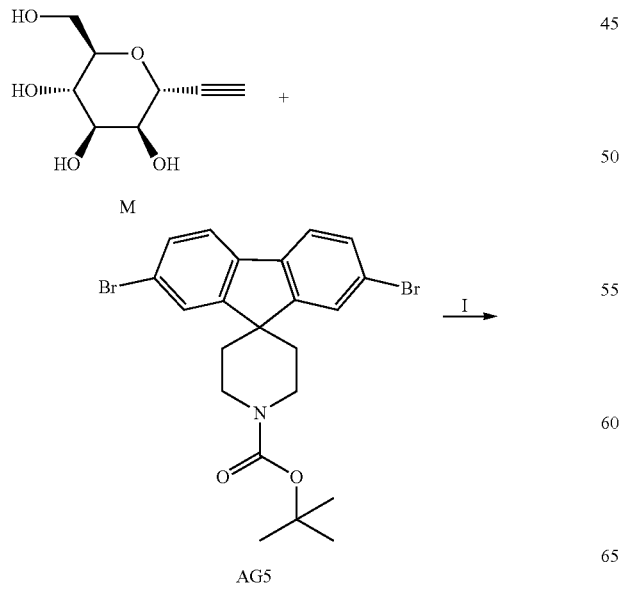

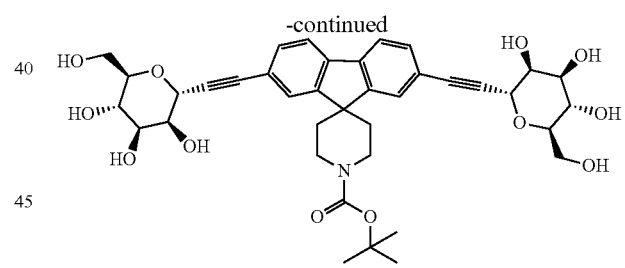

Compound 200 is prepared according to the procedure described for Compound 182 but using Intermediates AG5 (42.0 mg, 0.0850 mmol), M (400 µL of 0.53 M, 0.2130 mmol). The reaction mixture is sealed and heated at 100° C. for 2 h under N₂. Purification by reverse phase HPLC followed by lyophilisation afforded the title compound (11 mg, 18%) as a off-white solid. ¹H NMR (400 MHz, CD₃OD) δ 7.83-7.75 (m, 4H), 7.49 (d, J=7.8 Hz, 2H), 4.02 (d, J=2.4 Hz, 2H), 3.95 (dd, J=9.4, 3.1 Hz, 2H), 3.92-3.79 (m, 8H), 3.73 (dd, J=11.4, 5.5 Hz, 2H), 3.63 (t, J=9.4 Hz, 2H), 1.83 (s, 4H), 1.52 (s, 9H). (Two protons of C-1 sugar are underneath of solvent peak). ESI-MS m/z calc. 707.2942, found 708.22 (M+1)⁺.

Preparation of Compound 201 (Method D)

(2R,3S,4R,5S,6R)-2-(hydroxymethyl)-6-[2-[1'-methyl-7-[2-[(2R,3S,4R,5S,6R)-3,4,5-trihydroxy-6-(hydroxymethyl)tetrahydropyran-2-yl]ethynyl]spiro[fluorene-9,4'-piperidine]-2-yl]ethynyl]tetrahydropyran-3,4,5-triol

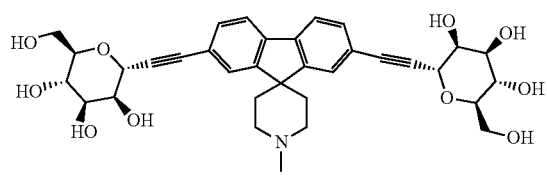 [SMILES: CN1CCC2(CC1)c1cc(C#C[C@H]3O[C@H](CO)[C@@H](O)[C@H](O)[C@@H]3O)ccc1-c1ccc(C#C[C@H]3O[C@H](CO)[C@@H](O)[C@H](O)[C@@H]3O)cc12]

Compound 201 is prepared according to the procedure described for Compound 182 but using Intermediates AG14. $^1$H NMR (400 MHz, CD$_3$OD) δ 7.88-7.80 (m, 4H), 7.54 (d, J=7.9 Hz, 2H), 4.04-4.00 (m, 2H), 3.93 (dd, J=9.4, 3.2 Hz, 2H), 3.91-3.80 (m, 4H), 3.74 (dd, J=11.4, 5.7 Hz, 2H), 3.63 (t, J=9.4 Hz, 2H), 3.52-3.44 (m, 4H), 3.00 (s, 3H), 2.20-1.98 (m, 4H). (two protons of C-1 sugar are underneath of solvent peak). ESI-MS m/z (M+H)$^+$ 622.59

Preparation of Compound 202 (Method D)

1-[2,7-Bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]ethanone

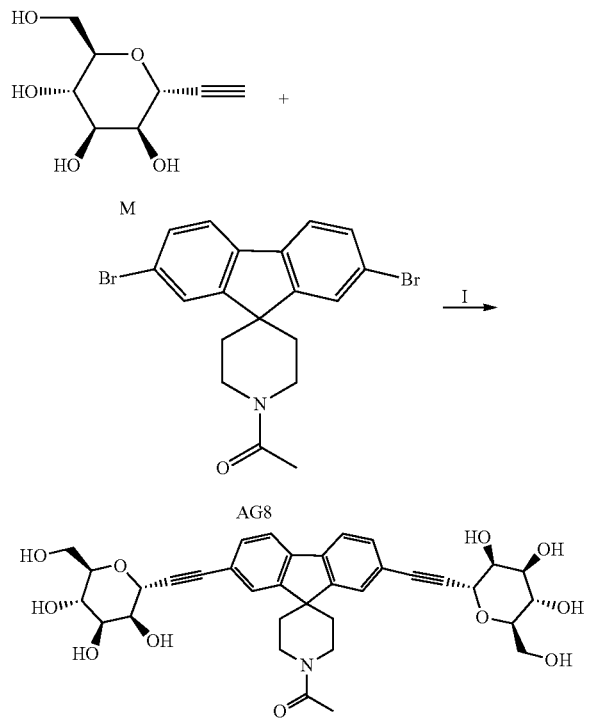

A mixture of Intermediates M (340 µL of 0.53 M, 0.1802 mmol), AG8, (35 mg, 0.080 mmol), Pd(dppf)Cl$_2$—CH$_2$Cl$_2$ (4.3 mg, 0.0053 mmol), CuI (4.6 mg, 0.024 mmol) in DMF (140 µL) is degassed (vacuum/N$_2$). To this is added DIPEA (112 µL, 0.6430 mmol), degassed. The reaction mixture is heated at 100° C. for 2 h, additional amount of Intermediate M (152 µL of 0.53 M, 0.080 mmol) is added and the resulting mixture is heated for an additional 2.5 h under N$_2$. The reaction mixture cooled to RT, filtered through metal scavenger (Si-DMT; Silicycle; SPE-R79030B-06P) cartridge, washed with DMF (1 mL). The filtrate is directly purified by reverse phase HPLC to afford the title compound (42 mg, 80%) as a white solid. $^1$H NMR (400 MHz, CD$_3$OD) δ 7.82-7.78 (m, 4H), 7.50 (d, J=8.0 Hz, 2H), 4.05-3.98 (m, 4H), 3.98-3.91 (m, 4H), 3.91-3.79 (m, 4H), 3.73 (dd, J=11.4, 5.6 Hz, 2H), 3.63 (t, J=9.4 Hz, 2H), 2.25-2.19 (m, 3H), 1.98-1.89 (m, 2H), 1.88-1.80 (m, 2H) (two protons of C-1 sugar are underneath solvent peak). ESI-MS m/z calc. 649.2523, found 650.6 (M+1)$^+$.

Alternative Preparation of Compound 202

1-[2,7-Bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]ethanone

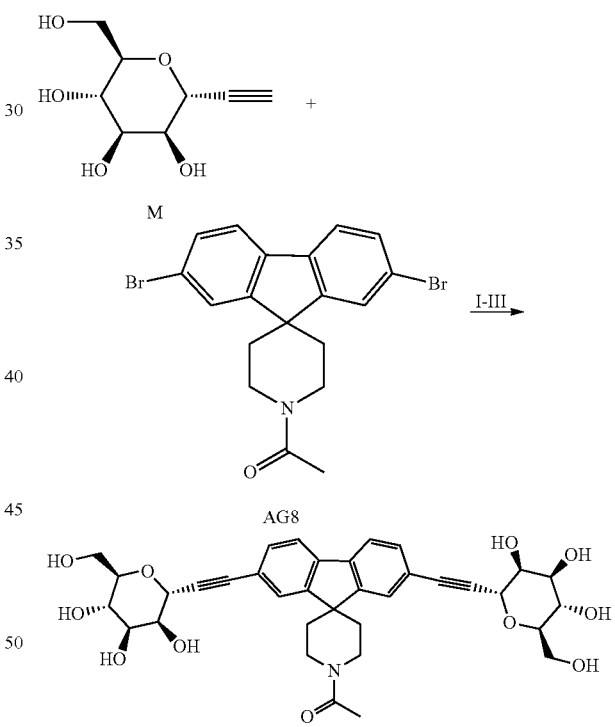

Step I: Crude Compound 202

A mixture of Intermediates M (12.8 mL of 0.468 M, 5.99 mmol), AG8, (875 mg, 1.999 mmol), Pd(dppf)Cl$_2$—CH$_2$Cl$_2$ (98 mg, 0.12 mmol), CuI (114 mg, 0.6 mmol) in DMF (3.0 mL) is degassed (vacuum/N$_2$ flush twice 5 min each). DIPEA (2.80 mL, 16.1 mmol) is added and the mixture is degassed twice. The final reaction mixture is heated at 100° C. for 2 h (LC-MS after 1 h showed complete conversion of AG8), cooled to RT and concentrated under vacuo at 40° C. to afford the title compound as dark brown oil.

Step II: [(2R,3R,4R,5R,6R)-3,4,5-triacetoxy-6-[2-[1'-acetyl-7-[2-[(2R,3R,4R,5R,6R)-3,4,5-triacetoxy-6-(acetoxymethyl)tetrahydropyran-2-yl]ethynyl]spiro[fluorene-9,4'-piperidine]-2-yl]ethynyl]tetrahydropyran-2-yl]methyl acetate To a stirred solution of the crude Compound 202 from Step I in pyridine (9 mL) at RT is sequentially added DMAP (12 mg, 0.098 mmol) and acetic anhydride (3.8 mL, 40.3 mmol) at RT. The mixture is stirred for 16 h, diluted with water (40 mL), extracted with EtOAc (3×30 mL). The combined extracts are washed with aqueous 1N HCl (3×20 mL), brine, passed through phase separator and concentrated. The residue is purified on Biotage™ SNAP silica gel cartridge (100 g) eluting with a gradient of EtOAC in Hex (10% to 20%, 8 CV; and 100%) as eluent to afford the title compound (1.690 g, 86%) as a beige foam. To a stirred solution of the latter in EtOAc (10 mL) is added 300 mg of SiliaMetS Thiol (Cat #R51030B from Silicycle) (1.42 mmol/g) and the mixture is stirred at RT for 3 h, filtered, washed with EtOAc (15 mL) and concentrated. The filtrate is treated one more time with SiliaMetS Thio to afford the title compound (1.600 g).

Step III: Compound 202

To a stirred solution of [(2R,3R,4R,5R,6R)-3,4,5-triacetoxy-6-[2-[1'-acetyl-7-[2-[(2R,3R,4R,5R,6R)-3,4,5-triacetoxy-6-(acetoxymethyl)tetrahydropyran-2-yl]ethynyl]spiro[fluorene-9,4'-piperidine]-2-yl]ethynyl]tetrahydropyran-2-yl]methyl acetate (1.600 g) from Step II in MeOH (15 mL) is added MeONa in MeOH (400 μL of 0.5 M, 0.200 mmol).

The mixture is stirred at RT for 7 h and quenched with AcOH (20 μL, 0.36 mmol). After stirring for 15 min, the resulting solid is filtered, washed with MeOH (10 mL), dried under vacuum oven at 40° C. for 40 h to afford the title compound (0.870 g, 65% overall yield from Step I) as off-white solid.

Preparation of Compound 203 to 205

Compounds 203, 204 and 205 are prepared according to the procedure described for Compound 182 but using the Intermediates AG42, AG43 and AG44 respectively.

| Compound | IUPAC name | $^1$H-NMR | LCMS m/z (M + H)$^+$ |
|---|---|---|---|
| 203 | (2R,3S,4R,5S,6R)-2-(hydroxymethyl)-6-[2-[4-hydroxy-7'-[2-[(2R,3S,4R,5S,6R)-3,4,5-trihydroxy-6-(hydroxymethyl)tetrahydropyran-2-yl]ethynyl]spiro[cyclohexane-1,9'-fluorene]-2'-yl]ethynyl]tetrahydropyran-3,4,5-triol | (400 MHz, CD$_3$OD) δ 7.92 (s, 1H), 7.76 (dd, J = 14.3, 7.9 Hz, 2H), 7.62 (s, 1H), 7.47 (ddd, J = 18.4, 7.9, 1.3 Hz, 2H), 4.89 (d, J = 2.1 Hz, 1H), 4.88 (d, 1H), 4.11-3.91 (m, 5H), 3.93-3.78 (m, 4H), 3.74 (ddd, J = 11.3, 5.5, 1.5 Hz, 2H), 3.63 (td, J = 9.4, 1.5 Hz, 2H), 2.14-2.04 (m, 2H), 2.02-1.92 (m, 4H), 1.67 (m, 2H). | 623.29 |
| 204 | (2R,3S,4R,5S,6R)-2-(hydroxymethyl)-6-[2-[1-hydroxy-1-methyl-7'-[2-[(2R,3S,4R,5S,6R)-3,4,5-trihydroxy-6-(hydroxymethyl)tetrahydropyran-2-yl]ethynyl]spiro[cyclohexane-4,9'-fluorene]-2'-yflethynyl]tetrahydropyran-3,4,5-triol | (400 MHz, CD$_3$OD) δ 7.82-7.65 (m, 4H), 7.47 (ddd, J = 10.5, 7.9, 1.4 Hz, 2H), 4.89 (m, 2H), 4.02 (dd, J = 3.3, 2.1 Hz, 2H), 3.96 (ddd, J = 9.3, 4.4, 3.3 Hz, 2H), 3.91-3.81 (m, 4H), 3.73 (dd, J = 11.4, 5.5 Hz, 2H), 3.63 (t, J = 9.4 Hz, 2H), 2.20-2.08 (m, 2H), 2.03-1.88 (m, 4H), 1.55-1.45 (m, 2H), 1.44 (s,3H). | 637.3 |
| 205 | (2R,3S,4R,5S,6R)-2-[2-[4-amino-7'-[2-[(2R,3S,4R,5S,6R)-3,4,5-trihydroxy-6-(hydroxymethyl)tetrahydropyran-2-yl]ethynyl]spiro[cyclohexane-1,9'-fluorene]-2'-yl]ethynyl]-6-(hydroxymethyl)tetrahydropyran-3,4,5-triol | (400 MHz, CDCl$_3$) δ 8.05-7.98 (s, 1H), 7.83 (d, J = 7.9 Hz, 1H), 7.76 (d, J = 7.9 Hz, 1H), 7.62 (s, 1H), 7.53 (dd, J = 7.9, 1.2 Hz, 1H), 7.46 (dd, J = 7.9, 1.3 Hz, 1H), 4.88 (d, J = 2.2 Hz, 1H), 4.86 (m, 1H), 4.01 (ddd, J = 7.3, 3.3, 2.1 Hz, 2H), 3.93 (ddd, J = 9.3, 3.3, 1.7 Hz, 2H), 3.91-3.77 (m, 4H), 3.77-3.68 (m, 2H), 3.62 (td, J = 9.4, 4.7 Hz, 2H), 3.48 (dd, J = 10.3, 5.1 Hz, 1H), 2.30-2.04 (m, 6H), 1.56 (d, J = 13.1 Hz, 2H). | 622.28 |

Preparation of Compound 206 (Method D)

1-[2,7-Bis[2-[(2R,3 S,4R,5S,6R)-3,4,5-trihydroxy-6-(hydroxymethyl)tetrahydropyran-2-yl]ethynyl]spiro[fluorene-9,4'-piperidine]-1'-yl]-2-hydroxy-2-methyl-propan-1-one

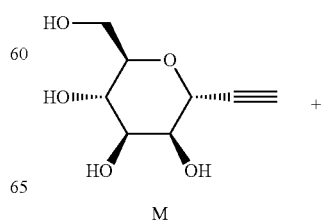

M

319
-continued

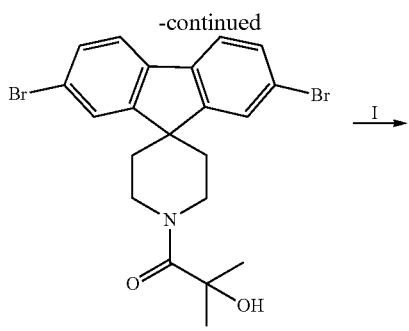

AG9

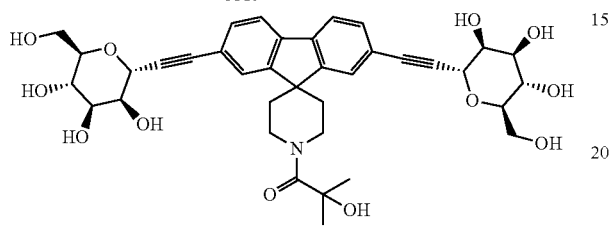

Compound 206 is prepared according to the procedure described for Compound 182 but using Intermediates M (275 μL of 0.53 M, 0.15 mmol) and AG9, (34 mg, 0.0622 mmol). The reaction mixture is heated at 100° C. for 2 h under $N_2$ and an additional amount of Intermediate M (120 μL of 0.53 M, 0.064 mmol) is added to complete the reaction. The reaction mixture is stirred at 100° C. for 2 h. Purification by reverse phase HPLC afforded the title compound (11 mg, 23%). $^1$H NMR (400 MHz, $CD_3OD$) δ 7.83-7.78 (m, 4H), 7.50 (dd, J=7.8, 1.3 Hz, 2H), 4.03-4.00 (m, 2H), 3.95 (dd, J=9.3, 3.3 Hz, 2H), 3.90-3.80 (m, 4H), 3.73 (dd, J=11.4, 5.6 Hz, 2H), 3.63 (t, J=9.4 Hz, 2H), 1.95-1.82 (m, 4H), 1.51 (s, 6H). Six protons are underneath solvent peaks. ESI-MS m/z calc. 693.2785, found 694.58 (M+1)$^+$.

Preparation of Compound 207 (Method D)

Methyl 2,7-bis[2-[(2R,3 S,4R,5S,6R)-3,4,5-trihydroxy-6-(hydroxymethyl)tetrahydropyran-2-yl]ethynyl]spiro[fluorene-9,4'-piperidine]-1'-carboxylate

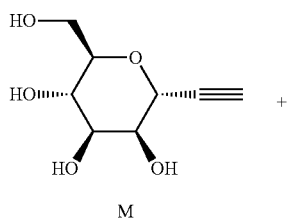

M

320
-continued

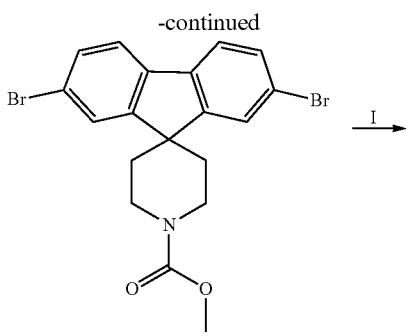

AG10

Compound 207 is prepared according to the procedure described for Compound 182 but using Intermediates M (375 μL of 0.53 M, 0.199 mmol) and AG10, (40 mg, 0.08405 mmol). The reaction mixture is heated at 100° C. for 2 h under $N_2$ and an additional amount of Intermediate M (160 μL of 0.53 M, 0.08480 mmol) is added to complete the reaction. The reaction mixture is stirred at 100° C. for 2 h. Purification by reverse phase HPLC afforded the title compound (31 mg, 54%). $^1$H NMR (400 MHz, $CD_3OD$) δ 7.82-7.77 (m, 4H), 7.49 (dd, J=7.9, 1.0 Hz, 2H), 4.03-4.00 (m, 2H), 3.95 (dd, J=9.4, 3.3 Hz, 2H), 3.93-3.80 (m, 8H), 3.76 (s, 3H), 3.73 (dd, J=11.4, 5.6 Hz, 2H), 3.63 (t, J=9.4 Hz, 2H), 1.89-1.79 (m, 4H). Two protons for C-1 sugar are under solvent peak. ESI-MS m/z calc. 665.24725, found 666.57 (M+1)$^+$.

Preparation of Compound 208 and 209

Compounds 208 and 209 are prepared according to the procedure described for Compound 207 but using the appropriate Intermediates prepared as described for Intermediates AG10

| Compound | IUPAC name | $^1$H-NMR | LCMS m/z (M + H)$^+$ |
|---|---|---|---|
| 208 | isopropyl 2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-carboxylate | (400 MHz, $CD_3OD$) δ 7.81-7.75 (m, 4H), 7.49 (dd, J = 7.9, 1.3 Hz, 2H), 4.99-4.90 (m, 1H), 4.88 (d, J = 2.1 Hz, 2H), 4.02 (dd, J = 3.2, 2.2 Hz, 2H), 3.95 (dd, J = 9.3, 3.3 Hz, 2H), 3.92-3.80 (m, 8H), 3.73 (dd, J = 11.4, 5.6 Hz, 2H), 3.63 (t, J = 9.4 Hz, | 694.27 |

| Compound | IUPAC name | ¹H-NMR | LCMS m/z (M + H)⁺ |
|---|---|---|---|
| 209 | ethyl 2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-carboxylate | 2H), 1.88-1.77 (m, 4H), 1.30 (d, J = 6.2 Hz, 6H). (400 MHz, CD₃OD) δ 7.82-7.74 (m, 4H), 7.49 (dd, J = 7.8, 1.3 Hz, 2H), 4.88 (d, J = 2.2 Hz, 2H), 4.19 (q, J = 7.1 Hz, 2H), 4.02 (dd, J = 3.2, 2.2 Hz, 2H), 3.95 (dd, J = 9.3, 3.3 Hz, 2H), 3.93-3.80 (m, 8H), 3.73 (dd, J = 11.4, 5.6 Hz, 2H), 3.63 (t, J = 9.4 Hz, 2H), 1.87-1.78 (m, 4H), 1.31 (t, J = 7.1 Hz, 3H). | 680.26 |

Preparation of Compound 210 (Method D)

(2R,3S,4R,5S,6R)-2-(hydroxymethyl)-6-[2-[1'-methylsulfonyl-7-[2-[(2R,3S,4R,5S,6R)-3,4,5-trihydroxy-6-(hydroxymethyl)tetrahydropyran-2-yl]ethynyl]spiro[fluorene-9,4'-piperidine]-2-yl]ethynyl]tetrahydropyran-3,4,5-triol

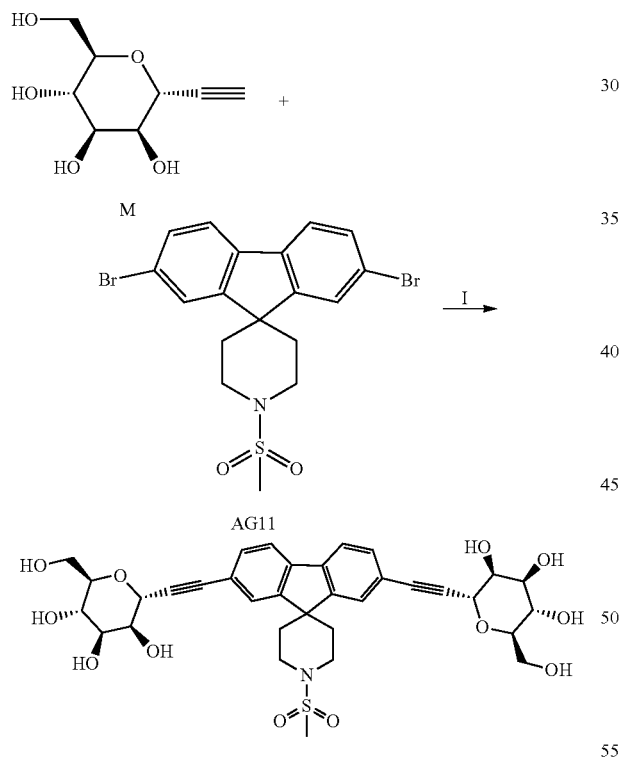

Compound 210 is prepared according to the procedure described for Compound 182 but using Intermediates M (350 μL of 0.53 M, 0.186 mmol) and AG11, (40 mg, 0.08 mmol). The reaction mixture is stirred at 100° C. for 2 h under N₂ then an additional amount of Intermediate M (150 μL of 0.53 M, 0.08 mmol) is added and the final mixture is stirred at 100° C. for 2 h. Purification by reverse phase HPLC afforded the title compound (23 mg, 41%). ¹H NMR (400 MHz, CD₃OD) δ 7.85-7.77 (m, 4H), 7.51 (d, J=9.1 Hz, 2H), 4.02 (dd, J=3.2, 2.2 Hz, 2H), 3.95 (dd, J=9.3, 3.3 Hz, 2H), 3.90-3.81 (m, 4H), 3.76-3.66 (m, 6H), 3.63 (t, J=9.4 Hz, 2H), 3.06 (s, 3H), 2.03-1.95 (m, 4H). Two protons of C-1 sugar are under the solvent peak. ESI-MS m/z calc. 685.2193, found 686.55 (M+1)⁺.

Preparation of Compound 211 (Method D)

[9-(acetoxymethyl)-2,7-bis[2-[(2R,3S,4R,5S,6R)-3,4,5-trihydroxy-6-(hydroxymethyl)tetrahydropyran-2-yl]ethynyl]fluoren-9-yl]methyl acetate

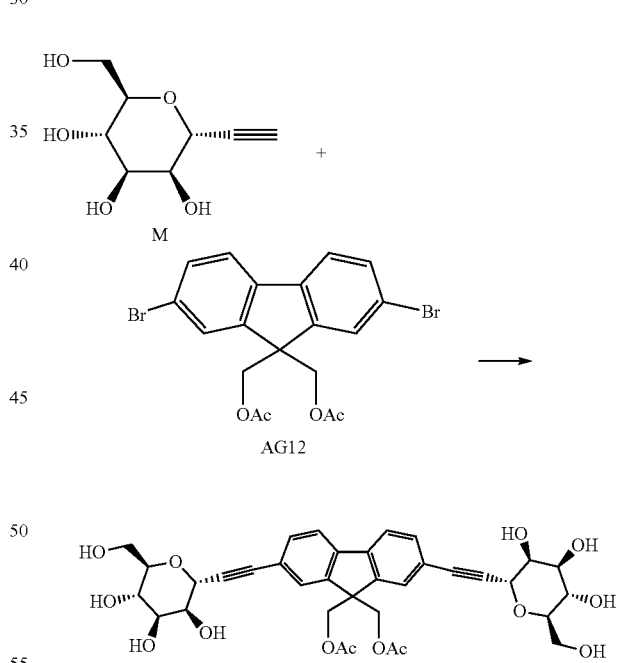

Compound 211 is prepared according to the procedure described for Compound 182 but using Intermediates M (1 mL of 0.53 M, 0.53 mmol) and AG12 (80 mg, 0.17 mmol). Purification by reverse phase HPLC afforded the title compound (36 mg, 29%). ¹H NMR (400 MHz, CD₃OD) δ 7.82 (d, J=7.9 Hz, 2H), 7.71 (s, 2H), 7.55 (d, J=7.9 Hz, 2H), 4.88 (d, J=2.1 Hz, 2H), 4.40 (s, 4H), 4.02 (dd, J=3.2, 2.2 Hz, 2H), 3.95 (dd, J=9.3, 3.3 Hz, 2H), 3.90-3.80 (m, 4H), 3.73 (dd, J=11.4, 5.5 Hz, 2H), 3.63 (t, J=9.4 Hz, 2H), 1.98 (s, 6H).

ESI-MS m/z calc. 682.22614, found 683.22 (M+1)⁺.

Preparation of Compound 212 (Method D)

(2R,3S,4R,5S,6R)-2-(hydroxymethyl)-6-[2-[7-[2-[(2R,3S,4R,5S,6R)-3,4,5-trihydroxy-6-(hydroxymethyl)tetrahydropyran-2-yl]ethynyl]-1H-indazol-5-yl]ethynyl]tetrahydropyran-3,4,5-triol

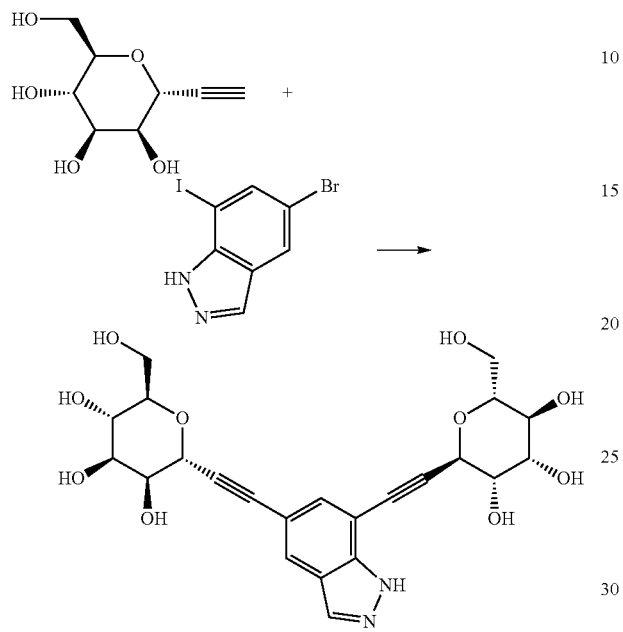

To a reaction tube charged with 5-bromo-7-iodo-1H-indazole (45.0 mg, 0.139 mmol) prepared following the procedure described in PCT Int. Appl., 2007117465, Pd(dppf)Cl$_2$. CH$_2$Cl$_2$ (6.0 mg, 0.0082 mmol) and CuI (6.0 mg, 0.032 mmol), capped and degassed (vacuum then nitrogen flush, 2×) is added Intermediate M (500 μL of 0.53 M, 0.265 mmol) as a solution in DMF and DIPEA (400 μL). The reaction tube is degassed again, transferred to a preheated (80° C.) oil bath and stirred overnight. After cooling down to RT, the reaction mixture is passed through a 200 mg Si-DMT cartridge, rinsed with portions of MeOH and purified by reverse phase HPLC. The fractions are combined and freeze-dried, providing the title compound (18.2 mg, 27% yield) as a fluffy white solid. $^1$H NMR (400 MHz, CD3OD) δ 8.14 (s, 1H), 7.97 (d, J=1.3 Hz, 1H), 7.60 (d, J=1.2 Hz, 1H), 5.01 (d, J=2.1 Hz, 1H), 4.93-4.78 (m, 1H), 4.16-4.09 (m, 1H), 4.06-4.01 (m, 1H), 4.01-3.81 (m, 6H), 3.80-3.70 (m, 2H), 3.69-3.58 (m, 2H). ESI-MS m/z: 491.44 (M+1)$^+$

Preparation of Compounds 213 to 216

Compounds 213-216 are prepared according to the procedure described for Compound 182 but using the Intermediates AG30 to AG33 respectively

| Compound | IUPAC name | $^1$H-NMR | LCMS m/z (M + H)$^+$ |
|---|---|---|---|
| 213 | (2R,3S,4R,5S,6R)-2-[2-[9-[2-(dimethylamino)ethyl-methyl-amino]-7-[2-(2R,3S,4R,5S,6R)-3,4,5-trihydroxy-6-(hydroxymethyl)tetrahydropyran-2-yl]ethynyl]-9H-fluoren-2-yl]ethynyl]-6-(hydroxymethyl)tetrahydropyran-3,4,5-triol | (400 MHz, CD$_3$OD) δ 7.79 (d, J = 7.6 Hz, 4H), 7.53 (d, J = 7.8 Hz, 2H), 5.03 (s, 1H), 4.87 (s, 2H), 4.00 (t, J = 2.7 Hz, 2H), 3.95-3.88 (m, 3H), 3.86 (d, J = 2.2 Hz, 1H), 3.85-3.79 (m, 2H), 3.73 (ddd, J = 11.4, 5.9, 1.4 Hz, 2H), 3.63 (td, J = 9.5, 1.0 Hz, 2H), 3.23-3.17 (m, 2H), 2.81 (s, 6H), 2.34 (s, 3H). | 639.31 |
| 214 | (2R,3S,4R,5S,6R)-2-[2-[9-(cyclopentylmethyl)-9-hydroxy-7-[2-[(2R,3S,4R,5S,6R)-3,4,5-trihydroxy-6-(hydroxymethyl)tetrahydropyran-2-yl]ethynyl]fluoren-2-yl]ethynyl]-6-(hydroxymethyl)tetrahydropyran-3,4,5-triol | (400 MHz, CD$_3$OD) δ 7.67 (d, J = 7.8 Hz, 2H), 7.58-7.53 (m, 2H), 7.47 (dd, J = 7.8, 1.4 Hz, 2H), 4.88 (d, J = 2.4 Hz, 2H), 4.02 (ddt, J = 3.0, 2.0, 1.0 Hz, 2H), 3.95 (dt, J = 9.3, 3.2 Hz, 2H), 3.91-3.88 (m, 1H), 3.87-3.80 (m, 3H), 3.73 (dd, J = 11.2, 5.6 Hz, 2H), 3.63 (t, J = 9.5 Hz, 2H), 2.29 (d, J = 6.2 Hz, 2H), 1.43-1.33 (m, 2H), 1.21-1.04 (m, 4H), 1.03-0.92 (m, 1H), 0.82-0.70 (m, 2H). | 637.27 |
| 215 | (2R,3S,4R,5S,6R)-2-[2-[9-(cyclohexylmethyl)-9-hydroxy-7-[2-[(2R,3S,4R,5S,6R)-3,4,5-trihydroxy-6-(hydroxymethyl)tetrahydropyran-2-yl]ethynyl]fluoren-2-yl]ethynyl]-6-(hydroxymethyl)tetrahydropyran-3,4,5-triol | (400 MHz, CD$_3$OD) δ 7.68 (d, J = 7.8 Hz, 2H), 7.55 (s, 2H), 7.47 (dd, J = 7.8, 1.3 Hz, 2H), 4.89 (d, J = 2.2 Hz, 2H), 4.06-4.00 (m, 2H), 3.95 (dt, J = 9.3, 3.5 Hz, 2H), 3.91-3.80 (m, 4H), 3.73 (dd, J = 11.3, 5.5 Hz, 2H), 3.63 (t, J = 9.4 Hz, 2H), 2.15-2.07 (m, 2H), 1.46-1.36 (m, 3H), 1.11 (d, J = 10.3 Hz, 2H), 1.04-0.90 (m, 1H), 0.90-0.80 (m, 2H), 0.74 (td, J = 15.7, 12.7, 5.1 Hz, 2H), 0.69-0.58 (m, 1H). | 651.27 |

-continued

| Compound | IUPAC name | ¹H-NMR | LCMS m/z (M + H)⁺ |
|---|---|---|---|
| 216 | (2R,3S,4R,5S,6R)-2-[2-[9-hydroxy-9-(2-hydroxyethyl)-7-[2-[(2R,3S,4R,5S,6R)-3,4,5-trihydroxy-6-(hydroxymethyl)tetrahydropyran-2-yl]ethynyl]fluoren-2-yl]ethynyl]-6-(hydroxymethyl)tetrahydropyran-3,4,5-triol | (400 MHz, CD₃OD) δ 7.68 (d, J = 7.9 Hz, 2H), 7.62-7.59 (m, 2H), 7.48 (dd, J = 7.9, 1.4 Hz, 2H), 4.88 (d, J = 1.1 Hz, 2H), 4.03-4.00 (m, 2H), 3.96-3.92 (m, 2H), 3.90-3.79 (m, 4H), 3.73 (dd, J = 11.5, 5.6 Hz, 2H), 3.63 (t, J = 9.5 Hz, 2H), 3.17-3.08 (m, 2H), 2.41-2.32 (m, 2H). | 599.27 |

Preparation of Compound 217

(2R,3S,4R,5S,6R)-2-[2-[9,9-Bis(hydroxymethyl)-7-[2-[(2R,3S,4R,5S,6R)-3,4,5-trihydroxy-6-(hydroxymethyl)tetrahydropyran-2-yl]ethynyl]fluoren-2-yl]ethynyl]-6-(hydroxymethyl)tetrahydropyran-3,4,5-triol

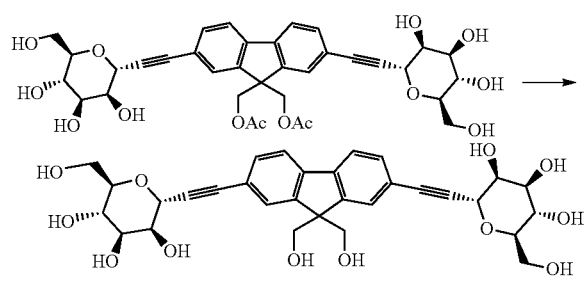

To a stirred solution of Compound 214 (23 mg, 0.03201 mmol) in MeOH (1 mL) is added MeONa in MeOH (100 μL of 0.5 M, 0.05 mmol), reaction mixture is stirred at RT overnight, quenched with DOWEX 50WX4 hydrogen form resin until pH 4-5, filtered and concentrated to afford the title compound (15 mg, 68%) as off-white solid. ¹H NMR (400 MHz, CD₃OD) δ 7.77 (d, J=7.9 Hz, 2H), 7.72 (s, 2H), 7.49 (dd, J=7.9, 1.3 Hz, 2H), 4.03-3.99 (m, 2H), 3.95 (dd, J=9.3, 3.3 Hz, 2H), 3.90-3.80 (m, 8H), 3.73 (dd, J=11.3, 5.4 Hz, 2H), 3.63 (t, J=9.4 Hz, 2H), two protons for C1-H sugar is under the solvent peak. ESI-MS m/z calc. 598.205, found 599.53 (M+1)⁺

Preparation of Compound 218 (Method D)

2,7-bis[2-[(2R,3S,4R,5S,6R)-3,4,5-trihydroxy-6-(hydroxymethyl)tetrahydropyran-2-yl]ethynyl]spiro[fluorene-9,5'-oxepane]-2'-one

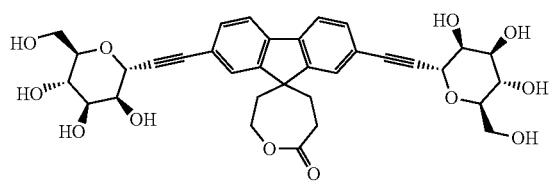 [SMILES: O=C1CCC2(CCO1)c1cc(C#C[C@H]3O[C@H](CO)[C@@H](O)[C@H](O)[C@@H]3O)ccc1-c1ccc(C#C[C@H]3O[C@H](CO)[C@@H](O)[C@H](O)[C@@H]3O)cc12]

Compound 218 is prepared according to the procedure described for Compound 182 but using the Intermediates AG13. ¹H NMR (400 MHz, CD₃OD) δ 7.90 (s, 1H), 7.84-7.75 (m, 2H), 7.60-7.46 (m, 3H), 4.81-4.70 (m, 1H), 4.04-4.00 (m, 2H), 3.99-3.93 (m, 2H), 3.91-3.81 (m, 4H), 3.73 (dd, J=11.2, 5.4 Hz, 2H), 3.63 (t, J=9.4 Hz, 2H), 3.21-3.12 (m, 1H), 2.85-2.74 (m, 1H), 2.44-1.94 (m, 4H), 1.44-1.34 (m, 1H). C-1 sugar protons are under the solvent peak. ESI-MS m/z calc. 637.27 (M+H)⁺.

Preparation of Compound 219

3-[9-(2-hydroxyethyl)-2,7-bis[2-[(2R,3S,4R,5S,6R)-3,4,5-trihydroxy-6-(hydroxymethyl)tetrahydropyran-2-yl]ethynyl]fluoren-9-yl]propanoic acid

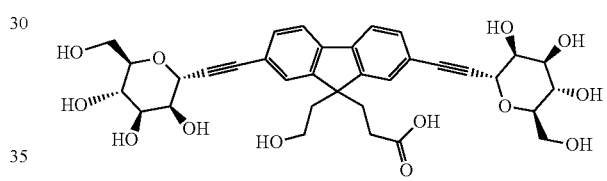

To a suspension of Compound 218 (0.075 mmol) in 1,4-dioxane (0.5 mL) is added aqueous LiOH in Water (100 μL of 1 M, 0.100 mmol). The resulting reaction mixture is stirred at RT for 5 h, quenched with AcOH (20 μL), purified by reverse phase HPLC to afford the title compound (7 mg, 14%) as white solid. ¹H NMR (400 MHz, CD₃OD) δ 7.77 (d, J=7.9 Hz, 2H), 7.58 (s, 2H), 7.49 (d, J=7.9 Hz, 2H), 4.04-4.00 (m, 2H), 3.96 (dd, J=9.3, 3.1 Hz, 2H), 3.91-3.81 (m, 4H), 3.73 (dd, J=11.3, 5.4 Hz, 2H), 3.63 (t, J=9.4 Hz, 2H), 2.84-2.73 (m, 2H), 2.46-2.29 (m, 4H), 1.48-1.34 (m, 2H). C-1 Sugar protons are under the solvent peak. ESI-MS m/z calc. 655.21 (M+H)⁺.

Preparation of Compound 220 (Method D)

[2,7-Bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-cyclopropyl-methanone

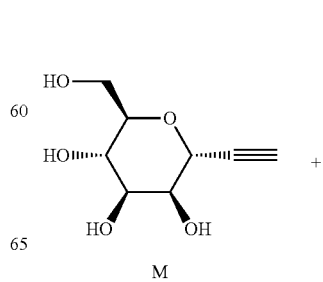

M

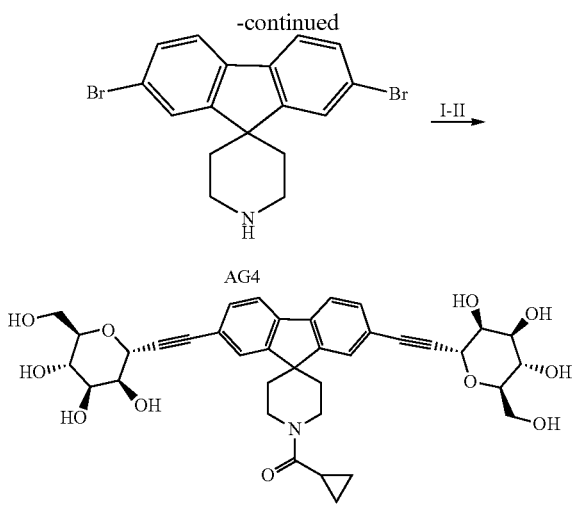

Step I: Crude Compound 192

A mixture of Intermediates AG4, (84 mg, 0.186 mmol), M (1.1 mL of 0.53 M, 0.583 mmol), Pd(dppf)Cl$_2$—CH$_2$Cl$_2$ (10.0 mg, 0.0123 mmol), CuI (11 mg, 0.058 mmol) in DMF (320 μL) is degassed (vacuum/N$_2$). To the reaction mixture is added DIPEA (260 μL, 1.493 mmol), degassed. The reaction mixture is placed on preheated oil bath at 100° C., stirred for 2 h under N$_2$, cooled to RT to afford the title compound. This crude reaction mixture is used as such in the next step without further workup.

Step II: Compound 220

To ⅓ of the crude reaction mixture from Step I (0.062 mmol, 0.55 mL) is added to a mixture of HATU (25.5 mg, 0.067 mmol) and cyclopropanecarboxylic acid (5.8 mg, 0.067 mmol) at RT. The reaction mixture is stirred for 2 h. The crude reaction mixture is filtered through metal scavenger (Si-DMT; Silicycle; SPE-R79030B-06P), washed with 0.5 mL of DMF. The filtrate is directly purified by reverse phase HPLC to afford the title compound (18 mg, 50%). $^1$H NMR (400 MHz, CD$_3$OD) δ 7.83-7.77 (m, 4H), 7.50 (dd, J=8.0, 1.0 Hz, 2H), 4.88 (d, J=2.1 Hz, 2H), 4.24-4.15 (m, 2H), 4.06-3.99 (m, 4H), 3.95 (dd, J=9.3, 3.3 Hz, 2H), 3.90-3.80 (m, 4H), 3.73 (dd, J=11.4, 5.6 Hz, 2H), 3.63 (t, J=9.4 Hz, 2H), 2.14-2.04 (m, 1H), 1.99-1.90 (m, 2H), 1.89-1.80 (m, 2H), 1.00-0.94 (m, 2H), 0.90-0.82 (m, 2H). ESI-MS m/z calc. 675.26794, found 676.51 (M+1)$^+$.

Preparation of Compounds 221 to 245

Compounds 221 to 245 are prepared according to the procedure described for Compound 220 but using the appropriate commercially available carboxylic acid.

| Compound | IUPAC name | $^1$H-NMR | LCMS m/z (M + H)$^+$ |
|---|---|---|---|
| 221 | 1-[2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-2-morphohno-ethanone | (400 MHz, CD$_3$OD) δ 8.27 (s, 1H), 7.84-7.77 (m, 4H), 7.51 (d, J = 7.9 Hz, 2H), 4.10-3.43 (m, 22H), 2.82-2.65 (m, 4H), 1.99-1.80 (m, 4H). [1] | 735.62 |
| 222 | 1-[2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-2-(dimethylamino)ethanone | (400 MHz, CD$_3$OD) δ 8.45 (s, 1H), 7.81-7.74 (m, 4H), 7.50 (d, J = 7.9 Hz, 2H), 4.22 (s, 2H), 4.07-3.99 (m, 4H), 3.93 (dd, J = 9.3, 3.2 Hz, 2H), 3.87-3.79 (m, 4H), 3.73 (dd, J = 11.4, 5.6 Hz, 2H), 3.63 (t, J = 9.4 Hz, 2H), 2.91 (s, 6H), 1.98-1.80 (m, 4H). | 693.47 |
| 223 | 1-[2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]propan-1-one | (400 MHz, CD$_3$OD) δ 7.82-7.77 (m, 4H), 7.50 (d, J = 8.0 Hz, 2H), 4.05-3.98 (m, 4H), 3.98-3.92 (m, 4H), 3.90-3.80 (m, 4H), 3.73 (dd, J = 11.4, 5.6 Hz, 2H), 3.63 (t, J = 9.4 Hz, 2H), 2.54 (q, J = 7.4 Hz, 2H), 1.95-1.79 (m, 4H), 1.19 (t, J = 7.5 Hz, 3H). C-1 sugar protons are under the solvent peak. | 664.18 |
| 224 | 1-[2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-2-methyl-propan-1-one | (400 MHz, CD$_3$OD) δ 7.83-7.78 (m, 4H), 7.50 (d, J = 8.0 Hz, 2H), 4.07-3.97 (m, 6H), 3.95 (dd, J = 9.4, 3.3 Hz, 2H), 3.90-3.80 (m, 4H), 3.73 (dd, J = 11.4, 5.6 Hz, 2H), 3.63 (t, J = 9.4 Hz, 2H), 3.14-3.02 (m, 1H), 1.95-1.81 (m, 4H), 1.19 (d, J = 6.7 Hz, 6H). C-1 sugar protons are under the solvent peak. | 678.18 |
| 225 | [2,7-bis[2-[(2R,3S,4R,5S,6R)-3,4,5-trihydroxy-6-(hydroxymethyl)tetrahydropyran- | (400 MHz, CD$_3$OD) δ 7.86-7.76 (m, 4H), 7.50 (d, J = 7.8 Hz, 2H), 4.18-3.99 (m, 6H), | 690.21 |

| Compound | IUPAC name | ¹H-NMR | LCMS m/z (M + H)⁺ |
|---|---|---|---|
| | 2-yl]ethynyl]spiro[fluorene-9,4'-piperidine]-1'-yl]-(1-methylcyclopropyl)methanone | 3.99-3.91 (m, 2H), 3.91-3.78 (m, 4H), 3.73 (dd, J = 11.3, 5.5 Hz, 2H), 3.63 (t, J = 9.4 Hz, 2H), 1.96-1.79 (m, 4H), 1.40 (s, 3H), 1.08-0.98 (m, 2H), 0.74-0.60 (m, 2H). C-1 sugar protons are under the solvent peak. | |
| 226 | [2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-cyclobutyl-methanone | (400 MHz, CD₃OD) δ 7.83-7.75 (m, 4H), 7.50 (d, J = 7.9 Hz, 2H), 4.04-3.97 (m, 4H), 3.94 (dd, J = 9.3, 3.3 Hz, 2H), 3.90-3.80 (m, 6H), 3.73 (dd, J = 11.4, 5.6 Hz, 2H), 3.63 (t, J = 9.4 Hz, 2H), 3.58-3.46 (m, 1H), 2.45-2.32 (m, 2H), 2.29-2.19 (m, 2H), 2.11-1.97 (m, 1H), 1.93-1.78 (m, 5H). C-1 sugar protons are under the solvent peak. | 690.21 |
| 227 | [2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-(1-hydroxycyclopropyl)methanone | (400 MHz, CD₃OD) δ 7.85-7.76 (m, 4H), 7.50 (d, J = 7.9 Hz, 2H), 4.42-3.9 (br m, 4H), 4.06-3.99 (m, 2H), 3.95 (dd, J = 9.4, 3.2 Hz, 2H), 3.91-3.80 (m, 4H), 3.78-3.70 (m, 2H), 3.63 (t, J = 9.4 Hz, 2H), 1.99-1.83 (m, 4H), 1.19-1.10 (m, 2H), 0.98-0.89 (m, 2H). C-1 sugar protons are under the solvent peak. | 692.19 |
| 228 | 1-[2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-2,2-dimethyl-propan-1-one | (400 MHz, CD₃OD) δ 7.83-7.78 (m, 4H), 7.53-7.47 (m, 2H), 4.13-4.05 (m, 4H), 4.04-4.00 (m, 2H), 3.95 (dd, J = 9.3, 3.3 Hz, 2H), 3.91-3.80 (m, 4H), 3.73 (dd, J = 11.4, 5.6 Hz, 2H), 3.63 (t, J = 9.4 Hz, 2H), 1.93-1.81 (m, 4H), 1.37 (s, 9H). C-1 sugar protons are under the solvent peak. | 692.22 |
| 229 | (2R)-1-[2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-2-methoxy-propan-1-one | (400 MHz, CD₃OD) δ 7.84-7.76 (m, 4H), 7.51 (d, J = 7.8 Hz, 2H), 4.39 (q, J = 6.6 Hz, 1H), 4.11-4.00 (m, 6H), 3.94 (dd, J = 9.4, 3.3 Hz, 2H), 3.90-3.79 (m, 4H), 3.73 (dd, J = 11.4, 5.6 Hz, 2H), 3.63 (t, J = 9.4 Hz, 2H), 3.40 (s, 3H), 1.98-1.81 (m, 4H), 1.42 (d, J = 6.7 Hz, 3H). C-1 sugar protons are under the solvent peak. | 694.21 |
| 230 | 1-[2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-carbonyl]cyclopropanecarbonitrile | (400 MHz, CD₃OD) δ 7.84 (s, 2H), 7.81 (d, J = 7.9 Hz, 2H), 7.52 (d, J = 7.9 Hz, 2H), 4.36-3.99 (m, 6H), 3.95 (dd, J = 9.3, 3.2 Hz, 2H), 3.90-3.80 (m, 4H), 3.73 (dd, J = 11.3, 5.5 Hz, 2H), 3.63 (t, J = 9.3 Hz, 2H), 2.08-1.81 (m, 4H), 1.73-1.58 (m, 4H). C-1 sugar protons are under the solvent peak. | 701.16 |
| 231 | [2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-(1H-pyrazol-5-yl)methanone | (400 MHz, CD₃OD) δ 7.85 (s, 2H), 7.80 (d, J = 7.9 Hz, 2H), 7.77-7.72 (m, 1H), 7.50 (d, J = 7.9 Hz, 2H), 6.70 (d, J = 2.4 Hz, 1H), 4.35-4.14 (m, 4H), 4.05-4.00 (m, 2H), 3.96 (dd, J = 9.3, 3.3 Hz, 2H), 3.91-3.80 (m, 4H), 3.73 (dd, J = 11.3, 5.4 Hz, 2H), 3.63 (t, J = 9.4 Hz, 2H), 2.01-1.88 (m, 4H). C-1 sugar protons are under the solvent peak. | 702.17 |

| Compound | IUPAC name | ¹H-NMR | LCMS m/z (M + H)⁺ |
|---|---|---|---|
| 232 | [2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-isoxazol-5-yl-methanone | (400 MHz, CD$_3$OD) δ 8.53 (d, 1H), 7.87 (s, 2H), 7.81 (d, J = 7.9 Hz, 2H), 7.51 (d, J = 7.8 Hz, 2H), 6.92 (d, 1H), 4.24-4.16 (m, 2H), 4.12-4.05 (m, 2H), 4.04-4.00 (m, 2H), 3.98-3.92 (m, 2H), 3.90-3.81 (m, 4H), 3.78-3.69 (m, 2H), 3.63 (t, J = 9.3 Hz, 2H), 2.03-1.93 (m, 4H). C-1 sugar protons are under the solvent peak. | 703.15 |
| 233 | [2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-[(2R)-tetrahydrofuran-2-yl]methanone | (400 MHz, CD$_3$OD) δ 7.86-7.76 (m, 4H), 7.54-7.48 (m, 2H), 4.15-3.79 (m, 15H), 3.73 (dd, J = 11.3, 5.6 Hz, 2H), 3.63 (t, J = 9.4 Hz, 2H), 2.32-1.71 (m, 8H). C-1 sugar protons are under the solvent peak. | 706.2 |
| 234 | 4-[2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-4-oxo-butanamide | (400 MHz, CD$_3$OD) δ 7.92 (d, J = 7.9 Hz, 2H), 7.83 (s, 2H), 7.48 (d, J = 7.8 Hz, 2H), 7.31 (s, 1H), 6.74 (s, 1H), 4.95 (d, J = 4.3 Hz, 2H), 4.78 (d, J = 5.8 Hz, 2H), 4.75-4.67 (m, 4H), 4.47 (t, J = 5.9 Hz, 2H), 3.89-3.33 (m, 16H), 2.62 (t, J = 7.1 Hz, 2H), 2.36 (t, J = 7.0 Hz, 2H), 1.90-1.79 (m, 2H), 1.77-1.65 (m, 2H). | 707.18 |
| 235 | [2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-(2,2-difluorocyclopropyl)methanone | (400 MHz, CD$_3$OD) δ 7.84 (s, 1H), 7.81 (d, J = 8.0 Hz, 2H), 7.73 (s, 1H), 7.51 (d, J = 7.9 Hz, 2H), 4.16-3.99 (m, 6H), 3.95 (dd, J = 9.3, 3.1 Hz, 2H), 3.89-3.80 (m, 4H), 3.73 (dd, J = 11.2, 5.2 Hz, 2H), 3.63 (t, J = 9.3 Hz, 2H), 3.13-3.02 (m, 1H), 2.13-1.78 (m, 6H). C-1 sugar protons are under the solvent peak. | 712.18 |
| 236 | [2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-pyrazin-2-yl-methanone | (400 MHz, CD$_3$OD) δ 8.96 (s, 1H), 8.71 (d, J = 2.5 Hz, 1H), 8.68 (d, J = 1.5 Hz, 1H), 7.88 (s, 2H), 7.81 (d, J = 7.9 Hz, 2H), 7.51 (d, J = 7.8 Hz, 2H), 4.28-4.19 (m, 2H), 4.05-4.01 (m, 2H), 3.99-3.93 (m, 4H), 3.91-3.80 (m, 4H), 3.77-3.70 (m, 2H), 3.63 (t, J = 9.2 Hz, 2H), 2.06-1.88 (m, 4H). C-1 sugar protons are under the solvent peak | 714.16 |
| 237 | [2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-(2-methylpyrazol-3-yl)methanone | (400 MHz, CD$_3$OD) δ 7.88 (s, 2H), 7.81 (d, J = 7.9 Hz, 2H), 7.55-7.48 (m, 3H), 6.63 (d, J = 1.9 Hz, 1H), 4.26-4.14 (m, 2H), 4.05-4.00 (m, 4H), 4.00 (s, 3H), 3.95 (dd, J = 9.3, 3.2 Hz, 2H), 3.91-3.81 (m, 4H), 3.73 (dd, J = 11.3, 5.4 Hz, 2H), 3.63 (t, J = 9.3 Hz, 2H), 2.03-1.82 (m, 4H). C-1 sugar protons are under the solvent peak. | 716.18 |
| 238 | [2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-(1-methylpyrazol-3-yl)methanone | (400 MHz, CD$_3$OD) δ 7.85 (s, 2H), 7.81 (d, J = 7.9 Hz, 2H), 7.67 (brs, 1H), 7.51 (d, J = 7.9 Hz, 2H), 6.67 (brs, 1H), 4.38-4.29 (m, 2H), 4.23-4.14 (m, 2H), 4.02 (dd, J = 3.2, 2.1 Hz, 2H), 3.98-3.92 (m, 5H), 3.90-3.81 (m, 4H), 3.73 (dd, J = | 716.21 |

-continued

| Compound | IUPAC name | ¹H-NMR | LCMS m/z (M + H)⁺ |
|---|---|---|---|
| | | 11.4, 5.6 Hz, 2H), 3.63 (t, J = 9.4 Hz, 2H), 2.00-1.88 (m, 4H). C-1 sugar protons are under the solvent peak. | |
| 239 | [2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-(6-methyl-2-pyridyl)methanone | (400 MHz, CD$_3$OD) δ 7.92-7.83 (m, 3H), 7.80 (d, J = 7.9 Hz, 2H), 7.53-7.46 (m, 3H), 7.39 (d, J = 7.8 Hz, 1H), 4.89 (d, J = 1.9 Hz, 2H), 4.25-4.17 (m, 2H), 4.05-4.01 (m, 2H), 3.96 (dd, J = 9.3, 3.1 Hz, 2H), 3.92-3.71 (m, 8H), 3.64 (t, J = 9.4 Hz, 2H), 2.59 (s, 3H), 2.03-1.96 (m, 2H), 1.93-1.84 (m, 2H). | 727.2 |
| 240 | 1-[2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-3-pyrazol-1-yl-propan-1-one | (400 MHz, CD$_3$OD) δ 7.79 (d, J = 7.9 Hz, 2H), 7.74 (s, 2H), 7.71 (d, J = 2.3 Hz, 1H), 7.55 (d, J = 1.9 Hz, 1H), 7.49 (dd, J = 7.9, 1.1 Hz, 2H), 6.34 (t, J = 2.1 Hz, 1H), 4.88 (d, J = 2.1 Hz, 3H), 4.54 (t, J = 6.6 Hz, 2H), 4.04-4.01 (m, 2H), 4.00-3.93 (m, 4H), 3.91-3.80 (m, 6H), 3.73 (dd, J = 11.3, 5.4 Hz, 2H), 3.63 (t, J = 9.4 Hz, 2H), 3.08 (t, J = 6.6 Hz, 2H), 1.81-1.73 (m, 4H). | 730.22 |
| 241 | 1-[2-[2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-2-oxo-ethyl]pyrrolidin-2-one | (400 MHz, CD$_3$OD) δ 7.92 (d, J = 7.8 Hz, 2H), 7.85 (s, 2H), 7.48 (d, J = 7.9 Hz, 2H), 4.95 (d, J = 4.2 Hz, 2H), 4.83-4.66 (m, 6H), 4.47 (t, J = 6.0 Hz, 2H), 4.18 (s, 2H), 3.91-3.34 (m, 18H), 2.25 (t, J = 8.0 Hz, 2H), 1.97 (d, J = 7.6 Hz, 2H), 1.85 (s, 2H), 1.75 (s, 2H). | 733.21 |
| 242 | [2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-[(2S)-tetrahydrofuran-2-yl]methanone | (400 MHz, CD$_3$OD) δ 7.85-7.76 (m, 4H), 7.52-7.48 (m, 2H), 4.16-3.80 (m, 15H), 3.73 (dd, J = 11.3, 5.5 Hz, 2H), 3.63 (t, J = 9.4 Hz, 2H), 2.33-1.75 (m, 8H). C-1 sugar protons are under the solvent peak | 706.2 |
| 243 | (5R)-5-[2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-carbonyl]pyrrolidin-2-one | (400 MHz, DMSO-d6) δ 7.97-7.89 (m, 3H), 7.78 (s, 1H), 7.74 (s, 1H), 7.49 (d, J = 8.4 Hz, 2H), 4.98-4.92 (m, 2H), 4.82-4.76 (m, 2H), 4.73 (d, J = 2.1 Hz, 2H), 4.70 (dd, J = 5.9, 2.1 Hz, 2H), 4.65-4.59 (m, 1H), 4.51-4.44 (m, 2H), 3.97-3.34 (m, 16H), 2.38-1.67 (m, 8H). | 719.2 |
| 244 | (5S)-5-[2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-carbonyl]pyrrolidin-2-one | (400 MHz, DMSO-d6) 8.16-8.13 (m, 1H), 8.00-7.88 (m, 3H), 7.78 (s, 1H), 7.74 (s, 1H), 7.49 (d, J = 8.0 Hz, 2H), 5.02-4.89 (m, 2H), 4.83-4.56 (m, 7H), 4.54-4.41 (m, 2H), 3.98-3.35 (m, 16H), 2.16-1.61 (m, 8H). | 719.2 |
| 245 | [2,7-bis[2-[(2R,3S,4R,5S,6R)-3,4,5-trihydroxy-6-(hydroxymethyl)tetrahydropyran-2-yl]ethynyl]spiro[fluorene-9,4'-piperidine]-1'-yl]-(1-methylpyrazol-4-yl)methanone | (400 MHz, CD$_3$OD) δ 8.05 (s, 1H), 7.88-7.79 (m, 5H), 7.51 (dd, J = 7.9, 1.3 Hz, 2H), 4.21-4.11 (m, 4H), 4.01 (dd, J = 3.2, 2.1 Hz, 2H), 3.97-3.94 (m, 2H), 3.93 (s, 3H), 3.91-3.80 (m, 4H), 3.77-3.69 (m, 2H), 3.63 (t, J = 9.4 Hz, 2H), 1.98-1.90 (m, 4H). | 716.21 |

Differential Scanning Calorimetry of Compound 162

Differential scanning calorimetry of Compound 162 crystalline form A can be measured using the TA Instrument DSC Q200 (Asset V012390). A sample (1.02 mg) is weighed in a pre-punched pinhole aluminum hermetic pan and heated from ambient temperature to 350° C. at 10° C./min. The DSC result seen in Figure A shows there is one endothermic peak observed, one at 258° C. (onset temperature of 254° C., enthalpy 50.7 J/g).

XRPD of Compound 162

The XRPD can be recorded at room temperature in reflection mode using Bruker D8 Discover system (Asset Tag V012842) equipped with a sealed tube source and a Hi-Star area detector (Bruker AXS, Madison, Wis.). The X-Ray generator operates at a tension of 40 kV and a current of 35 mA. The powder sample is placed on a Si zero-background wafer. Two frames are registered with an exposure time of 120 s each. The data are subsequently integrated over the range of 3°-41° 2-theta with a step size of 0.02° and merged into one continuous pattern. Figure C shows the X-ray powder diffractogram of the sample.

Representative XRPD peaks from Compound 162:

| Peak (2-Theta) | Intensity |
| --- | --- |
| 16.86 | 66.6 |
| 17.51 | 99.6 |
| 18.07 | 66.9 |
| 20.44 | 67.4 |
| 20.82 | 62.8 |
| 21.97 | 69.2 |
| 22.37 | 89.1 |
| 24.41 | 63 |
| 25.07 | 67.6 |
| 26.0 | 66.7 |
| 26.87 | 62.8 |
| 31.89 | 59.1 |

Thermo Analysis of Compound 202

A thermal gravimetric analysis of Compound 202 was performed to determine the percent weight loss as a function of time using the TA Instrument TGA Q500 (Asset V014840). A sample (1.29 mg) is added to a pre-tared aluminum pan and heated from ambient temperature to 350° C. at 10° C./min. Weight loss ca. 2.2% was observed upon heating to 130° C. with degradation being observed at >250° C. The TGA result is shown in Figure D.

XRPD of Compound 202

The XRPD of Compound 202 was recorded at room temperature in reflection mode using Bruker D8 Discover system (Asset Tag V012842) equipped with a sealed tube source and a Hi-Star area detector (Bruker AXS, Madison, Wis.). The X-Ray generator was operating at a tension of 40 kV and a current of 35 mA. The powder sample was placed on a Si zero-background wafer. Two frames were registered with an exposure time of 120 s each. The data were subsequently integrated over the range of 3.5°-39° 2-theta with a step size of 0.02° and merged into one continuous pattern. Figure D shows the X-ray powder diffractogram of the sample.

Representative XRPD peaks from Compound 202

| Peak (2-Theta) | Intensity |
| --- | --- |
| 7.42 | 38 |
| 9.39 | 65.8 |
| 14.29 | 91.6 |
| 14.9 | 100 |
| 16.24 | 78.7 |

Differential Scanning Calorimetry of Compound 202

Differential scanning calorimetry of Compound 202 crystalline form A can be measured using the TA Instrument DSC Q2000 (Asset V012390). A sample (1.94 mg) is weighed in a pre-punched pinhole aluminum hermetic pan and run with a modulation amplitude of +/−1° C./min using a ramp rate of 3° C./min to 300° C. The DSC result seen in figure E shows there is a glass transition observed at ca. 143° C. followed by a melting endothermic peak at 242° C. (onset temperature of 239.7° C., enthalpy 17.3 J/g).

Competitive Binding Assay

The first 177 amino acids of the FimH protein are expressed as a fusion protein with thrombin in a pET21b plasmid in bacteria. This FimH protein sequence contains the carbohydrate recognition domain (CRD) and shall be termed FimH-CRD. Following bacterial expression of the protein, the FimH-CRD protein is purified to homogeneity and the thrombin tag removed by protease cleavage. A competitive binding assay by fluorescence polarization is performed using 5 nM of the Alexa 647 mannoside probe and 60 nM of the FimH-CRD. The samples are assayed in a low volume 384 well microtiter plate in a final volume of 20 µl. The final assay buffer conditions are the following, 50 mM Tris-C$_1$, ph 7.0, 100 mM NaCl, 1 mM EDTA, 5 mM β-mercaptoethanol, 0.05% BSA and 2.5% DMSO. Two assays are performed for FimH, termed assay 1 or assay 2. The assay conditions are the same for both assays except the following: assay 1 has compounds prepared by manual dilution in a serial dilution factor with 12-point dose response while assay 2 has compounds prepared by a robotics system also through a serial dilution factor (12 point dose response) and initially prepared in duplicate in 384 well-Corning polypropylene round bottom plates. The assay 2 plates have compound which is then frozen and must be thawed prior to use. Initially the Alexa 647 probe and the FimH-CRD are added to the assay buffer and then 0.5 µl of test compound (assay 1 or 2) between 0.4 nM to 75 µM final concentration are added (12 point titration with 3-fold serial dilution). Control wells for the Alexa 647 probe are prepared with the same conditions except for the addition of the FimH-CRD protein. Plates are then incubated for 5 hrs at room temperature in the dark and under humid conditions to prevent drying. Plates are read using the SpectraMax Paradigm multi-mode plate reader and the appropriate fluorescent polarization detection cartridge (Alexa-647).

Alexa 647 mannoside probe is prepared using the similar procedure reported for FAM mannoside (Han, Z. et. al., 2010, J. Med. Chem., 53, 4779) and is described in the scheme below.

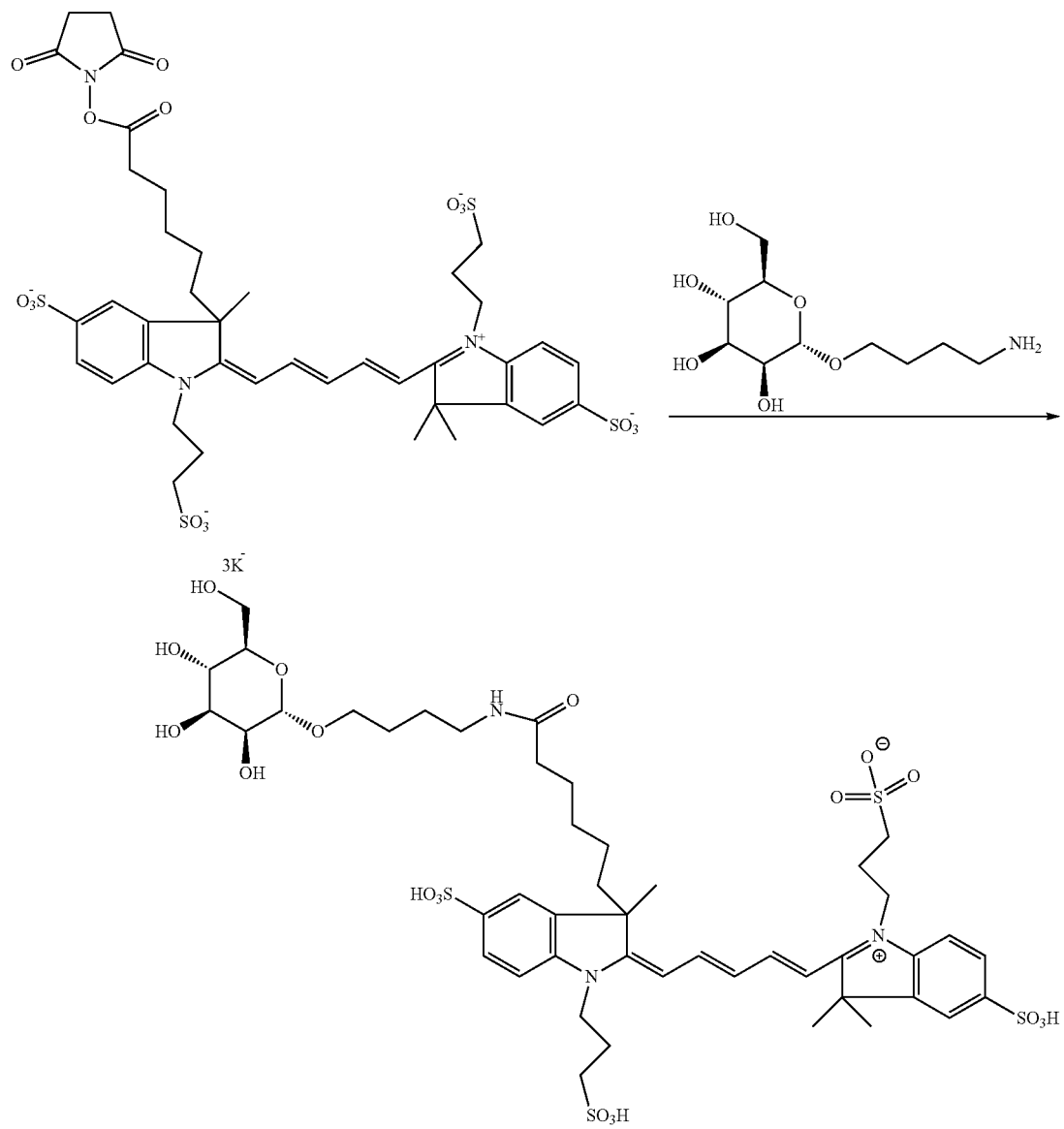

Alexa647 mannoside

To a blue colored stirred solution of (2S,3S,4S,5S,6R)-2-(4-aminobutoxy)-6-(hydroxymethyl)tetrahydropyran-3,4,5-triol (2.21 mg, 0.009 mmol) and the (2E)-2-[(2E,4E)-5-[3,3-dimethyl-5-sulfonato-1-(3-sulfonatopropyl)indol-1-ium-2-yl]penta-2,4-dienylidene]-3-[6-(2,5-dioxopyrrolidin-1-yl)oxy-6-oxo-hexyl]-3-methyl-1-(3-sulfonatopropyl)indoline-5-sulfonate (Potassium Ion (3)) (4.9 mg, 0.0044 mmol) in DMF (44 μL) is added Et$_3$N (5.4 mg, 7.0 μL, 0.053 mmol) at RT. The solution is stirred at room temperature over night, concentrated, dissolved in water and purified on 12 g C-18 silica gel cartridge on Isolera system using acetonitrile in water (0 to 40%, 10 CV) and followed by lyophilization to afford Alexa 647 mannoside probe (3.3 mg, 34%) as deep blue solid.

The $K_d$ values of the compounds are determined from dose response curves using twelve concentrations per compound in duplicate. Curves are fitted to data points using Fluorescence Polarization competitive displacement analysis, and Kds are interpolated from the resulting curves using GraphPad Prism software, version 50.4 (GraphPad software Inc., San Diego, Calif., USA). Table 1 below shows $K_d$ values obtained through both assay 1 and assay 2.

TABLE 1

| Compound No. | Assay 1 $K_d$ (uM) | Assay 2 $K_d$ (uM) |
|---|---|---|
| 1 | <0.005, 0.008, <0.005 | 0.013, 0.008 |
| 2 | 0.125, 0.062 | NT |
| 3 | 0.051, 0.04 | NT |
| 4 | 0.068, 0.096 | NT |
| 5 | <0.005, <0.005 | 0.049, <0.005, <0.005 |
| 6 | <0.005, <0.005 | <0.005, 0.023 |
| 7 | 0.017, 0.011 | NT |
| 8 | 0.016, 0.019 | NT |
| 9 | 0.007, 0.012 | 0.024 |
| 10 | 0.009, 0.015 | NT |

TABLE 1-continued

| Compound No. | Assay 1 $K_d$ (uM) | Assay 2 $K_d$ (uM) |
|---|---|---|
| 11 | <0.005, 0.011 | 0.016 |
| 12 | 0.014, 0.018 | NT |
| 13 | 0.017, 0.012 | NT |
| 14 | 0.011, 0.013 | 0.043, 0.006, 0.014 |
| 15 | 0.011, 0.015 | NT |
| 16 | <0.005, 0.006 | 0.026, <0.005, 0.009 |
| 17 | <0.005, 0.006 | NT |
| 18 | 1.062, 1.025 | NT |
| 19 | 0.006, <0.005 | NT |
| 20 | 0.058, 0.096 | NT |
| 21 | <0.005, <0.005, 0.009 | NT |
| 22 | <0.005, 0.012 | 0.014, <0.005, 0.011 |
| 23 | 0.009, 0.012 | 0.025, <0.005, 0.014 |
| 24 | <0.005, <0.005 | NT |
| 25 | <0.005, <0.005 | 0.021, 0.01, 0.012 |
| 26 | <0.005, <0.005 | NT |
| 27 | <0.005, <0.005 | NT |
| 28 | <0.005, <0.005 | NT |
| 29 | 0.006, 0.008 | NT |
| 30 | 0.007, <0.005 | NT |
| 31 | <0.005, <0.005 | NT |
| 32 | <0.005, <0.005 | NT |
| 33 | <0.005, <0.005 | NT |
| 34 | <0.005, 0.006 | NT |
| 35 | <0.005, 12.357, 0.007 | NT |
| 36 | 0.006, 0.014, <0.005 | NT |
| 37 | 0.007, 0.007 | 0.018, <0.005, 0.012 |
| 38 | <0.005, <0.005 | <0.005, <0.005, 0.021 |
| 39 | 0.029, 0.046 | NT |
| 40 | <0.005, 0.018 | 0.008, 0.01 |
| 41 | <0.005, <0.005 | <0.005, <0.005 |
| 42 | 0.114, 0.377 | 0.14, 0.145 |
| 43 | 0.02, 0.027 | NT |
| 44 | <0.005, <0.005 | 0.006 |
| 45 | NT | 0.707, 0.576, 0.558, 0.591 |
| 46 | NT | 0.011, 0.009, 0.016, 0.014 |
| 47 | NT | 0.044, 0.037, 0.051, 0.036 |
| 48 | NT | 0.079, 0.05, 0.063 |
| 49 | NT | 0.149, 0.087 |
| 50 | NT | 0.009, <0.005, <0.005 |
| 51 | NT | 0.015, <0.005 |
| 52 | NT | <0.005, <0.005 |
| 53 | NT | <0.005, <0.005 |
| 54 | NT | 0.016, 0.03 |
| 55 | NT | <0.005, 0.005 |
| 56 | NT | <0.005, <0.005 |
| 57 | NT | <0.005, <0.005 |
| 58 | NT | <0.005, <0.005 |
| 59 | NT | <0.005, <0.005 |
| 60 | NT | <0.005, <0.005 |

* NT means the compound was not tested

Bacterial Binding Assay

The purpose of the Bacterial Binding Assay (BBA) is to determine the inhibition activity of selective FimH antagonists on the bacterial strain LF82 binding to the glycoprotein BSA-(Mannose)$_3$.

Below is a list of the Materials used to run the BBA are described below.
1. LB broth: Supplier: Gibco, #10855
2. D-PBS: Supplier: Wisent, #311-425-CL
3. LB agar plates
4. 96-well black plate (high binding): Supplier: Costar, #3925
5. TopSeal™-A adhesive sealing films; Supplier PerkinElmer, #6005185
6. Carbonate-bicarbonate buffer pH 9.6 tablets, Supplier: Medicago, #09-8922-24
7. Water, Supplier: Gibco, #15230-162
8. Bovine serum albumin (BSA): Supplier: Sigma, #A-7888
9. (Man)3-BSA (α1-3, α1-6 Mannotriose-BSA, 1 mg), V-Labs, #NGP1336, lot #HGDX37-169-1
10. Tween 20: Supplier: Sigma, #P9416
11. Bright-Glo Luciferase Assay System: Supplier: Promega, #E2610
12. LF82/Luciferase strain: Invasive ability of an *Escherichia coli* strain isolated from the ileal mucosa of a patient with Crohn's disease. Boudeau J, Glasser A L, Masseret E, Joly B, Darfeuille-Michaud A, Infect Immun. 1999, 67(9), 4499-509

Solutions and buffers used to run the BBA are described below.
1. 0.04M carbonate-bicarbonate buffer (coating buffer)
2. 40 µg/mL BSA-(Man)$_3$: Dissolve 1 mg of (Man)3-BSA in 25 mL of water.
3. 4000 µg/mL BSA
4. 40 µg/mL BSA
5. 1 µg/mL BSA-(Man)$_3$: 150 µL of 40 µg/mL BSA-(Man)$_3$+5.85 mL of 40 µg/mL BSA
6. 0.5 µg/mL BSA-(Man)$_3$ in 0.02M carbonate-bicarbonate buffer.
7. 20 µg/mL BSA in 0.02M carbonate-bicarbonate buffer
8. Blocking buffer (2% BSA/DPBS): 1 g of BSA in 50 mL D-PBS
9. 2× binding buffer (0.2% BSA/D-PBS): 5 mL of blocking buffer+45 mL D-PBS.
10. Washing buffer (D-PBS/0.01% Tween 20): 10 µL of Tween 20 in 100 mL D-PBS.
11. 1× Bright-Glo Luciferase substrate: Dilute 1:1 the Bright-Glo Luciferase Assay System with D-PBS The experimental protocol to run the BBA is described below.

Overnight culture of LF82/Luciferase strain: Into two Falcon 50 mL tubes, add 20 mL of LB+20 µL of 50 mg/mL Kanamycin and inoculate with a loop from glycerol stock of the LF82/Luciferase strain. Incubate overnight at 37° C. with no shaking.

Glycoprotein coating of 96-well plates: Add 100 µL/well of 0.5-2 µg/mL BSA-(Man)$_3$. 20 µg/mL BSA is used as the control background. Seal plate using an adhesive sealing film and incubate overnight at room temperature. Wash the 96-well plate three times with 150 µL/well of D-PBS, add 170 µL/well of blocking solution and incubate 45 min (minimum) at room temperature.

Preparation of bacterial suspension: Mix the two cultures tubes (40 mL) and perform a 1:10 dilution in LB (900 µl LB+100 µl culture. Measure optical density (OD) of the bacterial cultures. OD1~5×10$^8$ cells/mL. Centrifuge LF82 culture for 20 min at 3500 rpm at room temperature. Re-suspend bacterial pellet in D-PBS and centrifuge again for 20 min at 3500 rpm. Re-suspend bacterial pellet in D-PBS to obtain a bacterial concentration of 2×10$^9$ bacteria/mL. Dilute 1/10 in D-PBS to obtain a final bacterial concentration of 2×10$^8$ bacteria/mL (=107 bacteria/50 µL). Perform 1/10 serial dilutions in LB of each bacterial suspension, plate 10 µL of dilutions on LB agar plates (final dilutions of 10-v) and incubate overnight at 37° C. and count CFUs to determine the actual bacteria density in the assay.

Bacterial binding assay: Add 147 µL 2× binding buffer to compound plate (containing 3 µL of compound). After blocking step is performed (at least 45 min), wash plates three times with 200 µL/well of D-PBS. With a 100 µL multichannel manual pipettor, add 50 µL/well of compound diluted in 2× binding buffer. With a 100 µL multichannel manual pipettor, add 50 µL/well of bacterial suspension. Agitate at slow speed for 1 min and incubate 40-75 min at room temperature. Wash 5 times with 150 µL/well of washing buffer and then once with D-PBS. Add 100 µL/well of 1× Bright-Glo Luciferase substrate. Read luminescence by using the Analyst HT plate reader or the Trilux 1450 microbeta plate reader. Table 2 below provides IC50 data for compounds 1-245 in the bacterial binding assay.

TABLE 2

Bacterial Binding Assay

| Compound | Bacterial Binding Assay IC$_{50}$ (μM) |
|---|---|
| 1 | 5.267 |
| 2 | 4.95 |
| 3 | NT |
| 4 | NT |
| 5 | 0.58 |
| 6 | 0.095 |
| 7 | NT |
| 8 | NT |
| 9 | NT |
| 10 | NT |
| 11 | NT |
| 12 | NT |
| 13 | NT |
| 14 | 4.10 |
| 15 | NT |
| 16 | 1.51 |
| 17 | NT |
| 18 | NT |
| 19 | 0.43 |
| 20 | NT |
| 21 | NT |
| 22 | 1.60 |
| 23 | 5.80 |
| 24 | 0.65 |
| 25 | 1.40 |
| 26 | 0.85 |
| 27 | 0.80 |
| 28 | 0.77 |
| 29 | 1.30 |
| 30 | 0.30 |
| 31 | NT |
| 32 | 0.34 |
| 33 | 0.39 |
| 34 | NT |
| 35 | NT |
| 36 | NT |
| 37 | 1.65 |
| 38 | 0.41 |
| 39 | NT |
| 40 | 0.043 |
| 41 | 0.55 |
| 42 | NT |
| 43 | NT |
| 44 | 0.48 |
| 45 | NT |
| 46 | NT |
| 47 | NT |
| 48 | NT |
| 49 | NT |
| 50 | 0.95 |
| 51 | 0.83 |
| 52 | 0.66 |
| 53 | 0.055 |
| 54 | 1.15 |
| 55 | 0.21 |
| 56 | 0.020 |
| 57 | 0.027 |
| 58 | 0.017 |
| 59 | 0.0082 |
| 60 | 0.013 |
| 62 | 0.067 |
| 63 | 0.112 |
| 64 | 0.015 |
| 65 | 0.055 |
| 66 | 0.034 |
| 67 | 0.040 |
| 68 | 0.0077 |
| 69 | 0.066 |
| 70 | 0.015 |
| 71 | 0.028 |

TABLE 2-continued

Bacterial Binding Assay

| Compound | Bacterial Binding Assay IC$_{50}$ (μM) |
|---|---|
| 72 | 0.018 |
| 73 | 0.021 |
| 74 | 0.0081 |
| 75 | 0.076 |
| 76 | 0.046 |
| 77 | 0.0040 |
| 78 | 0.063 |
| 79 | 0.037 |
| 80 | 0.011 |
| 81 | 0.009 |
| 82 | 0.018 |
| 83 | 0.0038 |
| 84 | 0.315 |
| 85 | 0.16 |
| 86 | 0.022 |
| 87 | 0.017 |
| 88 | 0.132 |
| 89 | 0.082 |
| 90 | 0.036 |
| 91 | 0.058 |
| 92 | 0.036 |
| 93 | 0.088 |
| 94 | 0.020 |
| 95 | 0.038 |
| 96 | 0.066 |
| 97 | 0.024 |
| 98 | 0.012 |
| 99 | 0.145 |
| 100 | 0.028 |
| 101 | 0.021 |
| 102 | 0.024 |
| 103 | 0.0074 |
| 104 | 0.034 |
| 105 | 0.046 |
| 106 | 0.0079 |
| 107 | 0.013 |
| 108 | 0.028 |
| 109 | 0.020 |
| 110 | 0.00089 |
| 111 | 0.0021 |
| 112 | 0.017 |
| 113 | 0.0055 |
| 114 | 0.0012 |
| 115 | 0.0039 |
| 116 | 0.0081 |
| 117 | 0.023 |
| 118 | 0.022 |
| 119 | 0.014 |
| 120 | 0.0012 |
| 121 | 0.012 |
| 122 | 0.029 |
| 123 | 0.041 |
| 124 | 0.027 |
| 125 | 0.054 |
| 126 | 0.124 |
| 127 | 0.043 |
| 128 | 0.022 |
| 129 | 1.245 |
| 130 | 0.067 |
| 131 | 0.128 |
| 132 | 0.052 |
| 133 | 0.028 |
| 134 | 0.044 |
| 135 | 0.58 |
| 136 | 0.145 |
| 137 | 0.70 |
| 138 | 0.031 |
| 139 | 0.046 |
| 140 | 0.353 |
| 141 | 0.34 |
| 142 | 0.091 |
| 143 | 0.24 |
| 144 | 0.235 |
| 145 | 0.43 |
| 146 | 0.165 |

TABLE 2-continued

Bacterial Binding Assay

| Compound | Bacterial Binding Assay IC$_{50}$ (μM) |
|---|---|
| 147 | 0.134 |
| 148 | 0.13 |
| 149 | 0.027 |
| 150 | 0.071 |
| 151 | 0.185 |
| 152 | 0.031 |
| 153 | 0.092 |
| 154 | 0.044 |
| 155 | 0.022 |
| 156 | 0.018 |
| 157 | 0.010 |
| 158 | 0.011 |
| 159 | 0.046 |
| 160 | 0.017 |
| 161 | 0.012 |
| 162 | 0.00011 |
| 163 | 0.018 |
| 164 | 0.035 |
| 165 | 0.0024 |
| 166 | 0.003 |
| 167 | 0.016 |
| 168 | 0.0031 |
| 169 | 0.00066 |
| 170 | 0.0075 |
| 171 | 0.013 |
| 172 | 0.188 |
| 173 | 0.0093 |
| 174 | 0.0047 |
| 175 | 0.0065 |
| 176 | 0.010 |
| 177 | 0.00066 |
| 178 | 0.0031 |
| 179 | 0.0071 |
| 180 | 0.0055 |
| 181 | 0.010 |
| 182 | 0.0014 |
| 183 | 0.00076 |
| 184 | 0.00083 |
| 185 | 0.0011 |
| 186 | 0.00028 |
| 187 | 0.0010 |
| 188 | 0.0043 |
| 189 | 0.0078 |
| 190 | 0.0011 |
| 191 | 0.00036 |
| 192 | 0.0032 |
| 193 | 0.00027 |
| 194 | 0.00027 |
| 195 | 0.018 |
| 196 | 0.028 |
| 197 | 0.00083 |
| 198 | 0.024 |
| 199 | 0.00021 |
| 200 | 0.00005 |
| 201 | 0.026 |
| 202 | 0.00007 |
| 203 | 0.00004 |
| 204 | 0.00080 |
| 205 | 0.00039 |
| 206 | 0.00008 |
| 207 | 0.00005 |
| 208 | 0.00003 |
| 209 | 0.00007 |
| 210 | 0.00016 |
| 211 | 0.0022 |
| 212 | 0.0049 |
| 213 | 0.0037 |
| 214 | 0.00045 |
| 215 | 0.0050 |
| 216 | 0.0099 |
| 217 | 0.020 |
| 218 | 0.00009 |
| 219 | 0.0038 |
| 220 | 0.00003 |
| 221 | 0.00004 |
| 222 | 0.00008 |
| 223 | 0.00006 |
| 224 | 0.00008 |
| 225 | 0.0012 |
| 226 | 0.00006 |
| 227 | 0.00006 |
| 228 | 0.00044 |
| 229 | 0.00035 |
| 230 | 0.00016 |
| 231 | 0.00008 |
| 232 | 0.00004 |
| 233 | 0.00005 |
| 234 | 0.00004 |
| 235 | 0.00003 |
| 236 | 0.00050 |
| 237 | 0.00022 |
| 238 | 0.00009 |
| 239 | 0.00035 |
| 240 | 0.00005 |
| 241 | 0.00003 |
| 242 | 0.00018 |
| 243 | 0.00022 |
| 244 | 0.00024 |
| 245 | 0.00014 |

Mouse Model of Inflammatory Bowel Disease (IBD):

Transgenic humanized-CEACAM6 mouse model may be used to test the compounds of the invention (Carvalho F A et al. (2009) J Exp Med. September 28; 206(10):2179-89). The Transgenic humanized-CEACAM6 mice are infected as described in Carvalho et al. The infected mice can then treated with compounds of the present invention.

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

What is claimed is:

1. A compound of the following formula (AG):

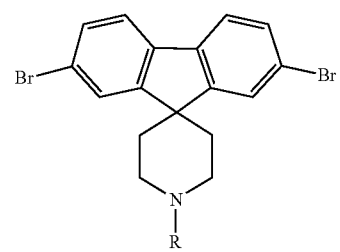

(AG)

wherein R is H (AG4), CH$_3$ (AG14), C(O)CH$_3$ (AG8), C(O)OCH$_3$ (AG10), C(O)OC(CH$_3$)$_3$ (AG5), C(O)C(CH$_3$)$_2$OH (AG9) or SO$_2$CH$_3$ (AG11).

2. The compound of claim 1, wherein R is C(O)CH$_3$ (AG8).

3. A process for preparing a compound of formula (AG5)

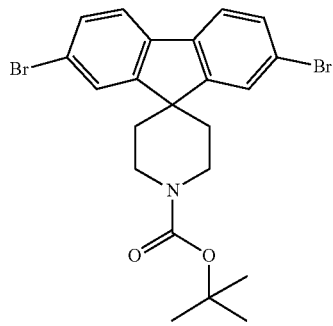
AG5 comprising the steps of:
reacting

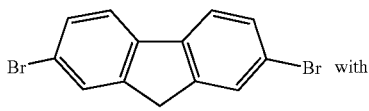 with

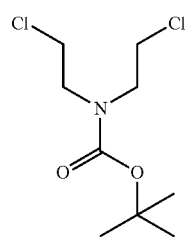

in the presence of a suitable base and a suitable solvent to form compound AG5.

4. The process of claim 3, wherein the suitable base is NaH.

5. The process of claim 3, wherein the suitable solvent is THF.

6. A process for preparing a compound of formula (AG4)

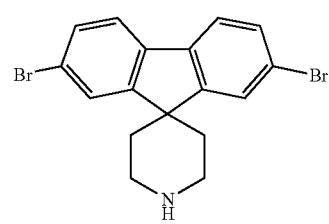
AG4 comprising the steps of reacting compound AG5

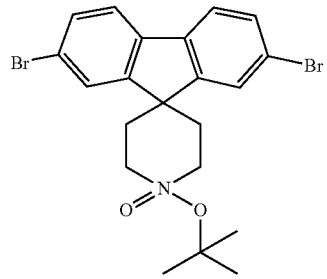
AG5 under acidic conditions to form compound AG4.

7. The process of claim 6, wherein acidic conditions correspond to HCl in dioxane.

8. A process for preparing a compound of formula (AG)

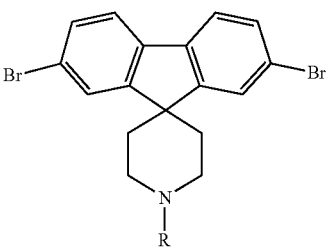
(AG)

wherein R is $C(O)CH_3$ (AG8), $C(O)OCH_3$ (AG10) or $SO_2CH_3$ (AG11), comprising the steps of reacting compound AG4

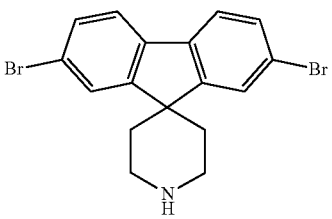
AG4 with R—Cl, a suitable base and a suitable solvent to form compound of formula (AG).

9. The process of claim 8, wherein the suitable base is triethylamine.

10. The process of claim 8, wherein the suitable solvent is chosen from DMF and $CH_2Cl_2$.

11. A process for preparing a compound of formula AG9:

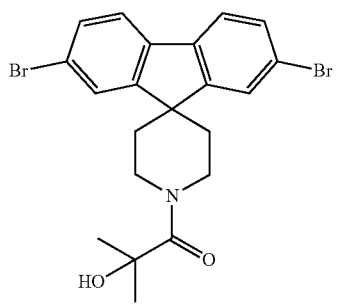

AG9 comprising the steps of reacting compound AG4 as defined in claim 6 with HATU, 2-hydroxy-2-methyl-propanoic acid, triethylamine and DMF to form compound of formula (AG9).

12. A process for preparing a compound of formula (AG14)

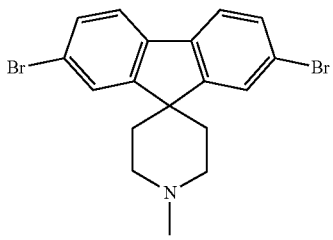

AG14 comprising the steps of reacting compound AG4 as defined in claim 6 with aqueous formaldehyde, sodium triacetoxyboranide and 1,2-dichloroethane to form compound of formula (AG14).

\* \* \* \* \*